US012673997B2

(12) United States Patent
Kang et al.

(10) Patent No.: US 12,673,997 B2
(45) Date of Patent: Jul. 7, 2026

(54) PD-1 BINDING PROTEINS, VEGF AND PD-1 BISPECIFIC BINDING PROTEINS, COMPOSITIONS, AND METHODS OF USE

(71) Applicant: Paragon Therapeutics, Inc., Waltham, MA (US)

(72) Inventors: Byong Ha Kang, Waltham, MA (US); Hussam Hisham Shaheen, Waltham, MA (US); Gopalan Raghunathan, Waltham, MA (US); Ghassan Najib Fayad, Waltham, MA (US); Mohammad Murshid Alam, Waltham, MA (US)

(73) Assignee: Paragon Therapeutics, Inc., Waltham, MA (US)

( * ) Notice: Subject to any disclaimer, the term of this patent is extended or adjusted under 35 U.S.C. 154(b) by 0 days.

(21) Appl. No.: 19/420,662

(22) Filed: Dec. 15, 2025

(65) Prior Publication Data

US 2026/0109769 A1    Apr. 23, 2026

Related U.S. Application Data

(63) Continuation of application No. PCT/US2025/047219, filed on Sep. 19, 2025.

(60) Provisional application No. 63/831,020, filed on Jun. 26, 2025, provisional application No. 63/788,196, filed on Apr. 14, 2025, provisional application No. 63/719,870, filed on Nov. 13, 2024, provisional application No. 63/697,436, filed on Sep. 20, 2024.

(51) Int. Cl.
| | |
|---|---|
| *C07K 16/28* | (2006.01) |
| *A61K 39/00* | (2006.01) |
| *C07K 16/22* | (2006.01) |

(52) U.S. Cl.
CPC .......... *C07K 16/2818* (2013.01); *C07K 16/22* (2013.01); *A61K 2039/505* (2013.01); *C07K 2317/31* (2013.01); *C07K 2317/73* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,751,173 | A | 5/1998 | McMahon et al. |
| 6,054,297 | A | 4/2000 | Carter et al. |
| 6,884,879 | B1 | 4/2005 | Baca et al. |
| 7,060,269 | B1 | 6/2006 | Baca et al. |
| 7,169,901 | B2 | 1/2007 | Baca et al. |
| 7,297,334 | B2 | 11/2007 | Baca et al. |
| 7,365,166 | B2 | 4/2008 | Baca et al. |
| 7,375,193 | B2 | 5/2008 | Baca et al. |
| 7,622,115 | B2 | 11/2009 | Fyfe et al. |
| 8,354,509 | B2 | 1/2013 | Carven et al. |
| 8,778,340 | B2 | 7/2014 | Dupont et al. |
| 8,900,587 | B2 | 12/2014 | Carven et al. |
| 8,952,136 | B2 | 2/2015 | Carven et al. |
| 9,079,953 | B2 | 7/2015 | Harding et al. |
| 9,220,776 | B2 | 12/2015 | Sharma et al. |
| 9,795,672 | B2 | 10/2017 | Fyfe et al. |
| 9,815,893 | B2 | 11/2017 | Akamatsu |
| 9,827,309 | B2 | 11/2017 | Strack et al. |
| 9,834,605 | B2 | 12/2017 | Carven et al. |
| 9,895,441 | B2 | 2/2018 | Maecker et al. |
| 10,087,251 | B2 | 10/2018 | Hermans et al. |
| 10,208,355 | B2 | 2/2019 | Bais et al. |
| 10,456,470 | B2 | 10/2019 | Bais et al. |
| 10,570,202 | B2 | 2/2020 | Martini et al. |
| 10,617,755 | B2 | 4/2020 | Bais et al. |
| 11,104,734 | B2 | 8/2021 | Xia et al. |
| 11,117,961 | B2 | 9/2021 | Carven et al. |
| 11,498,966 | B2 | 11/2022 | Kley et al. |
| 11,547,705 | B2 | 1/2023 | Denker et al. |
| 11,633,476 | B2 | 4/2023 | Sharma et al. |
| 12,083,112 | B2 | 9/2024 | Denker et al. |
| 12,122,834 | B2 | 10/2024 | Fayadat-Dilman et al. |
| 12,227,577 | B2 | 2/2025 | Alimzhanov et al. |
| 2016/0303231 | A1 | 10/2016 | Iannone et al. |
| 2019/0161549 | A1 | 5/2019 | Choong |
| 2020/0325228 | A1 | 10/2020 | Martini et al. |
| 2021/0317214 | A1 | 10/2021 | Chartash et al. |
| 2021/0317215 | A1 | 10/2021 | Reichert et al. |
| 2021/0380694 | A1 | 12/2021 | Forrest, Jr. et al. |
| 2021/0388090 | A1 | 12/2021 | Ishikura et al. |
| 2021/0403560 | A1 | 12/2021 | Carven et al. |
| 2022/0089738 | A1 | 3/2022 | Krishnamachari et al. |
| 2022/0251205 | A1 | 8/2022 | Brower et al. |

(Continued)

FOREIGN PATENT DOCUMENTS

| | | |
|---|---|---|
| AU | 2019/218433 A1 | 9/2020 |
| AU | 2019/332708 A1 | 4/2021 |

(Continued)

OTHER PUBLICATIONS

International Search Report and Written Opinion for Application No. PCT/US2025/047219, mailed Dec. 16, 2025.

(Continued)

*Primary Examiner* — Peter J Reddig

(74) *Attorney, Agent, or Firm* — Wolf, Greenfield & Sacks, P.C.

(57) ABSTRACT

Bispecific antibodies that bind VEGF and PD-1, pharmaceutical compositions thereof, and methods of use thereof, including methods of inhibiting VEGF and PD-1 biological activities.

19 Claims, 79 Drawing Sheets

Specification includes a Sequence Listing.

(56) References Cited

U.S. PATENT DOCUMENTS

| | | |
|---|---|---|
| 2022/0298247 A1 | 9/2022 | Choong |
| 2022/0380469 A1 | 12/2022 | Aktan et al. |
| 2023/0250182 A1 | 8/2023 | Perini et al. |
| 2023/0265196 A1 | 8/2023 | Lee et al. |
| 2024/0067711 A1 | 2/2024 | Jun et al. |

FOREIGN PATENT DOCUMENTS

| | | | |
|---|---|---|---|
| CN | 105175545 A | 12/2015 | |
| CN | 104195173 B | 3/2017 | |
| WO | WO 1995/009917 A1 | 4/1995 | |
| WO | WO 1998/045331 A2 | 10/1998 | |
| WO | WO 2008/156712 A1 | 12/2008 | |
| WO | WO 2013/181452 A1 | 12/2013 | |
| WO | WO 2015/088847 A1 | 6/2015 | |
| WO | WO 2017/106656 A1 | 6/2017 | |
| WO | WO 2017/165681 A1 | 9/2017 | |
| WO | WO 2018/036472 A1 | 3/2018 | |
| WO | WO-2019062642 A1 * | 4/2019 | .......... G01N 33/575 |
| WO | WO 2020/043184 A1 | 3/2020 | |
| WO | WO 2024/125417 A1 | 6/2024 | |

OTHER PUBLICATIONS

Lapeyre-Prost et al., Immunomodulatory Activity of VEGF in Cancer. Int Rev Cell Mol Biol. 2017:330:295-342. doi: 10.1016/bs.ircmb.2016.09.007. Epub Dec. 26, 2016.

Li et al., The enhanced antitumor activity of bispecific antibody targeting PD-1/PD-L1 signaling. Cell Commun Signal. Mar. 12, 2024;22(1):179. doi: 10.1186/s12964-024-01562-5.

Lu et al., Preclinical development of CR-001, a novel tetravalent PD-1 x VEGF bispecific antibody with cooperative pharmacology and potent anti-tumor activity. Crescent Biophrma. Presented at the SITC 40th Anniversary Annual Meeting, National Harbor, MD, USA, Nov. 7-9, 2025.

Xiong et al., Ivonescimab versus pembrolizumab for PD-L1-positive non-small cell lung cancer (HARMONi-2): a randomised, double-blind, phase 3 study in China. Lancet. Mar. 8, 2025;405(10481):839-849. doi: 10.1016/S0140-6736(24)02722-3.

Zhao et al., AK112, a novel PD-1/VEGF bispecific antibody, in combination with chemotherapy in patients with advanced non-small cell lung cancer (NSCLC): an open-label, multicenter, phase II trial. EClinicalMedicine. Aug. 3, 2023;62:102106. doi: 10.1016/j.eclinm.2023.102106. eCollection Aug. 2023.

Zhong et al., Design of a fragment crystallizable-engineered tetravalent bispecific antibody targeting programmed cell death-1 and vascular endothelial growth factor with cooperative biological effects. iScience. Dec. 31, 2024;28(3):111722. doi: 10.1016/j.isci.2024.111722. eCollection Mar. 21, 2025.

* cited by examiner

Promega PD-1/PD-L1 Blockade

—■— Pembrolizumab (IgG4 S228P)

······· Pembrolizumab (IgG4 S228P) YTE

—▽— Pembrolizumab IgG1 LALA YTE

—▼— Clone 2 IgG1 LALA YTE

—◆— Clone 3 IgG1 LALA YTE

\+ Isotype Control

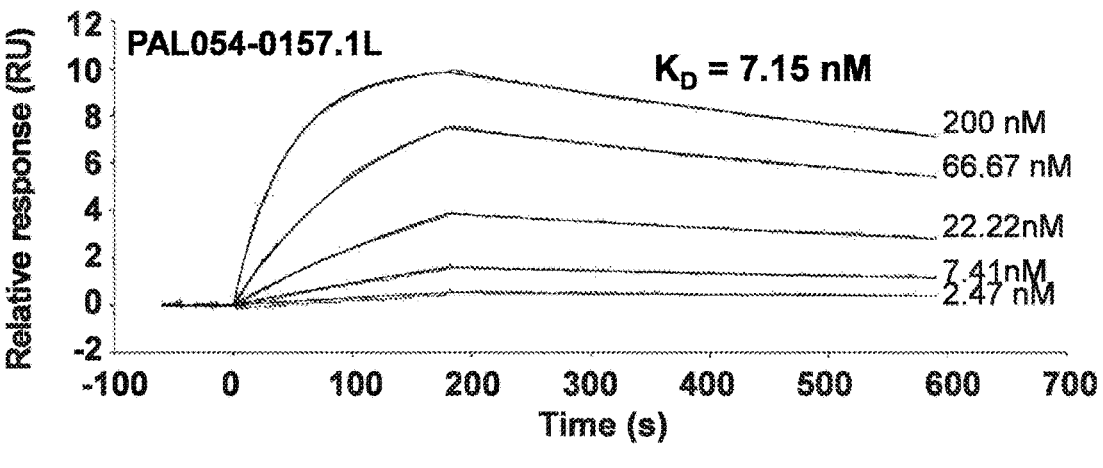
FIG. 6B
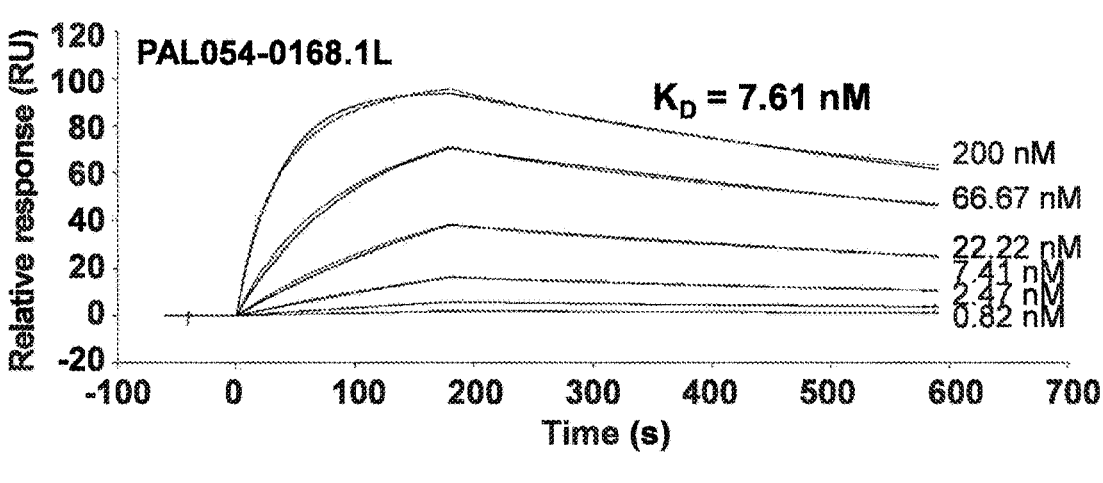
FIG. 6C
FIG. 6D

PAL054-0001.1L
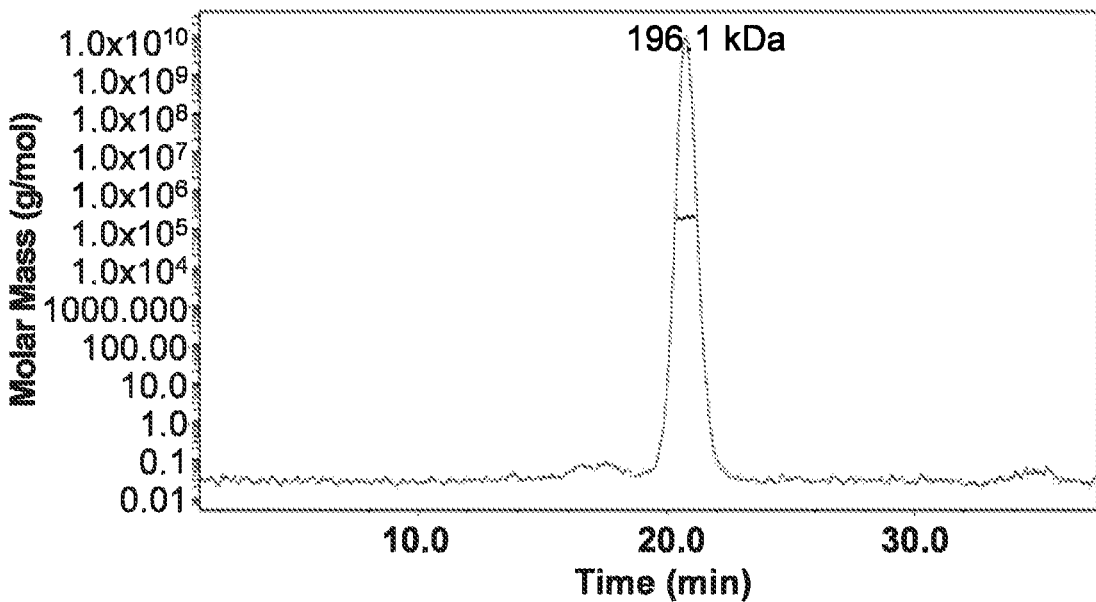
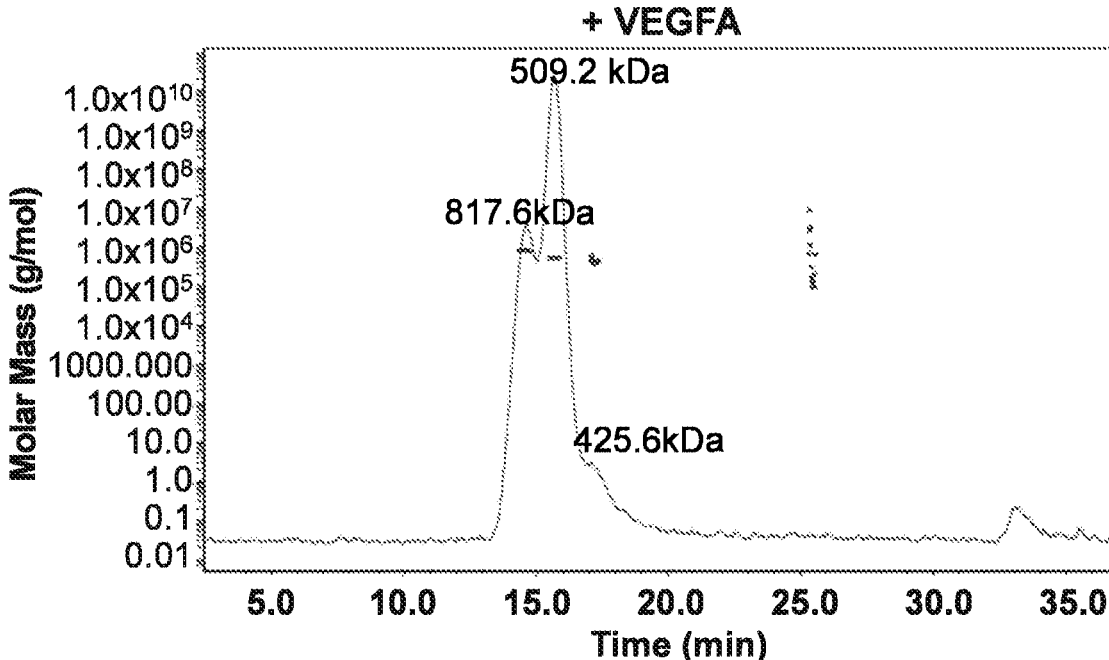
FIG. 7A

PAL054-0011.1La
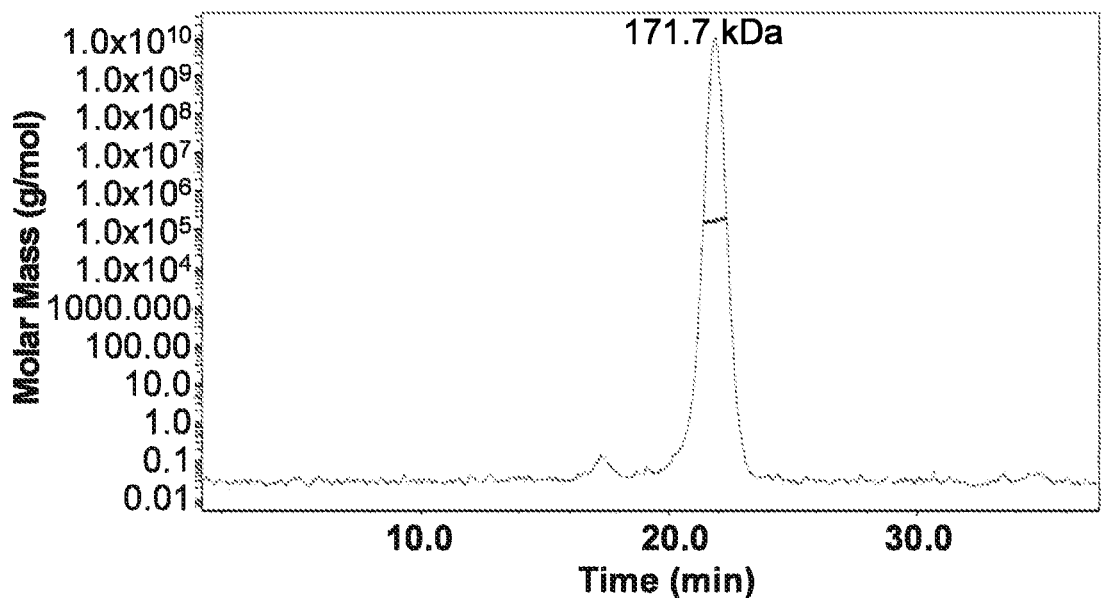
+ VEGFA
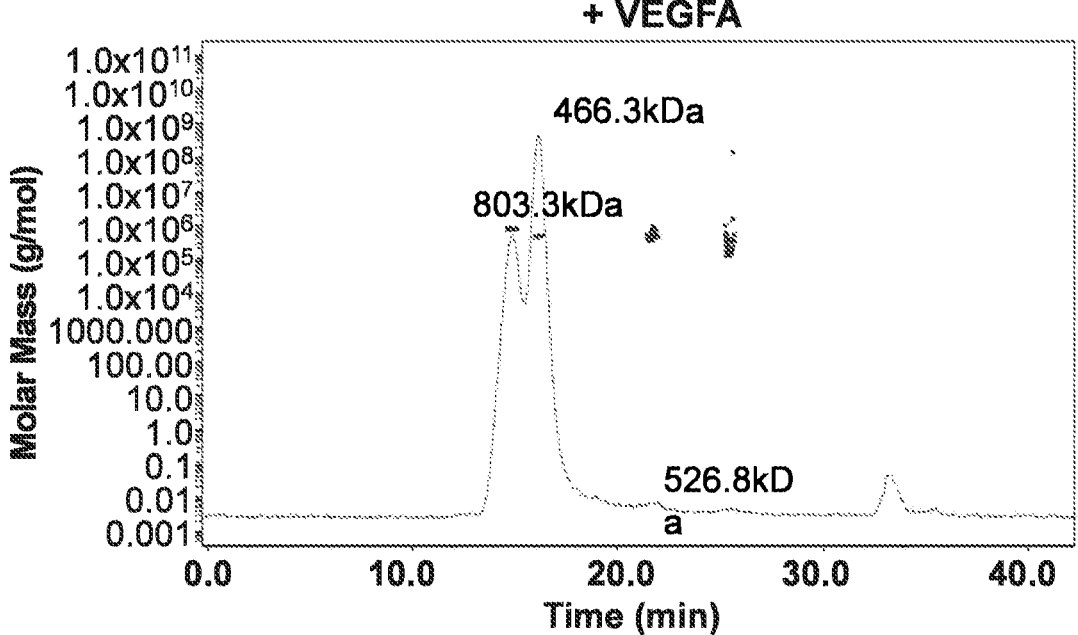
FIG. 7B

PAL054-0104.1La
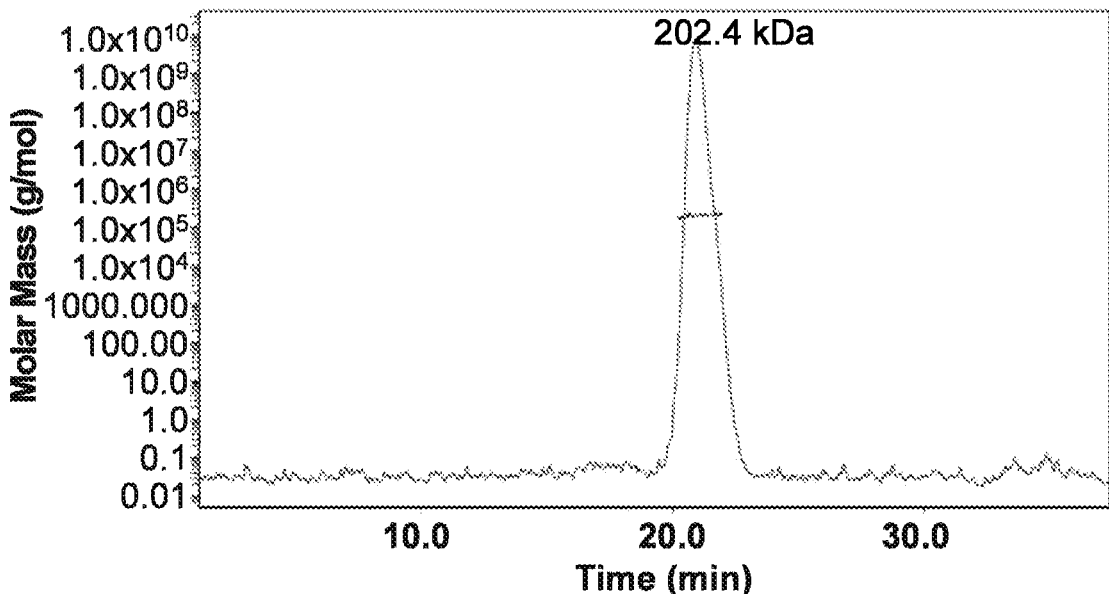
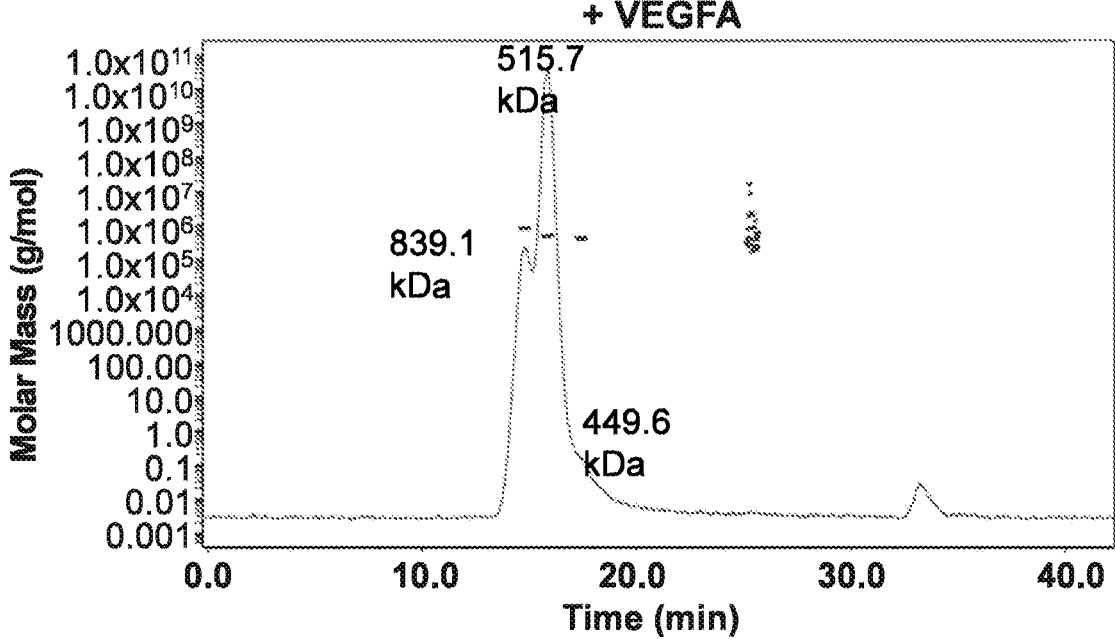
FIG. 7C

PAL054-0148.1La
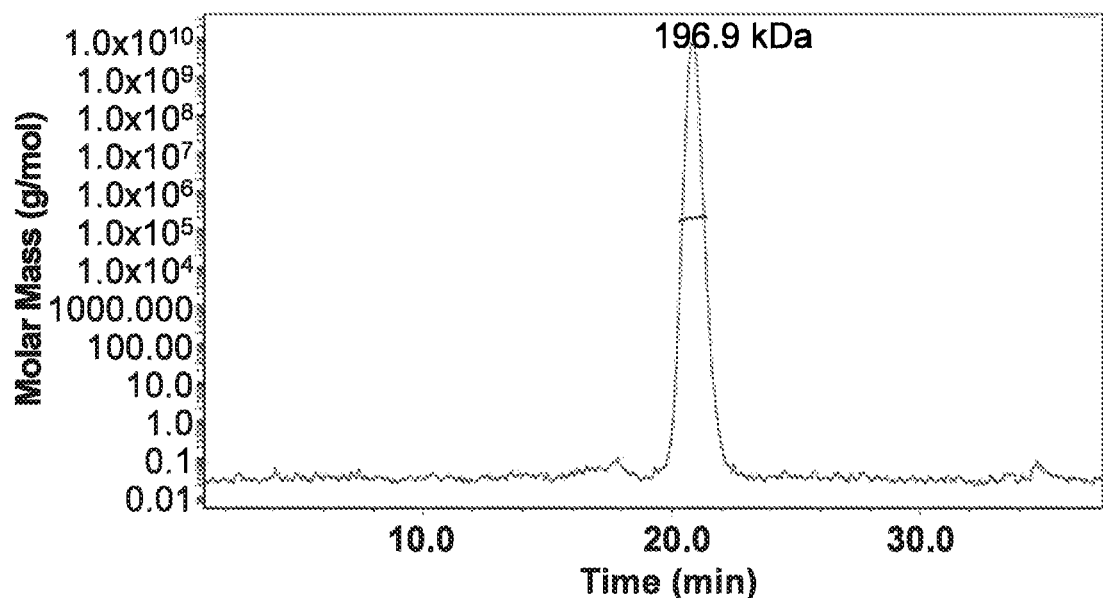
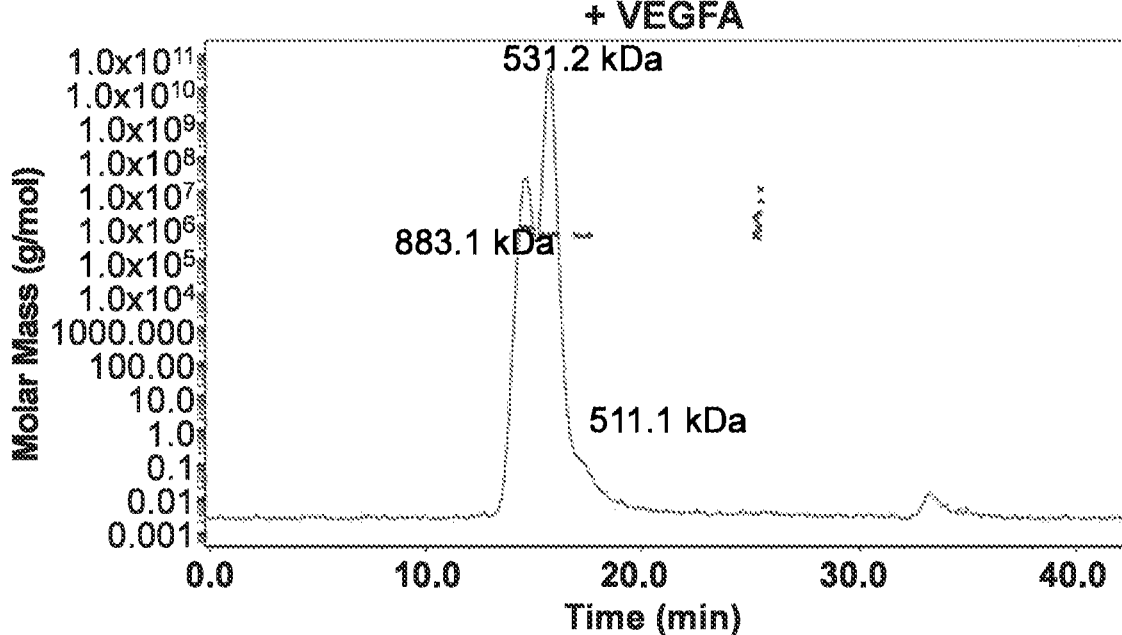
FIG. 7D

PAL054-0157.1La
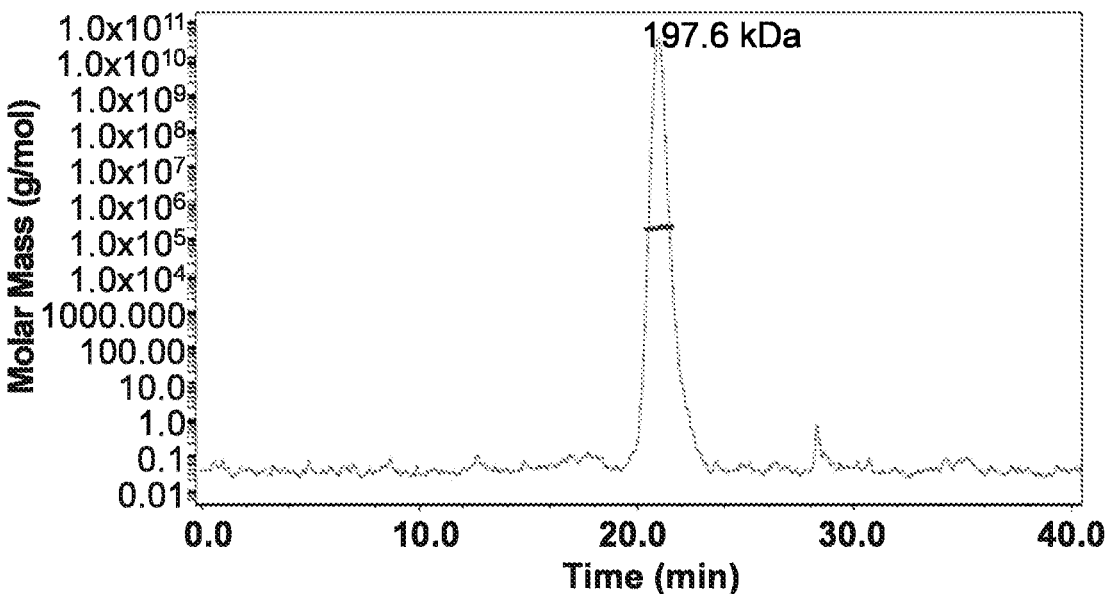
+ VEGFA
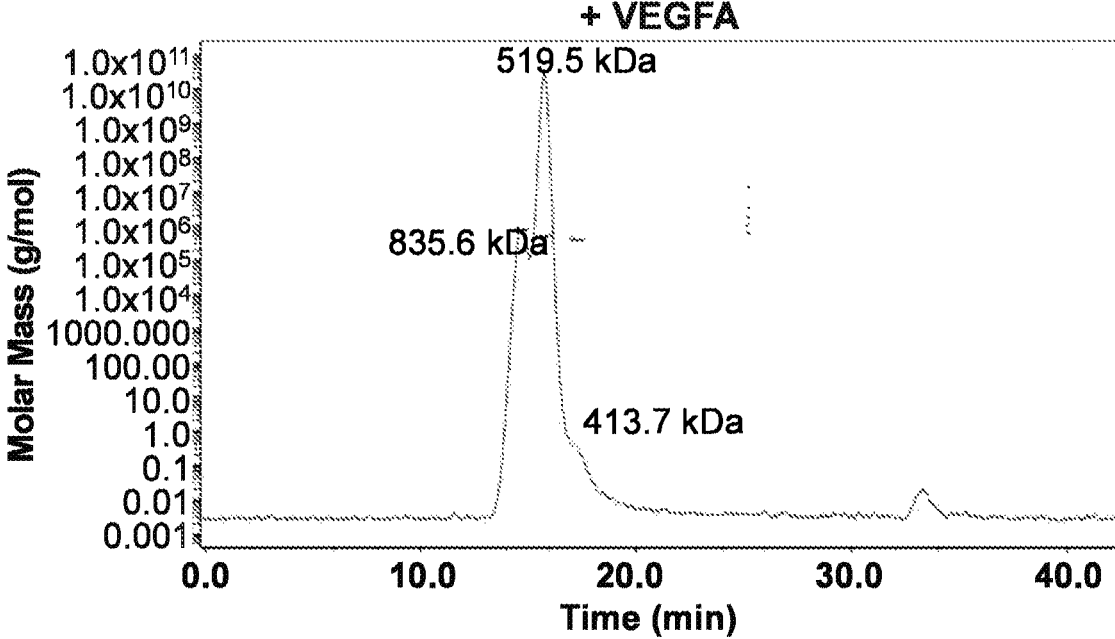
FIG. 7E

PAL054-0170.1L
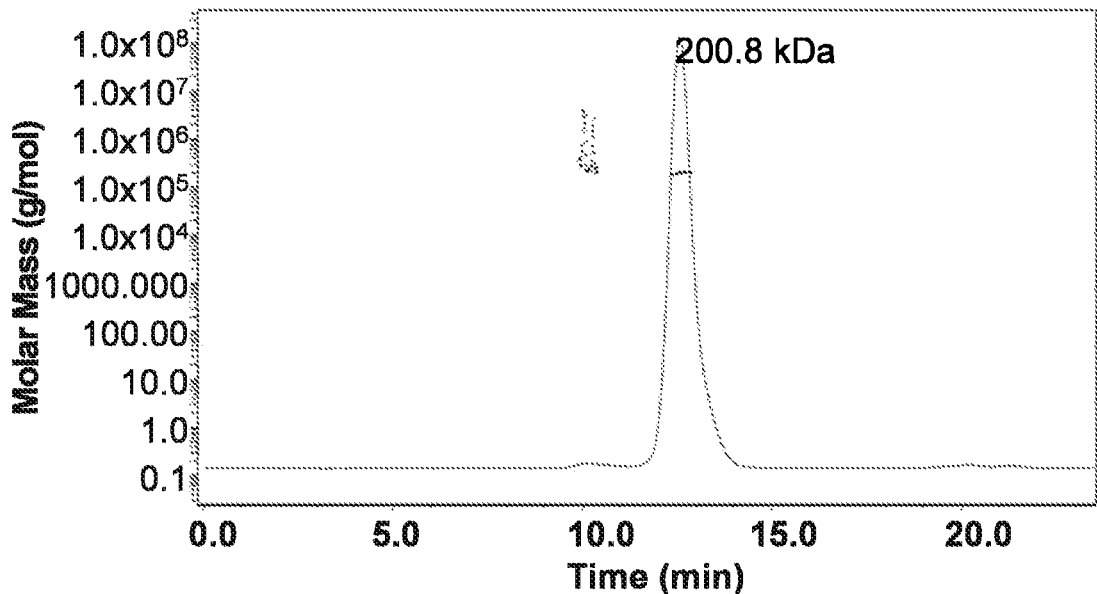
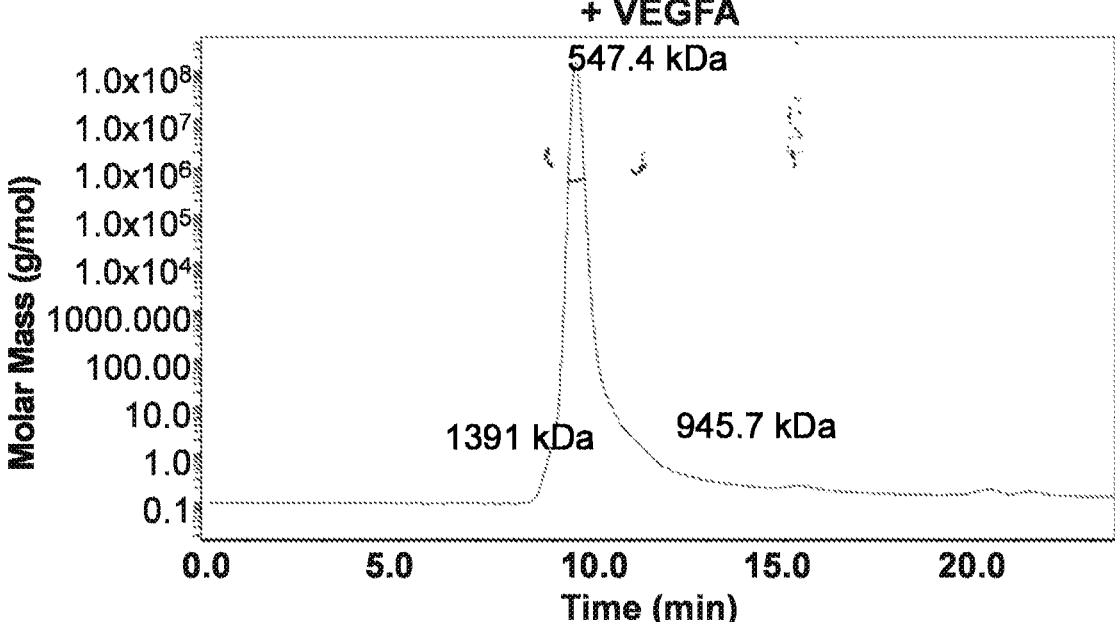
FIG. 7F

HC

EVQLVESGGGLVQPGGSLRLSCAASGYTFTNYGMNWVRQAPGKGLEWVGW
INTYTGEPTYAADFKRRFTFSLDTSKSTAYLQMNSLRAEDTAVYYCAKYP
HYYGSSHWYFDVWGQGTLVTVSSASTKGPSVFPLAPSSKSTSGGTAALGC
LVKDYFPEPVTVSWNSGALTSGVHTFPAVLQSSGLYSLSSVVTVPSSSLG
TQTYICNVNHKPSNTKVDKKVEPKSCDKTHTCPPCPAPEAAGGPSVFLFP
PKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPR
EPQVYTLPPSRDELTKNQVSLTCLVKGFYPSDIAVEWESNGQPENNYKTT
PPVLDSDGSFFLYSKLTVDKSRWQQGNVFSCSVMHEALHNHYTQKSLSLS
PGKGGGGSGGGGSGGGGSGGGGS<u>EVQLVESGGGLVQPGGSLRLSCAASGF</u>
<u>AFSSYDMSWVRQAPGKGLDWVATISGGGRYTYYPDSVKGRFTISRDNSKN</u>
<u>NLYLQMNSLRAEDTALYYCANRYGEAWFAYWGQGTLVTVSS</u>GGGGSGGGGG
SGGGGSGGGGS<u>DIQMTQSPSSMSASVGDRVTFTCRASQDINTYLSWFQQK</u>
<u>PGKSPKTLIYRANRLVSGVPSRFSGSGSGQDYTLTISSLQPEDMATYYCL</u>
<u>QYDEFPLTFGAGTKLELKR</u>

LC

DIQMTQSPSSLSASVGDRVTITCSASQDISNYLNWYQQKPGKAPKVLIYF
TSSLHSGVPSRFSGSGSGTDFTLTISSLQPEDFATYYCQQYSTVPWTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

Anti-VEGF (Avastin; bevacizumab)
Anti-PD-1 (<u>Penpulimab; AK105</u>)

FIG. 8

Anti-VEGF
Anti-PD-1 scFv

VEGFA (dimer)

Anti-VEGF Anti PD-1
VEGFA Interconnected
Complex

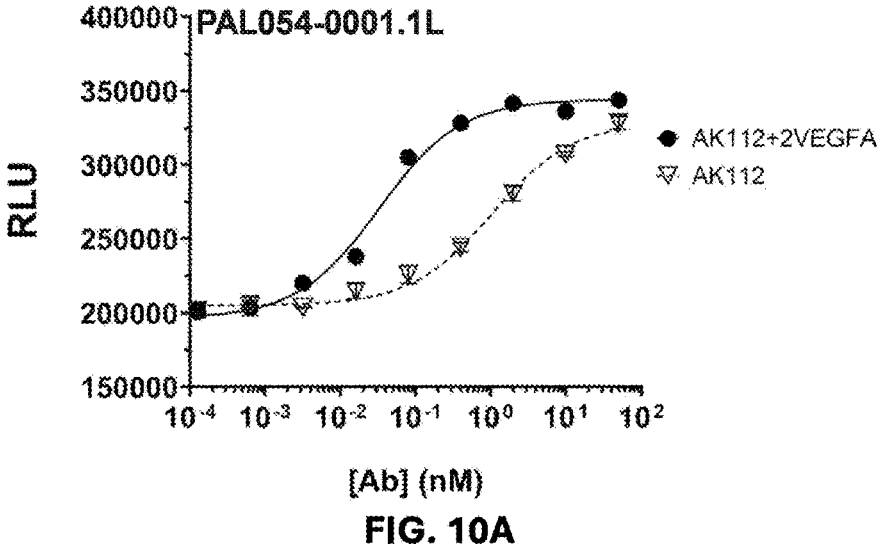
FIG. 10A
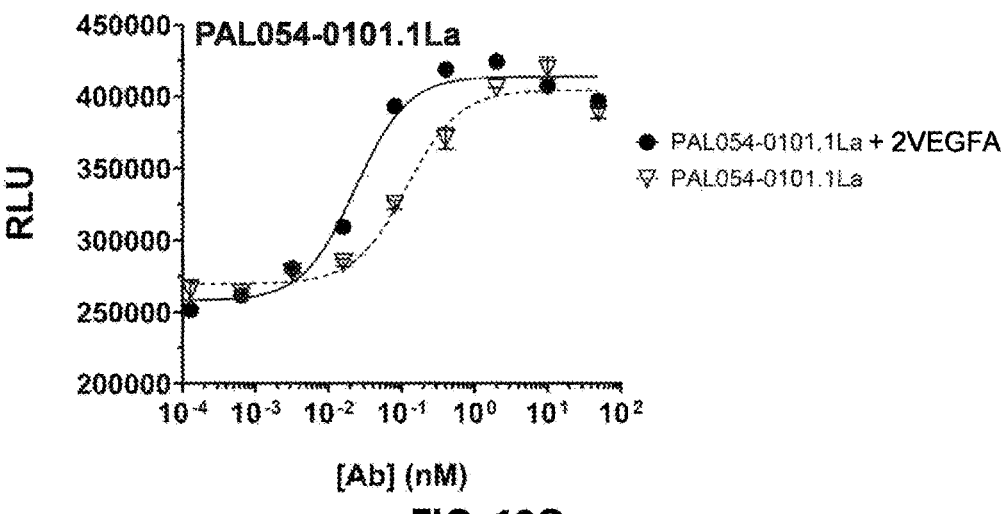
FIG. 10B
FIG. 10C

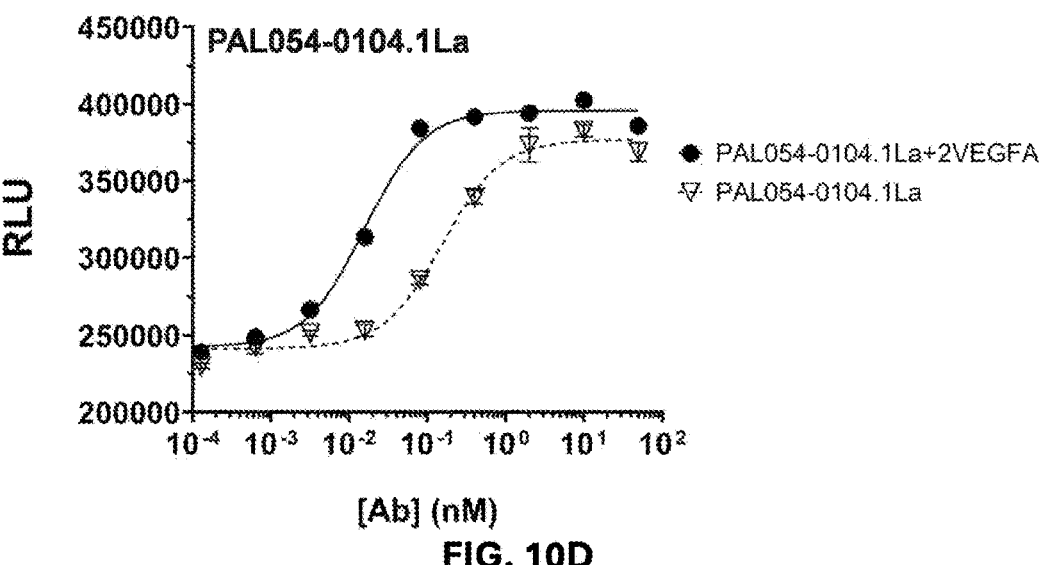
FIG. 10D
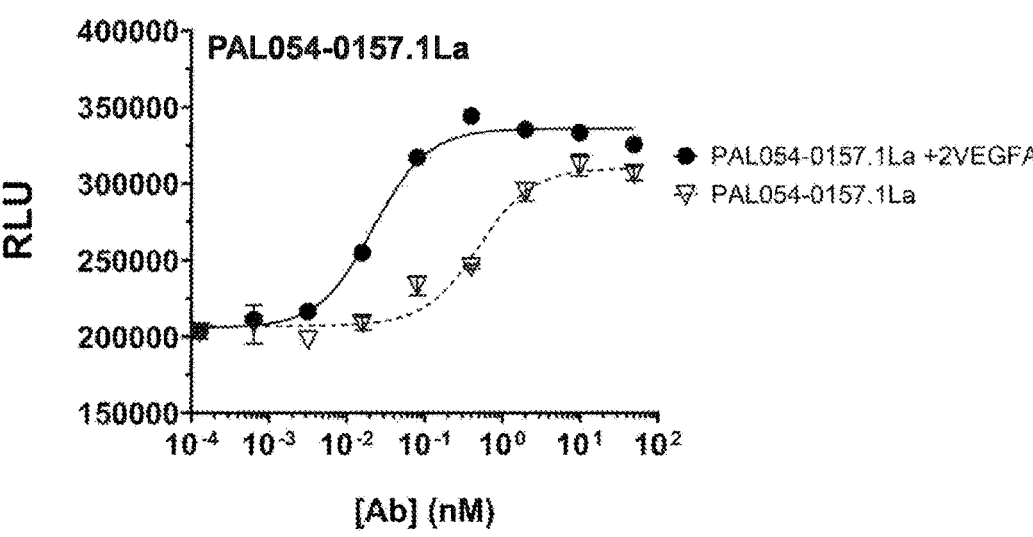
FIG. 10E
FIG. 10F

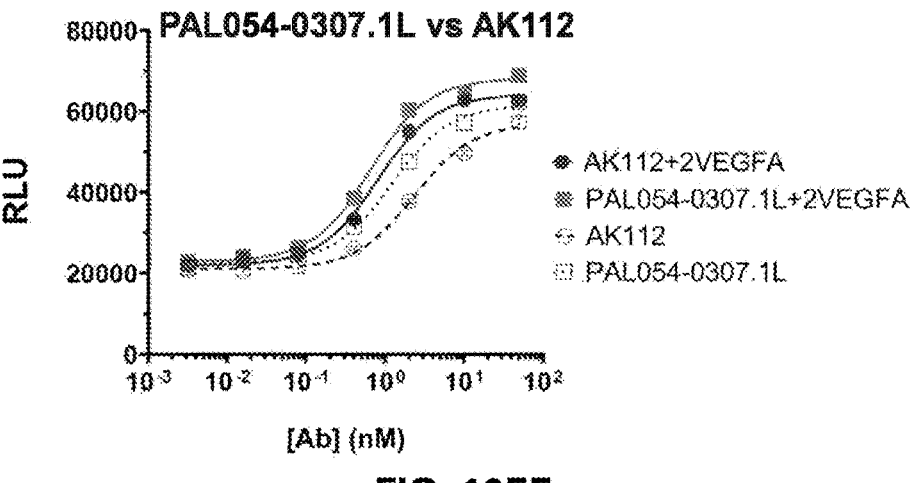
FIG. 10EE
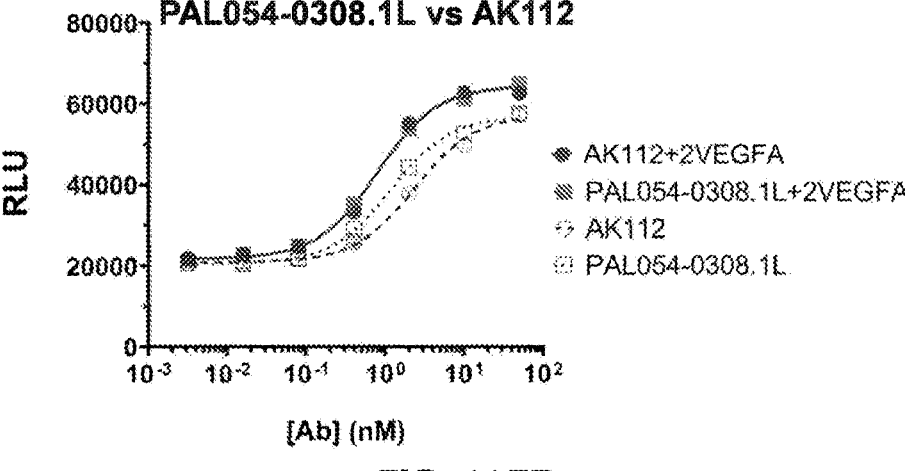
FIG. 10FF
PAL054-0309.1L vs AK112
FIG. 10GG

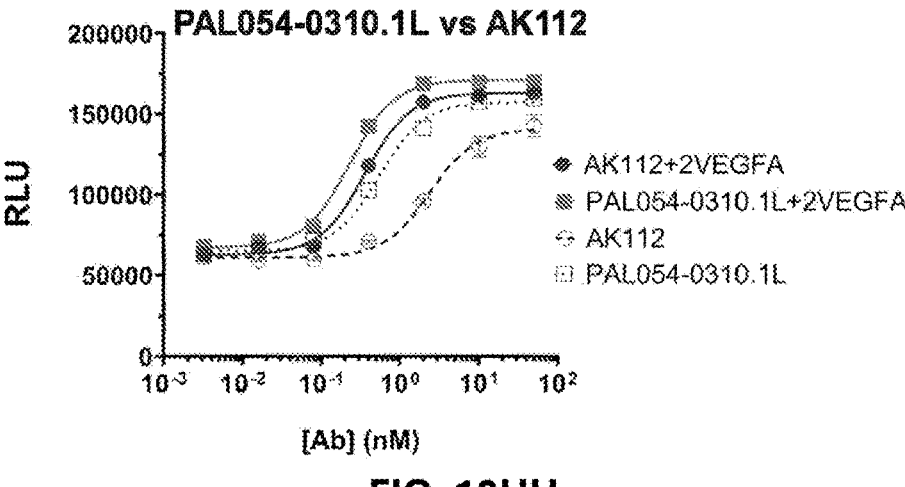
FIG. 10HH
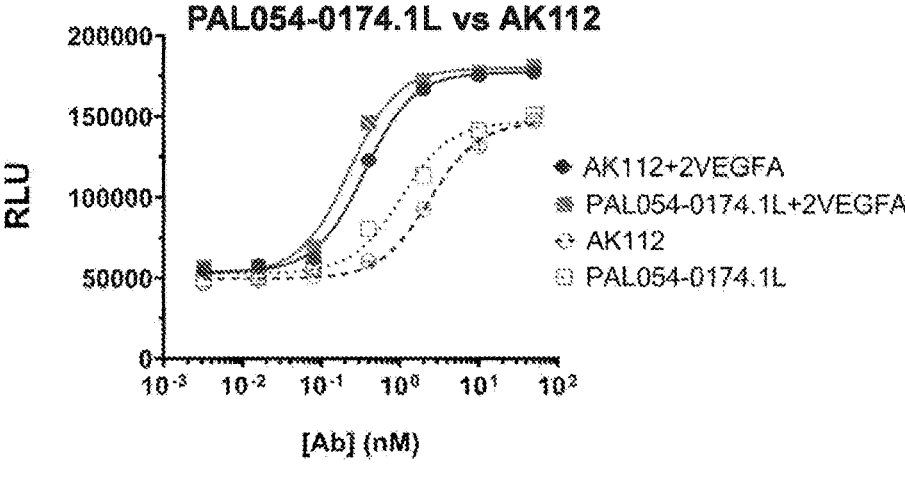
FIG. 10II
FIG. 10JJ

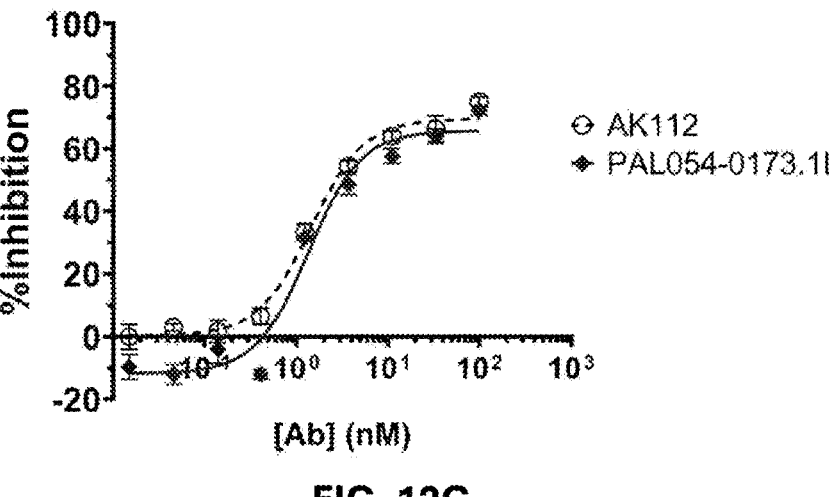
FIG. 12G
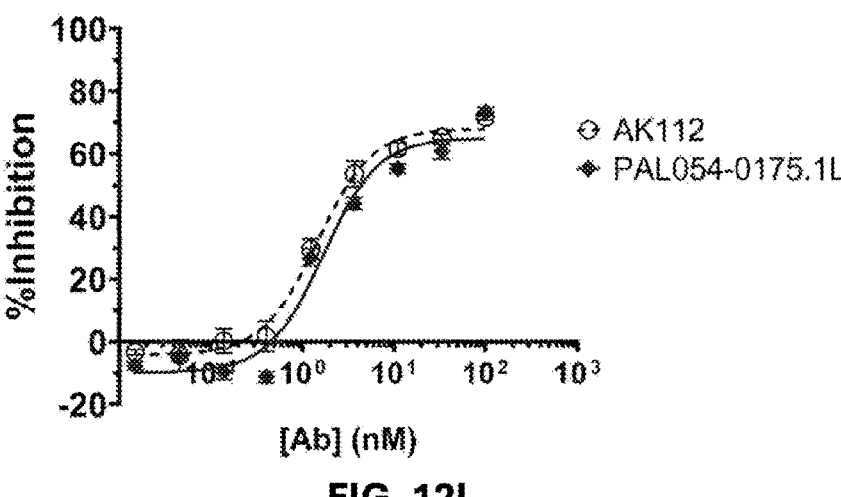
FIG. 12H
FIG. 12I

PAL054-0148.1La; PAL054-0145.1La vs AK112

● AK112+2VEGFA          ○ AK112                    [Ab]=200 nM
▩ PAL054-0145.1La+2VEGFA    ▤ PAL054-0145.1La
✳ PAL054-0148.1La+2VEGFA    ✳ PAL054-0148.1La

PAL054-0157.1La vs AK112

● AK112+2VEGFA          ○ AK112                    [Ab]=200 nM
▩ PAL054-0157.1La+2VEGFA    ▤ PAL054-0157.1La

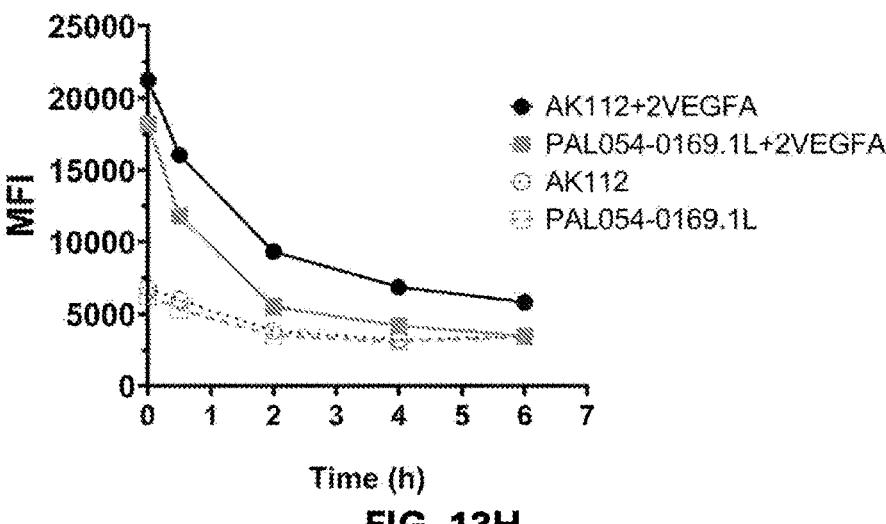
FIG. 13H
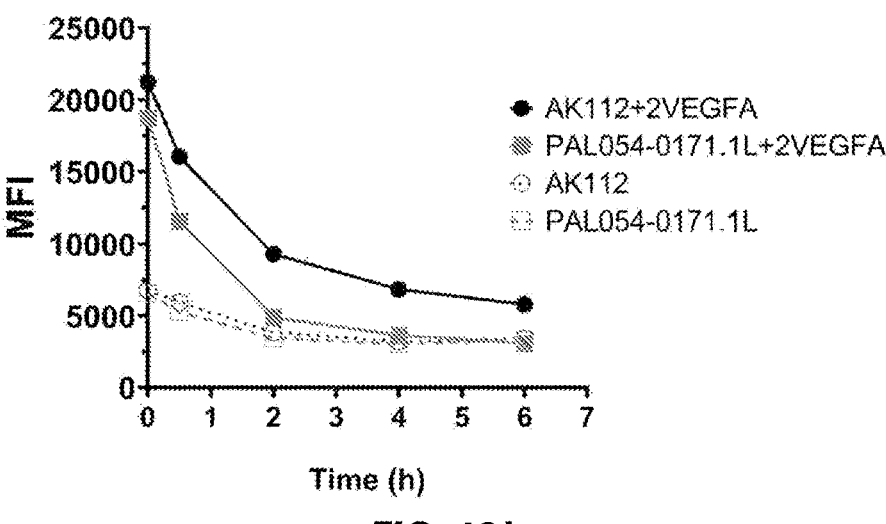
FIG. 13I
FIG. 13J

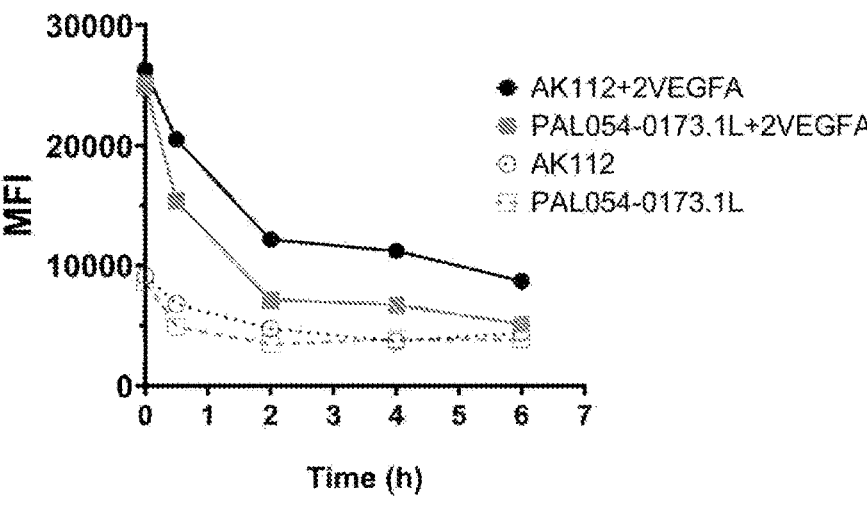
FIG. 13K
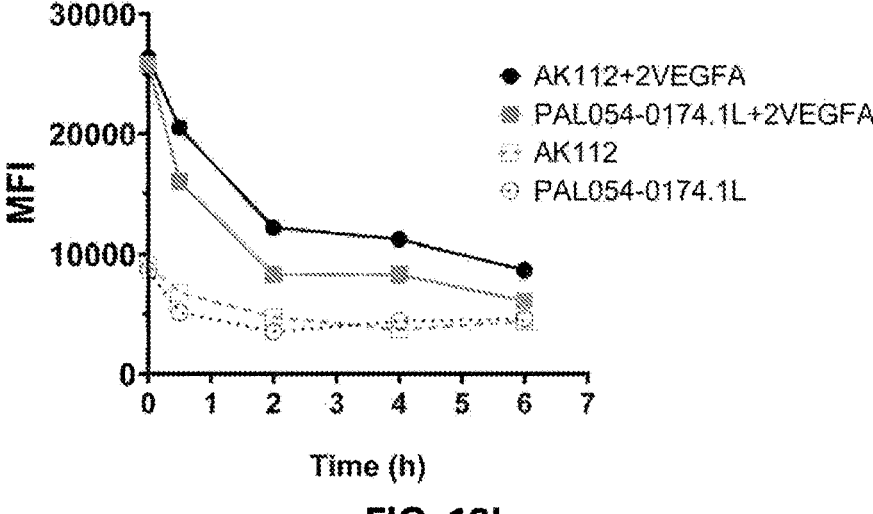
FIG. 13L
![FIG. 13M chart]
FIG. 13M

Anti-PD-1

Anti-VEGF

169.1L

170.1L

171.1L

172.1L

304.1L

305.1L

307.1L

308.1L

40° C stability at 10 mg/mL
Monomer % by time at 10 mg/mL, pH 6.0
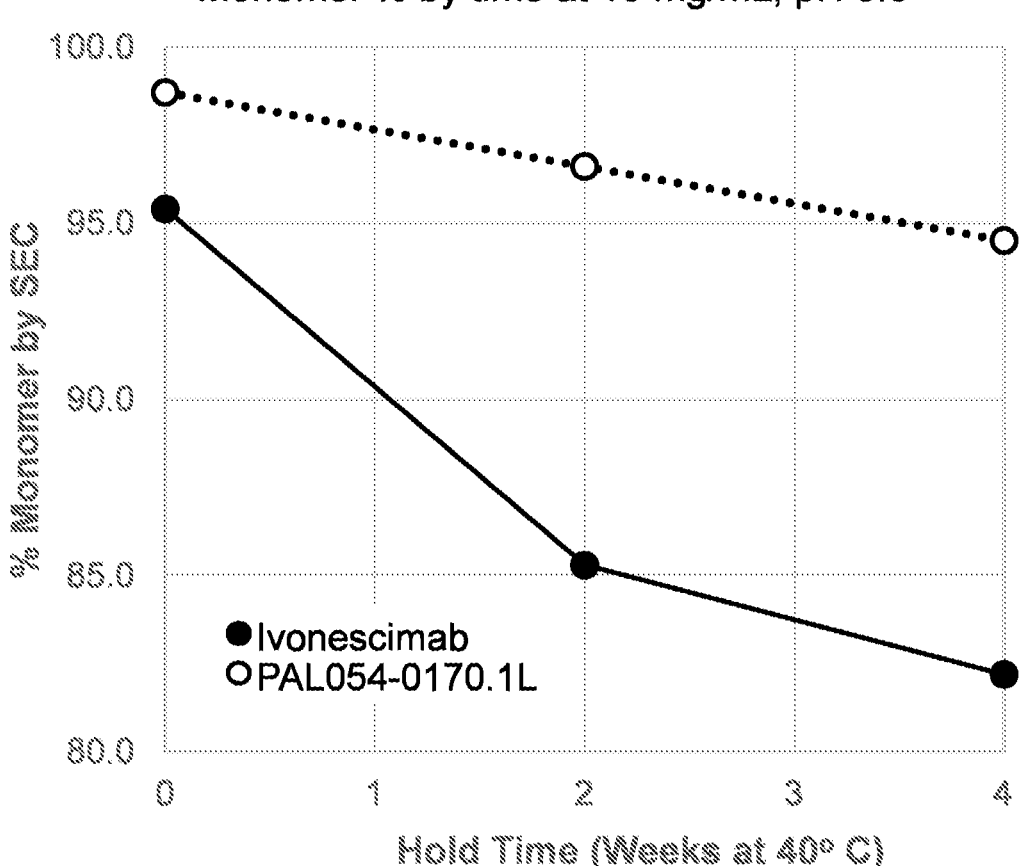
FIG. 17C

25° C stability at 150 mg/mL
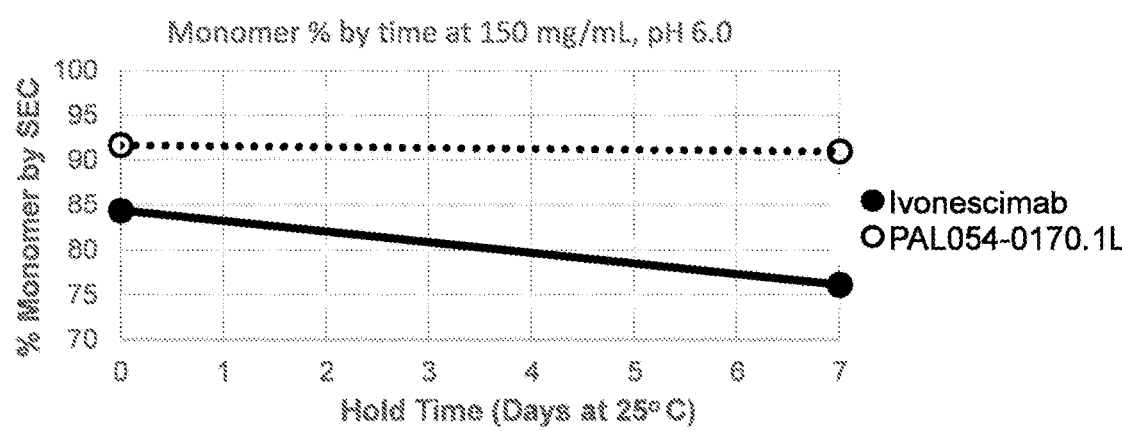
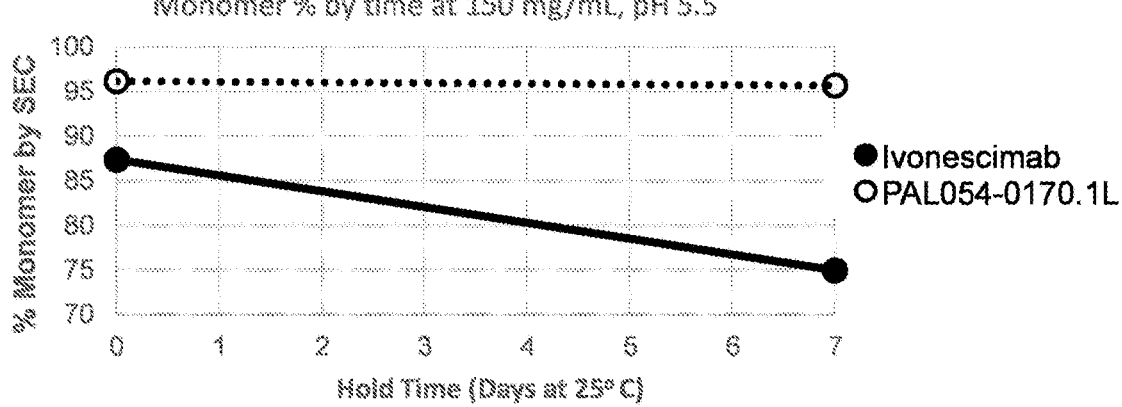
FIG. 17D

PD-1 BINDING PROTEINS, VEGF AND PD-1 BISPECIFIC BINDING PROTEINS, COMPOSITIONS, AND METHODS OF USE

RELATED APPLICATIONS

This Application is a continuation of international application number PCT/US2025/047219, filed Sep. 19, 2025, which claims benefit of U.S. provisional application Nos. 63/697,436, filed Sep. 20, 2024, 63/719,870, filed Nov. 13, 2024, 63/788,196, filed Apr. 14, 2025, and 63/831,020, filed Jun. 26, 2025.

REFERENCE TO AN ELECTRONIC SEQUENCE LISTING

The contents of the electronic sequence listing (C181870000US00-SEQ-LJG.xml; Size: 1,070,409 bytes; and Date of Creation: Dec. 19, 2025) are herein incorporated by reference in their entirety.

BACKGROUND

Vascular endothelial cell growth factor (VEGF) is a potent mitogen for vascular endothelial cells, has been reported as a pivotal regulator of both normal and abnormal angiogenesis. VEGF is a master regulator of angiogenesis during growth and development, as well as in disease states such as cancer, diabetes, and macular degeneration. It is also required for the cyclical blood vessel proliferation in the female reproductive tract and for bone growth and cartilage formation. Cancer is among the most common indications for current VEGF therapies, with FDA and EMA-approved therapies targeting various kinds of cancer. Some examples of current VEGF therapies to address these diseases and conditions include axitinib, bevacizumab, brolucizumab, cabozantinib, lapatinib, lenvatinib, pazopanib, ponatinib, ramucirumab, ranibizumab, regorafenib, sorafenib, sunitinib, and vandetanib.

Programmed death receptor 1 (PD-1) is an immunoinhibitory receptor primarily expressed on activated lymphocytes (e.g., peripheral CD4+ and CD8+ T cells, B cells and monocytes). Interaction with its ligands has been shown to attenuate T-cell responses both in vitro and in vivo.

The role of PD-1 in cancer is well established in the literature. The ligands for PD-1 (Programmed death-ligand 1 (PD-L1) and Programmed death-ligand 2 (PD-L2)) are constitutively expressed or can be induced in a variety of cell types, including non-hematopoietic tissues as well as various tumor types. Blockade of the interaction between PD-1 and PD-L1, for example, has been shown to enhance tumor-specific CD8+ T-cell immunity and may therefore be helpful in clearance of tumor cells by the immune system. Overall, the PD-1/PD-L1 pathway is a well-validated target for the development of antibody therapeutics for cancer treatment.

SUMMARY

The instant disclosure relates, in part, to PD-1 binding proteins and bispecific binding proteins that bind (1) VEGF and (2) PD-1.

In one aspect, provided are programmed death receptor 1 (PD-1) binding proteins comprising an anti-PD1 immunoglobulin heavy chain variable domain (anti-PD-1 VH) comprising complementary determining regions: CDR-H1 comprising the amino acid sequence of SEQ ID NO: 445; CDR-H2 comprising the amino acid sequence of SEQ ID NO: 456, 461, or 446; and CDR-H3 comprising the amino acid sequence of SEQ ID NO: 457 or 447; CDR-H1 comprising the amino acid sequence of SEQ ID NO: 451; CDR-H2 comprising the amino acid sequence of SEQ ID NO: 458, 462, or 452; and CDR-H3 comprising the amino acid sequence of SEQ ID NO: 459 or 453; or CDR-H1 comprising the amino acid sequence of SEQ ID NO: 443; CDR-H2 comprising the amino acid sequence of SEQ ID NO: 460, 463, or 455; and CDR-H3 comprising the amino acid sequence of SEQ ID NO: 457 or 447, provided that: if CDR-H2 comprises the amino acid sequence of SEQ ID NO: 446, then CDR-H3 does not comprise the amino acid sequence of 447; if CDR-H2 comprises the amino acid sequence of SEQ ID NO: 452, then CDR-H3 does not comprise the amino acid sequence of 453; and if CDR-H2 comprises the amino acid sequence of SEQ ID NO: 455, then CDR-H3 does not comprise the amino acid sequence of 447.

In some embodiments, the CDR-H1, CDR-H2, and CDR-H3 comprise the amino acid sequences of SEQ ID NOs 445, 456, and 457, respectively; SEQ ID NOs 451, 458, and 459, respectively; or SEQ ID NOs 443, 460, and 457, respectively. In some embodiments, the PD-1 binding protein further comprises an anti-PD1 immunoglobulin light chain variable domain (anti-PD-1 VL) comprising complementarity-determining regions: CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450; CDR-L1 comprising the amino acid sequence of SEQ ID NO: 454; CDR-L2 comprising the amino acid sequence of LAS; and CDR-L3 comprising the amino acid sequence of SEQ ID NO: 450; or CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450. In some embodiments, the anti-PD-1 VH and anti-PD-1 VL have amino acid sequences that are at least 85% identical to that of: SEQ ID NOs: 302 and 335, respectively; SEQ ID NOs: 302 and 336, respectively; SEQ ID NOs: 302 and 340, respectively; SEQ ID NOs: 302 and 342, respectively; SEQ ID NOs: 302 and 343, respectively; SEQ ID NOs: 302 and 346, respectively; SEQ ID NOs: 306 and 337, respectively; SEQ ID NOs: 306 and 339, respectively; SEQ ID NOs: 306 and 341, respectively; SEQ ID NOs: 306 and 344, respectively; SEQ ID NOs: 306 and 345, respectively; SEQ ID NOs: 306 and 347, respectively; SEQ ID NOs: 308 and 340, respectively; SEQ ID NOs: 309 and 341, respectively; SEQ ID NOs: 310 and 336, respectively; SEQ ID NOs: 311 and 337, respectively; SEQ ID NOs: 313 and 336, respectively; SEQ ID NOs: 313 and 342, respectively; SEQ ID NOs: 313 and 343, respectively; SEQ ID NOs: 316 and 337, respectively; SEQ ID NOs: 316 and 344, respectively; SEQ ID NOs: 316 and 345, respectively; SEQ ID NOs: 318 and 336, respectively; SEQ ID NOs: 318 and 340, respectively; SEQ ID NOs: 318 and 346, respectively; SEQ ID NOs: 319 and 336, respectively; SEQ ID NOs: 319 and 340, respectively; SEQ ID NOs: 319 and 346, respectively; SEQ ID NOs: 320 and 337, respectively; SEQ ID NOs: 320 and 341, respectively; SEQ ID NOs: 320 and 347, respectively; SEQ ID NOs: 320 and 743, respectively; SEQ ID NOs: 321 and 337, respectively; SEQ ID NOs: 321 and 341, respectively; or SEQ ID NOs: 321 and 347, respectively. In some embodiments, the anti-PD-1 VH and anti-PD-1 VL have amino acid sequences of: SEQ ID NOs: 302 and 335, respectively; SEQ ID NOs: 302 and 336, respectively; SEQ ID NOs: 302 and 340, respectively; SEQ ID NOs: 302 and 342, respectively;

SEQ ID NOs: 302 and 343, respectively; SEQ ID NOs: 302 and 346, respectively; SEQ ID NOs: 306 and 337, respectively; SEQ ID NOs: 306 and 339, respectively; SEQ ID NOs: 306 and 341, respectively; SEQ ID NOs: 306 and 344, respectively; SEQ ID NOs: 306 and 345, respectively; SEQ ID NOs: 306 and 347, respectively; SEQ ID NOs: 308 and 340, respectively; SEQ ID NOs: 309 and 341, respectively; SEQ ID NOs: 310 and 336, respectively; SEQ ID NOs: 311 and 337, respectively; SEQ ID NOs: 313 and 336, respectively; SEQ ID NOs: 313 and 342, respectively; SEQ ID NOs: 313 and 343, respectively; SEQ ID NOs: 316 and 337, respectively; SEQ ID NOs: 316 and 344, respectively; SEQ ID NOs: 316 and 345, respectively; SEQ ID NOs: 318 and 336, respectively; SEQ ID NOs: 318 and 340, respectively; SEQ ID NOs: 318 and 346, respectively; SEQ ID NOs: 319 and 336, respectively; SEQ ID NOs: 319 and 340, respectively; SEQ ID NOs: 319 and 346, respectively; SEQ ID NOs: 320 and 337, respectively; SEQ ID NOs: 320 and 341, respectively; SEQ ID NOs: 320 and 347, respectively; SEQ ID NOs: 320 and 743, respectively; SEQ ID NOs: 321 and 337, respectively; SEQ ID NOs: 321 and 341, respectively; or SEQ ID NOs: 321 and 347, respectively.

In some embodiments, the CDR-H1, CDR-H2, and CDR-H3 comprise the amino acid sequences of SEQ ID NOs 445, 456, and 447, respectively; SEQ ID NOs 451, 458, and 453, respectively; or SEQ ID NOs 443, 460, and 447, respectively. In some embodiments, the PD-1 binding protein further comprises an anti-PD1 immunoglobulin light chain variable domain (anti-PD-1 VL) comprising complementarity-determining regions: CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450; CDR-L1 comprising the amino acid sequence of SEQ ID NO: 454; CDR-L2 comprising the amino acid sequence of LAS; and CDR-L3 comprising the amino acid sequence of SEQ ID NO: 450; or CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450. In some embodiments, the anti-PD-1 VH and anti-PD-1 VL have amino acid sequences that are at least 85% identical to that of: SEQ ID NOs: 303 and 336, respectively; SEQ ID NOs: 325 and 347, respectively; or SEQ ID NOs: 325 and 743, respectively. In some embodiments, the anti-PD-1 VH and anti-PD-1 VL have amino acid sequences of: SEQ ID NOs: 303 and 336, respectively; SEQ ID NOs: 325 and 347, respectively; or SEQ ID NOs: 325 and 743, respectively.

In some embodiments, the CDR-H1, CDR-H2, and CDR-H3 comprise the amino acid sequences of SEQ ID NOs 445, 461, and 447, respectively; SEQ ID NOs 451, 462, and 453, respectively; or SEQ ID NOs 443, 463, and 447, respectively. In some embodiments, the PD-1 binding protein further comprises an anti-PD1 immunoglobulin light chain variable domain (anti-PD-1 VL) comprising complementarity-determining regions: CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450; CDR-L1 comprising the amino acid sequence of SEQ ID NO: 454; CDR-L2 comprising the amino acid sequence of LAS; and CDR-L3 comprising the amino acid sequence of SEQ ID NO: 450; or CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450. In some embodiments, the anti-PD-1 VH and anti-PD-1 VL have amino acid sequences that are at least 85% identical to that of: SEQ ID NOs: 326 and 347, respectively; or SEQ ID NOs: 326 and 743, respectively. In some embodiments, the anti-PD-1 VH and anti-PD-1 VL have amino acid sequences of: SEQ ID NOs: 326 and 347, respectively; or SEQ ID NOs: 326 and 743, respectively.

In some embodiments, the CDR-H1, CDR-H2, and CDR-H3 comprise the amino acid sequences of SEQ ID NOs 445, 446, and 457, respectively; SEQ ID NOs 451, 452, and 459, respectively; or SEQ ID NOs 443, 455, and 457, respectively. In some embodiments, the PD-1 binding protein further comprises an anti-PD1 immunoglobulin light chain variable domain (anti-PD-1 VL) comprising complementarity-determining regions: CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450; CDR-L1 comprising the amino acid sequence of SEQ ID NO: 454; CDR-L2 comprising the amino acid sequence of LAS; and CDR-L3 comprising the amino acid sequence of SEQ ID NO: 450; or CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450. In some embodiments, the anti-PD-1 VH and anti-PD-1 VL have amino acid sequences that are at least 85% identical to that of: SEQ ID NOs: 327 and 347, respectively; or SEQ ID NOs: 327 and 743, respectively. In some embodiments, the anti-PD-1 VH and anti-PD-1 VL have amino acid sequences of: SEQ ID NOs: 327 and 347, respectively; or SEQ ID NOs: 327 and 743, respectively.

In some embodiments, the CDR-H1, CDR-H2, and CDR-H3 comprise the amino acid sequences of SEQ ID NOs 445, 461, and 457, respectively; SEQ ID NOs 451, 462, and 459, respectively; or SEQ ID NOs 443, 463, and 457, respectively. In some embodiments, the PD-1 binding protein further comprises an anti-PD1 immunoglobulin light chain variable domain (anti-PD-1 VL) comprising complementarity-determining regions: CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450; CDR-L1 comprising the amino acid sequence of SEQ ID NO: 454; CDR-L2 comprising the amino acid sequence of LAS; and CDR-L3 comprising the amino acid sequence of SEQ ID NO: 450; or CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450. In some embodiments, the anti-PD-1 VH and anti-PD-1 VL have amino acid sequences that are at least 85% identical to that of: SEQ ID NOs: 303 and 335, respectively; SEQ ID NOs: 303 and 342, respectively; SEQ ID NOs: 303 and 343, respectively; SEQ ID NOs: 307 and 337, respectively; SEQ ID NOs: 307 and 344, respectively; SEQ ID NOs: 307 and 345, respectively; SEQ ID NOs: 314 and 336, respectively; SEQ ID NOs: 314 and 342, respectively; SEQ ID NOs: 314 and 343, respectively; SEQ ID NOs: 317 and 337, respectively; SEQ ID NOs: 317 and 344, respectively; SEQ ID NOs: 317 and 345, respectively; or SEQ ID NOs: 324 and 347, respectively. In some embodiments, the anti-PD-1 VH and anti-PD-1 VL have amino acid sequences of: SEQ ID NOs: 303 and 335, respectively; SEQ ID NOs: 303 and 342, respectively; SEQ ID NOs: 303 and 343, respectively; SEQ ID NOs: 307 and 337, respectively; SEQ ID NOs: 307 and 344, respectively; SEQ ID NOs: 307 and 345, respectively; SEQ ID NOs: 314 and 336, respectively; SEQ ID NOs: 314 and 342, respectively; SEQ ID NOs: 314 and 343, respectively; SEQ ID NOs: 317 and 337, respectively; SEQ ID NOs: 317 and 344, respectively; SEQ ID NOs: 317 and 345, respectively; or SEQ ID NOs: 324 and 347, respectively.

In some embodiments, the anti-PD-1 VH has a framework having an amino acid sequence at least 85% identical to that within any one of SEQ ID NO: 464-470 and the anti-PD-1 VL has a framework having an amino acid sequence at least 85% identical to that within any one of SEQ ID NO: 471-476.

In some embodiments, the anti-PD-1 VH has a framework having an amino acid sequence of that within any one of SEQ ID NO: 464-470 and the anti-PD-1 VL has a framework having an amino acid sequence of that within any one of SEQ ID NO: 471-476.

In some embodiments, the anti-PD-1 VH has a framework having an amino acid sequence of that within SEQ ID NO: 464 and the anti-PD-1 VL has a framework having an amino acid sequence of that within SEQ ID NO: 471.

In some embodiments, the anti-PD-1 VH has a framework having an amino acid sequence of that within SEQ ID NO: 465 and the anti-PD-1 VL has a framework having an amino acid sequence of that within SEQ ID NO: 472.

In some embodiments, the anti-PD-1 VH has a framework having an amino acid sequence of that within SEQ ID NO: 465 and the anti-PD-1 VL has a framework having an amino acid sequence of that within SEQ ID NO: 471.

In some embodiments, the anti-PD-1 VH has a framework having an amino acid sequence of that within SEQ ID NO: 465 and the anti-PD-1 VL has a framework having an amino acid sequence of that within SEQ ID NO: 473.

In some embodiments, the anti-PD-1 VH has a framework having an amino acid sequence of that within SEQ ID NO: 464 and the anti-PD-1 VL has a framework having an amino acid sequence of that within SEQ ID NO: 472.

In some embodiments, the anti-PD-1 VH has a framework having an amino acid sequence of that within SEQ ID NO: 464 and the anti-PD-1 VL has a framework having an amino acid sequence of that within SEQ ID NO: 473.

In some embodiments, the anti-PD-1 VH has a framework having an amino acid sequence of that within SEQ ID NO: 464 and the anti-PD-1 VL has a framework having an amino acid sequence of that within SEQ ID NO: 474.

In some embodiments, the anti-PD-1 VH has a framework having an amino acid sequence of that within SEQ ID NO: 464 and the anti-PD-1 VL has a framework having an amino acid sequence of that within SEQ ID NO: 475.

In some embodiments, the anti-PD-1 VH has a framework having an amino acid sequence of that within SEQ ID NO: 467 and the anti-PD-1 VL has a framework having an amino acid sequence of that within SEQ ID NO: 471.

In some embodiments, the anti-PD-1 VH has a framework having an amino acid sequence of that within SEQ ID NO: 467 and the anti-PD-1 VL has a framework having an amino acid sequence of that within SEQ ID NO: 474.

In some embodiments, the anti-PD-1 VH has a framework having an amino acid sequence of that within SEQ ID NO: 467 and the anti-PD-1 VL has a framework having an amino acid sequence of that within SEQ ID NO: 475.

In some embodiments, the anti-PD-1 VH has a framework having an amino acid sequence of that within SEQ ID NO: 468 and the anti-PD-1 VL has a framework having an amino acid sequence of that within SEQ ID NO: 471.

In some embodiments, the anti-PD-1 VH has a framework having an amino acid sequence of that within SEQ ID NO: 468 and the anti-PD-1 VL has a framework having an amino acid sequence of that within SEQ ID NO: 474.

In some embodiments, the anti-PD-1 VH has a framework having an amino acid sequence of that within SEQ ID NO: 468 and the anti-PD-1 VL has a framework having an amino acid sequence of that within SEQ ID NO: 475.

In some embodiments, the anti-PD-1 VH has a framework having an amino acid sequence of that within SEQ ID NO: 466 and the anti-PD-1 VL has a framework having an amino acid sequence of that within SEQ ID NO: 471.

In some embodiments, the anti-PD-1 VH has a framework having an amino acid sequence of that within SEQ ID NO: 470 and the anti-PD-1 VL has a framework having an amino acid sequence of that within SEQ ID NO: 474.

In some embodiments, the anti-PD-1 VH has a framework having an amino acid sequence of that within SEQ ID NO: 469 and the anti-PD-1 VL has a framework having an amino acid sequence of that within SEQ ID NO: 476.

In some embodiments, the anti-PD-1 VH has a framework having an amino acid sequence of that within SEQ ID NO: 465 except for one amino acid substitution; and the anti-PD-1 VL has a framework having an amino acid sequence of that within SEQ ID NO: 472 except for one amino acid substitution; the anti-PD-1 VH has a framework having an amino acid sequence of that within SEQ ID NO: 465 except for one amino acid substitution; and the anti-PD-1 VL has a framework having an amino acid sequence of that within SEQ ID NO: 471 except for one amino acid substitution; the anti-PD-1 VH has a framework having an amino acid sequence of that within SEQ ID NO: 465 except for one amino acid substitution; and the anti-PD-1 VL has a framework having an amino acid sequence of that within SEQ ID NO: 473 except for one amino acid substitution; the anti-PD-1 VH has a framework having an amino acid sequence of that within SEQ ID NO: 464 except for one amino acid substitution; and the anti-PD-1 VL has a framework having an amino acid sequence of that within SEQ ID NO: 472 except for one amino acid substitution; the anti-PD-1 VH has a framework having an amino acid sequence of that within SEQ ID NO: 464 except for one amino acid substitution; and the anti-PD-1 VL has a framework having an amino acid sequence of that within SEQ ID NO: 473 except for one amino acid substitution; the anti-PD-1 VH has a framework having an amino acid sequence of that within SEQ ID NO: 464 except for one amino acid substitution; and the anti-PD-1 VL has a framework having an amino acid sequence of that within SEQ ID NO: 474 except for one amino acid substitution; the anti-PD-1 VH has a framework having an amino acid sequence of that within SEQ ID NO: 464 except for one amino acid substitution; and the anti-PD-1 VL has a framework having an amino acid sequence of that within SEQ ID NO: 475 except for one amino acid substitution; the anti-PD-1 VH has a framework having an amino acid sequence of that within SEQ ID NO: 467 except for one amino acid substitution; and the anti-PD-1 VL has a framework having an amino acid sequence of that within SEQ ID NO: 471 except for one amino acid substitution; the anti-PD-1 VH has a framework having an amino acid sequence of that within SEQ ID NO: 467 except for one amino acid substitution; and the anti-PD-1 VL has a framework having an amino acid sequence of that within SEQ ID NO: 474 except for one amino acid substitution; the anti-PD-1 VH has a framework having an amino acid sequence of that within SEQ ID NO: 467 except for one amino acid substitution; and the anti-PD-1 VL has a framework having an amino acid sequence of that within SEQ ID NO: 475 except for one amino acid substitution; the anti-PD-1 VH has a framework having an amino acid sequence of that within SEQ ID NO: 468 except for one amino acid substitution; and the anti-PD-1 VL has a framework having an amino acid sequence of that within SEQ ID NO: 471 except for one amino acid substitution; the anti-PD-1 VH has a framework having an amino acid sequence of that within SEQ ID NO: 468 except for one amino acid substitution; and the anti-PD-1 VL has a framework having an amino acid sequence of that within SEQ ID NO: 474 except for one amino acid substitution; the anti-PD-1 VH has a framework having an amino acid sequence of that within SEQ ID NO: 468 except for one amino acid substitution; and the anti-PD-1 VL has a framework having an amino acid sequence of that within SEQ ID NO: 475 except for one amino acid substitution; the anti-PD-1 VH has a framework having an amino acid sequence of that within SEQ ID NO: 468 except for one amino acid substitution; and the anti-PD-1 VL has a framework having an amino acid sequence of that within SEQ ID NO: 475 except for one amino acid substitution; the anti-PD-1 VH has a framework having an amino acid sequence of that within SEQ ID NO: 466 except for one amino acid substitution; and the anti-PD-1 VL has a framework having an amino acid sequence of that within SEQ ID NO: 471 except for one amino acid substitution; or the anti-PD-1 VH has a framework having an amino acid sequence of that within SEQ ID NO: 470 except for one amino acid substitution; and the anti-PD-1 VL has a framework having an amino acid sequence of that within SEQ ID NO: 474 except for one amino acid substitution, wherein the one amino acid substitution in the VH is from a non-cysteine residue to a cysteine residue and the one amino acid substitution in the VL is from a non-cysteine residue to a cysteine residue.

In some embodiments, the one amino acid substitution in the anti-PD-1 VH is at residue H44 and the one amino acid substitution in the anti-PD-1 VL is at residue L100, wherein numbering is according to Kabat.

In one aspect provided are PD-1 binding proteins comprising (a) an anti-PD-1 immunoglobulin heavy chain variable domain (anti-PD-1 VH) comprising complementary determining regions CDR-H1, CDR-H2, and CDR-H3 which comprise the amino acid sequences of (1) SEQ ID NOs 445, 456, and 447, respectively; (2) SEQ ID NOs 451, 458, and 453, respectively; or (3) SEQ ID NOs 443, 460, and 457, respectively, and (b) an anti-PD1 immunoglobulin light chain variable domain (anti-PD-1 VL) comprising complementary determining regions CDR-L1, CDR-L2, and CDR-L3 which comprise the amino acid sequences of (1) SEQ ID NOs 448, 449, and 450, respectively; (2) SEQ ID NO: 454, LAS, and SEQ ID NO: 450, respectively; or (3) SEQ ID NOs 448, 449, and 450 respectively. In some embodiments, (a) the anti-PD-1 VH has an amino acid sequence at least 85% identical to that of SEQ ID NO: 325; and (b) the anti-PD-1 VL has an amino acid sequence at least 85% identical to that of SEQ ID NO: 347. In some embodiments, (a) the anti-PD-1 VH has an amino acid sequence of SEQ ID NO: 325; and (b) the anti-PD-1 VL has an amino acid sequence of SEQ ID NO: 347.

In one aspect, provided are a PD-1 binding proteins comprising (a) an anti-PD-1 immunoglobulin heavy chain variable domain (anti-PD-1 VH) comprising complementary determining regions CDR-H1, CDR-H2, and CDR-H3 which comprise the amino acid sequences of (1) SEQ ID NOs 445, 456, and 457, respectively; (2) SEQ ID NOs 451, 458, and 459, respectively; or (3) SEQ ID NOs 443, 460, and 457, respectively, and (b) an anti-PD1 immunoglobulin light chain variable domain (anti-PD-1 VL) comprising complementary determining regions CDR-L1, CDR-L2, and CDR-L3 which comprise the amino acid sequences of (1) SEQ ID NOs 448, 449, and 450, respectively; (2) SEQ ID NO: 454, LAS, and SEQ ID NO: 450, respectively; or (3) SEQ ID NOs 448, 449, and 450 respectively. In some embodiments, (a) the anti-PD-1 VH has an amino acid sequence at least 85% identical to that of SEQ ID NO: 320; and (b) the anti-PD-1 VL has an amino acid sequence at least 85% identical to that of SEQ ID NO: 347. In some embodiments, (a) the anti-PD-1 VH has an amino acid sequence of SEQ ID NO: 320; and (b) the anti-PD-1 VL has an amino acid sequence of SEQ ID NO: 347.

In one aspect, provided are PD-1 binding proteins comprising (a) an anti-PD-1 immunoglobulin heavy chain variable domain (anti-PD-1 VH) comprising complementary determining regions CDR-H1, CDR-H2, and CDR-H3 which comprise the amino acid sequences of (1) SEQ ID NOs 445, 461, and 457, respectively; (2) SEQ ID NOs 451, 462, and 459, respectively; or (3) SEQ ID NOs 443, 463, and 457, respectively, and (b) an anti-PD1 immunoglobulin light chain variable domain (anti-PD-1 VL) comprising complementary determining regions CDR-L1, CDR-L2, and CDR-L3 which comprise the amino acid sequences of (1) SEQ ID NOs 448, 449, and 450, respectively; (2) SEQ ID NO: 454, LAS, and SEQ ID NO: 450, respectively; or (3) SEQ ID NOs 448, 449, and 450 respectively. In some embodiments, (a) the anti-PD-1 VH has an amino acid sequence at least 85% identical to that of SEQ ID NO: 324; and (b) the anti-PD-1 VL has an amino acid sequence at least 85% identical to that of SEQ ID NO: 347. In some embodiments, (a) the anti-PD-1 VH has an amino acid sequence of SEQ ID NO: 324; and (b) the anti-PD-1 VL has an amino acid sequence of SEQ ID NO: 347.

In one aspect, provided are PD-1 binding proteins comprising (a) an anti-PD-1 immunoglobulin heavy chain variable domain (anti-PD-1 VH) comprising complementary determining regions CDR-H1, CDR-H2, and CDR-H3 which comprise the amino acid sequences of (1) SEQ ID NOs 445, 461, and 447, respectively; (2) SEQ ID NOs 451, 462, and 453, respectively; or (3) SEQ ID NOs 443, 463, and 447, respectively, and (b) an anti-PD1 immunoglobulin light chain variable domain (anti-PD-1 VL) comprising complementary determining regions CDR-L1, CDR-L2, and CDR-L3 which comprise the amino acid sequences of (1) SEQ ID NOs 448, 449, and 450, respectively; (2) SEQ ID NO: 454, LAS, and SEQ ID NO: 450, respectively; or (3) SEQ ID NOs 448, 449, and 450 respectively. In some embodiments, (a) the anti-PD-1 VH has an amino acid sequence at least 85% identical to that of SEQ ID NO: 326; and (b) the anti-PD-1 VL has an amino acid sequence at least 85% identical to that of SEQ ID NO: 347. In some embodiments, (a) the anti-PD-1 VH has an amino acid sequence of SEQ ID NO: 326; and (b) the anti-PD-1 VL has an amino acid sequence of SEQ ID NO: 347.

In one aspect, provided are PD-1 binding proteins comprising an anti-PD-1 immunoglobulin heavy chain variable domain (anti-PD-1 VH) comprising complementary determining regions CDR-H1, CDR-H2, and CDR-H3 which comprise the amino acid sequences of SEQ ID NOs 445, 446, and 457, respectively; SEQ ID NOs 451, 452, and 459, respectively; or SEQ ID NOs 443, 455, and 457, respectively, and an anti-PD1 immunoglobulin light chain variable domain (anti-PD-1 VL) comprising complementary determining regions CDR-L1, CDR-L2, and CDR-L3 which comprise the amino acid sequences of SEQ ID NOs 448, 449, and 450, respectively; SEQ ID NO: 454, LAS, and SEQ ID NO: 450, respectively; or SEQ ID NOs 448, 449, and 450 respectively.

In some embodiments, the anti-PD-1 VH has an amino acid sequence at least 85% identical to that of SEQ ID NO: 327; and the anti-PD-1 VL has an amino acid sequence at least 85% identical to that of SEQ ID NO: 347.

In some embodiments, the anti-PD-1 VH has an amino acid sequence of SEQ ID NO: 327; and the anti-PD-1 VL has an amino acid sequence of SEQ ID NO: 347.

In some embodiments, the anti-PD-1 VH has a framework having an amino acid sequence of that within SEQ ID NO: 467 except for up to one amino acid substitution; and the anti-PD-1 VL has a framework having an amino acid sequence of that within SEQ ID NO: 475 except for up to one amino acid substitution.

In some embodiments, the one amino acid substitutions in the anti-PD-1 VH and the anti-PD-1 VL are collectively H44-L100 cysteine mutations.

In one aspect, provided are programmed death receptor 1 (PD-1) binding proteins comprising an anti-PD1 immunoglobulin heavy chain variable domain (anti-PD-1 VH) and an anti-PD1 immunoglobulin light chain variable domain (anti-PD-1 VL), wherein: the anti-PD-1 VH comprises complementary determining regions CDR-H1 comprising the amino acid sequence of SEQ ID NO: 445; CDR-H2 comprising the amino acid sequence of SEQ ID NO: 446; and CDR-H3 comprising the amino acid sequence of SEQ ID NO: 447; CDR-H1 comprising the amino acid sequence of SEQ ID NO: 451; CDR-H2 comprising the amino acid sequence of SEQ ID NO: 452; and CDR-H3 comprising the amino acid sequence of SEQ ID NO: 453; or CDR-H1 comprising the amino acid sequence of SEQ ID NO: 443; CDR-H2 comprising the amino acid sequence of SEQ ID NO: 455; and CDR-H3 comprising the amino acid sequence of SEQ ID NO: 447; the anti-PD-1 VL comprises complementary determining regions CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450; CDR-L1 comprising the amino acid sequence of SEQ ID NO: 454; CDR-L2 comprising the amino acid sequence of LAS; and CDR-L3 comprising the amino acid sequence of SEQ ID NO: 450; or CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450, and wherein the anti-PD-1 VH has a framework having an amino acid sequence of that within SEQ ID NO: 465; and the anti-PD-1 VL has a framework having an amino acid sequence of that within SEQ ID NO: 472, the anti-PD-1 VH has a framework having an amino acid sequence of that within SEQ ID NO: 465; and the anti-PD-1 VL has a framework having an amino acid sequence of that within SEQ ID NO: 471, the anti-PD-1 VH has a framework having an amino acid sequence of that within SEQ ID NO: 465; and the anti-PD-1 VL has a framework having an amino acid sequence of that within SEQ ID NO: 473, the anti-PD-1 VH has a framework having an amino acid sequence of that within SEQ ID NO: 464; and the anti-PD-1 VL has a framework having an amino acid sequence of that within SEQ ID NO: 472, the anti-PD-1 VH has a framework having an amino acid sequence of that within SEQ ID NO: 464; and the anti-PD-1 VL has a framework having an amino acid sequence of that within SEQ ID NO: 473, the anti-PD-1 VH has a framework having an amino acid sequence of that within SEQ ID NO: 464; and the anti-PD-1 VL has a framework having an amino acid sequence of that within SEQ ID NO: 474, the anti-PD-1 VH has a framework having an amino acid sequence of that within SEQ ID NO: 464; and the anti-PD-1 VL has a framework having an amino acid sequence of that within SEQ ID NO: 475, the anti-PD-1 VH has a framework having an amino acid sequence of that within SEQ ID NO: 467; and the anti-PD-1 VL has a framework having an amino acid sequence of that within SEQ ID NO: 471, the anti-PD-1 VH has a framework having an amino acid sequence of that within SEQ ID NO: 467; and the anti-PD-1 VL has a framework having an amino acid sequence of that within SEQ ID NO: 474, the anti-PD-1 VH has a framework having an amino acid sequence of that within SEQ ID NO: 467; and the anti-PD-1 VL has a framework having an amino acid sequence of that within SEQ ID NO: 475, the anti-PD-1 VH has a framework having an amino acid sequence of that within SEQ ID NO: 468; and the anti-PD-1 VL has a framework having an amino acid sequence of that within SEQ ID NO: 471, the anti-PD-1 VH has a framework having an amino acid sequence of that within SEQ ID NO: 468; and the anti-PD-1 VL has a framework having an amino acid sequence of that within SEQ ID NO: 474, the anti-PD-1 VH has a framework having an amino acid sequence of that within SEQ ID NO: 468; and the anti-PD-1 VL has a framework having an amino acid sequence of that within SEQ ID NO: 475, the anti-PD-1 VH has a framework having an amino acid sequence of that within SEQ ID NO: 468; and the anti-PD-1 VL has a framework having an amino acid sequence of that within SEQ ID NO: 475, the anti-PD-1 VH has a framework having an amino acid sequence of that within SEQ ID NO: 466; and the anti-PD-1 VL has a framework having an amino acid sequence of that within SEQ ID NO: 471, or the anti-PD-1 VH has a framework having an amino acid sequence of that within SEQ ID NO: 470; and the anti-PD-1 VL has a framework having an amino acid sequence of that within SEQ ID NO: 474.

In one aspect, provided are programmed death receptor 1 (PD-1) binding proteins comprising an anti-PD1 immunoglobulin heavy chain variable domain (anti-PD-1 VH) and an anti-PD1 immunoglobulin light chain variable domain (anti-PD-1 VL), wherein the anti-PD-1 VH comprises complementary determining regions CDR-H1 comprising the amino acid sequence of SEQ ID NO: 445; CDR-H2 comprising the amino acid sequence of SEQ ID NO: 446; and CDR-H3 comprising the amino acid sequence of SEQ ID NO: 447; CDR-H1 comprising the amino acid sequence of SEQ ID NO: 451; CDR-H2 comprising the amino acid sequence of SEQ ID NO: 452; and CDR-H3 comprising the amino acid sequence of SEQ ID NO: 453; or CDR-H1 comprising the amino acid sequence of SEQ ID NO: 443; CDR-H2 comprising the amino acid sequence of SEQ ID NO: 455; and CDR-H3 comprising the amino acid sequence of SEQ ID NO: 447, the anti-PD-1 VL comprises complementary determining regions CDR-LT comprising the amino acid sequence of SEQ ID NO: 448; CDR-L2 comprising the amino acid sequence of SEQ ID NO: 449; and CDR-L3 comprising the amino acid sequence of SEQ ID NO: 450; CDR-LT comprising the amino acid sequence of SEQ ID NO: 454; CDR-L2 comprising the amino acid sequence of LAS; and CDR-L3 comprising the amino acid sequence of SEQ ID NO: 450; or CDR-LT comprising the amino acid sequence of SEQ ID NO: 448; CDR-L2 comprising the amino acid sequence of SEQ ID NO: 449; and CDR-L3 comprising the amino acid sequence of SEQ ID NO: 450, and wherein the anti-PD-1 VH has a framework having an amino acid sequence of that within SEQ ID NO: 465 except for one amino acid substitution; and the anti-PD-1 VL has a framework having an amino acid sequence of that within SEQ ID NO: 472 except for one amino acid substitution; the anti-PD-1 VH has a framework having an amino acid sequence of that within SEQ ID NO: 465 except for one amino acid substitution; and the anti-PD-1 VL has a framework having an amino acid sequence of that within SEQ ID NO: 471 except for one amino acid substitution; the anti-PD-1 VH has a framework having an amino acid sequence of that within SEQ ID NO: 465 except for one amino acid substitution; and the anti-PD-1 VL has a framework having an amino acid sequence of that within SEQ ID NO: 473 except for one amino acid substitution; the anti-PD-1 VH has a framework having an amino acid sequence of that within SEQ ID NO: 464 except for one amino acid substitution; and the anti-PD-1 VL has a framework having an amino acid sequence of that within SEQ ID NO: 472 except for one amino acid substitution; the anti-PD-1 VH has a framework having an amino acid sequence of that within SEQ ID NO: 464 except for one amino acid substitution; and the anti-PD-1 VL has a framework having an amino acid sequence of that within SEQ ID NO: 473 except for one amino acid substitution; the anti-PD-1 VH has a framework having an amino acid sequence of that within SEQ ID NO: 464 except for one amino acid substitution; and the anti-PD-1 VL has a framework having an amino acid sequence of that within SEQ ID NO: 474 except for one amino acid substitution; the anti-PD-1 VH has a framework having an amino acid sequence of that within SEQ ID NO: 464 except for one amino acid substitution; and the anti-PD-1 VL has a framework having an amino acid sequence of that within SEQ ID NO: 475 except for one amino acid substitution; the anti-PD-1 VH has a framework having an amino acid sequence of that within SEQ ID NO: 467 except for one amino acid substitution; and the anti-PD-1 VL has a framework having an amino acid sequence of that within SEQ ID NO: 471 except for one amino acid substitution; the anti-PD-1 VH has a framework having an amino acid sequence of that within SEQ ID NO: 467 except for one amino acid substitution; and the anti-PD-1 VL has a framework having an amino acid sequence of that within SEQ ID NO: 474 except for one amino acid substitution; the anti-PD-1 VH has a framework having an amino acid sequence of that within SEQ ID NO: 467 except for one amino acid substitution; and the anti-PD-1 VL has a framework having an amino acid sequence of that within SEQ ID NO: 475 except for one amino acid substitution; the anti-PD-1 VH has a framework having an amino acid sequence of that within SEQ ID NO: 468 except for one amino acid substitution; and the anti-PD-1 VL has a framework having an amino acid sequence of that within SEQ ID NO: 471 except for one amino acid substitution; the anti-PD-1 VH has a framework having an amino acid sequence of that within SEQ ID NO: 468 except for one amino acid substitution; and the anti-PD-1 VL has a framework having an amino acid sequence of that within SEQ ID NO: 474 except for one amino acid substitution; the anti-PD-1 VH has a framework having an amino acid sequence of that within SEQ ID NO: 468 except for one amino acid substitution; and the anti-PD-1 VL has a framework having an amino acid sequence of that within SEQ ID NO: 475 except for one amino acid substitution; the anti-PD-1 VH has a framework having an amino acid sequence of that within SEQ ID NO: 468 except for one amino acid substitution; and the anti-PD-1 VL has a framework having an amino acid sequence of that within SEQ ID NO: 475 except for one amino acid substitution; the anti-PD-1 VH has a framework having an amino acid sequence of that within SEQ ID NO: 466 except for one amino acid substitution; and the anti-PD-1 VL has a framework having an amino acid sequence of that within SEQ ID NO: 471 except for one amino acid substitution; or the anti-PD-1 VH has a framework having an amino acid sequence of that within SEQ ID NO: 470 except for one amino acid substitution; and the anti-PD-1 VL has a framework having an amino acid sequence of that within SEQ ID NO: 474 except for one amino acid substitution, wherein the one amino acid substitution in the VH is from a non-cysteine residue to a cysteine residue and the one amino acid substitution in the VL is from a non-cysteine residue to a cysteine residue.

In some embodiments, the one amino acid substitution in the anti-PD-1 VH is at residue H44 and the one amino acid substitution in the anti-PD-1 VL is at residue L100, wherein numbering is according to Kabat.

In one aspect, provided are programmed death receptor 1 (PD-1) binding proteins comprising an anti-PD1 immunoglobulin heavy chain variable domain (anti-PD-1 VH) and an anti-PD1 immunoglobulin light chain variable domain (anti-PD-1 VL), wherein: the anti-PD-1 VH comprises complementary determining regions CDR-H1 comprising the amino acid sequence of SEQ ID NO: 445; CDR-H2 comprising the amino acid sequence of SEQ ID NO: 446; and CDR-H3 comprising the amino acid sequence of SEQ ID NO: 447; CDR-H1 comprising the amino acid sequence of SEQ ID NO: 451; CDR-H2 comprising the amino acid sequence of SEQ ID NO: 452; and CDR-H3 comprising the amino acid sequence of SEQ ID NO: 453; or CDR-H1 comprising the amino acid sequence of SEQ ID NO: 443; CDR-H2 comprising the amino acid sequence of SEQ ID NO: 455; and CDR-H3 comprising the amino acid sequence of SEQ ID NO: 447; the anti-PD-1 VL comprises complementary determining regions CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450; CDR-L1 comprising the amino acid sequence of SEQ ID NO: 454; CDR-L2 comprising the amino acid sequence of LAS; and CDR-L3 comprising the amino acid sequence of SEQ ID NO: 450; or CDR-L1 comprising the amino acid sequence of SEQ ID NO: 448; CDR-L2 comprising the amino acid sequence of SEQ ID NO: 449; and CDR-L3 comprising the amino acid sequence of SEQ ID NO: 450, and wherein the anti-PD-1 VH and anti-PD-1 VL have amino acid sequences that are at least 85% identical to that of: SEQ ID NOs: 301 and 335, respectively; SEQ ID NOs: 301 and 336, respectively; SEQ ID NOs: 301 and 342, respectively; SEQ ID NOs: 301 and 343, respectively; SEQ ID NOs: 301 and 348, respectively; SEQ ID NOs: 305 and 337, respectively; SEQ ID NOs: 305 and 344, respectively; SEQ ID NOs: 305 and 345, respectively; SEQ ID NOs: 312 and 335, respectively; SEQ ID NOs: 312 and 336, respectively; SEQ ID NOs: 312 and 342, respectively; SEQ ID NOs: 312 and 343, respectively; SEQ ID NOs: 315 and 337, respectively; SEQ ID NOs: 315 and 344, respectively; SEQ ID NOs: 315 and 345, respectively; SEQ ID NOs: 322 and 346, respectively; SEQ ID NOs: 323 and 347, respectively; or SEQ ID NOs: 323 and 743, respectively.

In some embodiments, the anti-PD-1 VH and anti-PD-1 VL have amino acid sequences of: SEQ ID NOs: 301 and 335, respectively; SEQ ID NOs: 301 and 336, respectively; SEQ ID NOs: 301 and 342, respectively; SEQ ID NOs: 301 and 343, respectively; SEQ ID NOs: 301 and 348, respectively; SEQ ID NOs: 305 and 337, respectively; SEQ ID NOs: 305 and 344, respectively; SEQ ID NOs: 305 and 345, respectively; SEQ ID NOs: 312 and 335, respectively; SEQ ID NOs: 312 and 336, respectively; SEQ ID NOs: 312 and 342, respectively; SEQ ID NOs: 312 and 343, respectively; SEQ ID NOs: 315 and 337, respectively; SEQ ID NOs: 315 and 344, respectively; SEQ ID NOs: 315 and 345, respectively; SEQ ID NOs: 322 and 346, respectively; SEQ ID NOs: 323 and 347, respectively; or SEQ ID NOs: 323 and 743, respectively.

In some embodiments, the PD-1 binding protein further comprises an Fc region.

In some embodiments, the Fc region comprises a means for extending the half-life of the PD-1 binding protein.

In some embodiments, the half-life extending means comprises an Fc modification.

In some embodiments, the Fc modification is selected from the group consisting of M252Y/S254T/T256E (YTE), M428L/N434S (LS), M428L/N434A (LA), H433K/N434F (KF), and L309D/Q311H/N434S (DHS).

In some embodiments, the Fc modification is M252Y/S254T/T256E (YTE) or M428L/N434S (LS).

In some embodiments, the Fc modification is M428L/N434S (LS).

In some embodiments, the Fc region is an IgG1, IgG2, or IgG4 Fc region.

In some embodiments, the PD-1 binding protein is an antibody or antigen-binding fragment thereof.

In some embodiments, the PD-1 binding protein is a human or humanized antibody or antigen-binding fragment thereof.

In some embodiments, the antigen-binding fragment is a Fab, a F(ab')2, a Fab', a single-chain Fv (scFv), an Fv fragment, a Fd fragment, or a diabody.

In one aspect, provided are bispecific proteins comprising a PD-1 binding protein described herein and a VEGF-binding region comprising an anti-VEGF immunoglobulin heavy chain variable domain (anti-VEGF VH) comprising complementary determining regions CDR-H1 comprising the amino acid sequence of SEQ ID NO: 433; CDR-H2 comprising the amino acid sequence of SEQ ID NO: 434; and CDR-H3 comprising the amino acid sequence of SEQ ID NO: 435; CDR-H1 comprising the amino acid sequence of SEQ ID NO: 439; CDR-H2 comprising the amino acid sequence of SEQ ID NO: 440; and CDR-H3 comprising the amino acid sequence of SEQ ID NO: 441; or CDR-H1 comprising the amino acid sequence of SEQ ID NO: 443; CDR-H2 comprising the amino acid sequence of SEQ ID NO: 444; and CDR-H3 comprising the amino acid sequence of SEQ ID NO: 435.

In some embodiments, the bispecific protein further comprises an anti-VEGF immunoglobulin light chain variable domain (anti-VEGF VL) comprising complementarity-determining regions: CDR-LT comprising the amino acid sequence of SEQ ID NO: 436; CDR-L2 comprising the amino acid sequence of SEQ ID NO: 437; and CDR-L3 comprising the amino acid sequence of SEQ ID NO: 438; CDR-LT comprising the amino acid sequence of SEQ ID NO: 442; CDR-L2 comprising the amino acid sequence of FTS; and CDR-L3 comprising the amino acid sequence of SEQ ID NO: 438; or CDR-LT comprising the amino acid sequence of SEQ ID NO: 436; CDR-L2 comprising the amino acid sequence of SEQ ID NO: 437; and CDR-L3 comprising the amino acid sequence of SEQ ID NO: 438.

In some embodiments, the anti-VEGF VH has an amino acid sequence at least 85% identical to that of SEQ ID NO: 431; and the anti-VEGF VL has an amino acid sequence at least 85% identical to that of SEQ ID NO: 432.

In some embodiments, the anti-VEGF VH has an amino acid sequence of SEQ ID NO: 431; and the anti-VEGF-1 VL has an amino acid of SEQ ID NO: 432.

In one aspect, provided are bispecific proteins comprising a PD-1 binding region and a VEGF-binding region, wherein (a) the PD-1 binding region comprises (i) an anti-PD-1 immunoglobulin heavy chain variable domain (anti-PD-1 VH) comprising complementary determining regions CDR-H1, CDR-H2, and CDR-H3 which comprise the amino acid sequences of (1) SEQ ID NOs 445, 456, and 447, respectively; (2) SEQ ID NOs 451, 458, and 453, respectively; or (3) SEQ ID NOs 443, 460, and 447, respectively, and (ii) an anti-PD1 immunoglobulin light chain variable domain (anti-PD-1 VL) comprising complementary determining regions CDR-L1, CDR-L2, and CDR-L3 which comprise the amino acid sequences of (1) SEQ ID NOs 448, 449, and 450, respectively; (2) SEQ ID NO: 454, LAS, and SEQ ID NO: 450, respectively; or (3) SEQ ID NOs 448, 449, and 450 respectively; and (b) the VEGF-binding region comprises (i) an anti-VEGF immunoglobulin heavy chain variable domain (anti-VEGF VH) comprising complementary determining regions CDR-H1, CDR-H2, and CDR-H3 which comprise the amino acid sequences of (1) SEQ ID NOs: 433, 434, and 435, respectively; (2) SEQ ID NOs: 439, 440, and 441, respectively; or (3) SEQ ID NOs: 443, 444, and 435, respectively, and (ii) an anti-VEGF immunoglobulin light chain variable domain (anti-VEGF VL) comprising complementary determining regions CDR-L1, CDR-L2, and CDR-L3 which comprise the amino acid sequences of (1) SEQ ID NOs: 436, 437, and 438, respectively; (2) SEQ ID NO: 442, FTS, and SEQ ID NO: 438, respectively; or (3) SEQ ID NOs: 436, 437, and 438, respectively. In some embodiments, (a) the anti-PD-1 VH has an amino acid sequence at least 85% identical to that of SEQ ID NO: 325; and the anti-PD-1 VL has an amino acid sequence at least 85% identical to that of SEQ ID NO: 347; and (b) the anti-VEGF VH has an amino acid sequence at least 85% identical to that of SEQ ID NO: 431; and the anti-VEGF-1 VL has an amino acid sequence at least 85% identical to that of SEQ ID NO: 432. In some embodiments, (a) the anti-PD-1 VH has an amino acid sequence of SEQ ID NO: 325; and the anti-PD-1 VL has an amino acid sequence of SEQ ID NO: 347; and (b) the anti-VEGF VH has an amino acid sequence of SEQ ID NO: 431; and the anti-VEGF-1 VL has an amino acid sequence of SEQ ID NO: 432.

In one aspect, provided are bispecific proteins comprising a PD-1 binding region and a VEGF-binding region, wherein (a) the PD-1 binding region comprises (i) an anti-PD-1 immunoglobulin heavy chain variable domain (anti-PD-1 VH) comprising complementary determining regions CDR-H1, CDR-H2, and CDR-H3 which comprise the amino acid sequences of (1) SEQ ID NOs 445, 456, and 457, respectively; (2) SEQ ID NOs 451, 458, and 459, respectively; or (3) SEQ ID NOs 443, 460, and 457, respectively, and (b) an anti-PD1 immunoglobulin light chain variable domain (anti-PD-1 VL) comprising complementary determining regions CDR-L1, CDR-L2, and CDR-L3 which comprise the amino acid sequences of (1) SEQ ID NOs 448, 449, and 450, respectively; (2) SEQ ID NO: 454, LAS, and SEQ ID NO: 450, respectively; or (3) SEQ ID NOs 448, 449, and 450 respectively; and (b) the VEGF-binding region comprises (i) an anti-VEGF immunoglobulin heavy chain variable domain (anti-VEGF VH) comprising complementary determining regions CDR-H1, CDR-H2, and CDR-H3 which comprise the amino acid sequences of (1) SEQ ID NOs: 433, 434, and 435, respectively; (2) SEQ ID NOs: 439, 440, and 441, respectively; or (3) SEQ ID NOs: 443, 444, and 435, respectively, and (ii) an anti-VEGF immunoglobulin light chain variable domain (anti-VEGF VL) comprising complementary determining regions CDR-L1, CDR-L2, and CDR-L3 which comprise the amino acid sequences of (1) SEQ ID NOs: 436, 437, and 438, respectively; (2) SEQ ID NO: 442, FTS, and SEQ ID NO: 438, respectively; or (3) SEQ ID NOs: 436, 437, and 438, respectively. In some embodiments, (a) the anti-PD-1 VH has an amino acid sequence at least 85% identical to that of SEQ ID NO: 320; and the anti-PD-1 VL has an amino acid sequence at least 85% identical to that of SEQ ID NO: 347; and (b) the anti-VEGF VH has an amino acid sequence at least 85% identical to that of SEQ ID NO: 431; and the anti-VEGF-1 VL has an amino acid sequence at least 85% identical to that of SEQ ID NO: 432. In some embodiments, (a) the anti-PD-1 VH has an amino acid sequence of SEQ ID NO: 320; and the anti-PD-1 VL has an amino acid sequence of SEQ ID NO: 347; and (b) the anti-VEGF VH has an amino acid sequence of SEQ ID NO: 431; and the anti-VEGF-1 VL has an amino acid sequence of SEQ ID NO: 432.

In one aspect, provided are bispecific proteins comprising a PD-1 binding region and a VEGF-binding region, wherein (a) the PD-1 binding region comprises (i) an anti-PD-1 immunoglobulin heavy chain variable domain (anti-PD-1 VH) comprising complementary determining regions CDR-H1, CDR-H2, and CDR-H3 which comprise the amino acid sequences of (1) SEQ ID NOs 445, 461, and 457, respectively; (2) SEQ ID NOs 451, 462, and 459, respectively; or (3) SEQ ID NOs 443, 463, and 457, respectively, and (ii) an anti-PD1 immunoglobulin light chain variable domain (anti-PD-1 VL) comprising complementary determining regions CDR-L1, CDR-L2, and CDR-L3 which comprise the amino acid sequences of (1) SEQ ID NOs 448, 449, and 450, respectively; (2) SEQ ID NO: 454, LAS, and SEQ ID NO: 450, respectively; or (3) SEQ ID NOs 448, 449, and 450 respectively; and (a) the VEGF-binding region comprises (i) an anti-VEGF immunoglobulin heavy chain variable domain (anti-VEGF VH) comprising complementary determining regions CDR-H1, CDR-H2, and CDR-H3 which comprise the amino acid sequences of (1) SEQ ID NOs: 433, 434, and 435, respectively; (2) SEQ ID NOs: 439, 440, and 441, respectively; or (3) SEQ ID NOs: 443, 444, and 435, respectively, and (ii) an anti-VEGF immunoglobulin light chain variable domain (anti-VEGF VL) comprising complementary determining regions CDR-L1, CDR-L2, and CDR-L3 which comprise the amino acid sequences of (1) SEQ ID NOs: 436, 437, and 438, respectively; (2) SEQ ID NO: 442, FTS, and SEQ ID NO: 438, respectively; or (3) SEQ ID NOs: 436, 437, and 438, respectively. In some embodiments, (a) the anti-PD-1 VH has an amino acid sequence at least 85% identical to that of SEQ ID NO: 324; and the anti-PD-1 VL has an amino acid sequence at least 85% identical to that of SEQ ID NO: 347; and (b) the anti-VEGF VH has an amino acid sequence at least 85% identical to that of SEQ ID NO: 431; and the anti-VEGF-1 VL has an amino acid sequence at least 85% identical to that of SEQ ID NO: 432. In some embodiments, (a) the anti-PD-1 VH has an amino acid sequence of SEQ ID NO: 324; and the anti-PD-1 VL has an amino acid sequence of SEQ ID NO: 347; and (b) the anti-VEGF VH has an amino acid sequence of SEQ ID NO: 431; and the anti-VEGF-1 VL has an amino acid sequence of SEQ ID NO: 432.

In one aspect, provided are bispecific proteins comprising a PD-1 binding region and a VEGF-binding region, wherein (a) the PD-1 binding region comprises (i) an anti-PD-1 immunoglobulin heavy chain variable domain (anti-PD-1 VH) comprising complementary determining regions CDR-H1, CDR-H2, and CDR-H3 which comprise the amino acid sequences of (1) SEQ ID NOs 445, 461, and 447, respectively; (2) SEQ ID NOs 451, 462, and 453, respectively; or (3) SEQ ID NOs 443, 463, and 447, respectively, and (ii) an anti-PD1 immunoglobulin light chain variable domain (anti- PD-1 VL) comprising complementary determining regions CDR-L1, CDR-L2, and CDR-L3 which comprise the amino acid sequences of (1) SEQ ID NOs 448, 449, and 450, respectively; (2) SEQ ID NO: 454, LAS, and SEQ ID NO: 450, respectively; or (3) SEQ ID NOs 448, 449, and 450 respectively; and (a) the VEGF-binding region comprises (i) an anti-VEGF immunoglobulin heavy chain variable domain (anti-VEGF VH) comprising complementary determining regions CDR-H1, CDR-H2, and CDR-H3 which comprise the amino acid sequences of (1) SEQ ID NOs: 433, 434, and 435, respectively; (2) SEQ ID NOs: 439, 440, and 441, respectively; or (3) SEQ ID NOs: 443, 444, and 435, respectively, and (ii) an anti-VEGF immunoglobulin light chain variable domain (anti-VEGF VL) comprising complementary determining regions CDR-L1, CDR-L2, and CDR-L3 which comprise the amino acid sequences of (1) SEQ ID NOs: 436, 437, and 438, respectively; (2) SEQ ID NO: 442, FTS, and SEQ ID NO: 438, respectively; or (3) SEQ ID NOs: 436, 437, and 438, respectively. In some embodiments, (a) the anti-PD-1 VH has an amino acid sequence at least 85% identical to that of SEQ ID NO: 326; and the anti-PD-1 VL has an amino acid sequence at least 85% identical to that of SEQ ID NO: 347; and (b) the anti-VEGF VH has an amino acid sequence at least 85% identical to that of SEQ ID NO: 431; and the anti-VEGF-1 VL has an amino acid sequence at least 85% identical to that of SEQ ID NO: 432. In some embodiments, (a) the anti-PD-1 VH has an amino acid sequence of SEQ ID NO: 326; and the anti-PD-1 VL has an amino acid sequence of SEQ ID NO: 347; and (b) the anti-VEGF VH has an amino acid sequence of SEQ ID NO: 431; and the anti-VEGF-1 VL has an amino acid sequence of SEQ ID NO: 432.

In one aspect, provided are bispecific proteins comprising a PD-1 binding region and a VEGF-binding region, wherein the PD-1 binding region comprises an anti-PD-1 immunoglobulin heavy chain variable domain (anti-PD-1 VH) comprising complementary determining regions CDR-H1, CDR-H2, and CDR-H3 which comprise the amino acid sequences of (1) SEQ ID NOs 445, 446, and 457, respectively; (2) SEQ ID NOs 451, 452, and 459, respectively; or (3) SEQ ID NOs 443, 455, and 457, respectively, and (an anti-PD1 immunoglobulin light chain variable domain (anti-PD-1 VL) comprising complementary determining regions CDR-L1, CDR-L2, and CDR-L3 which comprise the amino acid sequences of (1) SEQ ID NOs 448, 449, and 450, respectively; (2) SEQ ID NO: 454, LAS, and SEQ ID NO: 450, respectively; or (3) SEQ ID NOs 448, 449, and 450 respectively; and the VEGF-binding region comprises an anti-VEGF immunoglobulin heavy chain variable domain (anti-VEGF VH) comprising complementary determining regions CDR-H1, CDR-H2, and CDR-H3 which comprise the amino acid sequences of (1) SEQ ID NOs: 433, 434, and 435, respectively; (2) SEQ ID NOs: 439, 440, and 441, respectively; or (3) SEQ ID NOs: 443, 444, and 435, respectively, and an anti-VEGF immunoglobulin light chain variable domain (anti-VEGF VL) comprising complementary determining regions CDR-L1, CDR-L2, and CDR-L3 which comprise the amino acid sequences of (1) SEQ ID NOs: 436, 437, and 438, respectively; (2) SEQ ID NO: 442, FTS, and SEQ ID NO: 438, respectively; or (3) SEQ ID NOs: 436, 437, and 438, respectively.

In some embodiments, the anti-PD-1 VH has an amino acid sequence at least 85% identical to that of SEQ ID NO: 327; and the anti-PD-1 VL has an amino acid sequence at least 85% identical to that of SEQ ID NO: 347; and the anti-VEGF VH has an amino acid sequence at least 85% identical to that of SEQ ID NO: 431; and the anti-VEGF-1 VL has an amino acid sequence at least 85% identical to that of SEQ ID NO: 432.

In some embodiments, the anti-PD-1 VH has an amino acid sequence of SEQ ID NO: 327; and the anti-PD-1 VL has an amino acid sequence of SEQ ID NO: 347; and the anti-VEGF VH has an amino acid sequence of SEQ ID NO: 431; and the anti-VEGF-1 VL has an amino acid sequence of SEQ ID NO: 432.

In some embodiments, the bispecific protein further comprises an Fc region.

In some embodiments, the Fc region comprises a means for extending the half-life of the PD-1 binding protein.

In some embodiments, the half-life extending means comprises an Fc modification.

In some embodiments, the Fc modification is selected from the group consisting of M252Y/S254T/T256E (YTE), M428L/N434S (LS), M428L/N434A (LA), H433K/N434F (KF), and L309D/Q311H/N434S (DHS).

In some embodiments, the Fc modification is M252Y/S254T/T256E (YTE) or M428L/N434S (LS).

In some embodiments, the Fc modification is M428L/N434S (LS).

In some embodiments, the Fc region is an IgG1, IgG2, or IgG4 Fc region.

In some embodiments, the bispecific protein is an antibody or antigen-binding fragment thereof.

In some embodiments, the bispecific protein is a human or humanized antibody or antigen-binding fragment thereof.

In some embodiments, the antigen-binding fragment is a Fab, a F(ab')2, a Fab', a single-chain Fv (scFv), an Fv fragment, a Fd fragment, or a diabody.

In some embodiments, bispecific protein comprises two PD-1 binding regions and two VEGF binding regions.

In some embodiments, the bispecific protein comprises two PD-1 binding regions and one VEGF binding region.

In some embodiments, the bispecific protein comprises one PD-1 binding region and two VEGF binding regions.

In some embodiments, each PD-1 binding region is an scFv.

In some embodiments, each VEGF binding region comprises an anti-VEGF VH on a first polypeptide chain and an anti-VEGF VL on a second polypeptide chain, an anti-VEGF VH and an anti-VEGF VL within a Fab, or an anti-VEGF VH and an anti-VEGF VL within a CrossFab.

In some embodiments, each VEGF binding region is an scFv.

In some embodiments, each PD-1 binding region comprises an anti-PD1 VH on a first polypeptide chain and an anti-PD1 VL on a second polypeptide chain, an anti-PD1 VH and an anti-PD1 VL within a Fab, or an anti-PD1 VH and an anti-PD1 VL within a CrossFab.

In some embodiments, each PD-1 binding region is a VHH.

In some embodiments, each VEGF binding region comprises an anti-VEGF VH on a first polypeptide chain and an anti-VEGF VL on a second polypeptide chain, an anti-VEGF VH and an anti-VEGF VL within a Fab, or an anti-VEGF VH and an anti-VEGF VL within a CrossFab.

In one aspect, provided are bispecific proteins comprising at least one PD-1 binding region and at least one VEGF-binding region, comprising a first polypeptide chain having the sequence of SEQ ID NO: 92 and a second polypeptide chain having the sequence of SEQ ID NO: 239.

In one aspect, provided are bispecific proteins comprising at least one PD-1 binding region and at least one VEGF-binding region, comprising a first polypeptide chain having the sequence of SEQ ID NO: 73 and a second polypeptide chain having the sequence of SEQ ID NO: 220.

In one aspect, provided are bispecific proteins comprising at least one PD-1 binding region and at least one VEGF-binding region, comprising a first polypeptide chain having the sequence of SEQ ID NO: 91 and a second polypeptide chain having the sequence of SEQ ID NO: 238.

In one aspect, provided are bispecific proteins comprising at least one PD-1 binding region and at least one VEGF-binding region, comprising a first polypeptide chain having the sequence of SEQ ID NO: 94 and a second polypeptide chain having the sequence of SEQ ID NO: 241.

In one aspect, provided are bispecific proteins comprising at least one PD-1 binding region and at least one VEGF-binding region, comprising a first polypeptide chain having the sequence of SEQ ID NO: 96 and a second polypeptide chain having the sequence of SEQ ID NO: 243.

In some embodiments, the bispecific protein forms a dimer.

In various aspects, provided are isolated nucleic acids encoding one or more chains of a PD-1 binding protein or a bispecific protein as disclosed herein, expression vectors comprising said isolated nucleic acids, and host cells comprising said isolated nucleic acids or expression vectors.

In various aspects, provided are sets of isolated nucleic acids collectively encoding a PD-1 binding protein or a bispecific protein as disclosed herein, sets of expression vectors collectively comprising said sets of isolated nucleic acids, and host cells comprising said sets of isolated nucleic acids or said sets of expression vectors.

In one aspect, provided are pharmaceutical compositions comprising a PD-1 binding protein or bispecific protein as disclosed herein and a pharmaceutically acceptable carrier.

In one aspect, provided are methods comprising a step of administering to a subject in need thereof an effective amount of a PD-1 binding protein, bispecific protein, or pharmaceutical composition as disclosed herein.

In some embodiments, the subject has or is at risk of having a disease or condition associated with aberrant PD-1 and/or VEGF expression or signaling.

In some embodiments, the disease or condition is a cancer.

In some embodiments, the cancer is a lung cancer.

In some embodiments, the lung cancer is non-small cell lung cancer.

In some embodiments, the cancer is a gastrointestinal cancer.

In some embodiments, the gastrointestinal cancer is colorectal cancer, biliary cancer, gastric cancer, or hepatocellular cancer.

In some embodiments, the cancer is a reproductive cancer.

In some embodiments, the reproductive cancer is cervical cancer, endometrial cancer, or ovarian cancer.

In some embodiments, the step of administering comprises systemic administration of the PD-1 binding protein, bispecific protein, or pharmaceutical composition.

In some embodiments, systemic administration comprises intravenous administration of the PD-1 binding protein, bispecific protein, or pharmaceutical composition.

In some embodiments, systemic administration comprises subcutaneous administration of the PD-1 binding protein, bispecific protein, or pharmaceutical composition.

BRIEF DESCRIPTION OF THE DRAWINGS

These and other features, aspects, and advantages of the present invention will become better understood with regard to the following description, and accompanying drawing, where:

FIGS. 6A-6D depict the SPR curves for binding of the indicated antibodies to cynomolgus PD-1.

FIGS. 7A-7F depict SEC-MALS complex profiles for the indicated antibodies.

FIG. 8 depicts the heavy and light chain sequences (SEQ ID NOs: 128 and 275, respectively) and format for ivonescimab ("AK112"). The variable domains from penpulimab ("AK105") are underlined.

FIGS. 17C-17D depict stability data at 40° C. (FIG. 17C) and 25° C. (FIG. 17D).

DETAILED DESCRIPTION

Definitions

Figure 1A:
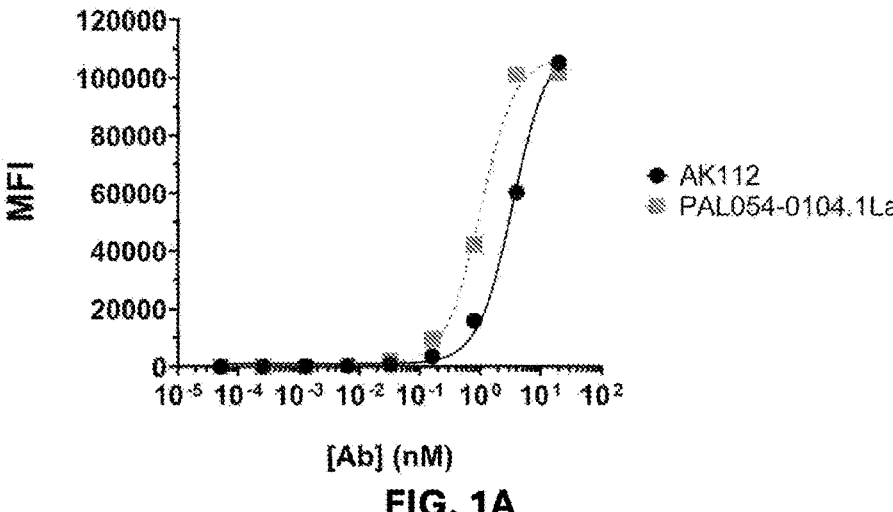
FIGS. 1A-1CC depict binding activity of the indicated antibodies to PD-1 expressing cells.

Unless otherwise defined, all terms of art, notations and other scientific terminology used herein are intended to have the meanings commonly understood by those of skill in the art. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., Molecular Cloning: A Laboratory Manual 4th ed. (2012) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

As used herein, the singular form "a," "an," and "the" includes plural references unless indicated otherwise.

It is understood that aspects and embodiments of the invention described herein include "comprising," "consisting," and "consisting essentially of" aspects and embodiments.

For all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as "consisting essentially of" a component, the composition may additionally contain any amount of pharmaceutically acceptable carriers, vehicles, or diluents and other such components which do not substantially affect the condition being treated.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which an exogenous nucleic acid has been introduced, and the progeny of such cells. Host cells include "transformants" (or "transformed cells") and "transfectants" (or "transfected cells"), which each include the primary transformed or transfected cell and progeny derived therefrom. Such progeny may not be completely identical in nucleic acid content to a parent cell, and may contain mutations. A "recombinant host cell" or "host cell" refers to a cell that includes an exogenous polynucleotide, regardless of the method used for insertion, for example, direct uptake, transduction, f-mating, or other methods known in the art to create recombinant host cells.

An "effective amount" or "therapeutically effective amount" as used herein refers to an amount of therapeutic compound, such as an anti-VEGF antibody, administered to an individual, either as a single dose or as part of a series of doses, which is effective to produce or contribute to a desired therapeutic effect, either alone or in combination with another therapeutic modality. Examples of a desired therapeutic effect is enhancing an immune response, slowing or delaying tumor development; stabilization of disease; amelioration of one or more symptoms. An effective amount may be given in one or more dosages.

The term "treating" (and variations thereof such as "treat" or "treatment") refers to clinical intervention in an attempt to alter the natural course of a disease or condition in a subject in need thereof. Treatment can be performed during the course of clinical pathology. Desirable effects of treatment include preventing recurrence of disease, alleviation of symptoms, diminishment of any direct or indirect pathological consequences of the disease, preventing metastasis, decreasing the rate of disease progression, amelioration or palliation of the disease state, and remission or improved prognosis.

The term "sufficient amount" means an amount sufficient to produce a desired effect, e.g., an amount sufficient to modulate an immune response in a subject.

The terms "recipient", "individual", "subject", "host", and "patient", are used interchangeably herein and in some embodiments, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human. None of these terms require the supervision of medical personnel. As used herein, the term "effective amount" refers to the amount of a compound (e.g., a compound of the present disclosure) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating, slowing or preventing a symptom thereof. As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA (1975).

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "about" indicates and encompasses an indicated value and a range above and below that value. In certain embodiments, the term "about" indicates the designated value±10%, ±5%, or ±1%. In certain embodiments, where applicable, the term "about" indicates the designated value(s)±one standard deviation of that value(s).

The term "optionally" is meant, when used sequentially, to include from one to all of the enumerated combinations and contemplates all sub-combinations.

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The term "affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope).

The term "$k_d$" (sec-1), as used herein, refers to the dissociation rate constant of a particular antibody-antigen interaction. This value is also referred to as the $k_{off}$ value.

The term "$k_a$" (M-1×sec-1), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D=k_d/k_a$. In some embodiments, the affinity of an antibody is described in terms of the $K_D$ for an interaction between such antibody and its antigen. For clarity, as known in the art, a smaller $K_D$ value indicates a higher affinity interaction, while a larger $K_D$ value indicates a lower affinity interaction.

The term "$K_A$" (M-1), as used herein, refers to the association equilibrium constant of a particular antibody-antigen interaction. $K_A=k_a/k_d$.

As used herein, unless otherwise indicated, the term "antibody" is understood to mean an intact antibody (e.g., an intact monoclonal antibody), or a fragment thereof, such as a Fc fragment of an antibody (e.g., an Fc fragment of a monoclonal antibody), or an antigen-binding fragment of an antibody (e.g., an antigen-binding fragment of a monoclonal antibody), including an intact antibody, antigen-binding fragment, or Fc fragment that has been modified, engineered, or chemically conjugated. In general, antibodies are multimeric proteins that contain four polypeptide chains. Two of the polypeptide chains are called immunoglobulin heavy chains (H chains), and two of the polypeptide chains are called immunoglobulin light chains (L chains). The immunoglobulin heavy and light chains are connected by an interchain disulfide bond. The immunoglobulin heavy chains are connected by interchain disulfide bonds. A light chain consists of one variable region (VL) and one constant region (CL). The heavy chain consists of one variable region (VH) and at least three constant regions (CH1, CH2 and CH3). The variable regions determine the binding specificity of the antibody. Each variable region contains three hypervariable regions known as complementarity determining regions (CDRs) flanked by four relatively conserved regions known as framework regions (FRs). The extent of the FRs and CDRs has been defined (Kabat, E. A., et al. (1991) Sequences of Proteins of Immunological Interest, Fifth Edition, U.S. Department of Health and Human Services, NIH Publication No. 91-3242; and Chothia, C. et al. (1987) J. Mol. Biol. 196:901-917). The three CDRs, referred to as CDR1, CDR2, and CDR3, contribute to the antibody binding specificity. Naturally occurring antibodies have been used as starting material for engineered antibodies, such as chimeric antibodies and humanized antibodies. Examples of antibody-based antigen-binding fragments include Fab, Fab', (Fab')2, Fv, single chain antibodies (e.g., scFv), minibodies, and diabodies. Examples of antibodies that have been modified or engineered include chimeric antibodies, humanized antibodies, and multispecific antibodies (e.g., bispecific antibodies). An example of a chemically conjugated antibody is an antibody conjugated to a toxin moiety.

A "VEGF antibody" or "VEGF specific antibody" is an antibody, as provided herein, which specifically binds to VEGF. A "VEGF binder" or "VEGF specific binder" is a binder, as provided herein, which specifically binds to VEGF.

A "PD-1 antibody," "PD1 antibody" or "PD1 specific antibody" is an antibody, as provided herein, which specifically binds to PD1. A "PD-1 binder," "PD1 binder" or "PD1 specific binder" is an binder, as provided herein, which specifically binds to PD1.

The term "epitope" means a portion of an antigen that specifically binds to an antibody.

The term "hypervariable region" or "HVR," as used herein, refers to each of the regions of an antibody variable domain which are hypervariable in sequence and/or form structurally defined loops ("hypervariable loops").

The term "antigen-binding domain" means the portion of an antibody that is capable of specifically binding to an antigen or epitope.

The term "chimeric antibody" refers to an antibody in which a portion of the heavy and/or light chain is derived from a particular source or species, while the remainder of the heavy and/or light chain is derived from a different source or species.

The term "human antibody" refers to an antibody which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

The term "humanized antibody" refers to a protein having a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject.

The term "multispecific antibody" refers to an antibody that comprises two or more different antigen-binding domains that collectively specifically bind two or more different epitopes.

A "bispecific antibody" is an antibody that comprises two different antigen binding domains that each bind different epitopes.

A "monospecific antibody" is an antibody that comprises one or more binding sites that specifically bind to a single epitope. An example of a monospecific antibody is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "single-chain" refers to a molecule comprising amino acid monomers linearly linked by peptide bonds. In a particular such embodiment, the C-terminus of the Fab light chain is connected to the N-terminus of the Fab heavy chain in the single-chain Fab molecule. As described in more detail herein, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain.

The "Fab fragment" (also referred to as fragment antigen-binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region.

"F(ab')2" fragments contain two Fab' fragments joined, near the hinge region, by disulfide bonds. F(ab')2 fragments may be generated, for example, by recombinant methods or by pepsin digestion of an intact antibody. The F(ab') fragments can be dissociated, for example, by treatment with ß-mercaptoethanol.

"Fv" fragments comprise a non-covalently-linked dimer of one heavy chain variable domain and one light chain variable domain.

"Single-chain Fv" or "sFv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in The Pharmacology of Monoclonal Antibodies, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

"scFv-Fc" fragments comprise an scFv attached to an Fc domain. For example, an Fc domain may be attached to the C-terminal of the scFv. The Fc domain may follow the VH or VL, depending on the orientation of the variable domains in the scFv (i.e., VH-VL or VL-VH). Any suitable Fc domain known in the art or described herein may be used. In some cases, the Fc domain comprises an IgG4 Fc domain.

The term "single domain antibody" or "sdAb" refers to a molecule in which one variable domain of an antibody specifically binds to an antigen without the presence of the other variable domain. Single domain antibodies, and fragments thereof, are described in Arabi Ghahroudi et al. (1998) *FEBS Letters* 414:521-526 and Muyldermans et al. (2001) *Trends in Biochem. Sci.* 26:230-245, each of which is incorporated by reference in its entirety. Single domain antibodies are also known as sdAbs, VHH, or nanobodies. sdAbs are fairly stable and easy to express as fusion partner with the Fc chain of an antibody (Harmsen M M, De Haard H J (2007) "Properties, production, and applications of camelid single-domain antibody fragments" *Appl. Microbiol Biotechnol.* 77(1): 13-22).

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "antibody fragment" refers to an antibody that comprises a portion of an intact antibody, such as the antigen-binding or variable region of an intact antibody. Antibody fragments include, for example, Fv fragments, Fab fragments, F(ab')₂ fragments, Fab' fragments, scFv (sFv) fragments, and scFv-Fc fragments.

The term "Fc domain" or "Fc region" herein is used to define a C-terminal region of an immunoglobulin heavy chain that contains at least a portion of the constant region. The term includes native sequence Fc regions and variant Fc regions.

The term "substantially purified" refers to a construct described herein, or variant thereof that may be substantially or essentially free of components that normally accompany or interact with the protein as found in its naturally occurring environment, i.e. a native cell, or host cell in the case of recombinantly produced antibody that in certain embodiments, is substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., using publicly available computer software such as BLAST, BLASTP, BLASTN, BLAST-2, ALIGN, MEGALIGN (DNASTAR), CLUST-ALW, CLUSTAL OMEGA, or MUSCLE software or other algorithms available to persons of skill) or by visual inspection. Software for performing BLAST analyses (Altschul et al. (1990) *J. Mol. Biol.* 215:403-410) is publicly available through the National Center for Biotechnology Information (ncbi.nlm.nih.gov). Those skilled in the art can determine appropriate parameters for aligning sequences, including any algorithms needed to achieve maximal alignment over the full length of the sequences being compared. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman (1981) *Adv. Appl. Math.* 2:482, by the homology alignment algorithm of Needleman & Wunsch (1970) *J. Mol. Biol.* 48:443, by the search for similarity method of Pearson & Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

It must be noted that, as used in the specification and the appended claims, the singular forms "a," "an" and "the" include plural referents unless the context clearly dictates otherwise.

PD-1 Antibodies and Bispecific Anti-VEGF/PD-1 Antibodies

Basic Antibody Structure

The recognized immunoglobulin (antibody) genes include the kappa, lambda, alpha, gamma, delta, epsilon, and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

An exemplary immunoglobulin structural unit is composed of two pairs of polypeptide chains, each pair having one "light" (about 25 kD) and one "heavy" chain (about 50-70 kD). The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises of the VH, CH1, CH2, and CH3 domains respectively from the N- to C-terminus. The light chain comprises of the VL and CL domains from N- to C-terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain found in an antibody provided herein, is from or derived from an immunoglobulin based construct such as a diabody or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody, or any chimeric antibody.

In some embodiments, the antibodies provided herein comprise a heavy chain. In one embodiment, the heavy chain is an IgA. In one embodiment, the heavy chain is an IgD. In one embodiment, the heavy chain is an IgE. In one embodiment, the heavy chain is an IgG. In one embodiment, the heavy chain is an IgM. In one embodiment, the heavy chain is an IgG1. In one embodiment, the heavy chain is an IgG2. In one embodiment, the heavy chain is an IgG3. In one embodiment, the heavy chain is an IgG4. In one embodiment, the heavy chain is an IgA1. In one embodiment, the heavy chain is an IgA2.

In some embodiments, an antibody is an IgG1 antibody. In some embodiments, an antibody is an IgG3 antibody. In some embodiments, an antibody is an IgG2 antibody. In some embodiments, an antibody is an IgG4 antibody.

Generally, native four-chain antibodies comprise six hypervariable regions (HVRs); three in the VH (H1, H2, and H3), and three in the VL (L1, L2, and L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. HVRs are also referred to as CDRs, and these terms are used herein interchangeably in reference to portions of the variable region that form the antigen-binding regions. This particular region has been described by Kabat et al. (1983) U.S. Dept. of Health and Human Services, Sequences of Proteins of Immunological Interest and by Chothia et al. (1987) *J Mol Biol* 196:901-917, where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The amino acid sequence boundaries of a CDR can be determined by one of skill in the art using any of a number of known numbering schemes, including those described by Kabat et al., supra ("Kabat" numbering scheme); Al-Lazikani et al. (1997) *J. Mol. Biol.,* 273:927-948 ("Chothia" numbering scheme); MacCallum et al. (1996) *J. Mol. Biol.* 262:732-745 ("Contact" numbering scheme); Lefranc et al. (2003) *Dev. Comp. Immunol.* 27:55-77 ("IMGT" numbering scheme); and Honegge and Plückthun (2001) *J. Mol. Biol.* 309:657-70 ("AHo" numbering scheme); each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at bioinf.org.uk/abs/abnum/, and described in Abhinandan and Martin (2008) *Immunology,* 45:3832-3839, incorporated by reference in its entirety.

TABLE 1

Residues in CDRs according to Kabat and Chothia numbering schemes.
Table 1

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

One example of an antigen-binding domain is an antigen-binding domain formed by a VH-VL dimer of an antibody. Another example of an antigen-binding domain is an antigen-binding domain formed by diversification of certain loops from the tenth fibronectin type III domain of an Adnectin. An antigen-binding domain can include CDRs 1, 2, and 3 from a heavy chain in that order; and CDRs 1, 2, and 3 from a light chain in that order.

Epitopes frequently consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding and other amino acid residues, which are not directly involved in the binding. The epitope to which an antibody binds can be determined using known techniques for epitope determination such as, for example, testing for antibody binding to VEGF variants with different point-mutations or to chimeric VEGF variants.

To screen for antibodies which bind to an epitope on a target antigen bound by an antibody of interest (e.g., VEGF or PD-1), a routine cross-blocking assay such as that described in Antibodies, A Laboratory Manual, Cold Spring Harbor Laboratory, Ed Harlow and David Lane (1988), can be performed. Alternatively, or additionally, epitope mapping can be performed by methods known in the art.

Chimeric antibodies are antibodies in which a portion of the heavy and/or light chain is derived from a particular source or species, while the remainder of the heavy and/or light chain is derived from a different source or species.

Human antibodies are antibodies which possess an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies can be found in U.S. Pat. Nos. 6,054,297, 5,886,152 and 5,877,293. For further details, see Jones et al. (1986) *Nature* 321:522-525; Riechmann et al. (1988) *Nature* 332:323-329; and Presta (1992) *Curr. Op. Struct. Biol.* 2:593-596, each of which is incorporated by reference in its entirety.

The two or more different epitopes may be epitopes on the same antigen (e.g., a single VEGF) or on different antigens (e.g., different VEGF molecules, or a VEGF molecule and a non-VEGF molecule). In some embodiments, a multi-specific antibody binds two different epitopes (i.e., a "bispecific antibody"). In some embodiments, a multi-specific antibody binds three different epitopes (i.e., a "trispecific antibody").

Anti-VEGF or PD-1 antibodies can include those described herein such as the clones set forth in the drawings and/or tables. In some embodiments, the binding protein comprises an alternative scaffold. In some embodiments, the binding protein consists of an alternative scaffold. In some embodiments, the binding protein consists essentially of an alternative scaffold. In some embodiments, the binding protein comprises an antibody fragment. In some embodiments, the binding protein consists of an antibody fragment. In some embodiments, the binding protein consists essentially of an antibody fragment.

In some embodiments the bispecific antibodies are monoclonal antibodies.

In some embodiments the bispecific antibodies are polyclonal antibodies.

In some embodiments the bispecific antibodies are produced by hybridomas. In other embodiments, the bispecific antibodies are produced by recombinant cells engineered to express the desired variable and constant domains.

In some embodiments the bispecific antibodies may be single chain antibodies or other antibody derivatives retaining the antigen specificity and the lower hinge region or a variant thereof.

In some embodiments the bispecific antibodies may be polyfunctional antibodies, recombinant antibodies, human antibodies, humanized antibodies, fragments or variants thereof. In particular embodiments, the antibody fragment or a derivative thereof is selected from a Fab fragment, a Fab'₂ fragment, a CDR, and scFv.

In some embodiments, the bispecific antibodies are capable of forming an immune complex. For example, an immune complex can be a tumor cell covered by bispecific antibodies.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Bispecific Antibody Structure

The present application provides proteins that bind VEGF and PD-1, as well as compositions (e.g., pharmaceutical compositions thereof). Bispecific antibodies disclosed herein can be of any structure known in the art.

Disclosed bispecific binding proteins can take any format, including but not limited to those described herein.

In one exemplary bispecific format, the bispecific binding protein comprises (a) two immunoglobulin heavy chains which each comprise, from N- to C-terminus: (1) a heavy chain variable domain, (2) an Fc (hinge-CH2-CH3) domain, which immunoglobulin heavy chains are each linked at their C-termini to an scFv; and (b) two immunoglobulin light chains which each comprise, from N- to C-terminus: (1) a light chain variable domain and (2) a light chain constant domain. Linkers (e.g., amino acid linkers) may be used between any of the aforementioned domains within a given immunoglobulin chain, within an scFv, and/or between the immunoglobulin heavy chain and the scFv. In this format, a heavy chain variable domain and a light chain variable domain together form a first binding region, and the scFv comprises a second binding region. In some embodiments, the first binding region is a VEGF binding region and the second binding region is a PD-1 binding region. In some embodiments, the first binding region is a PD-1 binding region and the second binding region is a VEGF binding region. Thus, for example, in this format, the bispecific binding protein comprises two VEGF binding regions and two PD-1 binding regions per construct.

However, additional formats, such as formats comprising different numbers of each binding region, are also contemplated, e.g., two VEGF binding regions and one PD-1 binding region, one VEGF binding region and two PD-1 binding regions, or one VEGF binding region and one PD-1 binding region.

Another format is a bispecific binding protein that includes a first immunoglobulin heavy chain, a second immunoglobulin heavy chain and an immunoglobulin light chain. In this format, (1) the first immunoglobulin heavy chain includes a first Fc (hinge-CH2-CH3) domain, a first variable heavy chain domain and an optional first CH1 heavy chain domain, (2) the immunoglobulin light chain includes a variable light chain domain and a constant light chain domain; and (3) together with the first immunoglobulin heavy chain, the immunoglobulin light chain forms an antigen-binding site that binds VEGF. In this format, the second immunoglobulin heavy chain comprises a second Fc (hinge-CH2-CH3) domain, a second variable heavy chain domain and a second CH1 heavy chain domain that may pair with an immunoglobulin light chain identical to the one that pairs with the first immunoglobulin heavy chain, except that when immunoglobulin light chain is paired with the second immunoglobulin heavy chain, the resulting antigen binding site binds to PD-1.

In some embodiments, the bispecific binding protein is in the Triomab form, which is a trifunctional, bispecific binding protein that maintains an IgG-like shape. This chimera consists of two half antibodies, each with one light and one heavy chain, that originate from two parental antibodies.

In some embodiments, the bispecific binding protein is the KiH Common Light Chain (LC) form, which involves the knobs-into-holes (KIHs) technology. The KIH involves engineering $C_H3$ domains to create either a "knob" or a "hole" in each heavy chain to promote heterodimerization. The concept behind the "Knobs-into-Holes (KiH)" Fc technology was to introduce a "knob" in one CH3 domain (CH3A) by substitution of a small residue with a bulky one (e.g., $T366W_{CH3A}$ in EU numbering). To accommodate the "knob," a complementary "hole" surface was created on the other CH3 domain (CH3B) by replacing the closest neighboring residues to the knob with smaller ones (e.g., T366S/L368A/$Y407V_{CH3B}$). The "hole" mutation was optimized by structured-guided phage library screening (Atwell et al. (1997) "Stable heterodimers from remodeling the domain interface of a homodimer using a phage display library," *J. Mol. Biol.* 270(1):26-35). X-ray crystal structures of KiH Fc variants (Elliott et al. (2014) "Antiparallel conformation of knob and hole aglycosylated half-antibody homodimers is mediated by a CH2-CH3 hydrophobic interaction," *J. Mol. Biol.* 426(9):1947-57; Mimoto et al. (2014) "Crystal structure of a novel asymmetrically engineered Fc variant with improved affinity for FcgammaRs," *Mol. Immunol.* 58(1): 132-8) demonstrated that heterodimerization is thermodynamically favored by hydrophobic interactions driven by steric complementarity at the inter-CH3 domain core interface, whereas the knob-knob and the hole-hole interfaces do not favor homodimerization owing to steric hindrance and disruption of the favorable interactions, respectively.

In some embodiments, the bispecific binding protein is in the Orthogonal Fab interface (Ortho-Fab) form. In the ortho-Fab IgG approach (Lewis et al. (2014) "Generation of bispecific IgG antibodies by structure-based design of an orthogonal Fab interface," *Nat. Biotechnol.* 32(2):191-8), structure-based regional design introduces complementary mutations at the LC and $HC_{VH-CH1}$ interface in only one Fab, without any changes being made to the other Fab.

In some embodiments, the bispecific binding protein is in the 2-in-1 Ig format. In some embodiments, the bispecific binding protein is in the ES form, which is a heterodimeric construct containing two different Fabs binding to targets 1 and target 2 fused to the Fc. Heterodimerization is ensured by electrostatic steering mutations in the Fc. In some embodiments, the bispecific binding protein is in the κλ-Body form, which is a heterodimeric construct with two different Fabs fused to Fc stabilized by heterodimerization mutations: Fab1 targeting antigen 1 contains kappa LC, while second Fab targeting antigen 2 contains lambda LC.

In some embodiments, the bispecific binding protein is in Fab Arm Exchange form (antibodies that exchange Fab arms by swapping a heavy chain and attached light chain (half-molecule) with a heavy-light chain pair from another molecule, which results in bispecific antibodies). In some embodiments, the bispecific binding protein is in the SEED Body form. The strand-exchange engineered domain (SEED) platform was designed to generate asymmetric and bispecific binding protein-like molecules, a capability that expands therapeutic applications of natural antibodies. This protein engineered platform is based on exchanging structurally related sequences of immunoglobulin within the conserved CH3 domains. The SEED design allows efficient generation of AG/GA heterodimers, while disfavoring homodimerization of AG and GA SEED CH3 domains. (Muda M. et al. (2011) *Protein Eng. Des. Sel.* 24(5):447-54). In some embodiments, the bispecific binding protein is in the LuZ-Y form, in which a leucine zipper is used to induce heterodimerization of two different HCs. (Wranik et al. (2012) *J. Biol. Chem.* 287:43331-9).

In some embodiments, the bispecific binding protein is in the Cov-X-Body form. In bispecific CovX-Bodies, two different peptides are joined together using a branched azetidinone linker and fused to the scaffold binding protein under mild conditions in a site-specific manner. Whereas the pharmacophores are responsible for functional activities, the binding protein scaffold imparts long half-life and Ig-like distribution. The pharmacophores can be chemically optimized or replaced with other pharmacophores to generate optimized or unique bispecific antibodies. (Doppalapudi et al. (2010) *PNAS* 107(52): 22611-22616).

In some embodiments, the bispecific binding protein is in an Oasc-Fab heterodimeric form that includes Fab binding to target 1, and scFab binding to target 2 fused to Fc. Heterodimerization is ensured by mutations in the Fc.

In some embodiments, the bispecific binding protein is in a DuetMab form, which is an heterodimeric construct containing two different Fabs binding to antigens 1 and 2, and Fc stabilized by heterodimerization mutations. Fab 1 and 2 contain differential S—S bridges that ensure correct LC and HC pairing.

In some embodiments, the bispecific binding protein is in a CrossmAb form, which is an heterodimeric construct with two different Fabs binding to targets 1 and 2, fused to Fc stabilized by heterodimerization. CL and CH1 domains and VH and VL domains are switched, e.g., CH1 is fused in-line with VL, while CL is fused in-line with VH.

In some embodiments, the bispecific binding protein is in a Fit-Ig form, which is a homodimeric construct where Fab binding to antigen 2 is fused to the N terminus of HC of Fab that binds to antigen 1. The construct contains wild-type Fc.

Tables 2A-2B lists sequences of heavy chains and light chains that, in combination, can bind to VEGF and/or PD-1. Sequences of PD-1 Antibodies and Bispecific Anti-VEGF/PD-1 Binding Proteins Provided herein are binding proteins that bind programmed death receptor 1 (PD-1). PD-1 binding proteins generally comprise one or more PD-1 binding regions, as further discussed herein.

Also provided herein are bispecific binding proteins that bind vascular endothelial growth factor (VEGF) and programmed death receptor 1 (PD-1). Provided bispecific binding proteins generally comprise one or more VEGF binding regions and one or more PD-1 binding regions.

Exemplary Characteristic Sequences of VEGF Binding Regions

VEGF binding regions are capable of binding to VEGF. In some embodiments, VEGF binding regions are capable of binding to an epitope of human VEGF, such as a human VEGF-A isoform. In some embodiments, VEGF binding regions are capable of binding to all human VEGF-A isoforms. In some embodiments, VEGF binding regions antagonize VEGF, e.g., by blocking binding of VEGF to its receptor.

In some embodiments, VEGF binding regions comprise a heavy chain variable domain comprising complementarity determining regions CDR-H1, CDR-H2, and CDR-H3 with sequences as shown in Table 2. In some embodiments, VEGF binding regions further comprise a light chain variable domain comprising complementarity determining regions CDR-L1, CDR-L2, and CDR-L3 with sequences as shown in Table 2.

In some embodiments, VEGF binding regions comprise a heavy chain variable domain with a heavy chain variable domain sequence as shown in Table 2. In some embodiments, VEGF binding regions comprise a heavy chain variable domain which is a variant of the heavy chain variable sequence shown in Table 2, in that the heavy chain variable domain has (1) CDR-H1, CDR-H2, and CDR-H3 with sequences as shown in Table 2 and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the heavy chain variable domain sequence shown in Table 2.

In some embodiments, VEGF binding regions comprise a heavy chain variable domain as described herein in Table 2 (or a variant thereof, as described herein) and further comprise a light chain variable region which has (1) CDR-L1, CDR-L2, and CDR-L3 with sequences as shown in Table 2 and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the light chain variable domain sequence shown in Table 2.

shown in Table 5A. In some embodiments, VEGF binding regions further comprise a light chain variable domain comprising complementarity determining regions CDR-L1, CDR-L2, and CDR-L3 with sequences as shown within a light chain variable domain sequence in Table 6A.

In some embodiments, VEGF binding regions comprise a heavy chain variable domain with a heavy chain variable sequence as shown in Table 5A. In some embodiments, VEGF binding regions comprise a heavy chain variable domain which is a variant of the heavy chain variable sequence shown in Table 5A, in that the heavy chain variable domain has (1) CDR-H1, CDR-H2, and CDR-H3 with sequences within a given heavy chain variable domain sequence shown in Table 5A and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the same heavy chain variable domain sequence shown in Table 5A.

In some embodiments, VEGF binding regions comprise a heavy chain variable domain as described herein in Table 5A (or a variant thereof, as described herein) and further comprise a light chain variable region which has (1) CDR-L1, CDR-L2, and CDR-L3 within a light chain variable domain sequence as shown in Table 6A and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the same light chain variable domain sequence shown in Table 6A.

TABLE 2

Characteristic sequences of exemplary VEGF binding regions

| Heavy chain Variable domain | Light chain Variable domain |
|---|---|
| EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSS (SEQ ID NO: 431) | DIQMTQSPSSLSASVGDRVTITCSASQDISNY LNWYQQKPGKAPKVLIYFTSSLHSGVPSRFSG SGSGTDFTLTISSLQPEDFATYYCQQYSTVPW TFGQGTKVEIK (SEQ ID NO: 432) |
| Kabat CDRs CDR-H1: NYGMN (SEQ ID NO: 433) CDR-H2: WINTYTGEPTYAADFKR (SEQ ID NO: 434) CDR-H3: YPHYYGSSHWYFDV (SEQ ID NO: 435) | Kabat CDRs CDR-L1: SASQDISNYLN (SEQ ID NO: 436) CDR-L2: FTSSLHS (SEQ ID NO: 437) CDR-L3: QQYSTVPWT (SEQ ID NO: 438) |
| IMGT CDRs CDR-H1: GYTFTNYG (SEQ ID NO: 439) CDR-H2: INTYTGEP (SEQ ID NO: 440) CDR-H3: AKYPHYYGSSHWYFDV (SEQ ID NO: 441) | IMGT CDRs CDR-L1: QDISNY (SEQ ID NO: 442) CDR-L2: FTS CDR-L3: QQYSTVPWT (SEQ ID NO: 438) |
| Chothia CDRs CDR-H1: GYTFTNY (SEQ ID NO: 443) CDR-H2: NTYTGE (SEQ ID NO: 444) CDR-H3: YPHYYGSSHWYFDV (SEQ ID NO: 435) | Chothia CDRs CDR-L1: SASQDISNYLN (SEQ ID NO: 436) CDR-L2: FTSSLHS (SEQ ID NO: 437) CDR-L3: QQYSTVPWT (SEQ ID NO: 438) |

In some embodiments, VEGF binding regions comprise a heavy chain variable domain comprising complementarity determining regions CDR-H1, CDR-H2, and CDR-H3 with sequences within a heavy chain variable domain sequence Exemplary Characteristic Sequences of PD-1-Binding Regions PD-1 binding regions are capable of binding to PD-1. In some embodiments, PD-1 binding regions are capable of binding to an epitope of human PD-1. In some embodiments, PD-1 binding regions antagonize PD-1, e.g., by blocking binding of PD-1 to PD-L1.

In some embodiments, PD-1 binding regions comprise a heavy chain variable domain comprising complementarity determining regions CDR-H1, CDR-H2, and CDR-H3 with sequences as shown for a given set in Table 3A. In some embodiments, PD-1 binding regions further comprise a light chain variable domain comprising complementarity determining regions CDR-L1, CDR-L2, and CDR-L3 with sequences as shown in the same set in Table 3A.

TABLE 3A

Exemplary sequences of complementarity-determining regions
within PD-1 binding regions

| Heavy chain | Light chain |
|---|---|
| Set 1 | |
| Kabat CDRs | Kabat CDRs |
| CDR-H1: NYYMY | CDR-L1: RASKGVSTSGYSYLH |
| (SEQ ID NO: 445) | (SEQ ID NO: 448) |
| CDR-H2: GINPSNGGTNFNEKFKN | CDR-L2: LASYLES |
| (SEQ ID NO: 446) | (SEQ ID NO: 449) |
| CDR-H3: RDYRFDMGFDY | CDR-L3: QHSRDLPLT |
| (SEQ ID NO: 447) | (SEQ ID NO: 450) |
| | |
| IMGT CDRs | IMGT CDRs |
| CDR-H1: GYTFTNYY | CDR-L1: KGVSTSGYSY |
| (SEQ ID NO: 451) | (SEQ ID NO: 454) |
| CDR-H2: INPSNGGT | CDR-L2: LAS |
| (SEQ ID NO: 452) | CDR-L3: QHSRDLPLT |
| CDR-H3: ARRDYRFDMGFDY | (SEQ ID NO: 450) |
| (SEQ ID NO: 453) | |
| | |
| Chothia CDRs | Chothia CDRs |
| CDR-H1: GYTFTNY | CDR-L1: RASKGVSTSGYSYLH |
| (SEQ ID NO: 443) | (SEQ ID NO: 448) |
| CDR-H2: NPSNGG | CDR-L2: LASYLES |
| (SEQ ID NO: 455) | (SEQ ID NO: 449) |
| CDR-H3: RDYRFDMGFDY | CDR-L3: QHSRDLPLT |
| (SEQ ID NO: 447) | (SEQ ID NO: 450) |
| Set 2 | |
| Kabat CDRs | Kabat CDRs |
| CDR-H1: NYYMY | CDR-L1: RASKGVSTSGYSYLH |
| (SEQ ID NO: 445) | (SEQ ID NO: 448) |
| CDR-H2: GINPSQGGTNFNEKFKN | CDR-L2: LASYLES |
| (SEQ ID NO: 456) | (SEQ ID NO: 449) |
| CDR-H3: RDYRFDLGFDY | CDR-L3: QHSRDLPLT |
| (SEQ ID NO: 457) | (SEQ ID NO: 450) |
| | |
| IMGT CDRs | IMGT CDRs |
| CDR-H1: GYTFTNYY | CDR-L1: KGVSTSGYSY |
| (SEQ ID NO: 451) | (SEQ ID NO: 454) |
| CDR-H2: INPSQGGT | CDR-L2: LAS |
| (SEQ ID NO: 458) | CDR-L3: QHSRDLPLT |
| CDR-H3: ARRDYRFDLGFDY | (SEQ ID NO: 450) |
| (SEQ ID NO: 459) | |
| | |
| Chothia CDRs | Chothia CDRs |
| CDR-H1: GYTFTNY | CDR-L1: RASKGVSTSGYSYLH |
| (SEQ ID NO: 443) | (SEQ ID NO: 448) |
| CDR-H2: NPSQGG | CDR-L2: LASYLES |
| (SEQ ID NO: 460) | (SEQ ID NO: 449) |
| CDR-H3: RDYRFDLGFDY | CDR-L3: QHSRDLPLT |
| (SEQ ID NO: 457) | (SEQ ID NO: 450) |
| Set 3 | |
| Kabat CDRs | Kabat CDRs |
| CDR-H1: NYYMY | CDR-L1: RASKGVSTSGYSYLH |
| (SEQ ID NO: 445) | (SEQ ID NO: 448) |
| CDR-H2: GINPSQGGTNFNEKFKN | CDR-L2: LASYLES |
| (SEQ ID NO: 456) | (SEQ ID NO: 449) |
| CDR-H3: RDYRFDMGFDY | CDR-L3: QHSRDLPLT |
| (SEQ ID NO: 447) | (SEQ ID NO: 450) |
| | |
| IMGT CDRs | IMGT CDRs |
| CDR-H1: GYTFTNYY | CDR-L1: KGVSTSGYSY |
| (SEQ ID NO: 451) | (SEQ ID NO: 454) |

TABLE 3A-continued

Exemplary sequences of complementarity-determining regions
within PD-1 binding regions

| Heavy chain | Light chain |
|---|---|
| CDR-H2: INP SQGGT<br>(SEQ ID NO: 458)<br>CDR-H3: ARRDYRFDMGFDY<br>(SEQ ID NO: 453) | CDR-L2: LAS<br>CDR-L3: QHSRDLPLT<br>(SEQ ID NO: 450) |
| Chothia CDRs<br>CDR-H1: GYTFTNY<br>(SEQ ID NO: 443)<br>CDR-H2: NPSQGG<br>(SEQ ID NO: 460)<br>CDR-H3: RDYRFDMGFDY<br>(SEQ ID NO: 447) | Chothia CDRs<br>CDR-L1: RASKGVSTSGYSYLH<br>(SEQ ID NO: 448)<br>CDR-L2: LASYLES<br>(SEQ ID NO: 449)<br>CDR-L3: QHSRDLPLT<br>(SEQ ID NO: 450) |

Set 4

| Kabat CDRs<br>CDR-H1: NYYMY<br>(SEQ ID NO: 445)<br>CDR-H2: GINPSRGGTNFNEKFKN<br>(SEQ ID NO: 461)<br>CDR-H3: RDYRFDMGFDY<br>(SEQ ID NO: 447) | Kabat CDRs<br>CDR-L1: RASKGVSTSGYSYLH<br>(SEQ ID NO: 448)<br>CDR-L2: LASYLES<br>(SEQ ID NO: 449)<br>CDR-L3: QHSRDLPLT<br>(SEQ ID NO: 450) |
|---|---|
| IMGT CDRs<br>CDR-H1: GYTFTNYY<br>(SEQ ID NO: 451)<br>CDR-H2: INPSRGGT<br>(SEQ ID NO: 462)<br>CDR-H3: ARRDYRFDMGFDY<br>(SEQ ID NO: 453) | IMGT CDRs<br>CDR-L1: KGVSTSGYSY<br>(SEQ ID NO: 454)<br>CDR-L2: LAS<br>CDR-L3: QHSRDLPLT<br>(SEQ ID NO: 450) |
| Chothia CDRs<br>CDR-H1: GYTFTNY<br>(SEQ ID NO: 443)<br>CDR-H2: NPSRGG<br>(SEQ ID NO: 463)<br>CDR-H3: RDYRFDMGFDY<br>(SEQ ID NO: 447) | Chothia CDRs<br>CDR-L1: RASKGVSTSGYSYLH<br>(SEQ ID NO: 448)<br>CDR-L2: LASYLES<br>(SEQ ID NO: 449)<br>CDR-L3: QHSRDLPLT<br>(SEQ ID NO: 450) |

Set 5

| Kabat CDRs<br>CDR-H1: NYYMY<br>(SEQ ID NO: 445)<br>CDR-H2: GINPSNGGTNFNEKFKN<br>(SEQ ID NO: 446)<br>CDR-H3: RDYRFDLGFDY<br>(SEQ ID NO: 457) | Kabat CDRs<br>CDR-L1: RASKGVSTSGYSYLH<br>(SEQ ID NO: 448)<br>CDR-L2: LASYLES<br>(SEQ ID NO: 449)<br>CDR-L3: QHSRDLPLT<br>(SEQ ID NO: 450) |
|---|---|
| IMGT CDRs<br>CDR-H1: GYTFTNYY<br>(SEQ ID NO: 451)<br>CDR-H2: INPSNGGT<br>(SEQ ID NO: 452)<br>CDR-H3: ARRDYRFDLGFDY<br>(SEQ ID NO: 459) | IMGT CDRs<br>CDR-L1: KGVSTSGYSY<br>(SEQ ID NO: 454)<br>CDR-L2: LAS<br>CDR-L3: QHSRDLPLT<br>(SEQ ID NO: 450) |
| Chothia CDRs<br>CDR-H1: GYTFTNY<br>(SEQ ID NO: 443)<br>CDR-H2: NPSNGG<br>(SEQ ID NO: 455)<br>CDR-H3: RDYRFDLGFDY<br>(SEQ ID NO: 457) | Chothia CDRs<br>CDR-L1: RASKGVSTSGYSYLH<br>(SEQ ID NO: 448)<br>CDR-L2: LASYLES<br>(SEQ ID NO: 449)<br>CDR-L3: QHSRDLPLT<br>(SEQ ID NO: 450) |

Set 6

| Kabat CDRs<br>CDR-H1: NYYMY<br>(SEQ ID NO: 445)<br>CDR-H2: GINPSRGGTNFNEKFKN<br>(SEQ ID NO: 461)<br>CDR-H3: RDYRFDLGEFDY<br>(SEQ ID NO: 457) | Kabat CDRs<br>CDR-L1: RASKGVSTSGYSYLH<br>(SEQ ID NO: 448)<br>CDR-L2: LASYLES<br>(SEQ ID NO: 449)<br>CDR-L3: QHSRDLPLT<br>(SEQ ID NO: 450) |
|---|---|

TABLE 3A-continued

Exemplary sequences of complementarity-determining regions
within PD-1 binding regions

| Heavy chain | Light chain |
|---|---|
| IMGT CDRs | IMGT CDRs |
| CDR-H1: GYTFTNYY | CDR-L1: KGVSTSGYSY |
| (SEQ ID NO: 451) | (SEQ ID NO: 454) |
| CDR-H2: INPSRGGT | CDR-L2: LAS |
| (SEQ ID NO: 462) | CDR-L3: QHSRDLPLT |
| CDR-H3: ARRDYRFDLGFDY | (SEQ ID NO: 450) |
| (SEQ ID NO: 459) | |
| | |
| Chothia CDRs | Chothia CDRs |
| CDR-H1: GYTFTNY | CDR-L1: RASKGVSTSGYSYLH |
| (SEQ ID NO: 443) | (SEQ ID NO: 448) |
| CDR-H2: NPSRGG | CDR-L2: LASYLES |
| (SEQ ID NO: 463) | (SEQ ID NO: 449) |
| CDR-H3: RDYRFDLGFDY | CDR-L3: QHSRDLPLT |
| (SEQ ID NO: 457) | (SEQ ID NO: 450) |

In some embodiments, PD-1 binding regions comprise a heavy chain variable domain comprising complementarity determining regions CDR-H1, CDR-H2, and CDR-H3 with sequences within a heavy chain variable domain sequence shown in Table 5B. In some embodiments, PD-1 binding regions further comprise a light chain variable domain comprising complementarity determining regions CDR-L1, CDR-L2, and CDR-L3 with sequences as shown within a light chain variable domain sequence in Table 6B.

In some embodiments, PD-1 binding regions comprise a heavy chain variable domain with a heavy chain variable sequence as shown in Table 5B. In some embodiments, PD-1 binding regions comprise a heavy chain variable domain which is a variant of the heavy chain variable sequence shown in Table 5B, in that the heavy chain variable domain has (1) CDR-H1, CDR-H2, and CDR-H3 with sequences within a given heavy chain variable domain sequence shown in Table 5B and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the same heavy chain variable domain sequence shown in Table 5B.

In some embodiments, PD-1 binding regions comprise a heavy chain variable domain as described herein in Table 5B (or a variant thereof, as described herein) and further comprise a light chain variable region which has (1) CDR-L1, CDR-L2, and CDR-L3 within a light chain variable domain sequence as shown in Table 6B and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the same light chain variable domain sequence shown in Table 6B.

Tables 3B and 3C depict exemplary VH and VL sequences, respectively, of PD-1 binding regions, which illustrate representative heavy chain variable domain and light chain variable domain framework sequences within PD-1 binding regions of the present disclosure. Exemplary CDR sequences (as defined by Kabat) within these VH and VL sequences are shown within boxes. However, it is understood by those of ordinary skill in the art that the exact borders between CDRs and framework regions may vary depending on the antibody annotation system used. For example, CDRs may be defined as described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Other CDR definitions, such as according to IMGT, Chothia, Contact residues, may also be used. The exact residue numbers which encompass a particular CDR will vary depending on the sequence and size of the CDR. Those skilled in the art can routinely determine which residues comprise a particular CDR given the variable region amino acid sequence of the antibody.

In some embodiments, PD-1 binding regions comprise: (1) a set of CDRs as described herein for PD-1 binding regions, (2) a heavy chain variable domain having a sequence that has at least 75%, at least 80%, at least 85%, at least 90%, at least 92.5%, at least 95%, at least 97.5%, at least 98%, or at least 99% amino acid sequence identity with the sequence of a VH sequence shown in Table 3B, and (3) a light chain variable domain having a sequence that has at least 75%, at least 80%, at least 85%, at least 90%, at least 92.5%, at least 95%, at least 97.5%, at least 98%, or at least 99% amino acid sequence identity with the sequence of a VL sequence shown in Table 3C.

In some embodiments, PD-1 binding regions comprise a heavy chain variable domain framework sequence as shown within a VH sequence shown in Table 3B and a light chain variable domain framework sequence as shown within a VL sequence as shown in Table 3C.

In some embodiments, PD-1 binding regions comprise a heavy chain variable domain framework sequence as shown within a VH sequence shown in Table 3B and a variant of a light chain variable domain framework sequence as shown within a VL sequence as shown in Table 3C. In some embodiments, PD-1 binding regions comprise a variant of a heavy chain variable domain framework sequence as shown within a VH sequence shown in Table 3B and a light chain variable domain framework sequence as shown within a VL sequence as shown in Table 3C. In some embodiments, PD-1 binding regions comprise a variant of a heavy chain variable domain framework sequence as shown within a VH sequence shown in Table 3B and a variant of a light chain variable domain framework sequence as shown within a VL sequence as shown in Table 3C.

Examples of variants of disclosed framework sequences include, but are not limited to: (1) sequences that have at least 75%, at least 80%, at least 85%, at least 90%, at least 92.5%, at least 95%, at least 97.5%, at least 98%, or at least 99% amino acid sequence identity across framework region residues (not including CDR residues, according to any definition of CDRs used by those of skill in the art) with a disclosed framework sequence and (2) sequences that are nearly identical to a disclosed framework sequence except for a specific framework mutation or set of framework mutations (e.g., up to four, three, two, or one amino acid substitutions, deletions, or insertions within a given immunoglobulin framework region) as discussed herein. Non-limiting examples of specific framework mutations include stabilizing mutations and/or cysteine mutations (e.g., at H44 and/or L100).

Any combination of the heavy chain framework sequences and light chain framework sequences disclosed herein may be used in PD-1 binding regions of the present disclosure. Non-limiting examples of pairs of heavy chain and light chain framework sequences that can be used within PD-1 binding regions include:

(1) VH0 and VL0 framework regions (within SEQ ID NOs: 464 and 471, respectively), or variants thereof;

(2) VH1 and VL1 framework regions (within SEQ ID NOs: 465 and 472, respectively), or variants thereof;

(3) VH1 and VL0 framework regions (within SEQ ID NOs: 465 and 471, respectively), or variants thereof;

(4) VH1 and VL2 framework regions (within SEQ ID NOs: 465 and 473, respectively), or variants thereof;

(5) VH0 and VL1 framework regions (within SEQ ID NOs: 464 and 472, respectively), or variants thereof;

(6) VH0 and VL2 framework regions (within SEQ ID NOs: 464 and 473, respectively), or variants thereof;

(7) VH0 and VL3 framework regions (within SEQ ID NOs: 464 and 474, respectively), or variants thereof;

(8) VH0 and VL4 framework regions (within SEQ ID NOs: 464 and 475, respectively), or variants thereof;

(9) VH3 and VL0 framework regions (within SEQ ID NOs: 467 and 471, respectively), or variants thereof;

(10) VH3 and VL3 framework regions (within SEQ ID NOs: 467 and 474, respectively), or variants thereof;

(11) VH3 and VL4 framework regions (within SEQ ID NOs: 467 and 475, respectively), or variants thereof;

(12) VH4 and VL0 framework regions (within SEQ ID NOs: 468 and 471, respectively), or variants thereof;

(13) VH4 and VL3 framework regions (within SEQ ID NOs: 468 and 474, respectively), or variants thereof;

(14) VH4 and VL4 framework regions (within SEQ ID NOs: 468 and 475, respectively), or variants thereof;

(15) VH2 and VL0 framework regions (within SEQ ID NOs: 466 and 471, respectively), or variants thereof;

(16) VH6 and VL framework regions (within SEQ ID NOs: 470 and 474, respectively), or variants thereof; and

(17) VH5 and VL5 framework regions (within SEQ ID NOs: 469 and 476, respectively), or variants thereof;

Any of the framework sequences disclosed herein may be combined with any set of CDRs for PD-1 binding regions as described herein, or any of the CDRs within the VH and VL sequences shown with Tables 5B and 6B.

TABLE 3B

Exemplary VH sequences of PD-1 binding regions

| VH | SEQ ID NO | Sequence |
|---|---|---|
| VH0 | 464 | QVQLVQSGVEVKKPGASVKVSCKASGYTFT[NYYMY]WVRQAPGQGLEWMG[GIN][PSNGGTNFNEKFKN]RVTLTTDSSTTTAYMELKSLQFDDTAVYYCARR[DYRFD][MGFDY]WGQGTTVTVSS |
| VH1 | 465 | QVQLVQSGVEVKKPGASVKVSCKASGYTFT[NYYMY]WVRQAPGQGLEWMG[GIN][PSNGGTNFNEKFKN]RVTLTTDSSTTTAYMELKSLRFDDTAVYYCARR[DYRFD][MGFDY]WGQGTTVTVSS |
| VH2 | 466 | QVQLVQSGVEVKKPGASVKVSCKASGYTFT[NYYMY]WVRQAPGQGLEWMG[GIN][PSQGGTNFNEKFKN]RVTLTTDSSTTTAYMELKSLQFDDTAVYYCARRDYRFD[LGFDY]WGQGTGVRVSS |
| VH3 | 467 | EVQLVQSGAEVKKPGASVKVSCKASGYTFT[NYYMY]WVRQAPGQGLEWMG[GIN][PSQGGTNFNEKFKN]RVTLTTDSSTSTAYMELSSLRSEDTAVYYCARR[DYRFD][LGFDY]WGQGTTVTVSS |
| VH4 | 468 | EVQLLESGGGLVQPGGSLRLSCKASGYTFT[NYYMY]WVRQAPGKGLEWMG[GIN][PSQGGTNFNEKFKN]RVTLSTDSSKNTAYLQMNSLRAEDTAVYYCARRDYRFD[LGFDY]WGQGTTVTVSS |
| VH5 | 469 | QVQLVQSGVEVKKPGASVKVSCKASGYTFT[NYYMY]WVRQAPGQCLEWMG[GIN][PSQGGTNFNEKFKN]RVTLTTDSSTTTAYMELKSLQFDDTAVYYCARR[DYRFD][LGFDY]WGQGTTVTVSS |

TABLE 3B-continued

| | | Exemplary VH sequences of PD-1 binding regions |
|---|---|---|
| VH | SEQ ID NO | Sequence |
| VH6 | 470 | EVQLVESSGGGLVQPGGSLRLSCAASGYTFT[NYYMY]WVRQAPGLGLEWMG[GIN] [PSQGGTNFNEKFKN]RFTISRDNSKNTLYLQMNSLRAEDTAVYYCAR[RDYRFD] [LGFDY]WGQGTLVTVSS |

TABLE 3C

| | | Exemplary VL sequences of PD-1 binding regions |
|---|---|---|
| VL | SEQ ID NO | Sequence |
| VL0 | 471 | EIVLTQSPATLSLSPGERATLSC[RASKGVSTSGYSYLH]WYQQKPGQAPRLLI Y[LASYLES]GVPARFSGSGSGTDFTLTISSLEPEDFAVYYC[QHSRDLPLT]FGG GTKVEIKR |
| VL1 | 472 | EIVLTQSPSTLSLSPGERATLSC[RASKGVSTSGYSYLH]WYQQKPGQAPRLLI Y[LASYLES]GVPARFSGSGSGTDFTLTISSLEPEDFAVYYC[QHSRDLPLT]FGG GTKVEIKR |
| VL2 | 473 | EIVLTQSPSTLSLSPGERATLSC[RASKGVSTSGYSYLH]WYQQKPGQAPRLLI Y[LASYLES]GVPARFSGSGSGTDFTLTISGLEPEDFAVYYC[QHSRDLPLT]FGG GTKVEIKR |
| VL3 | 474 | EIVLTQSPATLSVSPGERATLSC[RASKGVSTSGYSYLH]WYQQKPGQAPRLLI Y[LASYLES]GIPARFSGSGSGTEFTLTISSLQSEDFAVYYC[QHSRDLPLT]FGG GTKVEIKR |
| VL4 | 475 | DIQLTQSPSSLSASVGDRVTITC[RASKGVSTSGYSYLH]WYQQKPGKAPKLLI Y[LASYLES]GVPSRFSGSGSGTDFTLTISSLQPEDFATYYC[QHSRDLPLT]FGG GTKVEIKR |
| VL5 | 476 | EIVLTQSPATLSLSPGERATLSCRASKGVSTSGYSYLHWYQQKPGQAPRLLIY [LASYLES]GVPARFSGSGSGTDFTLTISSLEPEDFAVYYCQHSRDLPLTFGCG TKVEIKR |

Heavy Chain and Light Chain Domains

In some embodiments, the binding protein comprises a heavy chain comprising an amino acid sequence having at least 80% sequence identity with an amino acid sequence according to any one of SEQ ID NOs: 1-147, 656-678, and 702-713; and a light chain sequence comprising a sequence having at least 80% sequence identity to the amino acid sequence of any one of SEQ ID NOs: 148-194, 679-701, and 714-737. In some embodiments, the binding protein comprises a heavy chain comprising an amino acid sequence having at least 85% sequence identity with an amino acid sequence according to any one of SEQ ID NOs: 1-147, 656-678, and 702-713; and a light chain sequence comprising a sequence having at least 85% sequence identity to the amino acid sequence of any one of SEQ ID NOs: 148-194, 679-701, and 714-737. In some embodiments, the binding protein comprises a heavy chain comprising an amino acid sequence having at least 90% sequence identity with an amino acid sequence according to any one of SEQ ID NOs: 1-147, 656-678, and 702-713; and a light chain sequence comprising a sequence having at least 90% sequence identity to the amino acid sequence of any one of SEQ ID NOs: 148-194, 679-701, and 714-737. In some embodiments, the binding protein comprises a heavy chain comprising an amino acid sequence having at least 95% sequence identity with an amino acid sequence according to any one of SEQ ID NOs: 1-147, 656-678, and 702-713; and a light chain sequence comprising a sequence having at least 90% sequence identity to the amino acid sequence of any one of SEQ ID NOs: 148-194, 679-701, and 714-737. In some embodiments, the binding protein comprises a heavy chain comprising an amino acid sequence having at least 96% sequence identity with an amino acid sequence according to any one of SEQ ID NOs: 1-147, 656-678, and 702-713; and a light chain sequence comprising a sequence having at least 96% sequence identity to the amino acid sequence of any one of SEQ ID NOs: 148-194, 679-701, and 714-737. In some embodiments, the binding protein comprises a heavy chain comprising an amino acid sequence having at least 97% sequence identity with an amino acid sequence according to any one of SEQ ID NOs: 1-147, 656-678, and 702-713; and a light chain sequence comprising a sequence having at least 97% sequence identity to the amino acid sequence of any one of SEQ ID NOs: 148-194, 679-701, and 714-737. In some embodiments, the binding protein comprises a heavy chain comprising an amino acid sequence having at least 98% sequence identity with an amino acid sequence according to any one of SEQ ID NOs: 1-147, 656-678, and 702-713; and a light chain sequence comprising a sequence having at least 98% sequence identity to the amino acid sequence of any one of SEQ ID NOs: 148-194, 679-701, and 714-737. In some embodiments, the binding protein comprises a heavy chain comprising an amino acid sequence having at least 99% sequence identity with an amino acid sequence according to any one of SEQ ID NOs: 1-147, 656-678, and 702-713; and a light chain sequence comprising a sequence having at least 99% sequence identity to the amino acid sequence of any one of SEQ ID NOs: 148-194, 679-701, and 714-737. In some embodiments, the binding protein comprises a heavy chain comprising an amino acid sequence having 100% sequence identity with an amino acid sequence according to any one of SEQ ID NOs: 1-147, 656-678, and 702-713; and a light chain sequence comprising a sequence having 100% sequence identity with the amino acid sequence of any one of SEQ ID NOs: 148-194, 679-701, and 714-737.

Provided herein, in certain embodiments, are bispecific binding proteins that bind vascular endothelial growth factor (VEGF) and programmed death receptor 1 (PD-1), comprising: a) a heavy chain sequence comprising a sequence having at least 90% sequence identity to the amino acid sequence of any one of SEQ ID NOs: 22-23, 60, 62, 65-67, 70-72, 75-77, 142-143, 667-678, and 702-713; and b) a light chain sequence comprising a sequence having at least 80% sequence identity to the amino acid sequence of any one of SEQ ID NOs: 148-194, 679-701, and 714-737.

Further provided herein, in certain embodiments, are bispecific binding proteins that bind vascular endothelial growth factor (VEGF) and programmed death receptor 1 (PD-1), comprising: a) a heavy chain sequence comprising a sequence having at least 95% sequence identity to the amino acid sequence of any one of SEQ ID NOs: 1-21, 24-57, 58, 59, 61, 63, 64, 68, 69, 73, 74, 78-97, 130-141, 144-147, and 656-666; and b) a light chain sequence comprising a sequence having at least 80% sequence identity to the amino acid sequence of any one of SEQ ID NOs: 148-194, 679-701, and 714-737.

Further provided herein, in certain embodiments, are bispecific binding proteins that bind vascular endothelial growth factor (VEGF) and programmed death receptor 1 (PD-1), comprising: a) a heavy chain sequence comprising the amino acid sequence of any one of SEQ ID NOs: 98-127 and 129; and b) a light chain sequence comprising a sequence having at least 80% sequence identity to the amino acid sequence of any one of SEQ ID NOs: 148-194, 679-701, and 714-737.

TABLE 4A

Sequences of Heavy Chains and Light Chains of Multispecific Binding Proteins

| Construct Name | SEQ ID NO | Heavy Chain | SEQ ID NO | Light Chain |
|---|---|---|---|---|
| PAL054-0101.1L | 1 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 148 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0101.1La | 2 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL | 149 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | | |
| PAL054-0101.1Lb | 3 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVLHEALHSHYTQKSLS LSPGKGGGGSGGGGSGGGGSGGGGSQVQLVQS GVEVKKPGASVKVSCKASGYTFTNYYMYWVRQ APGQGLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 150 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLILSKADYEKHKVYACEVTHQGLSSP VTKSFNRGEC |
| PAL054-0102.1L | 4 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 151 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0102.1La | 5 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL | 152 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | | |
| PAL054-0102.1Lb | 6 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVLHEALHSHYTQKSLS LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 153 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0103.1L | 7 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSRGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 154 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0103.1La | 8 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ | 155 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

| | | | | |
|---|---|---|---|---|
| Construct Name | SEQ ID NO | Heavy Chain | SEQ ID NO | Light Chain |

Sequences of Heavy Chains and Light Chains of Multispecific Binding Proteins

| Construct Name | SEQ ID NO | Heavy Chain | SEQ ID NO | Light Chain |
|---|---|---|---|---|
| | | APGQGLEWMGGINPSRGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | | |
| PAL054-0103.1Lb | 9 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVLHEALHSHYTQKSLS LSPGKGGGGSGGGGSGGGGSGGGGSQVQLVQS GVEVKKPGASVKVSCKASGYTFTNYYMYWVRQ APGQGLEWMGGINPSRGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 156 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0104.1L | 10 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 157 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0104.1La | 11 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSNGGTNFNEKFKNRVTLT TDSSTTTAYMELKSLQFDDTAVYYCARRDYRF DMGFDYWGQGTTVTVSSGGGGSGGGGSGGGGS | 158 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | | |
| PAL054-0104.1Lb | 12 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVLHEALHSHYTQKSLS LSPGKGGGGSGGGGSGGGGSGGGGSQVQLVQS GVEVKKPGASVKVSCKASGYTFTNYYMYWVRQ APGQCLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 159 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0105.1L | 13 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 160 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLILSKADYEKHKVYACEVTHQGLSSP VTKSFNRGEC |
| PAL054-0105.1La | 14 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT | 161 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSLHWYQQKPGQAPRLLIYLASYLE SGVPARFSGSGSGTDFTLTISSLEPEDFAVYY CQHSRDLPLTFGCGTKVEIKR | | |
| PAL054-0105.1Lb | 15 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVLHEALHSHYTQKSLS LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 162 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0106.1L | 16 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSRGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 163 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0106.1La | 17 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSRGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK | 164 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

| | SEQ ID | | SEQ | |
|---|---|---|---|---|
| Construct Name | NO | Heavy Chain | ID NO | Light Chain |
| | | GVSTSGYSYLHWYQQKPGQAPRLLIYLASYLE SGVPARFSGSGSGTDFTLTISSLEPEDFAVYY CQHSRDLPLTFGCGTKVEIKR | | |
| PAL054-0106.1Lb | 18 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVLHEALHSHYTQKSLS LSPGKGGGGSGGGGSGGGGSGGGGSQVQLVQS GVEVKKPGASVKVSCKASGYTFTNYYMYWVRQ APGQCLEWMGGINPSRGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 165 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0107.1L | 19 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEIVLTQS PATLSLSPGERATLSCRASKGVSTSGYSYLHW YQQKPGQAPRLLIYLASYLESGVPARFSGSGS GTDFTLTISSLEPEDFAVYYCQHSRDLPLTFG GGTKVEIKSSGGGGSGGGGSGGGGSGGGGSQV QLVQSGVEVKKPGASVKVSCKASGYTFTNYYM YWVRQAPGQGLEWMGGINPSQGGTNFNEKFKN RVTLTTDSSTTTAYMELKSLQFDDTAVYYCAR RDYRFDLGFDYWGQGTTVTVSS | 166 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0107.1La | 20 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEIVLTQS PATLSLSPGERATLSCRASKGVSTSGYSYLHW YQQKPGQAPRLLIYLASYLESGVPARFSGSGS GTDFTLTISSLEPEDFAVYYCQHSRDLPLTFG GGTKVEIKSSGGGGSGGGGSGGGGSGGGGSQV QLVQSGVEVKKPGASVKVSCKASGYTFTNYYM YWVRQAPGQGLEWMGGINPSQGGTNFNEKFKN RVTLTTDSSTTTAYMELKSLQFDDTAVYYCAR RDYRFDLGFDYWGQGTTVTVSS | 167 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| PAL054-0108.1La | 21 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEIVLTQS PATLSLSPGERATLSCRASKGVSTSGYSYLHW YQQKPGQAPRLLIYLASYLESGVPARFSGSGS GTDFTLTISSLEPEDFAVYYCQHSRDLPLTFG CGTKVEIKGGGGSGGGGSGGGGSGGGGSQVQL VQSGVEVKKPGASVKVSCKASGYTFTNYYMYW VRQAPGQCLEWMGGINPSQGGTNFNEKFKNRV TLTTDSSTTTAYMELKSLQFDDTAVYYCARRD YRFDLGFDYWGQGTTVTVSS | 168 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0109.1La | 22 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGYTFTNYYMYWVRQ APGKGLEWMGGINPSQGGTNFNEKFKNRFTIS RDNSKNTLYLQMNSLRAEDTAVYYCARRDYRF DLGFDYWGQGTLVTVSSGGGGSGGGGSGGGGS GGGGSEIVLTQSPATLSVSPGERATLSCRASK GVSTSGYSYLHWYQQKPGQAPRLLIYLASYLE SGIPARFSGSGSGTEFTLTISSLQSEDFAVYY CQHSRDLPLTFGGGTKVEIKR | 169 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0110.1La | 23 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGYTFTNYYMYWVRQ APGKCLEWMGGINPSQGGTNFNEKFKNRFTIS RDNSKNTLYLQMNSLRAEDTAVYYCARRDYRF DLGFDYWGQGTLVTVSSGGGGSGGGGSGGGGS GGGGSEIVLTQSPATLSVSPGERATLSCRASK GVSTSGYSYLHWYQQKPGQAPRLLIYLASYLE SGIPARFSGSGSGTEFTLTISSLQSEDFAVYY CQHSRDLPLTFGCGTKVEIKR | 170 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLILSKADYEKHKVYACEVTHQGLSSP VTKSFNRGEC |
| PAL054-0111.1La | 24 | EVQLVESGGGLVQPGGSLRLSCAASGYTFTNY GMNWVRQAPGKGLEWVGWINTYTGEPTYAADF | 171 | DIQMTQSPSSLSASVGDRVTITCSASQDISNYLN WYQQKPGKAPKVLIYFTSSLHSGVPSRFSGSGSG |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLQFDDTAVYYCARRDYRF DLGFDYWGQGTGVRSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | | TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLILSKADYEKHKVYACEVTHQGLSSP VTKSFNRGEC |
| PAL054-0112.1La | 25 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT TDSSTTTAYMELKSLQFDDTAVYYCARRDYRF DLGFDYWGQGTGVRSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 172 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0113.1La | 26 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSNGGTNFNEKFKNRVTLT TDSSTTTAYMELKSLRFDDTAVYYCARRDYRF DMGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 173 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0114.1L | 27 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV | 174 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | TVSWNSGALTSGVHTFPAVLQSSGLYSLSSVV<br>TVPSSSLGTQTYICNVNHKPSNTKVDKKVEPK<br>SCDKTHTCPPCPAPEAAGGPSVFLFPPKPKDT<br>LMISRTPEVTCVVVDVSHEDPEVKFNWYVDGV<br>EVHNAKTKPREEQYNSTYRVVSVLTVLHQDWL<br>NGKEYKCKVSNKALPAPIEKTISKAKGQPREP<br>QVYTLPPSRDELTKNQVSLTCLVKGFYPSDIA<br>VEWESNGQPENNYKTTPPVLDSDGSFFLYSKL<br>TVDKSRWQQGNVFSCSVMHEALHNHYTQKSLS<br>LSPGKGGGGSGGGGSGGGGSGGGGSQVQLVQS<br>GVEVKKPGASVKVSCKASGYTFTNYYMYWVRQ<br>APGQGLEWMGGINPSNGGTNFNEKFKNRVTLT<br>TDSSTTTAYMELKSLRFDDTAVYYCARRDYRF<br>DMGFDYWGQGTTVTVSSGGGGSGGGGSGGGGS<br>GGGGSEIVLTQSPATLSLSPGERATLSCRASK<br>GVSTSGYSYLHWYQQKPGQAPRLLIYLASYLE<br>SGVPARFSGSGSGTDFTLTISSLEPEDFAVYY<br>CQHSRDLPLTFGGGTKVEIKR | | STYSLSSTLTLSKADYEKHKVYACEVTHQGLSSP<br>VTKSFNRGEC |
| PAL054-0114.1La | 28 | EVQLVESGGGLVQPGGSLRLSCAASGYTFTNY<br>GMNWVRQAPGKGLEWVGWINTYTGEPTYAADF<br>KRRFTFSLDTSKSTAYLQMNSLRAEDTAVYYC<br>AKYPHYYGSSHWYFDVWGQGTLVTVSSASTKG<br>PSVFPLAPSSKSTSGGTAALGCLVKDYFPEPV<br>TVSWNSGALTSGVHTFPAVLQSSGLYSLSSVV<br>TVPSSSLGTQTYICNVNHKPSNTKVDKKVEPK<br>SCDKTHTCPPCPAPEAAGGPSVFLFPPKPKDT<br>LYITREPEVTCVVVDVSHEDPEVKFNWYVDGV<br>EVHNAKTKPREEQYNSTYRVVSVLTVLHQDWL<br>NGKEYKCKVSNKALPAPIEKTISKAKGQPREP<br>QVYTLPPSRDELTKNQVSLTCLVKGFYPSDIA<br>VEWESNGQPENNYKTTPPVLDSDGSFFLYSKL<br>TVDKSRWQQGNVFSCSVMHEALHNHYTQKSLS<br>LSPGKGGGGSGGGGSGGGGSGGGGSQVQLVQS<br>GVEVKKPGASVKVSCKASGYTFTNYYMYWVRQ<br>APGQGLEWMGGINPSNGGTNFNEKFKNRVTLT<br>TDSSTTTAYMELKSLRFDDTAVYYCARRDYRF<br>DMGFDYWGQGTTVTVSSGGGGSGGGGSGGGGS<br>GGGGSEIVLTQSPATLSLSPGERATLSCRASK<br>GVSTSGYSYLHWYQQKPGQAPRLLIYLASYLE<br>SGVPARFSGSGSGTDFTLTISSLEPEDFAVYY<br>CQHSRDLPLTFGGGTKVEIKR | 175 | DIQMTQSPSSLSASVGDRVTITCSASQDISNYLN<br>WYQQKPGKAPKVLIYFTSSLHSGVPSRFSGSGSG<br>TDFTLTISSLQPEDFATYYCQQYSTVPWTFGQGT<br>KVEIKRTVAAPSVFIFPPSDEQLKSGTASVVCLL<br>NNFYPREAKVQWKVDNALQSGNSQESVTEQDSKD<br>STYSLSSTLTLSKADYEKHKVYACEVTHQGLSSP<br>VTKSFNRGEC |
| PAL054-0115.1La | 29 | EVQLVESGGGLVQPGGSLRLSCAASGYTFTNY<br>GMNWVRQAPGKGLEWVGWINTYTGEPTYAADF<br>KRRFTFSLDTSKSTAYLQMNSLRAEDTAVYYC<br>AKYPHYYGSSHWYFDVWGQGTLVTVSSASTKG<br>PSVFPLAPSSKSTSGGTAALGCLVKDYFPEPV<br>TVSWNSGALTSGVHTFPAVLQSSGLYSLSSVV<br>TVPSSSLGTQTYICNVNHKPSNTKVDKKVEPK<br>SCDKTHTCPPCPAPEAAGGPSVFLFPPKPKDT<br>LYITREPEVTCVVVDVSHEDPEVKFNWYVDGV<br>EVHNAKTKPREEQYNSTYRVVSVLTVLHQDWL<br>NGKEYKCKVSNKALPAPIEKTISKAKGQPREP<br>QVYTLPPSRDELTKNQVSLTCLVKGFYPSDIA<br>VEWESNGQPENNYKTTPPVLDSDGSFFLYSKL<br>TVDKSRWQQGNVFSCSVMHEALHNHYTQKSLS<br>LSPGKGGGGSGGGGSGGGGSGGGGSQVQLVQS<br>GVEVKKPGASVKVSCKASGYTFTNYYMYWVRQ<br>APGQGLEWMGGINPSNGGTNFNEKFKNRVTLT<br>TDSSTTTAYMELKSLRFDDTAVYYCARRDYRF<br>DMGFDYWGQGTTVTVSSGGGGSGGGGSGGGGS<br>GGGGSEIVLTQSPSTLSLSPGERATLSCRASK<br>GVSTSGYSYLHWYQQKPGQAPRLLIYLASYLE<br>SGVPARFSGSGSGTDFTLTISGLEPEDFAVYY<br>CQHSRDLPLTFGGGTKVEIKR | 176 | DIQMTQSPSSLSASVGDRVTITCSASQDISNYLN<br>WYQQKPGKAPKVLIYFTSSLHSGVPSRFSGSGSG<br>TDFTLTISSLQPEDFATYYCQQYSTVPWTFGQGT<br>KVEIKRTVAAPSVFIFPPSDEQLKSGTASVVCLL<br>NNFYPREAKVQWKVDNALQSGNSQESVTEQDSKD<br>STYSLSSTLTLSKADYEKHKVYACEVTHQGLSSP<br>VTKSFNRGEC |
| PAL054-0116.1L | 30 | EVQLVESGGGLVQPGGSLRLSCAASGYTFTNY<br>GMNWVRQAPGKGLEWVGWINTYTGEPTYAADF<br>KRRFTFSLDTSKSTAYLQMNSLRAEDTAVYYC<br>AKYPHYYGSSHWYFDVWGQGTLVTVSSASTKG<br>PSVFPLAPSSKSTSGGTAALGCLVKDYFPEPV<br>TVSWNSGALTSGVHTFPAVLQSSGLYSLSSVV<br>TVPSSSLGTQTYICNVNHKPSNTKVDKKVEPK<br>SCDKTHTCPPCPAPEAAGGPSVFLFPPKPKDT | 177 | DIQMTQSPSSLSASVGDRVTITCSASQDISNYLN<br>WYQQKPGKAPKVLIYFTSSLHSGVPSRFSGSGSG<br>TDFTLTISSLQPEDFATYYCQQYSTVPWTFGQGT<br>KVEIKRTVAAPSVFIFPPSDEQLKSGTASVVCLL<br>NNFYPREAKVQWKVDNALQSGNSQESVTEQDSKD<br>STYSLSSTLTLSKADYEKHKVYACEVTHQGLSSP<br>VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | | |
| PAL054-0116.1La | 31 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 178 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0117.1La | 32 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISGLEPEDFAVYY CQHSRDLPLTFGGGTKVEIKR | 179 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0118.1La | 33 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP | 180 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLRFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | | |
| PAL054-0119.1La | 34 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLRFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 181 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0120.1La | 35 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLRFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISGLEPEDFAVYY CQHSRDLPLTFGGGIKVEIKR | 182 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0121.1La | 36 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS | 183 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | | |
| PAL054-0122.1La | 37 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISGLEPEDFAVYY CQHSRDLPLTFGGGTKVEIKR | 184 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0123.1La | 38 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSRGGTNFNEKFKNRVTLT TDSSTTTAYMELKSLRFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 185 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0124.1La | 39 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSRGGTNFNEKFKNRVTLT | 186 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

| Construct Name | SEQ ID NO | Heavy Chain | SEQ ID NO | Light Chain |
|---|---|---|---|---|
| | | TDSSTTTAYMELKSLRFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | | |
| PAL054-0125.1La | 40 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSRGGTNFNEKFKNRVTLT TDSSTTTAYMELKSLRFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 187 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0126.1La | 41 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSRGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 188 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0127.1La | 42 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSRGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPSTLSLSPGERATLSCRASK | 189 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | GVSTSGYSYLHWYQQKPGQAPRLLIYLASYLE SGVPARFSGSGSGTDFTLTISGLEPEDFAVYY CQHSRDLPLTFGGGTKVEIKR | | |
| PAL054-0128.1La | 43 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSNGGTNFNEKFKNRVTLT TDSSTTTAYMELKSLRFDDTAVYYCARRDYRF DMGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 190 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0129.1La | 44 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSNGGTNFNEKFKNRVTLT TDSSTTTAYMELKSLRFDDTAVYYCARRDYRF DMGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 191 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0130.1La | 45 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSNGGTNFNEKFKNRVTLT TDSSTTTAYMELKSLRFDDTAVYYCARRDYRF DMGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISGLEPEDFAVYY CQHSRDLPLTFGCGTKVEIKR | 192 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| PAL054-0131.1La | 46 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 193 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0132.1La | 47 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISGLEPEDFAVYY CQHSRDLPLTFGCGTKVEIKR | 194 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0133.1La | 48 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT TDSSTTTAYMELKSLRFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 195 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0134.1La | 49 | EVQLVESGGGLVQPGGSLRLSCAASGYTFTNY GMNWVRQAPGKGLEWVGWINTYTGEPTYAADF | 196 | DIQMTQSPSSLSASVGDRVTITCSASQDISNYLN WYQQKPGKAPKVLIYFTSSLHSGVPSRFSGSGSG |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT TDSSTTTAYMELKSLRFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | | TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0135.1La | 50 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT TDSSTTTAYMELKSLRFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISGLEPEDFAVYY CQHSRDLPLTFGCGTKVEIKR | 197 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0136.1La | 51 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 198 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLILSKADYEKHKVYACEVTHQGLSSP VTKSFNRGEC |
| PAL054-0137.1La | 52 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV | 199 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISGLEPEDFAVYY CQHSRDLPLTFGCGTKVEIKR | | STYSLSSTLTLSKADYEKHKVYACEVTHQGLSSP VTKSFNRGEC |
| PAL054-0138.1La | 53 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSRGGTNFNEKFKNRVTLT TDSSTTTAYMELKSLRFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 200 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0139.1La | 54 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSRGGTNFNEKFKNRVTLT TDSSTTTAYMELKSLRFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 201 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0140.1La | 55 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT | 202 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSRGGTNFNEKFKNRVTLT TDSSTTTAYMELKSLRFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISGLEPEDFAVYY CQHSRDLPLTFGCGTKVEIKR | | |
| PAL054-0141.1La | 56 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSRGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 203 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0142.1La | 57 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSRGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPSTLSLSPGERATLSCRASK GVSTSGYSYLHWYQQKPGQAPRLLIYLASYLE SGVPARFSGSGSGTDFTLTISGLEPEDFAVYY CQHSRDLPLTFGCGTKVEIKR | 204 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0143.1La | 58 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP | 205 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | | |
| PAL054-0144.1La | 59 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSVSPGERATLSCRASK GVSTSGYSYLHWYQQKPGQAPRLLIYLASYLE SGIPARFSGSGSGTEFTLTISSLQSEDFAVYY CQHSRDLPLTFGGGTKVEIKR | 206 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0145.1La | 60 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGGGTKVEIKR | 207 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0146.1La | 61 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS | 208 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | LSPGKGGGGSGGGGSGGGGSGGGGSEVQLVQS GAEVKKPGASVKVSCKASGYTFTNYYMYWVRQ APGQGLEWMGGINPSQGGTNFNEKFKNRVTLT TDSSTSTAYMELSSLRSEDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | | |
| PAL054-0147.1La | 62 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQGLEWMGGINPSQGGTNFNEKFKNRVTLT TDSSTSTAYMELSSLRSEDTAVYYCARRDYRF DLGFDYWGQGTTVTVSSGGGGSGGGGSGGGGS GGGGSEIVLTQSPATLSVSPGERATLSCRASK GVSTSGYSYLHWYQQKPGQAPRLLIYLASYLE SGIPARFSGSGSGTEFTLTISSLQSEDFAVYY CQHSRDLPLTFGGGIKVEIKR | 209 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0148.1L | 63 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQGLEWMGGINPSQGGTNFNEKFKNRVTLI TDSSTSTAYMELSSLRSEDTAVYYCARRDYRF DLGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGGGTKVEIKR | 210 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0148.1La | 64 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQGLEWMGGINPSQGGTNFNEKFKNRVTLT | 211 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | TDSSTSTAYMELSSLRSEDTAVYYCARRDYRF DLGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGGGTKVEIKR | | |
| PAL054-0149.1La | 65 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLLES GGGLVQPGGSLRLSCKASGYTFTNYYMYWVRQ APGKGLEWMGGINPSQGGTNFNEKFKNRVTLS TDSSKNTAYLQMNSLRAEDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 212 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0150.1La | 66 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLLES GGGLVQPGGSLRLSCKASGYTFTNYYMYWVRQ APGKGLEWMGGINPSQGGTNFNEKFKNRVTLS TDSSKNTAYLQMNSLRAEDTAVYYCARRDYRF DLGFDYWGQGTTVTVSSGGGGSGGGGSGGGGS GGGGSEIVLTQSPATLSVSPGERATLSCRASK GVSTSGYSYLHWYQQKPGQAPRLLIYLASYLE SGIPARFSGSGSGTEFTLTISSLQSEDFAVYY CQHSRDLPLTFGGGTKVEIKR | 213 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0151.1La | 67 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLLES GGGLVQPGGSLRLSCKASGYTFTNYYMYWVRQ APGKGLEWMGGINPSQGGTNFNEKFKNRVILS TDSSKNTAYLQMNSLRAEDTAVYYCARRDYRF DLGFDYWGQGTTVTVSSGGGGSGGGGSGGGGS GGGGSDIQLTQSPSSLSASVGDRVTITCRASK | 214 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | GVSTSGYSYLHWYQQKPGKAPKLLIYLASYLE SGVPSRFSGSGSGTDFTLTISSLQPEDFATYY CQHSRDLPLTFGGGTKVEIKR | | |
| PAL054-0152.1La | 68 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 215 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0153.1La | 69 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSVSPGERATLSCRASK GVSTSGYSYLHWYQQKPGQAPRLLIYLASYLE SGIPARFSGSGSGTEFTLTISSLQSEDFAVYY CQHSRDLPLTFGCGTKVEIKR | 216 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0154.1La | 70 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGCGTKVEIKR | 217 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| PAL054-0155.1La | 71 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSQGGTNFNEKFKNRVTLT TDSSTSTAYMELSSLRSEDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 218 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0156.1La | 72 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSQGGTNFNEKFKNRVTLT TDSSTSTAYMELSSLRSEDTAVYYCARRDYRF DLGFDYWGQGTTVTVSSGGGGSGGGGSGGGGS GGGGSEIVLTQSPATLSVSPGERATLSCRASK GVSTSGYSYLHWYQQKPGQAPRLLIYLASYLE SGIPARFSGSGSGTEFTLTISSLQSEDFAVYY CQHSRDLPLTFGCGTKVEIKR | 219 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0157.1L | 73 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSQGGTNFNEKFKNRVTLT TDSSTSTAYMELSSLRSEDTAVYYCARRDYRF DLGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGCGTKVEIKR | 220 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0157.1La | 74 | EVQLVESGGGLVQPGGSLRLSCAASGYTFTNY GMNWVRQAPGKGLEWVGWINTYTGEPTYAADF | 221 | DIQMTQSPSSLSASVGDRVTITCSASQDISNYLN WYQQKPGKAPKVLIYFTSSLHSGVPSRFSGSGSG |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSQGGTNFNEKFKNRVTLT TDSSTSTAYMELSSLRSEDTAVYYCARRDYRF DLGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGCGTKVEIKR | | TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLILSKADYEKHKVYACEVTHQGLSSP VTKSFNRGEC |
| PAL054-0158.1La | 75 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLLES GGGLVQPGGSLRLSCKASGYTFTNYYMYWVRQ APGKCLEWMGGINPSQGGTNFNEKFKNRVTLS TDSSKNTAYLQMNSLRAEDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 222 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0159.1La | 76 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLLES GGGLVQPGGSLRLSCKASGYTFTNYYMYWVRQ APGKCLEWMGGINPSQGGTNFNEKFKNRVTLS TDSSKNTAYLQMNSLRAEDTAVYYCARRDYRF DLGFDYWGQGTTVTVSSGGGGSGGGGSGGGGS GGGGSEIVLTQSPATLSVSPGERATLSCRASK GVSTSGYSYLHWYQQKPGQAPRLLIYLASYLE SGIPARFSGSGSGTEFTLTISSLQSEDFAVYY CQHSRDLPLTFGCGTKVEIKR | 223 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0160.1La | 77 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV | 224 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLLES GGGLVQPGGSLRLSCKASGYTFTNYYMYWVRQ APGKCLEWMGGINPSQGGTNFNEKFKNRVTLS TDSSKNTAYLQMNSLRAEDTAVYYCARRDYRF DLGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGCGTKVEIKR | | STYSLSSTLTLSKADYEKHKVYACEVTHQGLSSP VTKSFNRGEC |
| PAL054-0161.1L | 78 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEIVLTQS PATLSLSPGERATLSCRASKGVSTSGYSYLHW YQQKPGQAPRLLIYLASYLESGVPARFSGSGS GTDFTLTISSLEPEDFAVYYCQHSRDLPLTFG GGTKVEIKGGGGSGGGGSGGGGSGGGGSQVQL VQSGVEVKKPGASVKVSCKASGYTFTNYYMYW VRQAPGQGLEWMGGINPSNGGTNFNEKFKNRV TLTTDSSTTTAYMELKSLQFDDTAVYYCARRD YRFDMGFDYWGQGTTVTVSS | 225 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0161.1La | 79 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEIVLTQS PATLSLSPGERATLSCRASKGVSTSGYSYLHW YQQKPGQAPRLLIYLASYLESGVPARFSGSGS GTDFTLTISSLEPEDFAVYYCQHSRDLPLTFG GGTKVEIKGGGGSGGGGSGGGGSGGGGSQVQL VQSGVEVKKPGASVKVSCKASGYTFTNYYMYW VRQAPGQGLEWMGGINPSNGGTNFNEKFKNRV TLTTDSSTTTAYMELKSLQFDDTAVYYCARRD YRFDMGFDYWGQGTTVTVSS | 226 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0162.1L | 80 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT | 227 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEIVLTQS PATLSLSPGERATLSCRASKGVSTSGYSYLHW YQQKPGQAPRLLIYLASYLESGVPARFSGSGS GTDFTLTISSLEPEDFAVYYCQHSRDLPLTFG GGTKVEIKGGGGSGGGGSGGGGSGGGGSQVQL VQSGVEVKKPGASVKVSCKASGYTFTNYYMYW VRQAPGQGLEWMGGINPSRGGTNFNEKFKNRV TLTTDSSTTTAYMELKSLQFDDTAVYYCARRD YRFDLGFDYWGQGTTVTVSS | | |
| PAL054-0162.1La | 81 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEIVLTQS PATLSLSPGERATLSCRASKGVSTSGYSYLHW YQQKPGQAPRLLIYLASYLESGVPARFSGSGS GTDFTLTISSLEPEDFAVYYCQHSRDLPLTFG GGTKVEIKGGGGSGGGGSGGGGSGGGGSQVQL VQSGVEVKKPGASVKVSCKASGYTFTNYYMYW VRQAPGQGLEWMGGINPSRGGTNFNEKFKNRV TLTTDSSTTTAYMELKSLQFDDTAVYYCARRD YRFDLGFDYWGQGTTVTVSS | 228 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0163.1L | 82 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEIVLTQS PATLSLSPGERATLSCRASKGVSTSGYSYLHW YQQKPGQAPRLLIYLASYLESGVPARFSGSGS GTDFTLTISSLEPEDFAVYYCQHSRDLPLTFG GGTKVEIKGGGGSGGGGSGGGGSGGGGSQVQL VQSGVEVKKPGASVKVSCKASGYTFTNYYMYW VRQAPGQGLEWMGGINPSNGGTNFNEKFKNRV TLTTDSSTTTAYMELKSLRFDDTAVYYCARRD YRFDMGFDYWGQGTTVTVSS | 229 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0163.1La | 83 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP | 230 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEIVLTQS PATLSLSPGERATLSCRASKGVSTSGYSYLHW YQQKPGQAPRLLIYLASYLESGVPARFSGSGS GTDFTLTISSLEPEDFAVYYCQHSRDLPLTFG GGTKVEIKGGGGSGGGGSGGGGSGGGGSQVQL VQSGVEVKKPGASVKVSCKASGYTFTNYYMYW VRQAPGQGLEWMGGINPSNGGTNFNEKFKNRV TLTTDSSTTTAYMELKSLRFDDTAVYYCARRD YRFDMGFDYWGQGTTVTSS | | |
| PAL054-0164.1L | 84 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEIVLTQS PSTLSLSPGERATLSCRASKGVSTSGYSYLHW YQQKPGQAPRLLIYLASYLESGVPARFSGSGS GTDFTLTISSLEPEDFAVYYCQHSRDLPLTFG GGTKVEIKGGGGSGGGGSGGGGSGGGGSQVQL VQSGVEVKKPGASVKVSCKASGYTFTNYYMYW VRQAPGQGLEWMGGINPSNGGTNFNEKFKNRV TLTTDSSTTTAYMELKSLQFDDTAVYYCARRD YRFDMGFDYWGQGTTVTSS | 231 | DIQMTQSPSSLSASVGDRVTITCSASQDISNYLN WYQQKPGKAPKVLIYFTSSLHSGVPSRFSGSGSG IDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0164.1La | 85 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEIVLTQS PSTLSLSPGERATLSCRASKGVSTSGYSYLHW YQQKPGQAPRLLIYLASYLESGVPARFSGSGS GTDFTLTISSLEPEDFAVYYCQHSRDLPLTFG GGTKVEIKGGGGSGGGGSGGGGSGGGGSQVQL VQSGVEVKKPGASVKVSCKASGYTFTNYYMYW VRQAPGQGLEWMGGINPSNGGTNFNEKFKNRV TLTTDSSTTTAYMELKSLQFDDTAVYYCARRD YRFDMGFDYWGQGTTVTSS | 232 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLILSKADYEKHKVYACEVTHQGLSSP VTKSFNRGEC |
| PAL054-0165.1L | 86 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS | 233 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | LSPGKGGGGSGGGGSGGGGSGGGGSEVQLVQS GAEVKKPGASVKVSCKASGYTFTNYYMYWVRQ APGQGLEWMGGINPSNGGTNFNEKFKNRVTLT TDSSTSTAYMELSSLRSEDTAVYYCARRDYRF DMGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGGGTKVEIKR | | |
| PAL054-0165.1La | 87 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQGLEWMGGINPSNGGTNFNEKFKNRVTLT TDSSTSTAYMELSSLRSEDTAVYYCARRDYRF DMGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGGGTKVEIKR | 234 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0166.1L | 88 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSNGGTNFNEKFKNRVTLT TDSSTSTAYMELSSLRSEDTAVYYCARRDYRF DMGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGCGTKVEIKR | 235 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0166.1La | 89 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSNGGTNFNEKFKNRVTLT | 236 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | TDSSTSTAYMELSSLRSEDTAVYYCARRDYRF DMGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGCGTKVEIKR | | |
| PAL054-0167.1L | 90 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSRGGTNFNEKFKNRVTLT TDSSTSTAYMELSSLRSEDTAVYYCARRDYRF DLGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGCGTKVEIKR | 237 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0167.1La | 91 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSRGGTNFNEKFKNRVTLT TDSSTSTAYMELSSLRSEDTAVYYCARRDYRF DLGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGCGTKVEIKR | 238 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0168.1L | 92 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSQGGTNFNEKFKNRVTLT TDSSTSTAYMELSSLRSEDTAVYYCARRDYRF DMGFDYWGQGTTVTVSSGGGGSGGGGSGGGGS GGGGSDIQLTQSPSSLSASVGDRVTITCRASK | 239 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | GVSTSGYSYLHWYQQKPGKAPKLLIYLASYLE SGVPSRFSGSGSGTDFTLTISSLQPEDFATYY CQHSRDLPLTFGCGTKVEIKR | | |
| PAL054-0168.1La | 93 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSQGGTNFNEKFKNRVTLT TDSSTSTAYMELSSLRSEDTAVYYCARRDYRF DMGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGCGTKVEIKR | 240 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0169.1L | 94 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSRGGTNFNEKFKNRVTLT TDSSTSTAYMELSSLRSEDTAVYYCARRDYRF DMGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGCGTKVEIKR | 241 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0169.1La | 95 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSRGGTNFNEKFKNRVTLT TDSSTSTAYMELSSLRSEDTAVYYCARRDYRF DMGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGCGTKVEIKR | 242 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| PAL054-0170.1L | 96 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSNGGTNFNEKFKNRVTLT TDSSTSTAYMELSSLRSEDTAVYYCARRDYRF DLGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGCGTKVEIKR | 243 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0170.1La | 97 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVQS GAEVKKPGASVKVSCKASGYTFTNYYMYWVRQ APGQCLEWMGGINPSNGGTNFNEKFKNRVTLT TDSSTSTAYMELSSLRSEDTAVYYCARRDYRF DLGFDYWGQGTTVTVSSGGGGSGGGGSGGGGS GGGGSDIQLTQSPSSLSASVGDRVTITCRASK GVSTSGYSYLHWYQQKPGKAPKLLIYLASYLE SGVPSRFSGSGSGTDFTLTISSLQPEDFATYY CQHSRDLPLTFGCGTKVEIKR | 244 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0201.1L | 98 | QVQLVQSGVEVKKPGASVKVSCKASGYTFTNY YMYWVRQAPGQGLEWMGGINPSNGGTNFNEKF KNRVTLTTDSSTTTAYMELKSLQFDDTAVYYC ARRDYRFDMGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KGLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGQGTKVEIKR | 245 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLILSKADYEKHKVYACEVTHQG LSSPVTKSFNRGEC |
| PAL054-0201.1La | 99 | QVQLVQSGVEVKKPGASVKVSCKASGYTFTNY YMYWVRQAPGQGLEWMGGINPSNGGTNFNEKF | 246 | EIVLTQSPATLSLSPGERATLSCRASKGVSTSGY SYLHWYQQKPGQAPRLLIYLASYLESGVPARFSG |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | KNRVTLITDSSTTTAYMELKSLQFDDTAVYYC ARRDYRFDMGEDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLYI TREPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KGLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGQGTKVEIKR | | SGSGTDFTLTISSLEPEDFAVYYCQHSRDLPLTF GGGGTKVEIKRTVAAPSVFIFPPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| PAL054-0201.1Lb | 100 | QVQLVQSGVEVKKPGASVKVSCKASGYTFTNY YMYWVRQAPGQGLEWMGGINPSNGGTNFNEKF KNRVTLTTDSSTTTAYMELKSLQFDDTAVYYC ARRDYRFDMGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLIVD KSRWQQGNVFSCSVLHEALHSHYTQKSLSLSP GKGGGGSGGGGSGGGGSGGGGSEVQLVESGGG LVQPGGSLRLSCAASGYTFTNYGMNWVRQAPG KGLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGQGTKVEIKR | 247 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGGTKVEIKRTVAAPSVFIFPPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| PAL054-0202.1L | 101 | QVQLVQSGVEVKKPGASVKVSCKASGYTFTNY YMYWVRQAPGQGLEWMGGINPSQGGTNFNEKF KNRVTLTDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KGLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGQGTKVEIKR | 248 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGGTKVEIKRTVAAPSVFIFPPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| PAL054-0202.1La | 102 | QVQLVQSGVEVKKPGASVKVSCKASGYTFTNY YMYWVRQAPGQGLEWMGGINPSQGGTNFNEKF KNRVTLTTDSSTTTAYMELKSLQFDDTAVYYC ARRDYRFDLGFDYWGQGTTVTVSSASTKGPSV FPLAPSSKSTSGGTAALGCLVKDYFPEPVTVS | 249 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGGTKVEIKRTVAAPSVFIFPPPSDEQLKSGTASV VCLLNNFYPREAKVQWKVDNALQSGNSQESVTEQ |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLYI TREPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KGLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGQGTKVEIKR | | DSKDSTYSLSSTLTLSKADYEKHKVYACEVTHQG LSSPVTKSFNRGEC |
| PAL054-0202.1Lb | 103 | QVQLVQSGVEVKKPGASVKVSCKASGYTFTNY YMYWVRQAPGQGLEWMGGINPSQGGTNFNEKF KNRVTLTTDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVLHEALHSHYTQKSLSLSP GKGGGGSGGGGSGGGGSGGGGSEVQLVESGGG LVQPGGSLRLSCAASGYTFTNYGMNWVRQAPG KGLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGQGTKVEIKR | 250 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| PAL054-0203.1L | 104 | QVQLVQSGVEVKKPGASVKVSCKASGYTFTNY YMYWVRQAPGQGLEWMGGINPSRGGTNFNEKF KNRVTLTTDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KGLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGQGTKVEIKR | 251 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLILSKADYEKHKVYACEVTHQG LSSPVTKSFNRGEC |
| PAL054-0203.1La | 105 | QVQLVQSGVEVKKPGASVKVSCKASGYTFTNY YMYWVRQAPGQGLEWMGGINPSRGGINFNEKF KNRVTLTTDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLYI | 252 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | TREPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KGLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGQGTKVEIKR | | |
| PAL054-0203.1Lb | 106 | QVQLVQSGVEVKKPGASVKVSCKASGYTFTNY YMYWVRQAPGQGLEWMGGINPSRGGTNFNEKF KNRVTLTTDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVLHEALHSHYTQKSLSLSP GKGGGGSGGGGSGGGGSGGGGSEVQLVESGGG LVQPGGSLRLSCAASGYTFTNYGMNWVRQAPG KGLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGQGTKVEIKR | 253 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| PAL054-0204.1L | 107 | QVQLVQSGVEVKKPGASVKVSCKASGYTFTNY YMYWVRQAPGQGLEWMGGINPSNGGTNFNEKF KNRVTLTTDSSTTTAYMELKSLQFDDTAVYYC ARRDYRFDMGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KCLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGCGTKVEIKR | 254 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| PAL054-0204.1La | 108 | QVQLVQSGVEVKKPGASVKVSCKASGYTFTNY YMYWVRQAPGQGLEWMGGINPSNGGTNFNEKF KNRVTLTTDSSTTTAYMELKSLQFDDTAVYYC ARRDYRFDMGEDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLYI TREPEVTCVVVDVSHEDPEVKFNWYVDGVEVH NAKTKPREEQYNSTYRVVSVLTVLHQDWLNGK EYKCKVSNKALPAPIEKTISKAKGQPREPQVY | 255 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLILSKADYEKHKVYACEVTHQG LSSPVTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | TLPPSRDELTKNQVSLTCLVKGFYPSDIAVEW ESNGQPENNYKTTPPVLDSDGSFFLYSKLIVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KCLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGCGTKVEIKR | | |
| PAL054-0204.1Lb | 109 | QVQLVQSGVEVKKPGASVKVSCKASGYTFTNY YMYWVRQAPGQGLEWMGGINPSNGGTNFNEKF KNRVTLTTDSSTTAYMELKSLQFDDTAVYYC ARRDYRFDMGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVLHEALHSHYTQKSLSLSP GKGGGGSGGGGSGGGGSGGGGSEVQLVESGGG LVQPGGSLRLSCAASGYTFTNYGMNWVRQAPG KCLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGCGTKVEIKR | 256 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| PAL054-0205.1L | 110 | QVQLVQSGVEVKKPGASVKVSCKASGYTFTNY YMYWVRQAPGQGLEWMGGINPSQGGTNFNEKF KNRVTLITDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KCLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGCGTKVEIKR | 257 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| PAL054-0205.1La | 111 | QVQLVQSGVEVKKPGASVKVSCKASGYTFTNY YMYWVRQAPGQGLEWMGGINPSQGGTNFNEKF KNRVTLITDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLYI TREPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP | 258 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | GKGGGGSGGGGSGGGGSGGGGSEVQLVESGGG LVQPGGSLRLSCAASGYTFTNYGMNWVRQAPG KCLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGCGTKVEIKR | | |
| PAL054-0205.1Lb | 112 | QVQLVQSGVEVKKPGASVKVSCKASGYTFTNY YMYWVRQAPGQGLEWMGGINPSQGGTNFNEKF KNRVTLTTDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVLHEALHSHYTQKSLSLSP GKGGGGSGGGGSGGGGSGGGGSEVQLVESGGG LVQPGGSLRLSCAASGYTFTNYGMNWVRQAPG KCLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGCGTKVEIKR | 259 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| PAL054-0206.1L | 113 | QVQLVQSGVEVKKPGASVKVSCKASGYTFTNY YMYWVRQAPGQGLEWMGGINPSRGGTNFNEKF KNRVTLTTDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KCLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGCGTKVEIKR | 260 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| PAL054-0206.1La | 114 | QVQLVQSGVEVKKPGASVKVSCKASGYTFTNY YMYWVRQAPGQGLEWMGGINPSRGGTNFNEKF KNRVTLITDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLYI TREPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KCLEWVGWINTYTGEPTYAADFKRRFTFSLDT | 26 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLILSKADYEKHKVYACEVTHQG LSSPVTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGCGTKVEIKR | | |
| PAL054-0206.1Lb | 115 | QVQLVQSGVEVKKPGASVKVSCKASGYTFTNY YMYWVRQAPGQGLEWMGGINPSRGGTNFNEKF KNRVTLTTDSSTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLMI SRTPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVLHEALHSHYTQKSLSLSP GKGGGGSGGGGSGGGGSGGGGSEVQLVESGGG LVQPGGSLRLSCAASGYTFTNYGMNWVRQAPG KCLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGCGTKVEIKR | 262 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| PAL054-0301.1L | 116 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGSIASIHAMGWVRQ APGKEREWVSVITWSGGITYYADSVKGRFTIS RDNSKNTLYLQMNSLRAEDTAVYYCAGDKHQS SWYDYWGQGTLVTVSS | 263 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0301.1La | 117 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYIIREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGSIASIHAMGWVRQ APGKEREWVSVITWSGGITYYADSVKGRFTIS RDNSKNTLYLQMNSLRAEDTAVYYCAGDKHQS SWYDYWGQGTLVTVSS | 264 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0302.1L | 118 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG | 265 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGSIASIHAMGWVRQ APGKEREWVSVITWSGGITYYADSVKGRFTIS RDNSKNTVYLQMNSLRAEDTAVYYCAGDKHQS SWYDYWGQGTLVTVSS | | NNFYPREAKVQWKVDNALQSGNSQESVTEQDSKD STYSLSSTLTLSKADYEKHKVYACEVTHQGLSSP VTKSFNRGEC |
| PAL054-0302.1La | 119 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGSIASIHAMGWVRQ APGKEREWVSVITWSGGITYYADSVKGRFTIS RDNSKNTVYLQMNSLRAEDTAVYYCAGDKHQS SWYDYWGQGTLVTVSS | 266 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0303.1L | 120 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGSIASIHAMGWVRQ APGKEREFVSVITWSGGITYYADSVKGRFTIS RDNSKNTLYLQMNSLRAEDTAVYYCAGDKHQS SWYDYWGQGTLVTVSS | 267 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0303.1La | 121 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGSIASIHAMGWVRQ APGKEREFVSVITWSGGITYYADSVKGRFTIS RDNSKNTLYLQMNSLRAEDTAVYYCAGDKHQS SWYDYWGQGTLVTVSS | 268 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| PAL054-0304.1L | 122 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGSIASIHAMGWVRQ APGKEREFVSVITWSGGITYYADSVKGRFTIS RDNSKNTVYLQMNSLRAEDTAVYYCAGDKHQS SWYDYWGQGTLVTVSS | 269 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0304.1La | 123 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGSIASIHAMGWVRQ APGKEREFVSVITWSGGITYYADSVKGRFTIS RDNSKNTVYLQMNSLRAEDTAVYYCAGDKHQS SWYDYWGQGTLVTVSS | 270 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0305.1L | 124 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGSIASIHAMGWVRQ APGKEREFVAVITWSGGITYYADSVKGRFTIS RDNSKNTVYLQMNSLRAEDTAVYYCAGDKHQS SWYDYWGQGTLVTVSS | 271 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0305.1La | 125 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS | 272 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | LSPGKGGGGSGGGGSGGGGSGGGGSEVQLVES GGGLVQPGGSLRLSCAASGSIASIHAMGWVRQ APGKEREFVAVITWSGGITYYADSVKGRFTIS RDNSKNTVYLQMNSLRAEDTAVYYCAGDKHQS SWYDYWGQGTLVTVSS | | |
| PAL054-0306.1L | 126 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGSIASIHAMGWVRQ APGKEREWVAVITWSGGITYYADSVKGRFTIS RDNSKNTVYLQMNSLRAEDTAVYYCAGDKHQS SWYDYWGQGTLVTVSS | 273 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0306.1La | 127 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGSIASIHAMGWVRQ APGKEREWVAVITWSGGITYYADSVKGRFTIS RDNSKNTVYLQMNSLRAEDTAVYYCAGDKHQS SWYDYWGQGTLVTVSS | 274 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0001.1L | 128 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGFAFSSYDMSWVRQ APGKGLDWVATISGGGRYTYYPDSVKGRFTIS RDNSKNNLYLQMNSLRAEDTALYYCANRYGEA WFAYWGQGTLVTVSSGGGGSGGGGSGGGGSGG GGSDIQMTQSPSSMSASVGDRVTFTCRASQDI NTYLSWFQQKPGKSPKTLIYRANRLVSGVPSR FSGSGSGQDYTLTISSLQPEDMATYYCLQYDE FPLTFGAGTKLELKR | 275 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0001.1La | 129 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV | 276 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGFAFSSYDMSWVRQ APGKGLDWVATISGGGRYTYYPDSVKGRFTIS RDNSKNNLYLQMNSLRAEDTALYYCANRYGEA WFAYWGQGTLVTVSSGGGGSGGGGSGGGGSGG GGSDIQMTQSPSSMSASVGDRVTFTCRASQDI NTYLSWFQQKPGKSPKTLIYRANRLVSGVPSR FSGSGSGQDYTLTISSLQPEDMATYYCLQYDE FPLTFGAGTKLELKR | | STYSLSSTLTLSKADYEKHKVYACEVTHQGLSSP VTKSFNRGEC |
| PAL054-0101.1L | 130 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 277 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0101.1La | 131 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 278 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0102.1L | 132 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT | 279 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | | |
| PAL054-0102.1La | 133 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 280 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0103.1L | 134 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSRGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | 281 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0103.1La | 135 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP | 282 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQGLEWMGGINPSRGGINFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGGGTKVEIKR | | |
| PAL054-0104.1L | 136 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 283 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0104.1La | 137 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSNGGTNFNEKFKNRVTLT TDSSTTTAYMELKSLQFDDTAVYYCARRDYRF DMGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 284 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0105.1L | 138 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS | 285 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | | |
| PAL054-0105.1La | 139 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSQGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 286 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0106.1L | 140 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSRGGTNFNEKFKNRVTLT TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | 287 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0106.1La | 141 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSQVQLVQS GVEVKKPGASVKVSCKASGYTFTNYYMYWVRQ APGQCLEWMGGINPSRGGTNFNEKFKNRVTLT | 288 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | TDSSTTTAYMELKSLQFDDTAVYYCARRDYRF DLGFDYWGQGTTVTVSSGGGGSGGGGSGGGGS GGGGSEIVLTQSPATLSLSPGERATLSCRASK GVSTSGYSYLHWYQQKPGQAPRLLIYLASYLE SGVPARFSGSGSGTDFTLTISSLEPEDFAVYY CQHSRDLPLTFGCGTKVEIKR | | |
| PAL054-0109.1La | 142 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGYTFTNYYMYWVRQ APGKGLEWMGGINPSQGGTNFNEKFKNRFTIS RDNSKNTLYLQMNSLRAEDTAVYYCARRDYRF DLGFDYWGQGTLVTVSSGGGGSGGGGSGGGGS GGGGSEIVLTQSPATLSVSPGERATLSCRASK GVSTSGYSYLHWYQQKPGQAPRLLIYLASYLE SGIPARFSGSGSGTEFTLTISSLQSEDFAVYY CQHSRDLPLTFGGGTKVEIKR | 289 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0110.1La | 143 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGKGGGGSGGGGSGGGGSGGGGSEVQLVES GGGLVQPGGSLRLSCAASGYTFTNYYMYWVRQ APGKCLEWMGGINPSQGGTNFNEKFKNRFTIS RDNSKNTLYLQMNSLRAEDTAVYYCARRDYRF DLGFDYWGQGTLVTVSSGGGGSGGGGSGGGGS GGGGSEIVLTQSPATLSVSPGERATLSCRASK GVSTSGYSYLHWYQQKPGQAPRLLIYLASYLE SGIPARFSGSGSGTEFTLTISSLQSEDFAVYY CQHSRDLPLTFGCGTKVEIKR | 290 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0202.1La | 144 | QVQLVQSGVEVKKPGASVKVSCKASGYTFTNY YMYWVRQAPGQGLEWMGGINPSQGGTNFNEKF KNRVTLTTDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLYI TREPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KGLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ | 291 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | DISNYLNWYQQKPGKAPKVLIYFTSSLHSGVP SRFSGSGSGTDFTLTISSLQPEDFATYYCQQY STVPWTFGQGTKVEIKR | | |
| PAL054-0203.1La | 145 | QVQLVQSGVEVKKPGASVKVSCKASGYTFTNY YMYWVRQAPGQGLEWMGGINPSRGGTNFNEKF KNRVTLTTDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLYI TREPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KGLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGQGTKVEIKR | 292 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |
| PAL054-0205.1La | 146 | QVQLVQSGVEVKKPGASVKVSCKASGYTFTNY YMYWVRQAPGQGLEWMGGINPSQGGTNFNEKF KNRVTLTTDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLYI TREPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KCLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGCGTKVEIKR | 293 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLILSKADYEKHKVYACEVTHQG LSSPVTKSFNRGEC |
| PAL054-0206.1La | 147 | QVQLVQSGVEVKKPGASVKVSCKASGYTFTNY YMYWVRQAPGQGLEWMGGINPSRGGTNFNEKF KNRVTLTTDSSTTTAYMELKSLQFDDTAVYYC ARRDYRFDLGFDYWGQGTTVTVSSASTKGPSV FPLAPSSKSTSGGTAALGCLVKDYFPEPVTVS WNSGALTSGVHTFPAVLQSSGLYSLSSVVTVP SSSLGTQTYICNVNHKPSNTKVDKKVEPKSCD KTHTCPPCPAPEAAGGPSVFLFPPKPKDTLYI TREPEVTCVVVDVSHEDPEVKFNWYVDGVEVH NAKTKPREEQYNSTYRVVSVLTVLHQDWLNGK EYKCKVSNKALPAPIEKTISKAKGQPREPQVY TLPPSRDELTKNQVSLTCLVKGFYPSDIAVEW ESNGQPENNYKTTPPVLDSDGSFFLYSKLTVD KSRWQQGNVFSCSVMHEALHNHYTQKSLSLSP GKGGGGSGGGGSGGGGSGGGGSEVQLVESGGG LVQPGGSLRLSCAASGYTFTNYGMNWVRQAPG KCLEWVGWINTYTGEPTYAADFKRRFTFSLDT SKSTAYLQMNSLRAEDTAVYYCAKYPHYYGSS HWYFDVWGQGTLVTVSSGGGGSGGGGSGGGGS GGGGSDIQMTQSPSSLSASVGDRVTITCSASQ DISNYLNWYQQKPGKAPKVLIYFTSSLHSGVP SRFSGSGSGTDFTLTISSLQPEDFATYYCQQY STVPWTFGCGTKVEIKR | 294 | EIVLTQSPATLSLSPGERATLSCRASKGVSTSGY SYLHWYQQKPGQAPRLLIYLASYLESGVPARFSG SGSGTDFTLTISSLEPEDFAVYYCQHSRDLPLTF GGGTKVEIKRTVAAPSVFIFPPSDEQLKSGTASV VCLLNNFYPREAKVQWKVDNALQSGNSQESVTEQ DSKDSTYSLSSTLTLSKADYEKHKVYACEVTHQG LSSPVTKSFNRGEC |

TABLE 4A-continued

| Construct Name | SEQ ID NO | Heavy Chain | SEQ ID NO | Light Chain |
|---|---|---|---|---|
| | | Sequences of Heavy Chains and Light Chains of Multispecific Binding Proteins | | |
| PAL054-0171.1L | 656 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGGGSGGGGSGGGGSGGGGSEVQLVQSG AEVKKPGASVKVSCKASGYTFTNYYMYWVRQA PGQCLEWMGGINPSQGGTNFNEKFKNRVTLTT DSSTSTAYMELSSLRSEDTAVYYCARRDYRFD LGFDYWGQGTTVTVSSGGGGSGGGGSGGGGSG GGGSDIQLTQSPSSLSASVGDRVTITCRASKG VSTSGYSYLHWYQQKPGKAPKLLIYLASYLES GVPSRFSGSGSGTDFTLTISSLQPEDFATYYC QHSRDLPLTFGCGTKVEIK | 679 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0171.1La | 657 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGGGSGGGGSGGGGSGGGGSEVQLVQSG AEVKKPGASVKVSCKASGYTFTNYYMYWVRQA PGQCLEWMGGINPSQGGTNFNEKFKNRVILIT DSSTSTAYMELSSLRSEDTAVYYCARRDYRFD LGFDYWGQGTTVTVSSGGGGSGGGGSGGGGSG GGGSDIQLTQSPSSLSASVGDRVTITCRASKG VSTSGYSYLHWYQQKPGKAPKLLIYLASYLES GVPSRFSGSGSGTDFTLTISSLQPEDFATYYC QHSRDLPLTFGCGTKVEIK | 680 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0172.1L | 658 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGGGSGGGGSGGGGSGGGGSEVQLVQSG AEVKKPGASVKVSCKASGYTFTNYYMYWVRQA PGQCLEWMGGINPSNGGTNFNEKFKNRVTLTT DSSTSTAYMELSSLRSEDTAVYYCARRDYRFD MGFDYWGQGTTVTVSSGGGGSGGGGSGGGGSG GGGSDIQLTQSPSSLSASVGDRVTITCRASKG VSTSGYSYLHWYQQKPGKAPKLLIYLASYLES GVPSRFSGSGSGTDFTLTISSLQPEDFATYYC QHSRDLPLTFGCGTKVEIK | 681 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0172.1La | 659 | EVQLVESGGGLVQPGGSLRLSCAASGYTFTNY GMNWVRQAPGKGLEWVGWINTYTGEPTYAADF | 682 | DIQMTQSPSSLSASVGDRVTITCSASQDISNYLN WYQQKPGKAPKVLIYFTSSLHSGVPSRFSGSGSG |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGGGSGGGGSGGGGSGGGGSEVQLVQSG AEVKKPGASVKVSCKASGYTFTNYYMYWVRQA PGQCLEWMGGINPSNGGTNFNEKFKNRVTLTT DSSTSTAYMELSSLRSEDTAVYYCARRDYRFD MGFDYWGQGTTVTVSSGGGGSGGGGSGGGGSG GGGSDIQLTQSPSSLSASVGDRVTITCRASKG VSTSGYSYLHWYQQKPGKAPKLLIYLASYLES GVPSRFSGSGSGTDFTLTISSLQPEDFATYYC QHSRDLPLTFGCGTKVEIK | | TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0173.1L | 660 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGGGSGGGGSGGGGSGGGGSEVQLVQSG AEVKKPGASVKVSCKASGYTFTNYYMYWVRQA PGQCLEWMGGINPSQGGTNFNEKFKNRVTLTT DSSTSTAYMELSSLRSEDTAVYYCARRDYRFD MGFDYWGQGTTVTVSSGGGGSGGGGSGGGGSG GGGSDIQLTQSPSSLSASVGDRVTITCRASKG VSTSGYSYLHWYQQKPGKAPKLLIYLASYLES GVPSRFSGSGSGTDFTLTISSLQPEDFATYYC QHSRDLPLTFGCGTKVEIK | 683 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0174.1L | 661 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGGGSGGGGSGGGGSGGGGSEVQLVQSG AEVKKPGASVKVSCKASGYTFTNYYMYWVRQA PGQCLEWMGGINPSRGGTNFNEKFKNRVTLTT DSSTSTAYMELSSLRSEDTAVYYCARRDYRFD MGFDYWGQGTTVTVSSGGGGSGGGGSGGGGSG GGGSDIQLTQSPSSLSASVGDRVTITCRASKG VSTSGYSYLHWYQQKPGKAPKLLIYLASYLES GVPSRFSGSGSGTDFTLTISSLQPEDFATYYC QHSRDLPLTFGCGTKVEIK | 684 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0175.1L | 662 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV | 685 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGGGSGGGGSGGGGSGGGGSEVQLVQSG AEVKKPGASVKVSCKASGYTFTNYYMYWVRQA PGQCLEWMGGINPSNGGTNFNEKFKNRVTLTT DSSTSTAYMELSSLRSEDTAVYYCARRDYRFD LGFDYWGQGTTVTVSSGGGGSGGGGSGGGGSG GGGSDIQLTQSPSSLSASVGDRVTITCRASKG VSTSGYSYLHWYQQKPGKAPKLLIYLASYLES GVPSRFSGSGSGTDFTLTISSLQPEDFATYYC QHSRDLPLTFGCGTKVEIK | | STYSLSSTLTLSKADYEKHKVYACEVTHQGLSSP VTKSFNRGEC |
| PAL054-0307.1L | 663 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGGGSGGGGSGGGGSGGGGSEVQLVESG GGLVQPGGSLRLSCAASGSIASIHAMGWVRQA PGKEREFVAVITWSGGITYYADSVKGRFTISR DNSKNTVYLQMNSLRPEDTAVYYCAGDKHQSS WYDYWGQGTLVTVSS | 686 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0308.1L | 664 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGGGSGGGGSGGGGSGGGGSEVQLVESG GGLVQPGGSLRLSCAASGSIASIHAMGWVRQA PGKEREFVAVITWSGGITYYADSVKGRFTISR DNSKNTVYLQMNSLRPEDTALYYCAGDKHQSS WYDYWGQGTLVTVSS | 687 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0309.1L | 665 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGGGSGGGGSGGGGSGGGGSEVQLVESG GGLVQPGGSLRLSCAASGSIASIHAMGWERQA | 688 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

| | | | | |
|---|---|---|---|---|
| Construct Name | SEQ ID NO | Heavy Chain | SEQ ID NO | Light Chain |
| | | PGKEREFVAVITWSGGITYYADSVKGRFTISR DNSKNTVYLQMNSLRPEDTAVYYCAGDKHQSS WYDYWGQGTLVTVSS | | |
| PAL054-0310.1L | 666 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGGGSGGGGSGGGGSGGGGSEVQLVESG GGLVQPGGSLRLSCAASGSIASIHAMGWFRQA PGKEREFVAVITWSGGITYYADSVKGRFTISR DNSKNTVYLQMNSLRPEDTALYYCAGDKHQSS WYDYWGQGTLVTVSS | 689 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0501.1L | 667 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGSGGGGSGGGGSGGGGSEIVLTQSPAT LSLSPGERATLSCRASKGVSTSGYSYLHWYQQ KPGQAPRLLIYLASYLESGVPARFSGSGSGTD FTLTISSLEPEDFAVYYCQHSRDLPLTFGGGT KVEIKRTVAAPSVFIFPPSDEQLKSGTASVVC LLNNFYPREAKVQWKVDNALQSGNSQESVTEQ DSKDSTYSLSSTLTLSKADYEKHKVYACEVTH QGLSSPVTKSFNRGECGGSSGSGSGSTGTSSS GTGTSAGTTGTSASTSGSGSGGGGSGGGGSA GGTATAGASSGSGSVQLVQSGVEVKKPGASVKV SCKASGYTFTNYYMYWVRQAPGQGLEWMGGIN PSNGGTNFNEKFKNRVTLTTDSSTTTAYMELK SLQFDDTAVYYCARRDYRFDMGFDYWGQGTTV TVSSASTKGPSVFPLAPSSKSTSGGTAALGCL VKDYFPEPVTVSWNSGALTSGVHTFPAVLQSS GLYSLSSVVTVPSSSLGTQTYICNVNHKPSNT KVDKKVEPKSCDKTHT | 690 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0501.1La | 668 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGSGGGGSGGGGSGGGGSEIVLTQSPAT LSLSPGERATLSCRASKGVSTSGYSYLHWYQQ KPGQAPRLLIYLASYLESGVPARFSGSGSGTD FTLTISSLEPEDFAVYYCQHSRDLPLTFGGGT KVEIKRTVAAPSVFIFPPSDEQLKSGTASVVC | 691 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | LLNNFYPREAKVQWKVDNALQSGNSQESVTEQ DSKDSTYSLSSTLTLSKADYEKHKVYACEVTH QGLSSPVTKSFNRGECGGSSGSGSGSTGTSSS GTGTSAGTTGTSASTSGSGSGGGGGSGGGGSA GGTATAGASSGSQVQLVQSGVEVKKPGASVKV SCKASGYTFTNYYMYWVRQAPGQGLEWMGGIN PSNGGTNFNEKFKNRVTLTTDSSTTTAYMELK SLQFDDTAVYYCARRDYRFDMGEDYWGQGTTV TVSSASTKGPSVFPLAPSSKSTSGGTAALGCL VKDYFPEPVTVSWNSGALTSGVHTFPAVLQSS GLYSLSSVVTVPSSSLGTQTYICNVNHKPSNT KVDKKVEPKSCDKTHT | | |
| PAL054-0502.1L | 669 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGSGGGGSGGGGSGGGGSEIVLTQSPAT LSLSPGERATLSCRASKGVSTSGYSYLHWYQQ KPGQAPRLLIYLASYLESGVPARFSGSGSGTD FTLTISSLEPEDFAVYYCQHSRDLPLTFGGGT KVEIKRTVAAPSVFIFPPSDEQLKSGTASVVC LLNNFYPREAKVQWKVDNALQSGNSQESVTEQ DSKDSTYSLSSTLILSKADYEKHKVYACEVTH QGLSSPVTKSFNRGECGGSSGSGSGSTGTSSS GTGTSAGTTGTSASTSGSGSGGGGGSGGGGSA GGTATAGASSGSQVQLVQSGVEVKKPGASVKV SCKASGYTFTNYYMYWVRQAPGQGLEWMGGIN PSQGGTNFNEKFKNRVTLTTDSSTTTAYMELK SLQFDDTAVYYCARRDYRFDLGFDYWGQGTTV TVSSASTKGPSVFPLAPSSKSTSGGTAALGCL VKDYFPEPVTVSWNSGALTSGVHTFPAVLQSS GLYSLSSVVTVPSSSLGTQTYICNVNHKPSNT KVDKKVEPKSCDKTHT | 692 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0502.1La | 670 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGSGGGGSGGGGSGGGGSEIVLTQSPAT LSLSPGERATLSCRASKGVSTSGYSYLHWYQQ KPGQAPRLLIYLASYLESGVPARFSGSGSGTD FTLTISSLEPEDFAVYYCQHSRDLPLTFGGGT KVEIKRTVAAPSVFIFPPSDEQLKSGTASVVC LLNNFYPREAKVQWKVDNALQSGNSQESVTEQ DSKDSTYSLSSTLTLSKADYEKHKVYACEVTH QGLSSPVTKSFNRGECGGSSGSGSGSTGTSSS GTGTSAGTTGTSASTSGSGSGGGGGSGGGGSA GGTATAGASSGSQVQLVQSGVEVKKPGASVKV | 693 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | SCKASGYTFTNYYMWVRQAPGQGLEWMGGIN PSQGGTNFNEKFKNRVTLTTDSSTTTAYMELK SLQFDDTAVYYCARRDYRFDLGFDYWGQGTTV TVSSASTKGPSVFPLAPSSKSTSGGTAALGCL VKDYFPEPVTVSWNSGALTSGVHTFPAVLQSS GLYSLSSVVTVPSSSLGTQTYICNVNHKPSNT KVDKKVEPKSCDKTHT | | |
| PAL054-0503.1L | 671 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGSGGGGSGGGGSGGGGSEIVLTQSPAT LSLSPGERATLSCRASKGVSTSGYSYLHWYQQ KPGQAPRLLIYLASYLESGVPARFSGSGSGTD FTLTISSLEPEDFAVYYCQHSRDLPLTFGGGT KVEIKRTVAAPSVFIFPPSDEQLKSGTASVVC LLNNFYPREAKVQWKVDNALQSGNSQESVTEQ DSKDSTYSLSSTLTLSKADYEKHKVYACEVTH QGLSSPVTKSFNRGECGGSSGSGSGSTGTSSS GTGTSAGTTGTSASTSGSGSGGGGGSGGGGSA GGTATAGASSGSQVQLVQSGVEVKKPGASVKV SCKASGYTFTNYYMWVRQAPGQGLEWMGGIN PSRGGTNFNEKFKNRVTLTTDSSTTTAYMELK SLQFDDTAVYYCARRDYRFDLGFDYWGQGTTV TVSSASTKGPSVFPLAPSSKSTSGGTAALGCL VKDYFPEPVTVSWNSGALTSGVHTFPAVLQSS GLYSLSSVVTVPSSSLGTQTYICNVNHKPSNT KVDKKVEPKSCDKTHT | 694 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0503.1La | 672 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGSGGGGSGGGGSGGGGSEIVLTQSPAT LSLSPGERATLSCRASKGVSTSGYSYLHWYQQ KPGQAPRLLIYLASYLESGVPARFSGSGSGTD FTLTISSLEPEDFAVYYCQHSRDLPLTFGGGT KVEIKRTVAAPSVFIFPPSDEQLKSGTASVVC LLNNFYPREAKVQWKVDNALQSGNSQESVTEQ DSKDSTYSLSSTLTLSKADYEKHKVYACEVTH QGLSSPVTKSFNRGECGGSSGSGSGSTGTSSS GTGTSAGTTGTSASTSGSGSGGGGGSGGGGSA GGTATAGASSGSQVQLVQSGVEVKKPGASVKV SCKASGYTFTNYYMWVRQAPGQGLEWMGGIN PSRGGTNFNEKFKNRVTLTTDSSTTTAYMELK SLQFDDTAVYYCARRDYRFDLGFDYWGQGTTV TVSSASTKGPSVFPLAPSSKSTSGGTAALGCL VKDYFPEPVTVSWNSGALTSGVHTFPAVLQSS GLYSLSSVVTVPSSSLGTQTYICNVNHKPSNT KVDKKVEPKSCDKTHT | 695 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0504.1L | 673 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC | 696 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGSGGGGSGGGGSGGGGSDIQLTQSPSS LSASVGDRVTITCRASKGVSTSGYSYLHWYQQ KPGKAPKLLIYLASYLESGVPSRFSGSGSGTD FTLTISSLQPEDFATYYCQHSRDLPLTFGGGT KVEIKRTVAAPSVFIFPPSDEQLKSGTASVVC LLNNFYPREAKVQWKVDNALQSGNSQESVTEQ DSKDSTYSLSSTLTLSKADYEKHKVYACEVTH QGLSSPVTKSFNRGECGGSSGSGSGSTGTSSS GTGTSAGTTGTSASTSGSGSGGGGGSGGGGSA GGTATAGASSGSEVQLVQSGAEVKKPGASVKV SCKASGYTFTNYYMYWVRQAPGQGLEWMGGIN PSNGGTNFNEKFKNRVTLTTDSSTSTAYMELS SLRSEDTAVYYCARRDYRFDMGFDYWGQGTTV TVSSASTKGPSVFPLAPSSKSTSGGTAALGCL VKDYFPEPVTVSWNSGALTSGVHTFPAVLQSS GLYSLSSVVTVPSSSLGTQTYICNVNHKPSNT KVDKKVEPKSCDKTHT | | KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0504.1La | 674 | EVQLVESGGGLVQPGGSLRLSCAASGYTFTNY GMNWVRQAPGKGLEWVGWINTYTGEPTYAADF KRRPTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGSGGGGSGGGGSGGGGSDIQLTQSPSS LSASVGDRVTITCRASKGVSTSGYSYLHWYQQ KPGKAPKLLIYLASYLESGVPSRFSGSGSGTD FTLTISSLQPEDFATYYCQHSRDLPLTFGGGT KVEIKRTVAAPSVFIFPPSDEQLKSGTASVVC LLNNFYPREAKVQWKVDNALQSGNSQESVTEQ DSKDSTYSLSSTLILSKADYEKHKVYACEVTH QGLSSPVTKSFNRGECGGSSGSGSGSTGTSSS GTGTSAGTTGTSASTSGSGSGGGGGSGGGGSA GGTATAGASSGSEVQLVQSGAEVKKPGASVKV SCKASGYTFTNYYMYWVRQAPGQGLEWMGGIN PSNGGTNFNEKFKNRVTLTTDSSTSTAYMELS SLRSEDTAVYYCARRDYRFDMGFDYWGQGTTV TVSSASTKGPSVFPLAPSSKSTSGGTAALGCL VKDYFPEPVTVSWNSGALTSGVHTFPAVLQSS GLYSLSSVVTVPSSSLGTQTYICNVNHKPSNT KVDKKVEPKSCDKTHT | 697 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0505.1L | 675 | EVQLVESGGGLVQPGGSLRLSCAASGYTFTNY GMNWVRQAPGKGLEWVGWINTYTGEPTYAADF KRRPTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS | 698 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | LSPGGGSGGGGSGGGGSGGGGSDIQLTQSPSS LSASVGDRVTITCRASKGVSTSGYSYLHWYQQ KPGKAPKLLIYLASYLESGVPSRFSGSGSGTD FTLTISSLQPEDFATYYCQHSRDLPLTFGGGT KVEIKRTVAAPSVFIFPPSDEQLKSGTASVVC LLNNFYPREAKVQWKVDNALQSGNSQESVTEQ DSKDSTYSLSSTLTLSKADYEKHKVYACEVTH QGLSSPVTKSFNRGECGGSSGSGSGSGSTGTSSS GTGTSAGTTGTSASTSGSGSGGGGGSGGGGSA GGTATAGASSGSEVQLVQSGAEVKKPGASVKV SCKASGYTFTNYYMYWVRQAPGQGLEWMGGIN PSQGGTNFNEKFKNRVTLITDSSTSTAYMELS SLRSEDTAVYYCARRDYRFDLGFDYWGQGTTV TVSSASTKGPSVFPLAPSSKSTSGGTAALGCL VKDYFPEPVTVSWNSGALTSGVHTFPAVLQSS GLYSLSSVVTVPSSSLGTQTYICNVNHKPSNT KVDKKVEPKSCDKTHT | | |
| PAL054-0505.1La | 676 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGSGGGGSGGGGSGGGGSDIQLTQSPSS LSASVGDRVTITCRASKGVSTSGYSYLHWYQQ KPGKAPKLLIYLASYLESGVPSRFSGSGSGTD FTLTISSLQPEDFATYYCQHSRDLPLTFGGGT KVEIKRTVAAPSVFIFPPSDEQLKSGTASVVC LLNNFYPREAKVQWKVDNALQSGNSQESVTEQ DSKDSTYSLSSTLTLSKADYEKHKVYACEVTH QGLSSPVTKSFNRGECGGSSGSGSGSGSTGTSSS GTGTSAGTTGTSASTSGSGSGGGGGSGGGGSA GGTATAGASSGSEVQLVQSGAEVKKPGASVKV SCKASGYTFTNYYMYWVRQAPGQGLEWMGGIN PSQGGTNFNEKFKNRVILITDSSTSTAYMELS SLRSEDTAVYYCARRDYRFDLGFDYWGQGTTV TVSSASTKGPSVFPLAPSSKSTSGGTAALGCL VKDYFPEPVTVSWNSGALTSGVHTFPAVLQSS GLYSLSSVVTVPSSSLGTQTYICNVNHKPSNT KVDKKVEPKSCDKTHT | 699 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |
| PAL054-0506.1L | 677 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LMISRTPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGSGGGGSGGGGSGGGGSDIQLTQSPSS LSASVGDRVTITCRASKGVSTSGYSYLHWYQQ KPGKAPKLLIYLASYLESGVPSRFSGSGSGTD FTLTISSLQPEDFATYYCQHSRDLPLTFGGGT KVEIKRTVAAPSVFIFPPSDEQLKSGTASVVC LLNNFYPREAKVQWKVDNALQSGNSQESVTEQ DSKDSTYSLSSTLTLSKADYEKHKVYACEVTH QGLSSPVTKSFNRGECGGSSGSGSGSGSTGTSSS GTGTSAGTTGTSASTSGSGSGGGGGSGGGGSA GGTATAGASSGSEVQLVQSGAEVKKPGASVKV SCKASGYTFTNYYMYWVRQAPGQGLEWMGGIN | 700 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4A-continued

Sequences of Heavy Chains and Light Chains of Multispecific Binding Proteins

| Construct Name | SEQ ID NO | Heavy Chain | SEQ ID NO | Light Chain |
|---|---|---|---|---|
| | | PSRGGTNFNEKFKNRVTLTTDSSTSTAYMELS SLRSEDTAVYYCARRDYRFDLGFDYWGQGTTV TVSSASTKGPSVFPLAPSSKSTSGGTAALGCL VKDYFPEPVTVSWNSGALTSGVHTFPAVLQSS GLYSLSSVVTVPSSSLGTQTYICNVNHKPSNT KVDKKVEPKSCDKTHT | | |
| PAL054-0506.1La | 678 | EVQLVESGGGLVQPGGSLRLSCAASGYTFTNY GMNWVRQAPGKGLEWVGWINTYTGEPTYAADF KRRFTFSLDTSKSTAYLQMNSLRAEDTAVYYC AKYPHYYGSSHWYFDVWGQGTLVTVSSASTKG PSVFPLAPSSKSTSGGTAALGCLVKDYFPEPV TVSWNSGALTSGVHTFPAVLQSSGLYSLSSVV TVPSSSLGTQTYICNVNHKPSNTKVDKKVEPK SCDKTHTCPPCPAPEAAGGPSVFLFPPKPKDT LYITREPEVTCVVVDVSHEDPEVKFNWYVDGV EVHNAKTKPREEQYNSTYRVVSVLTVLHQDWL NGKEYKCKVSNKALPAPIEKTISKAKGQPREP QVYTLPPSRDELTKNQVSLTCLVKGFYPSDIA VEWESNGQPENNYKTTPPVLDSDGSFFLYSKL TVDKSRWQQGNVFSCSVMHEALHNHYTQKSLS LSPGGGSGGGGSGGGGSGGGGSDIQLTQSPSS LSASVGDRVTITCRASKGVSTSGYSYLHWYQQ KPGKAPKLLIYLASYLESGVPSRFSGSGSGTD FTLTISSLQPEDFATYYCQHSRDLPLTFGGGT KVEIKRTVAAPSVFIPPPSDEQLKSGTASVVC LLNNFYPREAKVQWKVDNALQSGNSQESVTEQ DSKDSTYSLSSTLTLSKADYEKHKVYACEVTH QGLSSPVTKSFNRGECGGSSGSGSGSGSTGTS SSGTGTSAGTTGTSASTSGSGSGGGGGSGGGGSA GGTATAGASSGSEVQLVQSGAEVKKPGASVKV SCKASGYTFTNYYMYWVRQAPGQGLEWMGGIN PSRGGTNFNEKFKNRVTLTTDSSTSTAYMELS SLRSEDTAVYYCARRDYRFDLGFDYWGQGTTV TVSSASTKGPSVFPLAPSSKSTSGGTAALGCL VKDYFPEPVTVSWNSGALTSGVHTFPAVLQSS GLYSLSSVVTVPSSSLGTQTYICNVNHKPSNT KVDKKVEPKSCDKTHT | 701 | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAPSVFIFPPSDEQLKSGTASVVCLL NNFYPREAKVQWKVDNALQSGNSQESVTEQDSKD STYSLSSTLTLSKADYEKHKVYACEVTHQGLSSP VTKSFNRGEC |

TABLE 4B

Sequences of Heavy Chains and Light Chains of Multispecific Binding Proteins

| Construct Name | SEQ ID NO | Heavy Chain | SEQ ID NO | Light Chain 1 | SEQ ID NO | Light Chain 2 |
|---|---|---|---|---|---|---|
| PAL054-0401.1L | 702 | EVQLVESGGGLVQPGGSLRLS CAASGYTFTNYGMNWVRQAPG KGLEWVGWINTYTGEPTYAAD FKRRFTFSLDTSKSTAYLQMN SLRAEDTAVYYCAKYPHYYGS SHWYFDVWGQGTLVTVSSAST KGPSVFPLAPSSKSTSGGTAA LGCLVKDYFPEPVTVSWNSGA LTSGVHTFPAVLQSSGLYSLS SVVTVPSSSLGTQTYICNVNH KPSNTKVDKKVEPKSCDKTHT CPPCPAPEAAGGPSVFLFPPK PKDTLMISRTPEVTCVVVDVS HEDPEVKFNWYVDGVEVHNAK TKPREEQYNSTYRVVSVLIVL HQDWLNGKEYKCKVSNKALPA PIEKTISKAKGQPREPQVYTL PPSRDELTKNQVSLTCLVKGF YPSDIAVEWESNGQPENNYKT TPPVLDSDGSFFLYSKLTVDK SRWQQGNVFSCSVMHEALHNH YTQKSLSLSPGGGSGGGGSGG GGSGGGGSQVQLVQSGVEVKK PGASVKVSCKASGYTFTNYYM YWVRQAPGQGLEWMGGINPSN GGTNFNEKFKNRVTLTTDSST | 714 | DIQMTQSPSSLSASVGDRVTI TCSASQDISNYLNWYQQKPGK APKVLIYFTSSLHSGVPSRFS GSGSGTDFTLTISSLQPEDFA TYYCQQYSTVPWTFGQGTKVE IKRTVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSEN RGEC | 726 | EIVLTQSPATLSLSPGERATL SCRASKGVSTSGYSYLHWYQQ KPGQAPRLLIYLASYLESGVP ARFSGSGSGTDFTLTISSLEP EDFAVYYCQHSRDLPLTFGGG TKVEIKSSASTKGPSVEPLAP SSKSTSGGTAALGCLVKDYFP EPVTVSWNSGALTSGVHTFPA VLQSSGLYSLSSVVTVPSSSL GTQTYICNVNHKPSNTKVDKK VEPKSC |

TABLE 4B-continued

Sequences of Heavy Chains and Light Chains of Multispecific Binding Proteins

| Construct Name | SEQ ID NO | Heavy Chain | SEQ ID NO | Light Chain 1 | SEQ ID NO | Light Chain 2 |
|---|---|---|---|---|---|---|
| | | TTAYMELKSLQFDDTAVYYCA RRDYRFDMGFDYWGQGTTVTV SSASVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | | | | |
| PAL054-0401.1La | 703 | EVQLVESGGGLVQPGGSLRLS CAASGYTFTNYGMNWVRQAPG KGLEWVGWINTYTGEPTYAAD FKRRFTFSLDTSKSTAYLQMN SLRAEDTAVYYCAKYPHYYGS SHWYFDVWGQGTLVTVSSAST KGPSVFPLAPSSKSTSGGTAA LGCLVKDYFPEPVTVSWNSGA LTSGVHTFPAVLQSSGLYSLS SVVTVPSSSLGTQTYICNVNH KPSNTKVDKKVEPKSCDKTHT CPPCPAPEAAGGPSVFLFPPK PKDTLYITREPEVTCVVVDVS HEDPEVKFNWYVDGVEVHNAK TKPREEQYNSTYRVVSVLTVL HQDWLNGKEYKCKVSNKALPA PIEKTISKAKGQPREPQVYTL PPSRDELTKNQVSLTCLVKGF YPSDIAVEWESNGQPENNYKT TPPVLDSDGSFFLYSKLTVDK SRWQQGNVFSCSVMHEALHNH YTQKSLSLSPGGGSGGGGSGG GGSGGGGSQVQLVQSGVEVKK PGASVKVSCKASGYTFTNYYM YWVRQAPGQGLEWMGGINPSN GGTNFNEKFKNRVTLTTDSST TTAYMELKSLQFDDTAVYYCA RRDYRFDMGFDYWGQGTTVTV SSASVAAPSVFIFPPSDEQLK SGTASVVCLLNNFYPREAKVQ WKVDNALQSGNSQESVTEQDS KDSTYSLSSTLILSKADYEKH KVYACEVTHQGLSSPVTKSFN RGEC | 715 | DIQMTQSPSSLSASVGDRVTI TCSASQDISNYLNWYQQKPGK APKVLIYFTSSLHSGVPSRFS GSGSGTDFTLTISSLQPEDFA TYYCQQYSTVPWTFGQGTKVE IKRTVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | 727 | EIVLTQSPATLSLSPGERATL SCRASKGVSTSGYSYLHWYQQ KPGQAPRLLIYLASYLESGVP ARFSGSGSGTDFTLTISSLEP EDFAVYYCQHSRDLPLTFGGG TKVEIKSSASTKGPSVEPLAP SSKSTSGGTAALGCLVKDYFP EPVTVSWNSGALTSGVHTFPA VLQSSGLYSLSSVVTVPSSSL GTQTYICNVNHKPSNTKVDKK VEPKSC |
| PAL054-0402.1L | 704 | EVQLVESGGGLVQPGGSLRLS CAASGYTFTNYGMNWVRQAPG KGLEWVGWINTYTGEPTYAAD FKRRFTFSLDTSKSTAYLQMN SLRAEDTAVYYCAKYPHYYGS SHWYFDVWGQGTLVTVSSAST KGPSVFPLAPSSKSTSGGTAA LGCLVKDYFPEPVTVSWNSGA LTSGVHTFPAVLQSSGLYSLS SVVTVPSSSLGTQTYICNVNH KPSNTKVDKKVEPKSCDKTHT CPPCPAPEAAGGPSVFLFPPK PKDTLMISRTPEVTCVVVDVS HEDPEVKFNWYVDGVEVHNAK TKPREEQYNSTYRVVSVLTVL HQDWLNGKEYKCKVSNKALPA PIEKTISKAKGQPREPQVYTL PPSRDELTKNQVSLTCLVKGF YPSDIAVEWESNGQPENNYKT TPPVLDSDGSFFLYSKLTVDK SRWQQGNVFSCSVMHEALHNH YTQKSLSLSPGGGSGGGGSGG GGSGGGGSQVQLVQSGVEVKK PGASVKVSCKASGYTFTNYYM YWVRQAPGQGLEWMGGINPSQ GGTNFNEKFKNRVTLTTDSST TTAYMELKSLQFDDTAVYYCA RRDYRFDLGFDYWGQGTTVTV SSASVAAPSVFIFPPSDEQLK SGTASVVCLLNNFYPREAKVQ WKVDNALQSGNSQESVTEQDS | 716 | DIQMTQSPSSLSASVGDRVTI TCSASQDISNYLNWYQQKPGK APKVLIYFTSSLHSGVPSRFS GSGSGTDFTLTISSLQPEDFA TYYCQQYSTVPWTFGQGTKVE IKRTVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | 728 | EIVLTQSPATLSLSPGERATL SCRASKGVSTSGYSYLHWYQQ KPGQAPRLLIYLASYLESGVP ARFSGSGSGTDFTLTISSLEP EDFAVYYCQHSRDLPLTFGGG TKVEIKSSASTKGPSVFPLAP SSKSTSGGTAALGCLVKDYFP EPVTVSWNSGALTSGVHTFPA VLQSSGLYSLSSVVTVPSSSL GTQTYICNVNHKPSNTKVDKK VEPKSC |

TABLE 4B-continued

Sequences of Heavy Chains and Light Chains of Multispecific Binding Proteins

| Construct Name | SEQ ID NO | Heavy Chain | SEQ ID NO | Light Chain 1 | SEQ ID NO | Light Chain 2 |
|---|---|---|---|---|---|---|
| | | KDSTYSLSSTLILSKADYEKH KVYACEVTHQGLSSPVTKSFN RGEC | | | | |
| PAL054- 0402.1La | 705 | EVQLVESGGGLVQPGGSLRLS CAASGYTFTNYGMNWVRQAPG KGLEWVGWINTYTGEPTYAAD FKRRFTFSLDTSKSTAYLQMN SLRAEDTAVYYCAKYPHYYGS SHWYFDVWGQGTLVTVSSAST KGPSVFPLAPSSKSTSGGTAA LGCLVKDYFPEPVTVSWNSGA LTSGVHTFPAVLQSSGLYSLS SVVTVPSSSLGTQTYICNVNH KPSNTKVDKKVEPKSCDKTHT CPPCPAPEAAGGPSVFLFPPK PKDTLYITREPEVTCVVVDVS HEDPEVKFNWYVDGVEVHNAK TKPREEQYNSTYRVVSVLTVL HQDWLNGKEYKCKVSNKALPA PIEKTISKAKGQPREPQVYTL PPSRDELTKNQVSLTCLVKGF YPSDIAVEWESNGQPENNYKT TPPVLDSDGSFFLYSKLTVDK SRWQQGNVFSCSVMHEALHNH YTQKSLSLSPGGGSGGGGSGG GGSGGGGSQVQLVQSGVEVKK PGASVKVSCKASGYTFTNYYM YWVRQAPGQGLEWMGGINPSQ GGTNFNEKFKNRVTLTTDSST TTAYMELKSLQFDDTAVYYCA RRDYRFDLGEDYWGQGTTVTV SSASVAAPSVFIFPPSDEQLK SGTASVVCLLNNFYPREAKVQ WKVDNALQSGNSQESVTEQDS KDSTYSLSSTLILSKADYEKH KVYACEVTHQGLSSPVTKSFN RGEC | 717 | DIQMTQSPSSLSASVGDRVTI TCSASQDISNYLNWYQQKPGK APKVLIYFTSSLHSGVPSRFS GSGSGTDFTLTISSLQPEDFA TYYCQQYSTVPWTFGQGTKVE IKRTVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | 729 | EIVLTQSPATLSLSPGERATL SCRASKGVSTSGYSYLHWYQQ KPGQAPRLLIYLASYLESGVP ARFSGSGSGTDFTLTISSLEP EDFAVYYCQHSRDLPLTFGGG TKVEIKSSASTKGPSVFPLAP SSKSTSGGTAALGCLVKDYFP EPVTVSWNSGALTSGVHTFPA VLQSSGLYSLSSVVTVPSSSL GTQTYICNVNHKPSNTKVDKK VEPKSC |
| PAL054- 0403.1L | 706 | EVQLVESGGGLVQPGGSLRLS CAASGYTFTNYGMNWVRQAPG KGLEWVGWINTYTGEPTYAAD FKRRFTFSLDTSKSTAYLQMN SLRAEDTAVYYCAKYPHYYGS SHWYFDVWGQGTLVTVSSAST KGPSVFPLAPSSKSTSGGTAA LGCLVKDYFPEPVTVSWNSGA LTSGVHTFPAVLQSSGLYSLS SVVTVPSSSLGTQTYICNVNH KPSNTKVDKKVEPKSCDKTHT CPPCPAPEAAGGPSVFLFPPK PKDTLMISRTPEVTCVVVDVS HEDPEVKFNWYVDGVEVHNAK TKPREEQYNSTYRVVSVLTVL HQDWLNGKEYKCKVSNKALPA PIEKTISKAKGQPREPQVYTL PPSRDELTKNQVSLTCLVKGE YPSDIAVEWESNGQPENNYKT TPPVLDSDGSFFLYSKLTVDK SRWQQGNVFSCSVMHEALHNH YTQKSLSLSPGGGSGGGGSGG GGSGGGGSQVQLVQSGVEVKK PGASVKVSCKASGYTFTNYYM YWVRQAPGQGLEWMGGINPSR GGTNFNEKFKNRVTLTTDSST TTAYMELKSLQFDDTAVYYCA RRDYRFDLGFDYWGQGTTVTV SSASVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | 718 | DIQMTQSPSSLSASVGDRVTI TCSASQDISNYLNWYQQKPGK APKVLIYFTSSLHSGVPSRFS GSGSGTDFTLTISSLQPEDFA TYYCQQYSTVPWTFGQGTKVE IKRTVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | 730 | EIVLIQSPATLSLSPGERATL SCRASKGVSTSGYSYLHWYQQ KPGQAPRLLIYLASYLESGVP ARFSGSGSGTDFTLTISSLEP EDFAVYYCQHSRDLPLTFGGG TKVEIKSSASTKGPSVFPLAP SSKSTSGGTAALGCLVKDYFP EPVTVSWNSGALTSGVHTFPA VLQSSGLYSLSSVVTVPSSSL GTQTYICNVNHKPSNTKVDKK VEPKSC |

TABLE 4B-continued

Sequences of Heavy Chains and Light Chains of Multispecific Binding Proteins

| Construct Name | SEQ ID NO | Heavy Chain | SEQ ID NO | Light Chain 1 | SEQ ID NO | Light Chain 2 |
|---|---|---|---|---|---|---|
| PAL054-0403.1La | 707 | EVQLVESGGGLVQPGGSLRLS CAASGYTFTNYGMNWVRQAPG KGLEWVGWINTYTGEPTYAAD FKRRFTFSLDTSKSTAYLQMN SLRAEDTAVYYCAKYPHYYGS SHWYFDVWGQGTLVTVSSAST KGPSVFPLAPSSKSTSGGTAA LGCLVKDYFPEPVTVSWNSGA LTSGVHTFPAVLQSSGLYSLS SVVTVPSSSLGTQTYICNVNH KPSNTKVDKKVEPKSCDKTHT CPPCPAPEAAGGPSVFLPPPK PKDTLYITREPEVTCVVVDVS HEDPEVKFNWYVDGVEVHNAK TKPREEQYNSTYRVVSVLIVL HQDWLNGKEYKCKVSNKALPA PIEKTISKAKGQPREPQVYTL PPSRDELTKNQVSLTCLVKGF YPSDIAVEWESNGQPENNYKT TPPVLDSDGSFFLYSKLTVDK SRWQQGNVFSCSVMHEALHNH YTQKSLSLSPGGGSGGGGSGG GGSGGGGSQVQLVQSGVEVKK PGASVKVSCKASGYTFTNYYM YWVRQAPGQGLEWMGGINPSR GGTNFNEKFKNRVTLTTDSST TTAYMELKSLQFDDTAVYYCA RRDYRFDLGFDYWGQGTTVTV SSASVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | 719 | DIQMTQSPSSLSASVGDRVTI TCSASQDISNYLNWYQQKPGK APKVLIYFTSSLHSGVPSRFS GSGSGTDFTLTISSLQPEDFA TYYCQQYSTVPWTFGQGTKVE IKRTVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | 731 | EIVLTQSPATLSLSPGERATL SCRASKGVSTSGYSYLHWYQQ KPGQAPRLLIYLASYLESGVP ARFSGSGSGTDFTLTISSLEP EDFAVYYCQHSRDLPLTFGGG TKVEIKSSASTKGPSVFPLAP SSKSTSGGTAALGCLVKDYFP EPVTVSWNSGALTSGVHTFPA VLQSSGLYSLSSVVTVPSSSL GTQTYICNVNHKPSNTKVDKK VEPKSC |
| PAL054-0404.1L | 708 | EVQLVESGGGLVQPGGSLRLS CAASGYTFTNYGMNWVRQAPG KGLEWVGWINTYTGEPTYAAD FKRRFTFSLDTSKSTAYLQMN SLRAEDTAVYYCAKYPHYYGS SHWYFDVWGQGTLVTVSSAST KGPSVFPLAPSSKSTSGGTAA LGCLVKDYFPEPVTVSWNSGA LTSGVHTFPAVLQSSGLYSLS SVVTVPSSSLGTQTYICNVNH KPSNTKVDKKVEPKSCDKTHT CPPCPAPEAAGGPSVFLPPPK PKDTLMISRTPEVTCVVVDVS HEDPEVKFNWYVDGVEVHNAK TKPREEQYNSTYRVVSVLTVL HQDWLNGKEYKCKVSNKALPA PIEKTISKAKGQPREPQVYTL PPSRDELTKNQVSLTCLVKGF YPSDIAVEWESNGQPENNYKT TPPVLDSDGSFFLYSKLTVDK SRWQQGNVFSCSVMHEALHNH YTQKSLSLSPGGGSGGGGSGG GGSGGGGSEVQLVQSGAEVKK PGASVKVSCKASGYTFTNYYM YWVRQAPGQGLEWMGGINPSN GGTNFNEKFKNRVTLTTDSST STAYMELSSLRSEDTAVYYCA RRDYRFDMGFDYWGQGTTVTV SSASVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | 720 | DIQMTQSPSSLSASVGDRVTI TCSASQDISNYLNWYQQKPGK APKVLIYFTSSLHSGVPSRFS GSGSGTDFTLTISSLQPEDFA TYYCQQYSTVPWTFGQGTKVE IKRTVAAPSVEIFPPSDEQLK SGTASVVCLLNNFYPREAKVQ WKVDNALQSGNSQESVTEQDS KDSTYSLSSTLILSKADYEKH KVYACEVTHQGLSSPVTKSFN RGEC | 732 | DIQLTQSPSSLSASVGDRVTI TCRASKGVSTSGYSYLHWYQQ KPGKAPKLLIYLASYLESGVP SRFSGSGSGTDFTLTISSLQP EDFATYYCQHSRDLPLTFGGG TKVEIKSSASTKGPSVFPLAP SSKSTSGGTAALGCLVKDYFP EPVTVSWNSGALTSGVHTFPA VLQSSGLYSLSSVVTVPSSSL GTQTYICNVNHKPSNTKVDKK VEPKSC |
| PAL054-0404.1La | 709 | EVQLVESGGGLVQPGGSLRLS CAASGYTFTNYGMNWVRQAPG KGLEWVGWINTYTGEPTYAAD FKRRFTFSLDTSKSTAYLQMN SLRAEDTAVYYCAKYPHYYGS | 721 | DIQMTQSPSSLSASVGDRVTI TCSASQDISNYLNWYQQKPGK APKVLIYFTSSLHSGVPSRFS GSGSGTDFTLTISSLQPEDFA TYYCQQYSTVPWTFGQGTKVE | 733 | DIQLTQSPSSLSASVGDRVTI TCRASKGVSTSGYSYLHWYQQ KPGKAPKLLIYLASYLESGVP SRFSGSGSGTDFTLTISSLQP EDFATYYCQHSRDLPLTFGGG |

TABLE 4B-continued

Sequences of Heavy Chains and Light Chains of Multispecific Binding Proteins

| Construct Name | SEQ ID NO | Heavy Chain | SEQ ID NO | Light Chain 1 | SEQ ID NO | Light Chain 2 |
|---|---|---|---|---|---|---|
| | | SHWYFDVWGQGTLVTVSSAST KGPSVFPLAPSSKSTSGGTAA LGCLVKDYFPEPVTVSWNSGA LTSGVHTFPAVLQSSGLYSLS SVVTVPSSSLGTQTYICNVNH KPSNTKVDKKVEPKSCDKTHT CPPCPAPEAAGGPSVFLFPPK PKDTLYITREPEVTCVVVDVS HEDPEVKFNWYVDGVEVHNAK TKPREEQYNSTYRVVSVLTVL HQDWLNGKEYKCKVSNKALPA PIEKTISKAKGQPREPQVYTL PPSRDELTKNQVSLTCLVKGF YPSDIAVEWESNGQPENNYKT TPPVLDSDGSFFLYSKLTVDK SRWQQGNVFSCSVMHEALHNH YTQKSLSLSPGGGSGGGGSGG GGSGGGGSEVQLVQSGAEVKK PGASVKVSCKASGYTFTNYYM YWVRQAPGQGLEWMGGINPSN GGTNFNEKFKNRVTLTTDSST STAYMELSSLRSEDTAVYYCA RRDYRFDMGFDYWGQGTTVTV SSASVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | | IKRTVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | | TKVEIKSSASTKGPSVFPLAP SSKSTSGGTAALGCLVKDYFP EPVTVSWNSGALTSGVHTFPA VLQSSGLYSLSSVVTVPSSSL GTQTYICNVNHKPSNTKVDKK VEPKSC |
| PAL054-0405.1L | 710 | EVQLVESGGGLVQPGGSLRLS CAASGYTFTNYGMNWVRQAPG KGLEWVGWINTYTGEPTYAAD FKRRFTFSLDTSKSTAYLQMN SLRAEDTAVYYCAKYPHYYGS SHWYFDVWGQGTLVTVSSAST KGPSVFPLAPSSKSTSGGTAA LGCLVKDYFPEPVTVSWNSGA LTSGVHTFPAVLQSSGLYSLS SVVTVPSSSLGTQTYICNVNH KPSNTKVDKKVEPKSCDKTHT CPPCPAPEAAGGPSVFLFPPK PKDTLMISRTPEVTCVVVDVS HEDPEVKFNWYVDGVEVHNAK TKPREEQYNSTYRVVSVLIVL HQDWLNGKEYKCKVSNKALPA PIEKTISKAKGQPREPQVYTL PPSRDELTKNQVSLTCLVKGF YPSDIAVEWESNGQPENNYKT TPPVLDSDGSFFLYSKLIVDK SRWQQGNVFSCSVMHEALHNH YTQKSLSLSPGGGSGGGGSGG GGSGGGGSEVQLVQSGAEVKK PGASVKVSCKASGYTFTNYYM YWVRQAPGQGLEWMGGINPSQ GGTNFNEKFKNRVTLTTDSST STAYMELSSLRSEDTAVYYCA RRDYRFDLGFDYWGQGTTVTV SSASVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | 722 | DIQMTQSPSSLSASVGDRVTI TCSASQDISNYLNWYQQKPGK APKVLIYFTSSLHSGVPSRFS GSGSGTDFTLTISSLQPEDFA TYYCQQYSTVPWTFGQGTKVE IKRTVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | 734 | DIQLTQSPSSLSASVGDRVTI TCRASKGVSTSGYSYLHWYQQ KPGKAPKLLIYLASYLESGVP SRFSGSGSGTDFTLTISSLQP EDFATYYCQHSRDLPLTFGGG TKVEIKSSASTKGPSVFPLAP SSKSTSGGTAALGCLVKDYFP EPVTVSWNSGALTSGVHTFPA VLQSSGLYSLSSVVTVPSSSL GTQTYICNVNHKPSNTKVDKK VEPKSC |
| PAL054-0405.1La | 711 | EVQLVESGGGLVQPGGSLRLS CAASGYTFTNYGMNWVRQAPG KGLEWVGWINTYTGEPTYAAD FKRRFTFSLDTSKSTAYLQMN SLRAEDTAVYYCAKYPHYYGS SHWYFDVWGQGTLVTVSSAST KGPSVFPLAPSSKSTSGGTAA LGCLVKDYFPEPVTVSWNSGA LTSGVHTFPAVLQSSGLYSLS SVVTVPSSSLGTQTYICNVNH | 723 | DIQMTQSPSSLSASVGDRVTI TCSASQDISNYLNWYQQKPGK APKVLIYFTSSLHSGVPSRFS GSGSGTDFTLTISSLQPEDFA TYYCQQYSTVPWTFGQGTKVE IKRTVAAPSVFIFPPSDEQLK SGTASVVCLLNNFYPREAKVQ WKVDNALQSGNSQESVTEQDS KDSTYSLSSTLILSKADYEKH KVYACEVTHQGLSSPVTKSFN | 735 | DIQLTQSPSSLSASVGDRVTI TCRASKGVSTSGYSYLHWYQQ KPGKAPKLLIYLASYLESGVP SRFSGSGSGTDFTLTISSLQP EDFATYYCQHSRDLPLTFGGG TKVEIKSSASTKGPSVFPLAP SSKSTSGGTAALGCLVKDYFP EPVTVSWNSGALTSGVHTFPA VLQSSGLYSLSSVVTVPSSSL GTQTYICNVNHKPSNTKVDKK |

TABLE 4B-continued

Sequences of Heavy Chains and Light Chains of Multispecific Binding Proteins

| Construct Name | SEQ ID NO | Heavy Chain | SEQ ID NO | Light Chain 1 | SEQ ID NO | Light Chain 2 |
|---|---|---|---|---|---|---|
| | | KPSNTKVDKKVEPKSCDKTHT CPPCPAPEAAGGPSVFLFPPK PKDTLYITREPEVTCVVVDVS HEDPEVKENWYVDGVEVHNAK TKPREEQYNSTYRVVSVLTVL HQDWLNGKEYKCKVSNKALPA PIEKTISKAKGQPREPQVYTL PPSRDELTKNQVSLTCLVKGF YPSDIAVEWESNGQPENNYKT TPPVLDSDGSFFLYSKLIVDK SRWQQGNVFSCSVMHEALHNH YTQKSLSLSPGGGSGGGGSGG GGSGGGGSEVQLVQSGAEVKK PGASVKVSCKASGYTFTNYYM YWVRQAPGQGLEWMGGINPSQ GGTNFNEKFKNRVTLTTDSST STAYMELSSLRSEDTAVYYCA RRDYRFDLGFDYWGQGTTVTV SSASVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | | RGEC | | VEPKSC |
| PAL054-0406.1L | 712 | EVQLVESGGGLVQPGGSLRLS CAASGYTFTNYGMNWVRQAPG KGLEWVGWINTYTGEPTYAAD FKRRFTFSLDTSKSTAYLQMN SLRAEDTAVYYCAKYPHYYGS SHWYFDVWGQGTLVTVSSAST KGPSVFPLAPSSKSTSGGTAA LGCLVKDYFPEPVTVSWNSGA LTSGVHTFPAVLQSSGLYSLS SVVTVPSSSLGTQTYICNVNH KPSNTKVDKKVEPKSCDKTHT CPPCPAPEAAGGPSVFLFPPK PKDTLMISRTPEVTCVVVDVS HEDPEVKFNWYVDGVEVHNAK TKPREEQYNSTYRVVSVLTVL HQDWLNGKEYKCKVSNKALPA PIEKTISKAKGQPREPQVYTL PPSRDELTKNQVSLTCLVKGF YPSDIAVEWESNGQPENNYKT TPPVLDSDGSFFLYSKLTVDK SRWQQGNVFSCSVMHEALHNH YTQKSLSLSPGGGSGGGGSGG GGSGGGGSEVQLVQSGAEVKK PGASVKVSCKASGYTFTNYYM YWVRQAPGQGLEWMGGINPSR GGTNFNEKFKNRVTLTTDSST STAYMELSSLRSEDTAVYYCA RRDYRFDLGFDYWGQGTTVTV SSASVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | 724 | DIQMTQSPSSLSASVGDRVTI TCSASQDISNYLNWYQQKPGK APKVLIYFTSSLHSGVPSRES GSGSGTDFTLTISSLQPEDFA TYYCQQYSTVPWTFGQGTKVE IKRTVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | 736 | DIQLTQSPSSLSASVGDRVTI TCRASKGVSTSGYSYLHWYQQ KPGKAPKLLIYLASYLESGVP SRFSGSGSGTDFTLTISSLQP EDFATYYCQHSRDLPLTFGGG TKVEIKSSASTKGPSVEPLAP SSKSTSGGTAALGCLVKDYFP EPVTVSWNSGALTSGVHTFPA VLQSSGLYSLSSVVTVPSSSL GTQTYICNVNHKPSNTKVDKK VEPKSC |
| PAL054-0406.1La | 713 | EVQLVESGGGLVQPGGSLRLS CAASGYTFTNYGMNWVRQAPG KGLEWVGWINTYTGEPTYAAD FKRRFTFSLDTSKSTAYLQMN SLRAEDTAVYYCAKYPHYYGS SHWYFDVWGQGTLVTVSSAST KGPSVFPLAPSSKSTSGGTAA LGCLVKDYFPEPVTVSWNSGA LTSGVHTFPAVLQSSGLYSLS SVVTVPSSSLGTQTYICNVNH KPSNTKVDKKVEPKSCDKTHT CPPCPAPEAAGGPSVFLFPPK PKDTLYITREPEVTCVVVDVS HEDPEVKFNWYVDGVEVHNAK TKPREEQYNSTYRVVSVLTVL | 725 | DIQMTQSPSSLSASVGDRVTI TCSASQDISNYLNWYQQKPGK APKVLIYFTSSLHSGVPSRES GSGSGTDFTLTISSLQPEDFA TYYCQQYSTVPWTFGQGTKVE IKRTVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | 737 | DIQLTQSPSSLSASVGDRVTI TCRASKGVSTSGYSYLHWYQQ KPGKAPKLLIYLASYLESGVP SRFSGSGSGTDFTLTISSLQP EDFATYYCQHSRDLPLTFGGG TKVEIKSSASTKGPSVEPLAP SSKSTSGGTAALGCLVKDYFP EPVTVSWNSGALTSGVHTFPA VLQSSGLYSLSSVVTVPSSSL GTQTYICNVNHKPSNTKVDKK VEPKSC |

TABLE 4B-continued

Sequences of Heavy Chains and Light Chains of Multispecific Binding Proteins

| Construct Name | SEQ ID NO | Heavy Chain | SEQ ID NO | Light Chain 1 | SEQ ID NO | Light Chain 2 |
|---|---|---|---|---|---|---|
| | | HQDWLNGKEYKCKVSNKALPA PIEKTISKAKGQPREPQVYTL PPSRDELTKNQVSLTCLVKGF YPSDIAVEWESNGQPENNYKT TPPVLDSDGSFFLYSKLTVDK SRWQQGNVFSCSVMHEALHNH YTQKSLSLSPGGGSGGGGSGG GGSGGGGSEVQLVQSGAEVKK PGASVKVSCKASGYTFTNYYM YWVRQAPGQGLEWMGGINPSR GGTNFNEKFKNRVTLTTDSST STAYMELSSLRSEDTAVYYCA RRDYRFDLGFDYWGQGTTVTV SSASVAAPSVFIFPPSDEQLK SGTASVVCLLNNFYPREAKVQ WKVDNALQSGNSQESVTEQDS KDSTYSLSSTLTLSKADYEKH KVYACEVTHQGLSSPVTKSFN RGEC | | | | |

VH Domains

In some embodiments, a binding protein provided herein comprises a first VH sequence selected from SEQ ID NOs: 295-296, 301-334, and 738-742 and a second VH sequence selected from SEQ ID NOs: 295-296, 301-334 and 738-742. In some embodiments, a binding protein provided herein comprises a first VH sequence selected from SEQ ID NOs: 295-296 and a second VH sequence selected from SEQ ID NOs: 301-334. In some embodiments, a binding protein provided herein comprises a first VH sequence comprising SEQ ID NO: 3 and a second VH sequence selected from SEQ ID NOs: 301-334.

In some embodiments, a binding protein provided herein comprises a first VH sequence having at least about 80%, 90%, 91%, 92%, 93%, 94%, 95%, 96%, 97%, 98% or 99% identity to a VH sequence selected from SEQ ID NOs: 295-296 and a second VH sequence selected from SEQ ID NOs: 301-334. In some embodiments, a binding protein provided herein comprises a first VH sequence having at least about 80%, 90%, 91%, 92%, 93%, 94%, 95%, 96%, 97%, 98% or 99% identity to a VH sequence comprising SEQ ID NO: 3 and a second VH sequence selected from SEQ ID NOs: 301-334. In some embodiments, a binding protein provided herein comprises a first VH sequence selected from SEQ ID NOs: 295-296 and a second VH sequence selected from SEQ ID NOs: 301-334, with up to 1, 2, 3, 4, 5, 6, 7, 8, 9, 10, 11, 12, 13, 14, 15, 16, 17, 18, 19, or 20 amino acid substitutions. In some embodiments, a binding protein provided herein comprises a first VH sequence comprising SEQ ID NO: 3 and a second VH sequence selected from SEQ ID NOs: 301-334, with up to 1, 2, 3, 4, 5, 6, 7, 8, 9, 10, 11, 12, 13, 14, 15, 16, 17, 18, 19, or 20 amino acid substitutions. In some embodiments, the amino acid substitutions are conservative amino acid substitutions. In some embodiments, the bispecific binding proteins described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining bispecific binding proteins.

TABLE 5A

Sequences of VEGF Heavy Chain Variable Regions (VH)

| SEQ ID NO | VH |
|---|---|
| 295 | EVQLVESGGGLVQPGGSLRLSCAASGYTFT NYGMNWVRQAPGKGLEWVGWINTYTGEPTY AADFKRRFTFSLDTSKSTAYLQMNSLRAED TAVYYCAKYPHYYGSSHWYFDVWGQGTLVT VSS |
| 296 | EVQLVESGGGLVQPGGSLRLSCAASGYTFT NYGMNWVRQAPGKCLEWVGWINTYTGEPTY AADFKRRFTFSLDTSKSTAYLQMNSLRAED TAVYYCAKYPHYYGSSHWYFDVWGQGTLVT VSS |

TABLE 5B

Sequences of PD-1 Heavy Chain Variable Regions (VH)

| SEQ ID NO | VH |
|---|---|
| 301 | QVQLVQSGVEVKKPGASVKVSCKASGYTFTNYYMYWVRQAPGQGLEWMGGINPS NGGTNFNEKFKNRVTLTTDSSTTTAYMELKSLQFDDTAVYYCARRDYRFDMGFD YWGQGTTVTVSS |

TABLE 5B-continued

Sequences of PD-1 Heavy Chain Variable Regions (VH)

| SEQ ID NO | VH |
|---|---|
| 302 | QVQLVQSGVEVKKPGASVKVSCKASGYTFTNYYMYWVRQAPGQGLEWMGGINPS QGGTNFNEKFKNRVTLTTDSSTTTAYMELKSLQFDDTAVYYCARRDYRFDLGFD YWGQGTTVTVSS |
| 303 | QVQLVQSGVEVKKPGASVKVSCKASGYTFTNYYMYWVRQAPGQGLEWMGGINPS RGGTNFNEKFKNRVTLTTDSSTTTAYMELKSLQFDDTAVYYCARRDYRFDLGFD YWGQGTTVTVSS |
| 304 | QVQLVQSGVEVKKPGASVKVSCKASGYTFTNYYMYWVRQAPGQGLEWMGGINPS NGGTNFNEKFKNRVTLTTDSSTTTAYMELKSLQFDDTAVYYCARRDYRFDMGFD YWGQGTTVTVSS |
| 305 | QVQLVQSGVEVKKPGASVKVSCKASGYTFTNYYMYWVRQAPGQCLEWMGGINPS NGGTNFNEKFKNRVTLTTDSSTTTAYMELKSLQFDDTAVYYCARRDYRFDMGFD YWGQGTTVTVSS |
| 306 | QVQLVQSGVEVKKPGASVKVSCKASGYTFTNYYMYWVRQAPGQCLEWMGGINPS QGGTNFNEKFKNRVTLTTDSSTTTAYMELKSLQFDDTAVYYCARRDYRFDLGFD YWGQGTTVTVSS |
| 307 | QVQLVQSGVEVKKPGASVKVSCKASGYTFTNYYMYWVRQAPGQCLEWMGGINPS RGGTNFNEKFKNRVTLTTDSSTTTAYMELKSLQFDDTAVYYCARRDYRFDLGFD YWGQGTTVTVSS |
| 308 | EVQLVESGGGLVQPGGSLRLSCAASGYTFTNYYMYWVRQAPGKGLEWMGGINPS QGGTNFNEKFKNRFTISRDNSKNTLYLQMNSLRAEDTAVYYCARRDYRFDLGFD YWGQGTLVTVSS |
| 309 | EVQLVESGGGLVQPGGSLRLSCAASGYTFTNYYMYWVRQAPGKCLEWMGGINPS QGGTNFNEKFKNRFTISRDNSKNTLYLQMNSLRAEDTAVYYCARRDYREDLGFD YWGQGTLVTVSS |
| 310 | QVQLVQSGVEVKKPGASVKVSCKASGYTFTNYYMYWVRQAPGQGLEWMGGINPS QGGTNFNEKFKNRVTLTTDSSTTTAYMELKSLQFDDTAVYYCARRDYRFDLGFD YWGQGTGVRVSS |
| 311 | QVQLVQSGVEVKKPGASVKVSCKASGYTFTNYYMYWVRQAPGQCLEWMGGINPS QGGTNFNEKFKNRVTLTTDSSTTTAYMELKSLQFDDTAVYYCARRDYREDLGFD YWGQGTGVRVSS |
| 312 | QVQLVQSGVEVKKPGASVKVSCKASGYTFTNYYMYWVRQAPGQGLEWMGGINPS NGGTNFNEKFKNRVTLTTDSSTTTAYMELKSLRFDDTAVYYCARRDYRFDMGFD YWGQGTTVTVSS |
| 313 | QVQLVQSGVEVKKPGASVKVSCKASGYTFTNYYMYWVRQAPGQGLEWMGGINPS QGGTNFNEKFKNRVTLTTDSSTTTAYMELKSLRFDDTAVYYCARRDYRFDLGFD YWGQGTTVTVSS |
| 314 | QVQLVQSGVEVKKPGASVKVSCKASGYTFTNYYMYWVRQAPGQGLEWMGGINPS RGGTNFNEKFKNRVTLTTDSSTTTAYMELKSLRFDDTAVYYCARRDYRFDLGFD YWGQGTTVTVSS |
| 315 | QVQLVQSGVEVKKPGASVKVSCKASGYTFTNYYMYWVRQAPGQCLEWMGGINPS NGGTNFNEKFKNRVTLTTDSSTTTAYMELKSLRFDDTAVYYCARRDYRFDMGFD YWGQGTTVTVSS |
| 316 | QVQLVQSGVEVKKPGASVKVSCKASGYTFTNYYMYWVRQAPGQCLEWMGGINPS QGGTNFNEKFKNRVTLTTDSSTTTAYMELKSLRFDDTAVYYCARRDYREDLGFD YWGQGTTVTVSS |
| 317 | QVQLVQSGVEVKKPGASVKVSCKASGYTFTNYYMYWVRQAPGQCLEWMGGINPS RGGTNFNEKFKNRVTLTTDSSTTTAYMELKSLRFDDTAVYYCARRDYREDLGFD YWGQGTTVTVSS |
| 318 | EVQLVQSGAEVKKPGASVKVSCKASGYTFTNYYMYWVRQAPGQGLEWMGGINPS QGGTNFNEKFKNRVTLTTDSSTSTAYMELSSLRSEDTAVYYCARRDYREDLGFD YWGQGTTVTVSS |
| 319 | EVQLLESGGGLVQPGGSLRLSCKASGYTFTNYYMYWVRQAPGKGLEWMGGINPS QGGTNFNEKFKNRVTLSTDSSKNTAYLQMNSLRAEDTAVYYCARRDYREDLGFD YWGQGTTVTVSS |
| 320 | EVQLVQSGAEVKKPGASVKVSCKASGYTFTNYYMYWVRQAPGQCLEWMGGINPS QGGTNFNEKFKNRVTLTTDSSTSTAYMELSSLRSEDTAVYYCARRDYRFDLGFD YWGQGTTVTVSS |

TABLE 5B-continued

Sequences of PD-1 Heavy Chain Variable Regions (VH)

| SEQ ID NO | VH |
|---|---|
| 321 | EVQLLESGGGLVQPGGSLRLSCKASGYTFTNYYMYWVRQAPGKCLEWMGGINPS QGGTNFNEKFKNRVTLSTDSSKNTAYLQMNSLRAEDTAVYYCARRDYREDLGFD YWGQGTTVTVSS |
| 322 | EVQLVQSGAEVKKPGASVKVSCKASGYTFTNYYMYWVRQAPGQGLEWMGGINPS NGGTNFNEKFKNRVTLTTDSSTSTAYMELSSLRSEDTAVYYCARRDYRFDMGFD YWGQGTTVTVSS |
| 323 | EVQLVQSGAEVKKPGASVKVSCKASGYTFTNYYMYWVRQAPGQCLEWMGGINPS NGGTNFNEKFKNRVTLTTDSSTSTAYMELSSLRSEDTAVYYCARRDYRFDMGFD YWGQGTTVTVSS |
| 324 | EVQLVQSGAEVKKPGASVKVSCKASGYTFTNYYMYWVRQAPGQCLEWMGGINPS RGGTNFNEKFKNRVTLTTDSSTSTAYMELSSLRSEDTAVYYCARRDYRFDLGFD YWGQGTTVTVSS |
| 325 | EVQLVQSGAEVKKPGASVKVSCKASGYTFTNYYMYWVRQAPGQCLEWMGGINPS QGGTNFNEKFKNRVTLTTDSSTSTAYMELSSLRSEDTAVYYCARRDYRFDMGFD YWGQGTTVTVSS |
| 326 | EVQLVQSGAEVKKPGASVKVSCKASGYTFTNYYMYWVRQAPGQCLEWMGGINPS RGGTNFNEKFKNRVTLTTDSSTSTAYMELSSLRSEDTAVYYCARRDYRFDMGFD YWGQGTTVTVSS |
| 327 | EVQLVQSGAEVKKPGASVKVSCKASGYTFTNYYMYWVRQAPGQCLEWMGGINPS NGGTNFNEKFKNRVTLTTDSSTSTAYMELSSLRSEDTAVYYCARRDYREDLGFD YWGQGTTVTVSS |
| 328 | EVQLVESGGGLVQPGGSLRLSCAASGSIASIHAMGWVRQAPGKEREWVSVITWS GGITYYADSVKGRFTISRDNSKNTLYLQMNSLRAEDTAVYYCAGDKHQSSWYDY WGQGTLVTVSS |
| 329 | EVQLVESGGGLVQPGGSLRLSCAASGSIASIHAMGWVRQAPGKEREWVSVITWS GGITYYADSVKGRFTISRDNSKNTVYLQMNSLRAEDTAVYYCAGDKHQSSWYDY WGQGTLVTVSS |
| 330 | EVQLVESGGGLVQPGGSLRLSCAASGSIASIHAMGWVRQAPGKEREFVSVITWS GGITYYADSVKGRFTISRDNSKNTLYLQMNSLRAEDTAVYYCAGDKHQSSWYDY WGQGTLVTVSS |
| 331 | EVQLVESGGGLVQPGGSLRLSCAASGSIASIHAMGWVRQAPGKEREFVSVITWS GGITYYADSVKGRFTISRDNSKNTVYLQMNSLRAEDTAVYYCAGDKHQSSWYDY WGQGTLVTVSS |
| 332 | EVQLVESGGGLVQPGGSLRLSCAASGSIASIHAMGWVRQAPGKEREFVAVITWS GGITYYADSVKGRFTISRDNSKNIVYLQMNSLRAEDTAVYYCAGDKHQSSWYDY WGQGTLVTVSS |
| 333 | EVQLVESGGGLVQPGGSLRLSCAASGSIASIHAMGWVRQAPGKEREWVAVITWS GGITYYADSVKGRFTISRDNSKNTVYLQMNSLRAEDTAVYYCAGDKHQSSWYDY WGQGTLVTVSS |
| 334 | EVQLVESGGGLVQPGGSLRLSCAASGFAFSSYDMSWVRQAPGKGLDWVATISGG GRYTYYPDSVKGRFTISRDNSKNNLYLQMNSLRAEDTALYYCANRYGEAWFAYW GQGTLVTVSS |
| 738 | EVQLVESGGGLVQPGGSLRLSCAASGSIASIHAMGWVRQAPGKEREFVAVITWS GGITYYADSVKGRFTISRDNSKNTVYLQMNSLRPEDTAVYYCAGDKHQSSWYDY WGQGTLVTVSS |
| 739 | EVQLVESGGGLVQPGGSLRLSCAASGSIASIHAMGWVRQAPGKEREFVAVITWS GGITYYADSVKGRFTISRDNSKNTVYLQMNSLRPEDTALYYCAGDKHQSSWYDY WGQGTLVTVSS |
| 740 | EVQLVESGGGLVQPGGSLRLSCAASGSIASIHAMGWFRQAPGKEREFVAVITWS GGITYYADSVKGRFTISRDNSKNTVYLQMNSLRPEDTAVYYCAGDKHQSSWYDY WGQGTLVTVSS |
| 741 | EVQLVESGGGLVQPGGSLRLSCAASGSIASIHAMGWFRQAPGKEREFVAVITWS GGITYYADSVKGRFTISRDNSKNIVYLQMNSLRPEDTALYYCAGDKHQSSWYDY WGQGTLVTVSS |

TABLE 5B-continued

| Sequences of PD-1 Heavy Chain Variable Regions (VH) |
| --- |

| SEQ ID NO | VH |
| --- | --- |
| 742 | EVQLVQSGAEVKKPGASVKVSCKASGYTFTNYYMYWVRQAPGQGLEWMGGINPS RGGTNFNEKFKNRVTLTTDSSTSTAYMELSSLRSEDTAVYYCARRDYRFDLGFD YWGQGTTVTVSS |

VL Domains

In some embodiments, a binding protein provided herein comprises a first VL sequence selected from SEQ ID NOs: 298-300, 335-349, and 743-744 and a second VL sequence selected from SEQ ID NOs: 298-300, 335-349, and 743-744. In some embodiments, a binding protein provided herein comprises a first VL sequence selected from SEQ ID NOs: 298-300 and a second VL sequence selected from SEQ ID NOs: 335-349 and 743-744. In some embodiments, a binding protein provided herein comprises a first VL sequence comprising SEQ ID NO: 298 and a second VL sequence selected from SEQ ID NOs: 335-349 and 743-744. In some embodiments, a binding protein provided herein comprises a first VL sequence having at least about 80%, 90%, 91%, 92%, 93%, 94%, 95%, 96%, 97%, 98% or 99% identity to a VL sequence comprising SEQ ID NO: 298 and a second VL sequence selected from SEQ ID NOs: 335-349 and 743-744. In some embodiments, a binding protein provided herein comprises a first VL sequence comprising SEQ ID NO: 299 and a second VL sequence selected from SEQ ID NOs: 335-349 and 743-744. In some embodiments, a binding protein provided herein comprises a first VL sequence having at least about 80%, 90%, 91%, 92%, 93%, 94%, 95%, 96%, 97%, 98% or 99% identity to a VL sequence comprising SEQ ID NO: 299 and a second VL sequence selected from SEQ ID NOs: 335-349 and 743-744. In some embodiments, a binding protein provided herein comprises a first VL sequence comprising SEQ ID NO: 300 and a second VL sequence selected from SEQ ID NOs: 335-349 and 743-744. In some embodiments, a binding protein provided herein comprises a first VL sequence having at least about 80%, 90%, 91%, 92%, 93%, 94%, 95%, 96%, 97%, 98% or 99% identity to a VL sequence comprising SEQ ID NO: 300 and a second VL sequence selected from SEQ ID NOs: 335-349 and 743-744.

In some embodiments, a binding protein provided herein comprises a first VL sequence selected from SEQ ID NOs: 298-300, and a second VL sequence selected from SEQ ID NOs: 335-349 and 743-744, with up to 1, 2, 3, 4, 5, 6, 7, 8, 9, 10, 11, 12, 13, 14, 15, 16, 17, 18, 19, or 20 amino acid substitutions. In some embodiments, a binding protein provided herein comprises a first VL sequence comprising SEQ ID NO: 298 and a second VL sequence selected from SEQ ID NOs: 335-349 and 743-744, with up to 1, 2, 3, 4, 5, 6, 7, 8, 9, 10, 11, 12, 13, 14, 15, 16, 17, 18, 19, or 20 amino acid substitutions.

TABLE 6A

| Sequences of VEGF Light Chain Variable Regions (VL) | |
| --- | --- |
| SEQ ID NO | VL |
| 298 | DIQMTQSPSSLSASVGDRVTITCSASQDIS NYLNWYQQKPGKAPKVLIYFTSSLHSGVPS RFSGSGSGTDFTLTISSLQPEDFATYYCQQ YSTVPWTFGQGTKVEIK |
| 299 | DIQMTQSPSSLSASVGDRVTITCSASQDIS NYLNWYQQKPGKAPKVLIYFTSSLHSGVPS RFSGSGSGTDFTLTISSLQPEDFATYYCQQ YSTVPWTFGQGTKVEIKR |
| 300 | DIQMTQSPSSLSASVGDRVTITCSASQDIS NYLNWYQQKPGKAPKVLIYFTSSLHSGVPS RFSGSGSGTDFTLTISSLQPEDFATYYCQQ YSTVPWTFGCGIKVEIKR |

TABLE 6B

| Sequences of PD-1 Light Chain Variable Regions (VL) |
| --- |

| SEQ ID NO | VL |
| --- | --- |
| 335 | EIVLTQSPATLSLSPGERATLSCRASKGVSTSGYSYLHWYQQKPGQAPRLLIYLA SYLESGVPARFSGSGSGTDFTLTISSLEPEDFAVYYCQHSRDLPLTFGGGTKVEI K |
| 336 | EIVLTQSPATLSLSPGERATLSCRASKGVSTSGYSYLHWYQQKPGQAPRLLIYLA SYLESGVPARFSGSGSGTDFTLTISSLEPEDFAVYYCQHSRDLPLTFGGGTKVEI KR |
| 337 | EIVLTQSPATLSLSPGERATLSCRASKGVSTSGYSYLHWYQQKPGQAPRLLIYLA SYLESGVPARFSGSGSGTDFTLTISSLEPEDFAVYYCQHSRDLPLTFGCGTKVEI KR |
| 338 | EIVLTQSPATLSLSPGERATLSCRASKGVSTSGYSYLHWYQQKPGQAPRLLIYLA SYLESGVPARFSGSGSGTDFTLTISSLEPEDFAVYYCQHSRDLPLTFGGGTKVEI KSS |

TABLE 6B-continued

| SEQ ID NO | VL |
|---|---|
| | Sequences of PD-1 Light Chain Variable Regions (VL) |
| 339 | EIVLTQSPATLSLSPGERATLSCRASKGVSTSGYSYLHWYQQKPGQAPRLLIYLA<br>SYLESGVPARFSGSGSGTDFTLTISSLEPEDFAVYYCQHSRDLPLTFGCGTKVEI<br>K |
| 340 | EIVLTQSPATLSVSPGERATLSCRASKGVSTSGYSYLHWYQQKPGQAPRLLIYLA<br>SYLESGIPARFSGSGSGTEFTLTISSLQSEDFAVYYCQHSRDLPLTFGGGTKVEI<br>KR |
| 341 | EIVLTQSPATLSVSPGERATLSCRASKGVSTSGYSYLHWYQQKPGQAPRLLIYLA<br>SYLESGIPARFSGSGSGTEFTLTISSLQSEDFAVYYCQHSRDLPLTFGCGTKVEI<br>KR |
| 342 | EIVLTQSPSTLSLSPGERATLSCRASKGVSTSGYSYLHWYQQKPGQAPRLLIYLA<br>SYLESGVPARFSGSGSGTDFTLTISSLEPEDFAVYYCQHSRDLPLTFGGGTKVEI<br>KR |
| 343 | EIVLTQSPSTLSLSPGERATLSCRASKGVSTSGYSYLHWYQQKPGQAPRLLIYLA<br>SYLESGVPARFSGSGSGTDFTLTISGLEPEDFAVYYCQHSRDLPLTFGGGTKVEI<br>KR |
| 344 | EIVLTQSPSTLSLSPGERATLSCRASKGVSTSGYSYLHWYQQKPGQAPRLLIYLA<br>SYLESGVPARFSGSGSGTDFTLTISSLEPEDFAVYYCQHSRDLPLTFGCGTKVEI<br>KR |
| 345 | EIVLTQSPSTLSLSPGERATLSCRASKGVSTSGYSYLHWYQQKPGQAPRLLIYLA<br>SYLESGVPARFSGSGSGTDFTLTISGLEPEDFAVYYCQHSRDLPLTFGCGTKVEI<br>KR |
| 346 | DIQLTQSPSSLSASVGDRVTITCRASKGVSTSGYSYLHWYQQKPGKAPKLLIYLA<br>SYLESGVPSRFSGSGSGTDFTLTISSLQPEDFATYYCQHSRDLPLTFGGGTKVEI<br>KR |
| 347 | DIQLTQSPSSLSASVGDRVTITCRASKGVSTSGYSYLHWYQQKPGKAPKLLIYLA<br>SYLESGVPSRFSGSGSGTDFTLTISSLQPEDFATYYCQHSRDLPLTFGCGTKVEI<br>KR |
| 348 | EIVLTQSPSTLSLSPGERATLSCRASKGVSTSGYSYLHWYQQKPGQAPRLLIYLA<br>SYLESGVPARFSGSGSGTDFTLTISSLEPEDFAVYYCQHSRDLPLTFGGGTKVEI<br>K |
| 349 | DIQMTQSPSSMSASVGDRVTFTCRASQDINTYLSWFQQKPGKSPKTLIYRANRLV<br>SGVPSRFSGSGSGQDYTLTISSLQPEDMATYYCLQYDEFPLTFGAGTKLELKR |
| 743 | DIQLTQSPSSLSASVGDRVTITCRASKGVSTSGYSYLHWYQQKPGKAPKLLIYLA<br>SYLESGVPSRFSGSGSGTDFTLTISSLQPEDFATYYCQHSRDLPLTFGCGTKVEI<br>K |
| 744 | DIQLTQSPSSLSASVGDRVTITCRASKGVSTSGYSYLHWYQQKPGKAPKLLIYLA<br>SYLESGVPSRFSGSGSGTDFTLTISSLQPEDFATYYCQHSRDLPLTFGGGTKVEI<br>K |

VH-VL Combinations

In some embodiments the CDR-H1, CDR-H2, and CDR-H3 of the VH within a PD-1 binding region (anti-PD1 VH) comprise the amino acid sequences of (a) SEQ ID NOs: 445, 456, and 457, respectively; (b) SEQ ID NOs: 451, 458, and 459, respectively; or (c) SEQ ID NOs: 443, 460, and 457, respectively, and the CDR-L1, CDR-L2, and CDR-HL of the VL within a PD-1 binding region (anti-PD1 VL) comprise the amino acid sequences of (a) SEQ ID NOs: 448, 449, and 450, respectively; (b) SEQ ID NO: 454, SAS, and SEQ ID NO: 450, respectively; or (c) SEQ ID NOs: 448, 449, or 450, respectively, and the anti-PD1 VH and anti-PD1 VL have amino acid sequences that are at least 85% identical to that of: (a) SEQ ID NOs: 302 and 335, respectively; (b) SEQ ID NOs: 302 and 336, respectively; (c) SEQ ID NOs: 302 and 340, respectively; (d) SEQ ID NOs: 302 and 342, respectively; (e) SEQ ID NOs: 302 and 343, respectively; (f) SEQ ID NOs: 302 and 346, respectively; (g) SEQ ID NOs: 306 and 337, respectively; (h) SEQ ID NOs: 306 and 339, respectively; (i) SEQ ID NOs: 306 and 341, respectively; (j) SEQ ID NOs: 306 and 344, respectively; (k) SEQ ID NOs: 306 and 345, respectively; (l) SEQ ID NOs: 306 and 347, respectively; (m) SEQ ID NOs: 308 and 340, respectively; (n) SEQ ID NOs: 309 and 341, respectively; (o) SEQ ID NOs: 310 and 336, respectively; (p) SEQ ID NOs: 311 and 337, respectively; (q) SEQ ID NOs: 313 and 336, respectively; (r) SEQ ID NOs: 313 and 342, respectively; (s) SEQ ID NOs: 313 and 343, respectively; (t) SEQ ID NOs: 316 and 337, respectively; (u) SEQ ID NOs: 316 and 344, respectively; (v) SEQ ID NOs: 316 and 345, respectively; (w) SEQ ID NOs: 318 and 336, respectively; (x) SEQ ID NOs: 318 and 340, respectively; (y) SEQ ID NOs: 318 and 346, respectively; (z) SEQ ID NOs: 319 and 336, respectively; (aa) SEQ ID NOs: 319 and 340, respectively; (bb) SEQ ID NOs: 319 and 346, respectively; (cc) SEQ ID NOs: 320 and 337, respectively; (dd) SEQ ID NOs: 320 and 341, respectively; (ee) SEQ ID NOs: 320 and 347, respectively; (ff) SEQ ID NOs: 320 and 743, respectively; (gg) SEQ ID NOs: 321 and 337, respectively; (hh) SEQ ID NOs: 321 and 341, respectively; or (ii) SEQ ID NOs: 321 and 347, respectively. In some embodiments, the anti-PD1 VH and anti-PD1 VL have amino acid sequences of: (a) SEQ ID NOs: 302 and 335, respectively; (b) SEQ ID NOs: 302 and 336, respectively; (c) SEQ ID NOs: 302 and 340, respectively; (d) SEQ ID NOs: 302 and 342, respectively; (e) SEQ ID NOs: 302 and 343, respectively; (f) SEQ ID NOs: 302 and 346, respectively; (g) SEQ ID NOs: 306 and 337, respectively; (h) SEQ ID NOs: 306 and 339, respectively; (i) SEQ ID NOs: 306 and 341, respectively; (j) SEQ ID NOs: 306 and 344, respectively; (k) SEQ ID NOs: 306 and 345, respectively; (l) SEQ ID NOs: 306 and 347, respectively; (m) SEQ ID NOs: 308 and 340, respectively; (n) SEQ ID NOs: 309 and 341, respectively; (o) SEQ ID NOs: 310 and 336, respectively; (p) SEQ ID NOs: 311 and 337, respectively; (q) SEQ ID NOs: 313 and 336, respectively; (r) SEQ ID NOs: 313 and 342, respectively; (s) SEQ ID NOs: 313 and 343, respectively; (t) SEQ ID NOs: 316 and 337, respectively; (u) SEQ ID NOs: 316 and 344, respectively; (v) SEQ ID NOs: 316 and 345, respectively; (w) SEQ ID NOs: 318 and 336, respectively; (x) SEQ ID NOs: 318 and 340, respectively; (y) SEQ ID NOs: 318 and 346, respectively; (z) SEQ ID NOs: 319 and 336, respectively; (aa) SEQ ID NOs: 319 and 340, respectively; (bb) SEQ ID NOs: 319 and 346, respectively; (cc) SEQ ID NOs: 320 and 337, respectively; (dd) SEQ ID NOs: 320 and 341, respectively; (ee) SEQ ID NOs: 320 and 347, respectively; (ff) SEQ ID NOs: 320 and 743, respectively; (gg) SEQ ID NOs: 321 and 337, respectively; (hh) SEQ ID NOs: 321 and 341, respectively; or (ii) SEQ ID NOs: 321 and 347, respectively.

In some embodiments the CDR-H1, CDR-H2, and CDR-H3 of the VH within a PD-1 binding region (anti-PD1 VH) comprise the amino acid sequences of (a) SEQ ID NOs: 445, 456, and 447, respectively; (b) SEQ ID NOs: 451, 458, and 453, respectively; or (c) SEQ ID NOs: 443, 460, and 447, respectively, and the CDR-L1, CDR-L2, and CDR-HL of the VL within a PD-1 binding region (anti-PD1 VL) comprise the amino acid sequences of (a) SEQ ID NOs: 448, 449, and 450, respectively; (b) SEQ ID NO: 454, SAS, and SEQ ID NO: 450, respectively; or (c) SEQ ID NOs: 448, 449, or 450, respectively, and the anti-PD1 VH and anti-PD1 VL have amino acid sequences that are at least 85% identical to that of: (a) SEQ ID NOs: 303 and 336, respectively; (b) SEQ ID NOs: 325 and 347, respectively; or (c) SEQ ID NOs: 325 and 743, respectively. In some embodiments, the anti-PD1 VH and anti-PD1 VL have amino acid sequences of: (a) SEQ ID NOs: 303 and 336, respectively; (b) SEQ ID NOs: 325 and 347, respectively; or (c) SEQ ID NOs: 325 and 743, respectively.

In some embodiments the CDR-H1, CDR-H2, and CDR-H3 of the VH within a PD-1 binding region (anti-PD1 VH) comprise the amino acid sequences of (a) SEQ ID NOs: 445, 461, and 447, respectively; (b) SEQ ID NOs: 451, 462, and 453, respectively; or (c) SEQ ID NOs: 443, 463, and 447, respectively, and the CDR-L1, CDR-L2, and CDR-HL of the VL within a PD-1 binding region (anti-PD1 VL) comprise the amino acid sequences of (a) SEQ ID NOs: 448, 449, and 450, respectively; (b) SEQ ID NO: 454, SAS, and SEQ ID NO: 450, respectively; or (c) SEQ ID NOs: 448, 449, or 450, respectively, and the anti-PD1 VH and anti-PD1 VL have amino acid sequences that are at least 85% identical to that of: SEQ ID NOs: 326 and 347, respectively; or SEQ ID NOs: 326 and 743, respectively. In some embodiments, the anti-PD1 VH and anti-PD1 VL have amino acid sequences of: SEQ ID NOs: 326 and 347, respectively; or SEQ ID NOs: 326 and 743, respectively.

In some embodiments the CDR-H1, CDR-H2, and CDR-H3 of the VH within a PD-1 binding region (anti-PD1 VH) comprise the amino acid sequences of (a) SEQ ID NOs: 445, 446, and 457, respectively; (b) SEQ ID NOs: 451, 452, and 459, respectively; or (c) SEQ ID NOs: 443, 455, and 457, respectively, and the CDR-L1, CDR-L2, and CDR-HL of the VL within a PD-1 binding region (anti-PD1 VL) comprise the amino acid sequences of (a) SEQ ID NOs: 448, 449, and 450, respectively; (b) SEQ ID NO: 454, SAS, and SEQ ID NO: 450, respectively; or (c) SEQ ID NOs: 448, 449, or 450, respectively, and the anti-PD1 VH and anti-PD1 VL have amino acid sequences that are at least 85% identical to that of: SEQ ID NOs: 327 and 347, respectively; or SEQ ID NOs: 327 and 743, respectively. In some embodiments, the anti-PD1 VH and anti-PD1 VL have amino acid sequences of: SEQ ID NOs: 327 and 347, respectively; or SEQ ID NOs: 327 and 743, respectively.

In some embodiments the CDR-H1, CDR-H2, and CDR-H3 of the VH within a PD-1 binding region (anti-PD1 VH) comprise the amino acid sequences of (a) SEQ ID NOs: 445, 461, and 457, respectively; (b) SEQ ID NOs: 451, 462, and 459, respectively; or (c) SEQ ID NOs: 443, 463, and 457, respectively, and the CDR-L1, CDR-L2, and CDR-HL of the VL within a PD-1 binding region (anti-PD1 VL) comprise the amino acid sequences of (a) SEQ ID NOs: 448, 449, and 450, respectively; (b) SEQ ID NO: 454, SAS, and SEQ ID NO: 450, respectively; or (c) SEQ ID NOs: 448, 449, or 450, respectively, and the anti-PD1 VH and anti-PD1 VL have amino acid sequences that are at least 85% identical to that of: (a) SEQ ID NOs: 303 and 335, respectively; (b) SEQ ID NOs: 303 and 342, respectively; (c) SEQ ID NOs: 303 and 343, respectively; (d) SEQ ID NOs: 307 and 337, respectively; (e) SEQ ID NOs: 307 and 344, respectively; (f) SEQ ID NOs: 307 and 345, respectively; (g) SEQ ID NOs: 314 and 336, respectively; (h) SEQ ID NOs: 314 and 342, respectively; (i) SEQ ID NOs: 314 and 343, respectively; (j) SEQ ID NOs: 317 and 337, respectively; (k) SEQ ID NOs: 317 and 344, respectively; (l) SEQ ID NOs: 317 and 345, respectively; or (m) SEQ ID NOs: 324 and 347, respectively. In some embodiments, the anti-PD1 VH and anti-PD1 VL have amino acid sequences of: (a) SEQ ID NOs: 303 and 335, respectively; (b) SEQ ID NOs: 303 and 342, respectively; (c) SEQ ID NOs: 303 and 343, respectively; (d) SEQ ID NOs: 307 and 337, respectively; (e) SEQ ID NOs: 307 and 344, respectively; (f) SEQ ID NOs: 307 and 345, respectively; (g) SEQ ID NOs: 314 and 336, respectively; (h) SEQ ID NOs: 314 and 342, respectively; (i) SEQ ID NOs: 314 and 343, respectively; (j) SEQ ID NOs: 317 and 337, respectively; (k) SEQ ID NOs: 317 and 344, respectively; (l) SEQ ID NOs: 317 and 345, respectively; or (m) SEQ ID NOs: 324 and 347, respectively.

In some embodiments the CDR-H1, CDR-H2, and CDR-H3 of the VH within a PD-1 binding region (anti-PD1 VH) comprise the amino acid sequences of (a) SEQ ID NOs: 445, 446, and 447, respectively; (b) SEQ ID NOs: 451, 452, and 453, respectively; or (c) SEQ ID NOs: 443, 455, and 447, respectively, and the CDR-L1, CDR-L2, and CDR-HL of the VL within a PD-1 binding region (anti-PD1 VL) comprise the amino acid sequences of (a) SEQ ID NOs: 448, 449, and 450, respectively; (b) SEQ ID NO: 454, SAS, and SEQ ID NO: 450, respectively; or (c) SEQ ID NOs: 448, 449, or 450, respectively, and the anti-PD1 VH and anti-PD1 VL have amino acid sequences that are at least 85% identical to that of: (a) SEQ ID NOs: 301 and 335, respectively; (b) SEQ ID NOs: 301 and 336, respectively; (c) SEQ ID NOs: 301 and 342, respectively; (d) SEQ ID NOs: 301 and 343, respectively; (e) SEQ ID NOs: 301 and 348, respectively; (f) SEQ ID NOs: 305 and 337, respectively; (g) SEQ ID NOs: 305 and 344, respectively; (h) SEQ ID NOs: 305 and 345, respectively; (i) SEQ ID NOs: 312 and 335, respectively; (j) SEQ ID NOs: 312 and 336, respectively; (k) SEQ ID NOs: 312 and 342, respectively; (l) SEQ ID NOs: 312 and 343, respectively; (m) SEQ ID NOs: 315 and 337, respectively; (n) SEQ ID NOs: 315 and 344, respectively; (o) SEQ ID NOs: 315 and 345, respectively; (p) SEQ ID NOs: 322 and 346, respectively; (q) SEQ ID NOs: 323 and 347, respectively; or (r) SEQ ID NOs: 323 and 743, respectively. In some embodiments, the anti-PD1 VH and anti-PD1 VL have amino acid sequences of: (a) SEQ ID NOs: 301 and 335, respectively; (b) SEQ ID NOs: 301 and 336, respectively; (c) SEQ ID NOs: 301 and 342, respectively; (d) SEQ ID NOs: 301 and 343, respectively; (e) SEQ ID NOs: 301 and 348, respectively; (f) SEQ ID NOs: 305 and 337, respectively; (g) SEQ ID NOs: 305 and 344, respectively; (h) SEQ ID NOs: 305 and 345, respectively; (i) SEQ ID NOs: 312 and 335, respectively; (j) SEQ ID NOs: 312 and 336, respectively; (k) SEQ ID NOs: 312 and 342, respectively; (l) SEQ ID NOs: 312 and 343, respectively; (m) SEQ ID NOs: 315 and 337, respectively; (n) SEQ ID NOs: 315 and 344, respectively; (o) SEQ ID NOs: 315 and 345, respectively; (p) SEQ ID NOs: 322 and 346, respectively; (q) SEQ ID NOs: 323 and 347, respectively; or (r) SEQ ID NOs: 323 and 743, respectively.

In some embodiments, a binding protein provided herein comprises a first VH sequence selected from SEQ ID NO: 295 or SEQ ID NO: 296 and a second VH sequence selected from SEQ ID NOs: 301-334 and 738-742; and a first VL sequence selected from SEQ ID NOs: 298-300, and a second VL sequence selected from SEQ ID NOs: 335-349 and 743-744. In some embodiments, a binding protein provided herein comprises a first VH sequence comprising SEQ ID NO: 295 and a second VH sequence selected from SEQ ID NOs: 301-334 and 738-742; and a first VL sequence comprising SEQ ID NOs: 298 and a second VL sequence selected from SEQ ID NOs: 335-349 and 743-744.

In certain aspects, any of SEQ ID NO: 295 or SEQ ID NO: 296 can be combined with any of SEQ ID NOs: 298-300, and any of SEQ ID NOs: 301-334 and 738-742 can be combined with any of SEQ ID NOs: 335-349 and 743-744.

In some embodiments, a binding protein provided herein comprises a first VH sequence having at least about 80%, 90%, 91%, 92%, 93%, 94%, 95%, 96%, 97%, 98% or 99% identity to a VH sequence provided in selected from SEQ ID NO: 295 or SEQ ID NO: 296 and a second VH sequence selected from SEQ ID NOs: 301-334 and 738-742; and a first VL sequence having at least about 80%, 90%, 91%, 92%, 93%, 94%, 95%, 96%, 97%, 98% or 99% identity to a VL sequence provided in SEQ ID NOs: 298-300 and a second VL sequence selected from SEQ ID NOs: 335-349 and 743-744. In some embodiments, a binding protein provided herein comprises a first VH sequence having at least about 80%, 90%, 91%, 92%, 93%, 94%, 95%, 96%, 97%, 98% or 99% identity to a VH sequence comprising SEQ ID NO: 295 and a second VH sequence selected from SEQ ID NOs 301-334 and 738-742; and a first VL sequence having at least about 80%, 90%, 91%, 92%, 93%, 94%, 95%, 96%, 97%, 98% or 99% identity to a VL sequence comprising SEQ ID NO: 298 and a second VL sequence selected from SEQ ID NOs: 335-349 and 743-744.

In some embodiments, a binding protein provided herein comprises a first VH sequence provided in SEQ ID NO: 295 or SEQ ID NO: 296 and a second VH sequence selected from SEQ ID NOs: 301-334 and 738-742, with up to 1, 2, 3, 4, 5, 6, 7, 8, 9, 10, 11, 12, 13, 14, 15, 16, 17, 18, 19, or 20 amino acid substitutions; and a first VL sequence provided in SEQ ID NOs: 298-300 and a second VL sequence selected from SEQ ID NOs: 335-349 and 743-744, with up to 1, 2, 3, 4, 5, 6, 7, 8, 9, 10, 11, 12, 13, 14, 15, 16, 17, 18, 19, or 20 amino acid substitutions. In some embodiments, a binding protein provided herein comprises a first VH sequence comprising SEQ ID NO: 295 and a second VH sequence selected from SEQ ID NOs: 301-334 and 738-742, with up to 1, 2, 3, 4, 5, 6, 7, 8, 9, 10, 11, 12, 13, 14, 15, 16, 17, 18, 19, or 20 amino acid substitutions; and a first VL sequence comprising SEQ ID NO: 298 and a second VL sequence selected from SEQ ID NOs: 335-349 and 743-744, with up to 1, 2, 3, 4, 5, 6, 7, 8, 9, 10, 11, 12, 13, 14, 15, 16, 17, 18, 19, or 20 amino acid substitutions. In some embodiments, the amino acid substitutions are conservative amino acid substitutions. In some embodiments, the binding proteins described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining binding proteins.

Bispecific Formats

In some embodiments, the format of the bispecific binding proteins disclosed herein have any of the bispecific antibody formats described herein. In some embodiments, the format of the bispecific binding proteins disclosed herein is selected from the group consisting of (a) single chain Fv (scFv), (b) tandem scFv format of bispecific T cell engager (BiTE), (c) disulfide-linked diabody format of dual affinity retargeting (DART) bsAb, (d) tandem diabody (TandAb), (e) single-domain antibody (VHH), (f) conventional immunoglobulin G (IgG), (g) IgGs with additional binding units such as scFv, (h) IgGs with additional binding units such as VHH, (i) dual variable domain immunoglobulin (DVD-Ig), (j) quadromab bsAb, (k) knobs-into-holes (KiH) bsAb with a common light chain, (l) KiH-CrossMabCH1-CL, and (m) bsAb by controlled Fab arm exchange (cFAE). (see Shim et al. (2020) *Biomolecules* 26; 10(3):360.) In some embodiments, the format of the bispecific binding proteins disclosed herein is selected from the group consisting of IgG-scFv, IgG-VHH, and DVD-Ig. In some embodiments, the format of the bispecific binding proteins disclosed herein is IgG-scFv. In some embodiments, the format of the bispecific binding proteins disclosed herein is IgG-VHH. In some embodiments, the format of the bispecific binding proteins disclosed herein is DVD-Ig. In some embodiments, the format of the bispecific binding proteins disclosed herein is kiH-CrossMabCH1-CL.

In some embodiments, bispecific binding proteins comprise an scFv which is characterized one or more stabilizing features, e.g., particular amino acid residues or sequences. In some embodiments, the one or more stabilizing features in the scFv are an engineered disulfide bond between the contact surface of the VH and VL domains. In some embodiments, the disulfide bond is at the position of H44-L100 (Kabat numbering).

In some embodiments, the binding protein comprises a heavy chain as disclosed in Table 4A or Table 4B and a light chain disclosed in Table 4A or Table 4B. In some embodiments, a binding protein provided herein comprises a first VH sequence as listed in Table 5A and second VH sequence as listed in Table 5B. In some embodiments, a binding protein provided herein comprises a first VL sequence as listed in Table 6A and second VL sequence as listed in Table 6B. In some embodiments, a binding protein provided herein comprises a heavy chain constant region as listed in Table 7. In some embodiments, a binding protein provided herein comprises a light chain constant region as listed in Table 8. In some embodiments, a binding protein provided herein comprises scFv or VHH sequence as listed in Table 9. In some embodiments, a binding protein provided herein comprises a first VH sequence as listed in Table 5A and second VH sequence as listed in Table 5B; a first VL sequence as listed in Table 6A and second VL sequence as listed in Table 6B; a heavy chain constant region as listed in Table 7; a light chain constant region as listed in Table 8; and a scFv or VHH sequence as listed in Table 9.

In some embodiments, the format of the bispecific binding proteins disclosed herein is IgG-scFv. In some embodiments, the bispecific format comprises a first VH sequence (VH1) comprising any one of SEQ ID NO: 295 or SEQ ID NO: 296, a heavy chain constant region (CH(1-3)) comprising any one of SEQ ID NOs: 350-352, and a first linker comprising at least 90% sequence identity to GGGGSGGGGSGGGGSGGGGS (SEQ ID NO: 1030), a first VL sequence (VL1) comprising any one of SEQ ID NOs: 298-300, a second linker comprising at least 90% sequence identity to GGGGSGGGGSGGGGSGGGGS (SEQ ID NO: 1030), a second VH (VH2) sequence comprising any one of SEQ ID NOs: 301-334 and 738-742, a second VL sequence (VL2) comprising any one of SEQ ID NOs: 335-349 and 743-744, and a light chain constant domain (CL) comprising SEQ ID NO: 353.

In some embodiments, the bispecific format comprises a first VH sequence (VH1) comprising any one of SEQ ID NOs: 301-334 and 738-742, a heavy chain constant region (CH(1-3)) comprising any one of SEQ ID NOs: 350-352, and a first linker comprising at least 90% sequence identity to GGGGSGGGGSGGGGSGGGGS (SEQ ID NO: 1030), a first VL sequence (VL1) comprising any one of SEQ ID NOs: 298-300, a second linker comprising at least 90% sequence identity to GGGGSGGGGSGGGGSGGGGS (SEQ ID NO: 1030), a second VH (VH2) sequence comprising any one of SEQ ID NO: 295 or SEQ ID NO: 296, a second VL sequence (VL2) comprising any one of SEQ ID NOs: 335-349 and 743-744, and a light chain constant domain (CL) comprising SEQ ID NO: 353.

In some embodiments, the bispecific format comprises a first VH sequence (VHT) comprising any one of SEQ ID NOs: 295-296, 301-334, and 738-742, a heavy chain constant region (CH(1-3)) comprising any one of SEQ ID NOs: 350-352, and a first linker comprising at least 90% sequence identity to GGGGSGGGGSGGGGSGGGGS (SEQ ID NO: 1030), a scFv or VHH comprising any one of SEQ ID NOs: 354-430, a first VL sequence comprising any one of SEQ ID Nos: 298-300, and a light chain constant domain (CL) comprising SEQ ID NO: 353.

TABLE 7

Sequences of Exemplary Heavy Chain Constant Regions 1-3

| SEQ ID NO | CH1-3 |
|---|---|
| 350 | ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPEAAGG PSVFLFPPKPKDTLMISRTPEVTCVVVDVS HEDPEVKENWYVDGVEVHNAKIKPREEQYN STYRVVSVLIVLHQDWLNGKEYKCKVSNKA LPAPIEKTISKAKGQPREPQVYTLPPSRDE LTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| 351 | ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPEAAGG PSVFLFPPKPKDTLYITREPEVTCVVVDVS HEDPEVKENWYVDGVEVHNAKIKPREEQYN STYRVVSVLIVLHQDWLNGKEYKCKVSNKA LPAPIEKTISKAKGQPREPQVYTLPPSRDE LIKNQVSLICLVKGFYPSDIAVEWESNGQP ENNYKTTPPVLDSDGSFFLYSKLTVDKSRW QQGNVFSCSVMHEALHNHYTQKSLSLSPGK |
| 352 | ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPEAAGG PSVFLFPPKPKDTLMISRTPEVTCVVVDVS HEDPEVKENWYVDGVEVHNAKIKPREEQYN STYRVVSVLIVLHQDWLNGKEYKCKVSNKA LPAPIEKTISKAKGQPREPQVYTLPPSRDE LTKNQVSLTCLVKGFYPSDIAVEWESNGQP ENNYKTTPPVLDSDGSFFLYSKLTVDKSRW QQGNVFSCSVLHEALHSHYTQKSLSLSPGK |

TABLE 8

Sequence of Exemplary Light Constant Region

| SEQ ID NO | CL |
|---|---|
| 353 | RTVAAPSVFIFPPSDEQLKSGTASVVCLLNNFY PREAKVQWKVDNALQSGNSQESVTEQDSKDSTY SLSSTLILSKADYEKHKVYACEVTHQGLSSPVT KSENRGEC |

TABLE 9

Exemplary scFv and VHH Sequences

| SEQ ID NO | scFV |
|---|---|
| 354 | QVQLVQSGVEVKKPGASVKVSCKASGYTFTNYYMYWVRQAPGQGLEWMGGINPSNGG TNFNEKFKNRVTLTIDSSTTTAYMELKSLQFDDTAVYYCARRDYRFDMGFDYWGQGT TVTVSSGGGGSGGGGSGGGGSGGGGSEIVLTQSPATLSLSPGERATLSCRASKGVST |

TABLE 9-continued

Exemplary scFv and VHH Sequences

| SEQ ID NO | scFV |
|---|---|

SGYSYLHWYQQKPGQAPRLLIYLASYLESGVPARFSGSGSGTDFTLTISSLEPEDFA
VYYCQHSRDLPLTFGGGTKVEIKR

355    QVQLVQSGVEVKKPGASVKVSCKASGYTFTNYYMYWVRQAPGQGLEWMGGINPSQGG
       TNFNEKFKNRVTLTTDSSTTTAYMELKSLQFDDTAVYYCARRDYRFDLGFDYWGQGT
       TVTVSSGGGGSGGGGSGGGGSGGGGSEIVLTQSPATLSLSPGERATLSCRASKGVST
       SGYSYLHWYQQKPGQAPRLLIYLASYLESGVPARFSGSGSGTDFTLTISSLEPEDFA
       VYYCQHSRDLPLTFGGGTKVEIKR

356    QVQLVQSGVEVKKPGASVKVSCKASGYTFTNYYMYWVRQAPGQGLEWMGGINPSRGG
       TNFNEKFKNRVTLTTDSSTTTAYMELKSLQFDDTAVYYCARRDYRFDLGFDYWGQGT
       TVTVSSGGGGSGGGGSGGGGSGGGGSEIVLTQSPATLSLSPGERATLSCRASKGVST
       SGYSYLHWYQQKPGQAPRLLIYLASYLESGVPARFSGSGSGTDFTLTISSLEPEDFA
       VYYCQHSRDLPLTFGGGTKVEIKR

357    QVQLVQSGVEVKKPGASVKVSCKASGYTFTNYYMYWVRQAPGQCLEWMGGINPSNGG
       TNFNEKFKNRVTLTTDSSTTTAYMELKSLQFDDTAVYYCARRDYRFDMGFDYWGQGT
       TVTVSSGGGGSGGGGSGGGGSGGGGSEIVLTQSPATLSLSPGERATLSCRASKGVST
       SGYSYLHWYQQKPGQAPRLLIYLASYLESGVPARFSGSGSGTDFTLTISSLEPEDFA
       VYYCQHSRDLPLTFGCGTKVEIKR

358    QVQLVQSGVEVKKPGASVKVSCKASGYTFTNYYMYWVRQAPGQCLEWMGGINPSQGG
       TNFNEKFKNRVTLTTDSSTTTAYMELKSLQFDDTAVYYCARRDYRFDLGEDYWGQGT
       TVTVSSGGGGSGGGGSGGGGSGGGGSEIVLTQSPATLSLSPGERATLSCRASKGVST
       SGYSYLHWYQQKPGQAPRLLIYLASYLESGVPARFSGSGSGTDFTLTISSLEPEDFA
       VYYCQHSRDLPLTFGCGTKVEIKR

359    QVQLVQSGVEVKKPGASVKVSCKASGYTFTNYYMYWVRQAPGQCLEWMGGINPSRGG
       TNFNEKFKNRVTLTTDSSTTTAYMELKSLQFDDTAVYYCARRDYRFDLGFDYWGQGT
       TVTVSSGGGGSGGGGSGGGGSGGGGSEIVLTQSPATLSLSPGERATLSCRASKGVST
       SGYSYLHWYQQKPGQAPRLLIYLASYLESGVPARFSGSGSGTDFTLTISSLEPEDFA
       VYYCQHSRDLPLTFGCGTKVEIKR

360    EIVLTQSPATLSLSPGERATLSCRASKGVSTSGYSYLHWYQQKPGQAPRLLIYLASY
       LESGVPARFSGSGSGTDFTLTISSLEPEDFAVYYCQHSRDLPLTFGGGTKVEIKSSG
       GGGSGGGGSGGGGSGGGGSQVQLVQSGVEVKKPGASVKVSCKASGYTFTNYYMYWVR
       QAPGQGLEWMGGINPSQGGTNFNEKFKNRVTLTTDSSTTTAYMELKSLQFDDTAVYY
       CARRDYRFDLGFDYWGQGTTVTVSS

361    EIVLTQSPATLSLSPGERATLSCRASKGVSTSGYSYLHWYQQKPGQAPRLLIYLASY
       LESGVPARFSGSGSGTDFTLTISSLEPEDFAVYYCQHSRDLPLTFGCGTKVEIKGGG
       GSGGGGSGGGGSGGGGSQVQLVQSGVEVKKPGASVKVSCKASGYTFTNYYMYWVRQA
       PGQCLEWMGGINPSQGGTNFNEKFKNRVTLTTDSSTTTAYMELKSLQFDDTAVYYCA
       RRDYRFDLGFDYWGQGTTVTVSS

362    EVQLVESGGGLVQPGGSLRLSCAASGYTFTNYYMYWVRQAPGKGLEWMGGINPSQGG
       TNFNEKFKNRFTISRDNSKNTLYLQMNSLRAEDTAVYYCARRDYREDLGFDYWGQGT
       LVTVSSGGGGSGGGGSGGGGSGGGGSEIVLTQSPATLSVSPGERATLSCRASKGVST
       SGYSYLHWYQQKPGQAPRLLIYLASYLESGIPARFSGSGSGTEFTLTISSLQSEDFA
       VYYCQHSRDLPLTFGGGTKVEIKR

363    EVQLVESGGGLVQPGGSLRLSCAASGYTFTNYYMYWVRQAPGKCLEWMGGINPSQGG
       TNFNEKFKNRFTISRDNSKNTLYLQMNSLRAEDTAVYYCARRDYRFDLGEDYWGQGT
       LVTVSSGGGGSGGGGSGGGGSGGGGSEIVLTQSPATLSVSPGERATLSCRASKGVST
       SGYSYLHWYQQKPGQAPRLLIYLASYLESGIPARFSGSGSGTEFTLTISSLQSEDFA
       VYYCQHSRDLPLTFGCGTKVEIKR

364    QVQLVQSGVEVKKPGASVKVSCKASGYTFTNYYMYWVRQAPGQGLEWMGGINPSQGG
       TNFNEKFKNRVTLTTDSSTTTAYMELKSLQFDDTAVYYCARRDYRFDLGEDYWGQGT
       GVRVSSGGGGSGGGGSGGGGSGGGGSEIVLTQSPATLSLSPGERATLSCRASKGVST
       SGYSYLHWYQQKPGQAPRLLIYLASYLESGVPARFSGSGSGTDFTLTISSLEPEDFA
       VYYCQHSRDLPLTFGGGTKVEIKR

365    QVQLVQSGVEVKKPGASVKVSCKASGYTFTNYYMYWVRQAPGQCLEWMGGINPSQGG
       TNFNEKFKNRVTLTTDSSTTTAYMELKSLQFDDTAVYYCARRDYRFDLGEDYWGQGT
       GVRVSSGGGGSGGGGSGGGGSGGGGSEIVLTQSPATLSLSPGERATLSCRASKGVST
       SGYSYLHWYQQKPGQAPRLLIYLASYLESGVPARFSGSGSGTDFTLTISSLEPEDFA
       VYYCQHSRDLPLTFGCGTKVEIKR

366    QVQLVQSGVEVKKPGASVKVSCKASGYTFTNYYMYWVRQAPGQGLEWMGGINPSNGG
       TNFNEKFKNRVTLTTDSSTTTAYMELKSLRFDDTAVYYCARRDYRFDMGFDYWGQGT
       TVTVSSGGGGSGGGGSGGGGSGGGGSEIVLTQSPSTLSLSPGERATLSCRASKGVST
       SGYSYLHWYQQKPGQAPRLLIYLASYLESGVPARFSGSGSGTDFTLTISSLEPEDFA
       VYYCQHSRDLPLTFGGGTKVEIKR

TABLE 9-continued

Exemplary scFv and VHH Sequences

| SEQ ID NO | scFV |
|---|---|
| 367 | QVQLVQSGVEVKKPGASVKVSCKASGYTFTNYYMYWVRQAPGQGLEWMGGINPSNGG<br>TNFNEKFKNRVTLTTDSSTTTAYMELKSLRFDDTAVYYCARRDYRFDMGFDYWGQGT<br>TVTVSSGGGGSGGGGSGGGGSGGGGSEIVLTQSPATLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGGGTKVEIKR |
| 368 | QVQLVQSGVEVKKPGASVKVSCKASGYTFTNYYMYWVRQAPGQGLEWMGGINPSNGG<br>TNFNEKFKNRVTLTTDSSTTTAYMELKSLRFDDTAVYYCARRDYRFDMGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISGLEPEDFA<br>VYYCQHSRDLPLTFGGGTKVEIKR |
| 369 | QVQLVQSGVEVKKPGASVKVSCKASGYTFTNYYMYWVRQAPGQGLEWMGGINPSNGG<br>TNFNEKFKNRVTLTTDSSTTTAYMELKSLQFDDTAVYYCARRDYRFDMGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGGGTKVEIKR |
| 370 | QVQLVQSGVEVKKPGASVKVSCKASGYTFTNYYMYWVRQAPGQGLEWMGGINPSNGG<br>TNFNEKFKNRVTLITDSSTTTAYMELKSLQFDDTAVYYCARRDYRFDMGEDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISGLEPEDFA<br>VYYCQHSRDLPLTFGGGTKVEIKR |
| 371 | QVQLVQSGVEVKKPGASVKVSCKASGYTFTNYYMYWVRQAPGQGLEWMGGINPSQGG<br>TNFNEKFKNRVTLTTDSSTTTAYMELKSLRFDDTAVYYCARRDYRFDLGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGGGTKVEIKR |
| 372 | QVQLVQSGVEVKKPGASVKVSCKASGYTFTNYYMYWVRQAPGQGLEWMGGINPSQGG<br>TNFNEKFKNRVTLITDSSTTTAYMELKSLREDDTAVYYCARRDYRFDLGFDYWGQGT<br>TVTVSSGGGGSGGGGSGGGGSGGGGSEIVLTQSPATLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGGGTKVEIKR |
| 373 | QVQLVQSGVEVKKPGASVKVSCKASGYTFTNYYMYWVRQAPGQGLEWMGGINPSQGG<br>TNFNEKFKNRVTLTTDSSTTTAYMELKSLRFDDTAVYYCARRDYRFFFFDLGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISGLEPEDFA<br>VYYCQHSRDLPLTFGGGTKVEIKR |
| 374 | QVQLVQSGVEVKKPGASVKVSCKASGYTFTNYYMYWVRQAPGQGLEWMGGINPSQGG<br>TNFNEKFKNRVTLTTDSSTTTAYMELKSLQFDDTAVYYCARRDYRFDLGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGGGTKVEIKR |
| 375 | QVQLVQSGVEVKKPGASVKVSCKASGYTFTNYYMYWVRQAPGQGLEWMGGINPSQGG<br>TNFNEKFKNRVTLTTDSSTTTAYMELKSLQFDDTAVYYCARRDYRFDLGEDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISGLEPEDFA<br>VYYCQHSRDLPLTFGGGTKVEIKR |
| 376 | QVQLVQSGVEVKKPGASVKVSCKASGYTFTNYYMYWVRQAPGQGLEWMGGINPSRGG<br>TNFNEKFKNRVTLTTDSSTTTAYMELKSLRFDDTAVYYCARRDYRFDLGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGGGTKVEIKR |
| 377 | QVQLVQSGVEVKKPGASVKVSCKASGYTFTNYYMYWVRQAPGQGLEWMGGINPSRGG<br>TNFNEKFKNRVTLTTDSSTTTAYMELKSLRFDDTAVYYCARRDYRFDLGFDYWGQGT<br>TVTVSSGGGGSGGGGSGGGGSGGGGSEIVLTQSPATLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGGGTKVEIKR |
| 378 | QVQLVQSGVEVKKPGASVKVSCKASGYTFTNYYMYWVRQAPGQGLEWMGGINPSRGG<br>TNFNEKFKNRVTLTTDSSTTTAYMELKSLRFDDTAVYYCARRDYREDLGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISGLEPEDFA<br>VYYCQHSRDLPLTFGGGTKVEIKR |
| 379 | QVQLVQSGVEVKKPGASVKVSCKASGYTFTNYYMYWVRQAPGQGLEWMGGINPSRGG<br>TNFNEKFKNRVTLITDSSTTTAYMELKSLQFDDTAVYYCARRDYRFDLGFDYWGQGT<br>TVTVSSGGGGSGGGGSGGGGSGGGGSEIVLTQSPSTLSLSPGERATLSCRASKGVST |

TABLE 9-continued

Exemplary scFv and VHH Sequences

| SEQ ID NO | scFV |
|---|---|
| | SGYSYLHWYQQKPGQAPRLLIYLASYLESGVPARFSGSGSGTDFTLTISSLEPEDFA<br>VYYCQHSRDLPLTFGGGTKVEIKR |
| 380 | QVQLVQSGVEVKKPGASVKVSCKASGYTFTNYYMYWVRQAPGQGLEWMGGINPSRGG<br>TNFNEKFKNRVTLTTDSSTTTAYMELKSLQFDDTAVYYCARRDYREDLGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGGGTKVEIKR |
| 381 | QVQLVQSGVEVKKPGASVKVSCKASGYTFTNYYMYWVRQAPGQCLEWMGGINPSNGG<br>TNFNEKFKNRVTLTTDSSTTTAYMELKSLRFDDTAVYYCARRDYRFDMGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGCGTKVEIKR |
| 382 | QVQLVQSGVEVKKPGASVKVSCKASGYTFTNYYMYWVRQAPGQCLEWMGGINPSNGG<br>TNFNEKFKNRVTLTTDSSTTTAYMELKSLRFDDTAVYYCARRDYRFDMGFDYWGQGT<br>TVTVSSGGGGSGGGGSGGGGSGGGGSEIVLTQSPATLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGCGTKVEIKR |
| 383 | QVQLVQSGVEVKKPGASVKVSCKASGYTFTNYYMYWVRQAPGQCLEWMGGINPSNGG<br>TNFNEKFKNRVTLTTDSSTTTAYMELKSLREDDTAVYYCARRDYRFDMGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISGLEPEDFA<br>VYYCQHSRDLPLTFGCGTKVEIKR |
| 384 | QVQLVQSGVEVKKPGASVKVSCKASGYTFTNYYMYWVRQAPGQCLEWMGGINPSNGG<br>TNFNEKFKNRVTLTTDSSTTTAYMELKSLQFDDTAVYYCARRDYRFDMGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGCGTKVEIKR |
| 385 | QVQLVQSGVEVKKPGASVKVSCKASGYTFTNYYMYWVRQAPGQCLEWMGGINPSNGG<br>TNFNEKFKNRVTLTIDSSTTTAYMELKSLQFDDTAVYYCARRDYRFDMGEDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISGLEPEDFA<br>VYYCQHSRDLPLTFGCGTKVEIKR |
| 386 | QVQLVQSGVEVKKPGASVKVSCKASGYTFTNYYMYWVRQAPGQCLEWMGGINPSQGG<br>TNFNEKFKNRVTLTTDSSTTTAYMELKSLRFDDTAVYYCARRDYRFDLGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGCGTKVEIKR |
| 387 | QVQLVQSGVEVKKPGASVKVSCKASGYTFTNYYMYWVRQAPGQCLEWMGGINPSQGG<br>TNFNEKFKNRVTLTTDSSTTTAYMELKSLRFDDTAVYYCARRDYRFDLGFDYWGQGT<br>TVTVSSGGGGSGGGGSGGGGSGGGGSEIVLTQSPATLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGCGTKVEIKR |
| 388 | QVQLVQSGVEVKKPGASVKVSCKASGYTFTNYYMYWVRQAPGQCLEWMGGINPSQGG<br>TNFNEKFKNRVTLTTDSSTTTAYMELKSLRFDDTAVYYCARRDYRFDLGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISGLEPEDFA<br>VYYCQHSRDLPLTFGCGTKVEIKR |
| 389 | QVQLVQSGVEVKKPGASVKVSCKASGYTFTNYYMYWVRQAPGQCLEWMGGINPSQGG<br>TNFNEKFKNRVTLTTDSSTTTAYMELKSLQFDDTAVYYCARRDYREDLGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGCGTKVEIKR |
| 390 | QVQLVQSGVEVKKPGASVKVSCKASGYTFTNYYMYWVRQAPGQCLEWMGGINPSQGG<br>TNFNEKFKNRVTLTTDSSTTTAYMELKSLQFDDTAVYYCARRDYREDLGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISGLEPEDFA<br>VYYCQHSRDLPLTFGCGTKVEIKR |
| 391 | QVQLVQSGVEVKKPGASVKVSCKASGYTFTNYYMYWVRQAPGQCLEWMGGINPSRGG<br>TNFNEKFKNRVTLTTDSSTTTAYMELKSLRFDDTAVYYCARRDYRFDLGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGCGTKVEIKR |

TABLE 9-continued

Exemplary scFv and VHH Sequences

| SEQ ID NO | scFV |
|---|---|
| 392 | QVQLVQSGVEVKKPGASVKVSCKASGYTFTNYYMYWVRQAPGQCLEWMGGINPSRGG<br>TNFNEKFKNRVTLTTDSSTTTAYMELKSLREDDTAVYYCARRDYREDLGFDYWGQGT<br>TVTVSSGGGGSGGGGSGGGGSGGGGSEIVLTQSPATLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGCGTKVEIKR |
| 393 | QVQLVQSGVEVKKPGASVKVSCKASGYTFTNYYMYWVRQAPGQCLEWMGGINPSRGG<br>TNFNEKFKNRVTLTTDSSTTTAYMELKSLRFDDTAVYYCARRDYRFDLGEDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISGLEPEDFA<br>VYYCQHSRDLPLTFGCGTKVEIKR |
| 394 | QVQLVQSGVEVKKPGASVKVSCKASGYTFTNYYMYWVRQAPGQCLEWMGGINPSRGG<br>TNFNEKFKNRVTLTTDSSTTTAYMELKSLQFDDTAVYYCARRDYRFDLGFDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGCGIKVEIKR |
| 395 | QVQLVQSGVEVKKPGASVKVSCKASGYTFTNYYMYWVRQAPGQCLEWMGGINPSRGG<br>TNFNEKFKNRVTLTTDSSTTTAYMELKSLQFDDTAVYYCARRDYRFDLGEDYWGQGT<br>TVTVSSGGGGSGGGGSGGGGSGGGGSEIVLTQSPSTLSLSPGERATLSCRASKGVST<br>SGYSYLHWYQQKPGQAPRLLIYLASYLESGVPARFSGSGSGTDFTLTISGLEPEDFA<br>VYYCQHSRDLPLIFGCGTKVEIKR |
| 396 | QVQLVQSGVEVKKPGASVKVSCKASGYTFTNYYMYWVRQAPGQGLEWMGGINPSQGG<br>TNFNEKFKNRVTLTTDSSTTTAYMELKSLQFDDTAVYYCARRDYRFDLGFDYWGQGT<br>TVTVSSGGGGSGGGGSGGGGSGGGGSEIVLTQSPATLSVSPGERATLSCRASKGVST<br>SGYSYLHWYQQKPGQAPRLLIYLASYLESGIPARFSGSGSGTEFTLTISSLQSEDFA<br>VYYCQHSRDLPLIFGGGTKVEIKR |
| 397 | QVQLVQSGVEVKKPGASVKVSCKASGYTFTNYYMYWVRQAPGQGLEWMGGINPSQGG<br>TNFNEKFKNRVTLTTDSSTTTAYMELKSLQFDDTAVYYCARRDYRFDLGFDYWGQGT<br>TVTVSSGGGGSGGGGSGGGGSGGGGSDIQLTQSPSSLSASVGDRVTITCRASKGVST<br>SGYSYLHWYQQKPGKAPKLLIYLASYLESGVPSRFSGSGSGTDFTLTISSLQPEDFA<br>TYYCQHSRDLPLTFGGGTKVEIKR |
| 398 | EVQLVQSGAEVKKPGASVKVSCKASGYTFTNYYMYWVRQAPGQGLEWMGGINPSQGG<br>TNFNEKFKNRVTLTTDSSTSTAYMELSSLRSEDTAVYYCARRDYRFDLGEDYWGQGT<br>TVTVSSGGGGSGGGGSGGGGSGGGGSEIVLTQSPATLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGGGTKVEIKR |
| 399 | EVQLVQSGAEVKKPGASVKVSCKASGYTFTNYYMYWVRQAPGQGLEWMGGINPSQGG<br>TNFNEKFKNRVTLTTDSSTSTAYMELSSLRSEDTAVYYCARRDYREDLGFDYWGQGT<br>TVTVSSGGGGSGGGGSGGGGSGGGGSEIVLTQSPATLSVSPGERATLSCRASKGVST<br>SGYSYLHWYQQKPGQAPRLLIYLASYLESGIPARFSGSGSGTEFTLTISSLQSEDFA<br>VYYCQHSRDLPLTFGGGTKVEIKR |
| 400 | EVQLVQSGAEVKKPGASVKVSCKASGYTFTNYYMYWVRQAPGQGLEWMGGINPSQGG<br>TNFNEKFKNRVTLTTDSSTSTAYMELSSLRSEDTAVYYCARRDYREDLGFDYWGQGT<br>TVTVSSGGGGSGGGGSGGGGSGGGGSDIQLTQSPSSLSASVGDRVTITCRASKGVST<br>SGYSYLHWYQQKPGKAPKLLIYLASYLESGVPSRFSGSGSGTDFTLTISSLQPEDFA<br>TYYCQHSRDLPLTFGGGTKVEIKR |
| 401 | EVQLLESGGGLVQPGGSLRLSCKASGYTFTNYYMYWVRQAPGKGLEWMGGINPSQGG<br>TNFNEKFKNRVTLSTDSSKNTAYLQMNSLRAEDTAVYYCARRDYRFDLGEDYWGQGT<br>TVTVSSGGGGSGGGGSGGGGSGGGGSEIVLTQSPATLSLSPGERATLSCRASKGVST<br>SGYSYLHWYQQKPGQAPRLLIYLASYLESGVPARFSGSGSGTDFTLTISSLEPEDFA<br>VYYCQHSRDLPLTFGGGTKVEIKR |
| 402 | EVQLLESGGGLVQPGGSLRLSCKASGYTFTNYYMYWVRQAPGKGLEWMGGINPSQGG<br>TNFNEKFKNRVTLSTDSSKNTAYLQMNSLRAEDTAVYYCARRDYRFDLGEDYWGQGT<br>TVTVSSGGGGSGGGGSGGGGSGGGGSEIVLTQSPATLSVSPGERATLSCRASKGVST<br>SGYSYLHWYQQKPGQAPRLLIYLASYLESGIPARFSGSGSGTEFTLTISSLQSEDFA<br>VYYCQHSRDLPLTFGGGTKVEIKR |
| 403 | EVQLLESGGGLVQPGGSLRLSCKASGYTFTNYYMYWVRQAPGKGLEWMGGINPSQGG<br>TNFNEKFKNRVTLSTDSSKNTAYLQMNSLRAEDTAVYYCARRDYRFDLGEDYWGQGT<br>TVTVSSGGGGSGGGGSGGGGSGGGGSDIQLTQSPSSLSASVGDRVTITCRASKGVST<br>SGYSYLHWYQQKPGKAPKLLIYLASYLESGVPSRFSGSGSGTDFTLTISSLQPEDFA<br>TYYCQHSRDLPLTFGGGTKVEIKR |
| 404 | QVQLVQSGVEVKKPGASVKVSCKASGYTFTNYYMYWVRQAPGQCLEWMGGINPSQGG<br>TNFNEKFKNRVTLTTDSSTTTAYMELKSLQFDDTAVYYCARRDYRFDLGFDYWGQGT<br>TVTVSSGGGGSGGGGSGGGGSGGGGSEIVLTQSPATLSVSPGERATLSCRASKGVST |

TABLE 9-continued

Exemplary scFv and VHH Sequences

| SEQ ID NO | scFV |
|---|---|
| | SGYSYLHWYQQKPGQAPRLLIYLASYLESGIPARFSGSGSGTEFTLTISSLQSEDFA VYYCQHSRDLPLTFGCGTKVEIKR |
| 405 | QVQLVQSGVEVKKPGASVKVSCKASGYTFTNYYMYWVRQAPGQCLEWMGGINPSQGG TNFNEKFKNRVTLTTDSSTTTAYMELKSLQFDDTAVYYCARRDYRFDLGFDYWGQGT TVTVSSGGGGSGGGGSGGGGSGGGGSDIQLTQSPSSLSASVGDRVTITCRASKGVST SGYSYLHWYQQKPGKAPKLLIYLASYLESGVPSRFSGSGSGTDFTLTISSLQPEDFA TYYCQHSRDLPLTFGCGTKVEIKR |
| 406 | EVQLVQSGAEVKKPGASVKVSCKASGYTFTNYYMYWVRQAPGQCLEWMGGINPSQGG TNFNEKFKNRVTLITDSSTSTAYMELSSLRSEDTAVYYCARRDYRFDLGFDYWGQGT TVTVSSGGGGSGGGGSGGGGSGGGGSEIVLTQSPATLSLSPGERATLSCRASKGVST SGYSYLHWYQQKPGQAPRLLIYLASYLESGVPARFSGSGSGTDFTLTISSLEPEDFA VYYCQHSRDLPLTFGCGTKVEIKR |
| 407 | EVQLVQSGAEVKKPGASVKVSCKASGYTFTNYYMYWVRQAPGQCLEWMGGINPSQGG TNFNEKFKNRVTLTTDSSTSTAYMELSSLRSEDTAVYYCARRDYREDLGFDYWGQGT TVTVSSGGGGSGGGGSGGGGSGGGGSEIVLTQSPATLSVSPGERATLSCRASKGVST SGYSYLHWYQQKPGQAPRLLIYLASYLESGIPARFSGSGSGTEFTLTISSLQSEDFA VYYCQHSRDLPLTFGCGTKVEIKR |
| 408 | EVQLVQSGAEVKKPGASVKVSCKASGYTFTNYYMYWVRQAPGQCLEWMGGINPSQGG TNFNEKFKNRVTLTTDSSTSTAYMELSSLRSEDTAVYYCARRDYRFDLGFDYWGQGT TVTVSSGGGGSGGGGSGGGGSGGGGSDIQLTQSPSSLSASVGDRVTITCRASKGVST SGYSYLHWYQQKPGKAPKLLIYLASYLESGVPSRFSGSGSGTDFTLTISSLQPEDFA TYYCQHSRDLPLTFGCGTKVEIKR |
| 409 | EVQLLESGGGLVQPGGSLRLSCKASGYTFTNYYMYWVRQAPGKCLEWMGGINPSQGG TNFNEKFKNRVTLSTDSSKNTAYLQMNSLRAEDTAVYYCARRDYRFDLGFDYWGQGT TVTVSSGGGGSGGGGSGGGGSGGGGSEIVLTQSPATLSLSPGERATLSCRASKGVST SGYSYLHWYQQKPGQAPRLLIYLASYLESGVPARFSGSGSGTDFTLTISSLEPEDFA VYYCQHSRDLPLTFGCGTKVEIKR |
| 410 | EVQLLESGGGLVQPGGSLRLSCKASGYTFTNYYMYWVRQAPGKCLEWMGGINPSQGG TNFNEKFKNRVTLSTDSSKNTAYLQMNSLRAEDTAVYYCARRDYRFDLGFDYWGQGT TVTVSSGGGGSGGGGSGGGGSGGGGSEIVLTQSPATLSVSPGERATLSCRASKGVST SGYSYLHWYQQKPGQAPRLLIYLASYLESGIPARFSGSGSGTEFTLTISSLQSEDFA VYYCQHSRDLPLTFGCGTKVEIKR |
| 411 | EVQLLESGGGLVQPGGSLRLSCKASGYTFTNYYMYWVRQAPGKCLEWMGGINPSQGG TNFNEKFKNRVTLSTDSSKNTAYLQMNSLRAEDTAVYYCARRDYRFDLGFDYWGQGT TVTVSSGGGGSGGGGSGGGGSGGGGSDIQLTQSPSSLSASVGDRVTITCRASKGVST SGYSYLHWYQQKPGKAPKLLIYLASYLESGVPSRFSGSGSGTDFTLTISSLQPEDFA TYYCQHSRDLPLTFGCGTKVEIKR |
| 412 | EIVLTQSPATLSLSPGERATLSCRASKGVSTSGYSYLHWYQQKPGQAPRLLIYLASY LESGVPARFSGSGSGIDFTLTISSLEPEDFAVYYCQHSRDLPLTFGGGTKVEIKGGG GSGGGGSGGGGSGGGGSQVQLVQSGVEVKKPGASVKVSCKASGYTFTNYYMYWVRQA PGQGLEWMGGINPSNGGTNFNEKFKNRVTLTIDSSTTTAYMELKSLQFDDTAVYYCA RRDYRFDMGFDYWGQGTTVTVSS |
| 413 | EIVLTQSPATLSLSPGERATLSCRASKGVSTSGYSYLHWYQQKPGQAPRLLIYLASY LESGVPARFSGSGSGTDFTLTISSLEPEDFAVYYCQHSRDLPLTFGGGTKVEIKGGG GSGGGGSGGGGSGGGGSQVQLVQSGVEVKKPGASVKVSCKASGYTFTNYYMYWVRQA PGQGLEWMGGINPSRGGTNFNEKFKNRVTLTTDSSTTTAYMELKSLQFDDTAVYYCA RRDYRFDLGFDYWGQGTTVTVSS |
| 414 | EIVLTQSPATLSLSPGERATLSCRASKGVSTSGYSYLHWYQQKPGQAPRLLIYLASY LESGVPARFSGSGSGTDFTLTISSLEPEDFAVYYCQHSRDLPLTFGGGTKVEIKGGG GSGGGGSGGGGSGGGGSQVQLVQSGVEVKKPGASVKVSCKASGYTFTNYYMYWVRQA PGQGLEWMGGINPSNGGTNFNEKFKNRVTLTTDSSTTTAYMELKSLRFDDTAVYYCA RRDYRFDMGFDYWGQGTTVTVSS |
| 415 | EIVLTQSPSTLSLSPGERATLSCRASKGVSTSGYSYLHWYQQKPGQAPRLLIYLASY LESGVPARFSGSGSGTDFTLTISSLEPEDFAVYYCQHSRDLPLTFGGGTKVEIKGGG GSGGGGSGGGGSGGGGSQVQLVQSGVEVKKPGASVKVSCKASGYTFTNYYMYWVRQA PGQGLEWMGGINPSNGGTNFNEKFKNRVTLTTDSSTTTAYMELKSLQFDDTAVYYCA RRDYRFDMGFDYWGQGTTVTVSS |
| 416 | EVQLVQSGAEVKKPGASVKVSCKASGYTFTNYYMYWVRQAPGQGLEWMGGINPSNGG TNFNEKFKNRVTLTTDSSTSTAYMELSSLRSEDTAVYYCARRDYRFDMGEDYWGQGT TVTVSSGGGGSGGGGSGGGGSGGGGSDIQLTQSPSSLSASVGDRVTITCRASKGVST SGYSYLHWYQQKPGKAPKLLIYLASYLESGVPSRFSGSGSGTDFTLTISSLQPEDFA TYYCQHSRDLPLTFGGGTKVEIKR |

TABLE 9-continued

Exemplary scFv and VHH Sequences

| SEQ ID NO | scFV |
|---|---|
| 417 | EVQLVQSGAEVKKPGASVKVSCKASGYTFTNYYMYWVRQAPGQCLEWMGGINPSNGG<br>TNFNEKFKNRVTLTTDSSTSTAYMELSSLRSEDTAVYYCARRDYRFDMGEDYWGQGT<br>TVTVSSGGGGSGGGGSGGGGSGGGGSDIQLTQSPSSLSASVGDRVTITCRASKGVST<br>SGYSYLHWYQQKPGKAPKLLIYLASYLESGVPSRFSGSGSGTDFTLTISSLQPEDFA<br>TYYCQHSRDLPLIFGCGTKVEIKR |
| 418 | EVQLVQSGAEVKKPGASVKVSCKASGYTFTNYYMYWVRQAPGQCLEWMGGINPSRGG<br>TNFNEKFKNRVTLTTDSSTSTAYMELSSLRSEDTAVYYCARRDYRFDLGEDYWGQGT<br>TVTVSSGGGGSGGGGSGGGGSGGGGSDIQLTQSPSSLSASVGDRVTITCRASKGVST<br>SGYSYLHWYQQKPGKAPKLLIYLASYLESGVPSRFSGSGSGTDFTLTISSLQPEDFA<br>TYYCQHSRDLPLTFGCGTKVEIKR |
| 419 | EVQLVQSGAEVKKPGASVKVSCKASGYTFTNYYMYWVRQAPGQCLEWMGGINPSQGG<br>TNFNEKFKNRVTLTTDSSTSTAYMELSSLRSEDTAVYYCARRDYRFDMGFDYWGQGT<br>TVTVSSGGGGSGGGGSGGGGSGGGGSDIQLTQSPSSLSASVGDRVTITCRASKGVST<br>SGYSYLHWYQQKPGKAPKLLIYLASYLESGVPSRFSGSGSGTDFTLTISSLQPEDFA<br>TYYCQHSRDLPLTFGCGTKVEIKR |
| 420 | EVQLVQSGAEVKKPGASVKVSCKASGYTFTNYYMYWVRQAPGQCLEWMGGINPSRGG<br>TNFNEKFKNRVTLTTDSSTSTAYMELSSLRSEDTAVYYCARRDYRFDMGFDYWGQGT<br>TVTVSSGGGGSGGGGSGGGGSGGGGSDIQLTQSPSSLSASVGDRVTITCRASKGVST<br>SGYSYLHWYQQKPGKAPKLLIYLASYLESGVPSRFSGSGSGTDFTLTISSLQPEDFA<br>TYYCQHSRDLPLTFGCGTKVEIKR |
| 421 | EVQLVQSGAEVKKPGASVKVSCKASGYTFTNYYMYWVRQAPGQCLEWMGGINPSNGG<br>TNFNEKFKNRVTLTTDSSTSTAYMELSSLRSEDTAVYYCARRDYRFDLGFDYWGQGT<br>TVTVSSGGGGSGGGGSGGGGSGGGGSDIQLTQSPSSLSASVGDRVTITCRASKGVST<br>SGYSYLHWYQQKPGKAPKLLIYLASYLESGVPSRFSGSGSGTDFTLTISSLQPEDFA<br>TYYCQHSRDLPLTFGCGTKVEIKR |
| 422 | EVQLVESGGGLVQPGGSLRLSCAASGYTFTNYGMNWVRQAPGKGLEWVGWINTYTGE<br>PTYAADFKRRFTFSLDISKSTAYLQMNSLRAEDTAVYYCAKYPHYYGSSHWYFDVWG<br>QGTLVTVSSGGGGSGGGGSGGGGSGGGGSDIQMTQSPSSLSASVGDRVTITCSASQD<br>ISNYLNWYQQKPGKAPKVLIYFTSSLHSGVPSRESGSGSGTDFTLTISSLQPEDFAT<br>YYCQQYSTVPWTFGQGTKVEIKR |
| 423 | EVQLVESGGGLVQPGGSLRLSCAASGYTFTNYGMNWVRQAPGKCLEWVGWINTYTGE<br>PTYAADFKRRFTFSLDTSKSTAYLQMNSLRAEDTAVYYCAKYPHYYGSSHWYFDVWG<br>QGTLVTVSSGGGGSGGGGSGGGGSGGGGSDIQMTQSPSSLSASVGDRVTITCSASQD<br>ISNYLNWYQQKPGKAPKVLIYFTSSLHSGVPSRFSGSGSGTDFTLTISSLQPEDFAT<br>YYCQQYSTVPWTFGCGTKVEIKR |
| 424 | EVQLVESGGGLVQPGGSLRLSCAASGSIASIHAMGWVRQAPGKEREWVSVITWSGGI<br>TYYADSVKGRFTISRDNSKNTLYLQMNSLRAEDTAVYYCAGDKHQSSWYDYWGQGTL<br>VTVSS |
| 425 | EVQLVESGGGLVQPGGSLRLSCAASGSIASIHAMGWVRQAPGKEREWVSVITWSGGI<br>TYYADSVKGRFTISRDNSKNIVYLQMNSLRAEDTAVYYCAGDKHQSSWYDYWGQGTL<br>VTVSS |
| 426 | EVQLVESGGGLVQPGGSLRLSCAASGSIASIHAMGWVRQAPGKEREFVSVITWSGGI<br>TYYADSVKGRFTISRDNSKNTLYLQMNSLRAEDTAVYYCAGDKHQSSWYDYWGQGTL<br>VTVSS |
| 427 | EVQLVESGGGLVQPGGSLRLSCAASGSIASIHAMGWVRQAPGKEREFVSVITWSGGI<br>TYYADSVKGRFTISRDNSKNTVYLQMNSLRAEDTAVYYCAGDKHQSSWYDYWGQGTL<br>VTVSS |
| 428 | EVQLVESGGGLVQPGGSLRLSCAASGSIASIHAMGWVRQAPGKEREFVAVITWSGGI<br>TYYADSVKGRFTISRDNSKNTVYLQMNSLRAEDTAVYYCAGDKHQSSWYDYWGQGTL<br>VTVSS |
| 429 | EVQLVESGGGLVQPGGSLRLSCAASGSIASIHAMGWVRQAPGKEREWVAVITWSGGI<br>TYYADSVKGRFTISRDNSKNIVYLQMNSLRAEDTAVYYCAGDKHQSSWYDYWGQGTL<br>VTVSS |
| 430 | EVQLVESGGGLVQPGGSLRLSCAASGFAFSSYDMSWVRQAPGKGLDWVATISGGGRY<br>TYYPDSVKGRFTISRDNSKNNLYLQMNSLRAEDTALYYCANRYGEAWFAYWGQGTLV<br>TVSSGGGGSGGGGSGGGGSGGGGSDIQMTQSPSSMSASVGDRVTFTCRASQDINTYL<br>SWFQQKPGKSPKTLIYRANRLVSGVPSRESGSGSGQDYTLTISSLQPEDMATYYCLQ<br>YDEFPLTFGAGTKLELKR |

Fc Modifications

Binding proteins (e.g., PD-1 binding proteins or bispecific PD-1/VEGF binding proteins) described herein typically comprise an immunoglobulin Fc region. Fc regions typically comprise one or more Fe polypeptides, such as a first Fc polypeptide and a second Fc polypeptide. An IgG Fc polypeptide typically contains two constant heavy domains (CH2 and CH-3) and a hinge region connected to the CH2 domain. Typical Fc regions comprise two Fc polypeptides which dimerize with one another; however, an Fc region may have a single Fc polypeptide or more than two Fc polypeptides, e.g., as may be present in some antibody formats.

In some embodiments, the binding proteins described herein comprise an IgG1 Fc region (e.g., human IgG1 Fc region), that is, except for having particular residue(s) at certain positions as noted herein, the Fc region has an amino acid sequence that is substantially similar to that of the Fc region within a wild type IgG1 Fc. In some embodiments, the wild type IgG1 Fc is a human IgG1 Fc, in which each Fc polypeptide comprises an amino acid sequence of SEQ ID NO: 792, 911, or 1022. In some embodiments, the binding proteins described herein comprise an Fc region, each Fc polypeptide of which has an amino acid sequence that is at least 85%, at least 87.5%, at least 90%, at least 91%, at least 92%, at least 93%, at least 94%, at least 95%, at least 96%, at least 97%, at least 98%, or at least 99% identical to that of an Fc polypeptide within a wild-type IgG1 Fc.

In certain embodiments, human IgG1 Fc regions include an SRDEL (SEQ ID NO: 1031) allotype or an SREEM (SEQ ID NO: 1032) allotype.

In some embodiments, the binding proteins described herein comprise an IgG2 Fc region (e.g., human IgG2 Fc region), that is, except for having particular residue(s) at certain positions as noted herein, the Fc region has an amino acid sequence that is substantially similar to that of the Fc region within a wild type IgG2 Fc. In some embodiments, the wild type IgG2 Fc is a human IgG2 Fc, in which each Fc polypeptide comprises an amino acid sequence of SEQ ID NO: 793 or 912. In some embodiments, the binding proteins described herein comprise an Fc region, each Fc polypeptide of which has an amino acid sequence that is at least 85%, at least 87.5%, at least 90%, at least 91%, at least 92%, at least 93%, at least 94%, at least 95%, at least 96%, at least 97%, at least 98%, or at least 99% identical to that of an Fc polypeptide within a wild-type IgG2 Fc.

In some embodiments, the binding proteins described herein comprise an IgG4 Fc region (e.g., human IgG4 Fc region), that is, except for having particular residue(s) at certain positions as noted herein, the Fc region has an amino acid sequence that is substantially similar to that of the Fc region within a wild type IgG4 Fc. In some embodiments, the wild type IgG4 Fc is a human IgG4 Fc, in which each Fc polypeptide comprises an amino acid sequence of SEQ ID NO: 794 or 913. In some embodiments, the binding proteins described herein comprise an Fc region, each Fc polypeptide of which has an amino acid sequence that is at least 85%, at least 87.5%, at least 90%, at least 91%, at least 92%, at least 93%, at least 94%, at least 95%, at least 96%, at least 97%, at least 98%, or at least 99% identical to that of an Fc polypeptide within a wild-type IgG4 Fc.

In some embodiments, the binding protein comprises a modified Fc comprising one or more modifications. In some embodiments, the one or more modifications are located in a Fc from IgG1 (e.g., human IgG1 (hIgG1). In some embodiments, the one or more modifications are located in a Fc from IgG4 (e.g., human IgG4 (hIgG4). In some embodiments, the one or more modifications are located in a Fc from IgG2. In some embodiments, the one or more modifications promote selective binding of Fc-gamma receptors. In any embodiment, a constant heavy chain region can include a C-terminal lysine.

Amino acid sequences of exemplary Fc regions are provided in Tables 10A and 10B. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

TABLE 10A

| Exemplary Fc Polypeptide Sequences | | |
|---|---|---|
| Name | SEQ ID NO | Fc polypeptide sequence |
| hIgG1 | 792 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG2 | 793 | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLMISRTPEV TCVVVDVSHEDPEVQFNWYVDGVEVHNAKTKPREEQFNSTERVVSV LTVVHQDWLNGKEYKCKVSNKGLPAPIEKTISKTKGQPREPQVYTL PPSREEMTKNQVSLTCLVKGFYPSDIAVEWESNGQPENNYKTTPPM LDSDGSFFLYSKLTVDKSRWQQGNVFSCSVMHEALHNHYTQKSLSL SPG |
| hIgG4 | 794 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPSCPAPEFLGGPSVFLFPPKPKDTLMISRTPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT |

TABLE 10A-continued

| | | |
|---|---|---|
| | | Exemplary Fc Polypeptide Sequences |

| Name | SEQ ID NO | Fc polypeptide sequence |
|---|---|---|
| | | LPPSQEEMTKNQVSLTCLVKGFYPSDIAVEWESNGQPENNYKTTPP VLDSDGSFFLYSRLTVDKSRWQEGNVFSCSVMHEALHNHYTQKSLS LSLG |
| IgG4-SP (S228P) | 795 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFLGGPSVFLFPPKPKDTLMISRTPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHNHYTQKSLS LSLG |
| IgG4-SPLE (S228P/ L235E) | 796 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEELGGPSVFLFPPKPKDTLMISRTPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHNHYTQKSLS LSLG |
| hIgG1- N297A | 797 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYASTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1- D265A | 798 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVAVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1- LALA (L234A/ L235A) | 799 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1- LAGA (L235A/ G237A) | 800 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1- LALAGA (L234A/ L235A/ G237A) | 801 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1- LALAPG (L234A/ L235A/ P329G) | 802 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |

TABLE 10A-continued

Exemplary Fc Polypeptide Sequences

| Name | SEQ ID NO | Fc polypeptide sequence |
|------|-----------|--------------------------|
| hIgG1-YTE (M252Y/ S254T/ T256E) | 803 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDILYITR EPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1- N297A/YTE | 804 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLYITR EPEVTCVVVDVSHEDPEVKFNWYVDGVEVHNAKTKPREEQYASTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1- D265A/YTE | 805 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLYITR EPEVTCVVVAVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1- LALA/YTE | 806 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLYITR EPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1- LAGA/YTE | 807 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLYITR EPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1- LALAGA/YTE | 808 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLYITR EPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1- LALAPG/YTE | 809 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLYITR EPEVTCVVVDVSHEDPEVKFNWYVDGVEVHNAKTKPREEQYNSTYR VVSVLTVLHQDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1-LS (M428L/ N434S) | 810 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHSHYTQK SLSLSPG |
| hIgG1- N297A/LS | 811 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT |

TABLE 10A-continued

Exemplary Fc Polypeptide Sequences

| Name | SEQ ID NO | Fc polypeptide sequence |
|------|-----------|-------------------------|

KVDKKVEPKSCDKTHTCPPCPAPELLGGPSVFLFPPKPKDTLMISR
TPEVTCVVVDVSHEDPEVKFNWYVDGVEVHNAKTKPREEQYASTYR
VVSVLTVLHQDWLNGKEYKCKVSNKALPAPIEKTISKAKGQPREPQ
VYTLPPSRDELTKNQVSLTCLVKGFYPSDIAVEWESNGQPENNYKT
TPPVLDSDGSFFLYSKLTVDKSRWQQGNVFSCSVLHEALHSHYTQK
SLSLSPG hIgG1-          812   ASTKGPSVFPLAPSSKSTSGGTAALGCLVKDYFPEPVTVSWNSGAL
D265A/LS              TSGVHTFPAVLQSSGLYSLSSVVTVPSSSLGTQTYICNVNHKPSNT
                      KVDKKVEPKSCDKTHTCPPCPAPELLGGPSVFLFPPKPKDTLMISR
                      TPEVTCVVVAVSHEDPEVKFNWYVDGVEVHNAKTKPREEQYNSTYR
                      VVSVLTVLHQDWLNGKEYKCKVSNKALPAPIEKTISKAKGQPREPQ
                      VYTLPPSRDELTKNQVSLTCLVKGFYPSDIAVEWESNGQPENNYKT
                      TPPVLDSDGSFFLYSKLTVDKSRWQQGNVFSCSVLHEALHSHYTQK
                      SLSLSPG hIgG1-          813   ASTKGPSVFPLAPSSKSTSGGTAALGCLVKDYFPEPVTVSWNSGAL
LALA/LS              TSGVHTFPAVLQSSGLYSLSSVVTVPSSSLGTQTYICNVNHKPSNT
                      KVDKKVEPKSCDKTHTCPPCPAPEAAGGPSVFLFPPKPKDTLMISR
                      TPEVTCVVVDVSHEDPEVKFNWYVDGVEVHNAKTKPREEQYNSTYR
                      VVSVLTVLHQDWLNGKEYKCKVSNKALPAPIEKTISKAKGQPREPQ
                      VYTLPPSRDELTKNQVSLTCLVKGFYPSDIAVEWESNGQPENNYKT
                      TPPVLDSDGSFFLYSKLTVDKSRWQQGNVFSCSVLHEALHSHYTQK
                      SLSLSPG hIgG1-          814   ASTKGPSVFPLAPSSKSTSGGTAALGCLVKDYFPEPVTVSWNSGAL
LAGA/LS              TSGVHTFPAVLQSSGLYSLSSVVTVPSSSLGTQTYICNVNHKPSNT
                      KVDKKVEPKSCDKTHTCPPCPAPELAGAPSVFLFPPKPKDTLMISR
                      TPEVTCVVVDVSHEDPEVKFNWYVDGVEVHNAKTKPREEQYNSTYR
                      VVSVLTVLHQDWLNGKEYKCKVSNKALPAPIEKTISKAKGQPREPQ
                      VYTLPPSRDELTKNQVSLTCLVKGFYPSDIAVEWESNGQPENNYKT
                      TPPVLDSDGSFFLYSKLTVDKSRWQQGNVFSCSVLHEALHSHYTQK
                      SLSLSPG hIgG1-          815   ASTKGPSVFPLAPSSKSTSGGTAALGCLVKDYFPEPVTVSWNSGAL
LALAGA/LS            TSGVHTFPAVLQSSGLYSLSSVVTVPSSSLGTQTYICNVNHKPSNT
                      KVDKKVEPKSCDKTHTCPPCPAPEAAGAPSVFLFPPKPKDTLMISR
                      TPEVTCVVVDVSHEDPEVKFNWYVDGVEVHNAKTKPREEQYNSTYR
                      VVSVLTVLHQDWLNGKEYKCKVSNKALPAPIEKTISKAKGQPREPQ
                      VYTLPPSRDELTKNQVSLTCLVKGFYPSDIAVEWESNGQPENNYKT
                      TPPVLDSDGSFFLYSKLTVDKSRWQQGNVFSCSVLHEALHSHYTQK
                      SLSLSPG hIgG1-          816   ASTKGPSVFPLAPSSKSTSGGTAALGCLVKDYFPEPVTVSWNSGAL
LALAPG/LS            TSGVHTFPAVLQSSGLYSLSSVVTVPSSSLGTQTYICNVNHKPSNT
                      KVDKKVEPKSCDKTHTCPPCPAPEAAGGPSVFLFPPKPKDTLMISR
                      TPEVTCVVVDVSHEDPEVKFNWYVDGVEVHNAKTKPREEQYNSTYR
                      VVSVLTVLHQDWLNGKEYKCKVSNKALGAPIEKTISKAKGQPREPQ
                      VYTLPPSRDELTKNQVSLTCLVKGFYPSDIAVEWESNGQPENNYKT
                      TPPVLDSDGSFFLYSKLTVDKSRWQQGNVFSCSVLHEALHSHYTQK
                      SLSLSPG hIgG1-DHS       817   ASTKGPSVFPLAPSSKSTSGGTAALGCLVKDYFPEPVTVSWNSGAL
(L309D/              TSGVHTFPAVLQSSGLYSLSSVVTVPSSSLGTQTYICNVNHKPSNT
Q311H/               KVDKKVEPKSCDKTHTCPPCPAPELLGGPSVFLFPPKPKDTLMISR
N434S)               TPEVTCVVVDVSHEDPEVKFNWYVDGVEVHNAKTKPREEQYNSTYR
                      VVSVLTVDHHDWLNGKEYKCKVSNKALPAPIEKTISKAKGQPREPQ
                      VYTLPPSRDELTKNQVSLTCLVKGFYPSDIAVEWESNGQPENNYKT
                      TPPVLDSDGSFFLYSKLTVDKSRWQQGNVFSCSVMHEALHSHYTQK
                      SLSLSPG hIgG1-          818   ASTKGPSVFPLAPSSKSTSGGTAALGCLVKDYFPEPVTVSWNSGAL
N297A/DHS            TSGVHTFPAVLQSSGLYSLSSVVTVPSSSLGTQTYICNVNHKPSNT
                      KVDKKVEPKSCDKTHTCPPCPAPELLGGPSVFLFPPKPKDTLMISR
                      TPEVTCVVVDVSHEDPEVKFNWYVDGVEVHNAKTKPREEQYASTYR
                      VVSVLTVDHHDWLNGKEYKCKVSNKALPAPIEKTISKAKGQPREPQ
                      VYTLPPSRDELTKNQVSLTCLVKGFYPSDIAVEWESNGQPENNYKT
                      TPPVLDSDGSFFLYSKLTVDKSRWQQGNVFSCSVMHEALHSHYTQK
                      SLSLSPG hIgG1-          819   ASTKGPSVFPLAPSSKSTSGGTAALGCLVKDYFPEPVTVSWNSGAL
D265A/DHS            TSGVHTFPAVLQSSGLYSLSSVVTVPSSSLGTQTYICNVNHKPSNT
                      KVDKKVEPKSCDKTHTCPPCPAPELLGGPSVFLFPPKPKDTLMISR
                      TPEVTCVVVAVSHEDPEVKFNWYVDGVEVHNAKTKPREEQYNSTYR
                      VVSVLTVDHHDWLNGKEYKCKVSNKALPAPIEKTISKAKGQPREPQ

TABLE 10A-continued

Exemplary Fc Polypeptide Sequences

| Name | SEQ ID NO | Fc polypeptide sequence |
|---|---|---|
| | | VYTLPPSRDELTKNQVSLTCLVKGFYPSDIAVEWESNGQPENNYKT TPPVLDSDGSFFLYSKLTVDKSRWQQGNVFSCSVMHEALHSHYTQK SLSLSPG |
| hIgG1-LALA/DHS | 820 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVDHHDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHSHYTQK SLSLSPG |
| hIgG1-LAGA/DHS | 821 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLTVDHHDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHSHYTQK SLSLSPG |
| hIgG1-LALAGA/DHS | 822 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR TPEVTCVVVDVSHEDPEVKFNWYVDGVEVHNAKTKPREEQYNSTYR VVSVLTVDHHDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHSHYTQK SLSLSPG |
| hIgG1-LALAPG/DHS | 823 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVDHHDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHSHYTQK SLSLSPG |
| hIgG4-YTE | 824 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPSCPAPEFLGGPSVFLFPPKPKDTLYITREPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHNHYTQKSLS LSLG |
| hIgG4-SP/YTE | 825 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFLGGPSVFLFPPKPKDTLYITREPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHNHYTQKSLS LSLG |
| hIgG4-SPLE/YTE | 826 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEELGGPSVFLFPPKPKDTLYITREPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHNHYTQKSLS LSLG |
| hIgG4-LS | 827 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPSCPAPEFLGGPSVFLFPPKPKDTLMISRTPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVLHEALHSHYTQKSLS LSLG |

TABLE 10A-continued

Exemplary Fc Polypeptide Sequences

| Name | SEQ ID NO | Fc polypeptide sequence |
|---|---|---|
| hIgG4-SP/LS | 828 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFLGGPSVFLFPPKPKDTLMISRTPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVLHEALHSHYTQKSLS LSLG |
| hIgG4-SPLE/LS | 829 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEELGGPSVFLFPPKPKDTLMISRTPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVLHEALHSHYTQKSLS LSLG |
| hIgG4-DHS | 830 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPSCPAPEFLGGPSVFLFPPKPKDTLMISRTPE VTCVVVDVSQEDPEVQFNWYVDGVEVHNAKTKPREEQFNSTYRVVS VLTVDHHDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHSHYTQKSLS LSLG |
| hIgG4-SP/DHS | 831 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFLGGPSVFLFPPKPKDTLMISRTPE VTCVVVDVSQEDPEVQFNWYVDGVEVHNAKTKPREEQFNSTYRVVS VLTVDHHDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHSHYTQKSLS LSLG |
| hIgG4-SPLE/DHS | 832 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEELGGPSVFLFPPKPKDTLMISRTPE VTCVVVDVSQEDPEVQFNWYVDGVEVHNAKTKPREEQFNSTYRVVS VLTVDHHDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHSHYTQKSLS LSLG |
| hIgG2-YTE | 833 | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLYITREPEV TCVVVDVSHEDPEVQFNWYVDGVEVHNAKTKPREEQFNSTFRVVSV LTVVHQDWLNGKEYKCKVSNKGLPAPIEKTISKTKGQPREPQVYTL PPSREEMTKNQVSLTCLVKGFYPSDIAVEWESNGQPENNYKTTPPM LDSDGSFFLYSKLTVDKSRWQQGNVFSCSVMHEALHNHYTQKSLSL SPG |
| hIgG2-LS | 834 | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLMISRTPEV TCVVVDVSHEDPEVQFNWYVDGVEVHNAKTKPREEQFNSTFRVVSV LTVVHQDWLNGKEYKCKVSNKGLPAPIEKTISKTKGQPREPQVYTL PPSREEMTKNQVSLTCLVKGFYPSDIAVEWESNGQPENNYKTTPPM LDSDGSFFLYSKLTVDKSRWQQGNVFSCSVLHEALHSHYTQKSLSL SPG |
| hIgG2-DHS | 835 | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLMISRTPEV TCVVVDVSHEDPEVQFNWYVDGVEVHNAKTKPREEQFNSTFRVVSV LTVDHHDWLNGKEYKCKVSNKGLPAPIEKTISKTKGQPREPQVYTL PPSREEMTKNQVSLTCLVKGFYPSDIAVEWESNGQPENNYKTTPPM LDSDGSFFLYSKLTVDKSRWQQGNVFSCSVMHEALHSHYTQKSLSL SPG |
| hIgG1-LA | 836 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR |

TABLE 10A-continued

| | SEQ | |
|---|---|---|
| Name | ID NO | Fc polypeptide sequence |
| | | TPEVTCVVVDVSHEDPEVKFNWYVDGVEVHNAKTKPREEQYNSTYR |
| | | VVSVLTVLHQDWLNGKEYKCKVSNKALPAPIEKTISKAKGQPREPQ |
| | | VYTLPPSRDELTKNQVSLTCLVKGFYPSDIAVEWESNGQPENNYKT |
| | | TPPVLDSDGSFFLYSKLTVDKSRWQQGNVFSCSVLHEALHAHYTQK |
| | | SLSLSPG |
| hIgG1- | 837 | ASTKGPSVFPLAPSSKSTSGGTAALGCLVKDYFPEPVTVSWNSGAL |
| N297A/LA | | TSGVHTFPAVLQSSGLYSLSSVVTVPSSSLGTQTYICNVNHKPSNT |
| | | KVDKKVEPKSCDKTHTCPPCPAPELLGGPSVFLFPPKPKDTLMISR |
| | | TPEVTCVVVDVSHEDPEVKFNWYVDGVEVHNAKTKPREEQYASTYR |
| | | VVSVLTVLHQDWLNGKEYKCKVSNKALPAPIEKTISKAKGQPREPQ |
| | | VYTLPPSRDELTKNQVSLTCLVKGFYPSDIAVEWESNGQPENNYKT |
| | | TPPVLDSDGSFFLYSKLTVDKSRWQQGNVFSCSVLHEALHAHYTQK |
| | | SLSLSPG |
| hIgG1- | 838 | ASTKGPSVFPLAPSSKSTSGGTAALGCLVKDYFPEPVTVSWNSGAL |
| D265A/LA | | TSGVHTFPAVLQSSGLYSLSSVVTVPSSSLGTQTYICNVNHKPSNT |
| | | KVDKKVEPKSCDKTHTCPPCPAPELLGGPSVFLFPPKPKDTLMISR |
| | | TPEVTCVVVAVSHEDPEVKFNWYVDGVEVHNAKTKPREEQYNSTYR |
| | | VVSVLTVLHQDWLNGKEYKCKVSNKALPAPIEKTISKAKGQPREPQ |
| | | VYTLPPSRDELTKNQVSLTCLVKGFYPSDIAVEWESNGQPENNYKT |
| | | TPPVLDSDGSFFLYSKLTVDKSRWQQGNVFSCSVLHEALHAHYTQK |
| | | SLSLSPG |
| hIgG1- | 839 | ASTKGPSVFPLAPSSKSTSGGTAALGCLVKDYFPEPVTVSWNSGAL |
| LALA/LA | | TSGVHTFPAVLQSSGLYSLSSVVTVPSSSLGTQTYICNVNHKPSNT |
| | | KVDKKVEPKSCDKTHTCPPCPAPEAAGGPSVFLFPPKPKDTLMISR |
| | | TPEVTCVVVDVSHEDPEVKFNWYVDGVEVHNAKTKPREEQYNSTYR |
| | | VVSVLTVLHQDWLNGKEYKCKVSNKALPAPIEKTISKAKGQPREPQ |
| | | VYTLPPSRDELTKNQVSLTCLVKGFYPSDIAVEWESNGQPENNYKT |
| | | TPPVLDSDGSFFLYSKLTVDKSRWQQGNVFSCSVLHEALHAHYTQK |
| | | SLSLSPG |
| hIgG1- | 840 | ASTKGPSVFPLAPSSKSTSGGTAALGCLVKDYFPEPVTVSWNSGAL |
| LAGA/LA | | TSGVHTFPAVLQSSGLYSLSSVVTVPSSSLGTQTYICNVNHKPSNT |
| | | KVDKKVEPKSCDKTHTCPPCPAPELAGAPSVFLFPPKPKDTLMISR |
| | | TPEVTCVVVDVSHEDPEVKFNWYVDGVEVHNAKTKPREEQYNSTYR |
| | | VVSVLTVLHQDWLNGKEYKCKVSNKALPAPIEKTISKAKGQPREPQ |
| | | VYTLPPSRDELTKNQVSLTCLVKGFYPSDIAVEWESNGQPENNYKT |
| | | TPPVLDSDGSFFLYSKLTVDKSRWQQGNVFSCSVLHEALHAHYTQK |
| | | SLSLSPG |
| hIgG1- | 841 | ASTKGPSVFPLAPSSKSTSGGTAALGCLVKDYFPEPVTVSWNSGAL |
| LALAGA/LA | | TSGVHTFPAVLQSSGLYSLSSVVTVPSSSLGTQTYICNVNHKPSNT |
| | | KVDKKVEPKSCDKTHTCPPCPAPEAAGAPSVFLFPPKPKDTLMISR |
| | | TPEVTCVVVDVSHEDPEVKFNWYVDGVEVHNAKTKPREEQYNSTYR |
| | | VVSVLTVLHQDWLNGKEYKCKVSNKALPAPIEKTISKAKGQPREPQ |
| | | VYTLPPSRDELTKNQVSLTCLVKGFYPSDIAVEWESNGQPENNYKT |
| | | TPPVLDSDGSFFLYSKLTVDKSRWQQGNVFSCSVLHEALHAHYTQK |
| | | SLSLSPG |
| hIgG1- | 842 | ASTKGPSVFPLAPSSKSTSGGTAALGCLVKDYFPEPVTVSWNSGAL |
| LALAPG/LA | | TSGVHTFPAVLQSSGLYSLSSVVTVPSSSLGTQTYICNVNHKPSNT |
| | | KVDKKVEPKSCDKTHTCPPCPAPEAAGGPSVFLFPPKPKDTLMISR |
| | | TPEVTCVVVDVSHEDPEVKFNWYVDGVEVHNAKTKPREEQYNSTYR |
| | | VVSVLIVLHQDWLNGKEYKCKVSNKALGAPIEKTISKAKGQPREPQ |
| | | VYTLPPSRDELTKNQVSLTCLVKGFYPSDIAVEWESNGQPENNYKT |
| | | TPPVLDSDGSFFLYSKLTVDKSRWQQGNVFSCSVLHEALHAHYTQK |
| | | SLSLSPG |
| hIgG1- | 843 | ASTKGPSVFPLAPSSKSTSGGTAALGCLVKDYFPEPVTVSWNSGAL |
| N434A | | TSGVHTFPAVLQSSGLYSLSSVVTVPSSSLGTQTYICNVNHKPSNT |
| | | KVDKKVEPKSCDKTHTCPPCPAPELLGGPSVFLFPPKPKDTLMISR |
| | | TPEVTCVVVDVSHEDPEVKFNWYVDGVEVHNAKTKPREEQYNSTYR |
| | | VVSVLTVLHQDWLNGKEYKCKVSNKALPAPIEKTISKAKGQPREPQ |
| | | VYTLPPSRDELTKNQVSLTCLVKGFYPSDIAVEWESNGQPENNYKT |
| | | TPPVLDSDGSFFLYSKLTVDKSRWQQGNVFSCSVMHEALHAHYTQK |
| | | SLSLSPG |
| hIgG1- | 844 | ASTKGPSVFPLAPSSKSTSGGTAALGCLVKDYFPEPVTVSWNSGAL |
| N297A/ | | TSGVHTFPAVLQSSGLYSLSSVVTVPSSSLGTQTYICNVNHKPSNT |
| N434A | | KVDKKVEPKSCDKTHTCPPCPAPELLGGPSVFLFPPKPKDTLMISR |
| | | TPEVTCVVVDVSHEDPEVKFNWYVDGVEVHNAKTKPREEQYASTYR |
| | | VVSVLTVLHQDWLNGKEYKCKVSNKALPAPIEKTISKAKGQPREPQ |
| | | VYTLPPSRDELTKNQVSLTCLVKGFYPSDIAVEWESNGQPENNYKT |

TABLE 10A-continued

Exemplary Fc Polypeptide Sequences

| Name | SEQ ID NO | Fc polypeptide sequence |
|---|---|---|
| | | TPPVLDSDGSFFLYSKLTVDKSRWQQGNVFSCSVMHEALHAHYTQK SLSLSPG |
| hIgG1-D265A/N434A | 845 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVAVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHAHYTQK SLSLSPG |
| hIgG1-LALA/N434A | 846 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHAHYTQK SLSLSPG |
| hIgG1-LAGA/N434A | 847 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHAHYTQK SLSLSPG |
| hIgG1-LALAGA/N434A | 848 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHAHYTQK SLSLSPG |
| hIgG1-LALAPG/N434A | 849 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHAHYTQK SLSLSPG |
| hIgG1-N434W | 850 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPG |
| hIgG1-N297A/N434W | 851 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYASTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPG |
| hIgG1-D265A/N434W | 852 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVAVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPG |

TABLE 10A-continued

| | | |
|---|---|---|
| | | Exemplary Fc Polypeptide Sequences |

| Name | SEQ ID NO | Fc polypeptide sequence |
|---|---|---|
| hIgG1-LALA/N434W | 853 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPG |
| hIgG1-LAGA/N434W | 854 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPG |
| hIgG1-LALAGA/N434W | 855 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPG |
| hIgG1-LALAPG/N434W | 856 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPG |
| hIgG1/DQ (T256D/T307Q) | 857 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVDVSHEDPEVKFNWYVDGVEVHNAKTKPREEQYNSTYR VVSVLQVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1-N297A/DQ | 858 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVDVSHEDPEVKFNWYVDGVEVHNAKTKPREEQYASTYR VVSVLQVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1-D265A/DQ | 859 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVAVSHEDPEVKFNWYVDGVEVHNAKTKPREEQYNSTYR VVSVLQVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1-LALA/DQ | 860 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR DPEVTCVVVDVSHEDPEVKFNWYVDGVEVHNAKTKPREEQYNSTYR VVSVLQVLHQDWLNGKEYKCKVSNKALPAPIEKTISKAKGQPREPQ VYTLPPSRDELTKNQVSLTCLVKGFYPSDIAVEWESNGQPENNYKI TPPVLDSDGSFFLYSKLTVDKSRWQQGNVFSCSVMHEALHNHYTQK SLSLSPG |
| hIgG1-LAGA/DQ | 861 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR |

TABLE 10A-continued

| | | |
|---|---|---|
| | | Exemplary Fc Polypeptide Sequences |
| Name | SEQ ID NO | Fc polypeptide sequence |

| Name | SEQ ID NO | Fc polypeptide sequence |
|---|---|---|
| | | DPEVTCVVVDVSHEDPEVKFNWYVDGVEVHNAKTKPREEQYNSTYR VVSVLQVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1-LALAGA/DQ | 862 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR DPEVTCVVVDVSHEDPEVKFNWYVDGVEVHNAKTKPREEQYNSTYR VVSVLQVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1-LALAPG/DQ | 863 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR DPEVTCVVVDVSHEDPEVKFNWYVDGVEVHNAKTKPREEQYNSTYR VVSVLQVLHQDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1/DW (T256D/ T307W) | 864 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVDVSHEDPEVKFNWYVDGVEVHNAKTKPREEQYNSTYR VVSVLWVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1-N297A/DW | 865 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVDVSHEDPEVKFNWYVDGVEVHNAKTKPREEQYASTYR VVSVLWVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1-D265A/DW | 866 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVAVSHEDPEVKFNWYVDGVEVHNAKTKPREEQYNSTYR VVSVLWVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1-LALA/DW | 867 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR DPEVTCVVVDVSHEDPEVKFNWYVDGVEVHNAKTKPREEQYNSTYR VVSVLWVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1-LAGA/DW | 868 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR DPEVTCVVVDVSHEDPEVKFNWYVDGVEVHNAKTKPREEQYNSTYR VVSVLWVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1-LALALAGA/DW | 869 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR DPEVTCVVVDVSHEDPEVKFNWYVDGVEVHNAKTKPREEQYNSTYR VVSVLWVLHQDWLNGKEYKCKVSNKALPAPIEKTISKAKGQPREPQ VYTLPPSRDELTKNQVSLTCLVKGFYPSDIAVEWESNGQPENNYKT |

TABLE 10A-continued

| | SEQ | |
|---|---|---|
| Name | ID NO | Fc polypeptide sequence |

|  |  | TPPVLDSDGSFFLYSKLTVDKSRWQQGNVFSCSVMHEALHNHYTQK<br>SLSLSPG |
| hIgG1-<br>LALAPG/DW | 870 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPEAAGGPSVFLFPPKPKDTLMISR<br>DPEVTCVVVDVSHEDPEVKFNWYVDGVEVHNAKTKPREEQYNSTYR<br>VVSVLWVLHQDWLNGKEYKCKVSNKALGAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPG |
| hIgG1/YD<br>(M252Y/T256D) | 871 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELLGGPSVFLFPPKPKDTLYISR<br>DPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPG |
| hIgG1-<br>N297A/YD | 872 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELLGGPSVFLFPPKPKDTLYISR<br>DPEVTCVVVDVSHEDPEVKFNWYVDGVEVHNAKTKPREEQYASTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPG |
| hIgG1-<br>D265A/YD | 873 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELLGGPSVFLFPPKPKDTLYISR<br>DPEVTCVVVAVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPG |
| hIgG1-<br>LALA/YD | 874 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPEAAGGPSVFLFPPKPKDTLYISR<br>DPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPG |
| hIgG1-<br>LAGA/YD | 875 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELAGAPSVFLFPPKPKDTLYISR<br>DPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPG |
| hIgG1-<br>LALAGA/YD | 876 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPEAAGAPSVFLFPPKPKDTLYISR<br>DPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPG |
| hIgG1-<br>LALAPG/YD | 877 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPEAAGGPSVFLFPPKPKDTLYISR<br>DPEVTCVVVDVSHEDPEVKFNWYVDGVEVHNAKTKPREEQYNSTYR<br>VVSVLTVLHQDWLNGKEYKCKVSNKALGAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPG |

TABLE 10A-continued

Exemplary Fc Polypeptide Sequences

| Name | SEQ ID NO | Fc polypeptide sequence |
|---|---|---|
| hIgG1/QVV (T307Q/ Q311V/ A378V) | 878 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNSTYR VVSVLQVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1- N297A/QVV | 879 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYASTYR VVSVLQVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1- D265A/QVV | 880 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVAVSHEDPEVKFNWYVDGVEVHNAKTKPREEQYNSTYR VVSVLQVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1- LALA/QVV | 881 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLQVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1- LAGA/QVV | 882 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLQVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1- LALAGA/QVV | 883 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR TPEVTCVVVDVSHEDPEVKFNWYVDGVEVHNAKTKPREEQYNSTYR VVSVLQVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1- LALAPG/QVV | 884 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLQVLHVDWLNGKEYKCKVSNKALGAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1/DDRVV (T256D/ N286D/ T307R/ Q311V/ A378V) | 885 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVDVSHEDPEVKFNWYVDGVEVDNAKTKPREEQYNSTYR VVSVLRVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1- N297A/DDRVV | 886 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR |

TABLE 10A-continued

| | | |
|---|---|---|
| | | Exemplary Fc Polypeptide Sequences |

| Name | SEQ ID NO | Fc polypeptide sequence |
|---|---|---|
| | | DPEVTCVVVDVSHEDPEVKFNWYVDGVEVDNAKTKPREEQYASTYR VVSVLRVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1-D265A/DDRVV | 887 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVAVSHEDPEVKFNWYVDGVEVDNAKTKPREEQYNSTYR VVSVLRVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1-LALA/DDRVV | 888 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR DPEVTCVVVDVSHEDPEVKFNWYVDGVEVDNAKTKPREEQYNSTYR VVSVLRVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1-LAGA/DDRVV | 889 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR DPEVTCVVVDVSHEDPEVKFNWYVDGVEVDNAKTKPREEQYNSTYR VVSVLRVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1-LALAGA/DDRVV | 890 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR DPEVTCVVVDVSHEDPEVKFNWYVDGVEVDNAKTKPREEQYNSTYR VVSVLRVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1-LALAPG/DDRVV | 891 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR DPEVTCVVVDVSHEDPEVKFNWYVDGVEVDNAKTKPREEQYNSTYR VVSVLRVLHVDWLNGKEYKCKVSNKALGAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPG |
| hIgG1-Q311R/M428L | 892 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHRDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPG |
| hIgG4-Q311R/M428L | 893 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPSCPAPEFLGGPSVFLFPPKPKDTLMISRTPE VTCVVVDVSQEDPEVQFNWYVDGVEVHNAKTKPREEQFNSTYRVVS VLTVLHRDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVLHEALHNHYTQKSLS LSLG |
| IgG4-SP/Q311R/M428L | 894 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFLGGPSVFLFPPKPKDTLMISRTPE VTCVVVDVSQEDPEVQFNWYVDGVEVHNAKTKPREEQFNSTYRVVS VLTVLHRDWLNGKEYKCKVSNKGLPSSIEKTISKAKGQPREPQVYT LPPSQEEMTKNQVSLTCLVKGFYPSDIAVEWESNGQPENNYKTTPP |

TABLE 10A-continued

| Name | SEQ ID NO | Fc polypeptide sequence |
|---|---|---|
| | | VLDSDGSFFLYSRLTVDKSRWQEGNVFSCSVLHEALHNHYTQKSLS LSLG |
| IgG4-SPLE/Q311R/M428L | 895 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEELGGPSVFLFPPKPKDTLMISRTPE VTCVVVDVSQEDPEVQFNWYVDGVEVHNAKTKPREEQFNSTYRVVS VLTVLHRDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVLHEALHNHYTQKSLS LSLG |
| IgG2-Q311R/M428L | 896 | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLMISRTPEV TCVVVDVSHEDPEVQFNWYVDGVEVHNAKTKPREEQFNSTFRVVSV LTVVHRDWLNGKEYKCKVSNKGLPAPIEKTISKTKGQPREPQVYTL PPSREEMTKNQVSLTCLVKGFYPSDIAVEWESNGQPENNYKITPPM LDSDGSFFLYSKLTVDKSRWQQGNVFSCSVLHEALHNHYTQKSLSL SPG |
| hIgG1-N297A/Q311R/M428L | 897 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYASTYR VVSVLTVLHRDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPG |
| hIgG1-D265A/Q311R/M428L | 898 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVAVSHEDPEVKFNWYVDGVEVHNAKTKPREEQYNSTYR VVSVLTVLHRDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPG |
| hIgG1-LALA/Q311R/M428L | 899 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHRDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPG |
| hIgG1-LAGA/Q311R/M428L | 900 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLTVLHRDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPG |
| hIgG1-LALALGA/Q311R/M428L | 901 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR TPEVTCVVVDVSHEDPEVKFNWYVDGVEVHNAKTKPREEQYNSTYR VVSVLTVLHRDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPG |
| hIgG1-LALALAPG/Q311R/M428L | 902 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHRDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPG |

TABLE 10A-continued

| Name | SEQ ID NO | Fc polypeptide sequence |
|------|-----------|-------------------------|
| hIgG1-variant | 903 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1 variant with (M428L/N434S) LS | 904 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVLHEALHSHYTQK SLSLSPG |
| hIgG1 variant with M252Y/S254T/ T256E (YTE) | 905 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLYITR EPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1 variant with M428L/N434A (LA) | 906 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVLHEALHAHYTQK SLSLSPG |
| hIgG1 variant with H433K/N434F (KF) | 907 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALKFHYTQK SLSLSPG |
| hIgG1 variant with L309D/Q311H/ N434S (DHS) | 908 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVDHHDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHSHYTQK SLSLSPG |
| hIgG1 variant with N297A | 909 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYASTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHNHYTQK SLSLSPG |
| hIgG1 variant with LALAGA/YTE/ D356E/L358M | 910 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLYITR EPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHNHYTQK SLSLSPG |

TABLE 10B

| | SEQ ID NO | Exemplary Fc polypeptide Sequences |
|---|---|---|
| Name | | Fc polypeptide sequence |
| hIgG1 with C-terminal lysine | 911 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELLGGPSVFLFPPKPKDTLMISR<br>TPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPGK |
| hIgG2 with C-terminal lysine | 912 | ASTKGPSVFPLAPCSRSTSESTAALGCLVKDYFPEPVTVSWNSGAL<br>TSGVHTFPAVLQSSGLYSLSSVVTVPSSNFGTQTYTCNVDHKPSNT<br>KVDKTVERKCCVECPPCPAPPVAGPSVFLFPPKPKDTLMISRTPEV<br>TCVVVDVSHEDPEVQFNWYVDGVEVHNAKTKPREEQFNSTFRVVSV<br>LTVVHQDWLNGKEYKCKVSNKGLPAPIEKTISKTKGQPREPQVYTL<br>PPSREEMTKNQVSLTCLVKGFYPSDIAVEWESNGQPENNYKTTPPM<br>LDSDGSFFLYSKLTVDKSRWQQGNVFSCSVMHEALHNHYTQKSLSL<br>SPGK |
| hIgG4 with C-terminal lysine | 913 | ASTKGPSVFPLAPCSRSTSESTAALGCLVKDYFPEPVTVSWNSGAL<br>TSGVHTFPAVLQSSGLYSLSSVVTVPSSSLGTKTYTCNVDHKPSNT<br>KVDKRVESKYGPPCPSCPAPEFLGGPSVFLFPPKPKDTLMISRTPE<br>VTCVVVDVSQEDPEVQFNWYVDGVEVHNAKTKPREEQFNSTYRVVS<br>VLTVLHQDWLNGKEYKCKVSNKGLPSSIEKTISKAKGQPREPQVYT<br>LPPSQEEMTKNQVSLTCLVKGFYPSDIAVEWESNGQPENNYKTTPP<br>VLDSDGSFFLYSRLTVDKSRWQEGNVFSCSVMHEALHNHYTQKSLS<br>LSLGK |
| IgG4-SP (S228P) with C-terminal lysine | 914 | ASTKGPSVFPLAPCSRSTSESTAALGCLVKDYFPEPVTVSWNSGAL<br>TSGVHTFPAVLQSSGLYSLSSVVTVPSSSLGTKTYTCNVDHKPSNT<br>KVDKRVESKYGPPCPPCPAPEFLGGPSVFLFPPKPKDTLMISRTPE<br>VTCVVVDVSQEDPEVQFNWYVDGVEVHNAKTKPREEQFNSTYRVVS<br>VLTVLHQDWLNGKEYKCKVSNKGLPSSIEKTISKAKGQPREPQVYT<br>LPPSQEEMTKNQVSLTCLVKGFYPSDIAVEWESNGQPENNYKITPP<br>VLDSDGSFFLYSRLTVDKSRWQEGNVFSCSVMHEALHNHYTQKSLS<br>LSLGK |
| IgG4-SPLE (S228P/L235E) with C-terminal lysine | 915 | ASTKGPSVFPLAPCSRSTSESTAALGCLVKDYFPEPVTVSWNSGAL<br>TSGVHTFPAVLQSSGLYSLSSVVTVPSSSLGTKTYTCNVDHKPSNT<br>KVDKRVESKYGPPCPPCPAPEELGGPSVFLFPPKPKDTLMISRTPE<br>VTCVVVDVSQEDPEVQFNWYVDGVEVHNAKTKPREEQFNSTYRVVS<br>VLTVLHQDWLNGKEYKCKVSNKGLPSSIEKTISKAKGQPREPQVYT<br>LPPSQEEMTKNQVSLTCLVKGFYPSDIAVEWESNGQPENNYKTTPP<br>VLDSDGSFFLYSRLTVDKSRWQEGNVFSCSVMHEALHNHYTQKSLS<br>LSLGK |
| hIgG1-N297A with C-terminal lysine | 916 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELLGGPSVFLFPPKPKDTLMISR<br>TPEVTCVVVDVSHEDPEVKFNWYVDGVEVHNAKTKPREEQYASTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPGK |
| hIgG1-D265A with C-terminal lysine | 917 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELLGGPSVFLFPPKPKDTLMISR<br>TPEVTCVVVAVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPGK |
| hIgG1-LALA (L234A/L235A) with C-terminal lysine | 918 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPEAAGGPSVFLFPPKPKDTLMISR<br>TPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPGK |
| hIgG1-LAGA | 919 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT |

TABLE 10B-continued

Exemplary Fc polypeptide Sequences

| Name | SEQ ID NO | Fc polypeptide sequence |
|---|---|---|
| (L235A/ G237A) with C- terminal lysine | | KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1- LALAGA (L234A/ L235A/ G237A) with C- terminal lysine | 920 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDILMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1- LALAPG (L234A/ L235A/ P329G) with C- terminal lysine | 921 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-YTE (M252Y/ S254T/ T256E) with C- terminal lysine | 922 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLYITR EPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1- N297A/YTE with C- terminal lysine | 923 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLYITR EPEVTCVVVDVSHEDPEVKFNWYVDGVEVHNAKTKPREEQYASTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1- D265A/YTE with C- terminal lysine | 924 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLYITR EPEVTCVVVAVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1- LALA/YTE with C- terminal lysine | 925 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLYITR EPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1- LAGA/YTE with C- terminal lysine | 926 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLYITR EPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1- LALAGA/ YTE with C- | 927 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLYITR EPEVTCVVVDVSHEDPEVKFNWYVDGVEVHNAKTKPREEQYNSTYR |

TABLE 10B-continued

Exemplary Fc polypeptide Sequences

| Name | SEQ ID NO | Fc polypeptide sequence |
|---|---|---|
| terminal lysine | | VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-LALAPG/YTE with C-terminal lysine | 928 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLYITR EPEVTCVVVDVSHEDPEVKFNWYVDGVEVHNAKTKPREEQYNSTYR VVSVLTVLHQDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-LS (M428L/N434S) with C-terminal lysine | 929 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHSHYTQK SLSLSPGK |
| hIgG1-N297A/LS with C-terminal lysine | 930 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYASTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHSHYTQK SLSLSPGK |
| hIgG1-D265A/LS with C-terminal lysine | 931 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVAVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHSHYTQK SLSLSPGK |
| hIgG1-LALA/LS with C-terminal lysine | 932 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHSHYTQK SLSLSPGK |
| hIgG1-LAGA/LS with C-terminal lysine | 933 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHSHYTQK SLSLSPGK |
| hIgG1-LALAGA/LS with C-terminal lysine | 934 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHSHYTQK SLSLSPGK |
| hIgG1-LALAPG/LS with C-terminal lysine | 935 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALGAPIEKTISKAKGQPREPQ VYTLPPSRDELTKNQVSLTCLVKGFYPSDIAVEWESNGQPENNYKT |

TABLE 10B-continued

Exemplary Fc polypeptide Sequences

| Name | SEQ ID NO | Fc polypeptide sequence |
|---|---|---|
| | | TPPVLDSDGSFFLYSKLTVDKSRWQQGNVFSCSVLHEALHSHYTQK SLSLSPGK |
| hIgG1-DHS (L309D/ Q311H/ N434S) with C-terminal lysine | 936 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVDHHDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHSHYTQK SLSLSPGK |
| hIgG1-N297A/DHS with C-terminal lysine | 937 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYASTYR VVSVLTVDHHDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHSHYTQK SLSLSPGK |
| hIgG1-D265A/DHS with C-terminal lysine | 938 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVAVSHEDPEVKFNWYVDGVEVHNAKTKPREEQYNSTYR VVSVLTVDHHDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHSHYTQK SLSLSPGK |
| hIgG1-LALA/DHS with C-terminal lysine | 939 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVDHHDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHSHYTQK SLSLSPGK |
| hIgG1-LAGA/DHS with C-terminal lysine | 940 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLTVDHHDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHSHYTQK SLSLSPGK |
| hIgG1-LALAGA/ DHS with C-terminal lysine | 941 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR TPEVTCVVVDVSHEDPEVKFNWYVDGVEVHNAKTKPREEQYNSTYR VVSVLTVDHHDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHSHYTQK SLSLSPGK |
| hIgG1-LALAPG/ DHS with C-terminal lysine | 942 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVDHHDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHSHYTQK SLSLSPGK |
| hIgG4-YTE with C-terminal lysine | 943 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPSCPAPEFLGGPSVFLFPPKPKDTLYITREPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHNHYTQKSLS LSLGK |

TABLE 10B-continued

| | SEQ ID NO | Fc polypeptide sequence |
|---|---|---|
| Exemplary Fc polypeptide Sequences | | |

| Name | SEQ ID NO | Fc polypeptide sequence |
|---|---|---|
| hIgG4-SP/YTE with C-terminal lysine | 944 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFLGGPSVFLFPPKPKDTLYITREPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHNHYTQKSLS LSLGK |
| hIgG4-SPLE/YTE with C-terminal lysine | 945 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEELGGPSVFLFPPKPKDTLYITREPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHNHYTQKSLS LSLGK |
| hIgG4-LS with C-terminal lysine | 946 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPSCPAPEFLGGPSVFLFPPKPKDTLMISRTPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVLHEALHSHYTQKSLS LSLGK |
| hIgG4-SP/LS with C-terminal lysine | 947 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFLGGPSVFLFPPKPKDTLMISRTPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVLHEALHSHYTQKSLS LSLGK |
| hIgG4-SPLE/LS with C-terminal lysine | 948 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEELGGPSVFLFPPKPKDTLMISRTPE VTCVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVLHEALHSHYTQKSLS LSLGK |
| hIgG4-DHS with C-terminal lysine | 949 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPSCPAPEFLGGPSVFLFPPKPKDTLMISRTPE VTCVVVDVSQEDPEVQFNWYVDGVEVHNAKTKPREEQFNSTYRVVS VLTVDHHDWLNGKEYKCKVSNKGLPSSIEKTISKAKGQPREPQVYT LPPSQEEMTKNQVSLTCLVKGFYPSDIAVEWESNGQPENNYKITPP VLDSDGSFFLYSRLTVDKSRWQEGNVFSCSVMHEALHSHYTQKSLS LSLGK |
| hIgG4-SP/DHS with C-terminal lysine | 950 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFLGGPSVFLFPPKPKDTLMISRTPE VTCVVVDVSQEDPEVQFNWYVDGVEVHNAKTKPREEQFNSTYRVVS VLTVDHHDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHSHYTQKSLS LSLGK |
| hIgG4-SPLE/DHS with C-terminal lysine | 951 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEELGGPSVFLFPPKPKDTLMISRTPE VTCVVVDVSQEDPEVQFNWYVDGVEVHNAKTKPREEQFNSTYRVVS VLTVDHHDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHSHYTQKSLS LSLGK |

TABLE 10B-continued

| | | |
|---|---|---|
| | | Exemplary Fc polypeptide Sequences |

| Name | SEQ ID NO | Fc polypeptide sequence |
|---|---|---|
| hIgG2-YTE with C-terminal lysine | 952 | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLYITREPEV TCVVVDVSHEDPEVQFNWYVDGVEVHNAKTKPREEQFNSTFRVVSV LTVVHQDWLNGKEYKCKVSNKGLPAPIEKTISKTKGQPREPQVYTL PPSREEMTKNQVSLTCLVKGFYPSDIAVEWESNGQPENNYKTTPPM LDSDGSFFLYSKLTVDKSRWQQGNVFSCSVMHEALHNHYTQKSLSL SPGK |
| hIgG2-LS with C-terminal lysine | 953 | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLMISRTPEV TCVVVDVSHEDPEVQFNWYVDGVEVHNAKTKPREEQFNSTFRVVSV LTVVHQDWLNGKEYKCKVSNKGLPAPIEKTISKTKGQPREPQVYTL PPSREEMTKNQVSLTCLVKGFYPSDIAVEWESNGQPENNYKITPPM LDSDGSFFLYSKLTVDKSRWQQGNVFSCSVLHEALHSHYTQKSLSL SPGK |
| hIgG2-DHS with C-terminal lysine | 954 | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLMISRTPEV TCVVVDVSHEDPEVQFNWYVDGVEVHNAKTKPREEQFNSTFRVVSV LTVDHHDWLNGKEYKCKVSNKGLPAPIEKTISKTKGQPREPQVYTL PPSREEMTKNQVSLTCLVKGFYPSDIAVEWESNGQPENNYKTTPPM LDSDGSFFLYSKLTVDKSRWQQGNVFSCSVMHEALHSHYTQKSLSL SPGK |
| hIgG1-LA with C-terminal lysine | 955 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHAHYTQK SLSLSPGK |
| hIgG1-N297A/LA with C-terminal lysine | 956 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYASTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHAHYTQK SLSLSPGK |
| hIgG1-D265A/LA with C-terminal lysine | 957 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVAVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHAHYTQK SLSLSPGK |
| hIgG1-LALA/LA with C-terminal lysine | 958 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHAHYTQK SLSLSPGK |
| hIgG1-LAGA/LA with C-terminal lysine | 959 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHAHYTQK SLSLSPGK |
| hIgG1-LALAGA/ | 960 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT |

TABLE 10B-continued

Exemplary Fc polypeptide Sequences

| Name | SEQ ID NO | Fc polypeptide sequence |
|---|---|---|
| LA with C-terminal lysine | | KVDKKVEPKSCDKTHTCPPCPAPEAAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHAHYTQK SLSLSPGK |
| hIgG1-LALAPG/ LA with C-terminal lysine | 961 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHAHYTQK SLSLSPGK |
| hIgG1-N434A with C-terminal lysine | 962 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHAHYTQK SLSLSPGK |
| hIgG1-N297A/ N434A with C-terminal lysine | 963 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYASTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHAHYTQK SLSLSPGK |
| hIgG1-D265A/ N434A with C-terminal lysine | 964 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVAVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHAHYTQK SLSLSPGK |
| hIgG1-LALA/ N434A with C-terminal lysine | 965 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDILMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHAHYTQK SLSLSPGK |
| hIgG1-LAGA/ N434A with C-terminal lysine | 966 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHAHYTQK SLSLSPGK |
| hIgG1-LALAGA/ N434A with C-terminal lysine | 967 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHAHYTQK SLSLSPGK |
| hIgG1-LALAPG/ N434A with C- | 968 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR |

TABLE 10B-continued

Exemplary Fc polypeptide Sequences

| Name | SEQ ID NO | Fc polypeptide sequence |
|---|---|---|
| terminal lysine | | VVSVLTVLHQDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHAHYTQK SLSLSPGK |
| hIgG1-N434W with C-terminal lysine | 969 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDILMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPGK |
| hIgG1-N297A/N434W with C-terminal lysine | 970 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYASTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPGK |
| hIgG1-D265A/N434W with C-terminal lysine | 971 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVAVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPGK |
| hIgG1-LALA/N434W with C-terminal lysine | 972 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPGK |
| hIgG1-LAGA/N434W with C-terminal lysine | 973 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPGK |
| hIgG1-LALAGA/N434W with C-terminal lysine | 974 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPGK |
| hIgG1-LALAPG/N434W with C-terminal lysine | 975 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHWHYTQK SLSLSPGK |
| hIgG1/DQ (T256D/T307Q) with C-terminal lysine | 976 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVDVSHEDPEVKFNWYVDGVEVHNAKTKPREEQYNSTYR VVSVLQVLHQDWLNGKEYKCKVSNKALPAPIEKTISKAKGQPREPQ VYTLPPSRDELTKNQVSLTCLVKGFYPSDIAVEWESNGQPENNYKT |

TABLE 10B-continued

Exemplary Fc polypeptide Sequences

| Name | SEQ ID NO | Fc polypeptide sequence |
|------|-----------|-------------------------|
| | | TPPVLDSDGSFFLYSKLTVDKSRWQQGNVFSCSVMHEALHNHYTQK SLSLSPGK |
| hIgG1-N297A/DQ with C-terminal lysine | 977 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVDVSHEDPEVKFNWYVDGVEVHNAKTKPREEQYASTYR VVSVLQVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-D265A/DQ with C-terminal lysine | 978 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVAVSHEDPEVKFNWYVDGVEVHNAKTKPREEQYNSTYR VVSVLQVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-LALA/DQ with C-terminal lysine | 979 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR DPEVTCVVVDVSHEDPEVKFNWYVDGVEVHNAKTKPREEQYNSTYR VVSVLQVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-LAGA/DQ with C-terminal lysine | 980 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR DPEVTCVVVDVSHEDPEVKFNWYVDGVEVHNAKTKPREEQYNSTYR VVSVLQVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-LALAGA/DQ with C-terminal lysine | 981 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDILMISR DPEVTCVVVDVSHEDPEVKFNWYVDGVEVHNAKTKPREEQYNSTYR VVSVLQVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-LALAPG/DQ with C-terminal lysine | 982 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR DPEVTCVVVDVSHEDPEVKFNWYVDGVEVHNAKTKPREEQYNSTYR VVSVLQVLHQDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1/DW (T256D/T307W) with C-terminal lysine | 983 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDILMISR DPEVTCVVVDVSHEDPEVKFNWYVDGVEVHNAKTKPREEQYNSTYR VVSVLWVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-N297A/DW with C-terminal lysine | 984 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVDVSHEDPEVKFNWYVDGVEVHNAKTKPREEQYASTYR VVSVLWVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |

TABLE 10B-continued

| | | |
|---|---|---|
| | | Exemplary Fc polypeptide Sequences |

| Name | SEQ ID NO | Fc polypeptide sequence |
|---|---|---|
| hIgG1-D265A/DW with C-terminal lysine | 985 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVAVSHEDPEVKFNWYVDGVEVHNAKTKPREEQYNSTYR VVSVLWVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-LALA/DW with C-terminal lysine | 986 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR DPEVTCVVVDVSHEDPEVKFNWYVDGVEVHNAKTKPREEQYNSTYR VVSVLWVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-LAGA/DW with C-terminal lysine | 987 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR DPEVTCVVVDVSHEDPEVKFNWYVDGVEVHNAKTKPREEQYNSTYR VVSVLWVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-LALAGA/DW with C-terminal lysine | 988 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR DPEVTCVVVDVSHEDPEVKFNWYVDGVEVHNAKTKPREEQYNSTYR VVSVLWVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-LALAPG/DW with C-terminal lysine | 989 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDILMISR DPEVTCVVVDVSHEDPEVKFNWYVDGVEVHNAKTKPREEQYNSTYR VVSVLWVLHQDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1/YD (M252Y/T256D) with C-terminal lysine | 990 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLYISR DPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-N297A/YD with C-terminal lysine | 991 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLYISR DPEVTCVVVDVSHEDPEVKFNWYVDGVEVHNAKTKPREEQYASTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1-D265A/YD with C-terminal lysine | 992 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLYISR DPEVTCVVVAVSHEDPEVKFNWYVDGVEVHNAKTKPREEQYNSTYR VVSVLTVLHQDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVMHEALHNHYTQK SLSLSPGK |

TABLE 10B-continued

Exemplary Fc polypeptide Sequences

| Name | SEQ ID NO | Fc polypeptide sequence |
|------|-----------|-------------------------|
| hIgG1-LALA/YD with C-terminal lysine | 993 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPEAAGGPSVFLFPPKPKDTLYISR<br>DPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPGK |
| hIgG1-LAGA/YD with C-terminal lysine | 994 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELAGAPSVFLFPPKPKDTLYISR<br>DPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPGK |
| hIgG1-LALALAGA/YD with C-terminal lysine | 995 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPEAAGAPSVFLFPPKPKDTLYISR<br>DPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPGK |
| hIgG1-LALAPG/YD with C-terminal lysine | 996 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPEAAGGPSVFLFPPKPKDTLYISR<br>DPEVTCVVVDVSHEDPEVKFNWYVDGVEVHNAKTKPREEQYNSTYR<br>VVSVLTVLHQDWLNGKEYKCKVSNKALGAPIEKTISKAKGQPREPQ<br>VYTLPPSRDELTKNQVSLTCLVKGFYPSDIAVEWESNGQPENNYKT<br>TPPVLDSDGSFFLYSKLTVDKSRWQQGNVFSCSVMHEALHNHYTQK<br>SLSLSPGK |
| hIgG1/QVV (T307Q/Q311V/A378V) with C-terminal lysine | 997 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELLGGPSVFLFPPKPKDTLMISR<br>TPEVTCVVVDVSHEDPEVKFNWYVDGVEVHNAKTKPREEQYNSTYR<br>VVSVLQVLHVDWLNGKEYKCKVSNKALPAPIEKTISKAKGQPREPQ<br>VYTLPPSRDELTKNQVSLTCLVKGFYPSDIVVEWESNGQPENNYKT<br>TPPVLDSDGSFFLYSKLTVDKSRWQQGNVFSCSVMHEALHNHYTQK<br>SLSLSPGK |
| hIgG1-N297A/QVV with C-terminal lysine | 998 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELLGGPSVFLFPPKPKDTLMISR<br>TPEVTCVVVDVSHEDPEVKFNWYVDGVEVHNAKTKPREEQYASTYR<br>VVSVLQVLHVDWLNGKEYKCKVSNKALPAPIEKTISKAKGQPREPQ<br>VYTLPPSRDELTKNQVSLTCLVKGFYPSDIVVEWESNGQPENNYKT<br>TPPVLDSDGSFFLYSKLTVDKSRWQQGNVFSCSVMHEALHNHYTQK<br>SLSLSPGK |
| hIgG1-D265A/QVV with C-terminal lysine | 999 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPELLGGPSVFLFPPKPKDTLMISR<br>TPEVTCVVVAVSHEDPEVKFNWYVDGVEVHNAKTKPREEQYNSTYR<br>VVSVLQVLHVDWLNGKEYKCKVSNKALPAPIEKTISKAKGQPREPQ<br>VYTLPPSRDELTKNQVSLTCLVKGFYPSDIVVEWESNGQPENNYKT<br>TPPVLDSDGSFFLYSKLTVDKSRWQQGNVFSCSVMHEALHNHYTQK<br>SLSLSPGK |
| hIgG1-LALA/QVV with C-terminal lysine | 1000 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSCDKTHTCPPCPAPEAAGGPSVFLFPPKPKDILMISR<br>TPEVTCVVVDVSHEDPEVKFNWYVDGVEVHNAKTKPREEQYNSTYR<br>VVSVLQVLHVDWLNGKEYKCKVSNKALPAPIEKTISKAKGQPREPQ<br>VYTLPPSRDELTKNQVSLTCLVKGFYPSDIVVEWESNGQPENNYKT<br>TPPVLDSDGSFFLYSKLTVDKSRWQQGNVFSCSVMHEALHNHYTQK<br>SLSLSPGK |
| hIgG1-LAGA/QVV | 1001 | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT |

TABLE 10B-continued

| | SEQ | |
| | ID | |
| Name | NO | Fc polypeptide sequence |
| --- | --- | --- |
| with C-terminal lysine | | KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLQVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPGK |
| hIgG1-LALAGA/QVV with C-terminal lysine | 1002 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR TPEVTCVVVDVSHEDPEVKFNWYVDGVEVHNAKTKPREEQYNSTYR VVSVLQVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPGK |
| hIgG1-LALAPG/QVV with C-terminal lysine | 1003 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDILMISR TPEVTCVVVDVSHEDPEVKFNWYVDGVEVHNAKTKPREEQYNSTYR VVSVLQVLHVDWLNGKEYKCKVSNKALGAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPGK |
| hIgG1/DDRVV (T256D/N286D/T307R/Q311V/A378V) with C-terminal lysine | 1004 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVDVSHEDPEVKFNWYVDGVEVDNAKTKPREEQYNSTYR VVSVLRVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPGK |
| hIgG1-N297A/DDRVV with C-terminal lysine | 1005 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVDVSHEDPEVKFNWYVDGVEVDNAKTKPREEQYASTYR VVSVLRVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPGK |
| hIgG1-D265A/DDRVV with C-terminal lysine | 1006 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR DPEVTCVVVAVSHEDPEVKFNWYVDGVEVDNAKTKPREEQYNSTYR VVSVLRVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPGK |
| hIgG1-LALA/DDRVV with C-terminal lysine | 1007 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR DPEVTCVVVDVSHEDPEVKFNWYVDGVEVDNAKTKPREEQYNSTYR VVSVLRVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPGK |
| hIgG1-LAGA/DDRVV with C-terminal lysine | 1008 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR DPEVTCVVVDVSHEDPEVKFNWYVDGVEVDNAKTKPREEQYNSTYR VVSVLRVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPGK |
| hIgG1-LALAGA/ | 1009 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT |

TABLE 10B-continued

Exemplary Fc polypeptide Sequences

| Name | SEQ ID NO | Fc polypeptide sequence |
|---|---|---|
| DDRVV with C-terminal lysine | | KVDKKVEPKSCDKTHTCPPCPAPEAAGAPSVFLFPPKPKDTLMISR DPEVTCVVVDVSHEDPEVKFNWYVDGVEVDNAKTKPREEQYNSTYR VVSVLRVLHVDWLNGKEYKCKVSNKALPAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPGK |
| hIgG1-LALAPG/DDRVV with C-terminal lysine | 1010 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR DPEVTCVVVDVSHEDPEVKFNWYVDGVEVDNAKTKPREEQYNSTYR VVSVLRVLHVDWLNGKEYKCKVSNKALGAPIEKTISKAKGQPREPQ VYTLPPSRDELTKNQVSLTCLVKGFYPSDIVVEWESNGQPENNYKT TPPVLDSDGSFFLYSKLTVDKSRWQQGNVFSCSVMHEALHNHYTQK SLSLSPGK |
| hIgG1-Q311R/M428L with C-terminal lysine | 1011 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHRDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPGK |
| hIgG4-Q311R/M428L with C-terminal lysine | 1012 | ASTKGPSVFPLAPCSRSTSESTAALGCLVKDYFPEPVTVSWNSGAL TSGVHTFPAVLQSSGLYSLSSVVTVPSSSLGIKTYTCNVDHKPSNT KVDKRVESKYGPPCPSCPAPEFLGGPSVFLFPPKPKDTLMISRTPE VTCVVVDVSQEDPEVQFNWYVDGVEVHNAKTKPREEQFNSTYRVVS VLTVLHRDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVLHEALHNHYTQKSLS LSLGK |
| IgG4-SP/Q311R/M428L with C-terminal lysine | 1013 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEFLGGPSVFLFPPKPKDTLMISRTPE VTCVVVDVSQEDPEVQFNWYVDGVEVHNAKTKPREEQFNSTYRVVS VLTVLHRDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVLHEALHNHYTQKSLS LSLGK |
| IgG4-SPLE/Q311R/M428L with C-terminal lysine | 1014 | ASTKGPSVFPLAPCSRSTSESTAALGCLVKDYFPEPVTVSWNSGAL TSGVHTFPAVLQSSGLYSLSSVVTVPSSSLGTKTYTCNVDHKPSNT KVDKRVESKYGPPCPPCPAPEELGGPSVFLFPPKPKDTLMISRTPE VTCVVVDVSQEDPEVQFNWYVDGVEVHNAKTKPREEQFNSTYRVVS VLTVLHRDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVLHEALHNHYTQKSLS LSLGK |
| IgG2-Q311R/M428L with C-terminal lysine | 1015 | ASTKGPSVFPLAPCSRSTSESTAALGCLVKDYFPEPVTVSWNSGAL TSGVHTFPAVLQSSGLYSLSSVVTVPSSNFGTQTYTCNVDHKPSNT KVDKTVERKCCVECPPCPAPPVAGPSVFLFPPKPKDTLMISRTPEV TCVVVDVSHEDPEVQFNWYVDGVEVHNAKTKPREEQFNSTERVVSV LTVVHRDWLNGKEYKCKVSNKGLPAPIEKTISKTKGQPREPQVYTL PPSREEMTKNQVSLTCLVKGFYPSDIAVEWESNGQPENNYKTTPPM LDSDGSFFLYSKLTVDKSRWQQGNVFSCSVLHEALHNHYTQKSLSL SPGK |
| hIgG1-N297A/Q311R/M428L with C-terminal lysine | 1016 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHRDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPGK |
| hIgG1-D265A/Q311R/M428L with C- | 1017 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELLGGPSVFLFPPKPKDTLMISR TPEVTCVVVAVSHEDPEVKFNWYVDGVEVHNAKTKPREEQYNSTYR |

TABLE 10B-continued

<u>Exemplary Fc polypeptide Sequences</u>

| Name | SEQ ID NO | Fc polypeptide sequence |
|---|---|---|
| terminal lysine | | VVSVLTVLHRDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPGK |
| hIgG1-LALA/ Q311R/M428L with C-terminal lysine | 1018 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHRDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPGK |
| hIgG1-LAGA/ Q311R/M428L with C-terminal lysine | 1019 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPELAGAPSVFLFPPKPKDTLMISR TPEVTCVVVDVSHEDPEVKFNWYVDGVEVHNAKTKPREEQYNSTYR VVSVLTVLHRDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPGK |
| hIgG1-LALALAGA/ Q311R/ M428L with C-terminal lysine | 1020 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLMISR TPEVTCVVVDVSHEDPEVKFNWYVDGVEVHNAKTKPREEQYNSTYR VVSVLTVLHRDWLNGKEYKCKVSNKALPAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPGK |
| hIgG1-LALAPG/ Q311R/ M428L with C-terminal lysine | 1021 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGGPSVFLFPPKPKDTLMISR TPEVTCVVVDVSHEDPEVKFNWYVDGVEVHNAKTKPREEQYNSTYR VVSVLTVLHRDWLNGKEYKCKVSNKALGAPIEKTISKAKGQPREPQ VYTLPPSRDELTKNQVSLTCLVKGFYPSDIAVEWESNGQPENNYKT TPPVLDSDGSFFLYSKLTVDKSRWQQGNVFSCSVLHEALHNHYTQK SLSLSPGK |
| hIgG1 - variant with C-terminal lysine | 1022 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1 variant with (M428L/ N434S) LS with C-terminal lysine | 1023 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVLHEALHSHYTQK SLSLSPGK |
| hIgG1 variant with M252Y/S254T/ T256E (YTE) with C-terminal lysine | 1024 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDILYITR EPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1 variant with M428L/ N434A (LA) | 1025 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYNSTYR |

TABLE 10B-continued

Exemplary Fc polypeptide Sequences

| Name | SEQ ID NO | Fc polypeptide sequence |
|------|-----------|-------------------------|
| with C-terminal lysine | | VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVLHEALHAHYTQK SLSLSPGK |
| hIgG1 variant with H433K/ N434F(KF) with C-terminal lysine | 1026 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALKFHYTQK SLSLSPGK |
| hIgG1 variant with L309D/Q311H/ N434S (DHS) with C-terminal lysine | 1027 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYNSTYR VVSVLTVDHHDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHSHYTQK SLSLSPGK |
| hIgG1 variant with N297A with C-terminal lysine | 1028 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKRVEPKSCDKTHTCPPCPAPELLGGPSVFLFPPKPKDTLMISR TPEVTCVVVDVSHEDPEVKFNWYVDGVEVHNAKTKPREEQYASTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHNHYTQK SLSLSPGK |
| hIgG1 variant with LALAGA/ YTE/ D356E/ L358M with C-terminal lysine | 1029 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNT KVDKKVEPKSCDKTHTCPPCPAPEAAGAPSVFLFPPKPKDTLYITR EPEVTCVVVDVSHEDPEVKFNWYVDGVEVHNAKTKPREEQYNSTYR VVSVLTVLHQDWLNGKEYKCKVSNKALPAPIEKTISKAKGQPREPQ VYTLPPSREEMTKNQVSLTCLVKGFYPSDIAVEWESNGQPENNYKT TPPVLDSDGSFFLYSKLTVDKSRWQQGNVFSCSVMHEALHNHYTQK SLSLSPGK |

In some embodiments, any binding protein described herein may comprise a Fc comprising one or more modifications with any one of the Fc modifications described herein. In some embodiments, any binding protein described herein can comprise any one of the Fc sequences in Tables 10A-10B (SEQ ID NOs: 792-1029). In some embodiments, the CH(1-3) domain of a binding protein in Table 7 is substituted with any one of the Fc sequences in Tables 10A-10B (SEQ ID NOs: 792-1029).

In some embodiments, one or more modifications in the modified Fc is selected from the group consisting of: S298A, E333A, K334A, K326A, F243L, R292P, Y300L, V305I, P396L, F243L, R292P, Y300L, L235V, P396L, F243L, S239D, I332E, A330L, S267E, L328F, D265S, S239E, K326A, A327H, G237F, K326E, G236A, D270L, H268D, S324T, L234F, N325L, V266L, and S267D. In some embodiments, one or more modifications in the modified Fc is selected from the group consisting of S228P, M252Y, S254T, T256E, T256D, T250Q, H285D, T307A, T307Q, T307R, T307W, L309D, Q411H, Q311V, A378V, E380A, M428L, N434A, N434S, N297A, D265A, L234A, L235A, and N434W.

In some embodiments, the modified Fc comprises a specific combination of amino acid substitutions selected from the group consisting of: L234A/L235A; V234A/ G237A; L235A/G237A/E318A; S228P/L236E; H268Q/ V309L/A330S/A331S; C220S/C226S/C229S/P238S; C226S/C229S/E3233P/L235V/L235A; L234F/L235E/ P331S; C226S/P230S; L234A/G237A; L234A/L235A/ G237A; and L234A/L235A/P329G.

In some embodiments, the modified Fc comprises a specific combination of amino acid substitutions selected from the group consisting of M428L/N434S (LS); M252Y/ S254T/T256E (YTE); T250Q/M428L; T307A/E380A/ N434A; T256D/T307Q (DQ); T256D/T307W (DW); M252Y/T256D (YD); T307Q/Q311V/A378V (QVV); T256D/H285D/T307R/Q311V/A378V (DDRVV); L309D/ Q311H/N434S (DHS); S228P/L235E (SPLE); L234A/ L235A (LALA); M428L/N434A (LA); L234A/G237A (LAGA); L234A/L235A/G237A (LALAGA); L234A/ L235A/P329G (LALAPG); N297A/YTE; D265A/YTE; LALA/YTE; LAGA/YTE; LALAGA/YTE; LALAPG/ YTE; N297A/LS; D265A/LS; LALA/LS; LAGA/LS; LALAGA/LS; LALAPG/LS; N297A/DHS; D265A/DHS; LALA/DHS; LAGA/DHS; LALAGA/DHS; LALAPG/ DHS; SP/YTE; SPLE/YTE; SP/LS; SPLE/LS; SP/DHS; SPLE/DHS; N297A/LA; D265A/LA; LALA/LA; LAGA/ LA; LALAGA/LA; LALAPG/LA; N297A/N434A; D265A/ N434A; LALA/N434A; LAGA/N434A; LALAGA/N434A; LALAPG/N434A; N297A/N434W; D265A/N434W;

LALA/N434W; LAGA/N434W; LALAGA/N434W; LALAPG/N434W; N297A/DQ; D265A/DQ; LALA/DQ; LAGA/DQ; LALAGA/DQ; LALAPG/DQ; N297A/DW; D265A/DW; LALA/DW; LAGA/DW; LALAGA/DW; LALAPG/DW; N297A/YD; D265A/YD; LALA/YD; LAGA/YD; LALAGA/YD; LALAPG/YD; N297A/QVV; D265A/QVV; LALA/QVV; LAGA/QVV, LALAGA/QVV; LALAPG/QVV; N297A/DDRVV; D265A/DDRVV; LALA/ DDRVV; LAGA/DDRVV; LALAGA/DDRVV; and LALAPG/DDRVV. In some embodiments, the modified Fc comprises a specific combination of amino acid substitutions selected from the group consisting of M428L/N434S (LS) and M252Y/S254T/T256E (YTE). In some embodiments, the modified Fc comprises M428L/N434S (LS) (e.g., SEQ ID NO: 810, 827, 834, 904, 929, 946, 953, or 1023) modifications. In some embodiments, the modified Fc comprises M252Y/S254T/T256E (YTE) modifications (e.g., SEQ ID NO: 803, 824, 833, 905, 922, 952, or 1024).

In some embodiments, the bispecific binding proteins described herein includes modifications to improve its ability to mediate effector function. Such modifications are known in the art and include afucosylation, or engineering of the affinity of the Fc towards an activating receptor, mainly FCGR3a for antibody-dependent cellular cytotoxicity (ADCC), and towards C1q for complement-dependent cytotoxicity (CDC).

In some embodiments, modifications to Fc regions reduce or abrogate effector functions, e.g., Fcγ receptor-mediated effector functions. Non-limiting examples of effector-reducing mutations or sets of mutations include, e.g., aglycosylation mutations (e.g., N297A or N297Q or N297G), L234A/ L235A (for IgG1 Fc regions), H268Q/V309L/A330S/P331S (for IgG2 Fc regions), and V234A/G237A/P238S/H268A/ V309L/A330S/P331S (for IgG2 Fc regions). In some embodiments, effector function is reduced by modifying the attached sugar structures. Non-limiting examples of effector-reducing sugar modifications include increasing sialylation or galactosylation of the sugar chains.

In some aspects, the bispecific binding proteins provided herein comprises a Fc domain (e.g., IgG1) with reduced fucose content at position Asn 297 (EU numbering) compared to a naturally occurring Fc domain. Such Fc domains are known to have improved ADCC. In some aspects, such binding proteins do not comprise any fucose at position Asn 297.

In some embodiments, the bispecific binding proteins described herein comprises an Fc region with one or more amino acid substitutions which improve ADCC, such as a substitution at one or more of positions 298, 333, and 334 of the Fc region. In some embodiments, the bispecific binding proteins provided herein comprises an Fc region with one or more amino acid substitutions at positions 239, 332, and 330.

In some embodiments, the Fc comprises an amino acid sequence having at least 80% sequence identity with the amino acid sequence according to any one of SEQ ID NOs in Table 10A or 10B. In some embodiments, the Fc comprises an amino acid sequence having at least 85% sequence identity with the amino acid sequence according to any one of SEQ ID NOs in Table 10A or 10B. In some embodiments, the Fc comprises an amino acid sequence having at least 90% sequence identity with the amino acid sequence according to any one of SEQ ID NOs in Table 10A or 10B. In some embodiments, the Fc comprises an amino acid sequence having at least 95% sequence identity with the amino acid sequence according to any one of SEQ ID NOs in Table 10A or 10B. In some embodiments, the Fc comprises an amino acid sequence having at least 96% sequence identity with the amino acid sequence according to any one of SEQ ID NOs in Table 10A or 10B. In some embodiments, the Fc comprises an amino acid sequence having at least 97% sequence identity with the amino acid sequence according to any one of SEQ ID NOs in Table 10A or 10B. In some embodiments, the Fc comprises an amino acid sequence having at least 98% sequence identity with the amino acid sequence according to any one of SEQ ID NOs in Table 10A or 10B. In some embodiments, the Fc comprises an amino acid sequence having at least 99% sequence identity with the amino acid sequence according to any one of SEQ ID NOs in Table 10A or 10B. In some embodiments, the Fc comprises the amino acid sequence according to any one of SEQ ID NOs in Table 10A or 10B.

In some embodiments, the bispecific binding proteins described herein comprise an Fc region with at least one galactose residue in the oligosaccharide attached to the Fc region. Such variants may have improved CDC function.

In some embodiments, the bispecific binding proteins described herein comprise one or more alterations that improves or diminishes C1q binding and/or CDC.

In certain embodiments, the Fc region comprises one or more amino acid substitutions, wherein the one or more substitutions result in an increase in one or more of antibody half-life, ADCC activity, ADCP activity, or CDC activity compared with the Fc without the one or more substitutions. In certain embodiments, the one or more amino acid substitutions results in increased antibody half-life at pH 6.0 compared to an antibody comprising a wild-type Fc region. In certain embodiments, the binding protein has an increased half-life that is about 10,000-fold, 1,000-fold, 500-fold, 100-fold, 50-fold, 20-fold, 10-fold, 9-fold, 8-fold, 7-fold, 6-fold, 5-fold, 4.5-fold, 4-fold, 3.5-fold, 3-fold, 2.5-fold, 2-fold, 1.95-fold, 1.9-fold, 1.85-fold, 1.8-fold, 1.75-fold, 1.7-fold, 1.65-fold, 1.6-fold, 1.55-fold, 1.50-fold, 1.45-fold, 1.4-fold, 1.35-fold, 1.3-fold, 1.25-fold, 1.2-fold, 1.15-fold, 1.1-fold, or 1.05-fold longer compared to an antibody comprising a wild-type Fc region.

In certain embodiments, the Fc region comprises one or more amino acid substitutions, wherein the one or more substitutions result in a decrease in one or more of ADCC activity, ADCP activity, or CDC activity compared with the Fc without the one or more substitutions.

In certain embodiments, the Fc region binds an Fcγ Receptor selected from the group consisting of: FcγRI, FcγRIIa, FcγRIIb, FcγRIIc, FcγRIIIa, and FcγRIIIb. In certain embodiments, the Fc region binds an Fcγ Receptor with higher affinity at pH 6.0 compared to an antibody comprising a wild-type Fc region.

In some embodiments, the bispecific binding proteins described herein comprise an extended half-life (i.e., serum half-life). In some embodiments, the bispecific binding proteins described herein comprise a half-life of at least about 14, 28, 42, 56, 70, 84, 96, or more than 96 weeks. In some embodiments, the binding protein described herein comprises a half-life in a range of about 14 days to about 96 days, about 14 days to about 84 days, about 14 days to about 70 days, about 14 days to about 56 days, about 14 days to about 42 days, about 14 days to about 28 days, of about 28 days to about 96 days, about 28 days to about 84 days, about 28 days to about 70 days, about 28 days to about 56 days, about 28 days to about 42 days, of about 42 days to about 96 days, about 42 days to about 84 days, about 42 days to about 70 days, or about 42 days to about 56 days. In some embodiments, the bispecific binding proteins described herein comprise a half-life in a range of about 42 days to about 56 days. In some embodiments, the bispecific binding proteins described herein comprise a half-life of at least about 50 days. In some embodiments, the bispecific binding proteins described herein comprise a half-life of about 50 days. Methods of measuring half-life are known in the art. In some embodiments, the half-life is measured in a non-human primate. In some embodiments, the half-life is measured in a human. In some embodiments, the half-life is measured following intravenous administration. In some embodiments, the half-life is measured following subcutaneous administration.

In some embodiments, the bispecific binding proteins described herein have a half-life that is at least 20% longer than a comparator antibody. In some embodiments, the comparator antibody comprises the same complementarity determining regions and variable regions but different Fc regions. In some embodiments, the half-life of the bispecific binding proteins described herein is at least 30%, at least 40%, at least 50%, at least 60%, at least 70%, at least 80%, or at least 90% longer than the half-life of the comparator antibody. In some embodiments, the half-life of the bispecific binding proteins described herein is longer than the half-life of the comparator antibody by at least 2 fold, at least 3 fold, at least 4 fold, at least 5 fold, at least 6 fold, at least 7 fold, at least 8 fold, at least 9 fold, or at least 10 fold.

Binding

The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule (i.e., VEGF or PD-1) and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule. In some embodiments, the affinity of a binding protein disclosed here in for a non-target molecule is less than about 50% of the affinity for VEGF or PD-1. In some embodiments, the affinity of a binding protein disclosed here in for a non-target molecule is less than about 40% of the affinity for VEGF or PD-1. In some embodiments, the affinity of a binding protein disclosed here in for a non-target molecule is less than about 40% of the affinity for VEGF or PD-1. In some embodiments, the affinity of a binding protein disclosed here in for a non-target molecule is less than about 20% of the affinity for VEGF or PD-1. In some embodiments, the affinity of a binding protein disclosed here in for a non-target molecule is less than about 10% of the affinity for VEGF or PD-1. In some embodiments, the affinity of a binding protein disclosed here in for a non-target molecule is less than about 1% of the affinity for VEGF or PD-1. In some embodiments, the affinity of a binding protein disclosed here in for a non-target molecule is less than about 0.1% of the affinity for VEGF or PD-1.

When used herein in the context of two or more binding proteins, the term "competes with" or "cross-competes with" indicates that the two or more binding proteins compete for binding to an antigen (e.g., VEGF). In one exemplary assay, VEGF is coated on a surface and contacted with a first anti-VEGF antibody, after which a second anti-VEGF antibody is added. In another exemplary assay, a first anti-VEGF antibody is coated on a surface and contacted with VEGF, and then a second anti-VEGF antibody is added. If the presence of the first anti-VEGF antibody reduces binding of the second anti-VEGF antibody, in either assay, then the binding proteins compete with each other. The term "competes with" also includes combinations of binding proteins where one antibody reduces binding of another antibody, but where no competition is observed when the binding proteins are added in the reverse order. However, in some embodiments, the first and second binding proteins inhibit binding of each other, regardless of the order in which they are added. In some embodiments, one antibody reduces binding of another antibody to its antigen by at least 25%, at least 50%, at least 60%, at least 70%, at least 80%, at least 85%, at least 90%, at least 95%, or at least 99% as measured in a competitive binding assay. A skilled artisan can select the concentrations of the binding proteins used in the competition assays based on the affinities of the binding proteins for VEGF and the valency of the binding proteins. The assays described in this definition are illustrative, and a skilled artisan can utilize any suitable assay to determine if binding proteins compete with each other. Suitable assays are described, for example, in Cox et al., "Immunoassay Methods," in Assay Guidance Manual [Internet], Updated Dec. 24, 2014 (ncbi.nlm.nih.gov/books/NBK92434/; accessed Sep. 29, 2015); Silman et al., *Cytometry*, 2001, 44:30-37; and Finco et al., J. Pharm. Biomed. Anal., 2011, 54:351-358; each of which is incorporated by reference in its entirety.

A test antibody competes with a reference antibody if an excess of a test antibody (e.g., at least 2×, 5×, 10×, 20×, or 100×) inhibits or blocks binding of the reference antibody by, e.g., at least 50%, 60%, 70%, 75%, 80%, 85%, 90%, 95%, or 99% as measured in a competitive binding assay. Binding proteins identified by competition assay (competing antibody) include binding proteins binding to the same epitope as the reference antibody and binding proteins binding to an adjacent epitope sufficiently proximal to the epitope bound by the reference antibody for steric hindrance to occur. For example, a second, competing antibody can be identified that competes for binding to VEGF with a first antibody described herein. In certain instances, the second antibody can block or inhibit binding of the first antibody by, e.g., at least 50%, 60%, 70%, 75%, 80%, 85%, 90%, 95%, or 99% as measured in a competitive binding assay. In certain instances, the second antibody can displace the first antibody by greater than 50%, 60%, 70%, 75%, 80%, 85%, 90%, 95%, or 99%.

In certain embodiments, the antibody binds a human VEGF and PD-1.

In some embodiments, the antibody provided herein binds VEGF or PD-1 with a $K_D$ of less than or equal to about 10, 9, 8, 7, 6, 5, 4.5, 4, 3.5, 3, 2.5, 2, 1.98, 1.95, 1.9, 1.85, 1.8, 1.75, 1.7, 1.65, 1.6, 1.55, 1.50, 1.45, 1.4, 1.3, 1.2, 1.1, 1, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, 0.01, 0.005, 0.001, 0.0005, or $0.0001 \times 10^{-8}$ M, or less, as measured by ELISA or any other suitable method known in the art. In some embodiments, the antibody provided herein binds VEGF or PD-1 with a $K_D$ between 5-3, 4-2, 3-1, 1.9-1.8, 1.8-1.7, 1.7-1.6, 1.6-1.5, 1.9-1.5, 1.5-1, 1-0.8, 1-0.5, 0.9-0.6, 0.7-0.4, 0.6-0.2, 0.5-0.3, 0.3-0.2, 0.2-0.1, 0.1-0.01, 0.01-0.001, or 0.001-0.0001×10$^{-8}$ M as measured by ELISA or any other suitable method known in the art.

Pharmaceutical Compositions

The present application provides compositions comprising the disclosed binding proteins (e.g., PD-1 binding proteins, or VEGF/PD-1 bispecific binding proteins) including pharmaceutical compositions with one or more pharmaceutically acceptable excipients. In some embodiments the composition is sterile. The pharmaceutical compositions generally comprise an effective amount of a binding protein.

These compositions can comprise, in addition to one or more of the binding proteins disclosed herein, a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

The binding protein that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16$^{th}$ edition, Osol, A. (ed), 1980.

A composition can be administered alone or in combination with other treatments, either simultaneously or sequentially dependent upon the condition to be treated.

Methods

Methods of Preparation

Methods for making binding proteins are known in the art. See Milstein and Cuello (1983) NATURE 305:537, International (PCT) Publication No. WO93/08829, and Traunecker et al. (1991) EMBO J., 10:3655. For further details of generating binding proteins see, for example, Suresh et al. (1986) METHODS ENZYMOL. 121:210. Binding proteins include cross-linked or "heteroconjugate" or "heterodimer" binding proteins. For example, one of the binding proteins in the heterodimer can be coupled to avidin, the other to biotin. Heterodimer binding proteins may be made using any convenient cross-linking method. Suitable cross-linking agents are well known in the art, and are disclosed in U.S. Pat. No. 4,676,980, along with a number of cross-linking techniques.

For example, binding proteins described herein can be produced using recombinant methods and compositions, e.g., as described in U.S. Pat. No. 4,816,567. In one embodiment, an isolated nucleic acid encoding a chain of a binding protein described herein is provided. Such a nucleic acid may encode an amino acid sequence comprising the VL sequence(s) and/or an amino acid sequence comprising the VH sequence(s) of the antibody (e.g., the light and/or heavy chains of the antibody). In a further embodiment, one or more vectors (e.g., expression vectors) comprising such nucleic acids are provided. In one embodiment, the nucleic acid is provided in a multicistronic vector. In a further embodiment, a host cell comprising such nucleic acid is provided. In one such embodiment, a host cell comprises (e.g., has been transformed with): (1) a vector comprising a nucleic acid that encodes an amino acid sequence comprising the VL sequence(s) of the antibody and an amino acid sequence comprising the VH sequence(s) of the antigen-binding polypeptide construct, or (2) a first vector comprising a nucleic acid that encodes an amino acid sequence comprising the VL sequence(s) of the antigen-binding polypeptide construct and a second vector comprising a nucleic acid that encodes an amino acid sequence comprising the VH sequence(s) of the antigen-binding polypeptide construct. In one embodiment, the host cell is eukaryotic, e.g., a Chinese Hamster Ovary (CHO) cell, or human embryonic kidney (HEK) cell, or lymphoid cell (e.g., Y0, NS0, Sp20 cell). In one embodiment, a method of making a binding protein is provided, wherein the method comprises culturing a host cell comprising nucleic acids each encoding at least one chain of the binding protein, as provided above, under conditions suitable for expression of the binding protein, and optionally recovering the binding protein from the host cell (or host cell culture medium).

For recombinant production of the binding protein, nucleic acid encoding at least one chain of an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

When a binding protein or variant thereof is recombinantly produced by the host cells, the protein in certain embodiments is present at about 30%, about 25%, about 20%, about 15%, about 10%, about 5%, about 4%, about 3%, about 2%, or about 1% or less of the dry weight of the cells. When the antibody or variant thereof is recombinantly produced by the host cells, the protein, in certain embodiments, is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. In certain embodiments, "substantially purified" antibody produced by the methods described herein, has a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

Suitable host cells for cloning or expression of antibody-encoding vectors include prokaryotic or eukaryotic cells described herein.

Recombinant host cells or host cells are cells that include an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome. Host cells can include CHO, derivatives of CHO, NS0, Sp20, CV-1, VERO-76, HeLa, HepG2, Per.C6, or BHK.

For example, antibody may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated binding proteins are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

In one embodiment, the binding proteins described herein are produced in stable mammalian cells, by a method comprising: transfecting at least one stable mammalian cell with: nucleic acid encoding the antibody, in a predetermined ratio; and expressing the nucleic acid in the at least one mammalian cell. In some embodiments, the predetermined ratio of nucleic acid is determined in transient transfection experiments to determine the relative ratio of input nucleic acids that results in the highest percentage of the antibody in the expressed product.

If required, the binding proteins can be purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and binding proteins, and these proteins can find use in the present invention for purification of binding proteins. For example, the bacterial proteins A and G bind to the Fc region. Likewise, the bacterial protein L binds to the Fab region of some binding proteins. Purification can often be enabled by a particular fusion partner. For example, binding proteins may be purified using glutathione resin if a GST fusion is employed, $Ni^{+2}$ affinity chromatography if a His-tag is employed or immobilized anti-flag antibody if a flag-tag is used. For general guidance in suitable purification techniques, see, e.g., incorporated entirely by reference Protein Purification: Principles and Practice, 3$^{rd}$ Ed., Scopes, Springer-Verlag, NY, 1994, incorporated entirely by reference. The degree of purification necessary will vary depending on the use of the binding proteins. In some instances, no purification is necessary.

In certain embodiments, the binding proteins are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments, the proteins described herein are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In addition, binding proteins described herein can be chemically synthesized using techniques known in the art (e.g., see Creighton, 1983, Proteins: Structures and Molecular Principles, W. H. Freeman & Co., N.Y and Hunkapiller et al., *Nature,* 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4diaminobutyric acid, alpha-amino isobutyric acid, 4aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, alanine, fluoro-amino acids, designer amino acids such as methyl amino acids, C-methyl amino acids, N-methyl amino acids, and amino acid analogs in general. Furthermore, the amino acid can be D (dextrorotary) or L (levorotary).

In certain embodiments, an antibody described herein has an aggregation temperature greater than about 69° C., greater than about 70° C., greater than about 71° C., greater than about 72° C., greater than about 73° C., greater than about 74° C., greater than about 75° C., or greater than about 76° C., for example, between about 69° C. and about 77° C., between about 70° C. and about 76° C., between about 71° C. and about 75° C. In certain embodiments, aggregation temperature is measured using DSF.

In certain embodiments, an antibody described herein has reduced hydrophobicity as compared to lebrikizumab as measured by hydrophobic interaction chromatography (HIC). In certain embodiments, the antibody exhibits an HIC retention time that is less than about 15.2 min. In certain embodiments, the antibody exhibits an HIC retention time that is between about 13 min and about 15 min.

Methods of Use/Methods of Treatment

In an aspect, the present application provides methods of contacting VEGF and/or PD-1 with a binding protein described herein.

In an aspect, the present application provides methods of using the binding proteins described herein or a pharmaceutical compositions thereof for treatment of a disorder or disease in a subject. In certain aspects, described herein is a method for treating a subject in need thereof, the method comprising administering to a mammalian subject a therapeutically effective amount of a binding protein described herein or pharmaceutical composition thereof. In certain embodiments, the present application provides methods of treating a disorder or disease associated with elevated levels of VEGF and/or PD-1 in a subject.

In certain aspects, described herein are methods for treating a pathology associated with VEGF and/or PD-1 activity, the method comprising administering to a subject a therapeutically effective amount a binding protein described herein or a pharmaceutical composition thereof.

Subjects

In certain embodiments, the subject is a mammal, such as a primate. In some embodiments, the subject is human.

The subject may be suffering from, exhibit at least one symptom of, diagnosed with, and/or identified as at risk of a disease or condition associated with aberrant VEGF and/or PD-1 expression and/or signaling. Non-limiting examples of such diseases or conditions include cancer (including solid tumors and liquid cancers), such as brain cancers (e.g., glioblastoma), chest and thoracic cancers (e.g., esophageal cancer, pleural mesothelioma, lung cancers (e.g., non-small cell lung cancer (NSCLC) including EGRm NSCLC, non-squamous NSCLC, and squamous NSCLC; and small cell lung cancer (SCLC)), gastrointestinal cancers (e.g., biliary cancer, colorectal cancer (all types, including MSI-H/dMMR and non-MSI-H/dMMR), gastric cancer, gastroesophageal junction (GEJ) cancer), hepatocellular cancer, or primary peritoneal cancel), head and neck cancers (e.g., head and neck squamous cell carcinoma, nasopharyngeal cancer, or thyroid cancer), hematological cancers (e.g., classical Hodgkin lymphoma or primary mediastinal large B-cell lymphoma (PMBCL)), kidney cancers (e.g., renal cell carcinoma), liver and biliary cancers (e.g., biliary tract cancer or hepatocellular carcinoma), reproductive cancers (e.g., breast cancer (including triple negative breast cancer), cervical cancer, endometrial cancer, fallopian tube cancer, ovarian cancer including epithelial ovarian cancer, and urothelial cancer), and soft tissue cancers (e.g., alveolar soft part carcinoma or soft tissue sarcoma).

Methods of Administration

In some embodiments, the methods provided herein are useful for the treatment of a disease or disorder in an individual. In an embodiment, the individual is a human and a binding protein described herein is administered to the human.

In some embodiments, a binding protein is administered intravenously, intramuscularly, subcutaneously, topically, orally, transdermally, intraperitoneally, intraorbitally, by implantation, by inhalation, intrathecally, intraventricularly, or intranasally. An effective amount of a binding protein may be administered for the treatment of a disease or disorder. The appropriate dosage of a binding protein may be determined based on the type of disease or disorder to be treated, the type of the binding protein, the severity and course of the disease or disorder, the clinical condition of the individual, the individual's clinical history and response to the treatment, and the discretion of the attending physician.

In some embodiments, an antibody provided herein is administered with at least one additional therapeutic agent. Any suitable additional therapeutic or immunotherapeutic agent may be administered with an antibody provided herein. Additional therapeutic agents include agents that are used to treat or prevent a disease or disorder such as, but not limited to, cancer, e.g., a cancer associated with elevated levels of VEGF and/or PD-1, a PD-1 expressing cancer, non-small cell lung cancer, etc.

The additional therapeutic agent can be administered by any suitable means. In some embodiments, an antibody provided herein and the additional therapeutic agent are included in the same pharmaceutical composition. In some embodiments, an antibody provided herein and the additional therapeutic agent are included in different pharmaceutical compositions.

In embodiments where a binding protein provided herein and the additional therapeutic agent are included in different pharmaceutical compositions, administration of the binding protein can occur prior to, simultaneously, and/or following, administration of the additional therapeutic agent. In some embodiments, administration of an antibody provided herein and the additional therapeutic agent occur within about one month of each other. In some embodiments, administration of a binding protein provided herein and the additional therapeutic agent occur within about one week of each other. In some embodiments, administration of a binding protein provided herein and the additional therapeutic agent occur within about one day of each other. In some embodiments, administration of a binding protein provided herein and the additional therapeutic agent occur within about twelve hours of each other. In some embodiments, administration of a binding protein provided herein and the additional therapeutic agent occur within about one hour of each other.

Kits and Articles of Manufacture

The present application provides kits comprising any one or more of the binding protein compositions described herein and instructions for use. In some embodiments, the kits further contain a component selected from any of secondary binding proteins, reagents for immunohistochemistry analysis, pharmaceutically acceptable excipient and instruction manual and any combination thereof. In one specific embodiment, the kit comprises a pharmaceutical composition comprising any one or more of the binding protein compositions described herein, with one or more pharmaceutically acceptable excipients.

The present application also provides articles of manufacture comprising any one of the binding protein compositions or kits described herein. Examples of an article of manufacture include vials (including sealed vials).

EXAMPLES

Provided herein are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual ($2^{nd}$ Edition, 1989); Methods In Enzymology (S. Colowick and N. Kaplan eds., Academic Press, Inc.); Remington's Pharmaceutical Sciences, $18^{th}$ Edition (Easton, Pennsylvania: Mack Publishing Company, 1990); Carey and Sundberg Advanced Organic Chemistry $3^{rd}$ Ed. (Plenum Press) Vols A and B (1992).

Methods

Gene Synthesis and Plasmid Construction

The coding sequences for HCs and LCs of the bispecific antibody were generated by DNA synthesis and PCR, subsequently subcloned into a plasmid for protein expression in mammalian cell system. The gene sequences in the expression vectors were confirmed by DNA sequencing.

Expression of Antibody Constructs

Bispecific constructs were engineered using methods known to those of ordinary skill in the art (e.g., transient expression of bispecific antibodies performed by co-transfection of paired HC and LC constructs into CHO cells using PEI method).

SEC-HPLC Analysis of Antibody Construct

Standard analytical SEC-HPLC was performed using Shimadzu LC-10 HPLC instrument (Shimadzu Corp.).

Measuring Antibody Binding Kinetics Using Surface Plasmon Resonance (SPR)

A Biacore 8K SPR system (GE HealthCare) equipped with Series S Sensor Chip Protein G was used to determine the binding kinetic rate and affinity constants using methods known to those of ordinary skill in the art. Samples were injected in a multi-cycle manner over freshly captured bispecific antibody, by regenerating the capture surfaces with injection of glycine. The data was processed and analyzed with Biacore Insight Evaluation Software Version 2.0.15.12933 (GE Healthcare). The responses from the two buffer blank injections were then subtracted from the reference subtracted data to yield double-referenced data, which were fit to a 1:1 binding model to determine the apparent association ($k_a$) and dissociation rate constants ($k_d$). Their ratio provides the apparent equilibrium dissociation constant or affinity constant ($K_D=k_d/k_a$).

For first-pass assays, SPR analysis was conducted on antibodies against PD-1-hFc and VEGFA for $K_D$, for example.

Assessing Blockade by Cell-Line-Based Assays

The blockade of the full signalling complex of VEGF and/or PD-1 was assessed using cell-line based assays and/or ELISA. Methods for conducting those assays are known to those of ordinary skill in the art.

PD-1 Cell Based Binding Assay

PD-1 binding was assessed in Jurkat-hPD-1 cells in the presence or absence of 2× conc. of VEGF (2×VEGF) by flow cytometry. Briefly, Jurkat-hPD-1 cells were resuspended in FACS buffer (2% FBS in IX PBS). Bispecific antibodies and 2×VEGFA were pre-incubated for 30 min at RT and added to the cells. Cells were incubated at 4° C. for 1 h and washed with FACS buffer. Cells were resuspended with 100 µL secondary antibody (1:500 dilution in FACS buffer) and incubated 4° C. for 1 h. After the incubation cells were washed with FACS buffer and analysed by FACS. The data was plotted and analyzed in GraphPad Prism 10.

PD-1 Reporter Assay

PD-1 signal blocking was assessed by reporter assay coculturing Jurkat-NFAT-hPD-1 and Hep3B-OS8-hPD-L1 cells. Briefly, Hep3B-OS8-PD-L1 cells and Jurkat (6C8)-NFAT-PD-1 cells were co-cultured in the presence of the bispecific antibody (+/−VEGF) and incubated in a humidified 37° C., 5% CO2 incubator for 6 hours. After the incubation, ONE-Glo™ Luciferase Assay System were added to each well to allow complete cell lysis and luminescence was measured by a Thermo Fisher Varioskan LUX multimode microplate reader. The data was plotted and analyzed in GraphPad Prism 10.

PD-1 Internalization Assay

PD1 internalization was assessed by measuring PD-1 level on PD-1-expressing Jurkat cells by flow cytometry. Briefly, Jurkat-hPD-1 cells were seeded into 96 well plate at 2E5 cells per well. Bispecific antibodies and 2× conc. of VEGF were pre-incubated for 30 min at RT. Cells were then treated with the antibodies (+/−VEGF) in warm culture medium at 37° C. for 0, 0.5, 2, 4 and 6 h. After incubation at 37° C., cells were kept on ice and fixed with PFA with a final concentration 2% for 15 min. Cells were then labeled with anti-human IgG Fc-Alexa 647 (1:500) at 4° C. for 1 h and analyzed by flow cytometry. The data was plotted and analyzed in GraphPad Prism 10.

VEGF Reporter Assay

VEGFA induced signal blocking was assessed by reporter assay using human VEGF R2 (Luc) HEK293 reporter cell. Briefly, human VEGF R2 (Luc.) HEK293 reporter cells were resuspended cell in assay medium and plated (3E4/ well) in 96-well one day before the assay. Bispecific antibodies and 2× conc. of VEGF were pre-incubated for 30 min at RT and added to the cells. Cells were incubated in a humidified 37° C., 5% CO2 incubator for 4 hours. After the incubation, ONE-Glo™ Luciferase Assay System were added to each well to allow complete cell lysis and luminescence was measured by a Thermo Fisher Varioskan LUX multimode microplate reader. The data was plotted and analyzed in GraphPad Prism 10.

Human Umbilical Vein Endothelial Cells (HUVEC) Proliferation Assay

Inhibition of VEGF-mediated cell proliferation was assessed in HUVEC culture. Briefly, HUVEC were digested with 3 ml TrypLE at 37° C. for 3 min and washed. Cells were then resuspended in assay medium and seeded in assay plate, and incubated at 37° C. overnight. Bispecific antibodies and 2× conc. of VEGF were pre-incubated for 30 min at RT.

Antibodies (+/−VEGFA) were added to the cells and incubated at 37° C. for 3 days. After the incubation CellTiter-Glo Luminescent buffer was added to the plate, and incubated at RT for 10 min. Luminescence was measured by Thermo Varioskan LUX afterwards. The data is plotted and analyzed in GraphPad Prism 10.

T Cell Activation in Human PBMC and Hepatocellular Carcinoma Cell Line Co-Culture T cell activation was assessed in human PBMC and Hep3B-OS8-hPD-L1 co-culture assay in the presence or absence of 2×VEGFA by measuring IL-2 secretion. Briefly, Hep3B-OS8-PD-L1 cells were resuspended with mitomycin, 10 ug/ml (in 5-10 ml 10% FBS+RPMI 1640 medium) and incubated at 37° C. for 1.5 hr. Bispecific antibodies and 2× conc. of VEGFA were pre-incubated for 30 min at RT. During incubation, PBMCs from healthy volunteers were resuspended in 10% FBS+RPMI 1640 medium. PBMC cells (5E4/well), Hep3B-OS8-PD-L1 cells (5E3/well) and antibodies (+/−VEGF) were added to 96 well plate in a humidified 37° C., 5% CO2 incubator for 72 hours. After 72 h, cell culture supernatants were collected, and concentration of IL-2 and IFN is measured by human IL-2 ELISA kit. The data was plotted and analyzed in GraphPad Prism 10.

T Cell Activation in Human Monocyte Derived Dendritic Cells and CD4+ T Cells Via Mixed Lymphocyte Reaction (MLR) Assay T cell activation was assessed in human monocyte derived dendritic cell (moDC) and CD4+ T cell mixed lymphocyte reaction (MLR) by measuring IL-2 and IFNγ secretion. Briefly, CD14+ monocyte were isolated from human PBMCs using the CD14 microbeads isolation kit (MILTE-NYI-130-050-201) according to the manufacturer protocol. The isolated CD14+ monocytes were then added to a 6-well plate followed by 2 mL/well of hGM-CSF & hIL-4 with assay media to induce dendritic cell differentiation. The plate was then incubated at 37° C. in 5% CO2 for 6 days.

After the incubation period, the cells were treated with rhGM-CSF (50 ng/mL), IL-4 (25 ng/ml) and LPS (1 μg/mL) to mature the dendritic cells (DCs). The DCs were then harvested and diluted into 0.2×106 cells/mL. CD4+ T cells were isolated from human PBMCs as well with the Human CD4+ T Cell Isolation Kit utilizing the manufacturer protocol. The isolated CD4+ T cells were resuspended at 2×10$^6$ cells/mL using assay media followed by distribution to a 96 well plate at 50 μL/well (0.1×106). Bispecific antibodies and 2× conc. of VEGF were pre-incubated for 30 min at RT. The antibody mixtures (+/−VEGFA) were transferred to the T cell culture, mixed well and incubated at 37° C. for 30 minutes. After incubation, the monocyte derived dendritic cells were added to the plate at a volume of 50 μL/well (0.2×106 cells/mL, 0.01×106 cells/well) and were incubated at 37° C., 5% CO2. After the 48-hour incubation period, 50 μL of the supernatant was transferred to a new 96-well plate for IL-2 quantification using the cytometric bead array (CBA) and a 96-hour incubation period, 50 μL of the supernatant was transferred to a new 96-well plate for IFNγ quantification via the CBA. The data is plotted and analyzed in GraphPad Prism 10.

Comparators

In some examples provided herein, comparators were used to evaluate bioactivity of the bispecific antibodies disclosed herein. In some cases, an ivonescimab (also referred to as PAL054-0001.1L or AK112 herein) antibody was used. AK112 is a PD-1/VEGF bispecific antibody comprising a heavy chain (SEQ ID NO: 128) and a light chain (SEQ ID NO: 275).

AK112 comprises VH and VL domains from bevacizumab and penpulimab (AK105) (FIG. 8).

Additional comparator sequences (controls and benchmarks are provided in Table 11).

TABLE 11

| Construct Name | HC Protein | SEQ ID NO | LC Protein | SEQ ID NO |
|---|---|---|---|---|
| | Benchmarks | | | |
| PAL054-0001.1L (Ivonescimab; AK112) | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNH KPSNTKVDKKVEPKSCDKTHTCPPCPAPEAAGGPS VFLFPPKPKDTLMISRTPEVTCVVVDVSHEDPEVK FNWYVDGVEVHNAKIKPREEQYNSTYRVVSVLTVL HQDWLNGKEYKCKVSNKALPAPIEKTISKAKGQPR EPQVYTLPPSRDELTKNQVSLTCLVKGFYPSDIAV EWESNGQPENNYKTTPPVLDSDGSFFLYSKLTVDK SRWQQGNVFSCSVMHEALHNHYTQKSLSLSPGKGG GGSGGGGSGGGGSGGGGSEVQLVESGGGLVQPGGS LRLSCAASGFAFSSYDMSWVRQAPGKGLDWVATIS GGGRYTYYPDSVKGRFTISRDNSKNNLYLQMNSLR AEDTALYYCANRYGEAWFAYWGQGTLVTVSSGGGG SGGGGSGGGGSGGGGSDIQMTQSPSSMSASVGDRV TFTCRASQDINTYLSWFQQKPGKSPKTLIYRANRL VSGVPSRFSGSGSGQDYTLTISSLQPEDMATYYCL QYDEFPLTFGAGTKLELKR | 128 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTVPWTF GQGTKVEIKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | 275 |
| PAL054-0001.1La | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNH KPSNTKVDKKVEPKSCDKTHTCPPCPAPEAAGGPS VFLFPPKPKDTLYITREPEVTCVVVDVSHEDPEVK FNWYVDGVEVHNAKTKPREEQYNSTYRVVSVLTVL | 129 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTVPWTF GQGTKVEIKRTVAA PSVFIFPPSDEQLK | 276 |

TABLE 11-continued

| Construct Name | HC Protein | SEQ ID NO | LC Protein | SEQ ID NO |
|---|---|---|---|---|
| | HQDWLNGKEYKCKVSNKALPAPIEKTISKAKGQPR EPQVYTLPPSRDELTKNQVSLTCLVKGFYPSDIAV EWESNGQPENNYKTTPPVLDSDGSFFLYSKLIVDK SRWQQGNVFSCSVMHEALHNHYTQKSLSLSPGKGG GGSGGGGSGGGGSGGGGSEVQLVESGGGLVQPGGS LRLSCAASGFAFSSYDMSWVRQAPGKGLDWVATIS GGGRYTYYPDSVKGRFTISRDNSKNNLYLQMNSLR AEDTALYYCANRYGEAWFAYWGQGTLVTVSSGGGG SGGGGSGGGGSGGGGSDIQMTQSPSSMSASVGDRV TFTCRASQDINTYLSWFQQKPGKSPKTLIYRANRL VSGVPSRFSGSGSGQDYTLTISSLQPEDMATYYCL QYDEFPLTFGAGTKLELKR | | SGTASVVCLLNNFY PREAKVQWKVDNAL QSGNSQESVTEQDS KDSTYSLSSTLILS KADYEKHKVYACEV THQGLSSPVTKSFN RGEC | |
| PAL054-0002.1L | EVQLVESGGGLVQPGGSLRLSCAASGFAFSSYDMS WVRQAPGKGLDWVATISGGGRYTYYPDSVKGRFTI SRDNSKNNLYLQMNSLRAEDTALYYCANRYGEAWF AYWGQGTLVTVSSASTKGPSVFPLAPSSKSTSGGT AALGCLVKDYFPEPVTVSWNSGALTSGVHTFPAVL QSSGLYSLSSVVTVPSSSLGTQTYICNVNHKPSNT KVDKKVEPKSCDKTHTCPPCPAPEAAGAPSVFLFP PKPKDTLMISRTPEVTCVVVDVSHEDPEVKENWYV DGVEVHNAKTKPREEQYNSTYRVVSVLTVLHQDWL NGKEYKCKVSNKALPAPIEKTISKAKGQPREPQVY TLPPSRDELTKNQVSLTCLVKGFYPSDIAVEWESN GQPENNYKTTPPVLDSDGSFFLYSKLTVDKSRWQQ GNVFSCSVMHEALHNHYTQKSLSLSPGK | 745 | DIQMTQSPSSMSAS VGDRVTFTCRASQD INTYLSWFQQKPGK SPKTLIYRANRLVS GVPSRFSGSGSGQD YTLTISSLQPEDMA TYYCLQYDEFPLTF GAGTKLELKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | 746 |
| PAL054-0003.1L | EPKSCDKTHTCPPCPAPEAAGGPSVFLFPPKPKDT LMISRTPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSR DELTKNQVSLTCLVKGFYPSDIAVEWESNGQPENN YKTTPPVLDSDGSFFLYSKLTVDKSRWQQGNVFSC SVMHEALHNHYTQKSLSLSPGKGGGGSGGGGSGGG GSGGGGSEVQLVESGGGLVQPGGSLRLSCAASGFA FSSYDMSWVRQAPGKGLDWVATISGGGRYTYYPDS VKGRFTISRDNSKNNLYLQMNSLRAEDTALYYCAN RYGEAWFAYWGQGTLVTVSSGGGGSGGGGSGGGGS GGGGSDIQMTQSPSSMSASVGDRVTFTCRASQDIN TYLSWFQQKPGKSPKTLIYRANRLVSGVPSRFSGS GSGQDYTLTISSLQPEDMATYYCLQYDEFPLTFGA GTKLELKR | 747 | | |
| PAL054-0004.4 (Pembroli zumab) | QVQLVQSGVEVKKPGASVKVSCKASGYTFTNYYMY WVRQAPGQGLEWMGGINPSNGGTNFNEKFKNRVTL TTDSSTTTAYMELKSLQFDDTAVYYCARRDYRFDM GFDYWGQGTTVTVSSASTKGPSVFPLAPCSRSTSE STAALGCLVKDYFPEPVTVSWNSGALTSGVHTFPA VLQSSGLYSLSSVVTVPSSSLGTKTYTCNVDHKPS NTKVDKRVESKYGPPCPPCPAPEFLGGPSVFLFPP KPKDTLMISRTPEVTCVVVDVSQEDPEVQFNWYVD GVEVHNAKTKPREEQFNSTYRVVSVLIVLHQDWLN GKEYKCKVSNKGLPSSIEKTISKAKGQPREPQVYT LPPSQEEMTKNQVSLTCLVKGFYPSDIAVEWESNG QPENNYKTTPPVLDSDGSFFLYSRLTVDKSRWQEG NVFSCSVMHEALHNHYTQKSLSLSLGK | 748 | EIVLTQSPATLSLS PGERATLSCRASKG VSTSGYSYLHWYQQ KPGQAPRLLIYLAS YLESGVPARFSGSG SGTDFTLTISSLEP EDFAVYYCQHSRDL PLTFGGGTKVEIKR TVAAPSVFIFPPSD EQLKSGTASVVCLL NNFYPREAKVQWKV DNALQSGNSQESVT EQDSKDSTYSLSST LTLSKADYEKHKVY ACEVTHQGLSSPVT KSFNRGEC | 749 |
| PAL054-0005.1L | EPKSCDKTHTCPPCPAPEAAGGPSVFLFPPKPKDT LMISRTPEVTCVVVDVSHEDPEVKENWYVDGVEVH NAKTKPREEQYNSTYRVVSVLIVLHQDWLNGKEYK CKVSNKALPAPIEKTISKAKGQPREPQVYTLPPSR DELTKNQVSLTCLVKGFYPSDIAVEWESNGQPENN YKTTPPVLDSDGSFFLYSKLTVDKSRWQQGNVFSC SVMHEALHNHYTQKSLSLSPGKGGGGSGGGGSGGG GSGGGGSGQVQLVQSGVEVKKPGASVKVSCKASGYT FTNYYMYWVRQAPGQGLEWMGGINPSNGGTNFNEK FKNRVTLTTDSSTTTAYMELKSLQFDDTAVYYCAR RDYRFDMGFDYWGQGTTVTVSSGGGGSGGGGSGGGG | 750 | | |

TABLE 11-continued

| Construct Name | HC Protein | SEQ ID NO | LC Protein | SEQ ID NO |
|---|---|---|---|---|
| | GSGGGGSEIVLTQSPATLSLSPGERATLSCRASKG VSTSGYSYLHWYQQKPGQAPRLLIYLASYLESGVP ARFSGSGSGTDFTLTISSLEPEDFAVYYCQHSRDL PLTFGGGTKVEIKR | | | |
| PAL054-0006.1L | EPKSCDKTHTCPPCPAPEAAGGPSVFLFPPKPKDT LMISRTPEVTCVVVDVSHEDPEVKENWYVDGVEVH NAKTKPREEQYNSTYRVVSVLTVLHQDWLNGKEYK CKVSNKALPAPIEKTISKAKGQPREPQVYTLPPSR DELTKNQVSLTCLVKGFYPSDIAVEWESNGQPENN YKTTPPVLDSDGSFFLYSKLTVDKSRWQQGNVFSC SVMHEALHNHYTQKSLSLSPGKGGGGSGGGGSGGG GSGGGGSQVQLVQSGVEVKKPGASVKVSCKASGYT FTNYYMYWVRQAPGQCLEWMGGINPSNGGINFNEK FKNRVTLTTDSSTTTAYMELKSLQFDDTAVYYCAR RDYRFDMGFDYWGQGTTVTVSSGGGGSGGGGSGGG GSGGGGSEIVLTQSPATLSLSPGERATLSCRASKG VSTSGYSYLHWYQQKPGQAPRLLIYLASYLESGVP ARFSGSGSGTDFTLTISSLEPEDFAVYYCQHSRDL PLTFGCGTKVEIKR | 751 | | |
| PAL054-0007.1 (Bevacizumab) | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNH KPSNTKVDKKVEPKSCDKTHTCPPCPAPELLGGPS VFLFPPKPKDTLMISRTPEVTCVVVDVSHEDPEVK FNWYVDGVEVHNAKTKPREEQYNSTYRVVSVLIVL HQDWLNGKEYKCKVSNKALPAPIEKTISKAKGQPR EPQVYTLPPSREEMTKNQVSLTCLVKGFYPSDIAV EWESNGQPENNYKTTPPVLDSDGSFFLYSKLTVDK SRWQQGNVFSCSVMHEALHNHYTQKSLSLSPGK | 752 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTVPWTF GQGTKVEIKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | 753 |
| PAL054-0008.1L | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNH KPSNTKVDKKVEPKSCDKTHTCPPCPAPEAAGGPS VFLFPPKPKDTLMISRTPEVTCVVVDVSHEDPEVK FNWYVDGVEVHNAKTKPREEQYNSTYRVVSVLIVL HQDWLNGKEYKCKVSNKALPAPIEKTISKAKGQPR EPQVYTLPPSRDELTKNQVSLTCLVKGFYPSDIAV EWESNGQPENNYKTTPPVLDSDGSFFLYSKLTVDK SRWQQGNVFSCSVMHEALHNHYTQKSLSLSPGKGG GGSGGGGSGGGGSGGGGSQVQLVESGGGVVQPGRS LRLDCKASGITFSNSGMHWVRQAPGKGLEWVAVIW YDGSKRYYADSVKGRFTISRDNSKNILFLQMNSLR AEDTAVYYCATNDDYWGQGTGVRVSSGGGGSGGGG SGGGGSGGGGSEIVLTQSPATLSLSPGERATLSCR ASQSVSSYLAWYQQKPGQAPRLLIYDASNRATGIP ARFSGSGSGTDFTLTISSLEPEDFAVYYCQQSSNW PRTFGQGTKVEIKR | 754 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTVPWTF GQGTKVEIKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | 755 |
| PAL054-0008.1La | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNH KPSNTKVDKKVEPKSCDKTHTCPPCPAPEAAGGPS VFLFPPKPKDTLYITREPEVTCVVVDVSHEDPEVK FNWYVDGVEVHNAKTKPREEQYNSTYRVVSVLTVL HQDWLNGKEYKCKVSNKALPAPIEKTISKAKGQPR EPQVYTLPPSRDELTKNQVSLTCLVKGFYPSDIAV EWESNGQPENNYKTTPPVLDSDGSFFLYSKLTVDK SRWQQGNVFSCSVMHEALHNHYTQKSLSLSPGKGG GGSGGGGSGGGGSGGGGSQVQLVESGGGVVQPGRS LRLDCKASGITFSNSGMHWVRQAPGKGLEWVAVIW YDGSKRYYADSVKGRFTISRDNSKNTLFLQMNSLR | 756 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTVPWTF GQGTKVEIKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | 757 |

TABLE 11-continued

| Construct Name | HC Protein | SEQ ID NO | LC Protein | SEQ ID NO |
|---|---|---|---|---|
| | AEDTAVYYCATNDDYWGQGTGVRVSSGGGGSGGGG SGGGGSGGGGSEIVLTQSPATLSLSPGERATLSCR ASQSVSSYLAWYQQKPGQAPRLLIYDASNRATGIP ARFSGSGSGTDFTLTISSLEPEDFAVYYCQQSSNW PRTFGQGTKVEIKR | | | |
| PAL054-0009.1L | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNH KPSNTKVDKKVEPKSCDKTHTCPPCPAPEAAGGPS VFLFPPKPKDTLMISRTPEVTCVVVDVSHEDPEVK FNWYVDGVEVHNAKIKPREEQYNSTYRVVSVLIVL HQDWLNGKEYKCKVSNKALPAPIEKTISKAKGQPR EPQVYTLPPSRDELTKNQVSLTCLVKGFYPSDIAV EWESNGQPENNYKTTPPVLDSDGSFFLYSKLTVDK SRWQQGNVFSCSVMHEALHNHYTQKSLSLSPGKGG GGSGGGGSGGGGSGGGGSEVQLLESGGVLVQPGGS LRLSCAASGFTFSNFGMTWVRQAPGKGLEWVSGIS GGGRDTYFADSVKGRFTISRDNSKNTLYLQMNSLK GEDTAVYYCVKWGNIYFDYWGQGTLVTVSSGGGGS GGGGGGGSGGGGSDIQMTQSPSSLSASVGDSIT ITCRASLSINTFLNWYQQKPGKAPNLLIYAASSLH GGVPSRFSGSGSGTDFTLTIRTLQPEDFATYYCQQ SSNTPFTFGPGTVVDFR | 758 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTVPWTF GQGTKVEIKRTVAA PSVFIFPPSDEQLK SGTASVVCLLNNFY PREAKVQWKVDNAL QSGNSQESVTEQDS KDSTYSLSSTLILS KADYEKHKVYACEV THQGLSSPVTKSFN RGEC | 759 |
| PAL054-0009.1La | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNH KPSNTKVDKKVEPKSCDKTHTCPPCPAPEAAGGPS VFLFPPKPKDTLYITREPEVTCVVVDVSHEDPEVK FNWYVDGVEVHNAKIKPREEQYNSTYRVVSVLTVL HQDWLNGKEYKCKVSNKALPAPIEKTISKAKGQPR EPQVYTLPPSRDELTKNQVSLTCLVKGFYPSDIAV EWESNGQPENNYKTTPPVLDSDGSFFLYSKLTVDK SRWQQGNVFSCSVMHEALHNHYTQKSLSLSPGKGG GGSGGGGSGGGGSGGGGSEVQLLESGGVLVQPGGS LRLSCAASGFTFSNFGMTWVRQAPGKGLEWVSGIS GGGRDTYFADSVKGRFTISRDNSKNTLYLQMNSLK GEDTAVYYCVKWGNIYFDYWGQGTLVTVSSGGGGS GGGGSGGGGSGGGGSDIQMTQSPSSLSASVGDSIT ITCRASLSINTFLNWYQQKPGKAPNLLIYAASSLH GGVPSRFSGSGSGTDFTLTIRTLQPEDFATYYCQQ SSNTPFTFGPGTVVDFR | 760 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTVPWTF GQGTKVEIKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | 761 |
| PAL054-0010.1La | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNH KPSNTKVDKKVEPKSCDKTHTCPPCPAPEAAGGPS VFLFPPKPKDTLYITREPEVTCVVVDVSHEDPEVK FNWYVDGVEVHNAKTKPREEQYNSTYRVVSVLTVL HQDWLNGKEYKCKVSNKALPAPIEKTISKAKGQPR EPQVYTLPPSRDELTKNQVSLTCLVKGFYPSDIAV EWESNGQPENNYKTTPPVLDSDGSFFLYSKLTVDK SRWQQGNVFSCSVMHEALHNHYTQKSLSLSPGKGG GGSGGGGSGGGGSGGGGSEVQLLESGGVLVQPGGS LRLSCAASGFTFSNFGMTWVRQAPGKCLEWVSGIS GGGRDTYFADSVKGRFTISRDNSKNTLYLQMNSLK GEDTAVYYCVKWGNIYFDYWGQGTLVTVSSGGGGS GGGGSGGGGSGGGGSDIQMTQSPSSLSASVGDSIT ITCRASLSINTFLNWYQQKPGKAPNLLIYAASSLH GGVPSRFSGSGSGTDFTLTIRTLQPEDFATYYCQQ SSNTPFTFGCGTVVDFR | 762 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTVPWTF GQGTKVEIKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | 763 |
| PAL054-0011.1L | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSSASTKGPSVFPLAPSSKS | 764 | DIQMTQSPSSLSAS VGDRVTITCSASQD ISNYLNWYQQKPGK APKVLIYFTSSLHS | 765 |

TABLE 11-continued

| Construct Name | HC Protein | SEQ ID NO | LC Protein | SEQ ID NO |
|---|---|---|---|---|
| | TSGGTAALGCLVKDYFPEPVTVSWNSGALTSGVHT FPAVLQSSGLYSLSSVVTVPSSSLGTQTYICNVNH KPSNTKVDKKVEPKSCDKTHTCPPCPAPEAAGGPS VFLFPPKPKDTLMISRTPEVTCVVVDVSHEDPEVK FNWYVDGVEVHNAKTKPREEQYNSTYRVVSVLTVL HQDWLNGKEYKCKVSNKALPAPIEKTISKAKGQPR EPQVYTLPPSRDELTKNQVSLTCLVKGFYPSDIAV EWESNGQPENNYKTTPPVLDSDGSFFLYSKLTVDK SRWQQGNVFSCSVMHEALHNHYTQKSLSLSPGKGG GGSGGGGSGGGGSGGGGSDVQLVESGGGVVQPGGS LRLSCAASGSIASIHAMGWFRQAPGKEREFVAVIT WSGGITYYADSVKGRFTISRDNSKNTVYLQMNSLR PEDTALYYCAGDKHQSSWYDYWGQGTLVTVSS | | GVPSRFSGSGSGTD FTLTISSLQPEDFA TYYCQQYSTVPWTF GQGTKVEIKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | |
| PAL054-0011.1La | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNH KPSNTKVDKKVEPKSCDKTHTCPPCPAPEAAGGPS VFLFPPKPKDTLYITREPEVTCVVVDVSHEDPEVK FNWYVDGVEVHNAKTKPREEQYNSTYRVVSVLIVL HQDWLNGKEYKCKVSNKALPAPIEKTISKAKGQPR EPQVYTLPPSRDELTKNQVSLTCLVKGFYPSDIAV EWESNGQPENNYKTTPPVLDSDGSFFLYSKLTVDK SRWQQGNVFSCSVMHEALHNHYTQKSLSLSPGKGG GGSGGGGSGGGGSGGGGSDVQLVESGGGVVQPGGS LRLSCAASGSIASIHAMGWFRQAPGKEREFVAVIT WSGGITYYADSVKGRFTISRDNSKNTVYLQMNSLR PEDTALYYCAGDKHQSSWYDYWGQGTLVTVSS | 766 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTVPWTF GQGTKVEIKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | 767 |
| PAL054-0012.1L | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNH KPSNTKVDKKVEPKSCDKTHTCPPCPAPEAAGGPS VFLFPPKPKDTLMISRTPEVTCVVVDVSHEDPEVK FNWYVDGVEVHNAKTKPREEQYNSTYRVVSVLTVL HQDWLNGKEYKCKVSNKALPAPIEKTISKAKGQPR EPQVYTLPPSRDELTKNQVSLTCLVKGFYPSDIAV EWESNGQPENNYKTTPPVLDSDGSFFLYSKLTVDK SRWQQGNVFSCSVMHEALHNHYTQKSLSLSPGGGG GSGGGGSGGEVQLQESGGGLVQPGGSLRLSCAASGF TFSSYWMYWLRQAPGKGLEWVSSINSDSSSTYYRD SVKGRFTISRDNAKNTLYLQMNSLKSEDTAVYYCA KDPGGYAKGQGTQVTVSS | 768 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTVPWTF GQGTKVEIKRTVAA PSVFIFPPSDEQLK SGTASVVCLLNNFY PREAKVQWKVDNAL QSGNSQESVTEQDS KDSTYSLSSTLILS KADYEKHKVYACEV THQGLSSPVTKSFN RGEC | 769 |
| PAL054-0013.1 | SDTGRPFVEMYSEIPEIIHMTEGRELVIPCRVTSP NITVTLKKFPLDTLIPDGKRIIWDSRKGFIISAAT YKEIGLLTCEATVNGHLYKTNYLTHRQTNTGGGGS GGGGSGGGGSEVQLVESGGGLVQPGGSLRLSCAAS GFTFSDSWIHWVRQAPGKGLEWVAWISPYGGSTYY ADSVKGRFTISADTSKNTAYLQMNSLRAEDTAVYY CARRHWPGGFDYWGQGTLVTVSSASTKGPSVFPLA PSSKSTSGGTAALGCLVKDYFPEPVTVSWNSGALT SGVHTFPAVLQSSGLYSLSSVVTVPSSSLGTQTYI CNVNHKPSNTKVDKRVEPKSCDKTHTCPPCPAPEL LGGPSVFLFPPKPKDTLMISRTPEVTCVVVDVSHE DPEVKFNWYVDGVEVHNAKTKPREEQYNATYRVVS VLTVLHQDWLNGKEYKCKVSNKALPAPIAATISKA KGQPREPQVYTLPPSREEMTKNQVSLTCLVKGFYP SDIAVEWESNGQPENNYKTTPPVLDSDGSFFLYSK LTVDKSRWQQGNVFSCSVMHEALHNHYTQKSLSLS PG | 770 | DIQMTQSPSSLSAS VGDRVTITCRASQD VSTAVAWYQQKPGK APKLLIYSASFLYS GVPSRFSGSGSGTD FTLTISSLQPEDFA TYYCQQYLYHPATF GQGTKVEIKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | 771 |
| PAL054-0014.1L | EVQLVESGGGLVQPGGSLRLSCAASGYTFTNYGMN WVRQAPGKGLEWVGWINTYTGEPTYAADFKRRFTF SLDTSKSTAYLQMNSLRAEDTAVYYCAKYPHYYGS SHWYFDVWGQGTLVTVSSASTKGPSVFPLAPSSKS TSGGTAALGCLVKDYFPEPVTVSWNSGALTSGVHT FPAVLQSSGLYSLSSVVTVPSSSLGTQTYICNVNH KPSNTKVDKKVEPKSCDKTHTCPPCPAPEAAGGPS VFLFPPKPKDTLMISRTPEVTCVVVDVSHEDPEVK | 772 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTVPWTF GQGTKVEIKRTVAA | 773 |

TABLE 11-continued

| Construct Name | HC Protein | SEQ ID NO | LC Protein | SEQ ID NO |
|---|---|---|---|---|
| | FNWYVDGVEVHNAKTKPREEQYNSTYRVVSVLIVL HQDWLNGKEYKCKVSNKALPAPIEKTISKAKGQPR EPQVYTLPPSRDELTKNQVSLTCLVKGFYPSDIAV EWESNGQPENNYKTTPPVLDSDGSFFLYSKLTVDK SRWQQGNVFSCSVMHEALHNHYTQKSLSLSPGGGG GSGGGGSGGGGSGGGGSEVQLVESGGGLVQPGGSL RLSCAVSGNIYNRNFMGWFRQAPGKGREGVSAIYT GTSRTYYADSVKGRFTISRDNAKNTVYLQMNSLRP EDTAVYYCAADLRDGFWDTGVWNTWGQGTLVTVSS | | PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | |
| PAL054-0015.1a | QVQLVQSGVEVKKPGASVKVSCKASGYTFTNYYMY WVRQAPGQGLEWMGGINPSNGGTNFNEKFKNRVTL TTDSSTTTAYMELKSLQFDDTAVYYCARRDYRFDM GFDYWGQGTTVTVSSASTKGPSVFPLAPSSKSTSG GTAALGCLVKDYFPEPVTVSWNSGALTSGVHTFPA VLQSSGLYSLSSVVTVPSSSLGTQTYICNVNHKPS NTKVDKKVEPKSCDKTHTCPPCPAPELLGGPSVFL FPPKPKDTLMISRTPEVTCVVVDVSHEDPEVKENW YVDGVEVHNAKTKPREEQYASTYRVVSVLIVLHQD WLNGKEYKCKVSNKALPAPIEKTISKAKGQPREPQ VYTLPPSRDELTKNQVSLLCLVKGFYPSDIAVEWE SNGQPENNYKTTPPVLRSDGSFFLYSKLTVDKSRW QQGNVFSCSVMHEALHNHYTQKSLSLSPGK | 774 | EIVLTQSPATLSLS PGERATLSCRASKG VSTSGYSYLHWYQQ KPGQAPRLLIYLAS YLESGVPARFSGSG SGTDFTLTISSLEP EDFAVYYCQHSRDL PLTFGGGTKVEIKR TVAAPSVFIFPPSD EQLKSGTASVVCLL NNFYPREAKVQWKV DNALQSGNSQESVT EQDSKDSTYSLSST LTLSKADYEKHKVY ACEVTHQGLSSPVT KSENRGEC | 775 |
| PAL054-0015.1b | EVQLVESGGGLVQPGGSLRLSCAASGFTISDYWIH WVRQAPGKGLEWVAGITPAGGYTYYADSVKGRFTI SADTSKNTAYLQMNSLRAEDTAVYYCARFVFFLPY AMDYWGQGTLVTVSSASTKGPSVFPLAPSSKSTSG GTAALGCLVKDYFPEPVTVSWNSGALTSGVHTFPA VLQSSGLYSLSSVVTVPSSSLGTQTYICNVNHKPS NTKVDKKVEPKSCDKTHTCPPCPAPELLGGPSVFL FPPKPKDTLMISRTPEVTCVVVDVSHEDPEVKENW YVDGVEVHNAKTKPREEQYASTYRVVSVLIVLHQD WLNGKEYKCKVSNKALPAPIEKTISKAKGQPREPQ VYTEPPSRDELTKNQVSLTCLVKGFYPSDIAVEWE SNGQPENNYKTTPPVLDSDGSFFLLSVLIVDKSRW QQGNVFSCSVMHEALHNHYTQKSLSLSPGK | 776 | DIQMTQSPSSLSAS VGDRVTITCRASQD VSTAVAWYQQKPGK APKLLIYSASFLYS GVPSRFSGSGSGTD FTLTISSLQPEDFA TYYCQQGYGNPFTF GQGTKVEIKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | 777 |
| PAL054-0016.1L | QVQLVESGGGLVQPGGSLRLSCAASGFAFSSYDMS WVRQAPGKCLEWVATISGGGRYTYYPDSVKGRFTI SRDNSKNNLYLQMNSLRAEDTAVYYCAVRYGETWF AYWGQGTLVTVSSGGGGGGGGSGGGGSGGGGSDI QMTQSPSSLSASVGDRVTITCRASQDINTYLAWFQ QKPGKAPKSLIYRANRLVSGVPSRFSGSGSGTDFT LTISSLQPEDMATYYCLQYDEFPLTFGCGTKLELK GGGASGGGGSGGGGSEVQLVESGGGLVQPGGSLRL SCAASGYTFTNYGMNWVRQAPGKGLEWVGWINTYT GEPTYAADFKRRFTFSLDISKSTAYLQMNSLRAED TAVYYCAKYPHYYGSSHWYFDVWGQGTLVTVSSAS TKGPSVFPLAPSSKSTSGGTAALGCLVKDYFPEPV TVSWNSGALTSGVHTFPAVLQSSGLYSLSSVVTVP SSSLGTQTYICNVNHKPSNTKVDKKVEPKSCDKTH TCPPCPAPEAAGGPSVFLFPPKPKDTLMISRTPEV TCVVVDVSHEDPEVKFNWYVDGVEVHNAKTKPREE QYNSTYRVVSVLTVLHQDWLNGKEYKCKVSNKALP APIEKTISKAKGQPREPQVYTLPPSREEMTKNQVS LTCLVKGFYPSDIAVEWESNGQPENNYKTTPPVLD SDGSFFLYSKLTVDKSRWQQGNVFSCSVMHEALHN HYTQKSLSLSPGK | 778 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTVPWTF GQGTKVEIKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | 779 |
| PAL054-0017.4 | EVQLVESGGGLVQPGGSLRLSCAASGFVFSNYDMS WVRQAPGKRLEWVATISGGGGYTYYSDSVKGRFTI SRDNAKNSLYLQMNSLRAEDTAVYYCASPYGHYGF EYWGQGTLVTVSSASTKGPSVFPLAPCSRSTSEST AALGCLVKDYFPEPVTVSWNSGALTSGVHTFPAVL QSSGLYSLSSVVTVPSSSLGTKTYTCNVDHKPSNT KVDKRVGGGSGGGGSGGGGSEVQLVESGGGLVQP GGSLRLSCAASGYDFTHYGMNWVRQAPGKGLEWVG WINTYTGEPTYAADFKRRFTFSLDISKSTAYLQMN SLRAEDTAVYYCAKYPYYYGTSHWYFDVWGQGTLV | 780 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTLPWTF GQGTKVEIKRTVAA PSVFIFPPSDEQLK SGTASVVCLLNNFY | 781 |

TABLE 11-continued

| Construct Name | HC Protein | SEQ ID NO | LC Protein | SEQ ID NO |
|---|---|---|---|---|
| | TVSSASTKGPSVFPLAPCSRSTSESTAALGCLVKD YPPEPVTVSWNSGALTSGVHTFPAVLQSSGLYSLS SVVTVPSSSLGTKTYTCNVDHKPSNTKVDKRVESK YGPPCPPCPAPEFLGGPSVFLFPPKPKDTLMISRT PEVTCVVVDVSQEDPEVQFNWYVDGVEVHNAKTKP REEQFNSTYRVVSVLTVLHQDWLNGKEYKCKVSNK GLPSSIEKTISKAKGQPREPQVYTLPPSQEEMTKN QVSLTCLVKGFYPSDIAVEWESNGQPENNYKTTPP VLDSDGSFFLYSRLTVDKSRWQEGNVFSCSVMHEA LHNHYTQKSLSLSLGK | | PREAKVQWKVDNAL QSGNSQESVTEQDS KDSTYSLSSTLTLS KADYEKHKVYACEV THQGLSSPVTKSFN RGEC | |
| PAL054-0018.1L | QVQLVESGGGLVQPGGSLRLSCATSGSRRSIYAMG WFRQAPGKGLEFVAGIGWAYATTYYADSVKGRETI SRDNTKNTLYLQMNSLRAEDTAVYYCAADLDHSGF DYWGQGTLVTVSSGGGGSGGGGSGGGGSEVQLVQS GGGVVQPGGSLRLSCAASGYTFTNYGMNWVRQAPG KGLEWVGWINTYTGEPTYAADFKRRFTFSLDISKS TAYLQMNSLRAEDTAVYYCAKYPHYYGSSHWYFDV WGQGTLVTVSSASTKGPSVFPLAPSSKSTSGGTAA LGCLVKDYFPEPVTVSWNSGALTSGVHTFPAVLQS SGLYSLSSVVTVPSSSLGTQTYICNVNHKPSNTKV DKKVEPKSCDKTHTCPPCPAPEAAGGPSVFLFPPK PKDTLMISRTPEVTCVVVDVSHEDPEVKENWYVDG VEVHNAKTKPREEQYNSTYRVVSVLTVLHQDWLNG KEYKCKVSNKALPAPIEKTISKAKGQPREPQVYTL PPSREEMTKNQVSLTCLVKGFYPSDIAVEWESNGQ PENNYKTTPPVLDSDGSFFLYSKLTVDKSRWQQGN VFSCSVMHEALHNHYTQKSLSLSPGK | 782 | DIQMTQSPSSLSAS VGDRVTITCSASQD ISNYLNWYQQKPGK APKVLIYFTSSLHS GVPSRFSGSGSGTD FTLTISSLQPEDFA TYYCQQYSTVPWTF GQGTKVEIKRTVAA PSVFIFPPSDEQLK SGTASVVCLLNNFY PREAKVQWKVDNAL QSGNSQESVTEQDS KDSTYSLSSTLTLS KADYEKHKVYACEV THQGLSSPVTKSFN RGEC | 783 |

Controls

| Construct Name | HC Protein | SEQ ID NO | LC Protein | SEQ ID NO |
|---|---|---|---|---|
| PAL054-0051.1La | QVQLVQSGVEVKKPGASVKVSCKASGYTFTNYYMY WVRQAPGQGLEWMGGINPSQGGTNFNEKFKNRVTL TTDSSTTTAYMELKSLQFDDTAVYYCARRDYREDL GFDYWGQGTTVTVSSASTKGPSVFPLAPSSKSTSG GTAALGCLVKDYFPEPVTVSWNSGALTSGVHTFPA VLQSSGLYSLSSVVTVPSSSLGTQTYICNVNHKPS NTKVDKKVEPKSCDKTHTCPPCPAPEAAGGPSVFL FPPKPKDTLYITREPEVTCVVVDVSHEDPEVKENW YVDGVEVHNAKTKPREEQYNSTYRVVSVLTVLHQD WLNGKEYKCKVSNKALPAPIEKTISKAKGQPREPQ VYTLPPSRDELTKNQVSLTCLVKGFYPSDIAVEWE SNGQPENNYKTTPPVLDSDGSFFLYSKLTVDKSRW QQGNVFSCSVMHEALHNHYTQKSLSLSPGK | 784 | EIVLTQSPATLSLS PGERATLSCRASKG VSTSGYSYLHWYQQ KPGQAPRLLIYLAS YLESGVPARFSGSG SGTDFTLTISSLEP EDFAVYYCQHSRDL PLTFGGGTKVEIKR TVAAPSVFIFPPSD EQLKSGTASVVCLL NNFYPREAKVQWKV DNALQSGNSQESVT EQDSKDSTYSLSST LTLSKADYEKHKVY ACEVTHQGLSSPVT KSENRGEC | 785 |
| PAL054-0052.1La | QVQLVQSGVEVKKPGASVKVSCKASGYTFTNYYMY WVRQAPGQGLEWMGGINPSRGGTNFNEKFKNRVTL TTDSSTTTAYMELKSLQFDDTAVYYCARRDYRFDL GFDYWGQGTTVTVSSASTKGPSVFPLAPSSKSTSG GTAALGCLVKDYFPEPVTVSWNSGALTSGVHTFPA VLQSSGLYSLSSVVTVPSSSLGTQTYICNVNHKPS NTKVDKKVEPKSCDKTHTCPPCPAPEAAGGPSVFL FPPKPKDTLYITREPEVTCVVVDVSHEDPEVKENW YVDGVEVHNAKTKPREEQYNSTYRVVSVLTVLHQD WLNGKEYKCKVSNKALPAPIEKTISKAKGQPREPQ VYTLPPSRDELTKNQVSLTCLVKGFYPSDIAVEWE SNGQPENNYKTTPPVLDSDGSFFLYSKLTVDKSRW QQGNVFSCSVMHEALHNHYTQKSLSLSPGK | 786 | EIVLTQSPATLSLS PGERATLSCRASKG VSTSGYSYLHWYQQ KPGQAPRLLIYLAS YLESGVPARFSGSG SGTDFTLTISSLEP EDFAVYYCQHSRDL PLTFGGGTKVEIKR TVAAPSVFIFPPSD EQLKSGTASVVCLL NNFYPREAKVQWKV DNALQSGNSQESVT EQDSKDSTYSLSST LTLSKADYEKHKVY ACEVTHQGLSSPVT KSFNRGEC | 787 |
| PAL054-0053.1La | EPKSCDKTHTCPPCPAPEAAGGPSVFLFPPKPKDT LYITREPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSR DELTKNQVSLTCLVKGFYPSDIAVEWESNGQPENN YKTTPPVLDSDGSFFLYSKLTVDKSRWQQGNVFSC SVMHEALHNHYTQKSLSLSPGKGGGGSGGGGSGGG GSGGGGSGGGGSQVQLVQSGVEVKKPGASVKVSCKASGYT FTNYYMYWVRQAPGQGLEWMGGINPSQGGINENEK FKNRVTLTTDSSTTTAYMELKSLQFDDTAVYYCAR RDYRFDLGFDYWGQGTTVTVSSGGGGSGGGGSGGG | 788 | | |

TABLE 11-continued

| Construct Name | HC Protein | SEQ ID NO | LC Protein | SEQ ID NO |
|---|---|---|---|---|
| | GSGGGGSEIVLTQSPATLSLSPGERATLSCRASKG VSTSGYSYLHWYQQKPGQAPRLLIYLASYLESGVP ARFSGSGSGTDFTLTISSLEPEDFAVYYCQHSRDL PLTFGGGTKVEIKR | | | |
| PAL054-0054.1La | EPKSCDKTHTCPPCPAPEAAGGPSVFLFPPKPKDT LYITREPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSR DELTKNQVSLTCLVKGFYPSDIAVEWESNGQPENN YKTTPPVLDSDGSFFLYSKLTVDKSRWQQGNVFSC SVMHEALHNHYTQKSLSLSPGKGGGGSGGGGSGGG GSGGGGSQVQLVQSGVEVKKPGASVKVSCKASGYT FTNYYMYWVRQAPGQGLEWMGGINPSRGGINENEK FKNRVTLTTDSSTTTAYMELKSLQFDDTAVYYCAR RDYRFDLGFDYWGQGTTVTVSSGGGGSGGGGSGGG GSGGGGSEIVLTQSPATLSLSPGERATLSCRASKG VSTSGYSYLHWYQQKPGQAPRLLIYLASYLESGVP ARFSGSGSGTDFTLTISSLEPEDFAVYYCQHSRDL PLTFGGGTKVEIKR | 789 | | |
| PAL054-0055.1La | EPKSCDKTHTCPPCPAPEAAGGPSVFLFPPKPKDT LYITREPEVTCVVVDVSHEDPEVKENWYVDGVEVH NAKTKPREEQYNSTYRVVSVLIVLHQDWLNGKEYK CKVSNKALPAPIEKTISKAKGQPREPQVYTLPPSR DELTKNQVSLTCLVKGFYPSDIAVEWESNGQPENN YKTTPPVLDSDGSFFLYSKLTVDKSRWQQGNVFSC SVMHEALHNHYTQKSLSLSPGKGGGGSGGGGSGGG GSGGGGSQVQLVQSGVEVKKPGASVKVSCKASGYT FTNYYMYWVRQAPGQCLEWMGGINPSQGGINENEK FKNRVTLTTDSSTTTAYMELKSLQFDDTAVYYCAR RDYRFDLGFDYWGQGTTVTVSSGGGGSGGGGSGGG GSGGGGSEIVLTQSPATLSLSPGERATLSCRASKG VSTSGYSYLHWYQQKPGQAPRLLIYLASYLESGVP ARFSGSGSGTDFTLTISSLEPEDFAVYYCQHSRDL PLTFGCGTKVEIKR | 790 | | |
| PAL054-0056.1La | EPKSCDKTHTCPPCPAPEAAGGPSVFLFPPKPKDT LYITREPEVTCVVVDVSHEDPEVKFNWYVDGVEVH NAKTKPREEQYNSTYRVVSVLTVLHQDWLNGKEYK CKVSNKALPAPIEKTISKAKGQPREPQVYTLPPSR DELTKNQVSLTCLVKGFYPSDIAVEWESNGQPENN YKITPPVLDSDGSFFLYSKLTVDKSRWQQGNVFSC SVMHEALHNHYTQKSLSLSPGKGGGGSGGGGSGGG GSGGGGSQVQLVQSGVEVKKPGASVKVSCKASGYT FTNYYMYWVRQAPGQCLEWMGGINPSRGGINENEK FKNRVTLTTDSSTTTAYMELKSLQFDDTAVYYCAR RDYRFDLGFDYWGQGTTVTVSSGGGGSGGGGSGGG GSGGGGSEIVLTQSPATLSLSPGERATLSCRASKG VSTSGYSYLHWYQQKPGQAPRLLIYLASYLESGVP ARFSGSGSGTDFTLTISSLEPEDFAVYYCQHSRDL PLTFGCGTKVEIKR | 791 | | |

Example 1: Determination of PD-1 Binding on PD-1 Expressing Cells

Figure 1B:
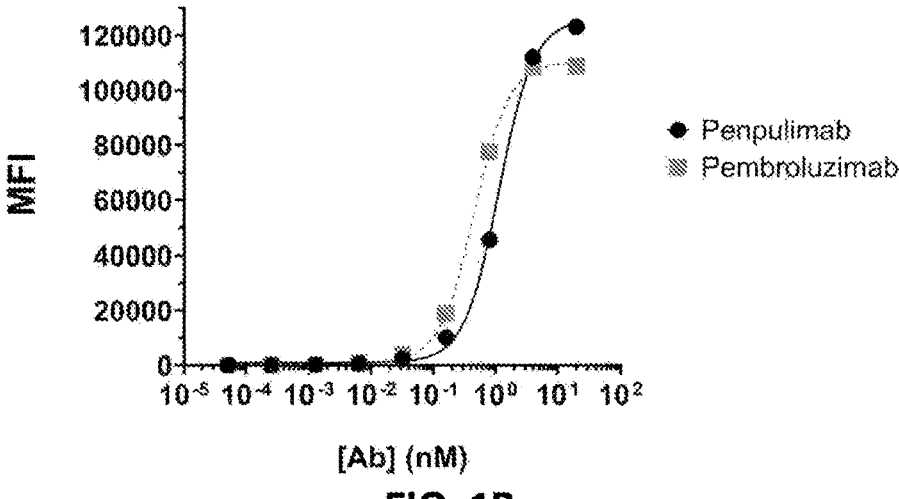
Figure 1C:
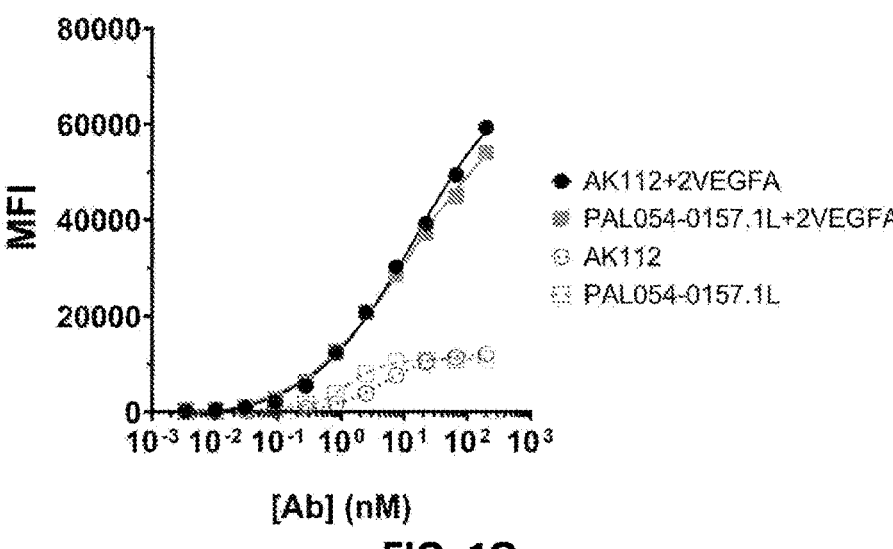
Figure 1D:
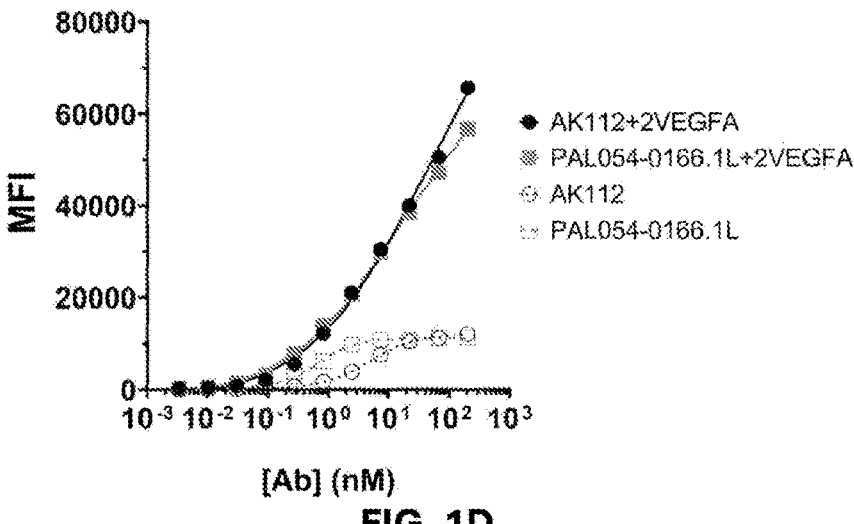
Figure 1E:
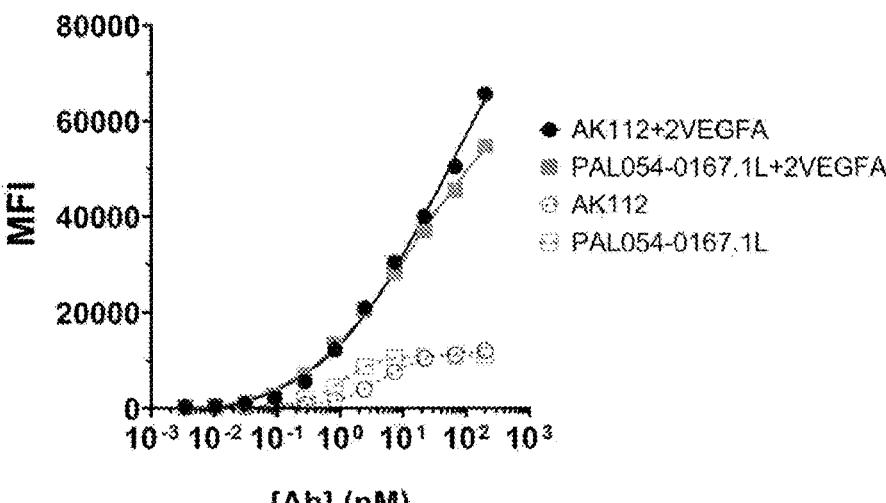
Figure 1F:
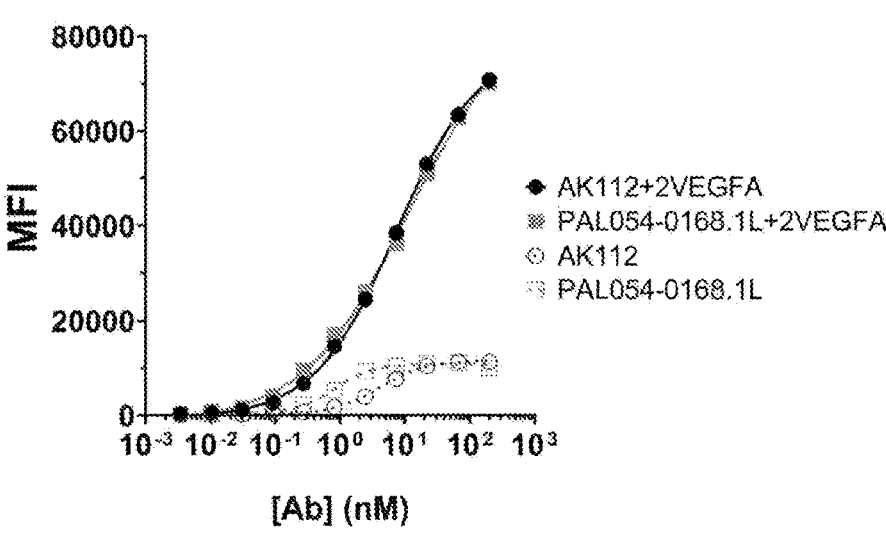
Figure 1G:
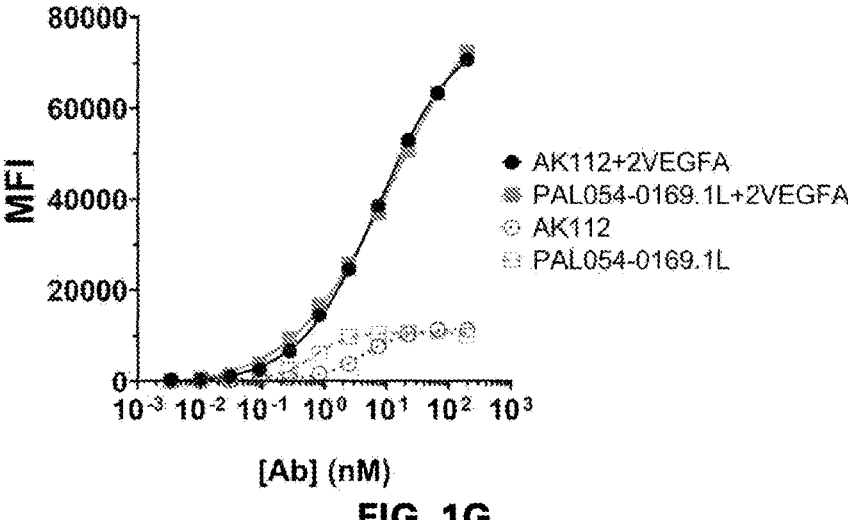
Figure 1H:
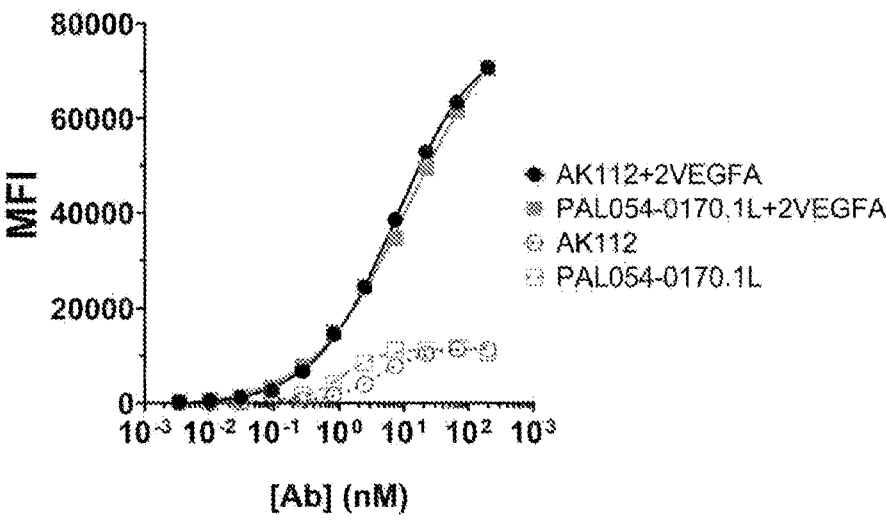
Figure 1I:
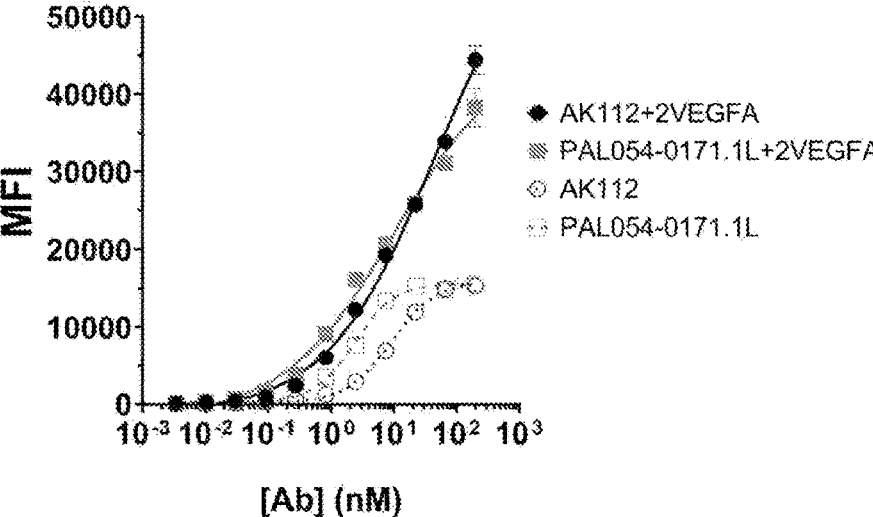
Figure 1J:
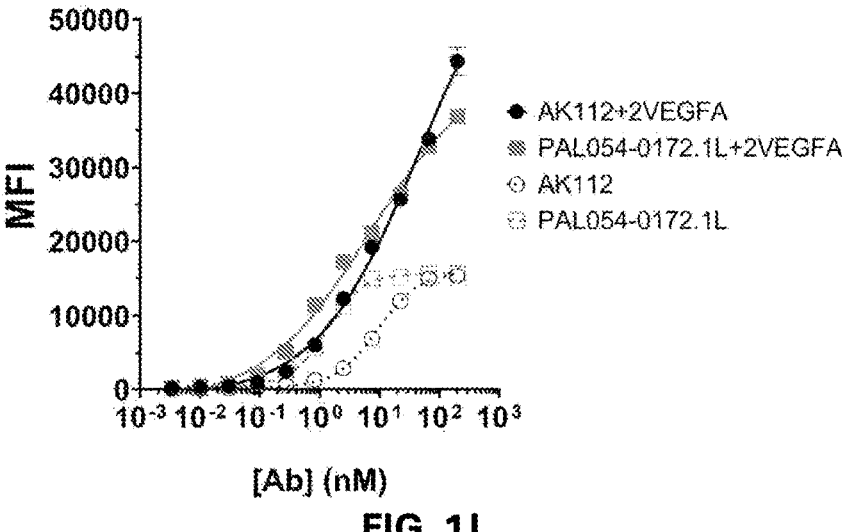
Figure 1K:
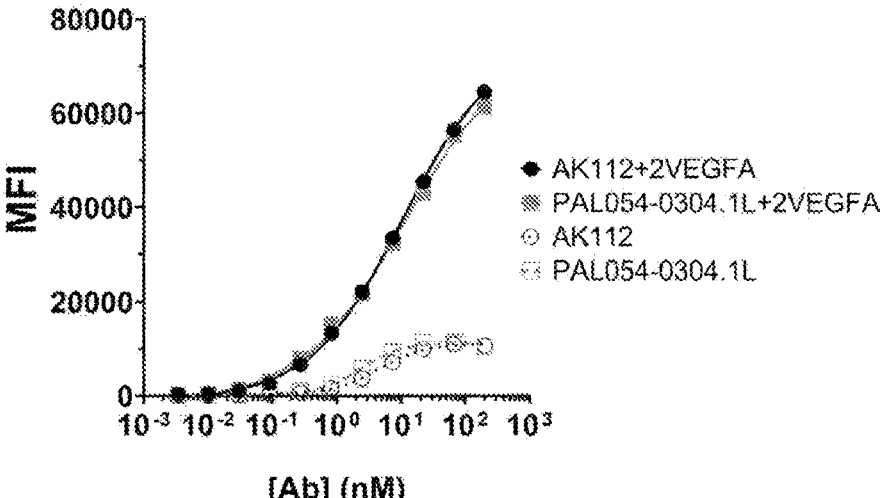
Figure 1L:
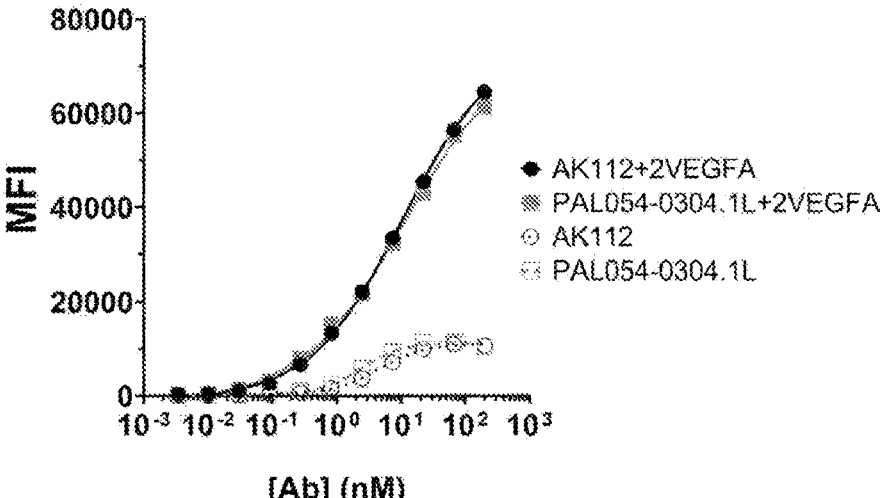
Figure 1M:
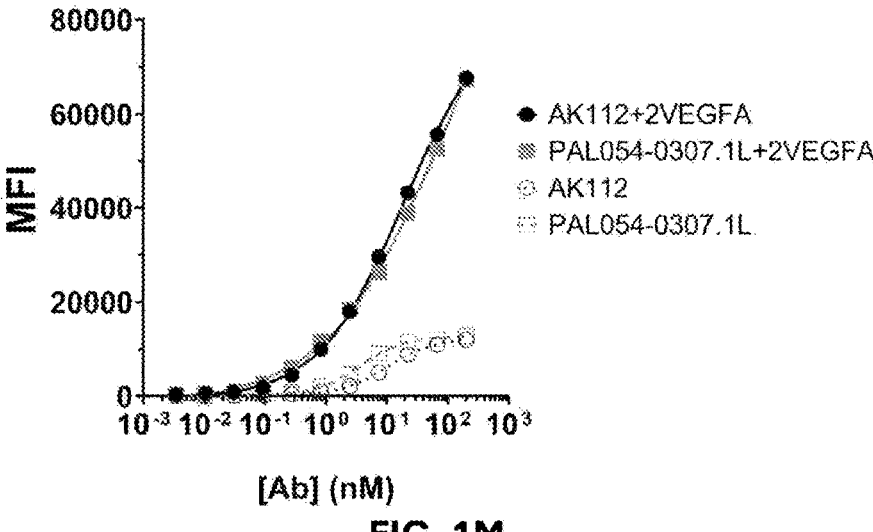
Figure 1N:
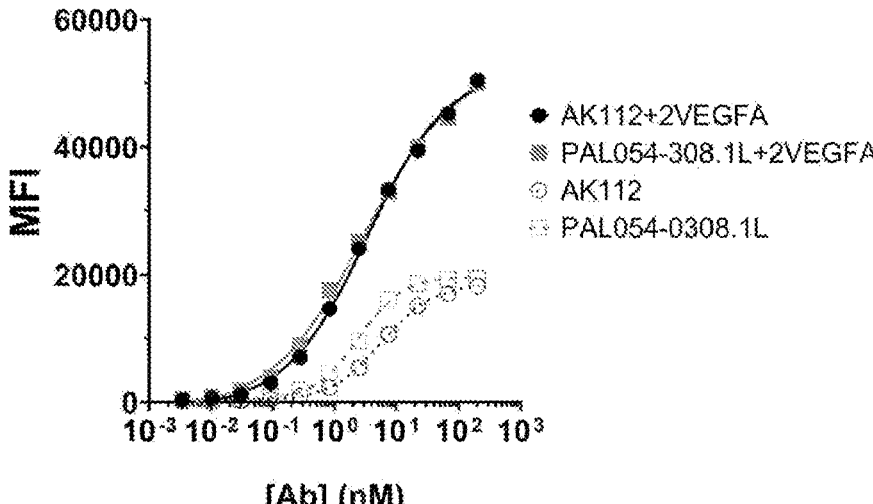
Figure 1O:
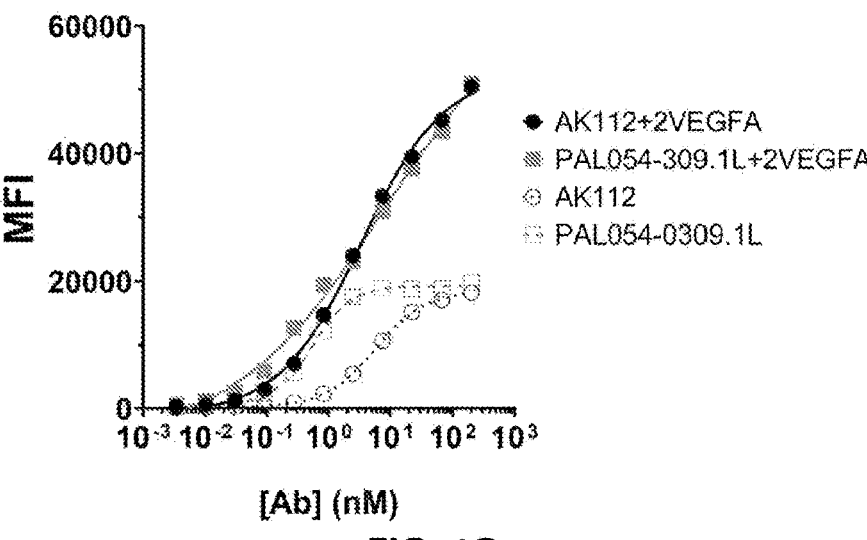
Figure 1P:
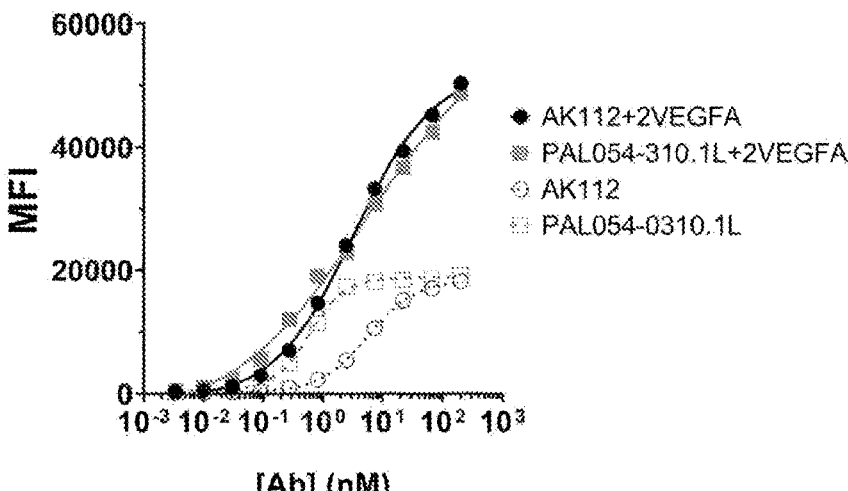
Figure 1Q:
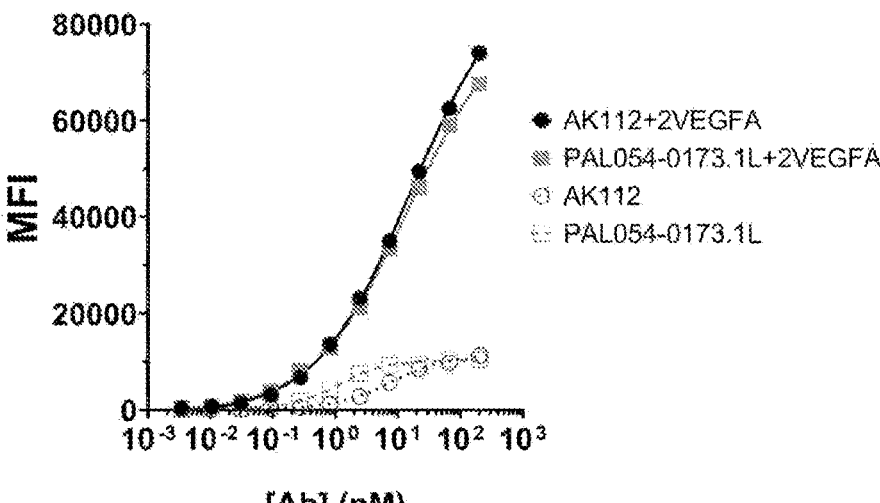
Figure 1R:
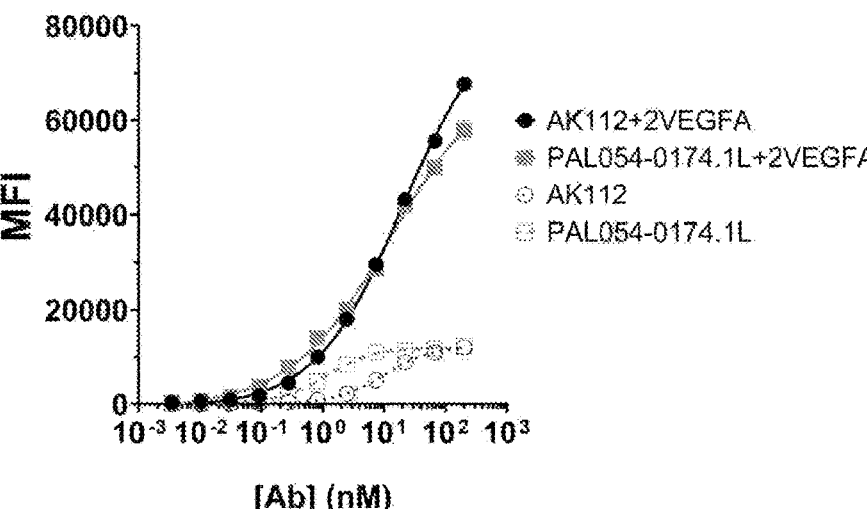
Figure 1S:
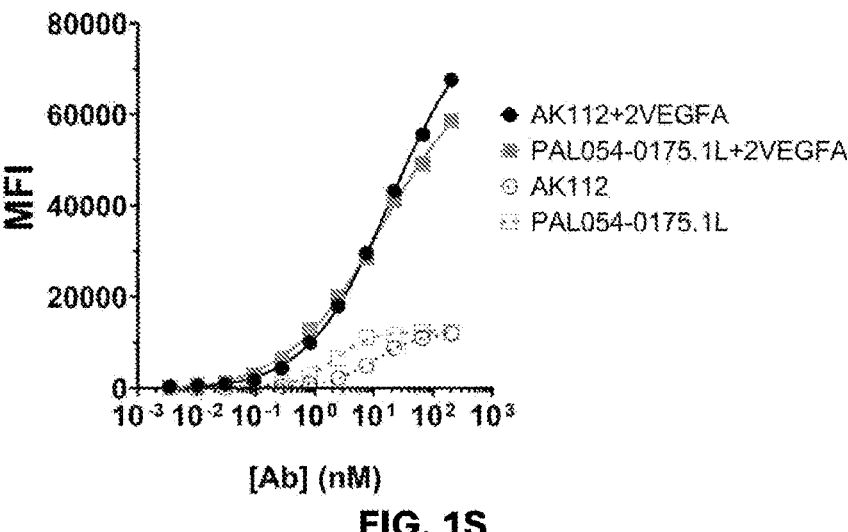
Figure 1T:
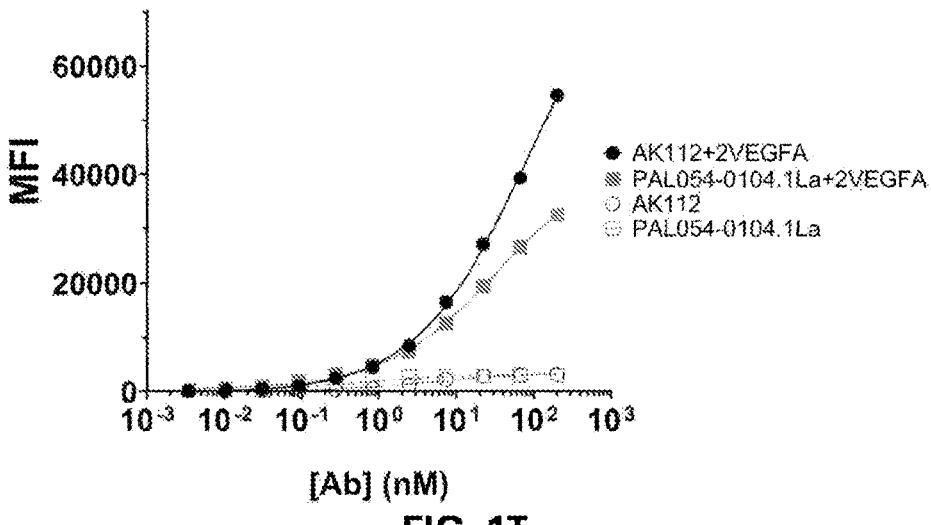
Figure 1U:
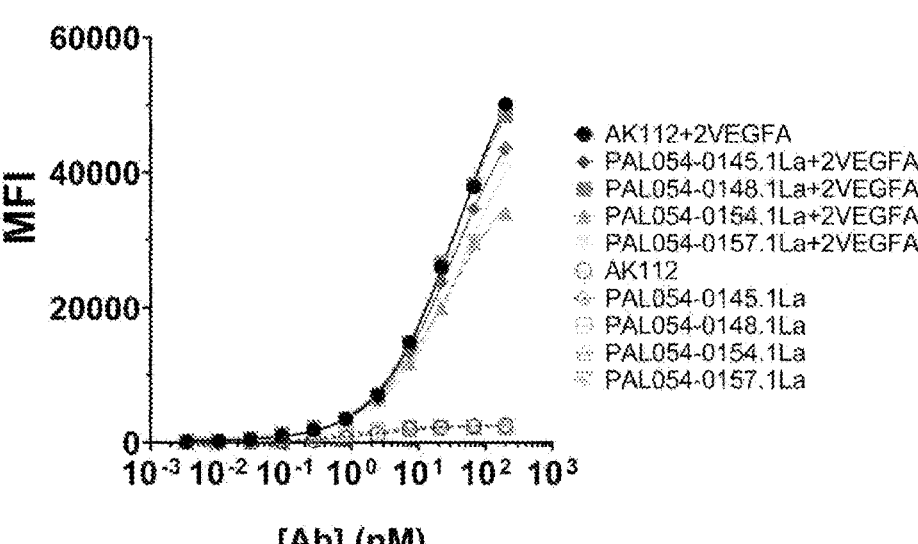
Figure 1V:
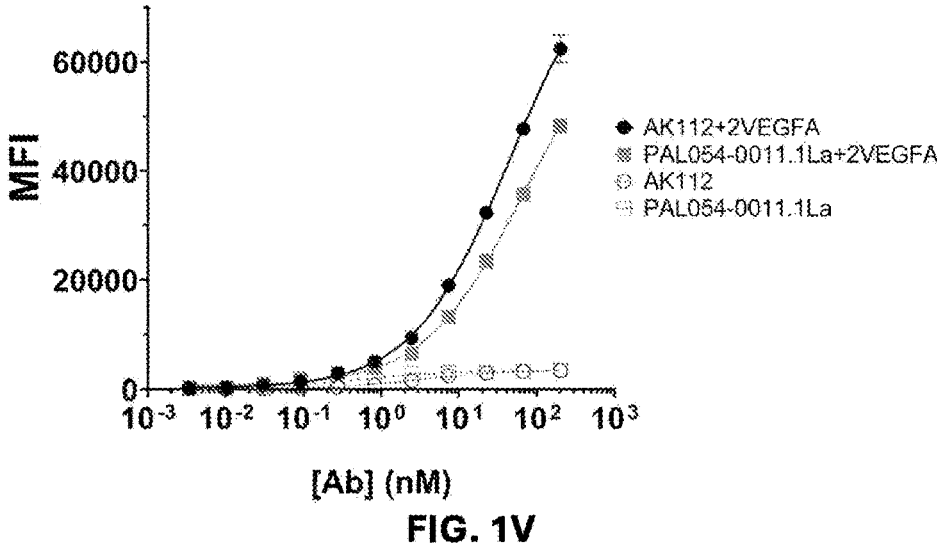
Figure 1W:
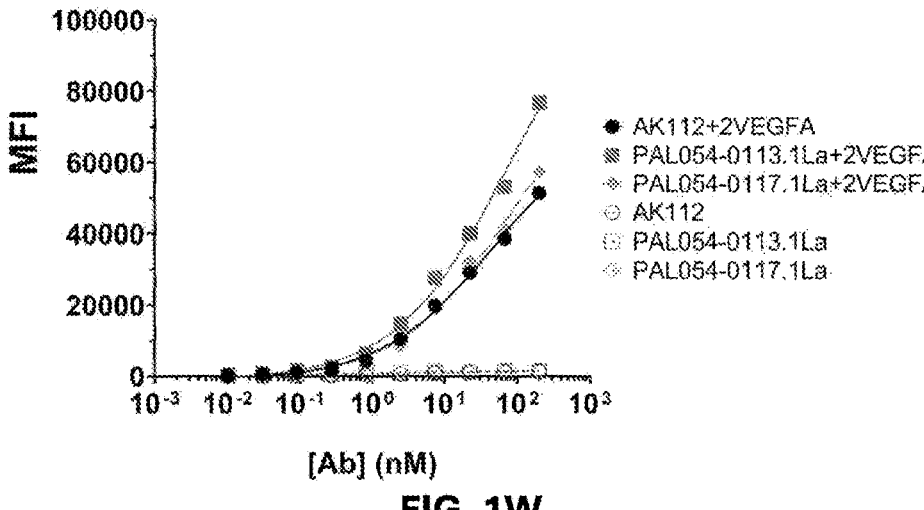
Figure 1X:
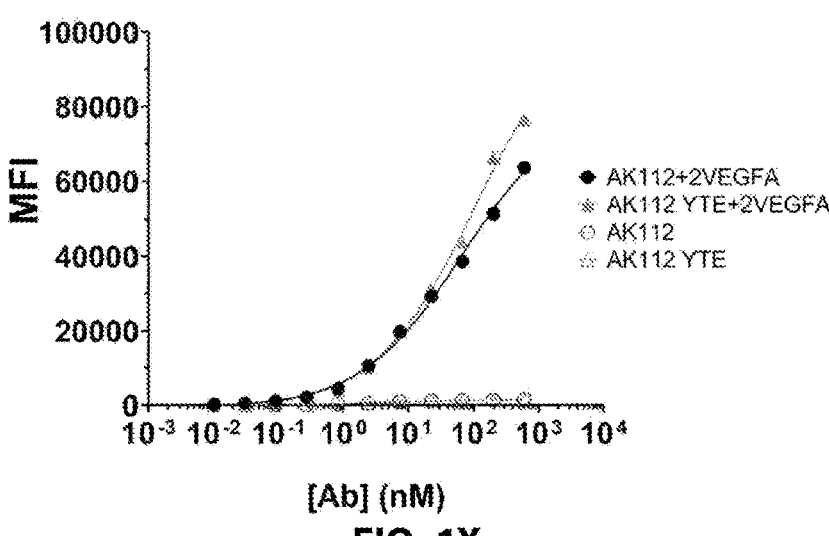
Figure 1Y:
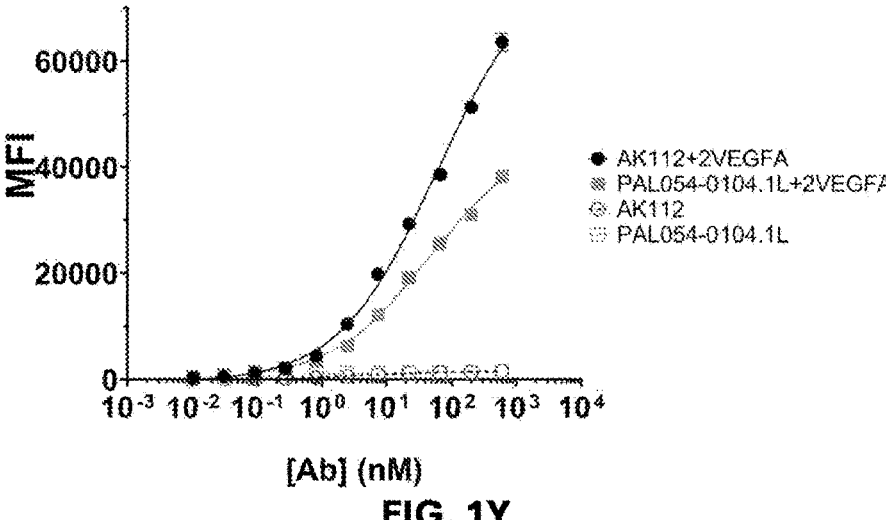
Figure 1Z:
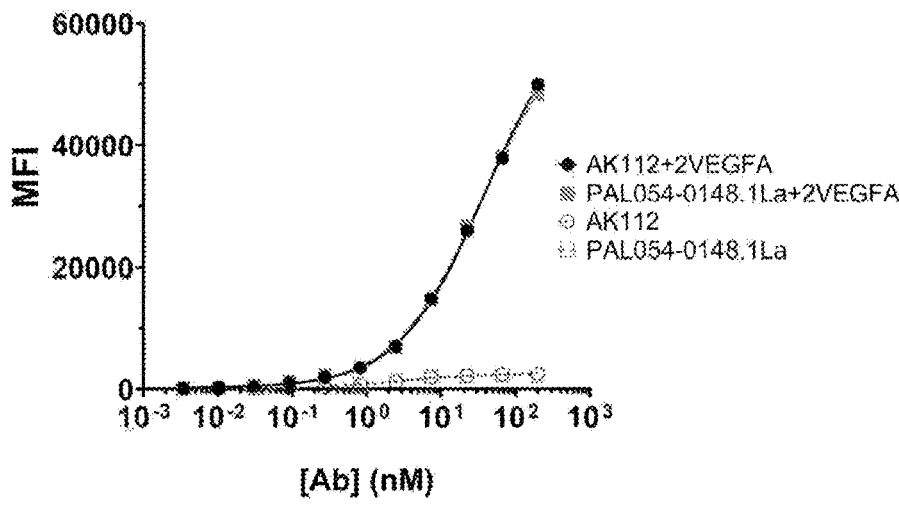
Figure 1A:
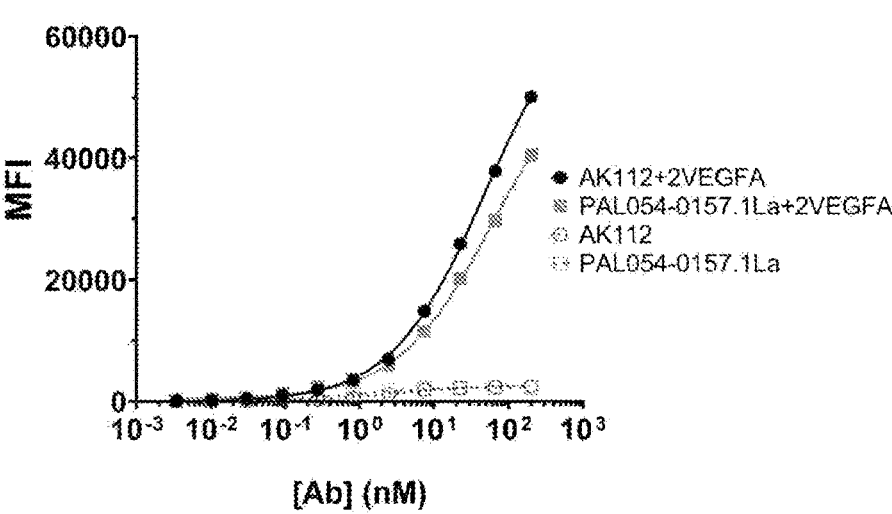
Figure 1B:
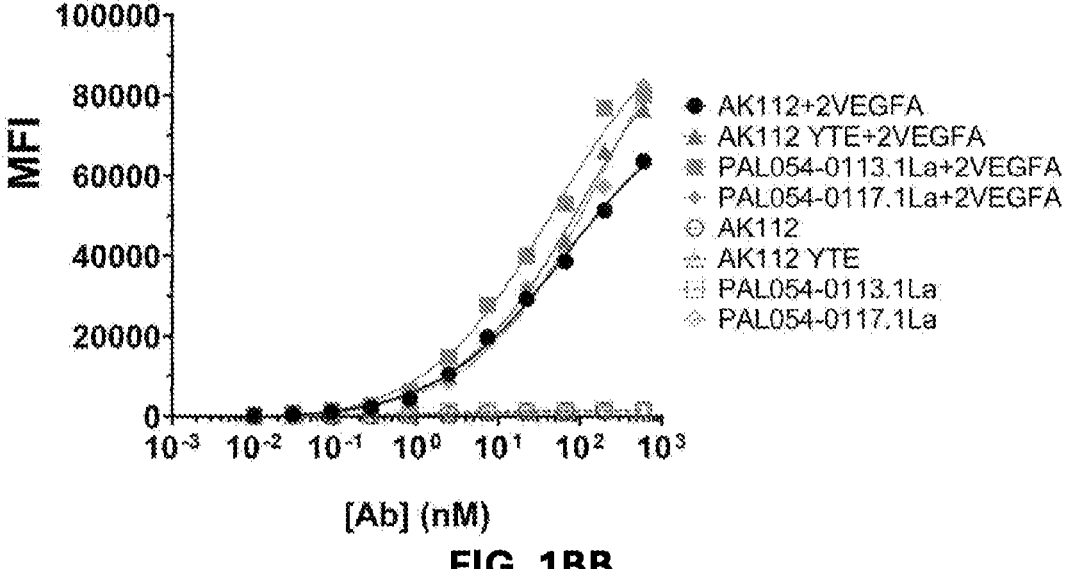
Figure 1C:
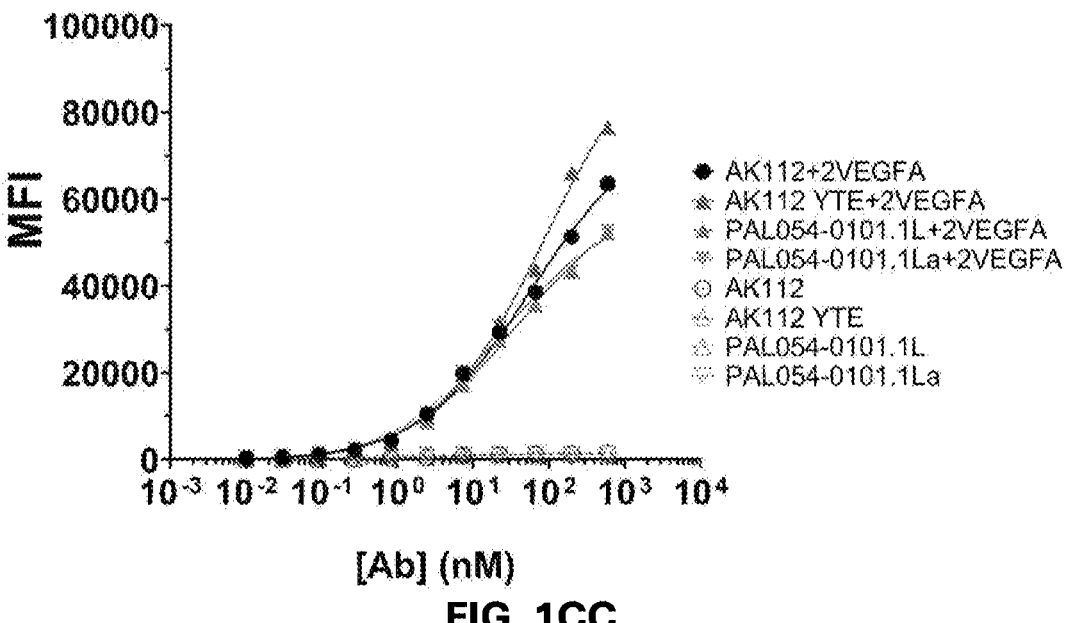

PD-1 binding was assessed in Jurkat-hPD-1 cells in the presence and absence of 2×VEGFA by flow cytometry as described above. Greater binding to PD-1 expressing cells was seen in the presence of VEGFA (referred to as VEGF or VEGFA interchangeably). The results are shown in FIGS. 1A-1CC and Table 12.

TABLE 12

| Bispecifics | Rel binding (MFI) at 200 nM (+VEGF) |
|---|---|
| PAL054-0001.1L (AK112) | 1 |
| PAL054-0145.1La | 0.9 |
| PAL054-0148.1La | 1 |

TABLE 12-continued

| Bispecifics | Rel binding (MFI) at 200 nM (+VEGF) |
|---|---|
| PAL054-0154.1La | 0.8 |
| PAL054-0157.1La | 0.8 |
| PAL054-0011.1La | 0.8 |
| PAL054-0104.1La | 0.6 |
| PAL054-0104.1L | 0.6 |
| PAL054-0001.1La (AK112 YTE) | 1.3 |
| PAL054-0113.1La | 1.5 |
| PAL054-0117.1La | 1.1 |
| PAL054-0157.1L | 0.9 |
| PAL054-0166.1L | 0.9 |
| PAL054-0167.1L | 0.8 |
| PAL054-0168.1L | 1 |
| PAL054-0169.1L | 1 |
| PAL054-0170.1L | 1 |
| PAL054-0171.1L | 0.9 |

TABLE 12-continued

| Bispecifics | Rel binding (MFI) at 200 nM (+VEGF) |
| --- | --- |
| PAL054-0172.1L | 0.8 |
| PAL054-0173.1L | 0.9 |
| PAL054-0174.1L | 0.9 |
| PAL054-0175.1L | 0.9 |
| PAL054-0304.1L | 1 |
| PAL054-0305.1L | 1 |
| PAL054-0307.1L | 1 |
| PAL054-0308.1L | 1 |
| PAL054-0309.1L | 1 |
| PAL054-0310.1L | 1 |

Example 2: Determination of Antibody Affinity to PD-1

Figure 2A:
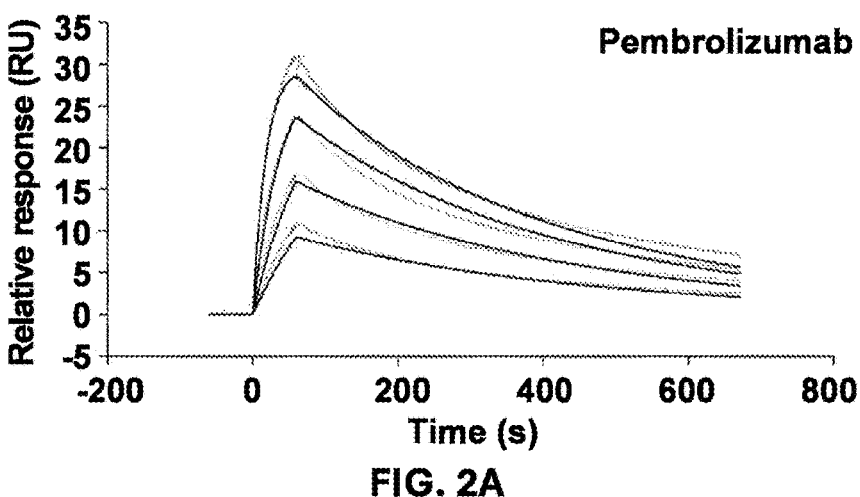
FIGS. 2A-2D depict the surface plasmon resonance (SPR) curves (FIGS. 2A-2C) and PD-1/PD-L1 blockade assay results (FIG. 2D) for the indicated antibodies.
Figure 2B:
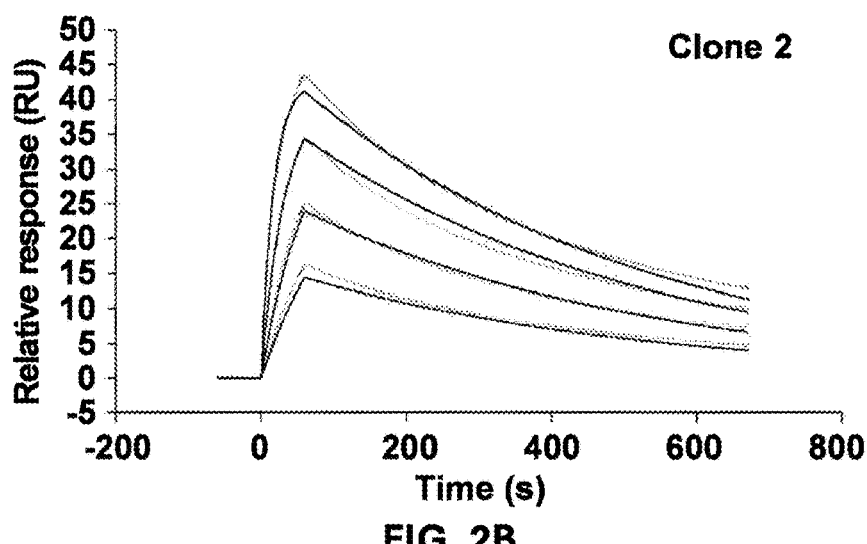
Figure 2C:
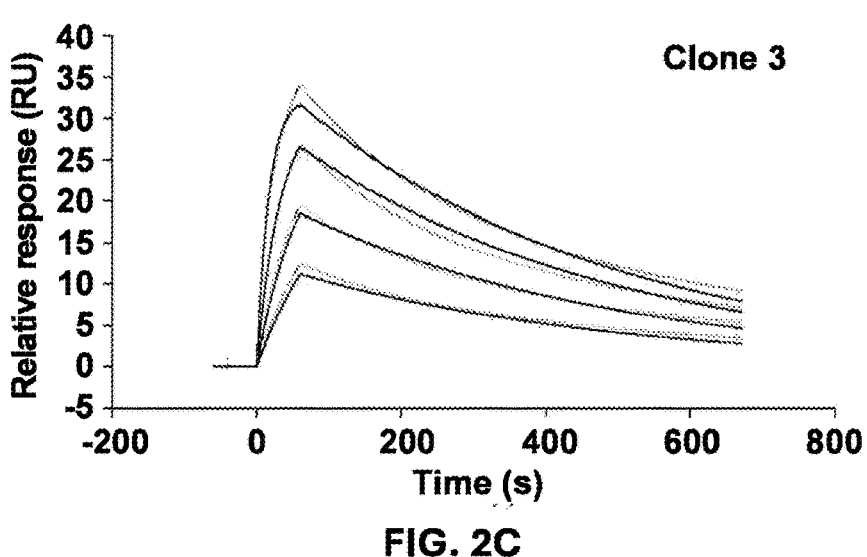
Figure 2D:
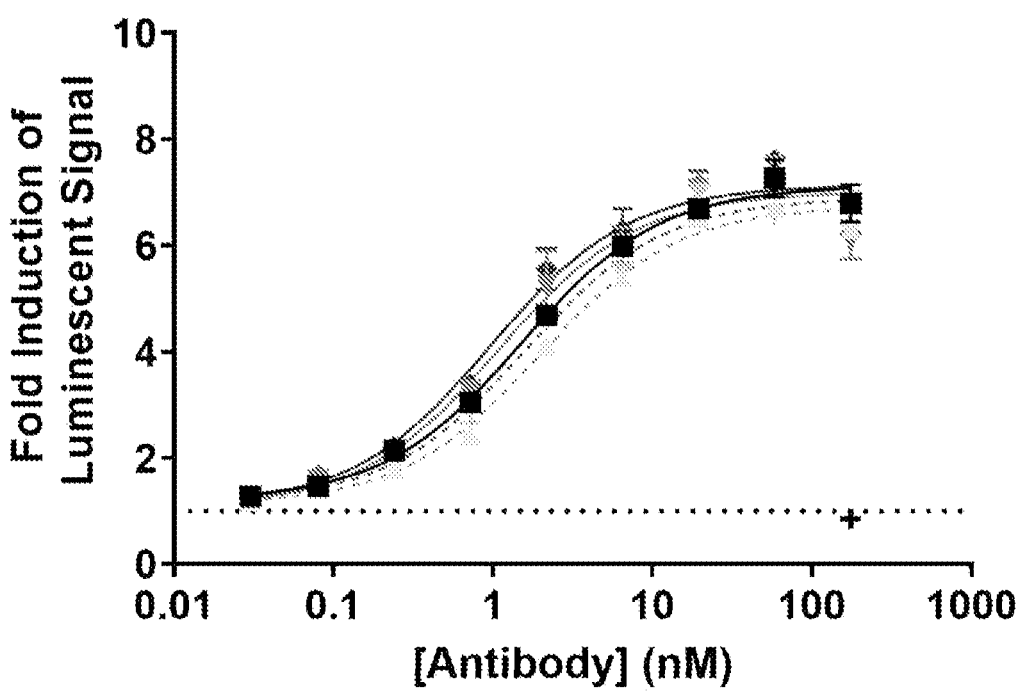

Binding affinity ($K_D$) of pembrolizumab and clone variants, with indicated Fc modifications, to PD-1 was determined by surface plasmon resonance (FIGS. 2A-2C and Table 13), and PD-1/PD-L1 blockade by the antibodies was analyzed by a PD-1 reporter assay (FIG. 2D).

TABLE 13

| Clone | ka (1/Ms) | kd (1/s) | KD (nM) |
| --- | --- | --- | --- |
| Pembrolizumab | 6.60E+05 | 3.10E−03 | 4.70 |
| Clone 2 (PAL054-0051.1La) | 5.73E+05 | 2.11E−03 | 3.69 |
| Clone 3 (PAL054-0052.1La) | 5.81E+05 | 2.27E−03 | 3.90 |

Figure 3A:
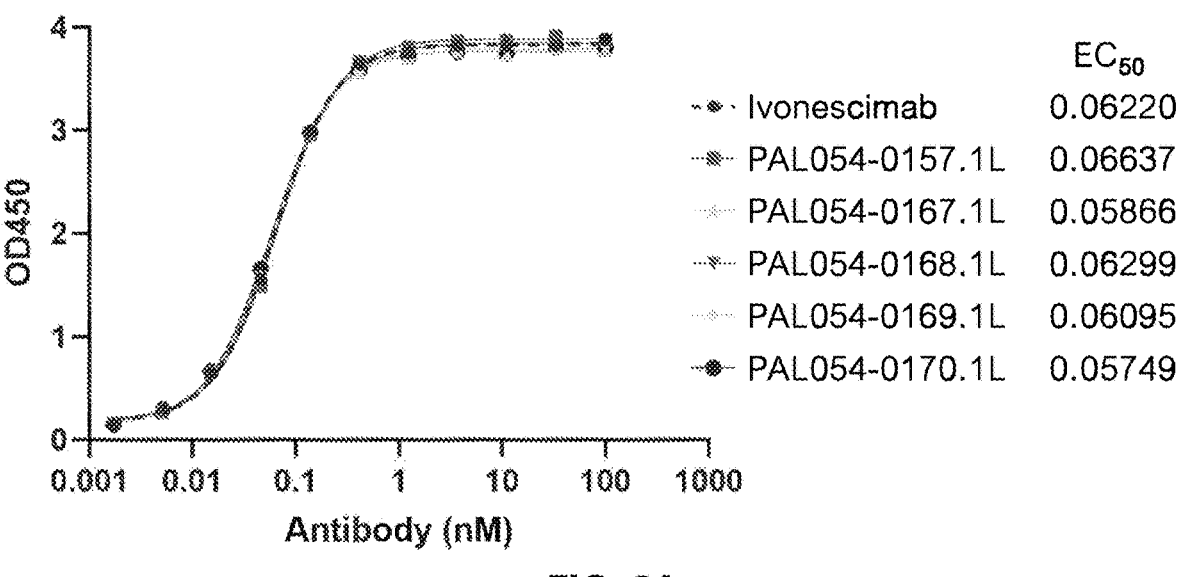
FIG. 3A depicts binding activity of the indicated antibodies to human VEGF determined by ELISA.
Figure 3B:
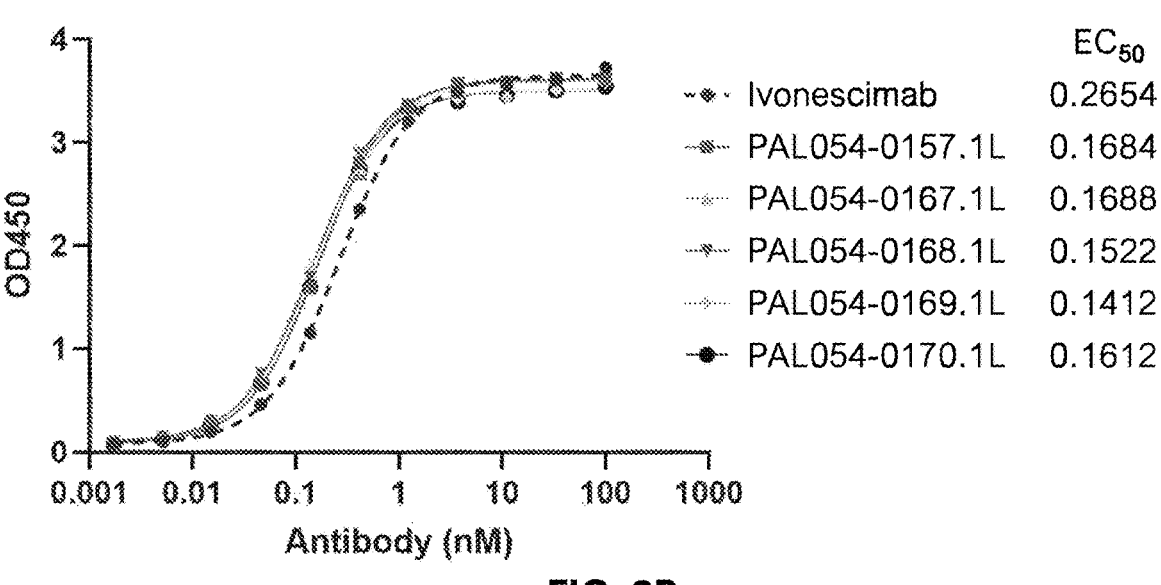
FIG. 3B depicts binding activity of the indicated antibodies to human PD-1 determined by ELISA.
Figure 3C:
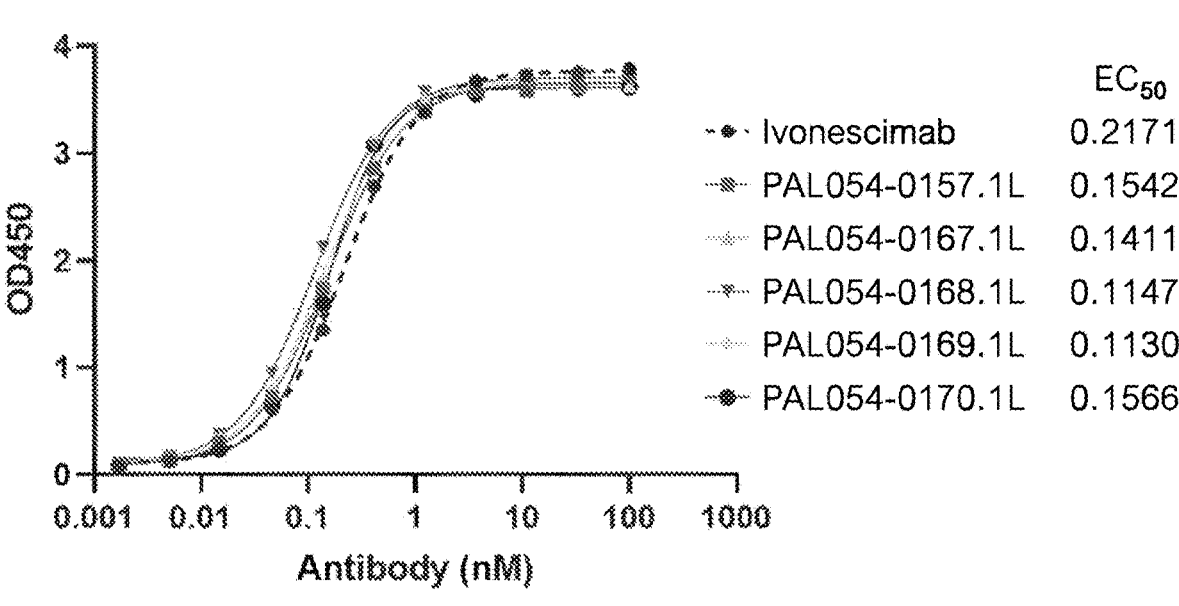
FIG. 3C depicts binding activity of the indicated antibodies to cynomolgus PD-1 determined by ELISA.
Figure 4A:
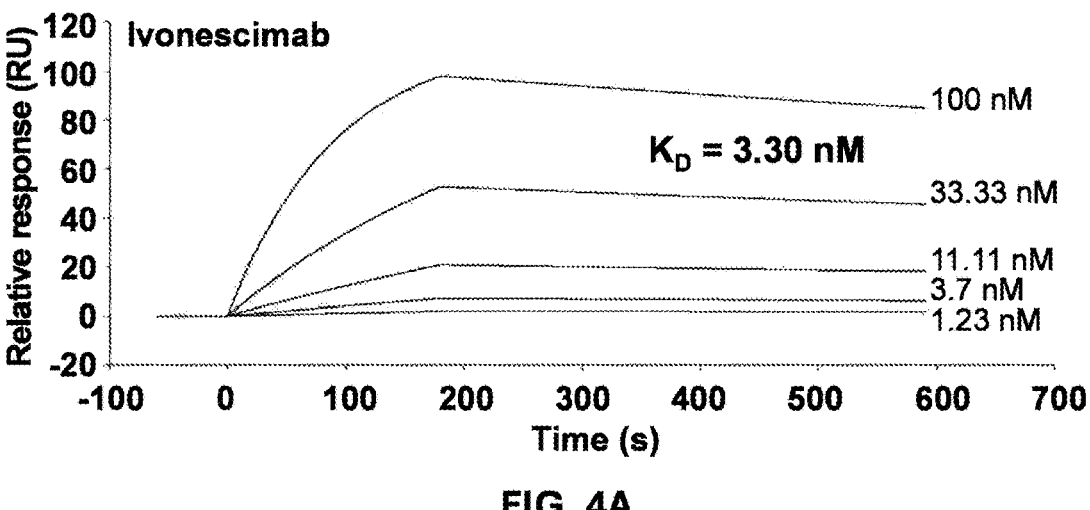
FIGS. 4A-4D depict the SPR curves for binding of the indicated antibodies to human VEGF.
Figure 4B:
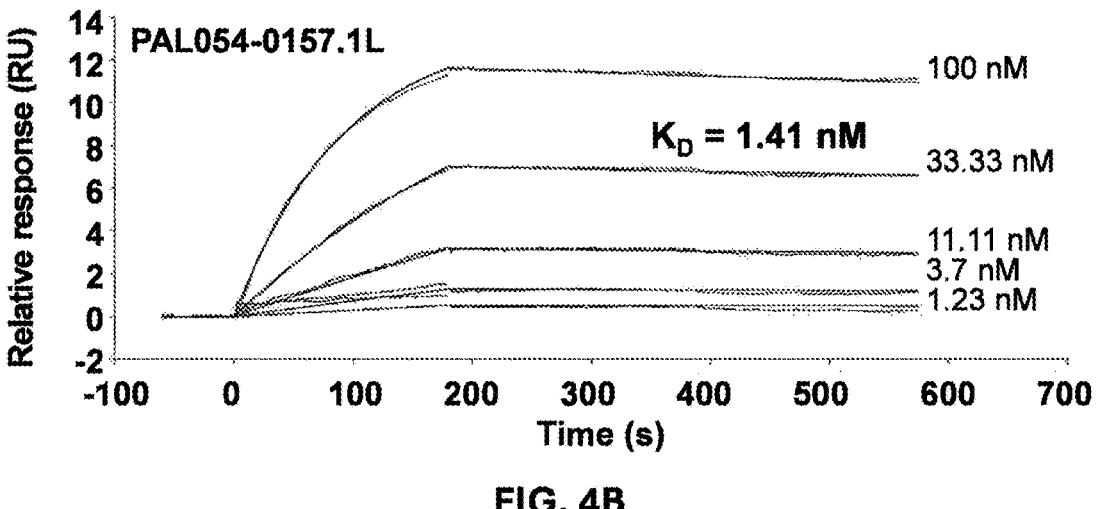
Figure 4C:
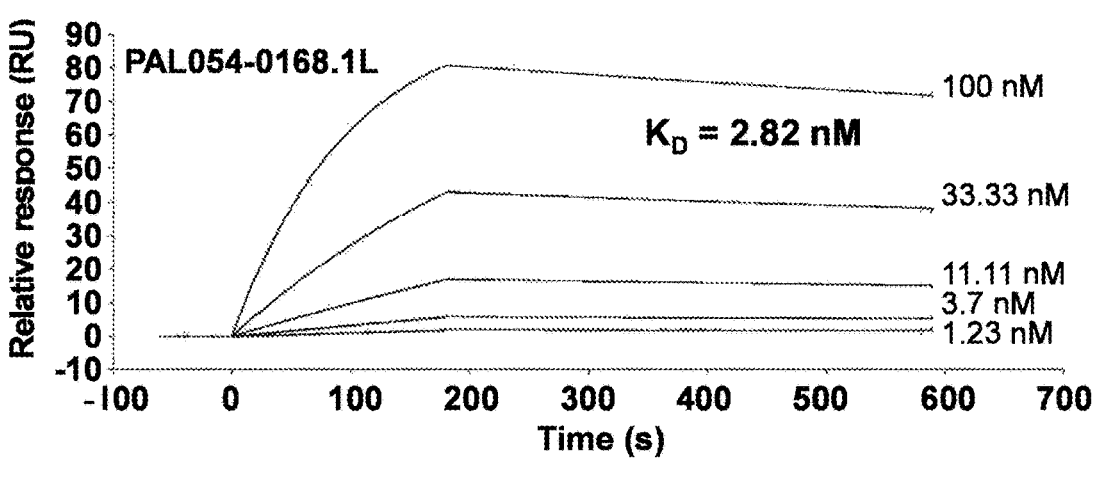
Figure 4D:
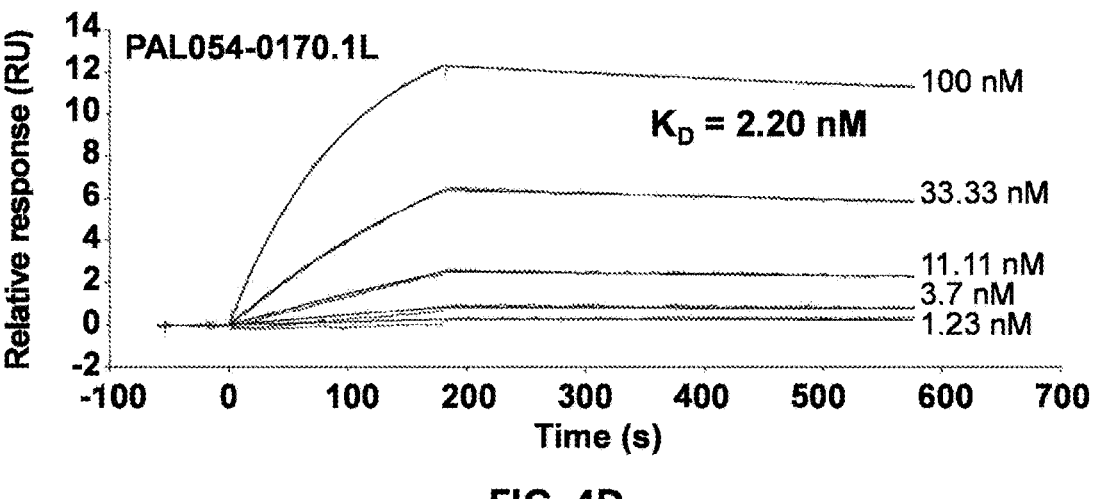
Figure 5A:
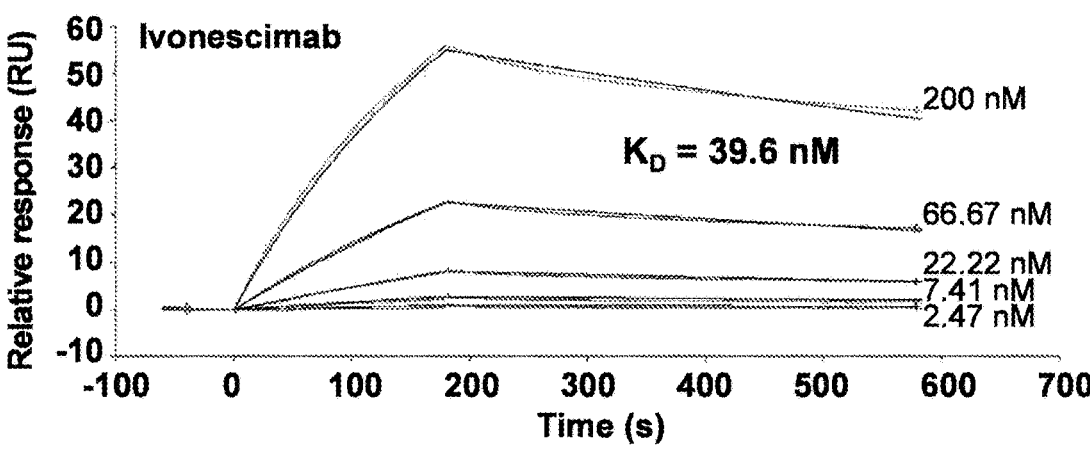
FIGS. 5A-5D depict the SPR curves for binding of the indicated antibodies to human PD-1.
Figure 5B:
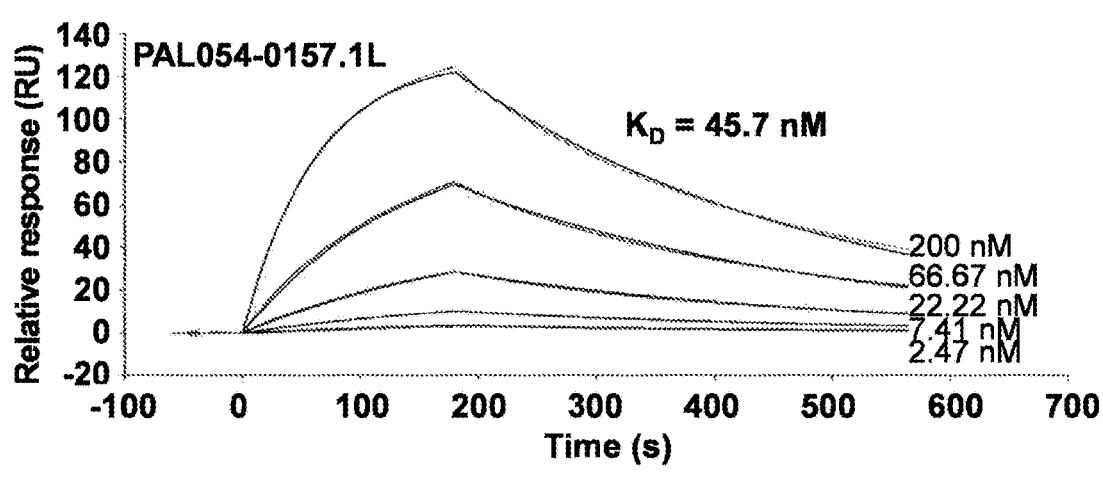
Figure 5C:
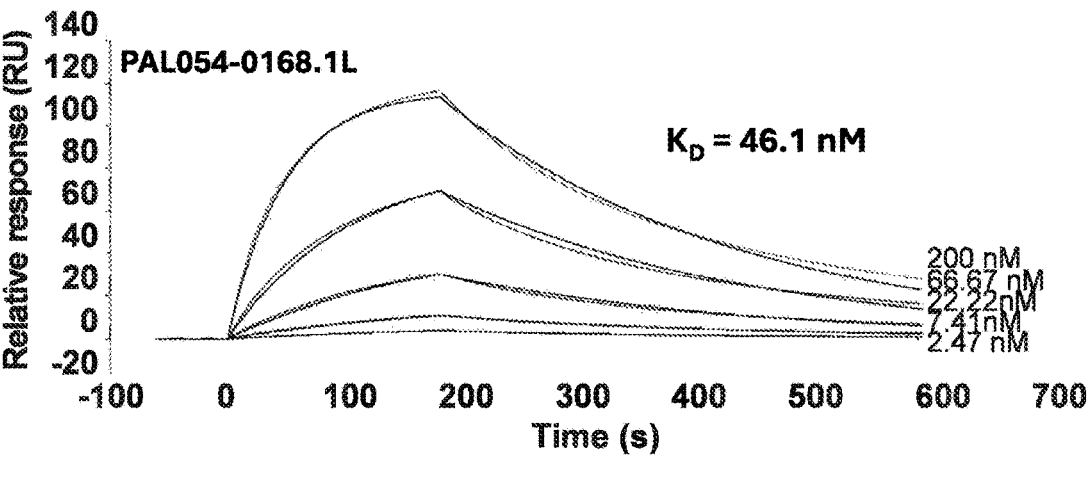
Figure 5D:
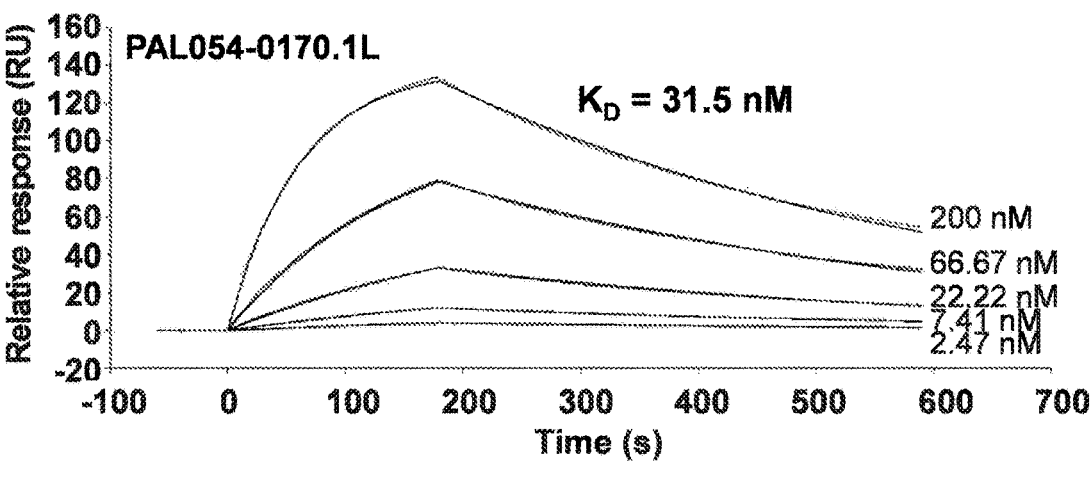
Figure 6A:
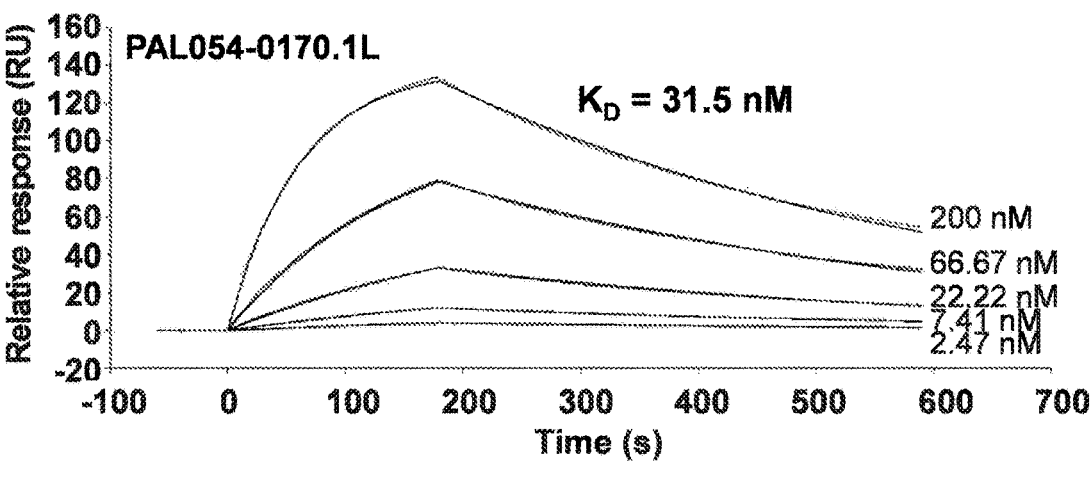

Example 3: Binding of Bispecific Antibody to Human VEGF, Human PD-1 and Cynomolgus PD-1 Determined by ELISA PD-1 binding assays were conducted to measure the affinity of AK112 and VEGF/PD-1 bispecific antibodies disclosed herein to PD-1 expressing cells. Half maximal effective concentration ($EC_{50}$) of binding of test articles to human VEGF, human PD-1, and cynomolgus PD-1 was determined by ELISA. Data is seen in FIGS. 3A-3C and Table 14.

TABLE 14

| | $EC_{50}$ (nM) | | |
| --- | --- | --- | --- |
| Test Article | Human VEGF | Human PD-1 | Cyno PD-1 |
| Ivonescimab | 0.0622 | 0.2654 | 0.2171 |
| PAL054-0157.1L | 0.06637 | 0.1684 | 0.1542 |
| PAL054-0167.1L | 0.05866 | 0.1688 | 0.1411 |
| PAL054-0168.1L | 0.06299 | 0.1522 | 0.1147 |
| PAL054-0169.1L | 0.06095 | 0.1412 | 0.1130 |
| PAL054-0170.1L | 0.05749 | 0.1612 | 0.1566 |

Example 4: Determination of Bispecific Antibody Affinity to Human VEGF

Binding affinity ($K_D$) of bispecific antibodies to human VEGF was determined by surface plasmon resonance by capturing test articles with Protein G chip and flowing human VEGF at 100, 33.33, 11.11, 3.7, and 1.23 nM (FIGS. 4A-4D and Table 15).

TABLE 15

| Test Article | Analyte | $k_a$ (1/Ms) | $k_d$ (1/s) | $K_D$ (M) |
| --- | --- | --- | --- | --- |
| Ivonescimab | Human VEGF165-His | 1.07E+05 | 3.55E−04 | 3.30E−09 |
| PAL054-0157.1L | Human VEGF165-His | 1.08E+05 | 1.52E−04 | 1.41E−09 |
| PAL054-0166.1L | Human VEGF165-His | 1.11E+05 | 2.83E−04 | 2.56E−09 |
| PAL054-0168.1L | Human VEGF165-His | 1.04E+05 | 2.92E−04 | 2.82E−09 |
| PAL054-0170.1L | Human VEGF165-His | 9.91E+04 | 2.18E−04 | 2.20E−09 |
| PAL054-0171.1L | Human VEGF165-His | 1.11E+05 | 3.54E−04 | 3.19E−09 |
| PAL054-0172.1L | Human VEGF165-His | 9.94E+04 | 3.02E−04 | 3.03E−09 |
| PAL054-0173.1L | Human VEGF165-His | 1.06E+05 | 2.89E−04 | 2.73E−09 |
| PAL054-0174.1L | Human VEGF165-His | 1.02E+05 | 2.97E−04 | 2.90E−09 |
| PAL054-0175.1L | Human VEGF165-His | 1.07E+05 | 3.40E−04 | 3.18E−09 |
| PAL054-0304.1L | Human VEGF165-His | 1.10E+05 | 2.87E−04 | 2.61E−09 |
| PAL054-0305.1L | Human VEGF165-His | 9.72E+04 | 2.92E−04 | 3.01E−09 |
| PAL054-0307.1L | Human VEGF165-His | 1.02E+05 | 2.73E−04 | 2.67E−09 |
| PAL054-0308.1L | Human VEGF165-His | 1.05E+05 | 2.94E−04 | 2.79E−09 |
| PAL054-0309.1L | Human VEGF165-His | 9.50E+04 | 2.97E−04 | 3.12E−09 |
| PAL054-0310.1L | Human VEGF165-His | 1.04E+05 | 2.97E−04 | 2.87E−09 |

Example 5: Determination of Bispecific Antibody Affinity to Human PD-1

Binding affinity ($K_D$) of bispecific antibodies to human PD-1 was determined by surface plasmon resonance by capturing test articles with Protein G chip and flowing human PD-1 at 200, 66.67, 22.22, 7.41, and 2.47 nM (FIGS. 5A-5D and Table 16).

TABLE 16

| Test Article | Analyte | $k_a$ (1/Ms) | $k_d$ (1/s) | $K_D$ (M) |
| --- | --- | --- | --- | --- |
| Ivonescimab | Human PD-1-His | 1.94E+04 | 7.69E−04 | 3.96E−08 |
| PAL054-0148.1L | Human PD-1-His | 5.39E+04 | 3.40E−03 | 6.31E−08 |
| PAL054-0157.1L | Human PD-1-His | 7.16E+04 | 3.27E−03 | 4.57E−08 |
| PAL054-0165.1L | Human PD-1-His | 9.17E+04 | 3.12E−03 | 3.40E−08 |
| PAL054-0166.1L | Human PD-1-His | 9.11E+04 | 2.96E−03 | 3.25E−08 |
| PAL054-0167.1L | Human PD-1-His | 6.71E+04 | 3.29E−03 | 4.91E−08 |
| PAL054-0168.1L | Human PD-1-His | 8.71E+04 | 4.01E−03 | 4.61E−08 |
| PAL054-0169.1L | Human PD-1-His | 8.54E+04 | 4.05E−03 | 4.74E−08 |
| PAL054-0170.1L | Human PD-1-His | 7.28E+04 | 2.29E−03 | 3.15E−08 |
| PAL054-0301.1L | Human PD-1-His | 4.96E+04 | 3.87E−03 | 7.80E−08 |
| PAL054-0302.1L | Human PD-1-His | 3.30E+04 | 2.59E−03 | 7.84E−08 |
| PAL054-0303.1L | Human PD-1-His | 2.77E+04 | 5.30E−03 | 1.91E−08 |
| PAL054-0304.1L | Human PD-1-His | 3.59E+04 | 5.36E−03 | 1.49E−08 |
| PAL054-0305.1L | Human PD-1-His | 3.73E+04 | 4.35E−04 | 1.16E−08 |
| PAL054-0306.1L | Human PD-1-His | 3.22E+04 | 2.69E−03 | 8.34E−08 |

Example 6: Determination of Bispecific Antibody Affinity to Cynomolgus PD-1

Binding affinity ($K_D$) of bispecific antibodies to cynomolgus PD-1 was determined by surface plasmon resonance by capturing test articles with Protein G chip and flowing cyno PD-1 at 200, 66.67, 22.22, 7.41, and 2.47 nM or at 200, 66.67, 22.22, 7.41, 2.47, and 0.82 nM (FIGS. 6A-6D and Table 17).

TABLE 17

| Test Article | Analyte | $k_a$ (1/Ms) | $k_d$ (1/s) | $K_D$ (M) |
|---|---|---|---|---|
| Ivonescimab | Cyno PD-1-His | 7.22E+04 | 9.01E−04 | 1.25E−08 |
| PAL054-0157.1L | Cyno PD-1-His | 1.11E+05 | 7.91E−04 | 7.15E−09 |
| PAL054-0166.1L | Cyno PD-1-His | 1.50E+05 | 7.70E−04 | 5.15E−09 |
| PAL054-0168.1L | Cyno PD-1-His | 1.35E+05 | 1.02E−03 | 7.61E−09 |
| PAL054-0170.1L | Cyno PD-1-His | 1.40E+05 | 6.08E−04 | 4.33E−09 |
| PAL054-0171.1L | Cyno PD-1-His | 9.93E+04 | 7.01E−04 | 7.06E−09 |
| PAL054-0172.1L | Cyno PD-1-His | 1.48E+05 | 7.49E−04 | 5.06E−09 |
| PAL054-0173.1L | Cyno PD-1-His | 1.29E+05 | 1.10E−03 | 8.52E−09 |
| PAL054-0174.1L | Cyno PD-1-His | 1.37E+05 | 1.11E−03 | 8.12E−09 |
| PAL054-0175.1L | Cyno PD-1-His | 1.15E+05 | 6.68E−04 | 5.82E−09 |
| PAL054-0304.1L | Cyno PD-1-His | 2.43E+04 | 3.51E−03 | 1.44E−07 |
| PAL054-0305.1L | Cyno PD-1-His | 3.06E+04 | 3.30E−03 | 1.08E−07 |
| PAL054-0307.1L | Cyno PD-1-His | 4.46E+04 | 4.39E−03 | 9.85E−08 |
| PAL054-0308.1L | Cyno PD-1-His | 3.20E+04 | 3.86E−03 | 1.20E−07 |
| PAL054-0309.1L | Cyno PD-1-His | 1.29E+05 | 6.00E−05 | 4.65E−10 |
| PAL054-0310.1L | Cyno PD-1-His | 1.18E+05 | 9.85E−05 | 8.35E−10 |

Figure 9:
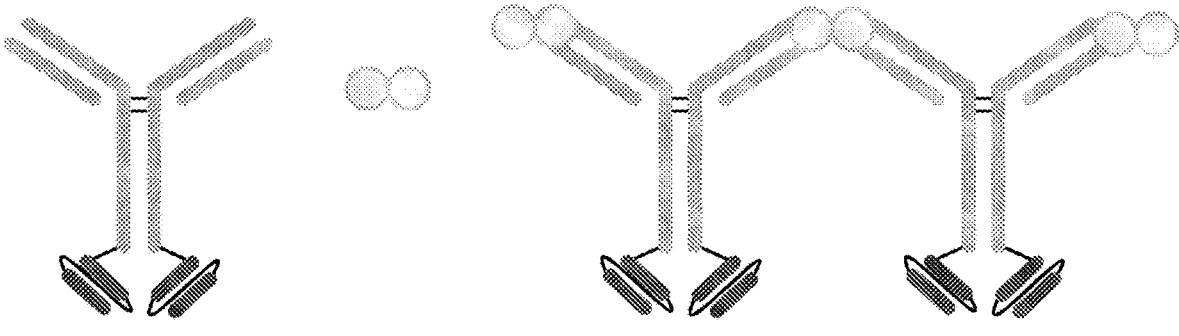
FIG. 9 demonstrates that bispecific antibodies can enhance PD-1 binding through VEGF daisy chaining.
Figure 10G:
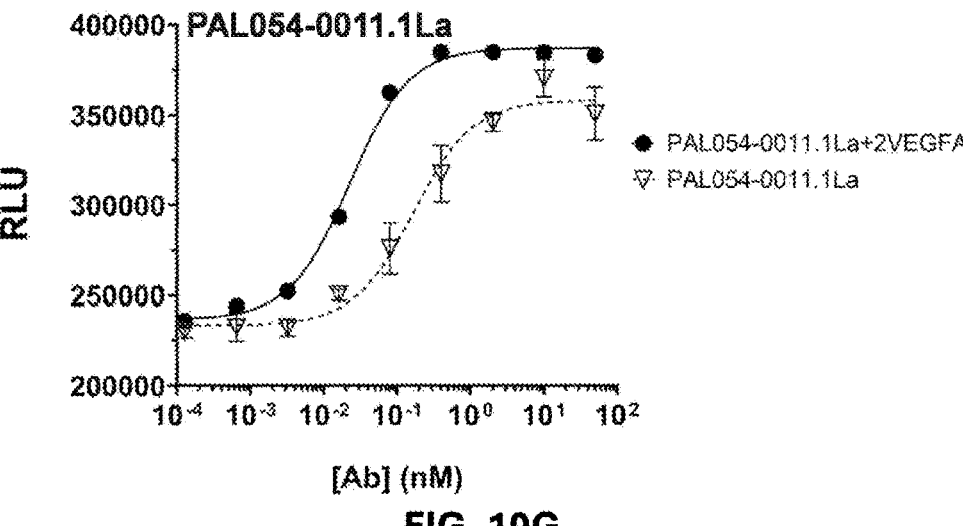
FIGS. 10A-10KK depict the PD-1 reporter assay results for the indicated antibodies.
Figure 10H:
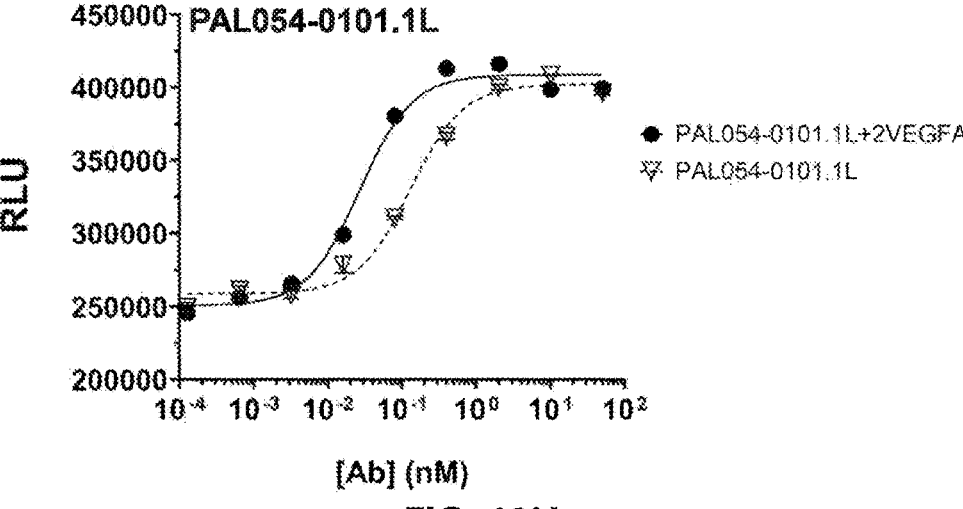
Figure 10I:
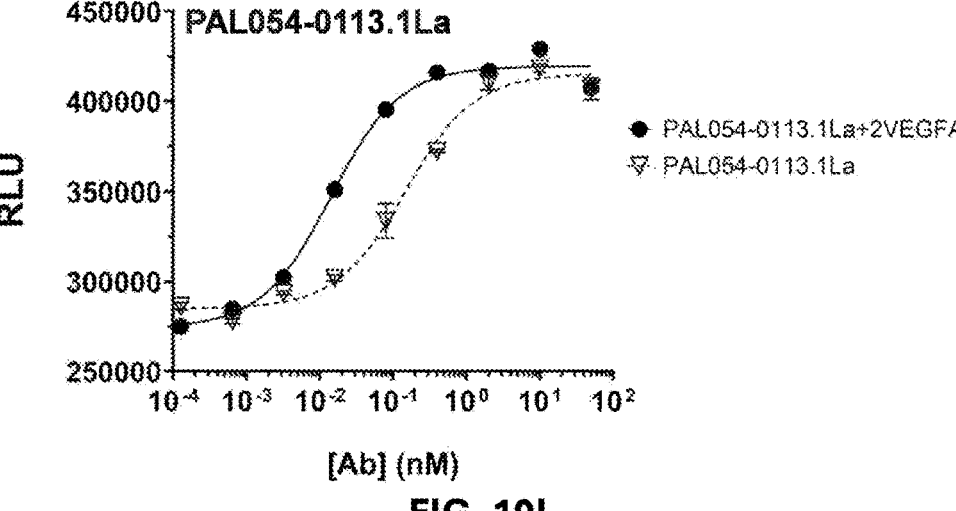
Figure 10J:
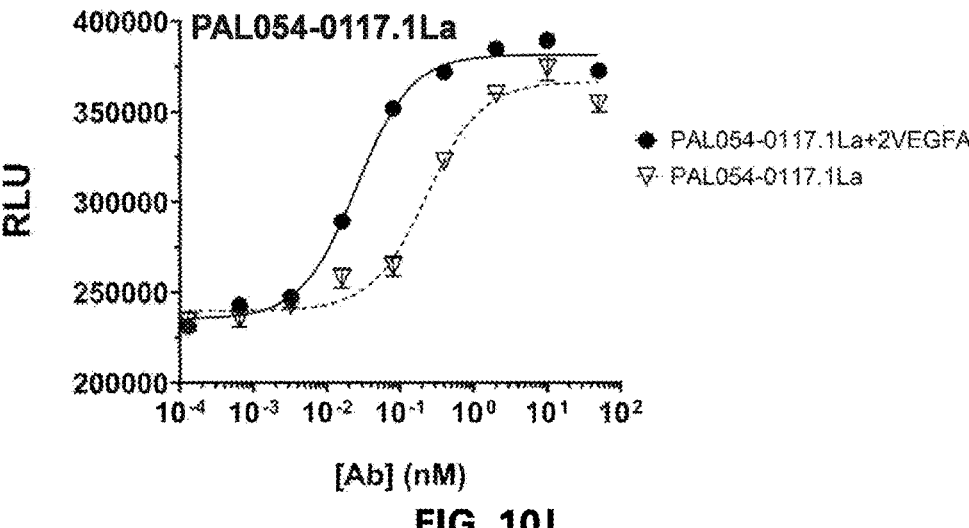
Figure 10K:
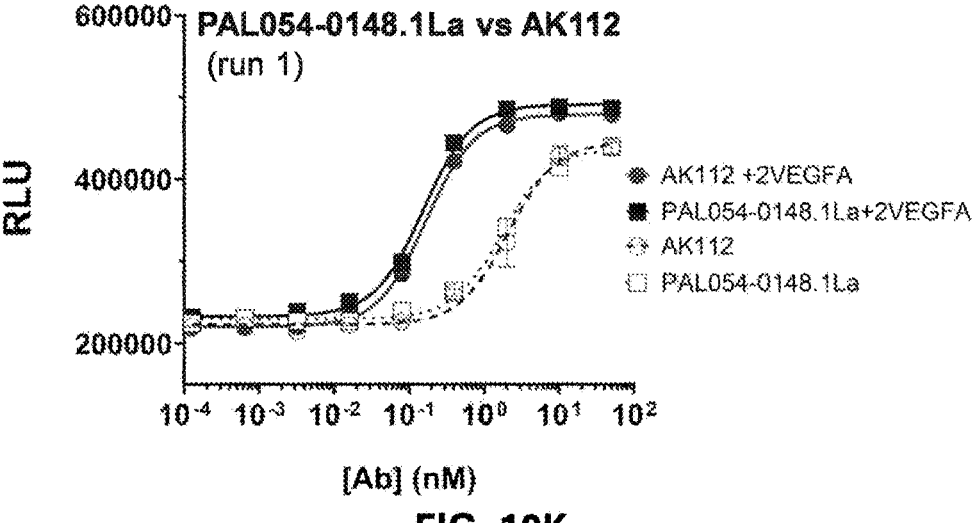
Figure 10L:
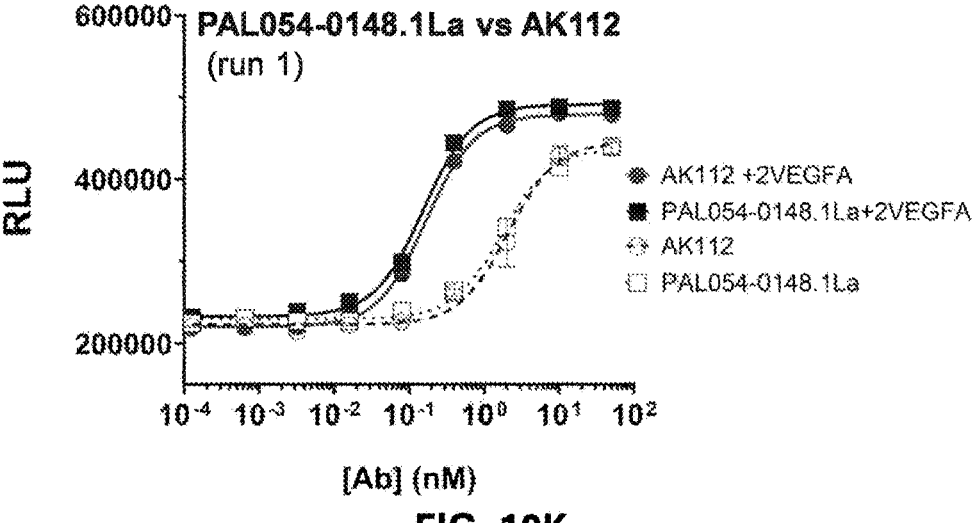
Figure 10M:
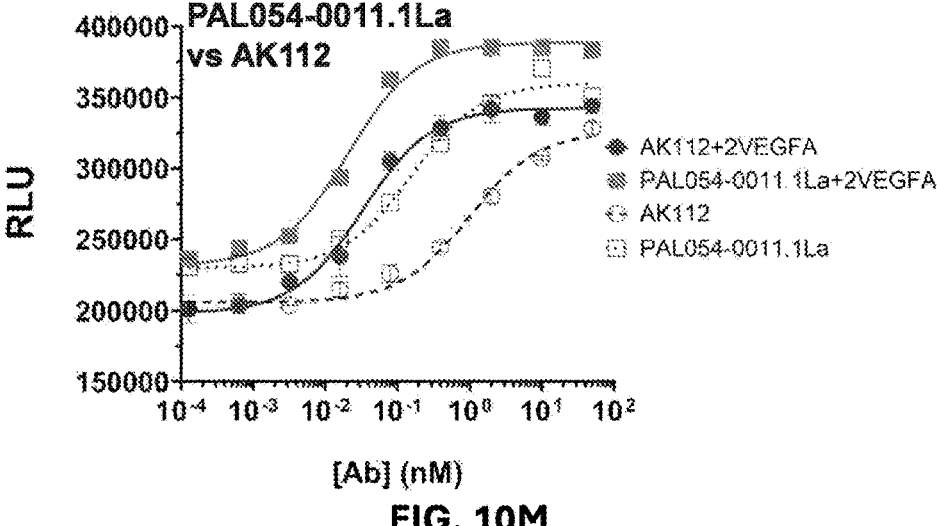
Figure 10N:
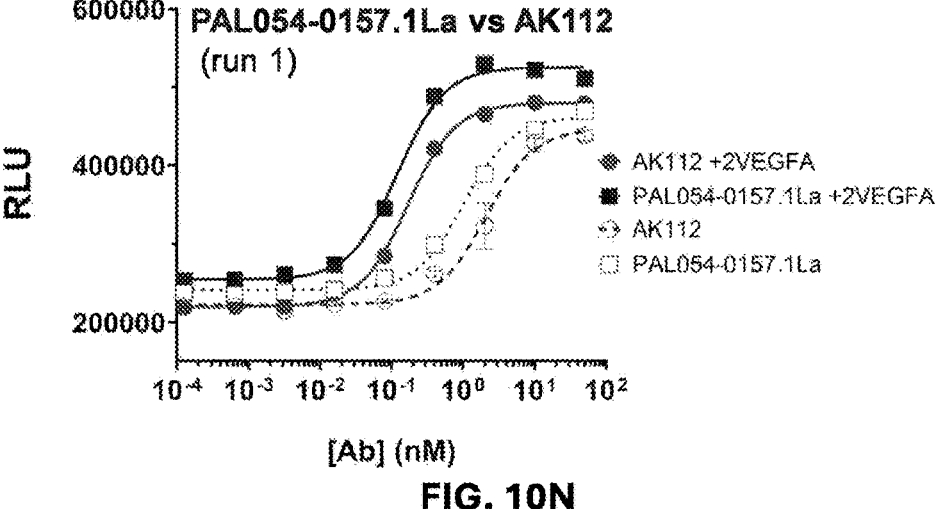
Figure 10O:
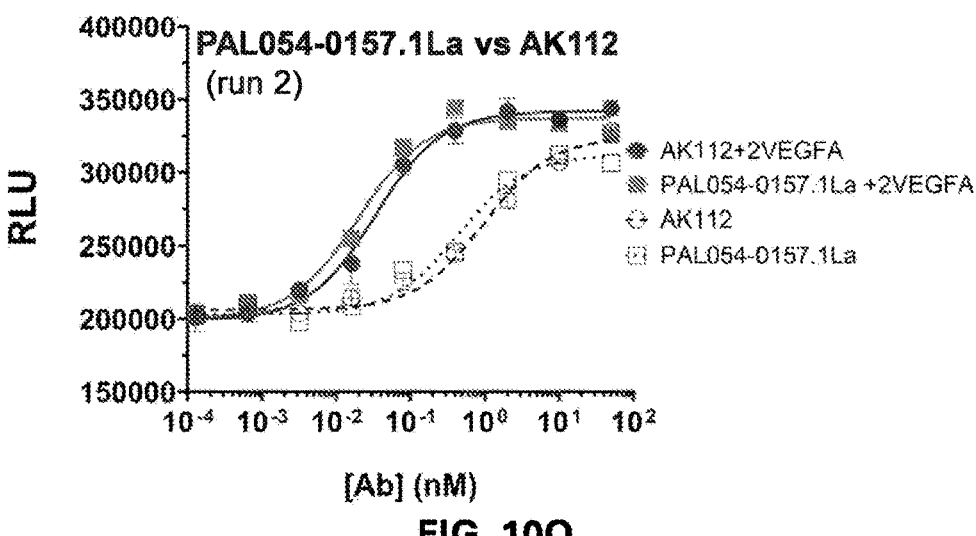
Figure 10P:
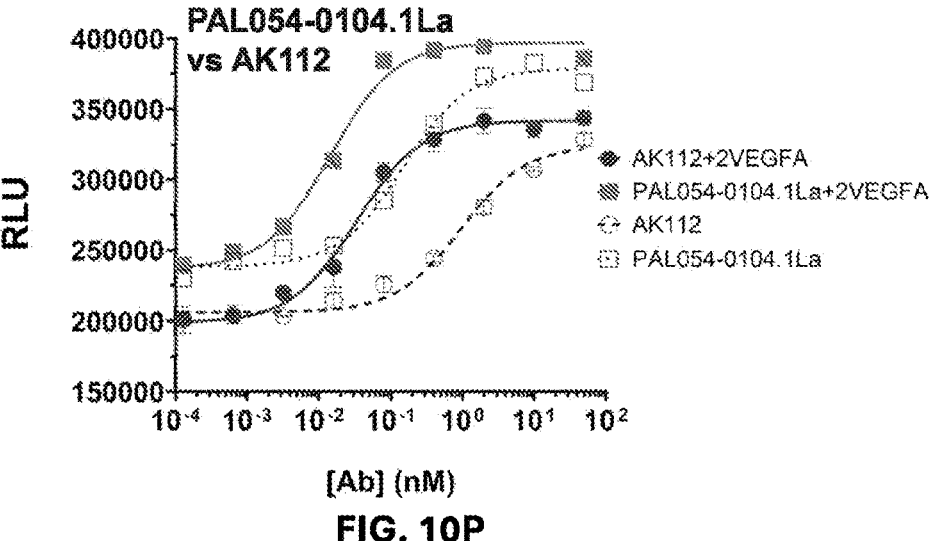
Figure 10Q:
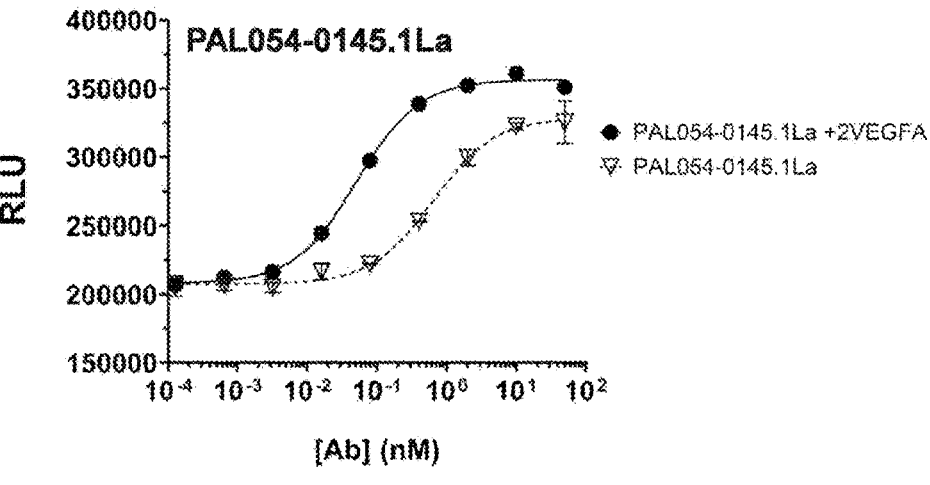
Figure 10R:
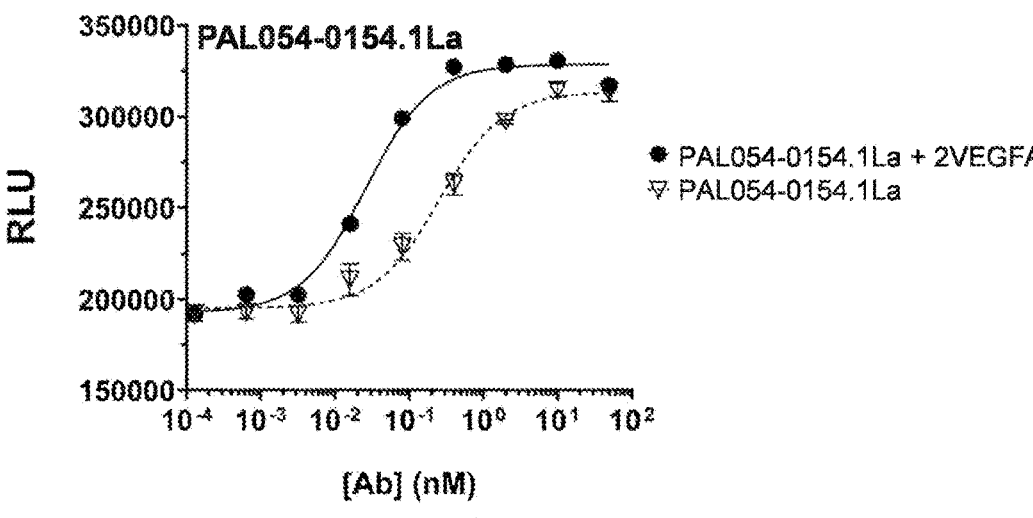
Figure 10S:
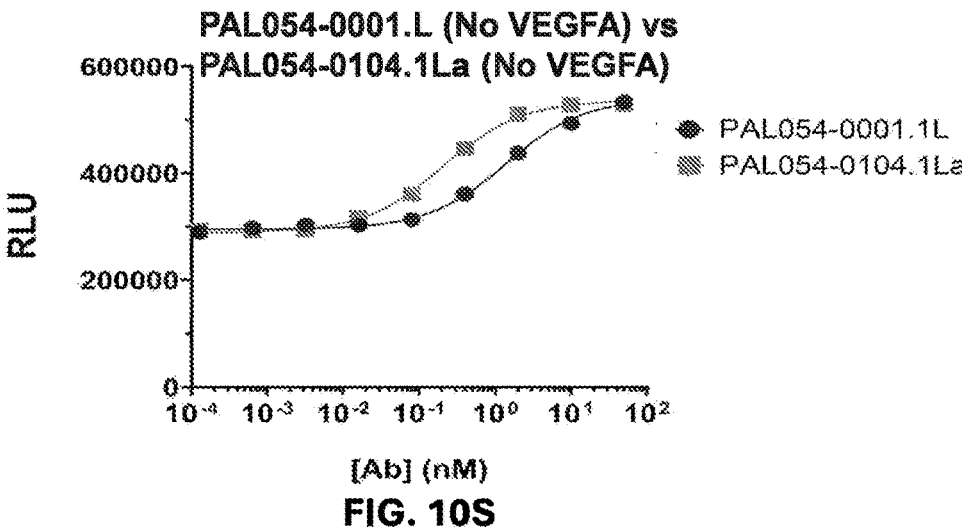
Figure 10T:
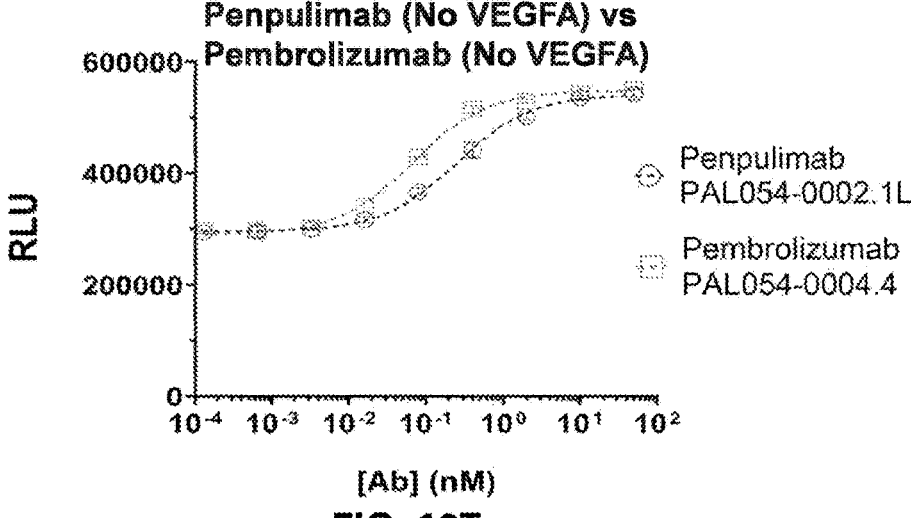
Figure 10U:
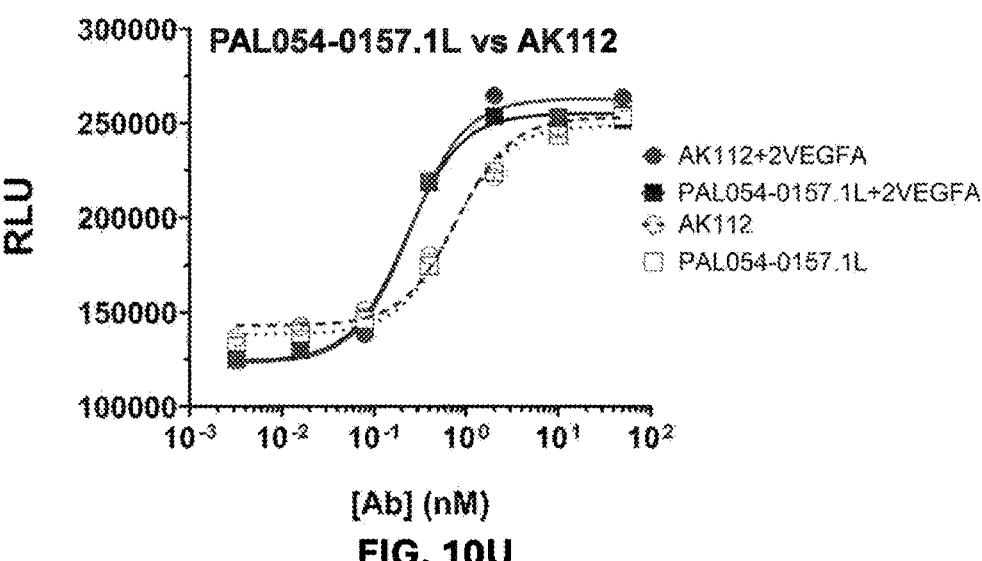
Figure 10V:
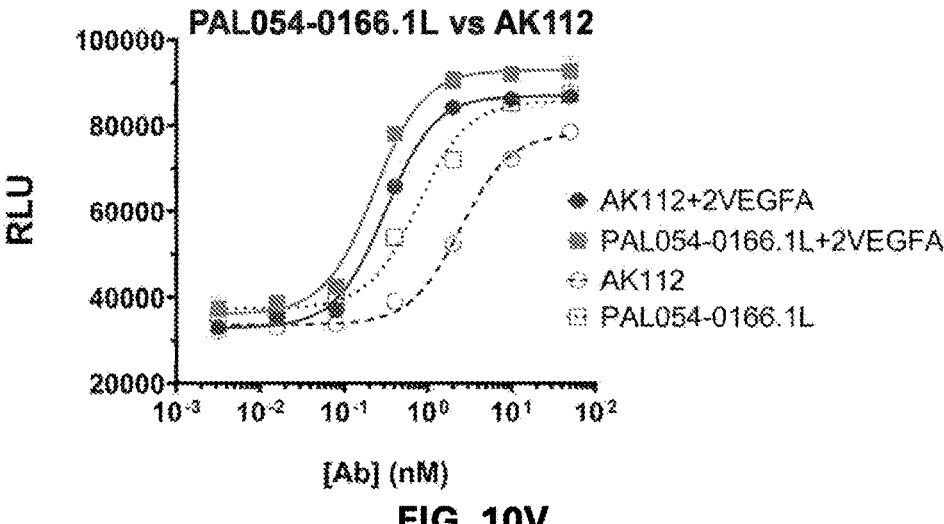
Figure 10W:
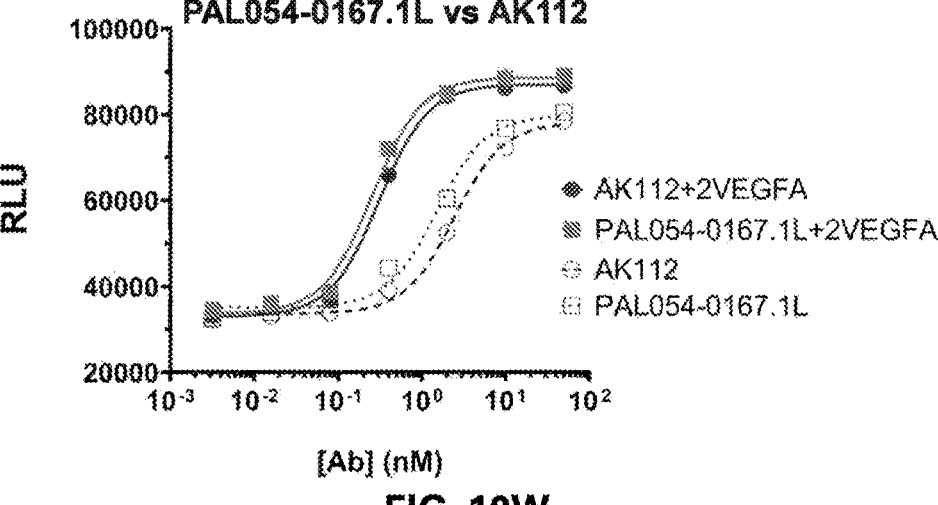
Figure 10X:
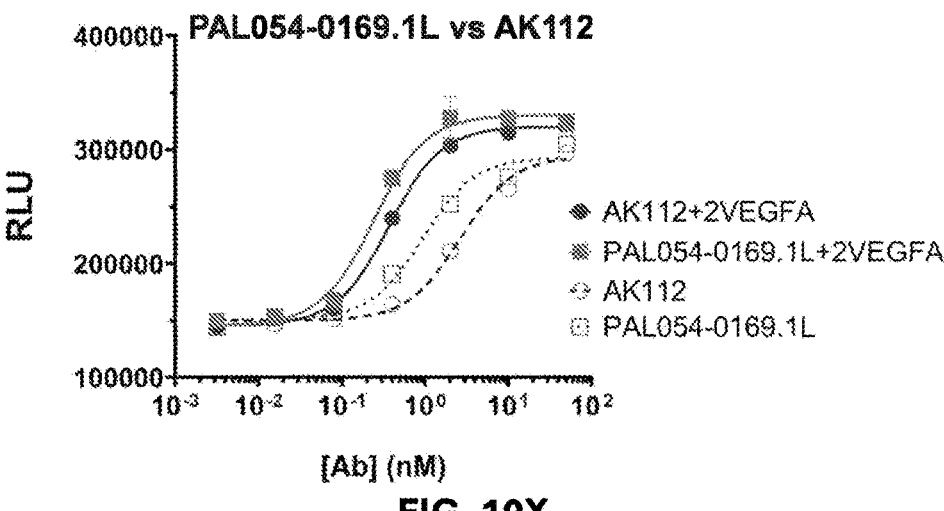
Figure 10Y:
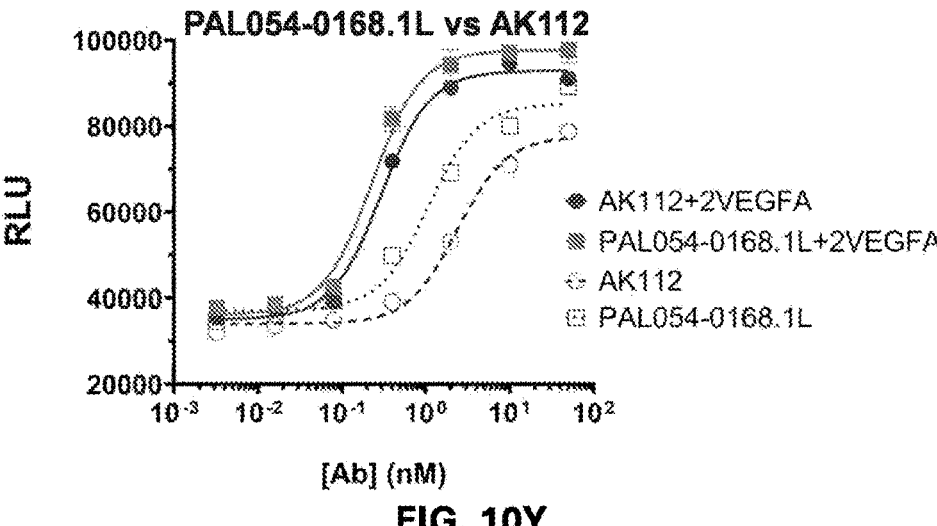
Figure 10Z:
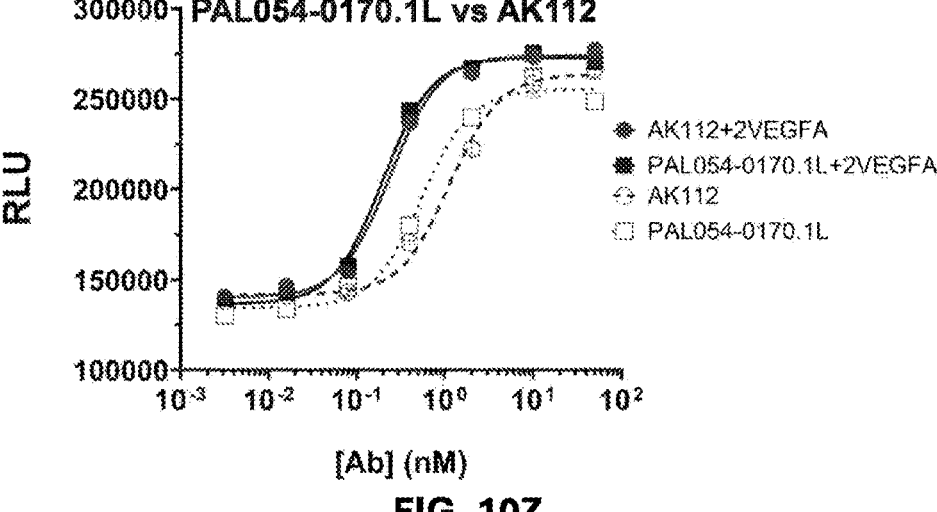
Figure 10A:
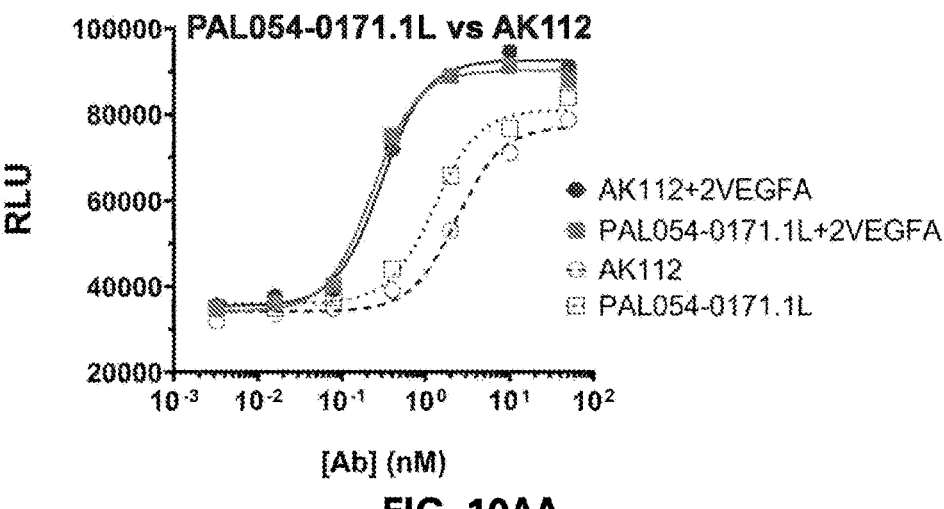
Figure 10B:
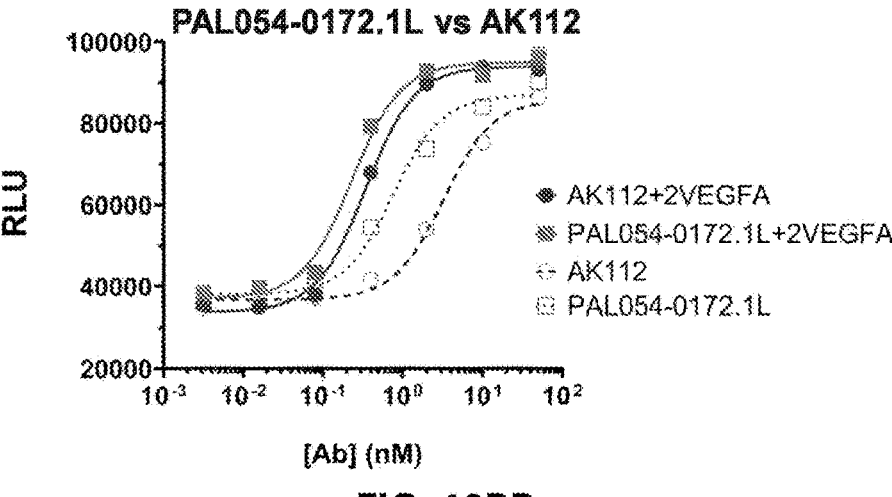
Figure 10C:
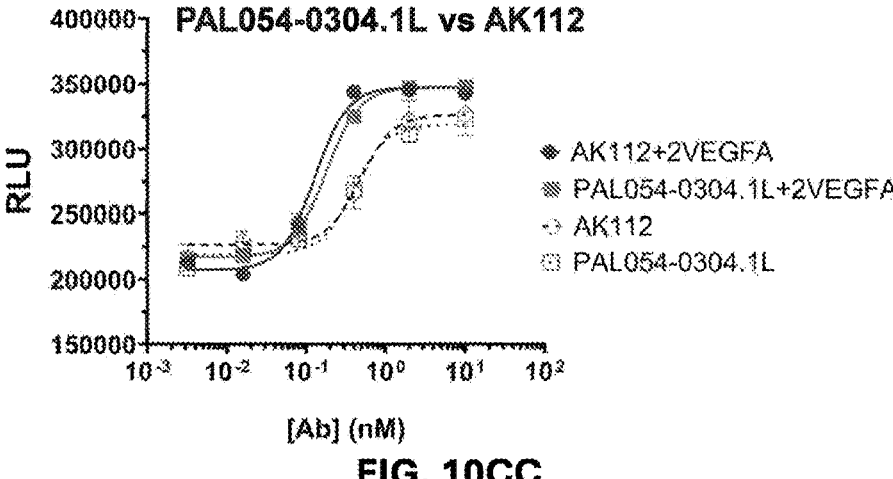
Figure 10D:
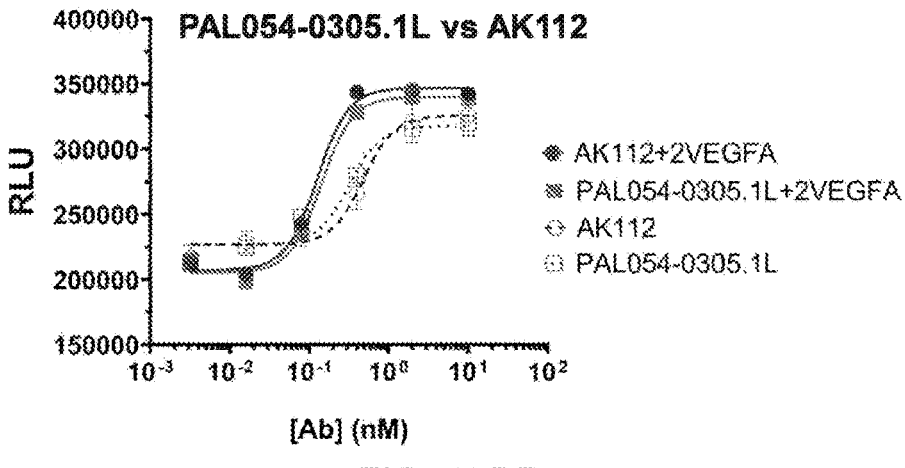
Figure 10K:
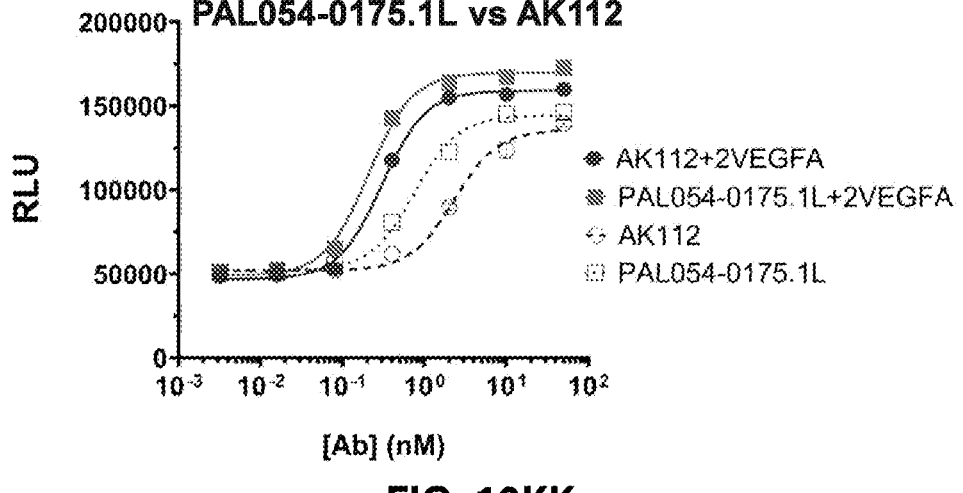

Example 7: Size Exclusion Chromatography of Bispecific Variants, Controls, and Benchmarks Size exclusion chromatography with multi-angle static light scattering (SEC-MALS) was used to characterize and compare benchmark bispecific, AK112, to controls and VEGF/PD-1 bispecific antibodies as disclosed herein. Exemplary clones disclosed herein exhibited similar SEC-MAL complex profiles to AK112 in the presence of VEGFA (FIGS. 7A-7F; Table 18). Without being bound by mechanism of action, the results strongly suggest that bispecific antibodies could enhance PD-1 binding through VEGFA daisy chaining (FIG. 9).

TABLE 18

| Sample name | Conc. (mg/ml) | SEC-MALS Loading (μl) | SEC-MALS Loading (nM) | Theoretical Mw (kDa) | Measured Mw (kDa) |
|---|---|---|---|---|---|
| VEGFA | 0.25 | 50 | 20 | 25 | / |
| PAL054-0001.1L | 2.88 | 50 | 5 | 201.1 | 196.1 |
| PAL054-0001.1La | 2.94 | 50 | 5 | 201.3 | 197.7 |
| PAL054-0011.1La | 4.43 | 50 | 5 | 174.9 | 171.7 |
| PAL054-0104.1La | 1.85 | 50 | 5 | 202.9 | 202.4 |
| PAL054-0148.1La | 2.38 | 50 | 5 | 202.5 | 196.9 |
| PAL054-0157.1La | 3.17 | 50 | 5 | 202.68 | 197.6 |
| PAL054-0170.1L | 4.72 | 50 | 2.5 | 202.50 | 200.8 |
| PAL054-0001.1L + VEGFA | / | 50 | 5 + 10 | / | 817.6, 509.2, 425.6 |
| PAL054-0001.1La + VEGFA | / | 50 | 5 + 10 | / | 882.1, 533.8, 595.7 |
| PAL054-0011.1La + VEGFA | / | 50 | 5 + 10 | / | 803.3, 466.3, 526.8 |
| PAL054-0104.1La + VEGFA | / | 50 | 5 + 10 | / | 839.1, 515.7, 449.6 |
| PAL054-0148.1La + VEGFA | / | 50 | 5 + 10 | / | 883.1, 531.2, 511.1 |
| PAL054-0157.1La + VEGFA | / | 50 | 5 + 10 | / | 835.6, 519.5, 413.7 |
| PAL054-0170.1L + VEGFA | / | 50 | 2.5 + 5 | / | 1391, 547.4, 945.7 |

Example 8: Functional Activity of Bispecific Antibodies in Reporter Assay

PD-1 Reporter Assays

A PD-1 reporter assay was conducted on VEGF/PD-1 bispecific antibodies as disclosed herein and revealed enhanced functional potency of VEGF/PD-1 bispecific antibodies to block PD-1/PD-L1 signaling pathway in the presence of VEGF (FIGS. 10A-10KK and Tables 19A-19C.

TABLE 19A

| | Run 1 | | |
|---|---|---|---|
| Bispecifics | PD-1 Reporter IC$_{50}$ (nM) (−VEGF) | PD-1 Reporter IC$_{50}$ (nM) (+VEGF) | Rel IC$_{50}$ PD-1 (+VEGF) |
| PAL054-0001.1L (AK112) | 2.08 | 0.17 | 1.0 |
| PAL054-0148.1La | 1.73 | 0.15 | 0.9 |
| PAL054-0157.1La | 1.04 | 0.12 | 0.7 |

TABLE 19B

| | Run 2 | | |
|---|---|---|---|
| Bispecifics | PD-1 Reporter IC$_{50}$ (nM) (−VEGF) | PD-1 Reporter IC$_{50}$ (nM) (+VEGF) | Rel IC$_{50}$ PD-1 (+VEGF) |
| PAL054-0001.1L (AK112) | 1.05 | 0.033 | 1.0 |
| PAL054-0148.1La | 0.73 | 0.056 | 1.7 |
| PAL054-0157.1La | 0.49 | 0.022 | 0.7 |

TABLE 19C

| | Run 3 | | |
|---|---|---|---|
| Bispecifics | PD-1 Reporter IC$_{50}$ (nM) (−VEGF) | PD-1 Reporter IC$_{50}$ (nM) (+VEGF) | Rel IC$_{50}$ PD-1 (+VEGF) |
| PAL054-0001.1L | 1 | 0.033 | 1 |
| PAL054-0145.1La | 0.64 | 0.052 | 1.7 |
| PAL054-0154.1La | 0.25 | 0.026 | 0.9 |
| PAL054-0011.1La | 0.17 | 0.022 | 0.7 |
| PAL054-0104.1La | 0.15 | 0.016 | 0.5 |
| PAL054-0001.1La | 0.73 | 0.033 | 1.1 |

TABLE 19C-continued

| | Run 3 | | |
| Bispecifics | PD-1 Reporter $IC_{50}$ (nM) (−VEGF) | PD-1 Reporter $IC_{50}$ (nM) (+VEGF) | Rel $IC_{50}$ PD-1 (+VEGF) |
| --- | --- | --- | --- |
| PAL054-0113.1La | 0.15 | 0.014 | 0.5 |
| PAL054-0117.1La | 0.23 | 0.025 | 0.8 |
| PAL054-0157.1L | 0.71 | 0.23 | 0.9 |
| PAL054-0166.1L | 0.77 | 0.23 | 0.7 |
| PAL054-0167.1L | 1.5 | 0.26 | 0.8 |
| PAL054-0168.1L | 1.1 | 0.23 | 0.8 |
| PAL054-0169.1L | 0.92 | 0.24 | 0.6 |
| PAL054-0170.1L | 0.55 | 0.2 | 0.8 |
| PAL054-0304.1L | 0.4 | 0.18 | 1.4 |
| PAL054-0305.1L | 0.31 | 0.14 | 1.1 |
| PAL054-0173.1L | 1.1 | 0.25 | 0.7 |
| PAL054-0174.1L | 1 | 0.23 | 0.6 |
| PAL054-0175.1L | 0.76 | 0.21 | 0.7 |
| PAL054-0307.1L | 1.2 | 0.65 | 0.8 |
| PAL054-0308.1L | 1.2 | 0.8 | 1.0 |
| PAL054-0309.1L | 0.42 | 0.22 | 0.6 |
| PAL054-0310.1L | 0.54 | 0.23 | 0.6 |
| PAL054-0171.1L | 1.3 | 0.23 | 0.8 |
| PAL054-0172.1L | 0.77 | 0.23 | 0.7 |

VEGF Reporter Assays

Figure 11A:
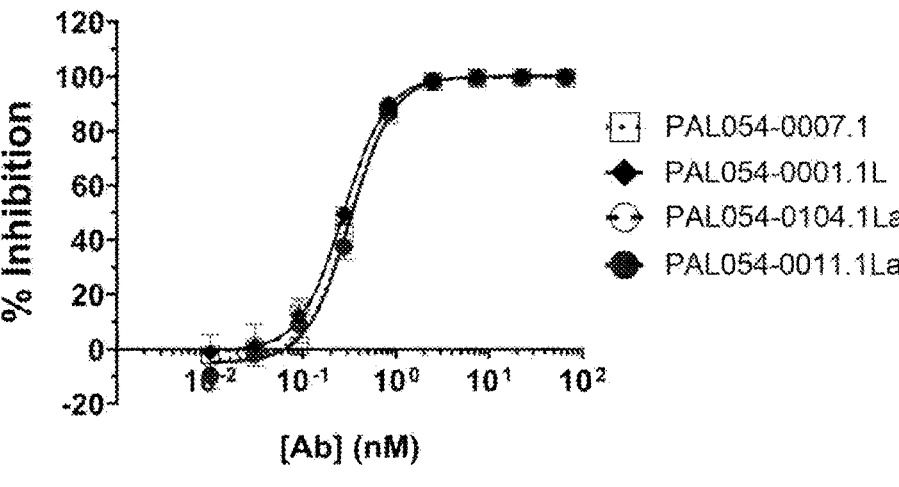
FIGS. 11A-11V depict VEGF reporter assay results for the indicated antibodies.
Figure 11B:
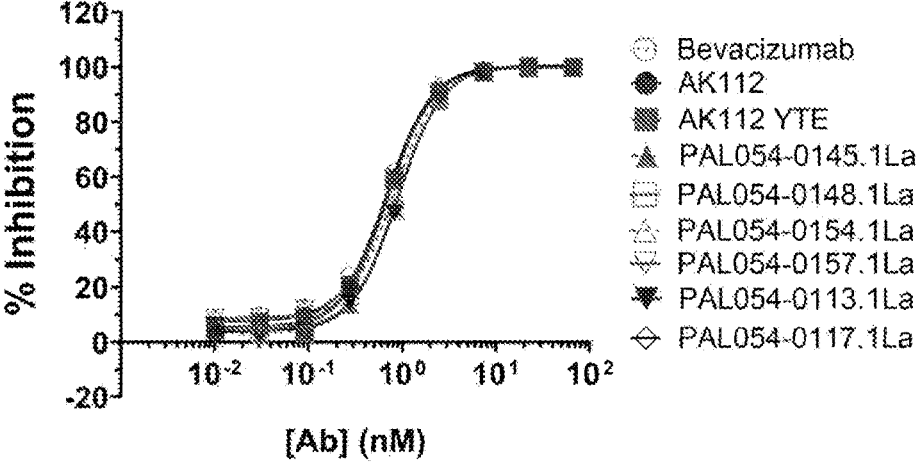
Figure 11C:
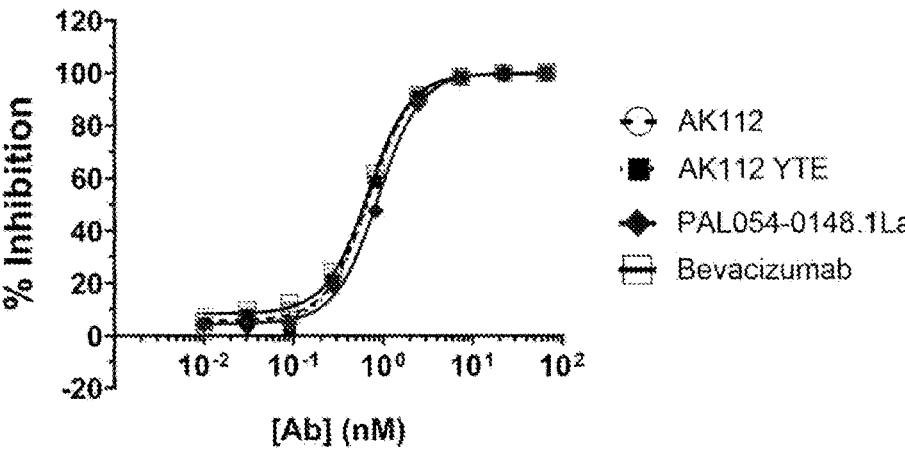
Figure 11D:
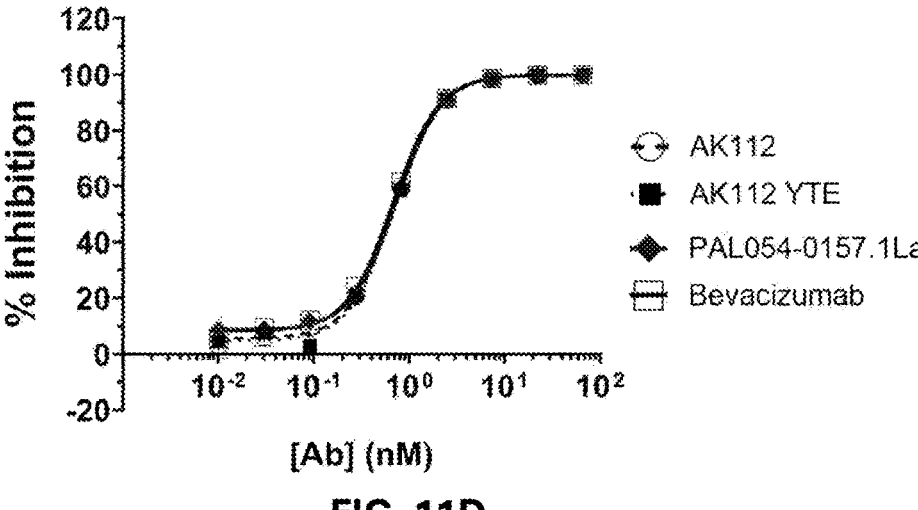
Figure 11E:
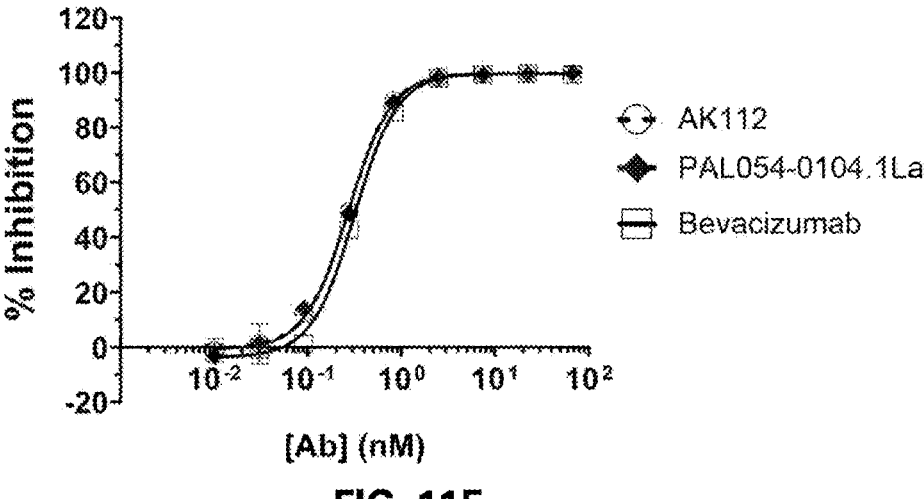
Figure 11F:
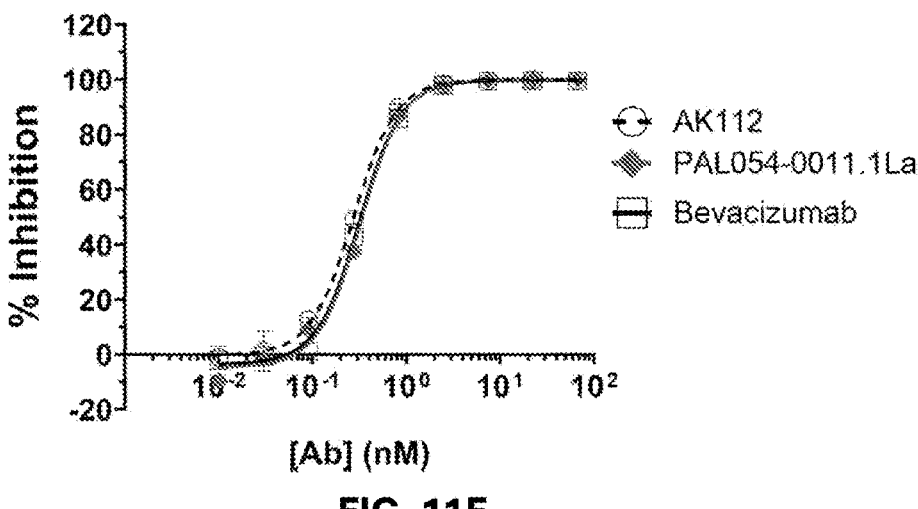
Figure 11G:
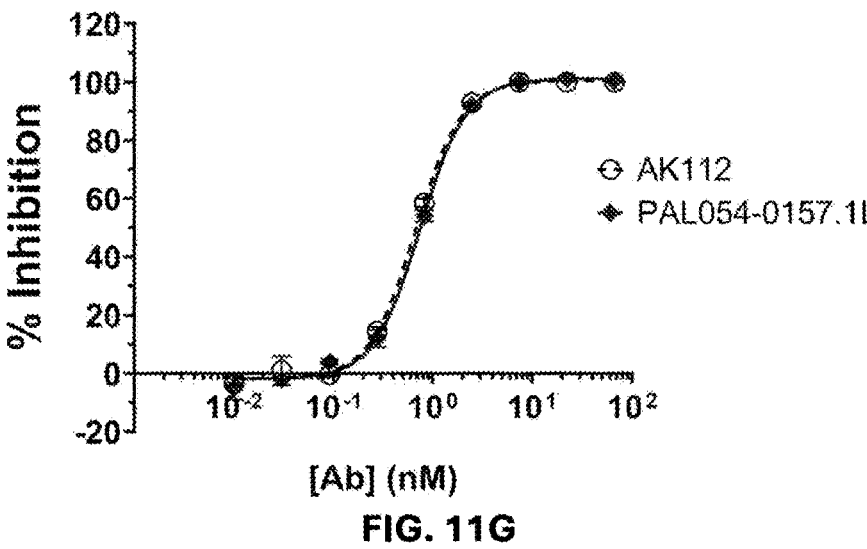
Figure 11H:
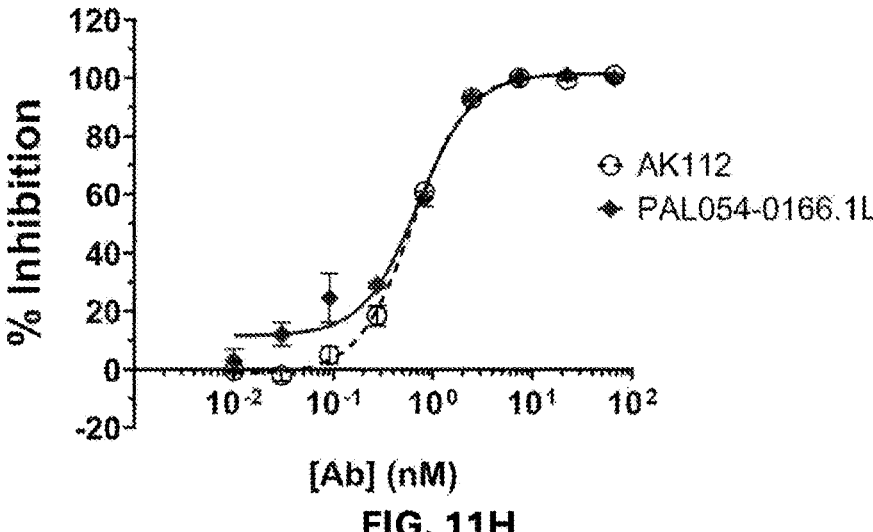
Figure 11I:
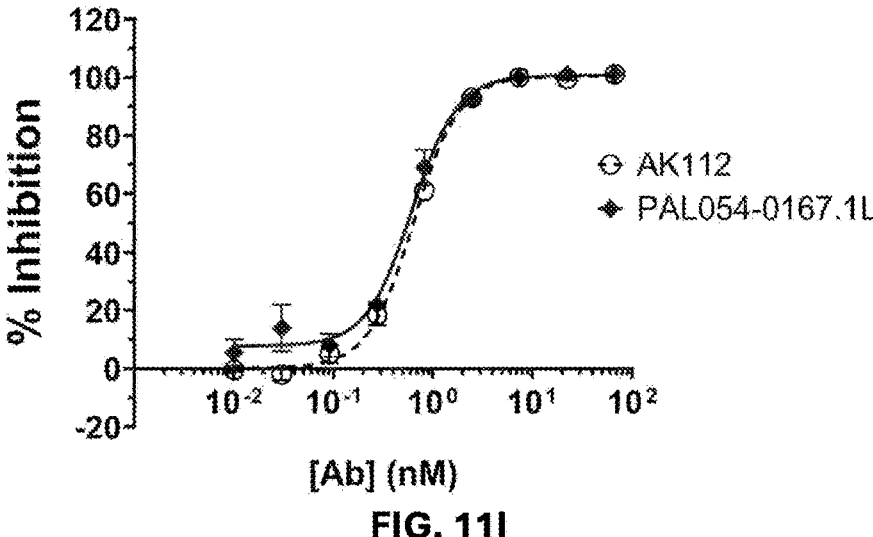
Figure 11J:
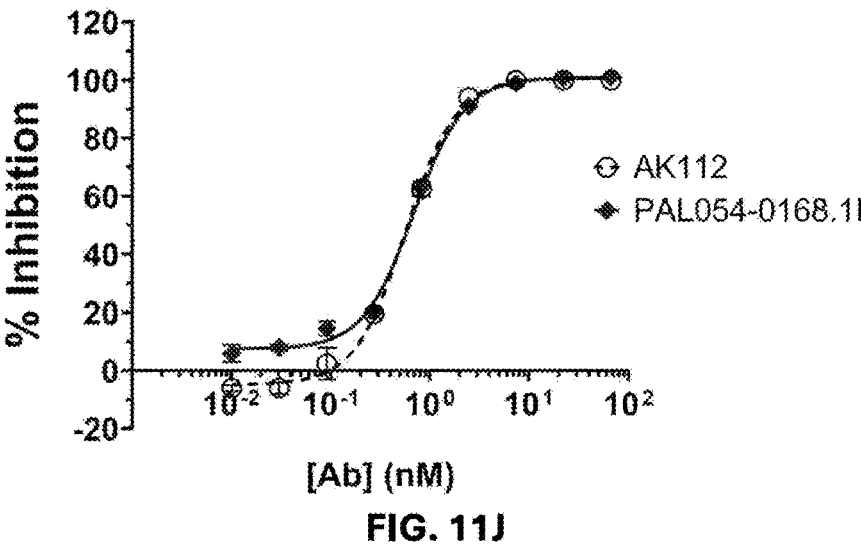
Figure 11K:
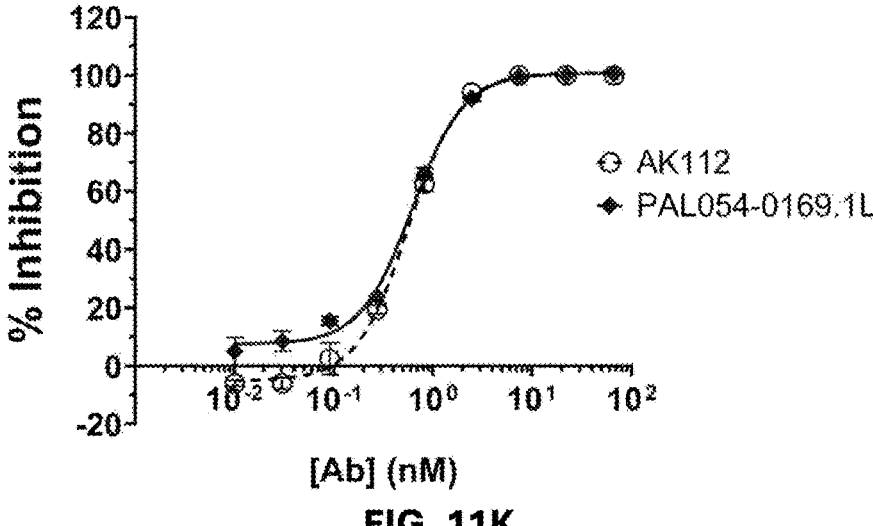
Figure 11L:
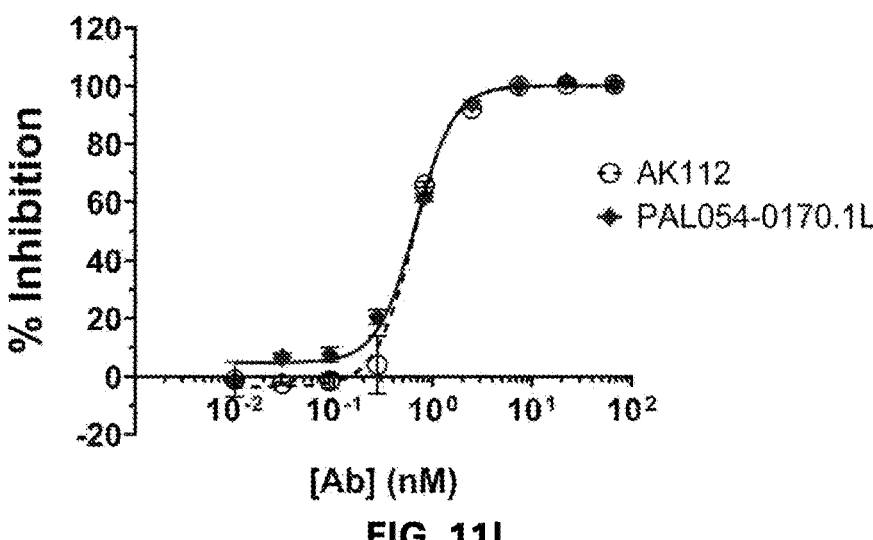
Figure 11M:
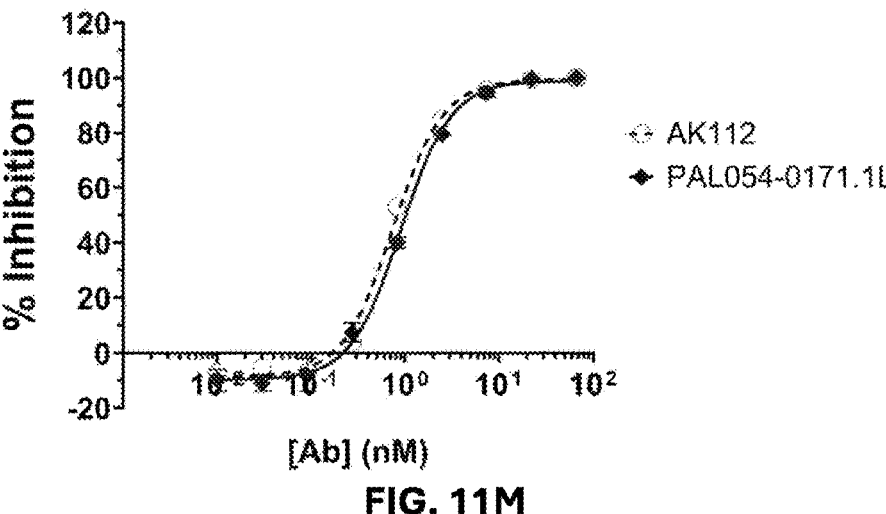
Figure 11N:
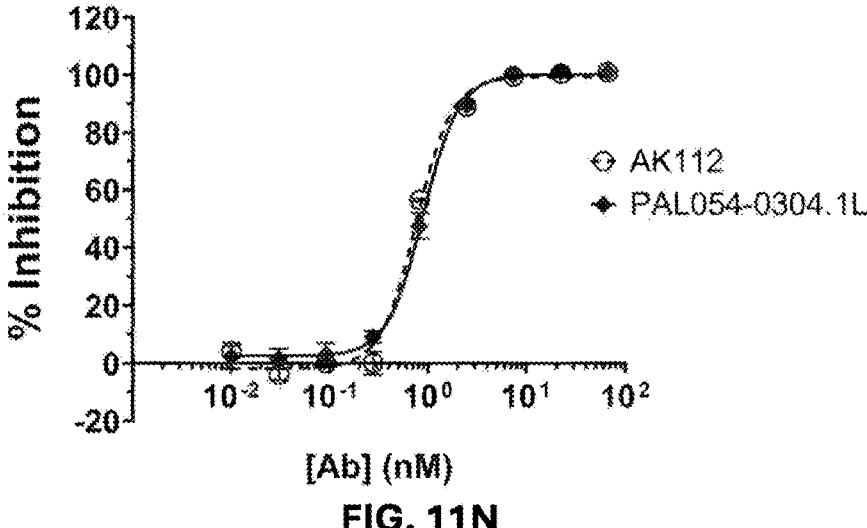
Figure 11O:
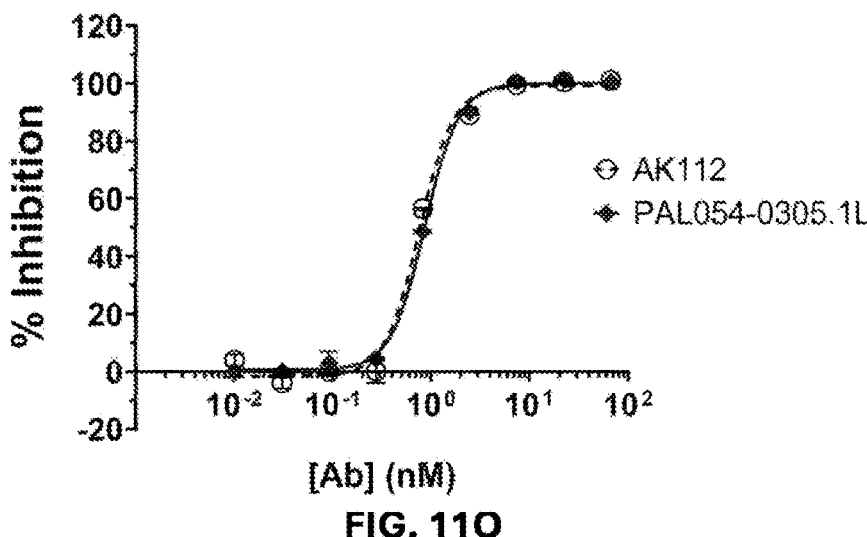
Figure 11P:
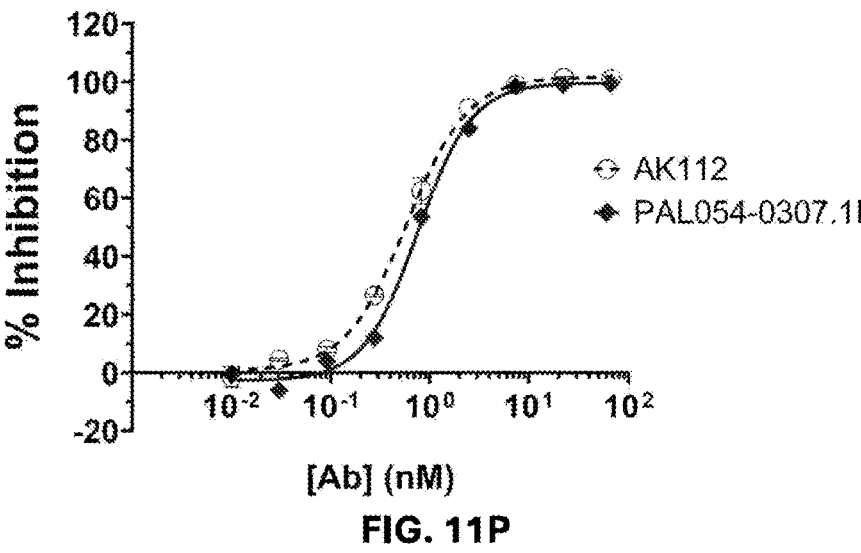
Figure 11Q:
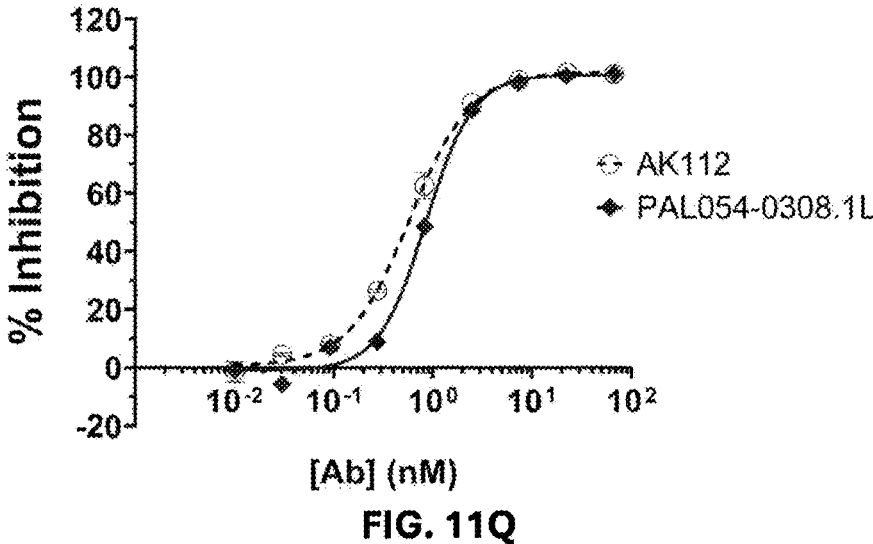
Figure 11R:
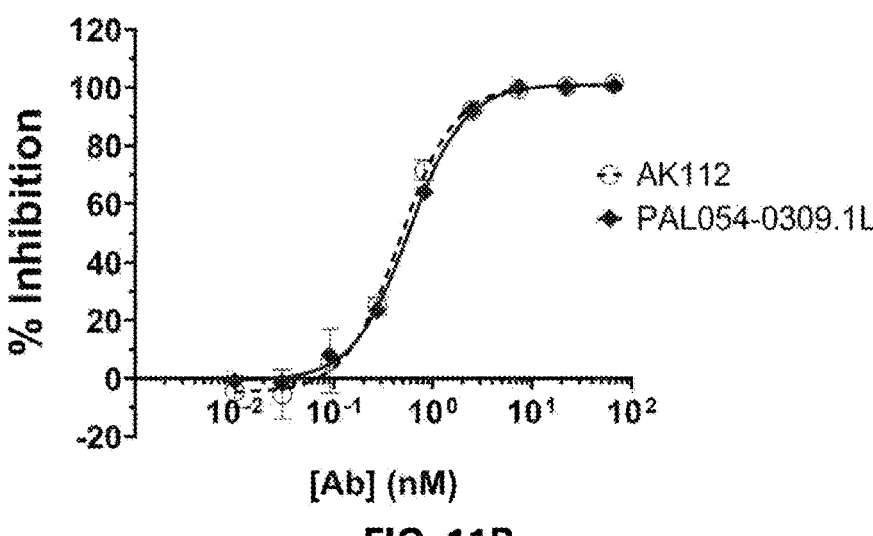
Figure 11S:
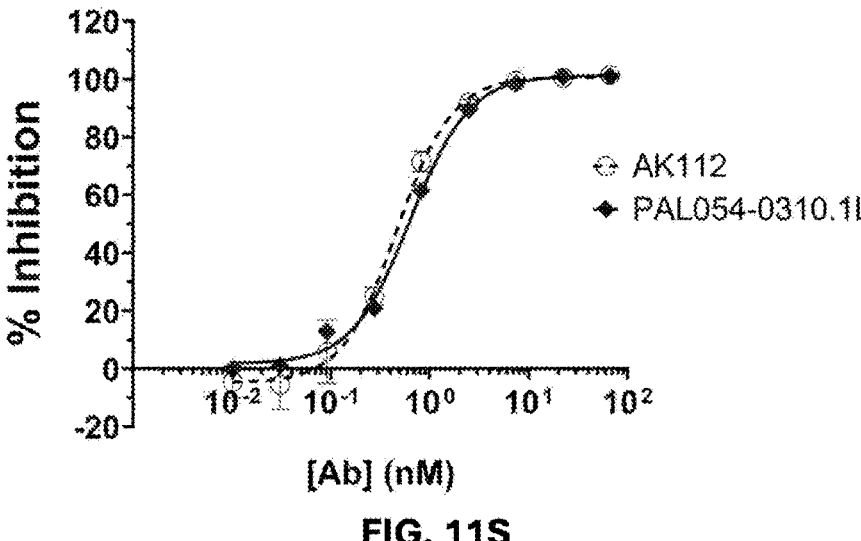
Figure 11T:
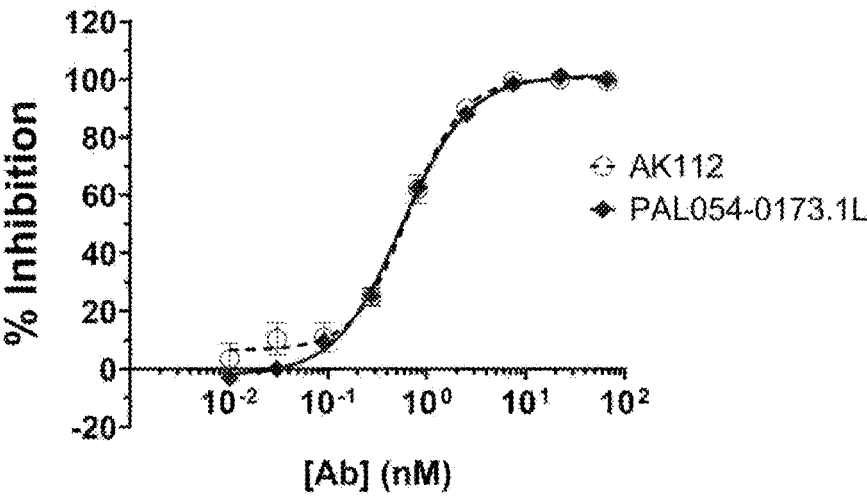
Figure 11U:
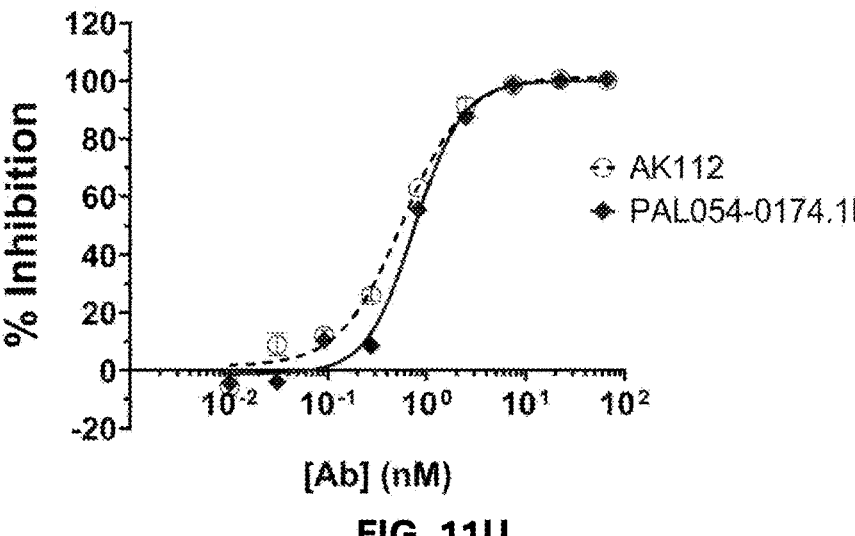
Figure 11V:
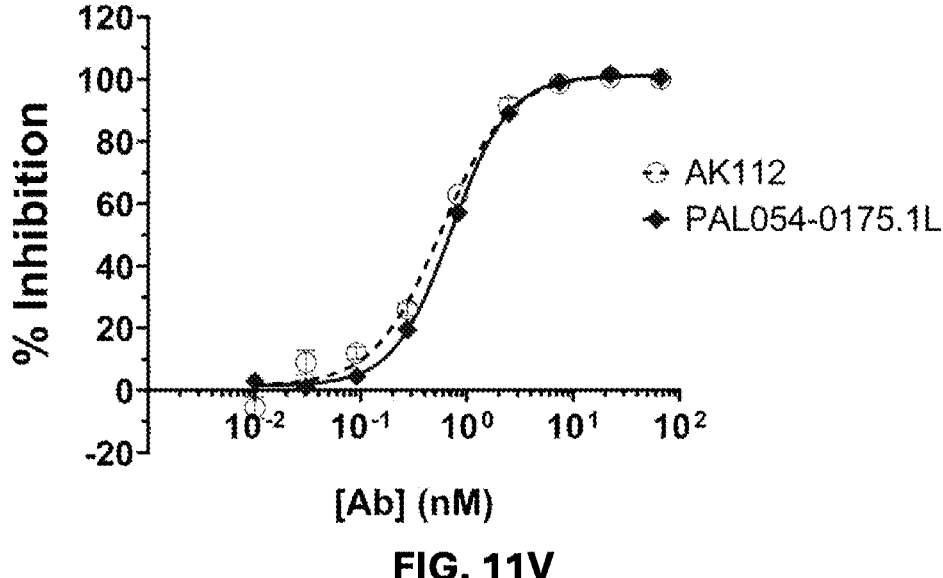

A VEGF reporter assay was conducted on VEGF/PD-1 bispecific antibodies as disclosed herein and the resultant $IC_{50}$ values are provided in FIGS. 11A-11V and Tables 20A and 20B.

TABLE 20A

| Bispecifics | Rel $IC_{50}$ (nM) |
| --- | --- |
| PAL054-0157.1L | 1.1 |
| Bevacizumab | 1.1 |
| PAL054-0166.1L | 1.2 |
| PAL054-0167.1L | 1.0 |
| PAL054-0168.1L | 1.2 |
| PAL054-0169.1L | 1.1 |
| PAL054-0170.1L | 1.0 |
| PAL054-0303.1L | 1.0 |
| PAL054-0304.1L | 1.2 |
| PAL054-0305.1L | 1.1 |
| PAL054-0173.1L | 0.9 |
| PAL054-0174.1L | 1.3 |
| PAL054-0175.1L | 1.2 |
| PAL054-0307.1L | 1.3 |
| PAL054-0308.1L | 1.4 |
| PAL054-0309.1L | 1.2 |
| PAL054-0310.1L | 1.4 |
| PAL054-0171.1L | 1.1 |

TABLE 20B

| Bispecifics | Rel $IC_{50}$ (nM) |
| --- | --- |
| PAL054-0001.1L (AK112) | 1.0 |
| PAL054-0001.1La (AK112 YTE) | 1.0 |
| PAL054-0145.1La | 1.3 |
| PAL054-0148.1La | 1.3 |
| PAL054-0154.1La | 1.2 |
| PAL054-0157.1La | 1.0 |
| PAL054-0011.1La | 1.2 |
| PAL054-0104.1La | 1.0 |
| PAL054-0001.1La | 1.0 |
| PAL054-0113.1La | 1.3 |
| PAL054-0117.1La | 1.0 |
| PAL054-0007.1 (Bevacizumab) | 1.2, 1.0 |

Example 9: VEGF Effect on HUVEC Proliferation

Figure 12A:
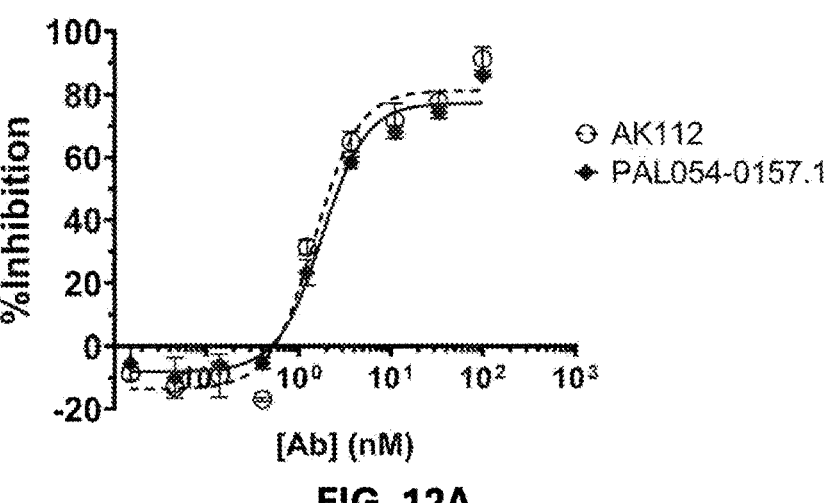
FIGS. 12A-12O depict inhibition of VEGF-mediated proliferation of human umbilical vein endothelial cells (HUVECs) by the indicated antibodies.
Figure 12B:
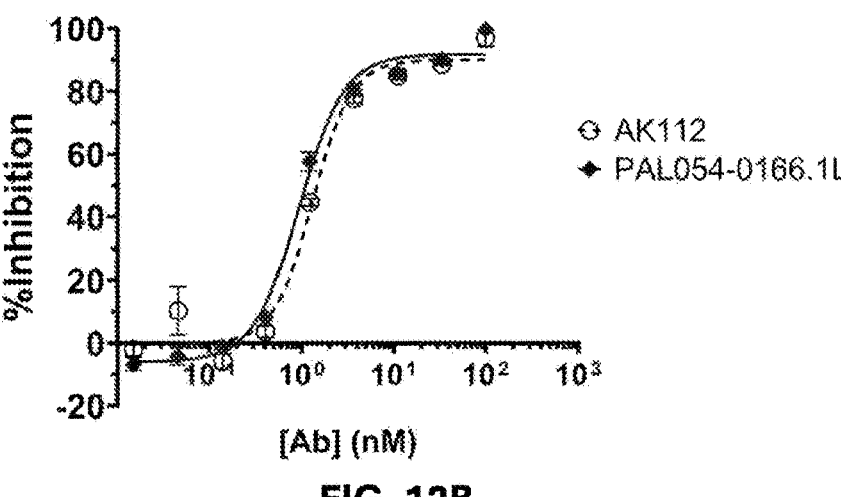
Figure 12C:
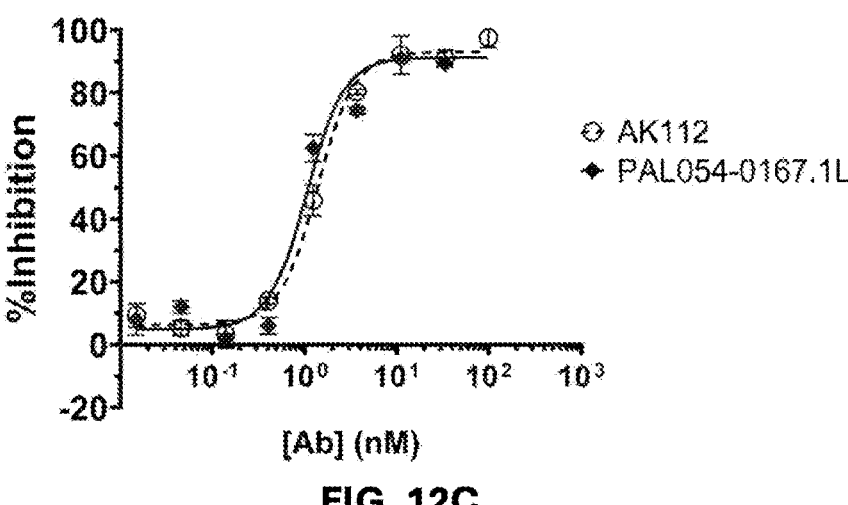
Figure 12D:
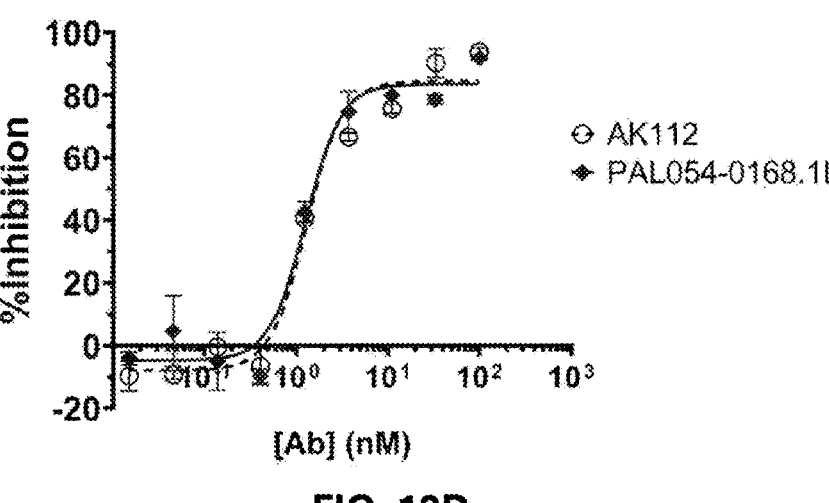
Figure 12E:
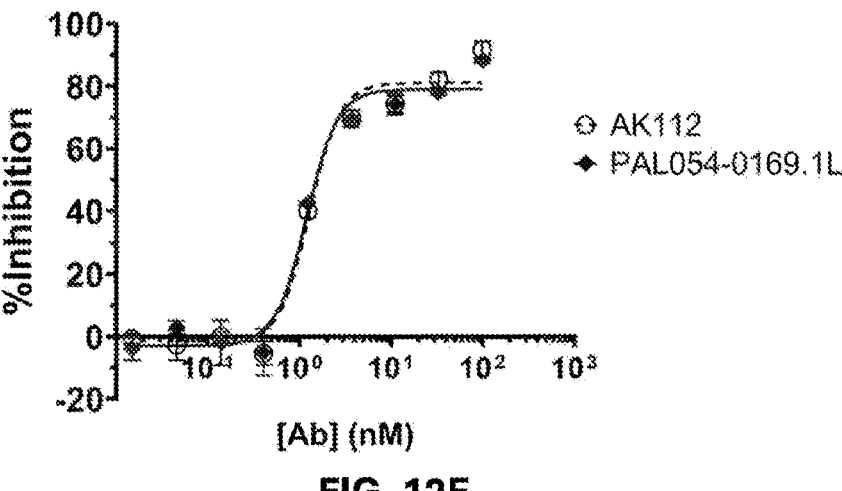
Figure 12F:
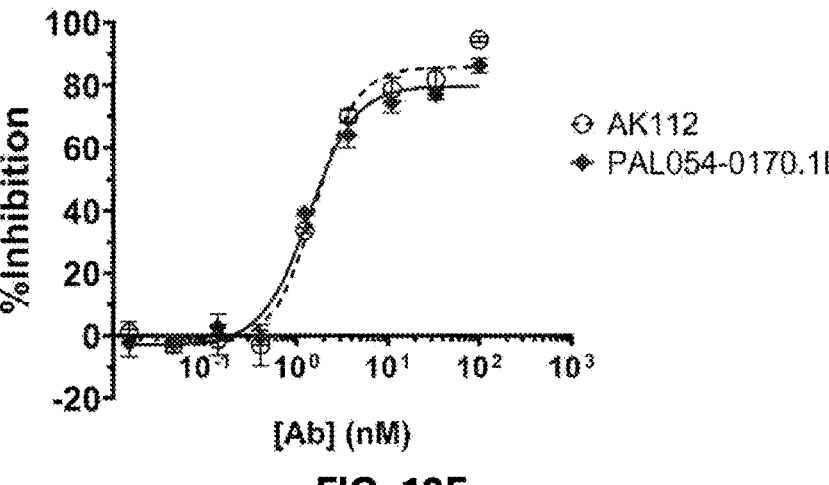
Figure 12J:
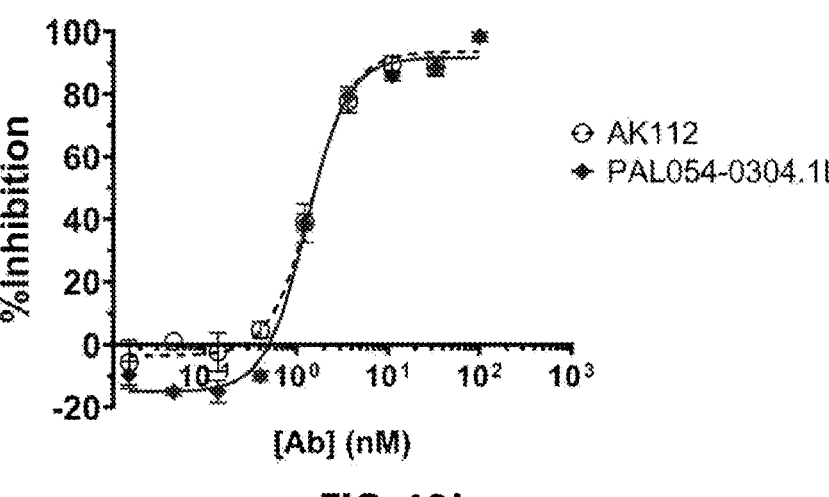
Figure 12K:
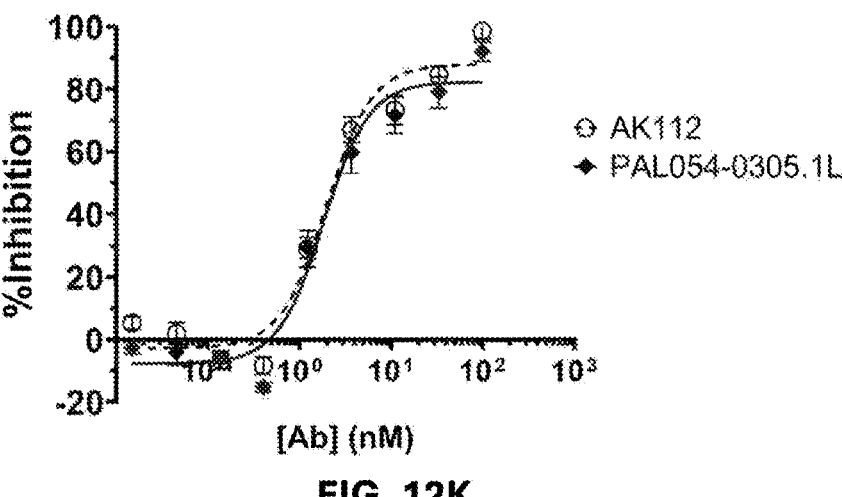
Figure 12L:
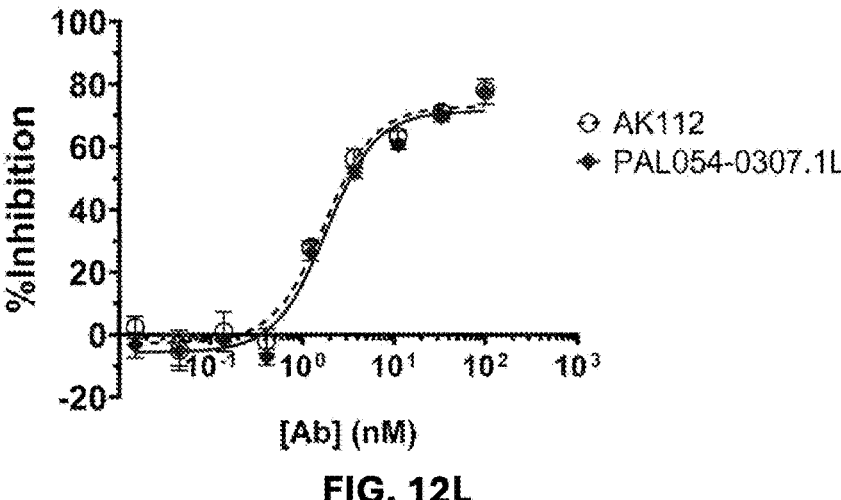
Figure 12M:
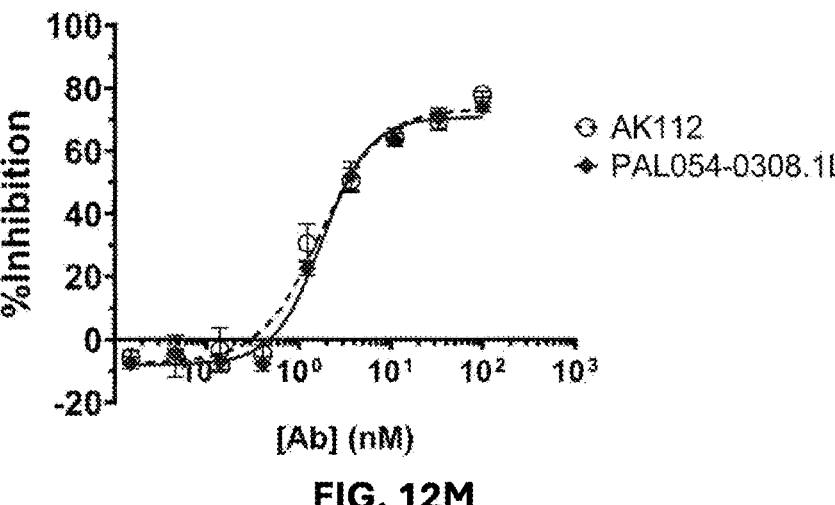
Figure 12N:
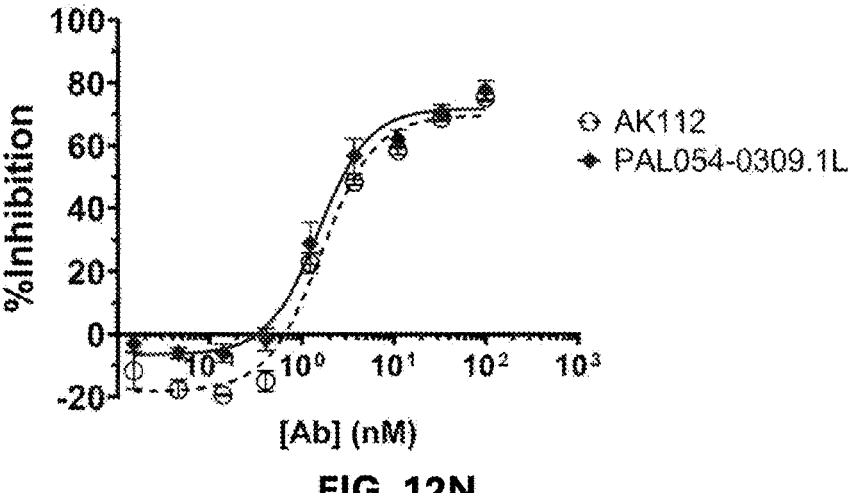
Figure 12O:
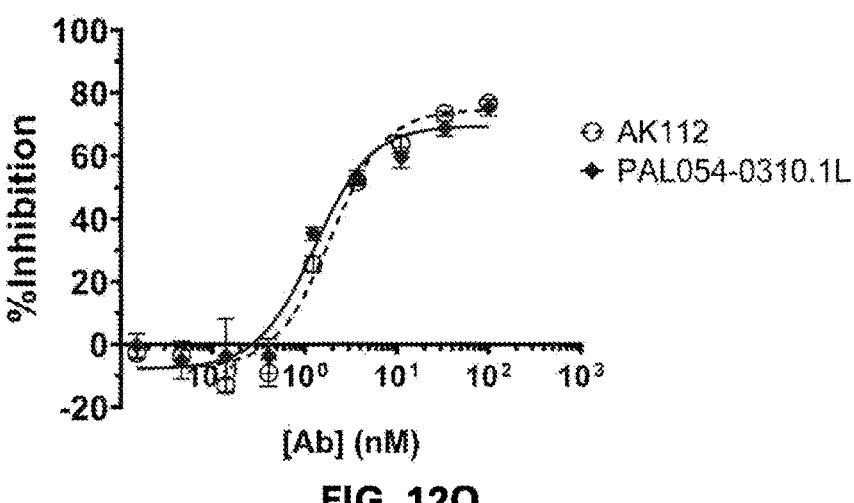

HUVEC proliferation assay was conducted on VEGF/PD-1 bispecific antibodies as disclosed herein and the resultant IC50 values are provided in FIGS. 12A-12O and Table 21.

TABLE 21

| HUVEC Proliferation $IC_{50}$ Values | | |
| Bispecifics | $IC_{50}$ (nM) | Positive control (AK112) $IC_{50}$ |
| --- | --- | --- |
| PAL054-0157.1L | 1.8 | 1.4 |
| PAL054-0170.1L | 1.4 | 1.6 |
| PAL054-0304.1L | 1.3 | 1.4 |
| PAL054-0305.1L | 1.8 | 2 |
| PAL054-0173.1L | 1.4 | 1.5 |
| PAL054-0174.1L | 1.4 | 1.6 |
| PAL054-0175.1L | 1.7 | 1.4 |
| PAL054-0307.1L | 1.8 | 1.7 |
| PAL054-0308.1L | 1.8 | 1.7 |
| PAL054-0309.1L | 1.5 | 1.6 |
| PAL054-0310.1L | 1.3 | 1.9 |
| PAL054-0166.1L | 0.9 | 1.3 |
| PAL054-0167.1L | 1.1 | 1.4 |
| PAL054-0168.1L | 1.3 | 1.3 |
| PAL054-0169.1L | 1.2 | 1.3 |

Example 10: VEGF Effect on PD-1 Internalization

Figure 13A:
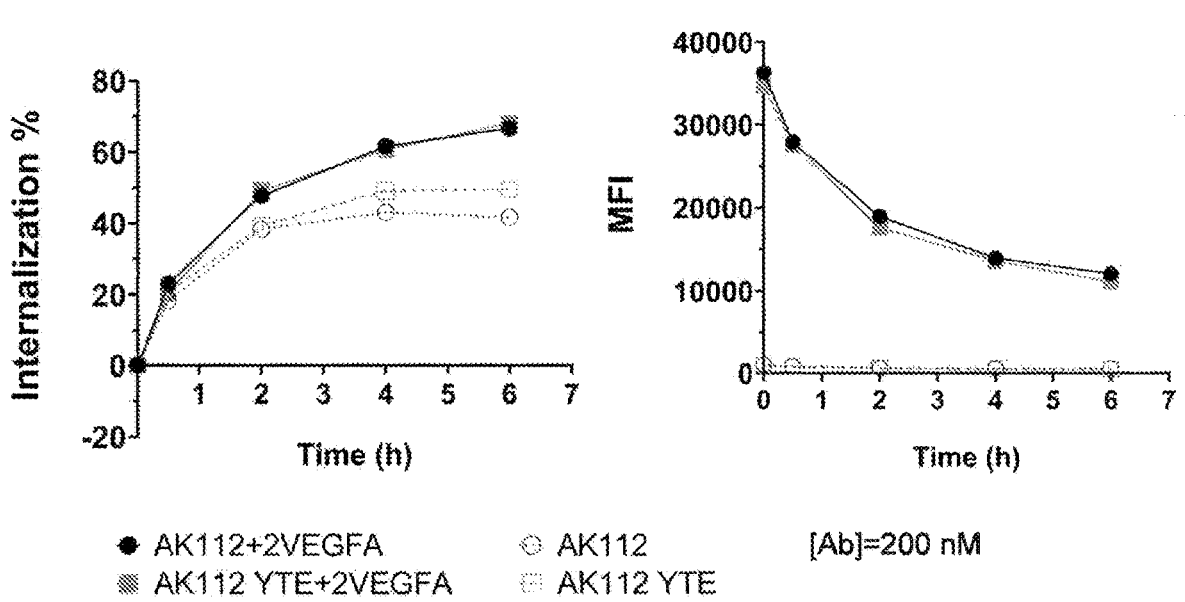
FIGS. 13A-13S depict PD-1 internalization results for the indicated antibodies.
Figure 13B:
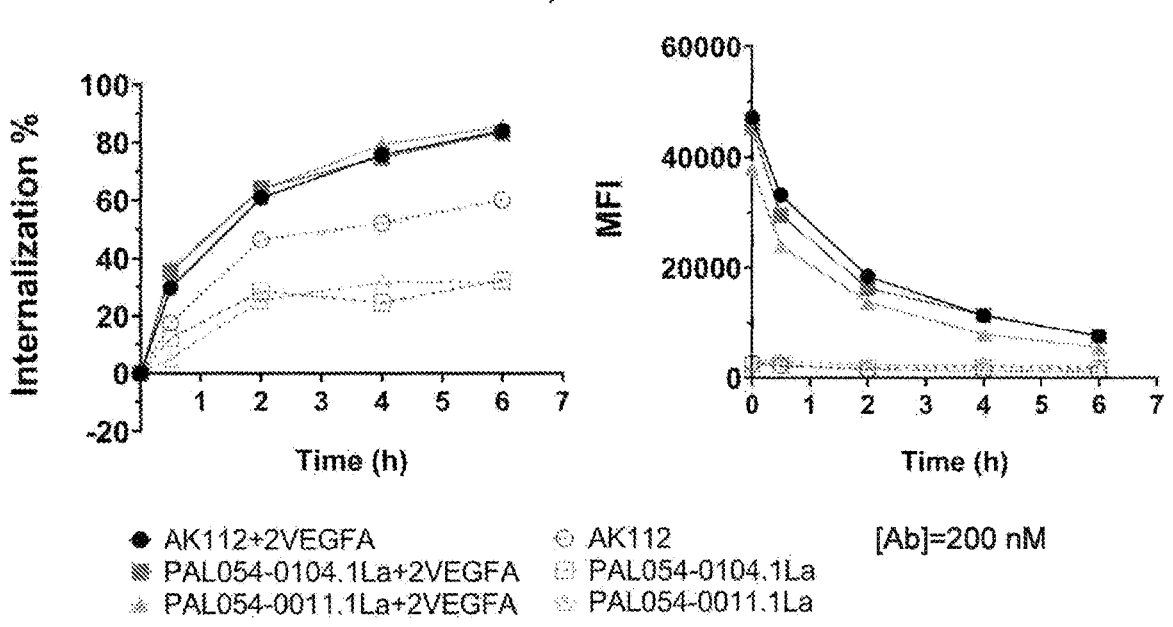
Figure 13C:
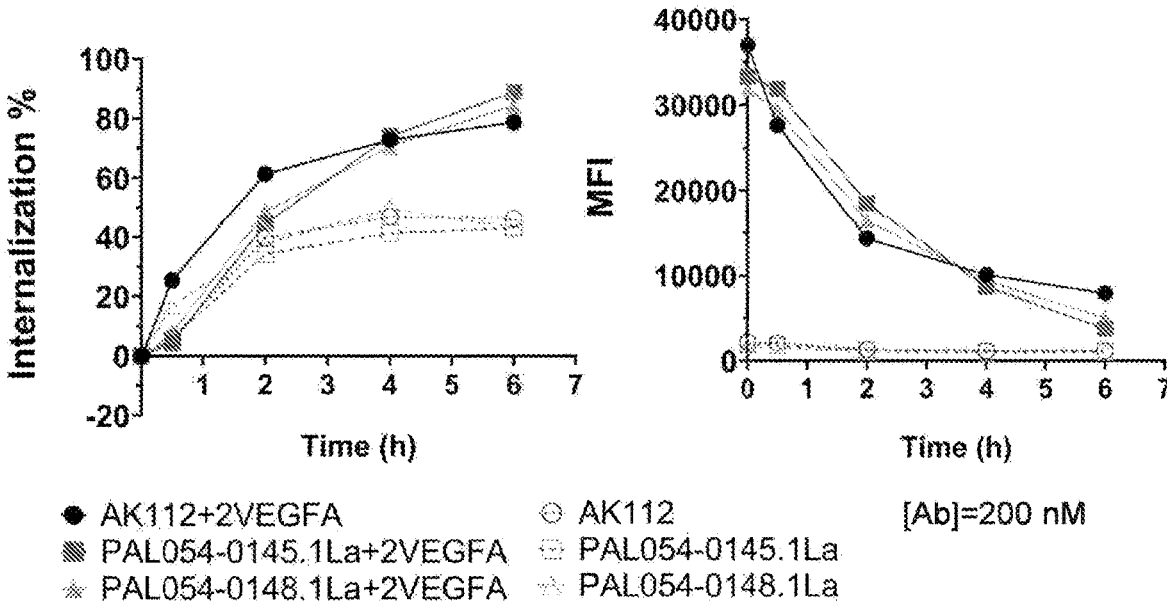
Figure 13D:
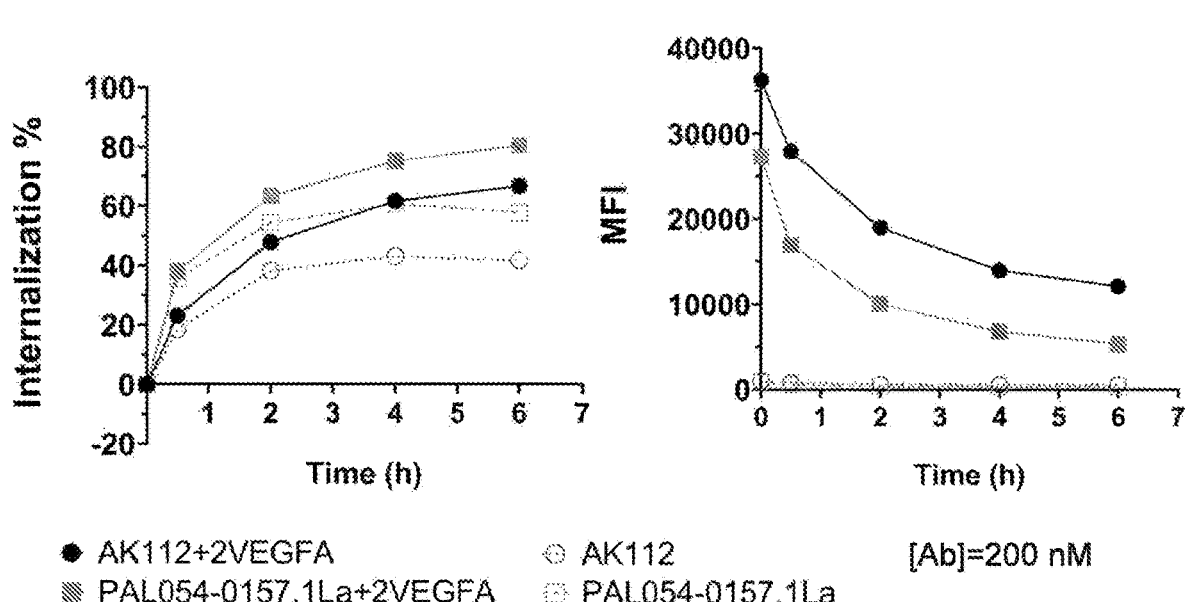
Figure 13E:
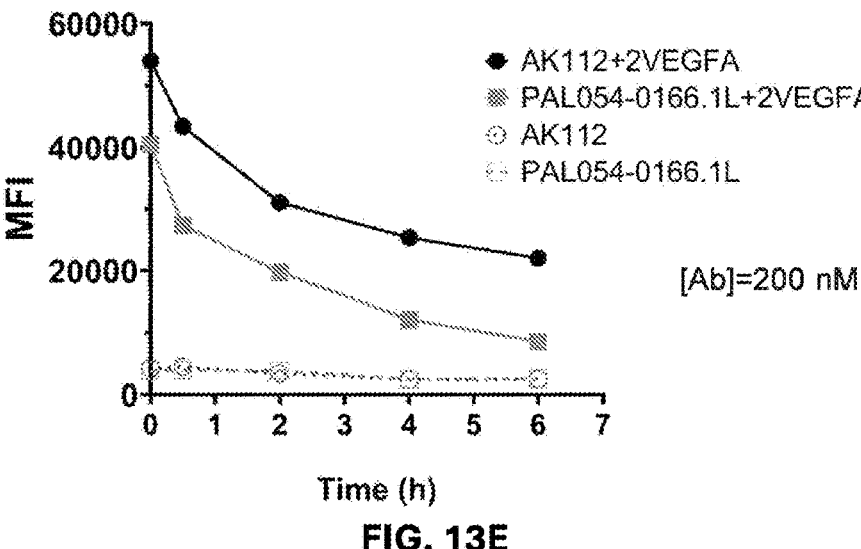
Figure 13F:
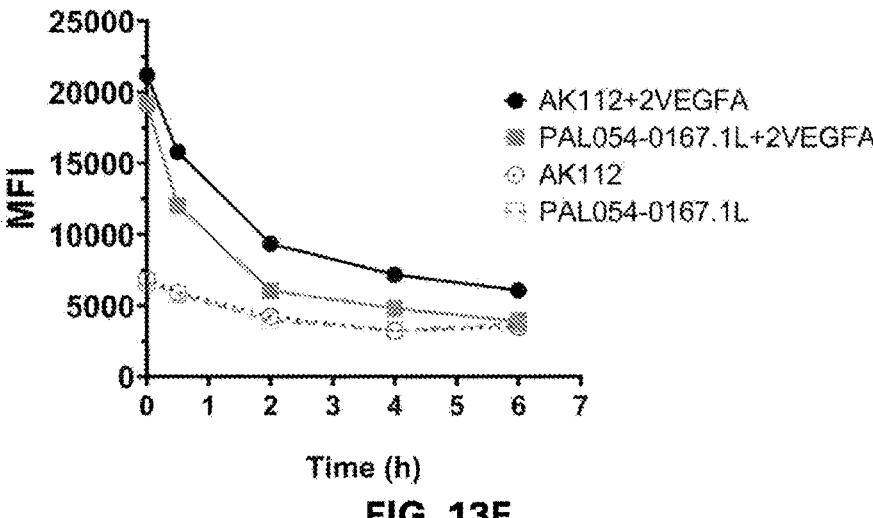
Figure 13G:
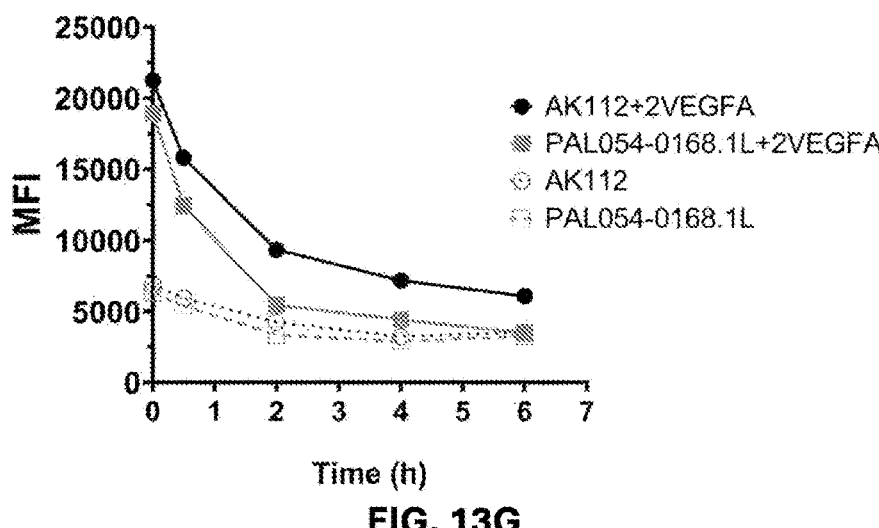
Figure 13N:
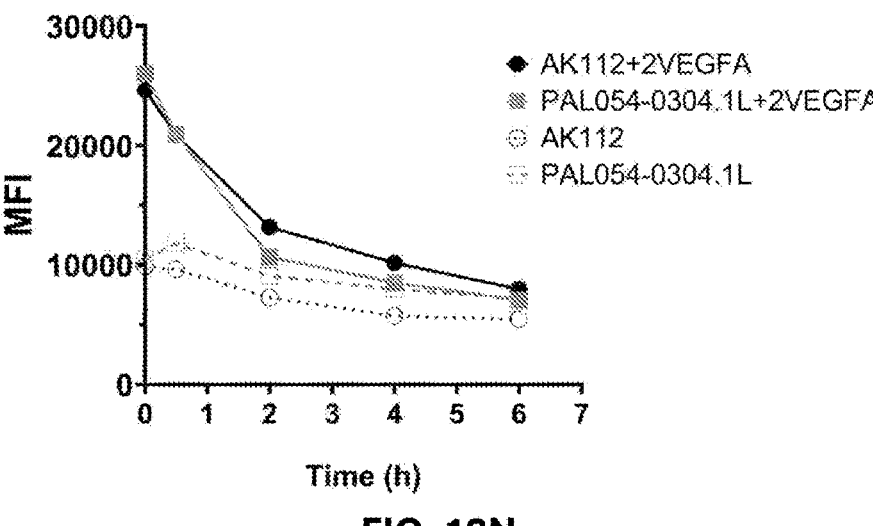
Figure 13O:
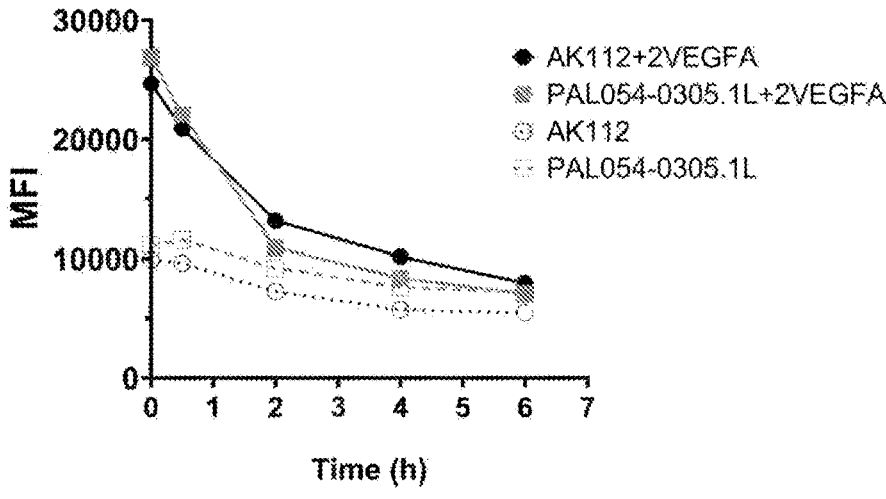
Figure 13P:
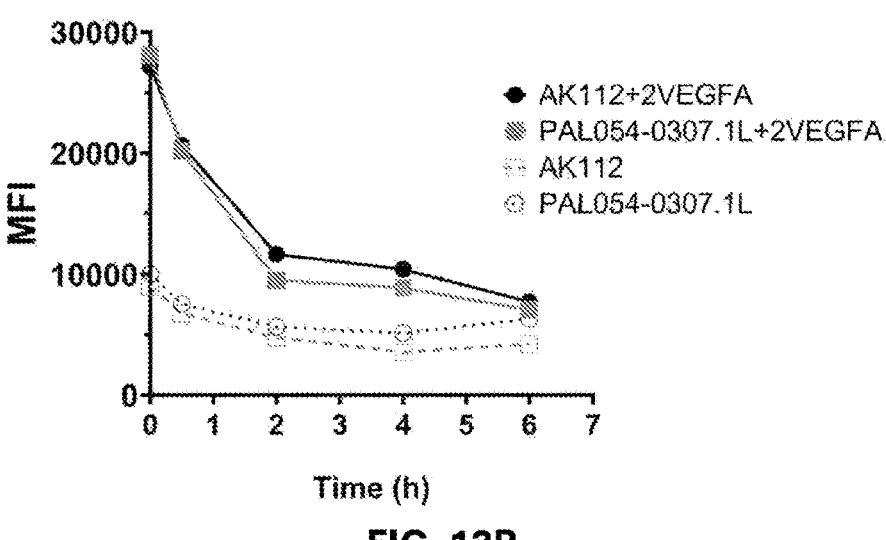
Figure 13Q:
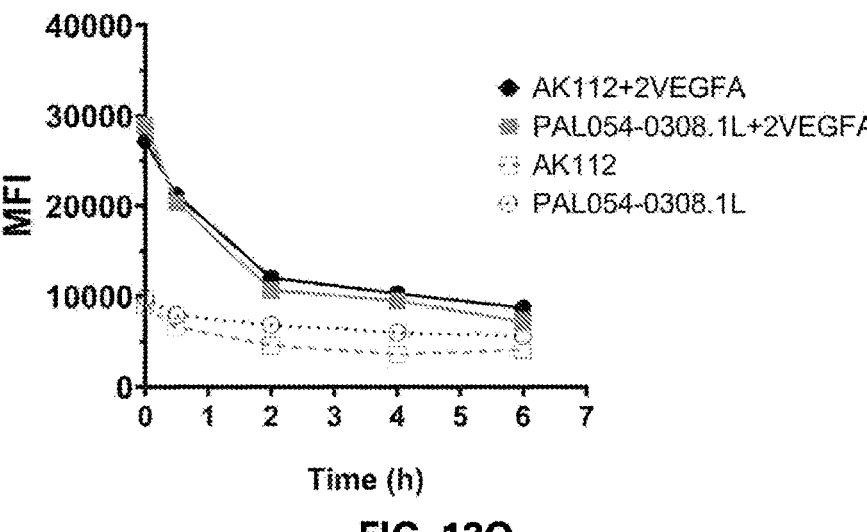
Figure 13R:
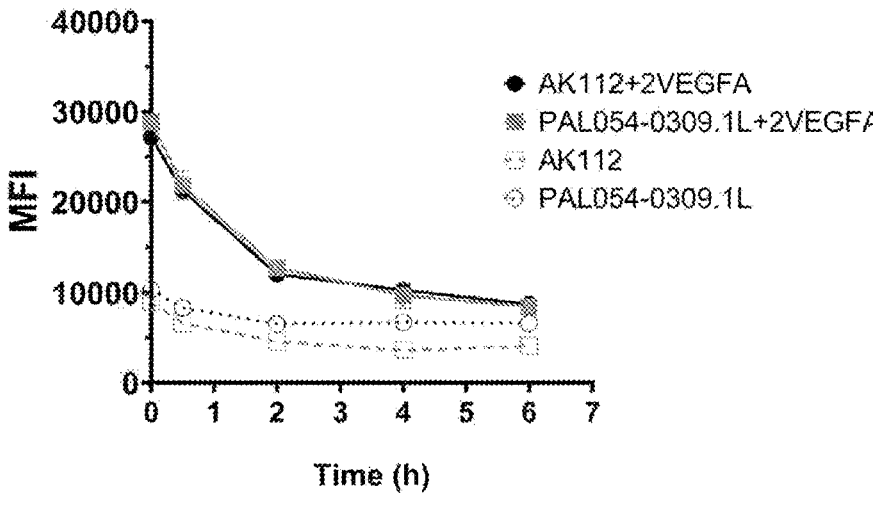
Figure 13S:
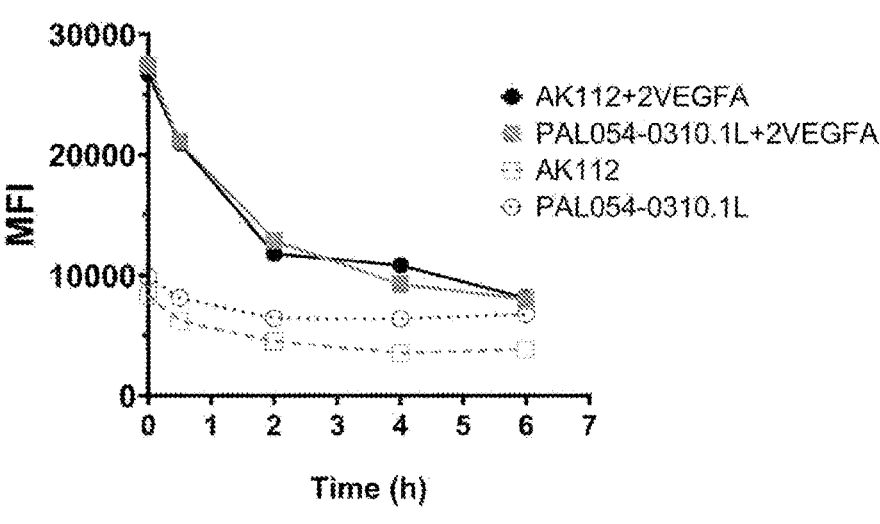

A PD-1 internalization assay was conducted on VEGF/PD-1 bispecific antibodies as disclosed herein and revealed enhanced internalization of PD-1 in the presence of VEGF. The results are shown in FIGS. 13A-13S.

Example 11: Binding and Activity of Bispecific Reverse Constructs

Figure 14A:
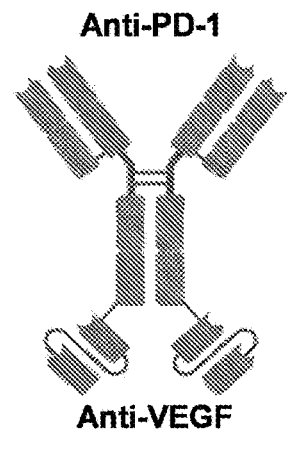
FIG. 14A depicts a PD-1-VEGF (scFv) bispecific reverse construct.
Figure 14B:
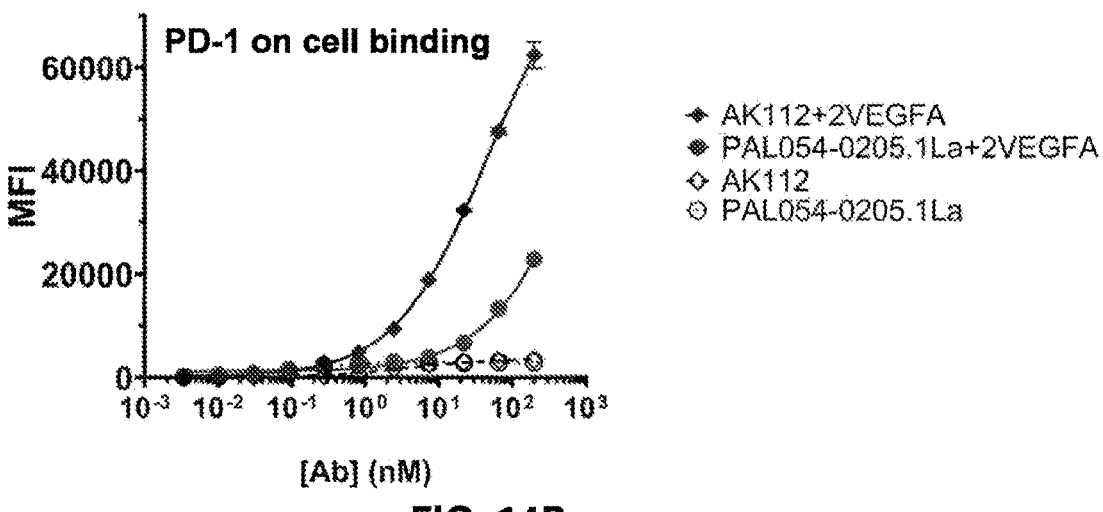
FIGS. 14B-14E depict results of PD-1 binding (FIG. 14B), PD-1 internalization (FIG. 14D), PD-1 reporter (FIG. 14C), and VEGF reporter (FIG. 14E) assays for the PD-1-VEGF (scFv) bispecific reverse construct.
Figure 14C:
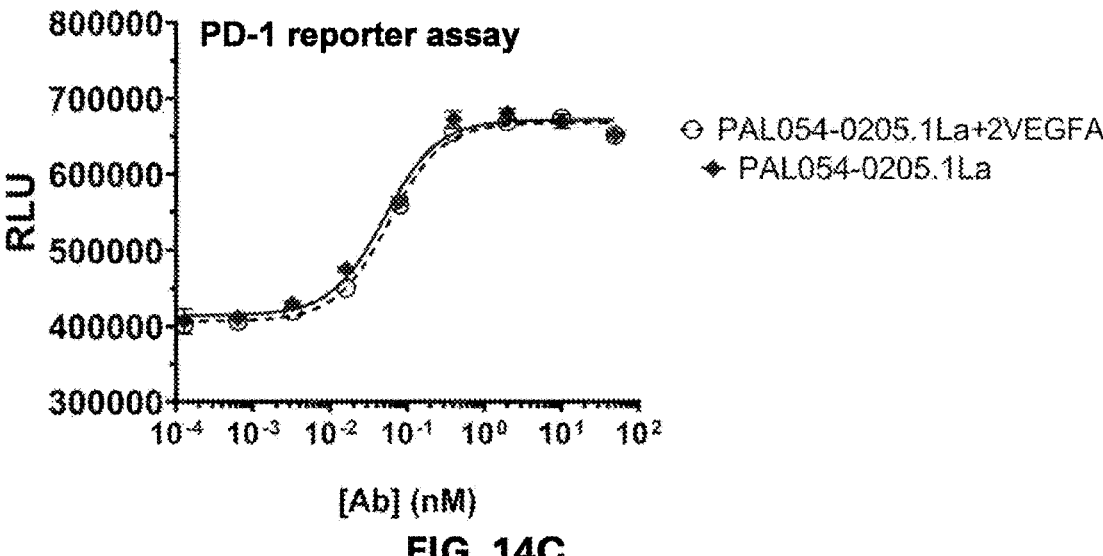
Figure 14D:
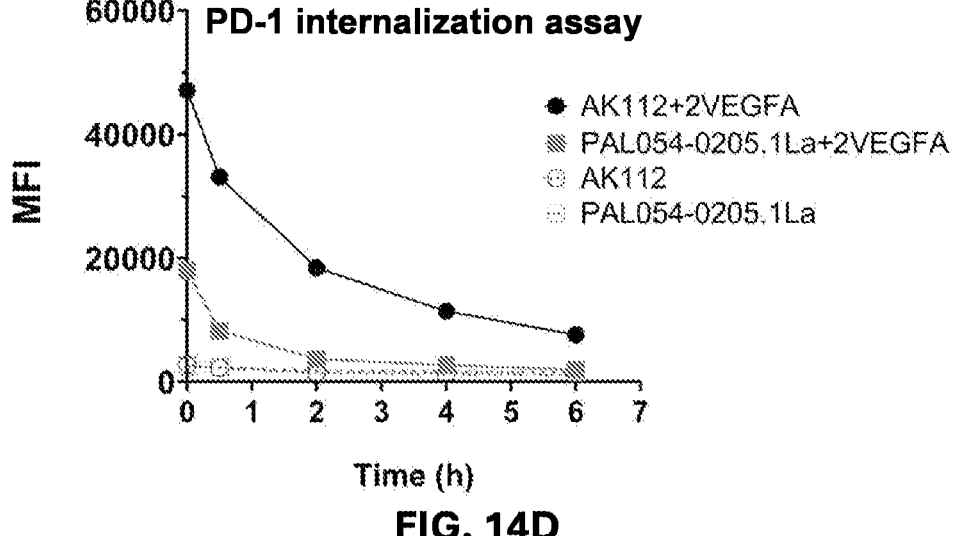
Figure 14E:
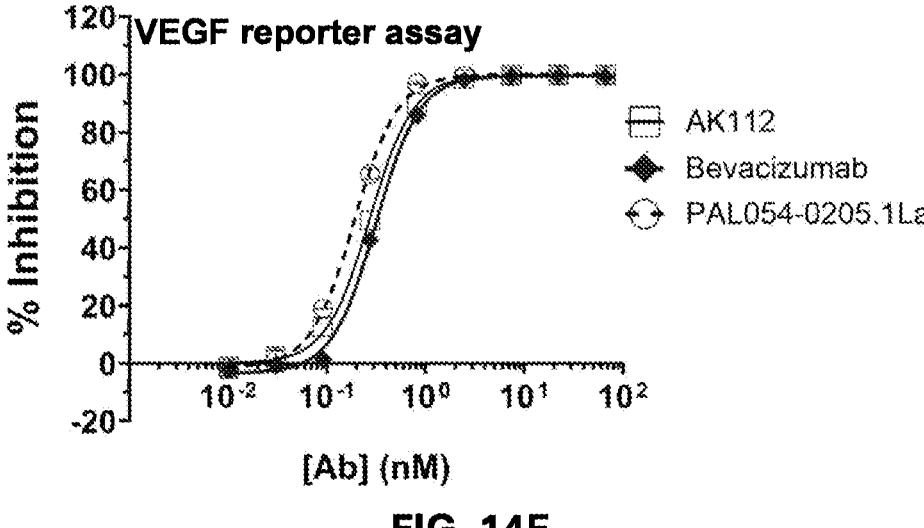

Cell binding, internalization, PD-1 reporter and VEGF reporter assays as known to those of ordinary skill in the art and described herein were conducted on PD-1-VEGF (scFv) reverse constructs (FIG. 14A), and the results are shown in FIGS. 14B-14E. The results did not show significant enhanced bioactivity of PD-1 in the presence of VEGFA.

Figure 15A:
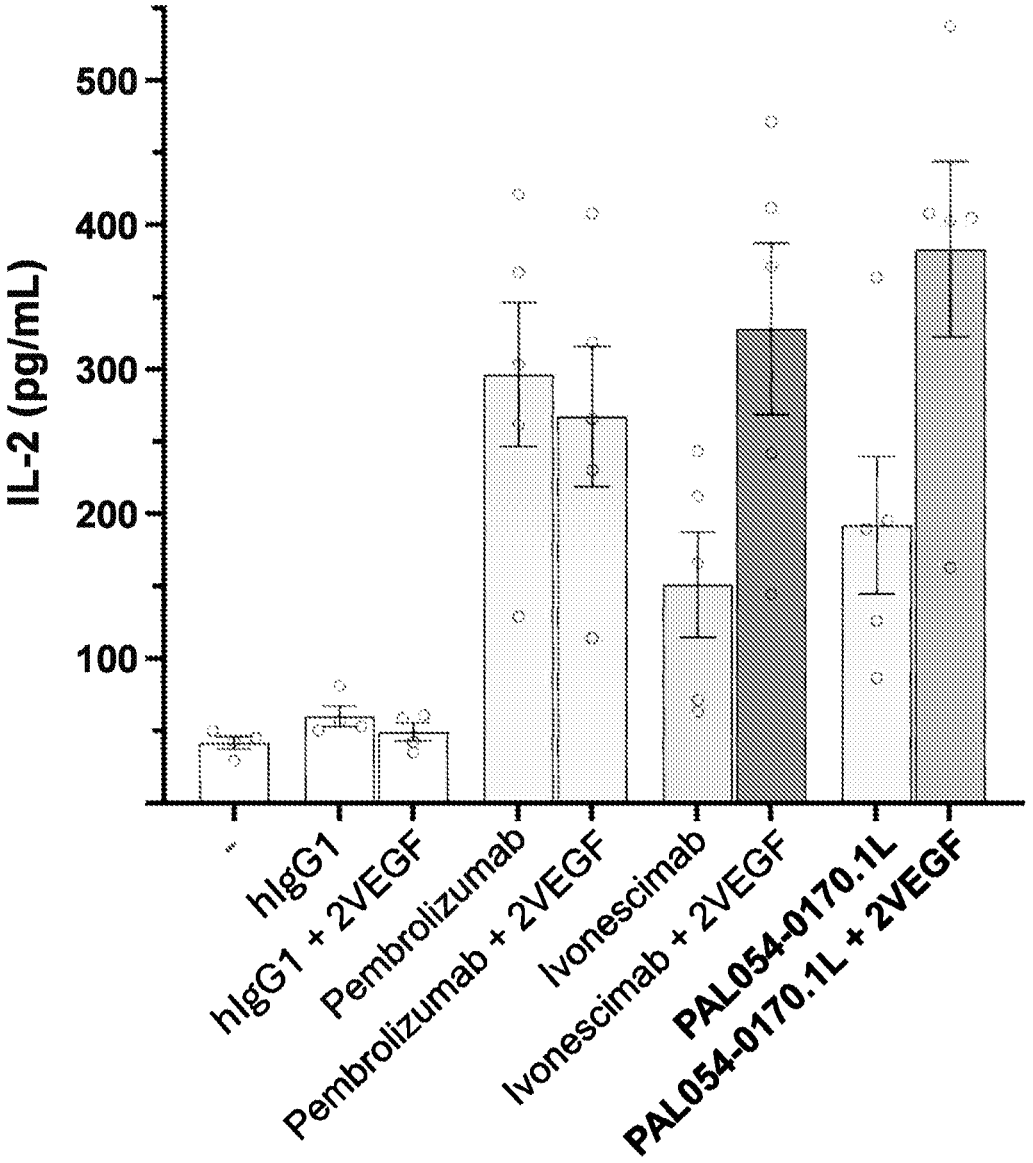
FIGS. 15A-15R depict data from T cell activation assessed in human PBMC and hepatocellular carcinoma co-culture assays with the indicated antibodies.
Figure 15B:
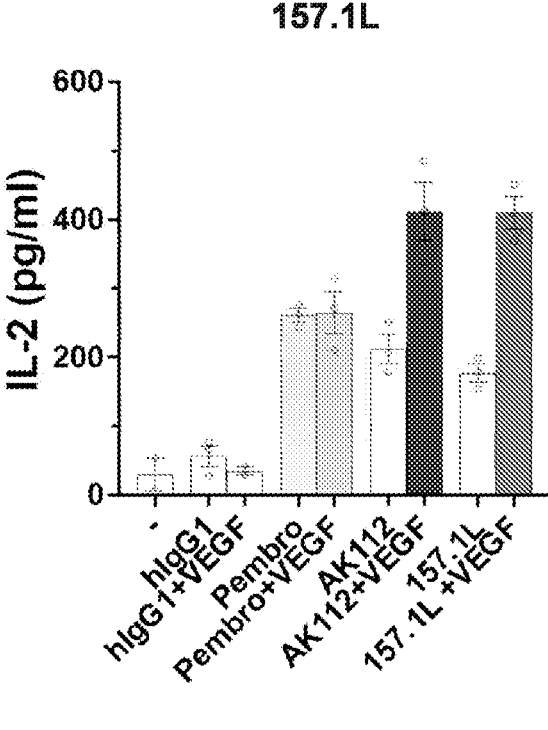
Figure 15C:
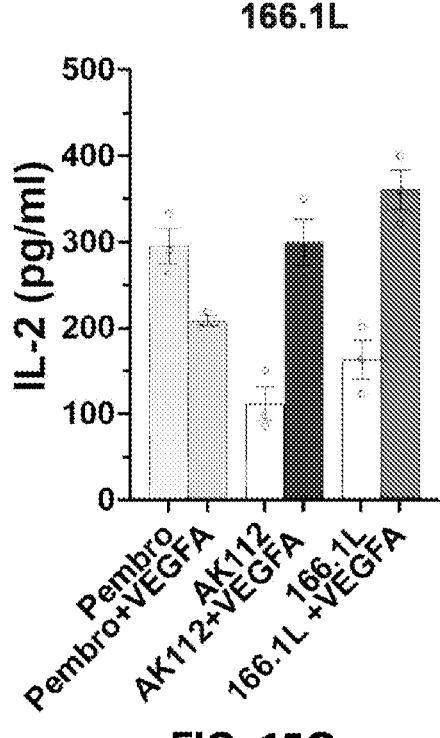
Figure 15D:
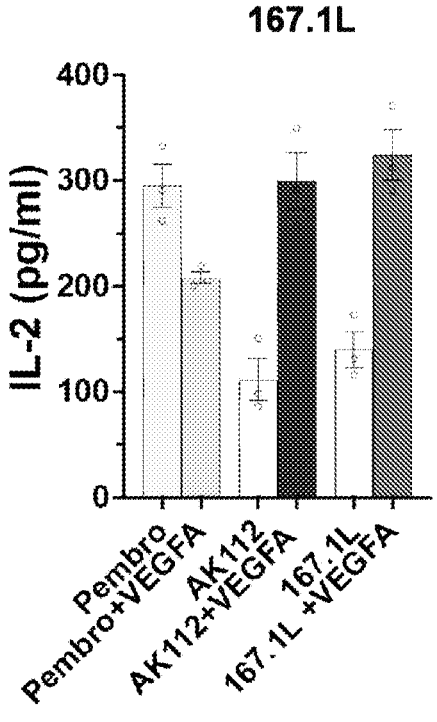
Figure 15E:
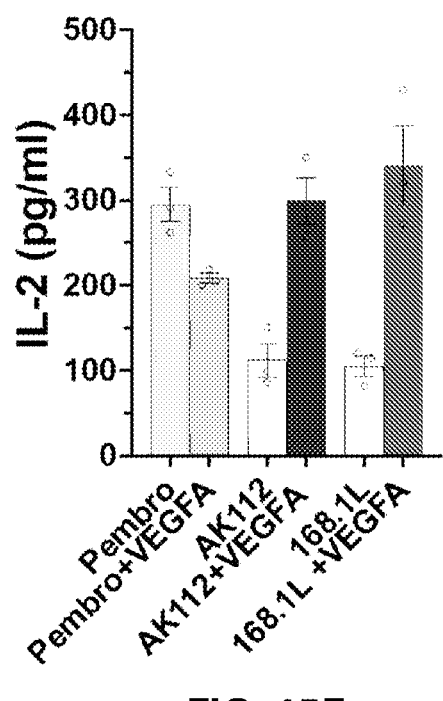
Figure 15F:
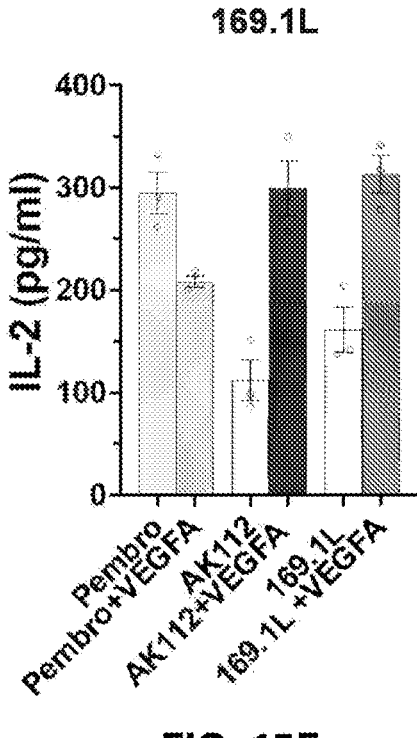
Figure 15G:
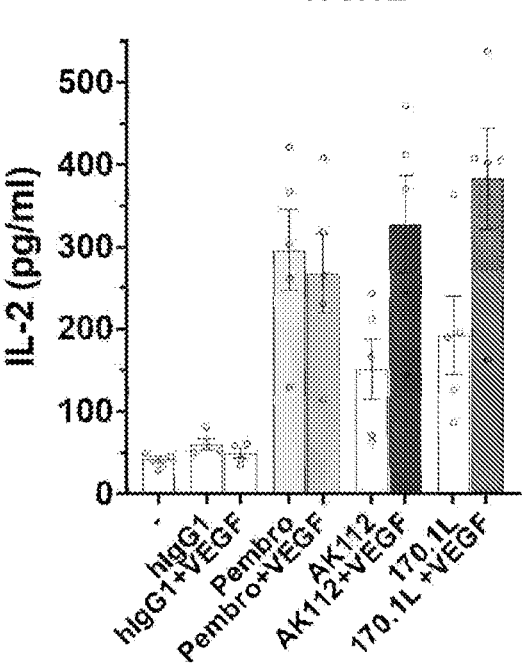
Figure 15H:
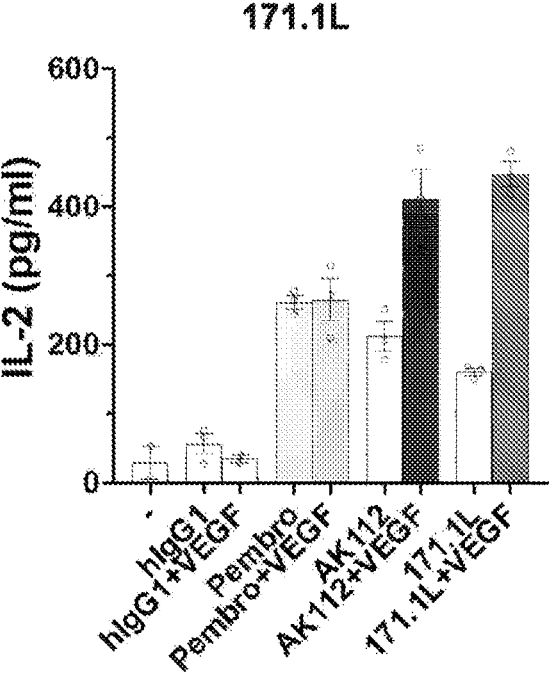
Figure 15I:
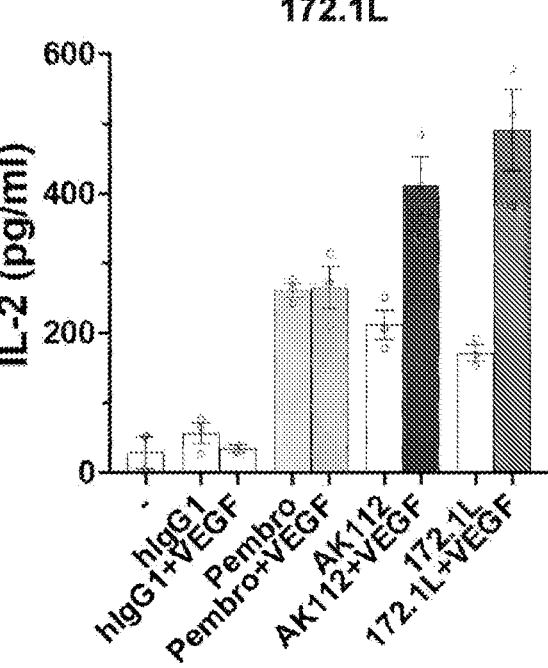
Figure 15J:
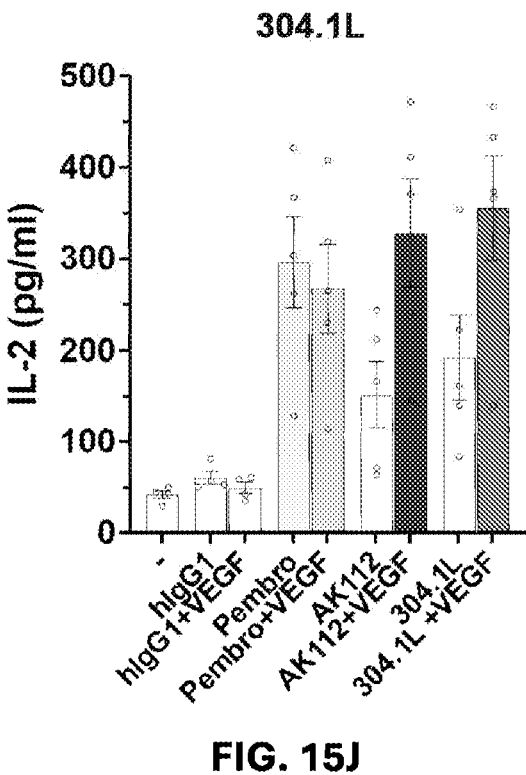
Figure 15K:
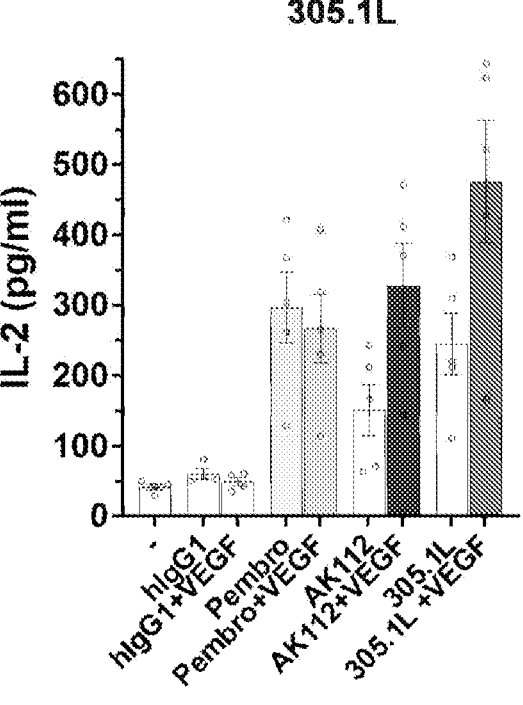
Figure 15L:
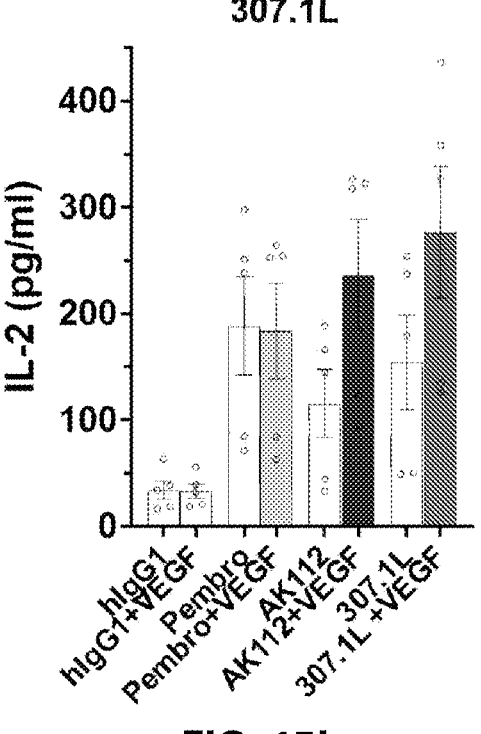
Figure 15M:
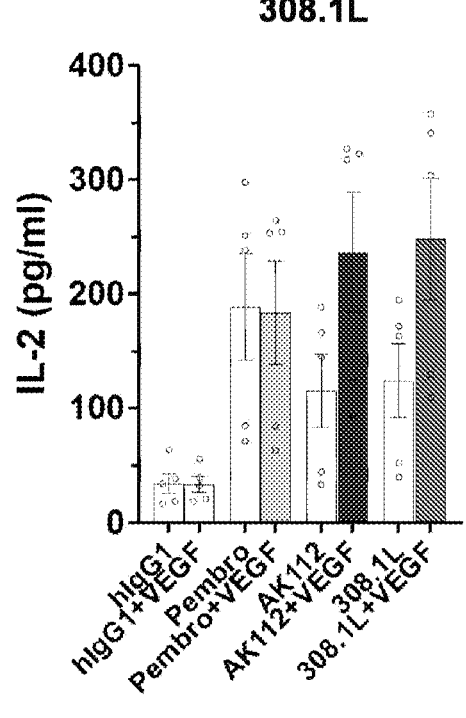
Figure 15N:
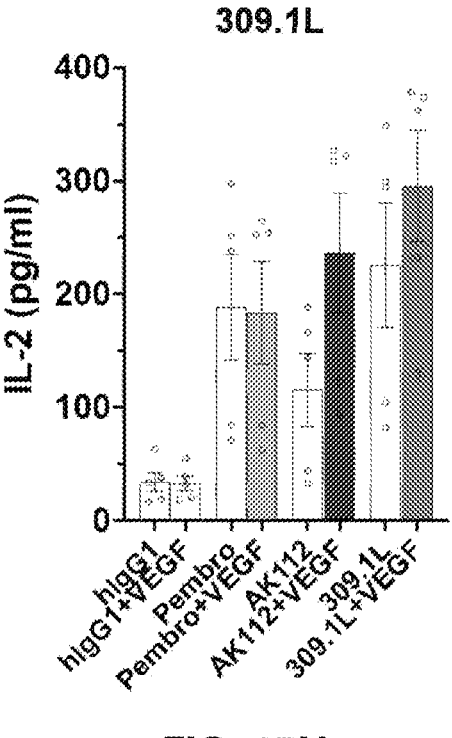
Figure 15O:
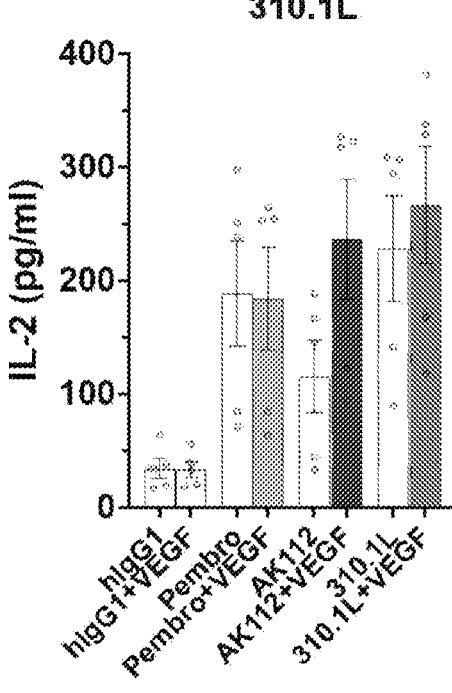
Figure 15P:
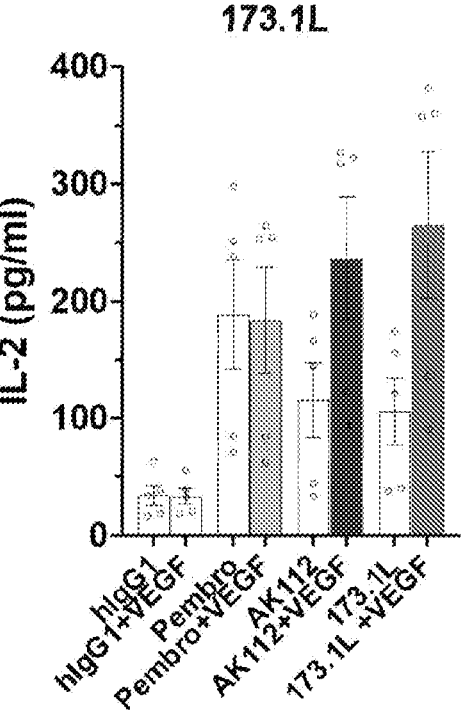
Figure 15Q:
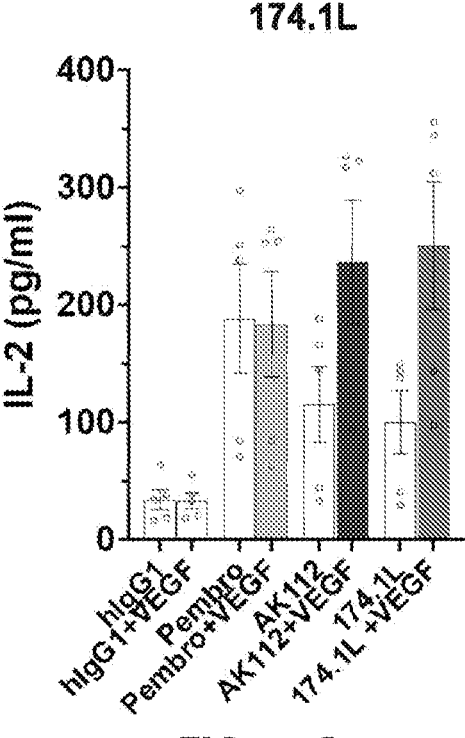
Figure 15R:
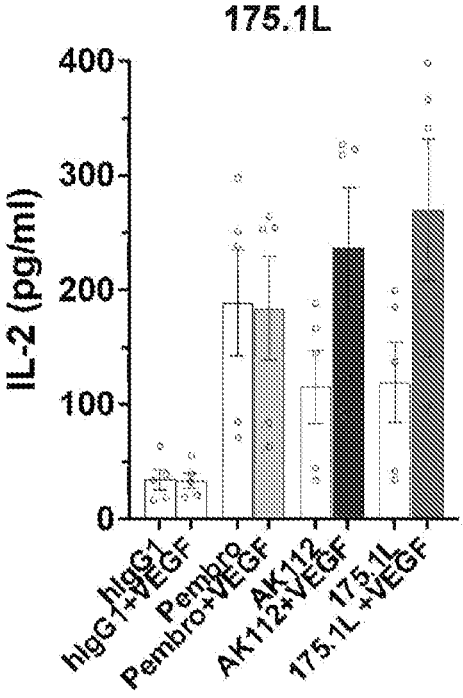
Figure 16A:
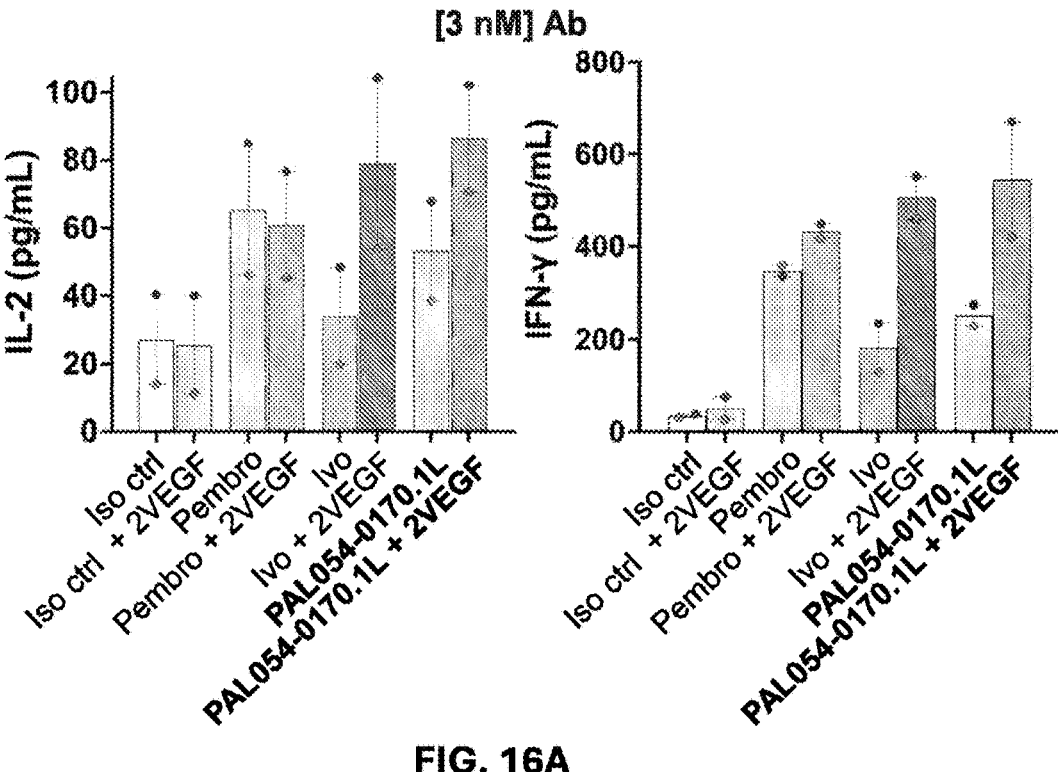
FIGS. 16A-16F depict data from T cell activation assessed in human monocyte derived dendritic cell and CD4+ T cell mixed lymphocyte reaction assays with the indicated antibodies.
Figure 16B:
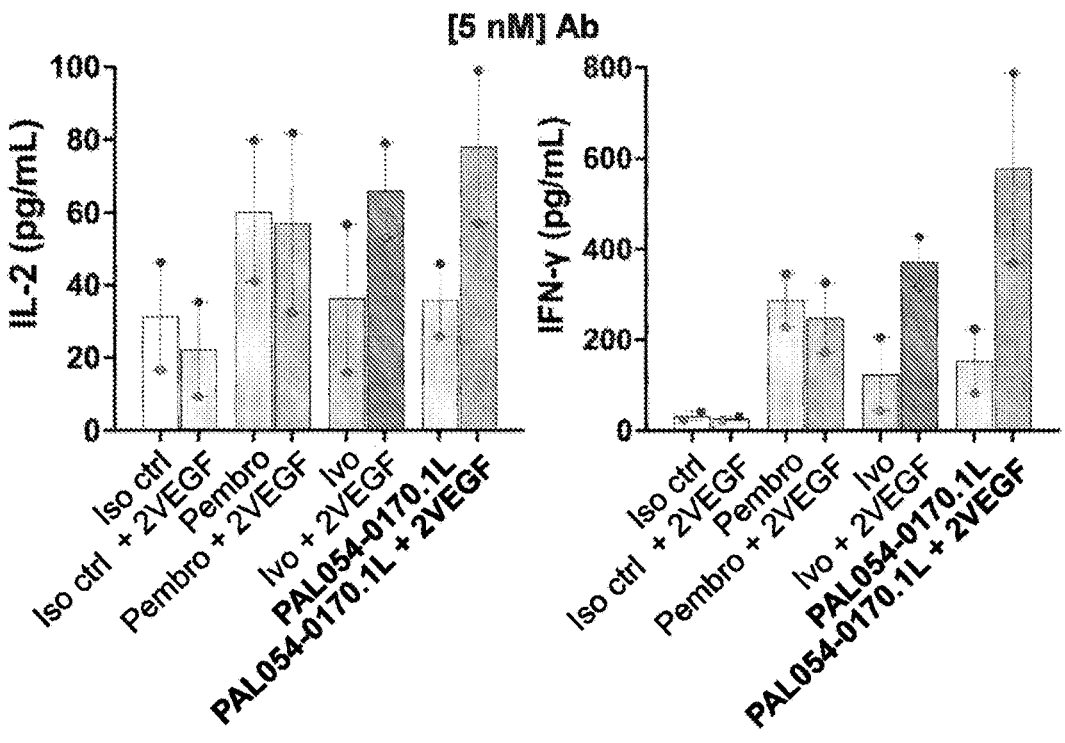
Figure 16C:
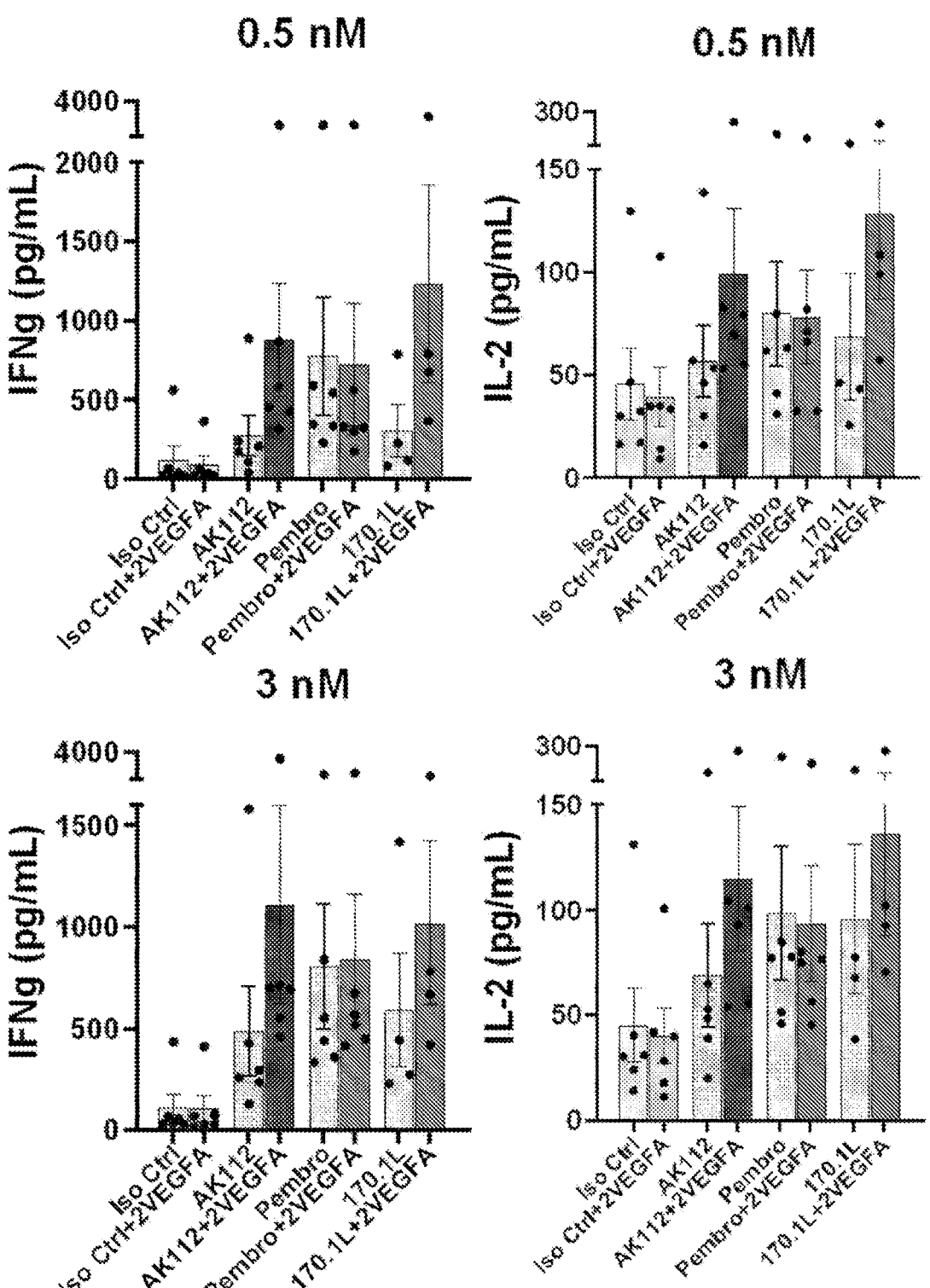
Figure 16D:
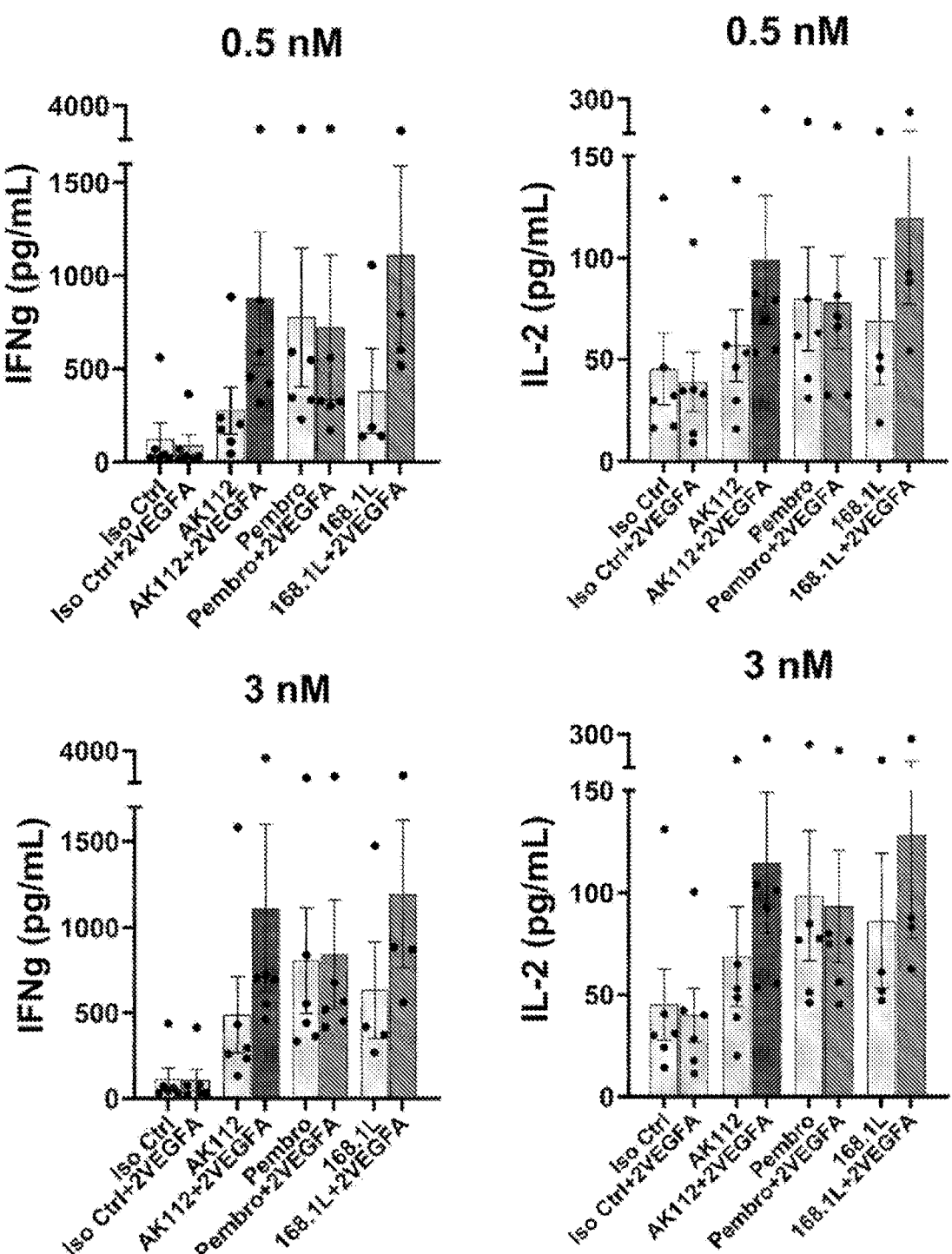
Figure 16E:
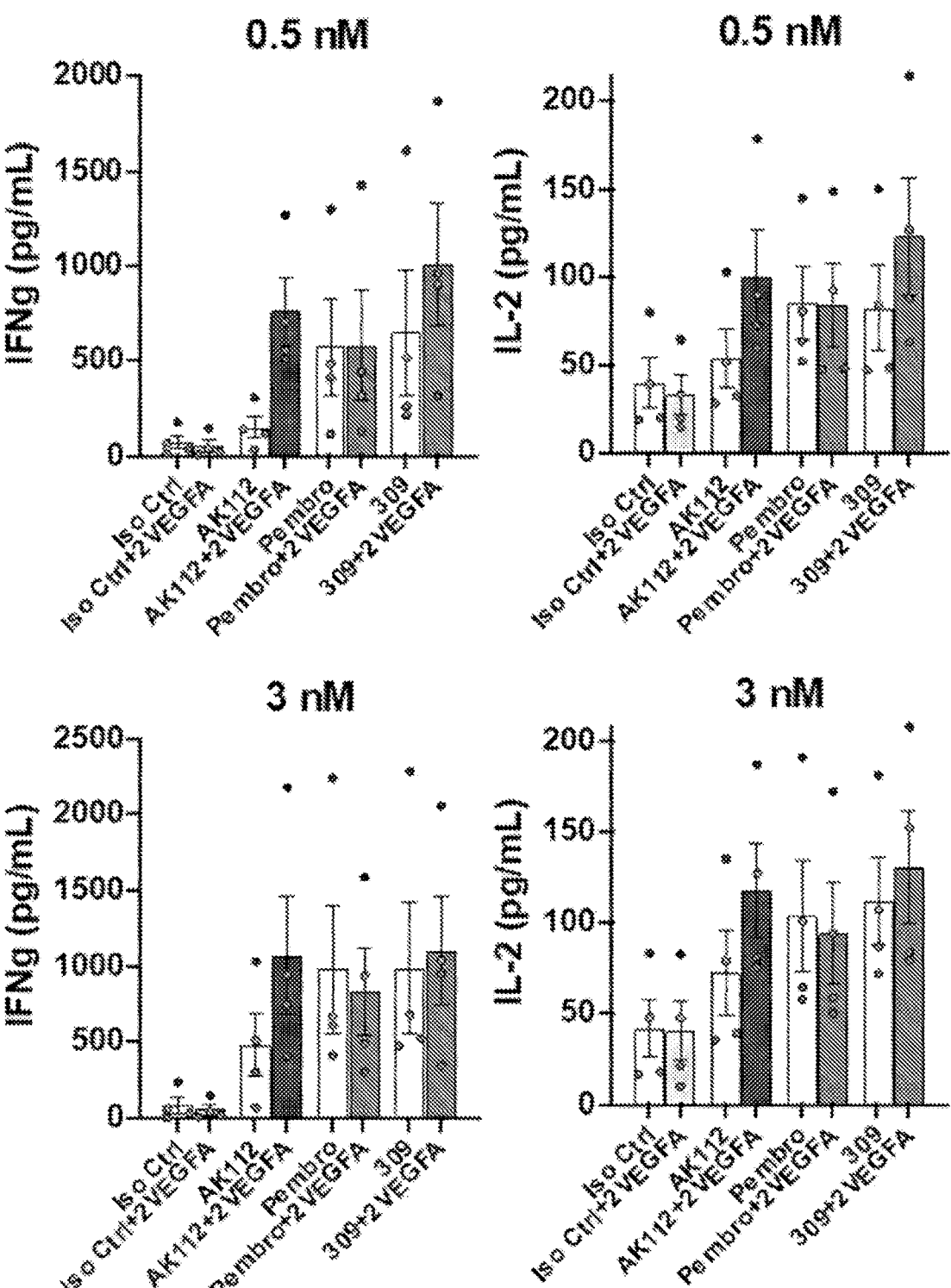
Figure 16F:
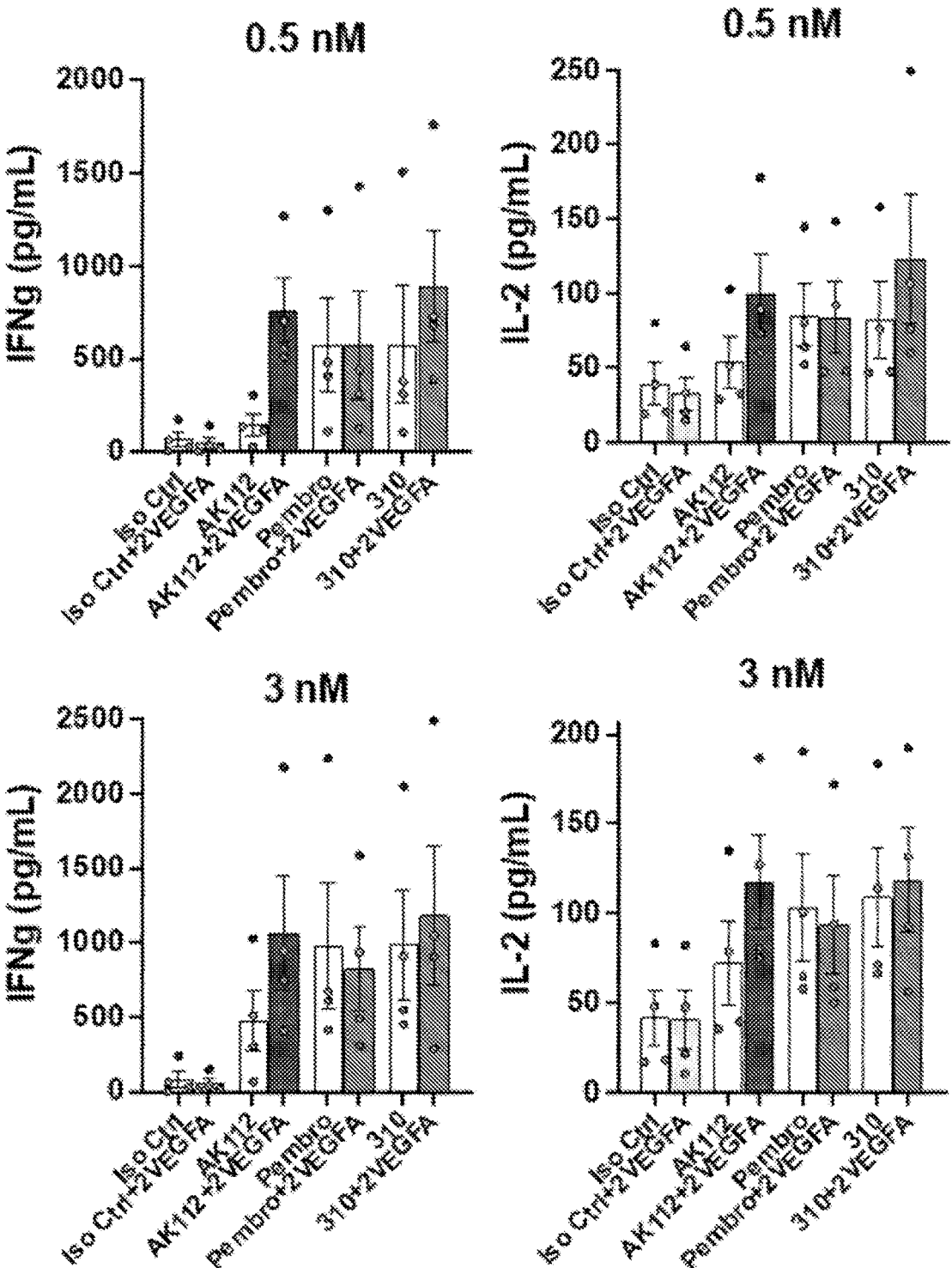

Example 12: T Cell Activation in Human PBMC and Hepatocellular Carcinoma Cell Line Co-Culture T cell activation was assessed in human PBMC and Hep3B-OS8-hPD-L1 co-culture assay in the presence or absence of 2×VEGFA (2VEGF) by measuring IL-2 secretion. For each bispecific clone, various controls were used including untreated (-), isotype control (hIgG1), PAL054-0004.4 (pembrolizumab), and/or PAL054-0001.1L (also referred to as ivonescimab or AKI 12) was tested. Data is seen in FIGS. 15A-15R. As seen in the data, bispecific-VEGF complex was found to enhance T cell activation in the co-culture assay.

Example 13: T Cell Activation in Human Monocyte Derived Dendritic Cells and CD4+ T Cells Via Mixed Lymphocyte Reaction (MLR) Assay Additionally, T cell activation was assessed in human monocyte derived dendritic cell (moDC) and CD4+ T cell mixed lymphocyte reaction (MLR) by measuring IL-2 and IFNγ secretion. Data collected from 4 independent donor pairs and is seen in FIGS. 16A-16F. As seen in the data, bispecific VEGF complex enhanced T cell activation in DC-CD4+ T cell MLR assay.

Example 14: Titer, Purity, and Thermal Stability Data for Benchmarks and Exemplary Bispecific Antibodies Titer, purity, and thermal stability data for benchmarks and bispecific antibodies as disclosed herein were determined. Titer and purity of the antibody samples were determined using standard analytical techniques well known in the art.

Thermal stability was determined using two different methods.

Method 1: Thermal Stability Determined Using UNCLE

To determine thermal stability, 9 microliters of each antibody sample were loaded into a Uni microcuvette designed specifically for use with the UNCLE instrument from Unchained Labs. Samples were subjected to a controlled thermal ramp from 20° C. to 95° C. at a rate of 0.5° C. per minute. Dynamic light scattering (DLS) measurements were performed both before and after the thermal ramp, with each measurement consisting of four acquisitions lasting five seconds each, to assess particle size and polydispersity. The melting temperature (Tm) of each sample was determined by the UNCLE software through analysis of the first derivative of the barycentric mean (BCM) of fluorescence intensity as a function of temperature. The aggregation onset temperature (Tagg) was calculated based on the intensity of scattered light measured at wavelengths of 266 nm or 473 nm. Size and polydispersity data were extracted from the DLS correlation function. This method provides a comprehensive assessment of antibody thermal stability and aggregation behavior. Data can be seen in Table 22.

were performed using the MicroCal™ VP-Capillary DSC automated data analysis software. The thermal transition midpoint (Tm) was determined by identifying the peak of the heat capacity curve, while the onset of unfolding (T_onset) was calculated based on the deviation from baseline preceding the transition peak.

This method enables precise quantification of protein thermal stability and unfolding characteristics under controlled conditions. Data corresponding to these measurements are presented in Table 23.

TABLE 23

| Clone | $T_m$Onset (° C.) | $T_m$1 (° C.) | $T_m$2 (° C.) | $T_m$3 (° C.) | $T_m$4 (° C.) |
|---|---|---|---|---|---|
| PAL054-0148.1L | 51.86 | 57.3 | 75.28 | 81.99 | 88.17 |
| PAL054-0165.1L | 57.26 | 61.87 | 75.7 | 81.86 | 87.15 |
| PAL054-0157.1L | 57.54 | 62.88 | 75.66 | 81.59 | N/A |
| PAL054-0166.1L | 60.56 | 66.42 | 75.73 | 81.74 | N/A |
| PAL054-0001.1L | 59.06 | 66.46 | 75.25 | 81.9 | 88.31 |
| PAL054-0167.1L | 52.9 | 62.7 | 75.3 | 81.7 | 87.0 |
| PAL054-0168.1L | 55.5 | 63.3 | 75.8 | 81.4 | 85.8 |
| PAL054-0169.1L | 54.5 | 62.8 | 75.9 | 81.4 | 85.6 |
| PAL054-0170.1L | 58.8 | 65.8 | 75.5 | 81.6 | 86.4 |
| PAL054-0171.1L | 51.6 | 61.8 | 75.0 | 81.7 | 88.4 |
| PAL054-0172.1L | 55.2 | 64.8 | 75.1 | 81.6 | 88.0 |

Figure 17A:
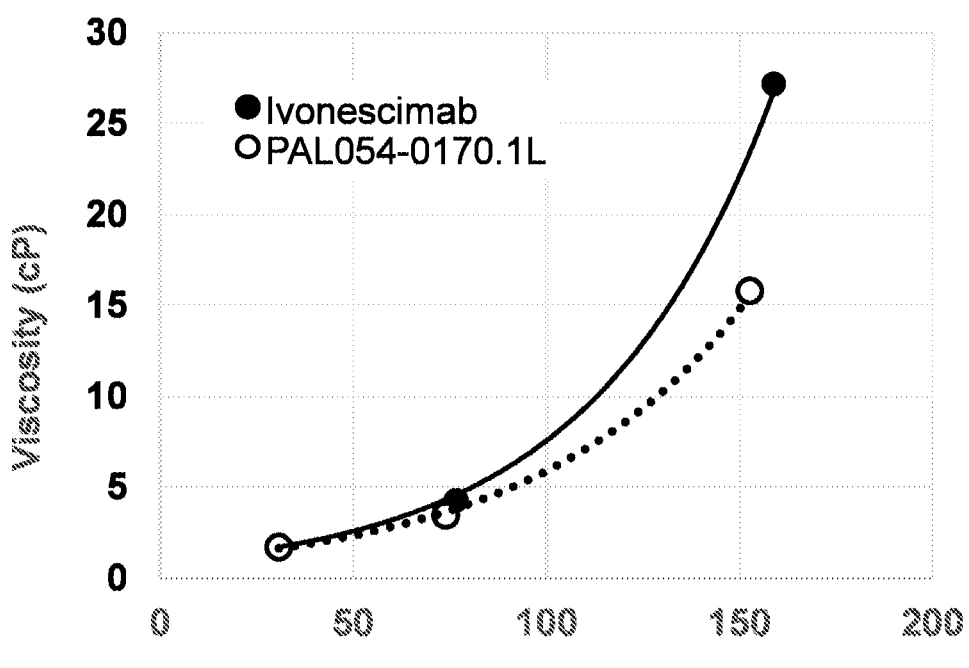
FIG. 17A depicts a graph of viscosity at varying protein concentrations at constant pH of 6.0.
Figure 17B:
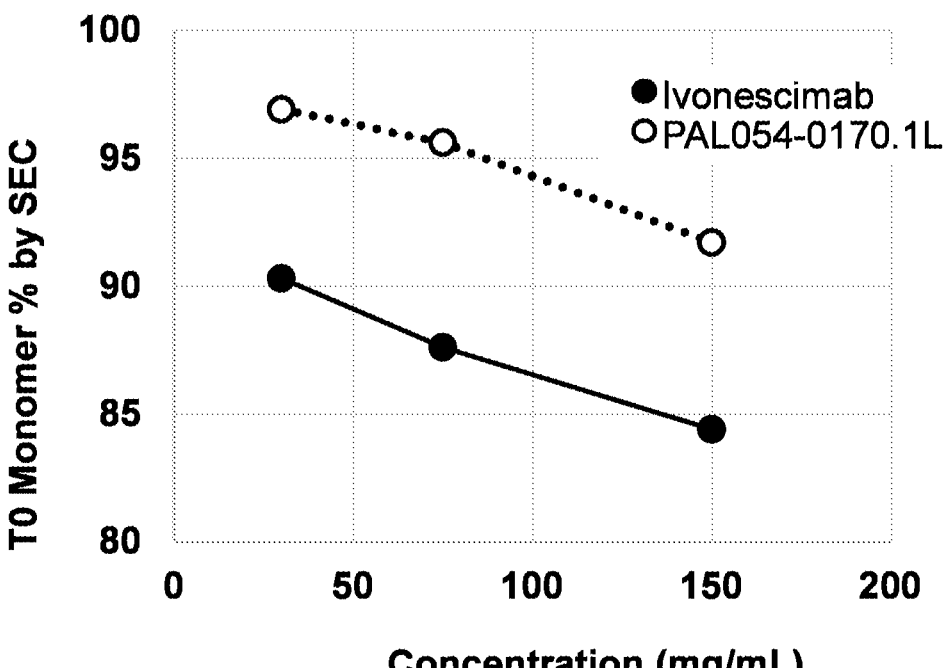
FIG. 17B depicts a graph of percent monomer by analytical size exclusion chromatography (SEC) at varying protein concentrations.

PAL054-0170.1L was further assayed for viscosity, aggregation, and stability. Data is seen in FIGS. 17A-17D that demonstrate PAL054-0170.1L has improved viscosity (FIG. 17A) and aggregation (FIG. 17B) as compared to ivonescimab as well as stability at 40° C. (FIG. 17C) and 25° C. (FIG. 17D).

TABLE 22

| Clone | Titer (mg/L) | SEC-HPLC (%) | Initial purity (%) | Purity after 3x F/T (%) | $T_m$1 (° C.) | $T_m$2 (° C.) | $T_m$3 (° C.) | $T_{agg}$266 (° C.) |
|---|---|---|---|---|---|---|---|---|
| PAL054-0001.1L | 1830 | 95.51 | 98.1 | 98.1 | 62.1 | 71.5 | — | 58.0 |
| PAL054-0001.1La | 1780 | 96.55 | 98.1 | 98.1 | 61.9 | 69.4 | — | 57.0 |
| PAL054-0008.1La | 764.1 | 87.39 | N/A | N/A | N/A | N/A | N/A | N/A |
| PAL054-0009.1La | 92.7 | N/A | N/A | N/A | N/A | N/A | N/A | N/A |
| PAL054-0011.1La | 1152.8 | 98.13 | 99.3 | 99.2 | 53.2 | 64.9 | — | 55.5 |
| PAL054-0101.1La | 1131.7 | 91.49 | N/A | N/A | N/A | N/A | N/A | N/A |
| PAL054-0104.1La | 256 | 98.19 | 99.3 | 99.3 | 48.8 | 64.7 | — | 46.6 |
| PAL054-0145.1La | 578.5 | 91.22 | 92.8 | 92.8 | 42.7 | 68.4 | 73.8 | 41.8 |
| PAL054-0148.1La | 2009.1 | 93.85 | 94.6 | 95.4 | 47.2 | 64.5 | 69.9 | 46.3 |
| PAL054-0154.1La | 376.4 | 97.4 | 98.2 | 98.2 | 47.6 | 67.4 | 71.9 | 48.3 |
| PAL054-0157.1La | 1561.7 | 97.92 | 98.4 | 98.5 | 51.5 | 65.1 | 72.8 | 51.00 |
| PAL054-0170.1L | 1647.0 | 98.6 | 100 | 98.8 | 54.0 | 63.4 | — | 52.4 |

Method 2: Thermal Stability Determined Using MicroCal™ VP DSC

To assess thermal stability and unfolding behavior, antibody samples were analyzed using the MicroCal™ VP-Capillary Differential Scanning Calorimeter (DSC) from Malvern. Prior to analysis, samples were diluted to a final concentration of 1 mg/mL using the respective reference buffer. A total of 400 microliters of reference buffer were dispensed into the odd-numbered wells of a 96-well plate, while 400 microliters of sample solution were added to the even-numbered wells.

The DSC instrument was programmed to execute a thermal scan from 10° C. to 110° C. at a constant scan rate of 200° C. per hour. Thermal transitions were monitored continuously throughout the scan. Data acquisition and analysis

Example 15: Pharmacokinetics in Non-Human Primates (NHP)

In vivo pharmacokinetic (PK) studies were performed on bispecific antibodies described herein as compared to Ivonescimab (AK112). Studies were performed using cynomolgus monkey (*Macaca fascicularis*), and antibodies were administered by intravenous (IV) injection. All animals were males, ranging from 2.5 to 3.9 kg in weight (n=5/group). Animals were administered PAL054-0001.1L (AK112), PAL054-0104.1L (104), PAL054-0157.1L (157), PAL054-0167.1L (167), PAL054-0168.1L (168), PAL054-0169.1L (169), PAL054-0170.1L (170), or PAL054-0171.1L (171), respectively, by intravenous (IV) bolus injection on Day 0, as shown in Table 24, and serum samples were taken regularly throughout the study. PK parameters were determined from cynomolgus serum samples up to day 28.

TABLE 24

| Antibody | Half-Life (Days) |
|---|---|
| AK112 (PAL054-0001.1L) | 1.50 |
| PAL054-0104.1L | 2.21 |
| PAL054-0157.1L | 2.97 |
| PAL054-0167.1L | 2.09 |
| PAL054-0168.1L | 3.12 |
| PAL054-0169.1L | 2.40 |
| PAL054-0170.1L | 3.57 |
| PAL054-0171.1L | 3.15 |

Receptor occupancy (RO) was determined by resuspending cyno PBMCs with FACS buffer and seeded at $2\times10^5$ cells/well into 96 well V bottom plate. Cells were then incubated with a saturating concentration (200 nM) of hIgG (isotype control) or test articles at 4° C. for 1 h. After the incubation, cells were washed and stained with Fixable Viability Stain 510, APC-Cy™7 Mouse Anti-Human CD3, Brilliant Violet 605™ anti-human CD4 Antibody, Alexa Fluor®700 anti-human CD8a Antibody, Brilliant Violet 421™ anti-human CD95 (Fas), goat F(ab')2 anti-human IgG-Fc (PE) and incubated at 4° C. for 45 min. Cells were then washed and resuspend in FACS buffer for FACS analysis. PD-1 RO was calculated following the below equation, RO (%)=[% CD3+CD95+(Control hIgG)/% CD3+CD95+(Bispecific)]×100

Figure 18A:
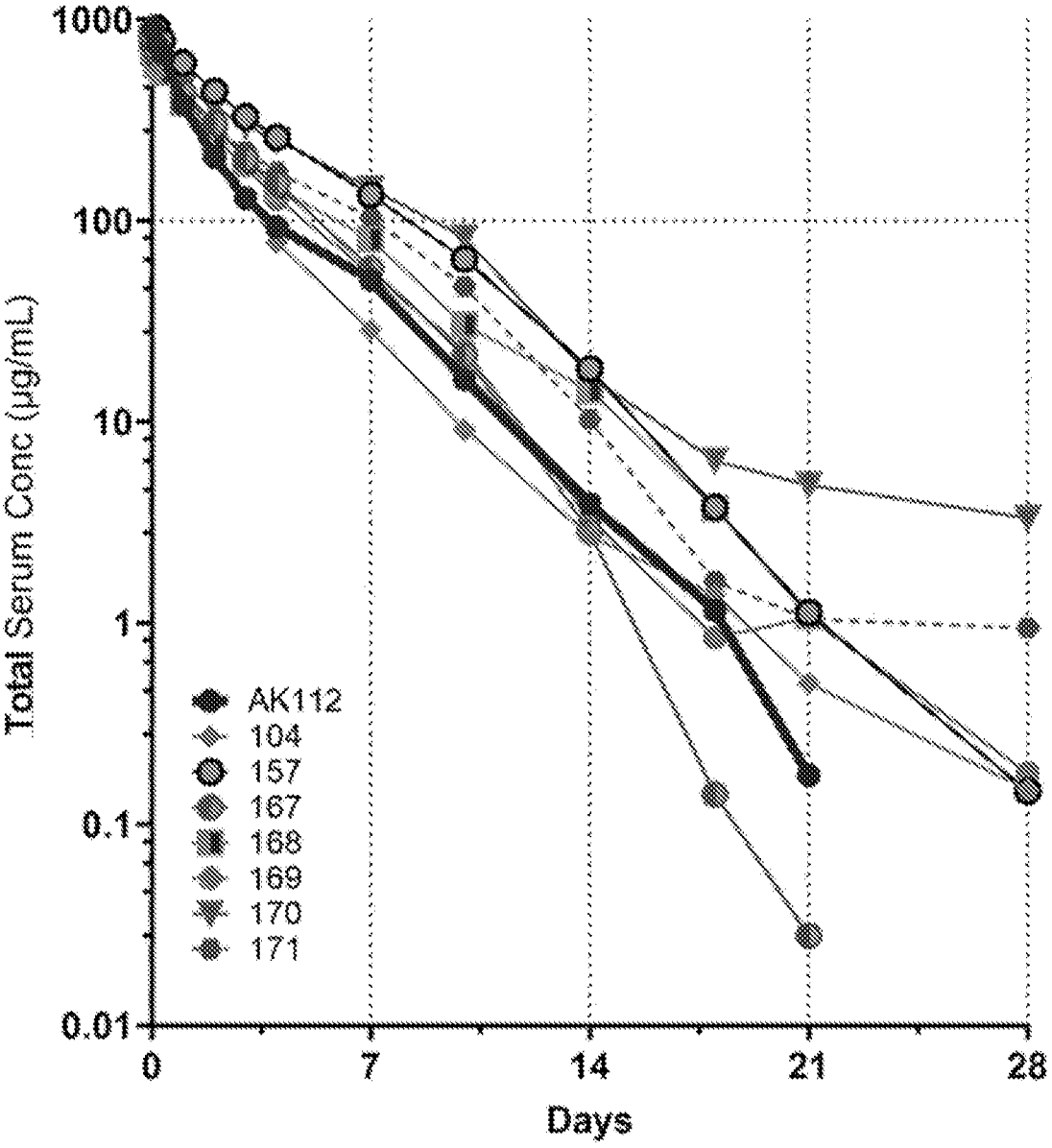
FIGS. 18A-18C depict pharmacokinetic data of the indicated antibodies.
Figure 18B:
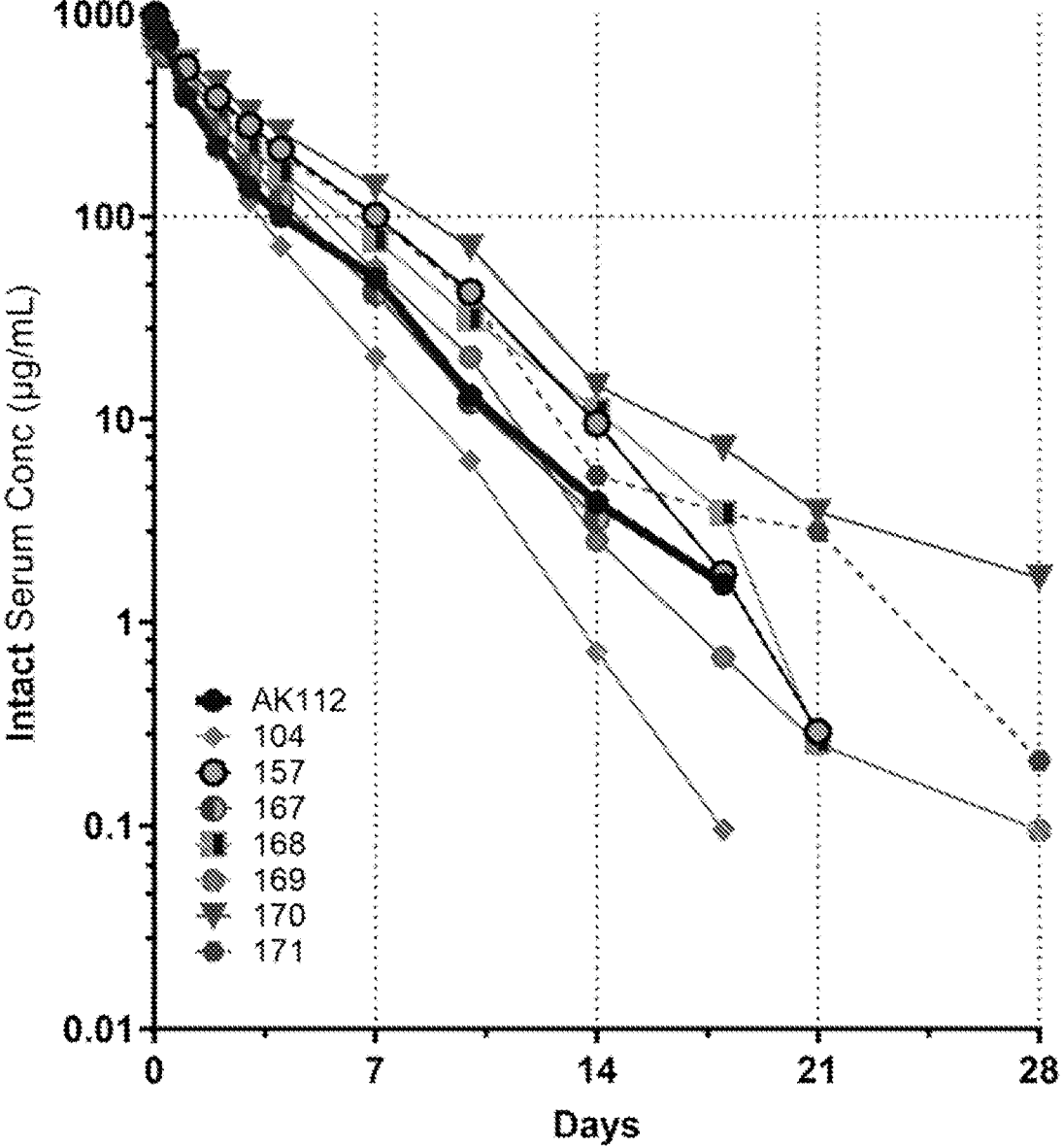
Figure 18C:
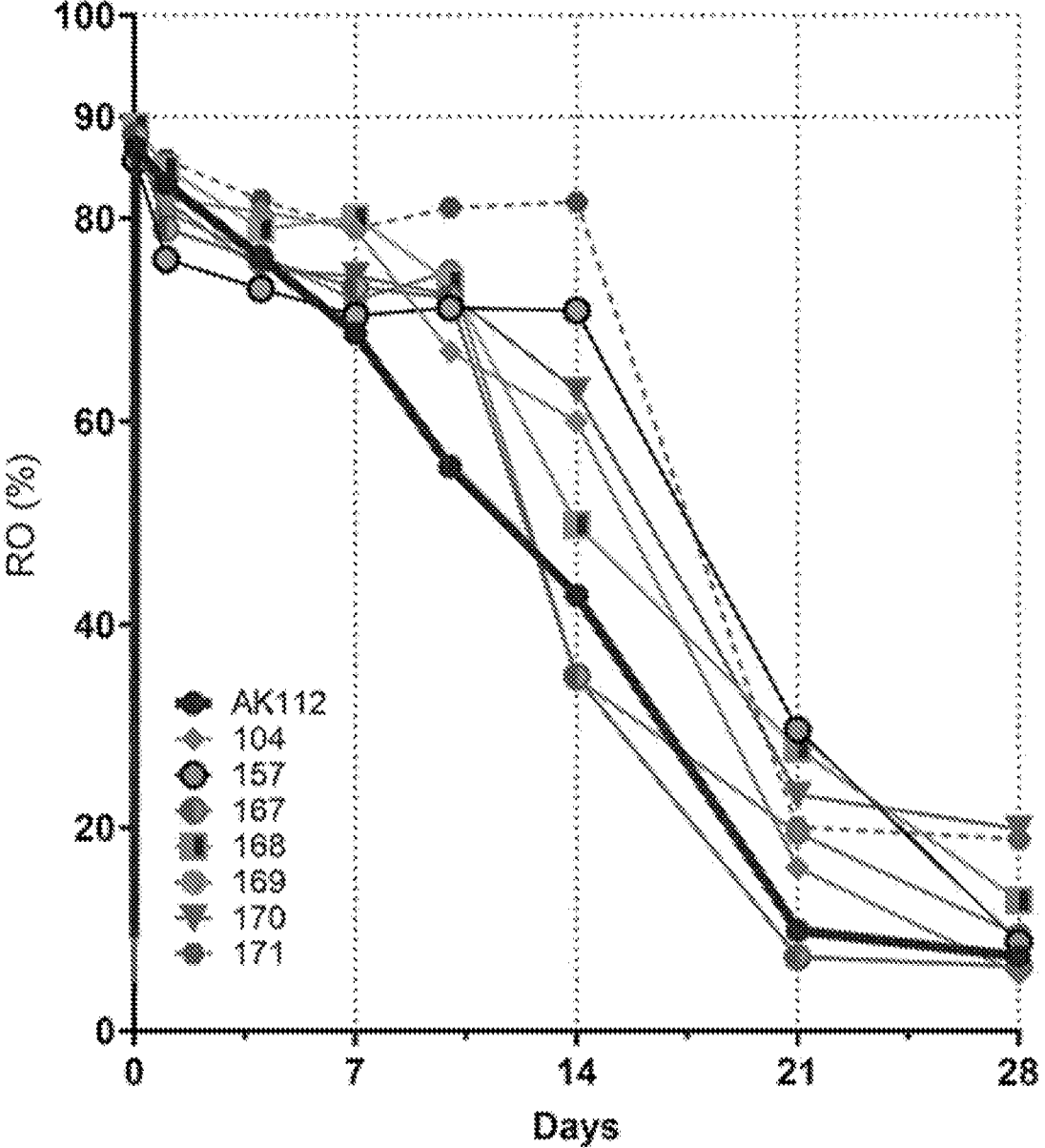

The results are summarized in FIGS. 18A-18C. The PK analysis demonstrated that PAL054-0170.1L had a half-life of 3.57 days, compared with 1.50 days for ivonescimab, and that ivonescimab and PAL054-0170.1L showed similar total and intact PK and receptor occupancy (RO) in NHP. The PK analysis demonstrated that the PAL054-0170.1L had improved half-life compared to those of ivonescimab (Table 24; FIGS. 18A-18B).

Example 16: Efficacy Study with hPBMC Co-Administered with HCC827 Subcutaneously in Mouse Tumor Model Seven to nine weeks old female SCID/Beige mice (Vital River Laboratory Animal Technology) divided into five groups with 8 mice per group were inoculated subcutaneously at the right hind flank with mixture of HCC827 tumor cells ($4\times10^6$), human PBMCs ($8\times10^5$) from healthy donor and indicated dose of antibody on day 0. Then the indicated antibodies (Table 25) were intravenously injected on day 7, 14, 21, 28, and 35. Tumor volume was measured twice a week up to day 68.

Figure 19:
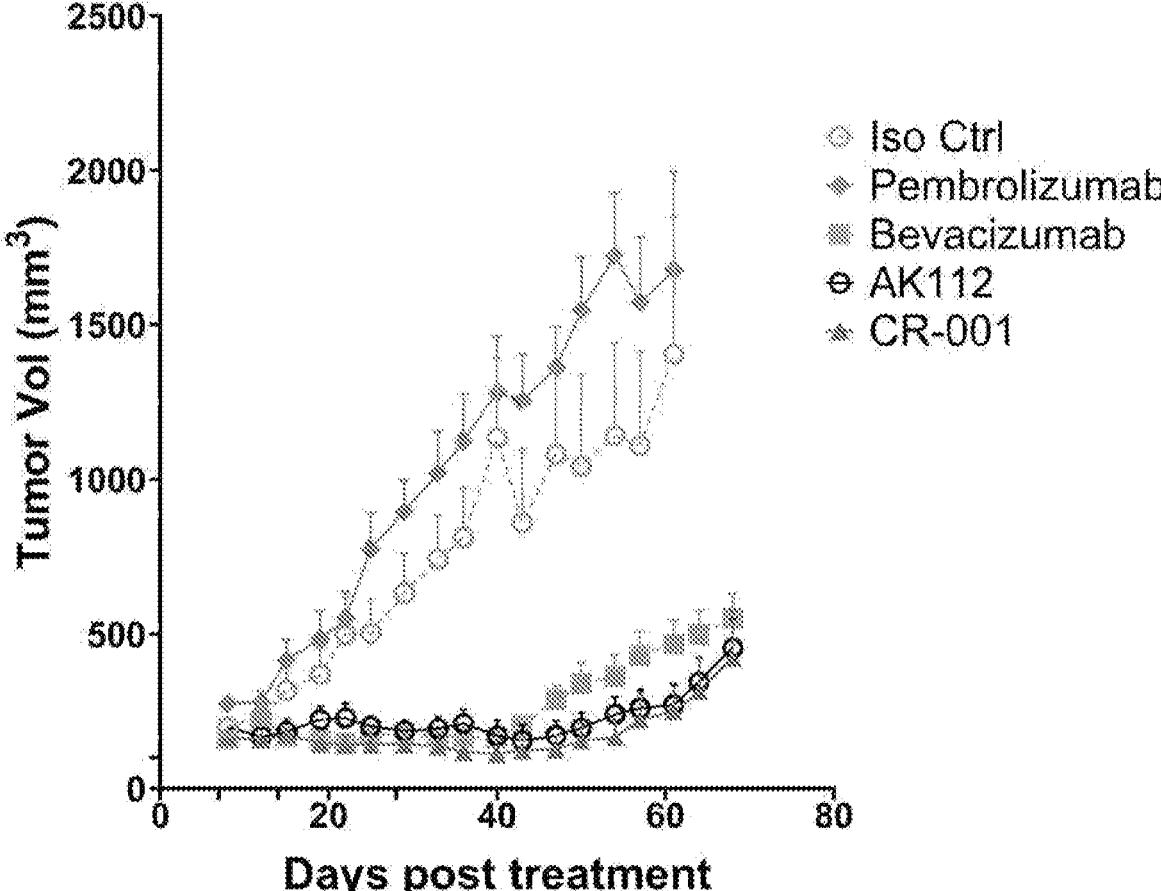
FIG. 19 depicts anti-tumor activity of the indicated antibodies.

Anti-tumor activity of VEGF/PD-1 bispecific was evaluated and compared with that of bevacizumab in PBMC humanized SCID/Beige mice with subcutaneous HCC827 xenograft tumors. Treatment with PAL054-0170.1L resulted in strong tumor growth inhibition. The anti-tumor effect was greater than bevacizumab at the equivalent molarity doses of 10 mg/kg (FIG. 19).

TABLE 25

Mice cohorts for the in vivo study

| Treatment groups | Dose mg/kg |
|---|---|
| PAL054-0007.1 (Bevacizumab) | 10 |
| PAL054-0004.4 (Pembrolizumab) | 10 |
| PAL054-0001.1L (AK112) | 14 |
| PAL054-0170.1L | 14 |
| Isotype control | 10 |

NUMBERED EMBODIMENTS

Embodiment 1. A bispecific antibody that binds vascular endothelial growth factor (VEGF) and programmed death receptor 1 (PD-1), comprising:
a) a heavy chain sequence comprising a sequence having at least 90% sequence identity to the amino acid sequence of any one of SEQ ID NOs: 22-23, 60, 62, 65-67, 70-72, 75-77, 142-143, 667-678, and 702-713; and
b) a light chain sequence comprising a sequence having at least 80% sequence identity to the amino acid sequence of any one of SEQ ID NOs: 148-194, 679-701, and 714-737.

Embodiment 2. The bispecific antibody of Embodiment 1, wherein the heavy chain sequence comprises a sequence having at least 90% sequence identity to the amino acid sequence of SEQ ID NO: 22; and the light chain sequence comprises a sequence having at least 80% sequence identity to the amino acid sequence of SEQ ID NO: 169.

Embodiment 3. The bispecific antibody of Embodiment 1, wherein the heavy chain sequence comprises a sequence having at least 90% sequence identity to the amino acid sequence of SEQ ID NO: 23; and the light chain sequence comprises a sequence having at least 80% sequence identity to the amino acid sequence of SEQ ID NO: 170.

Embodiment 4. The bispecific antibody of Embodiment 1, wherein the heavy chain sequence comprises a sequence having at least 90% sequence identity to the amino acid sequence of SEQ ID NO: 65; and the light chain sequence comprises a sequence having at least 80% sequence identity to the amino acid sequence of SEQ ID NO: 212.

Embodiment 5. The bispecific antibody of Embodiment 1, wherein the heavy chain sequence comprises a sequence having at least 90% sequence identity to the amino acid sequence of SEQ ID NO: 66; and the light chain sequence comprises a sequence having at least 80% sequence identity to the amino acid sequence of SEQ ID NO: 213.

Embodiment 6. The bispecific antibody of Embodiment 1, wherein the heavy chain sequence comprises a sequence having at least 90% sequence identity to the amino acid sequence of SEQ ID NO: 67; and the light chain sequence comprises a sequence having at least 80% sequence identity to the amino acid sequence of SEQ ID NO: 214.

Embodiment 7. The bispecific antibody of Embodiment 1, wherein the heavy chain sequence comprises a sequence having at least 90% sequence identity to the amino acid sequence of SEQ ID NO: 60; and the light chain sequence comprises a sequence having at least 80% sequence identity to the amino acid sequence of SEQ ID NO: 207.

Embodiment 8. The bispecific antibody of Embodiment 1, wherein the heavy chain sequence comprises a sequence having at least 90% sequence identity to the amino acid sequence of SEQ ID NO: 62; and the light chain sequence comprises a sequence having at least 80% sequence identity to the amino acid sequence of SEQ ID NO: 209.

Embodiment 9. The bispecific antibody of Embodiment 1, wherein the heavy chain sequence comprises a sequence having at least 90% sequence identity to the amino acid sequence of SEQ ID NO: 70; and the light chain sequence comprises a sequence having at least 80% sequence identity to the amino acid sequence of SEQ ID NO: 217.

Embodiment 10. The bispecific antibody of Embodiment 1, wherein the heavy chain sequence comprises a sequence having at least 90% sequence identity to the amino acid sequence of SEQ ID NO: 71; and the light chain sequence comprises a sequence having at least 80% sequence identity to the amino acid sequence of SEQ ID NO: 218.

Embodiment 11. The bispecific antibody of Embodiment 1, wherein the heavy chain sequence comprises a sequence having at least 90% sequence identity to the amino acid sequence of SEQ ID NO: 72; and the light chain sequence comprises a sequence having at least 80% sequence identity to the amino acid sequence of SEQ ID NO: 219.

Embodiment 12. The bispecific antibody of Embodiment 1, wherein the heavy chain sequence comprises a sequence having at least 90% sequence identity to the amino acid sequence of SEQ ID NO: 75; and the light chain sequence comprises a sequence having at least 80% sequence identity to the amino acid sequence of SEQ ID NO: 222.

Embodiment 13. The bispecific antibody of Embodiment 1, wherein the heavy chain sequence comprises a sequence having at least 90% sequence identity to the amino acid sequence of SEQ ID NO: 76; and the light chain sequence comprises a sequence having at least 80% sequence identity to the amino acid sequence of SEQ ID NO: 223.

Embodiment 14. The bispecific antibody of Embodiment 1, wherein the heavy chain sequence comprises a sequence having at least 90% sequence identity to the amino acid sequence of SEQ ID NO: 77; and the light chain sequence comprises a sequence having at least 80% sequence identity to the amino acid sequence of SEQ ID NO: 224.

Embodiment 15. The bispecific antibody of Embodiment 1, wherein the heavy chain sequence comprises a sequence having at least 90% sequence identity to the amino acid sequence of SEQ ID NO: 142; and the light chain sequence comprises a sequence having at least 80% sequence identity to the amino acid sequence of SEQ ID NO: 289.

Embodiment 16. The bispecific antibody of Embodiment 1, wherein the heavy chain sequence comprises a sequence having at least 90% sequence identity to the amino acid sequence of SEQ ID NO: 143; and the light chain sequence comprises a sequence having at least 80% sequence identity to the amino acid sequence of SEQ ID NO: 290.

Embodiment 17. The bispecific antibody of Embodiment 1, wherein the heavy chain sequence comprises a sequence having at least 90% sequence identity to the amino acid sequence of SEQ ID NO: 656; and the light chain sequence comprises a sequence having at least 80% sequence identity to the amino acid sequence of SEQ ID NO: 679.

Embodiment 18. The bispecific antibody of Embodiment 1, wherein the heavy chain sequence comprises a sequence having at least 90% sequence identity to the amino acid sequence of SEQ ID NO: 657; and the light chain sequence comprises a sequence having at least 80% sequence identity to the amino acid sequence of SEQ ID NO: 680.

Embodiment 19. The bispecific antibody of Embodiment 1, wherein the heavy chain sequence comprises a sequence having at least 90% sequence identity to the amino acid sequence of SEQ ID NO: 658; and the light chain sequence comprises a sequence having at least 80% sequence identity to the amino acid sequence of SEQ ID NO: 681.

Embodiment 20. The bispecific antibody of Embodiment 1, wherein the heavy chain sequence comprises a sequence having at least 90% sequence identity to the amino acid sequence of SEQ ID NO: 659; and the light chain sequence comprises a sequence having at least 80% sequence identity to the amino acid sequence of SEQ ID NO: 682.

Embodiment 21. The bispecific antibody of Embodiment 1, wherein the heavy chain sequence comprises a sequence having at least 90% sequence identity to the amino acid sequence of SEQ ID NO: 660; and the light chain sequence comprises a sequence having at least 80% sequence identity to the amino acid sequence of SEQ ID NO: 683.

Embodiment 22. The bispecific antibody of Embodiment 1, wherein the heavy chain sequence comprises a sequence having at least 90% sequence identity to the amino acid sequence of SEQ ID NO: 661; and the light chain sequence comprises a sequence having at least 80% sequence identity to the amino acid sequence of SEQ ID NO: 684.

Embodiment 23. The bispecific antibody of Embodiment 1, wherein the heavy chain sequence comprises a sequence having at least 90% sequence identity to the amino acid sequence of SEQ ID NO: 662; and the light chain sequence comprises a sequence having at least 80% sequence identity to the amino acid sequence of SEQ ID NO: 685.

Embodiment 24. The bispecific antibody of Embodiment 1, wherein the heavy chain sequence comprises a sequence having at least 90% sequence identity to the amino acid sequence of SEQ ID NO: 663; and the light chain sequence comprises a sequence having at least 80% sequence identity to the amino acid sequence of SEQ ID NO: 686.

Embodiment 25. The bispecific antibody of Embodiment 1, wherein the heavy chain sequence comprises a sequence having at least 90% sequence identity to the amino acid sequence of SEQ ID NO: 664; and the light chain sequence comprises a sequence having at least 80% sequence identity to the amino acid sequence of SEQ ID NO: 687.

Embodiment 26. The bispecific antibody of Embodiment 1, wherein the heavy chain sequence comprises a sequence having at least 90% sequence identity to the amino acid sequence of SEQ ID NO: 665; and the light chain sequence comprises a sequence having at least 80% sequence identity to the amino acid sequence of SEQ ID NO: 688.

Embodiment 27. The bispecific antibody of Embodiment 1, wherein the heavy chain sequence comprises a sequence having at least 90% sequence identity to the amino acid sequence of SEQ ID NO: 666; and the light chain sequence comprises a sequence having at least 80% sequence identity to the amino acid sequence of SEQ ID NO: 689.

Embodiment 28. The bispecific antibody of Embodiment 1, wherein the heavy chain sequence comprises a sequence having at least 90% sequence identity to the amino acid sequence of SEQ ID NO: 667; and the light chain sequence comprises a sequence having at least 80% sequence identity to the amino acid sequence of SEQ ID NO: 690.

Embodiment 29. The bispecific antibody of Embodiment 1, wherein the heavy chain sequence comprises a sequence having at least 90% sequence identity to the amino acid sequence of SEQ ID NO: 668; and the light chain sequence comprises a sequence having at least 80% sequence identity to the amino acid sequence of SEQ ID NO: 691.

Embodiment 30. The bispecific antibody of Embodiment 1, wherein the heavy chain sequence comprises a sequence having at least 90% sequence identity to the amino acid sequence of SEQ ID NO: 669; and the light chain sequence comprises a sequence having at least 80% sequence identity to the amino acid sequence of SEQ ID NO: 692.

Embodiment 31. The bispecific antibody of Embodiment 1, wherein the heavy chain sequence comprises a sequence having at least 90% sequence identity to the amino acid sequence of SEQ ID NO: 670; and the light chain sequence comprises a sequence having at least 80% sequence identity to the amino acid sequence of SEQ ID NO: 693.

Embodiment 32. The bispecific antibody of Embodiment 1, wherein the heavy chain sequence comprises a sequence having at least 90% sequence identity to the amino acid sequence of SEQ ID NO: 671; and the light chain sequence comprises a sequence having at least 80% sequence identity to the amino acid sequence of SEQ ID NO: 694.

Embodiment 33. The bispecific antibody of Embodiment 1, wherein the heavy chain sequence comprises a sequence having at least 90% sequence identity to the amino acid sequence of SEQ ID NO: 672; and the light chain sequence comprises a sequence having at least 80% sequence identity to the amino acid sequence of SEQ ID NO: 695.

Embodiment 34. The bispecific antibody of Embodiment 1, wherein the heavy chain sequence comprises a sequence having at least 90% sequence identity to the amino acid sequence of SEQ ID NO: 673; and the light chain sequence comprises a sequence having at least 80% sequence identity to the amino acid sequence of SEQ ID NO: 696.

Embodiment 35. The bispecific antibody of Embodiment 1, wherein the heavy chain sequence comprises a sequence having at least 90% sequence identity to the amino acid sequence of SEQ ID NO: 674; and the light chain sequence comprises a sequence having at least 80% sequence identity to the amino acid sequence of SEQ ID NO: 697.

Embodiment 36. The bispecific antibody of Embodiment 1, wherein the heavy chain sequence comprises a sequence having at least 90% sequence identity to the amino acid sequence of SEQ ID NO: 675; and the light chain sequence comprises a sequence having at least 80% sequence identity to the amino acid sequence of SEQ ID NO: 698.

Embodiment 37. The bispecific antibody of Embodiment 1, wherein the heavy chain sequence comprises a sequence having at least 90% sequence identity to the amino acid sequence of SEQ ID NO: 676; and the light chain sequence comprises a sequence having at least 80% sequence identity to the amino acid sequence of SEQ ID NO: 699.

Embodiment 38. The bispecific antibody of Embodiment 1, wherein the heavy chain sequence comprises a sequence having at least 90% sequence identity to the amino acid sequence of SEQ ID NO: 677; and the light chain sequence comprises a sequence having at least 80% sequence identity to the amino acid sequence of SEQ ID NO: 700.

Embodiment 39. The bispecific antibody of Embodiment 1, wherein the heavy chain sequence comprises a sequence having at least 90% sequence identity to the amino acid sequence of SEQ ID NO: 702; and a first light chain sequence comprises a sequence having at least 80% sequence identity to the amino acid sequence of SEQ ID NO: 714, and a second light chain sequence comprises a sequence having at least 80% sequence identity to the amino acid sequence of SEQ ID NO: 726.

Embodiment 40. The bispecific antibody of Embodiment 1, wherein the heavy chain sequence comprises a sequence having at least 90% sequence identity to the amino acid sequence of SEQ ID NO: 703; and a first light chain sequence comprises a sequence having at least 80% sequence identity to the amino acid sequence of SEQ ID NO: 715, and a second light chain sequence comprises a sequence having at least 80% sequence identity to the amino acid sequence of SEQ ID NO: 727.

Embodiment 41. The bispecific antibody of Embodiment 1, wherein the heavy chain sequence comprises a sequence having at least 90% sequence identity to the amino acid sequence of SEQ ID NO: 704; and a first light chain sequence comprises a sequence having at least 80% sequence identity to the amino acid sequence of SEQ ID NO: 716, and a second light chain sequence comprises a sequence having at least 80% sequence identity to the amino acid sequence of SEQ ID NO: 728.

Embodiment 42. The bispecific antibody of Embodiment 1, wherein the heavy chain sequence comprises a sequence having at least 90% sequence identity to the amino acid sequence of SEQ ID NO: 705; and a first light chain sequence comprises a sequence having at least 80% sequence identity to the amino acid sequence of SEQ ID NO: 717, and a second light chain sequence comprises a sequence having at least 80% sequence identity to the amino acid sequence of SEQ ID NO: 729.

Embodiment 43. The bispecific antibody of Embodiment 1, wherein the heavy chain sequence comprises a sequence having at least 90% sequence identity to the amino acid sequence of SEQ ID NO: 706; and a first light chain sequence comprises a sequence having at least 80% sequence identity to the amino acid sequence of SEQ ID NO: 718, and a second light chain sequence comprises a sequence having at least 80% sequence identity to the amino acid sequence of SEQ ID NO: 730.

Embodiment 44. The bispecific antibody of Embodiment 1, wherein the heavy chain sequence comprises a sequence having at least 90% sequence identity to the amino acid sequence of SEQ ID NO: 707; and a first light chain sequence comprises a sequence having at least 80% sequence identity to the amino acid sequence of SEQ ID NO: 719, and a second light chain sequence comprises a sequence having at least 80% sequence identity to the amino acid sequence of SEQ ID NO: 731.

Embodiment 45. The bispecific antibody of Embodiment 1, wherein the heavy chain sequence comprises a sequence having at least 90% sequence identity to the amino acid sequence of SEQ ID NO: 708; and a first light chain sequence comprises a sequence having at least 80% sequence identity to the amino acid sequence of SEQ ID NO: 720, and a second light chain sequence comprises a sequence having at least 80% sequence identity to the amino acid sequence of SEQ ID NO: 732.

Embodiment 46. The bispecific antibody of Embodiment 1, wherein the heavy chain sequence comprises a sequence having at least 90% sequence identity to the amino acid sequence of SEQ ID NO: 709; and a first light chain sequence comprises a sequence having at least 80% sequence identity to the amino acid sequence of SEQ ID NO: 721, and a second light chain sequence comprises a sequence having at least 80% sequence identity to the amino acid sequence of SEQ ID NO: 733.

Embodiment 47. The bispecific antibody of Embodiment 1, wherein the heavy chain sequence comprises a sequence having at least 90% sequence identity to the amino acid sequence of SEQ ID NO: 710; and a first light chain sequence comprises a sequence having at least 80% sequence identity to the amino acid sequence of SEQ ID NO: 722, and a second light chain sequence comprises a sequence having at least 80% sequence identity to the amino acid sequence of SEQ ID NO: 734.

Embodiment 48. The bispecific antibody of Embodiment 1, wherein the heavy chain sequence comprises a sequence having at least 90% sequence identity to the amino acid sequence of SEQ ID NO: 711; and a first light chain sequence comprises a sequence having at least 80% sequence identity to the amino acid sequence of SEQ ID NO: 723, and a second light chain sequence comprises a sequence having at least 80% sequence identity to the amino acid sequence of SEQ ID NO: 735.

Embodiment 49. The bispecific antibody of Embodiment 1, wherein the heavy chain sequence comprises a sequence having at least 90% sequence identity to the amino acid sequence of SEQ ID NO: 712; and a first light chain sequence comprises a sequence having at least 80% sequence identity to the amino acid sequence of SEQ ID NO: 724, and a second light chain sequence comprises a sequence having at least 80% sequence identity to the amino acid sequence of SEQ ID NO: 736.

Embodiment 50. The bispecific antibody of Embodiment 1, wherein the heavy chain sequence comprises a sequence having at least 90% sequence identity to the amino acid sequence of SEQ ID NO: 713; and a first light chain sequence comprises a sequence having at least 80% sequence identity to the amino acid sequence of SEQ ID NO: 725, and a second light chain sequence comprises a sequence having at least 80% sequence identity to the amino acid sequence of SEQ ID NO: 737.

Embodiment 51. The bispecific antibody of Embodiment 1, wherein the heavy chain sequence comprises a sequence having at least 90% sequence identity to the amino acid sequence of SEQ ID NO: 678; and the light chain sequence comprises a sequence having at least 80% sequence identity to the amino acid sequence of SEQ ID NO: 701.

Embodiment 52. A bispecific antibody that binds vascular endothelial growth factor (VEGF) and programmed death receptor 1 (PD-1), comprising:

a) a heavy chain sequence comprising a sequence having at least 95% sequence identity to the amino acid sequence of any one of SEQ ID NOs: 1-21, 24-57, 58, 59, 61, 63, 64, 68, 69, 73, 74, 78-97, 130-141, 144-147, and 656-666; and b) a light chain sequence comprising a sequence having at least 80% sequence identity to the amino acid sequence of any one of SEQ ID NOs: 148-194, 679-701, and 714-737.

Embodiment 53. The bispecific antibody of Embodiment 52, wherein the heavy chain sequence comprises a sequence having at least 95% sequence identity to the amino acid sequence of SEQ ID NO: 1; and the light chain sequence comprises a sequence having at least 80% sequence identity to the amino acid sequence of SEQ ID NO: 148.

Embodiment 54. The bispecific antibody of Embodiment 52, wherein the heavy chain sequence comprises a sequence having at least 95% sequence identity to the amino acid sequence of SEQ ID NO: 2; and the light chain sequence comprises a sequence having at least 80% sequence identity to the amino acid sequence of SEQ ID NO: 149.

Embodiment 55. The bispecific antibody of Embodiment 52, wherein the heavy chain sequence comprises a sequence having at least 95% sequence identity to the amino acid sequence of SEQ ID NO: 3; and the light chain sequence comprises a sequence having at least 80% sequence identity to the amino acid sequence of SEQ ID NO: 150.

Embodiment 56. The bispecific antibody of Embodiment 52, wherein the heavy chain sequence comprises a sequence having at least 95% sequence identity to the amino acid sequence of SEQ ID NO: 4; and the light chain sequence comprises a sequence having at least 80% sequence identity to the amino acid sequence of SEQ ID NO: 151.

Embodiment 57. The bispecific antibody of Embodiment 52, wherein the heavy chain sequence comprises a sequence having at least 95% sequence identity to the amino acid sequence of SEQ ID NO: 5; and the light chain sequence comprises a sequence having at least 80% sequence identity to the amino acid sequence of SEQ ID NO: 152.

Embodiment 58. The bispecific antibody of Embodiment 52, wherein the heavy chain sequence comprises a sequence having at least 95% sequence identity to the amino acid sequence of SEQ ID NO: 6; and the light chain sequence comprises a sequence having at least 80% sequence identity to the amino acid sequence of SEQ ID NO: 153.

Embodiment 59. The bispecific antibody of Embodiment 52, wherein the heavy chain sequence comprises a sequence having at least 95% sequence identity to the amino acid sequence of SEQ ID NO: 7; and the light chain sequence comprises a sequence having at least 80% sequence identity to the amino acid sequence of SEQ ID NO: 154.

Embodiment 60. The bispecific antibody of Embodiment 52, wherein the heavy chain sequence comprises a sequence having at least 95% sequence identity to the amino acid sequence of SEQ ID NO: 8; and the light chain sequence comprises a sequence having at least 80% sequence identity to the amino acid sequence of SEQ ID NO: 155.

Embodiment 61. The bispecific antibody of Embodiment 52, wherein the heavy chain sequence comprises a sequence having at least 95% sequence identity to the amino acid sequence of SEQ ID NO: 9; and the light chain sequence comprises a sequence having at least 80% sequence identity to the amino acid sequence of SEQ ID NO: 156.

Embodiment 62. The bispecific antibody of Embodiment 52, wherein the heavy chain sequence comprises a sequence having at least 95% sequence identity to the amino acid sequence of SEQ ID NO: 10; and the light chain sequence comprises a sequence having at least 80% sequence identity to the amino acid sequence of SEQ ID NO: 157.

Embodiment 63. The bispecific antibody of Embodiment 52, wherein the heavy chain sequence comprises a sequence having at least 95% sequence identity to the amino acid sequence of SEQ ID NO: 11; and the light chain sequence comprises a sequence having at least 80% sequence identity to the amino acid sequence of SEQ ID NO: 158.

Embodiment 64. The bispecific antibody of Embodiment 52, wherein the heavy chain sequence comprises a sequence having at least 95% sequence identity to the amino acid sequence of SEQ ID NO: 12; and the light chain sequence comprises a sequence having at least 80% sequence identity to the amino acid sequence of SEQ ID NO: 159.

Embodiment 65. The bispecific antibody of Embodiment 52, wherein the heavy chain sequence comprises a sequence having at least 95% sequence identity to the amino acid sequence of SEQ ID NO: 13; and the light chain sequence comprises a sequence having at least 80% sequence identity to the amino acid sequence of SEQ ID NO: 160.

Embodiment 66. The bispecific antibody of Embodiment 52, wherein the heavy chain sequence comprises a sequence having at least 95% sequence identity to the amino acid sequence of SEQ ID NO: 14; and the light chain sequence comprises a sequence having at least 80% sequence identity to the amino acid sequence of SEQ ID NO: 161.

Embodiment 67. The bispecific antibody of Embodiment 52, wherein the heavy chain sequence comprises a sequence having at least 95% sequence identity to the amino acid sequence of SEQ ID NO: 15; and the light chain sequence comprises a sequence having at least 80% sequence identity to the amino acid sequence of SEQ ID NO: 162.

Embodiment 68. The bispecific antibody of Embodiment 52, wherein the heavy chain sequence comprises a sequence having at least 95% sequence identity to the amino acid sequence of SEQ ID NO: 16; and the light chain sequence comprises a sequence having at least 80% sequence identity to the amino acid sequence of SEQ ID NO: 163.

Embodiment 69. The bispecific antibody of Embodiment 52, wherein the heavy chain sequence comprises a sequence having at least 95% sequence identity to the amino acid sequence of SEQ ID NO: 17; and the light chain sequence comprises a sequence having at least 80% sequence identity to the amino acid sequence of SEQ ID NO: 164.

Embodiment 70. The bispecific antibody of Embodiment 52, wherein the heavy chain sequence comprises a sequence having at least 95% sequence identity to the amino acid sequence of SEQ ID NO: 18; and the light chain sequence comprises a sequence having at least 80% sequence identity to the amino acid sequence of SEQ ID NO: 165.

Embodiment 71. The bispecific antibody of Embodiment 52, wherein the heavy chain sequence comprises a sequence having at least 95% sequence identity to the amino acid sequence of SEQ ID NO: 19; and the light chain sequence comprises a sequence having at least 80% sequence identity to the amino acid sequence of SEQ ID NO: 166.

Embodiment 72. The bispecific antibody of Embodiment 52, wherein the heavy chain sequence comprises a sequence having at least 95% sequence identity to the amino acid sequence of SEQ ID NO: 20; and the light chain sequence comprises a sequence having at least 80% sequence identity to the amino acid sequence of SEQ ID NO: 167.

Embodiment 73. The bispecific antibody of Embodiment 52, wherein the heavy chain sequence comprises a sequence having at least 95% sequence identity to the amino acid sequence of SEQ ID NO: 21; and the light chain sequence comprises a sequence having at least 80% sequence identity to the amino acid sequence of SEQ ID NO: 168.

Embodiment 74. The bispecific antibody of Embodiment 52, wherein the heavy chain sequence comprises a sequence having at least 95% sequence identity to the amino acid sequence of SEQ ID NO: 24; and the light chain sequence comprises a sequence having at least 80% sequence identity to the amino acid sequence of SEQ ID NO: 171.

Embodiment 75. The bispecific antibody of Embodiment 52, wherein the heavy chain sequence comprises a sequence having at least 95% sequence identity to the amino acid sequence of SEQ ID NO: 25; and the light chain sequence comprises a sequence having at least 80% sequence identity to the amino acid sequence of SEQ ID NO: 172.

Embodiment 76. The bispecific antibody of Embodiment 52, wherein the heavy chain sequence comprises a sequence having at least 95% sequence identity to the amino acid sequence of SEQ ID NO: 26; and the light chain sequence comprises a sequence having at least 80% sequence identity to the amino acid sequence of SEQ ID NO: 173.

Embodiment 77. The bispecific antibody of Embodiment 52, wherein the heavy chain sequence comprises a sequence having at least 95% sequence identity to the amino acid sequence of SEQ ID NO: 27; and the light chain sequence comprises a sequence having at least 80% sequence identity to the amino acid sequence of SEQ ID NO: 174.

Embodiment 78. The bispecific antibody of Embodiment 52, wherein the heavy chain sequence comprises a sequence having at least 95% sequence identity to the amino acid sequence of SEQ ID NO: 28; and the light chain sequence comprises a sequence having at least 80% sequence identity to the amino acid sequence of SEQ ID NO: 175.

Embodiment 79. The bispecific antibody of Embodiment 52, wherein the heavy chain sequence comprises a sequence having at least 95% sequence identity to the amino acid sequence of SEQ ID NO: 29; and the light chain sequence comprises a sequence having at least 80% sequence identity to the amino acid sequence of SEQ ID NO: 176.

Embodiment 80. The bispecific antibody of Embodiment 52, wherein the heavy chain sequence comprises a sequence having at least 95% sequence identity to the amino acid sequence of SEQ ID NO: 30; and the light chain sequence comprises a sequence having at least 80% sequence identity to the amino acid sequence of SEQ ID NO: 177.

Embodiment 81. The bispecific antibody of Embodiment 52, wherein the heavy chain sequence comprises a sequence having at least 95% sequence identity to the amino acid sequence of SEQ ID NO: 31; and the light chain sequence comprises a sequence having at least 80% sequence identity to the amino acid sequence of SEQ ID NO: 178.

Embodiment 82. The bispecific antibody of Embodiment 52, wherein the heavy chain sequence comprises a sequence having at least 95% sequence identity to the amino acid sequence of SEQ ID NO: 32; and the light chain sequence comprises a sequence having at least 80% sequence identity to the amino acid sequence of SEQ ID NO: 179.

Embodiment 83. The bispecific antibody of Embodiment 52, wherein the heavy chain sequence comprises a sequence having at least 95% sequence identity to the amino acid sequence of SEQ ID NO: 33; and the light chain sequence comprises a sequence having at least 80% sequence identity to the amino acid sequence of SEQ ID NO: 180.

Embodiment 84. The bispecific antibody of Embodiment 52, wherein the heavy chain sequence comprises a sequence having at least 95% sequence identity to the amino acid sequence of SEQ ID NO: 34; and the light chain sequence comprises a sequence having at least 80% sequence identity to the amino acid sequence of SEQ ID NO: 181.

Embodiment 85. The bispecific antibody of Embodiment 52, wherein the heavy chain sequence comprises a sequence having at least 95% sequence identity to the amino acid sequence of SEQ ID NO: 35; and the light chain sequence comprises a sequence having at least 80% sequence identity to the amino acid sequence of SEQ ID NO: 182.

Embodiment 86. The bispecific antibody of Embodiment 52, wherein the heavy chain sequence comprises a sequence having at least 95% sequence identity to the amino acid sequence of SEQ ID NO: 36; and the light chain sequence comprises a sequence having at least 80% sequence identity to the amino acid sequence of SEQ ID NO: 183.

Embodiment 87. The bispecific antibody of Embodiment 52, wherein the heavy chain sequence comprises a sequence having at least 95% sequence identity to the amino acid sequence of SEQ ID NO: 37; and the light chain sequence comprises a sequence having at least 80% sequence identity to the amino acid sequence of SEQ ID NO: 184.

Embodiment 88. The bispecific antibody of Embodiment 52, wherein the heavy chain sequence comprises a sequence having at least 95% sequence identity to the amino acid sequence of SEQ ID NO: 38; and the light chain sequence comprises a sequence having at least 80% sequence identity to the amino acid sequence of SEQ ID NO: 185.

Embodiment 89. The bispecific antibody of Embodiment 52, wherein the heavy chain sequence comprises a sequence having at least 95% sequence identity to the amino acid sequence of SEQ ID NO: 39; and the light chain sequence comprises a sequence having at least 80% sequence identity to the amino acid sequence of SEQ ID NO: 186.

Embodiment 90. The bispecific antibody of Embodiment 52, wherein the heavy chain sequence comprises a sequence having at least 95% sequence identity to the amino acid sequence of SEQ ID NO: 40; and the light chain sequence comprises a sequence having at least 80% sequence identity to the amino acid sequence of SEQ ID NO: 187.

Embodiment 91. The bispecific antibody of Embodiment 52, wherein the heavy chain sequence comprises a sequence having at least 95% sequence identity to the amino acid sequence of SEQ ID NO: 41; and the light chain sequence comprises a sequence having at least 80% sequence identity to the amino acid sequence of SEQ ID NO: 188.

Embodiment 92. The bispecific antibody of Embodiment 52, wherein the heavy chain sequence comprises a sequence having at least 95% sequence identity to the amino acid sequence of SEQ ID NO: 42; and the light chain sequence comprises a sequence having at least 80% sequence identity to the amino acid sequence of SEQ ID NO: 189.

Embodiment 93. The bispecific antibody of Embodiment 52, wherein the heavy chain sequence comprises a sequence having at least 95% sequence identity to the amino acid sequence of SEQ ID NO: 43; and the light chain sequence comprises a sequence having at least 80% sequence identity to the amino acid sequence of SEQ ID NO: 190.

Embodiment 94. The bispecific antibody of Embodiment 52, wherein the heavy chain sequence comprises a sequence having at least 95% sequence identity to the amino acid sequence of SEQ ID NO: 44; and the light chain sequence comprises a sequence having at least 80% sequence identity to the amino acid sequence of SEQ ID NO: 191.

Embodiment 95. The bispecific antibody of Embodiment 52, wherein the heavy chain sequence comprises a sequence having at least 95% sequence identity to the amino acid sequence of SEQ ID NO: 45; and the light chain sequence comprises a sequence having at least 80% sequence identity to the amino acid sequence of SEQ ID NO: 192.

Embodiment 96. The bispecific antibody of Embodiment 52, wherein the heavy chain sequence comprises a sequence having at least 95% sequence identity to the amino acid sequence of SEQ ID NO: 46; and the light chain sequence comprises a sequence having at least 80% sequence identity to the amino acid sequence of SEQ ID NO: 193.

Embodiment 97. The bispecific antibody of Embodiment 52, wherein the heavy chain sequence comprises a sequence having at least 95% sequence identity to the amino acid sequence of SEQ ID NO: 47; and the light chain sequence comprises a sequence having at least 80% sequence identity to the amino acid sequence of SEQ ID NO: 194.

Embodiment 98. The bispecific antibody of Embodiment 52, wherein the heavy chain sequence comprises a sequence having at least 95% sequence identity to the amino acid sequence of SEQ ID NO: 48; and the light chain sequence comprises a sequence having at least 80% sequence identity to the amino acid sequence of SEQ ID NO: 195.

Embodiment 99. The bispecific antibody of Embodiment 52, wherein the heavy chain sequence comprises a sequence having at least 95% sequence identity to the amino acid sequence of SEQ ID NO: 49; and the light chain sequence comprises a sequence having at least 80% sequence identity to the amino acid sequence of SEQ ID NO: 196.

Embodiment 100. The bispecific antibody of Embodiment 52, wherein the heavy chain sequence comprises a sequence having at least 95% sequence identity to the amino acid sequence of SEQ ID NO: 50; and the light chain sequence comprises a sequence having at least 80% sequence identity to the amino acid sequence of SEQ ID NO: 197.

Embodiment 101. The bispecific antibody of Embodiment 52, wherein the heavy chain sequence comprises a sequence having at least 95% sequence identity to the amino acid sequence of SEQ ID NO: 51; and the light chain sequence comprises a sequence having at least 80% sequence identity to the amino acid sequence of SEQ ID NO: 198.

Embodiment 102. The bispecific antibody of Embodiment 52, wherein the heavy chain sequence comprises a sequence having at least 95% sequence identity to the amino acid sequence of SEQ ID NO: 52; and the light chain sequence comprises a sequence having at least 80% sequence identity to the amino acid sequence of SEQ ID NO: 199.

Embodiment 103. The bispecific antibody of Embodiment 52, wherein the heavy chain sequence comprises a sequence having at least 95% sequence identity to the amino acid sequence of SEQ ID NO: 53; and the light chain sequence comprises a sequence having at least 80% sequence identity to the amino acid sequence of SEQ ID NO: 200.

Embodiment 104. The bispecific antibody of Embodiment 52, wherein the heavy chain sequence comprises a sequence having at least 95% sequence identity to the amino acid sequence of SEQ ID NO: 54; and the light chain sequence comprises a sequence having at least 80% sequence identity to the amino acid sequence of SEQ ID NO: 201.

Embodiment 105. The bispecific antibody of Embodiment 52, wherein the heavy chain sequence comprises a sequence having at least 95% sequence identity to the amino acid sequence of SEQ ID NO: 55; and the light chain sequence comprises a sequence having at least 80% sequence identity to the amino acid sequence of SEQ ID NO: 202.

Embodiment 106. The bispecific antibody of Embodiment 52, wherein the heavy chain sequence comprises a sequence having at least 95% sequence identity to the amino acid sequence of SEQ ID NO: 56; and the light chain sequence comprises a sequence having at least 80% sequence identity to the amino acid sequence of SEQ ID NO: 203.

Embodiment 107. The bispecific antibody of Embodiment 52, wherein the heavy chain sequence comprises a sequence having at least 95% sequence identity to the amino acid sequence of SEQ ID NO: 57; and the light chain sequence comprises a sequence having at least 80% sequence identity to the amino acid sequence of SEQ ID NO: 204.

Embodiment 108. The bispecific antibody of Embodiment 52, wherein the heavy chain sequence comprises a sequence having at least 95% sequence identity to the amino acid sequence of SEQ ID NO: 58; and the light chain sequence comprises a sequence having at least 80% sequence identity to the amino acid sequence of SEQ ID NO: 205.

Embodiment 109. The bispecific antibody of Embodiment 52, wherein the heavy chain sequence comprises a sequence having at least 95% sequence identity to the amino acid sequence of SEQ ID NO: 59; and the light chain sequence comprises a sequence having at least 80% sequence identity to the amino acid sequence of SEQ ID NO: 206.

Embodiment 110. The bispecific antibody of Embodiment 52, wherein the heavy chain sequence comprises a sequence having at least 95% sequence identity to the amino acid sequence of SEQ ID NO: 61; and the light chain sequence comprises a sequence having at least 80% sequence identity to the amino acid sequence of SEQ ID NO: 208.

Embodiment 111. The bispecific antibody of Embodiment 52, wherein the heavy chain sequence comprises a sequence having at least 95% sequence identity to the amino acid sequence of SEQ ID NO: 63; and the light chain sequence comprises a sequence having at least 80% sequence identity to the amino acid sequence of SEQ ID NO: 210.

Embodiment 112. The bispecific antibody of Embodiment 52, wherein the heavy chain sequence comprises a sequence having at least 95% sequence identity to the amino acid sequence of SEQ ID NO: 64; and the light chain sequence comprises a sequence having at least 80% sequence identity to the amino acid sequence of SEQ ID NO: 211.

Embodiment 113. The bispecific antibody of Embodiment 52, wherein the heavy chain sequence comprises a sequence having at least 95% sequence identity to the amino acid sequence of SEQ ID NO: 68; and the light chain sequence comprises a sequence having at least 80% sequence identity to the amino acid sequence of SEQ ID NO: 215.

Embodiment 114. The bispecific antibody of Embodiment 52, wherein the heavy chain sequence comprises a sequence having at least 95% sequence identity to the amino acid sequence of SEQ ID NO: 69; and the light chain sequence comprises a sequence having at least 80% sequence identity to the amino acid sequence of SEQ ID NO: 216.

Embodiment 115. The bispecific antibody of Embodiment 52, wherein the heavy chain sequence comprises a sequence having at least 95% sequence identity to the amino acid sequence of SEQ ID NO: 73; and the light chain sequence comprises a sequence having at least 80% sequence identity to the amino acid sequence of SEQ ID NO: 220.

Embodiment 116. The bispecific antibody of Embodiment 52, wherein the heavy chain sequence comprises a sequence having at least 95% sequence identity to the amino acid sequence of SEQ ID NO: 74; and the light chain sequence comprises a sequence having at least 80% sequence identity to the amino acid sequence of SEQ ID NO: 221.

Embodiment 117. The bispecific antibody of Embodiment 52, wherein the heavy chain sequence comprises a sequence having at least 95% sequence identity to the amino acid sequence of SEQ ID NO: 78; and the light chain sequence comprises a sequence having at least 80% sequence identity to the amino acid sequence of SEQ ID NO: 225.

Embodiment 118. The bispecific antibody of Embodiment 52, wherein the heavy chain sequence comprises a sequence having at least 95% sequence identity to the amino acid sequence of SEQ ID NO: 79; and the light chain sequence comprises a sequence having at least 80% sequence identity to the amino acid sequence of SEQ ID NO: 226.

Embodiment 119. The bispecific antibody of Embodiment 52, wherein the heavy chain sequence comprises a sequence having at least 95% sequence identity to the amino acid sequence of SEQ ID NO: 80; and the light chain sequence comprises a sequence having at least 80% sequence identity to the amino acid sequence of SEQ ID NO: 227.

Embodiment 120. The bispecific antibody of Embodiment 52, wherein the heavy chain sequence comprises a sequence having at least 95% sequence identity to the amino acid sequence of SEQ ID NO: 81; and the light chain sequence comprises a sequence having at least 80% sequence identity to the amino acid sequence of SEQ ID NO: 228.

Embodiment 121. The bispecific antibody of Embodiment 52, wherein the heavy chain sequence comprises a sequence having at least 95% sequence identity to the amino acid sequence of SEQ ID NO: 82; and the light chain sequence comprises a sequence having at least 80% sequence identity to the amino acid sequence of SEQ ID NO: 229.

Embodiment 122. The bispecific antibody of Embodiment 52, wherein the heavy chain sequence comprises a sequence having at least 95% sequence identity to the amino acid sequence of SEQ ID NO: 83; and the light chain sequence comprises a sequence having at least 80% sequence identity to the amino acid sequence of SEQ ID NO: 230.

Embodiment 123. The bispecific antibody of Embodiment 52, wherein the heavy chain sequence comprises a sequence having at least 95% sequence identity to the amino acid sequence of SEQ ID NO: 84; and the light chain sequence comprises a sequence having at least 80% sequence identity to the amino acid sequence of SEQ ID NO: 231.

Embodiment 124. The bispecific antibody of Embodiment 52, wherein the heavy chain sequence comprises a sequence having at least 95% sequence identity to the amino acid sequence of SEQ ID NO: 85; and the light chain sequence comprises a sequence having at least 80% sequence identity to the amino acid sequence of SEQ ID NO: 232.

Embodiment 125. The bispecific antibody of Embodiment 52, wherein the heavy chain sequence comprises a sequence having at least 95% sequence identity to the amino acid sequence of SEQ ID NO: 86; and the light chain sequence comprises a sequence having at least 80% sequence identity to the amino acid sequence of SEQ ID NO: 233.

Embodiment 126. The bispecific antibody of Embodiment 52, wherein the heavy chain sequence comprises a sequence having at least 95% sequence identity to the amino acid sequence of SEQ ID NO: 87; and the light chain sequence comprises a sequence having at least 80% sequence identity to the amino acid sequence of SEQ ID NO: 234.

Embodiment 127. The bispecific antibody of Embodiment 52, wherein the heavy chain sequence comprises a sequence having at least 95% sequence identity to the amino acid sequence of SEQ ID NO: 88; and the light chain sequence comprises a sequence having at least 80% sequence identity to the amino acid sequence of SEQ ID NO: 235.

Embodiment 128. The bispecific antibody of Embodiment 52, wherein the heavy chain sequence comprises a sequence having at least 95% sequence identity to the amino acid sequence of SEQ ID NO: 89; and the light chain sequence comprises a sequence having at least 80% sequence identity to the amino acid sequence of SEQ ID NO: 236.

Embodiment 129. The bispecific antibody of Embodiment 52, wherein the heavy chain sequence comprises a sequence having at least 95% sequence identity to the amino acid sequence of SEQ ID NO: 90; and the light chain sequence comprises a sequence having at least 80% sequence identity to the amino acid sequence of SEQ ID NO: 237.

Embodiment 130. The bispecific antibody of Embodiment 52, wherein the heavy chain sequence comprises a sequence having at least 95% sequence identity to the amino acid sequence of SEQ ID NO: 91; and the light chain sequence comprises a sequence having at least 80% sequence identity to the amino acid sequence of SEQ ID NO: 238.

Embodiment 131. The bispecific antibody of Embodiment 52, wherein the heavy chain sequence comprises a sequence having at least 95% sequence identity to the amino acid sequence of SEQ ID NO: 92; and the light chain sequence comprises a sequence having at least 80% sequence identity to the amino acid sequence of SEQ ID NO: 239.

Embodiment 132. The bispecific antibody of Embodiment 52, wherein the heavy chain sequence comprises a sequence having at least 95% sequence identity to the amino acid sequence of SEQ ID NO: 93; and the light chain sequence comprises a sequence having at least 80% sequence identity to the amino acid sequence of SEQ ID NO: 240.

Embodiment 133. The bispecific antibody of Embodiment 52, wherein the heavy chain sequence comprises a sequence having at least 95% sequence identity to the amino acid sequence of SEQ ID NO: 94; and the light chain sequence comprises a sequence having at least 80% sequence identity to the amino acid sequence of SEQ ID NO: 241.

Embodiment 134. The bispecific antibody of Embodiment 52, wherein the heavy chain sequence comprises a sequence having at least 95% sequence identity to the amino acid sequence of SEQ ID NO: 95; and the light chain sequence comprises a sequence having at least 80% sequence identity to the amino acid sequence of SEQ ID NO: 242.

Embodiment 135. The bispecific antibody of Embodiment 52, wherein the heavy chain sequence comprises a sequence having at least 95% sequence identity to the amino acid sequence of SEQ ID NO: 96; and the light chain sequence comprises a sequence having at least 80% sequence identity to the amino acid sequence of SEQ ID NO: 243.

Embodiment 136. The bispecific antibody of Embodiment 52, wherein the heavy chain sequence comprises a sequence having at least 95% sequence identity to the amino acid sequence of SEQ ID NO: 97; and the light chain sequence comprises a sequence having at least 80% sequence identity to the amino acid sequence of SEQ ID NO: 244.

Embodiment 137. The bispecific antibody of Embodiment 52, wherein the heavy chain sequence comprises a sequence having at least 95% sequence identity to the amino acid sequence of SEQ ID NO: 130; and the light chain sequence comprises a sequence having at least 80% sequence identity to the amino acid sequence of SEQ ID NO: 277.

Embodiment 138. The bispecific antibody of Embodiment 52, wherein the heavy chain sequence comprises a sequence having at least 95% sequence identity to the amino acid sequence of SEQ ID NO: 131; and the light chain sequence comprises a sequence having at least 80% sequence identity to the amino acid sequence of SEQ ID NO: 278.

Embodiment 139. The bispecific antibody of Embodiment 52, wherein the heavy chain sequence comprises a sequence having at least 95% sequence identity to the amino acid sequence of SEQ ID NO: 132; and the light chain sequence comprises a sequence having at least 80% sequence identity to the amino acid sequence of SEQ ID NO: 279.

Embodiment 140. The bispecific antibody of Embodiment 52, wherein the heavy chain sequence comprises a sequence having at least 95% sequence identity to the amino acid sequence of SEQ ID NO: 133; and the light chain sequence comprises a sequence having at least 80% sequence identity to the amino acid sequence of SEQ ID NO: 280.

Embodiment 141. The bispecific antibody of Embodiment 52, wherein the heavy chain sequence comprises a sequence having at least 95% sequence identity to the amino acid sequence of SEQ ID NO: 134; and the light chain sequence comprises a sequence having at least 80% sequence identity to the amino acid sequence of SEQ ID NO: 281.

Embodiment 142. The bispecific antibody of Embodiment 52, wherein the heavy chain sequence comprises a sequence having at least 95% sequence identity to the amino acid sequence of SEQ ID NO: 135; and the light chain sequence comprises a sequence having at least 80% sequence identity to the amino acid sequence of SEQ ID NO: 282.

Embodiment 143. The bispecific antibody of Embodiment 52, wherein the heavy chain sequence comprises a sequence having at least 95% sequence identity to the amino acid sequence of SEQ ID NO: 136; and the light chain sequence comprises a sequence having at least 80% sequence identity to the amino acid sequence of SEQ ID NO: 283.

Embodiment 144. The bispecific antibody of Embodiment 52, wherein the heavy chain sequence comprises a sequence having at least 95% sequence identity to the amino acid sequence of SEQ ID NO: 137; and the light chain sequence comprises a sequence having at least 80% sequence identity to the amino acid sequence of SEQ ID NO: 284.

Embodiment 145. The bispecific antibody of Embodiment 52, wherein the heavy chain sequence comprises a sequence having at least 95% sequence identity to the amino acid sequence of SEQ ID NO: 138; and the light chain sequence comprises a sequence having at least 80% sequence identity to the amino acid sequence of SEQ ID NO: 285.

Embodiment 146. The bispecific antibody of Embodiment 52, wherein the heavy chain sequence comprises a sequence having at least 95% sequence identity to the amino acid sequence of SEQ ID NO: 139; and the light chain sequence comprises a sequence having at least 80% sequence identity to the amino acid sequence of SEQ ID NO: 286.

Embodiment 147. The bispecific antibody of Embodiment 52, wherein the heavy chain sequence comprises a sequence having at least 95% sequence identity to the amino acid sequence of SEQ ID NO: 140; and the light chain sequence comprises a sequence having at least 80% sequence identity to the amino acid sequence of SEQ ID NO: 287.

Embodiment 148. The bispecific antibody of Embodiment 52, wherein the heavy chain sequence comprises a sequence having at least 95% sequence identity to the amino acid sequence of SEQ ID NO: 141; and the light chain sequence comprises a sequence having at least 80% sequence identity to the amino acid sequence of SEQ ID NO: 288.

Embodiment 149. The bispecific antibody of Embodiment 52, wherein the heavy chain sequence comprises a sequence having at least 95% sequence identity to the amino acid sequence of SEQ ID NO: 144; and the light chain sequence comprises a sequence having at least 80% sequence identity to the amino acid sequence of SEQ ID NO: 291.

Embodiment 150. The bispecific antibody of Embodiment 52, wherein the heavy chain sequence comprises a sequence having at least 95% sequence identity to the amino acid sequence of SEQ ID NO: 145; and the light chain sequence comprises a sequence having at least 80% sequence identity to the amino acid sequence of SEQ ID NO: 292.

Embodiment 151. The bispecific antibody of Embodiment 52, wherein the heavy chain sequence comprises a sequence having at least 95% sequence identity to the amino acid sequence of SEQ ID NO: 146; and the light chain sequence comprises a sequence having at least 80% sequence identity to the amino acid sequence of SEQ ID NO: 293.

Embodiment 152. The bispecific antibody of Embodiment 52, wherein the heavy chain sequence comprises a sequence having at least 95% sequence identity to the amino acid sequence of SEQ ID NO: 147; and the light chain sequence comprises a sequence having at least 80% sequence identity to the amino acid sequence of SEQ ID NO: 294.

Embodiment 153. The bispecific antibody of Embodiment 52, wherein the heavy chain sequence comprises a sequence having at least 95% sequence identity to the amino acid sequence of SEQ ID NO: 656; and the light chain sequence comprises a sequence having at least 80% sequence identity to the amino acid sequence of SEQ ID NO: 679.

Embodiment 154. The bispecific antibody of Embodiment 52, wherein the heavy chain sequence comprises a sequence having at least 95% sequence identity to the amino acid sequence of SEQ ID NO: 657; and the light chain sequence comprises a sequence having at least 80% sequence identity to the amino acid sequence of SEQ ID NO: 680.

Embodiment 155. The bispecific antibody of Embodiment 52, wherein the heavy chain sequence comprises a sequence having at least 95% sequence identity to the amino acid sequence of SEQ ID NO: 658; and the light chain sequence comprises a sequence having at least 80% sequence identity to the amino acid sequence of SEQ ID NO: 681.

Embodiment 156. The bispecific antibody of Embodiment 52, wherein the heavy chain sequence comprises a sequence having at least 95% sequence identity to the amino acid sequence of SEQ ID NO: 659; and the light chain sequence comprises a sequence having at least 80% sequence identity to the amino acid sequence of SEQ ID NO: 682.

Embodiment 157. The bispecific antibody of Embodiment 52, wherein the heavy chain sequence comprises a sequence having at least 95% sequence identity to the amino acid sequence of SEQ ID NO: 660; and the light chain sequence comprises a sequence having at least 80% sequence identity to the amino acid sequence of SEQ ID NO: 683.

Embodiment 158. The bispecific antibody of Embodiment 52, wherein the heavy chain sequence comprises a sequence having at least 95% sequence identity to the amino acid sequence of SEQ ID NO: 661; and the light chain sequence comprises a sequence having at least 80% sequence identity to the amino acid sequence of SEQ ID NO: 684.

Embodiment 159. The bispecific antibody of Embodiment 52, wherein the heavy chain sequence comprises a sequence having at least 95% sequence identity to the amino acid sequence of SEQ ID NO: 662; and the light chain sequence comprises a sequence having at least 80% sequence identity to the amino acid sequence of SEQ ID NO: 685.

Embodiment 160. The bispecific antibody of Embodiment 52, wherein the heavy chain sequence comprises a sequence having at least 95% sequence identity to the amino acid sequence of SEQ ID NO: 663; and the light chain sequence comprises a sequence having at least 80% sequence identity to the amino acid sequence of SEQ ID NO: 686.

Embodiment 161. The bispecific antibody of Embodiment 52, wherein the heavy chain sequence comprises a sequence having at least 95% sequence identity to the amino acid sequence of SEQ ID NO: 664; and the light chain sequence comprises a sequence having at least 80% sequence identity to the amino acid sequence of SEQ ID NO: 687.

Embodiment 162. The bispecific antibody of Embodiment 52, wherein the heavy chain sequence comprises a sequence having at least 95% sequence identity to the amino acid sequence of SEQ ID NO: 665; and the light chain sequence comprises a sequence having at least 80% sequence identity to the amino acid sequence of SEQ ID NO: 688.

Embodiment 163. The bispecific antibody of Embodiment 52, wherein the heavy chain sequence comprises a sequence having at least 95% sequence identity to the amino acid sequence of SEQ ID NO: 666; and the light chain sequence comprises a sequence having at least 80% sequence identity to the amino acid sequence of SEQ ID NO: 689.

Embodiment 164. A bispecific antibody that binds vascular endothelial growth factor (VEGF) and programmed death receptor 1 (PD-1), comprising:

a) a heavy chain sequence comprising the amino acid sequence of any one of SEQ ID NOs: 98-127 and 129; and b) a light chain sequence comprising a sequence having at least 80% sequence identity to the amino acid sequence of any one of SEQ ID NOs: 148-194, 679-701, and 714-737.

Embodiment 165. The bispecific antibody of Embodiment 164, wherein the heavy chain sequence comprises the amino acid sequence of SEQ ID NO: 98; and the light chain sequence comprises a sequence having at least 80% sequence identity to the amino acid sequence of SEQ ID NO: 245.

Embodiment 166. The bispecific antibody of Embodiment 164, wherein the heavy chain sequence comprises the amino acid sequence of SEQ ID NO: 99; and the light chain sequence comprises a sequence having at least 80% sequence identity to the amino acid sequence of SEQ ID NO: 246.

Embodiment 167. The bispecific antibody of Embodiment 164, wherein the heavy chain sequence comprises the amino acid sequence of SEQ ID NO: 100; and the light chain sequence comprises a sequence having at least 80% sequence identity to the amino acid sequence of SEQ ID NO: 247.

Embodiment 168. The bispecific antibody of Embodiment 164, wherein the heavy chain sequence comprises the amino acid sequence of SEQ ID NO: 101; and the light chain sequence comprises a sequence having at least 80% sequence identity to the amino acid sequence of SEQ ID NO: 248.

Embodiment 169. The bispecific antibody of Embodiment 164, wherein the heavy chain sequence comprises the amino acid sequence of SEQ ID NO: 102; and the light chain sequence comprises a sequence having at least 80% sequence identity to the amino acid sequence of SEQ ID NO: 249.

Embodiment 170. The bispecific antibody of Embodiment 164, wherein the heavy chain sequence comprises the amino acid sequence of SEQ ID NO: 103; and the light chain sequence comprises a sequence having at least 80% sequence identity to the amino acid sequence of SEQ ID NO: 250.

Embodiment 171. The bispecific antibody of Embodiment 164, wherein the heavy chain sequence comprises the amino acid sequence of SEQ ID NO: 104; and the light chain sequence comprises a sequence having at least 80% sequence identity to the amino acid sequence of SEQ ID NO: 251.

Embodiment 172. The bispecific antibody of Embodiment 164, wherein the heavy chain sequence comprises the amino acid sequence of SEQ ID NO: 105; and the light chain sequence comprises a sequence having at least 80% sequence identity to the amino acid sequence of SEQ ID NO: 252.

Embodiment 173. The bispecific antibody of Embodiment 164, wherein the heavy chain sequence comprises the amino acid sequence of SEQ ID NO: 106; and the light chain sequence comprises a sequence having at least 80% sequence identity to the amino acid sequence of SEQ ID NO: 253.

Embodiment 174. The bispecific antibody of Embodiment 164, wherein the heavy chain sequence comprises the amino acid sequence of SEQ ID NO: 107; and the light chain sequence comprises a sequence having at least 80% sequence identity to the amino acid sequence of SEQ ID NO: 254.

Embodiment 175. The bispecific antibody of Embodiment 164, wherein the heavy chain sequence comprises the amino acid sequence of SEQ ID NO: 108; and the light chain sequence comprises a sequence having at least 80% sequence identity to the amino acid sequence of SEQ ID NO: 255.

Embodiment 176. The bispecific antibody of Embodiment 164, wherein the heavy chain sequence comprises the amino acid sequence of SEQ ID NO: 109; and the light chain sequence comprises a sequence having at least 80% sequence identity to the amino acid sequence of SEQ ID NO: 256.

Embodiment 177. The bispecific antibody of Embodiment 164, wherein the heavy chain sequence comprises the amino acid sequence of SEQ ID NO: 110; and the light chain sequence comprises a sequence having at least 80% sequence identity to the amino acid sequence of SEQ ID NO: 257.

Embodiment 178. The bispecific antibody of Embodiment 164, wherein the heavy chain sequence comprises the amino acid sequence of SEQ ID NO: 111; and the light chain sequence comprises a sequence having at least 80% sequence identity to the amino acid sequence of SEQ ID NO: 258.

Embodiment 179. The bispecific antibody of Embodiment 164, wherein the heavy chain sequence comprises the amino acid sequence of SEQ ID NO: 112; and the light chain sequence comprises a sequence having at least 80% sequence identity to the amino acid sequence of SEQ ID NO: 259.

Embodiment 180. The bispecific antibody of Embodiment 164, wherein the heavy chain sequence comprises the amino acid sequence of SEQ ID NO: 113; and the light chain sequence comprises a sequence having at least 80% sequence identity to the amino acid sequence of SEQ ID NO: 260.

Embodiment 181. The bispecific antibody of Embodiment 164, wherein the heavy chain sequence comprises the amino acid sequence of SEQ ID NO: 114; and the light chain sequence comprises a sequence having at least 80% sequence identity to the amino acid sequence of SEQ ID NO: 261.

Embodiment 182. The bispecific antibody of Embodiment 164, wherein the heavy chain sequence comprises the amino acid sequence of SEQ ID NO: 115; and the light chain sequence comprises a sequence having at least 80% sequence identity to the amino acid sequence of SEQ ID NO: 262.

Embodiment 183. The bispecific antibody of Embodiment 164, wherein the heavy chain sequence comprises the amino acid sequence of SEQ ID NO: 116; and the light chain sequence comprises a sequence having at least 80% sequence identity to the amino acid sequence of SEQ ID NO: 263.

Embodiment 184. The bispecific antibody of Embodiment 164, wherein the heavy chain sequence comprises the amino acid sequence of SEQ ID NO: 117; and the light chain sequence comprises a sequence having at least 80% sequence identity to the amino acid sequence of SEQ ID NO: 264.

Embodiment 185. The bispecific antibody of Embodiment 164, wherein the heavy chain sequence comprises the amino acid sequence of SEQ ID NO: 118; and the light chain sequence comprises a sequence having at least 80% sequence identity to the amino acid sequence of SEQ ID NO: 265.

Embodiment 186. The bispecific antibody of Embodiment 164, wherein the heavy chain sequence comprises the amino acid sequence of SEQ ID NO: 119; and the light chain sequence comprises a sequence having at least 80% sequence identity to the amino acid sequence of SEQ ID NO: 266.

Embodiment 187. The bispecific antibody of Embodiment 164, wherein the heavy chain sequence comprises the amino acid sequence of SEQ ID NO: 120; and the light chain sequence comprises a sequence having at least 80% sequence identity to the amino acid sequence of SEQ ID NO: 267.

Embodiment 188. The bispecific antibody of Embodiment 164, wherein the heavy chain sequence comprises the amino acid sequence of SEQ ID NO: 121; and the light chain sequence comprises a sequence having at least 80% sequence identity to the amino acid sequence of SEQ ID NO: 268.

Embodiment 189. The bispecific antibody of Embodiment 164, wherein the heavy chain sequence comprises the amino acid sequence of SEQ ID NO: 122; and the light chain sequence comprises a sequence having at least 80% sequence identity to the amino acid sequence of SEQ ID NO: 269.

Embodiment 190. The bispecific antibody of Embodiment 164, wherein the heavy chain sequence comprises the amino acid sequence of SEQ ID NO: 123; and the light chain sequence comprises a sequence having at least 80% sequence identity to the amino acid sequence of SEQ ID NO: 270.

Embodiment 191. The bispecific antibody of Embodiment 164, wherein the heavy chain sequence comprises the amino acid sequence of SEQ ID NO: 124; and the light chain sequence comprises a sequence having at least 80% sequence identity to the amino acid sequence of SEQ ID NO: 271.

Embodiment 192. The bispecific antibody of Embodiment 164, wherein the heavy chain sequence comprises the amino acid sequence of SEQ ID NO: 125; and the light chain sequence comprises a sequence having at least 80% sequence identity to the amino acid sequence of SEQ ID NO: 272.

Embodiment 193. The bispecific antibody of Embodiment 164, wherein the heavy chain sequence comprises the amino acid sequence of SEQ ID NO: 126; and the light chain sequence comprises a sequence having at least 80% sequence identity to the amino acid sequence of SEQ ID NO: 273.

Embodiment 194. The bispecific antibody of Embodiment 164, wherein the heavy chain sequence comprises the amino acid sequence of SEQ ID NO: 127; and the light chain sequence comprises a sequence having at least 80% sequence identity to the amino acid sequence of SEQ ID NO: 274.

Embodiment 195. The bispecific antibody of Embodiment 164, wherein the heavy chain sequence comprises the amino acid sequence of SEQ ID NO: 129; and the light chain sequence comprises a sequence having at least 80% sequence identity to the amino acid sequence of SEQ ID NO: 276.

Embodiment 196. The bispecific antibody of any one of Embodiments 1-195, wherein the bispecific antibody is a humanized, human, or chimeric antibody.

Embodiment 197. The bispecific antibody of any one of Embodiments 1-196, wherein the bispecific antibody is a humanized antibody.

Embodiment 198. The bispecific antibody of any one of Embodiments 1-197, wherein the bispecific antibody comprises a heavy chain human constant region of a class selected from IgG, IgA, IgD, IgE, and IgM.

Embodiment 199. The bispecific antibody of Embodiment 198, wherein the human Fc region comprises a human heavy chain constant region of the class IgG and a subclass selected from IgG1, IgG2, IgG3, and IgG4.

Embodiment 200. The bispecific antibody of Embodiment 199, wherein the human Fc region comprises a human IgG1 Fc.

Embodiment 201. The bispecific antibody of Embodiment 199, wherein the human Fc region comprises a human IgG4 Fc.

Embodiment 202. The bispecific antibody of Embodiment 199, wherein the human Fc region comprises a human IgG2 Fc.

Embodiment 203. The bispecific antibody of any one of Embodiments 1-195 for use in the treatment of disease or condition.

Embodiment 204. The bispecific antibody of Embodiment 203, wherein the disease or disorder is cancer.

Embodiment 205. The bispecific antibody of Embodiment 204, wherein the cancer is a PD-1 expressing cancer.

Embodiment 206. The bispecific antibody of Embodiment 204, wherein the cancer is non-small cell lung cancer.

Embodiment 207. An isolated polynucleotide or set of polynucleotides encoding the bispecific antibody of any of Embodiments 1-195, a VH thereof, a VL thereof, a light chain thereof, a heavy chain thereof, or an antigen-binding portion thereof, and optionally, wherein the polynucleotide or set of polynucleotides comprises cDNA.

Embodiment 208. A vector or set of vectors comprising the polynucleotide or set of polynucleotides of Embodiment 207.

Embodiment 209. A host cell comprising the polynucleotide or set of polynucleotides of Embodiment 207 or the vector or set of vectors of Embodiment 208.

Embodiment 210. A method of producing an antibody, the method comprising expressing the bispecific antibody with the host cell of Embodiment 209 and isolating the expressed bispecific antibody.

Embodiment 211. A pharmaceutical composition comprising the bispecific antibody of any one of Embodiments 1-195 and a pharmaceutically acceptable excipient.

Embodiment 212. A kit comprising the bispecific antibody of any one of Embodiments 1-Embodiment 195 or a pharmaceutical composition of Embodiment 211 and instructions for use.

Embodiment 213. A method for treating a disease or condition in a mammalian subject in need thereof, the method comprising administering to the mammalian subject a therapeutically effective amount the bispecific antibody of any one of Embodiments 1-195 or a pharmaceutical composition of Embodiment 211.

Embodiment 214. The method of Embodiment 213, wherein the disease or disorder is cancer.

Embodiment 215. The method of Embodiment 214, wherein the cancer is a PD-1 expressing cancer.

Embodiment 216. The method of Embodiment 214, wherein the cancer is non-small cell lung cancer.

---

SEQUENCE LISTING

```
Sequence total quantity: 1032
SEQ ID NO: 1            moltype = AA  length = 725
FEATURE                 Location/Qualifiers
source                  1..725
                        mol_type = protein
                        organism = synthetic construct
SEQUENCE: 1
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQGLEW MGGINPSNGG TNFNEKFKNR  540
VTLTTDSSTT TAYMELKSLQ FDDTAVYYCA RRDYRFDMGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGGGTK  720
VEIKR                                                             725

SEQ ID NO: 2            moltype = AA  length = 725
FEATURE                 Location/Qualifiers
source                  1..725
                        mol_type = protein
                        organism = synthetic construct
SEQUENCE: 2
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
```

-continued

```
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQGLEW MGGINPSNGG TNFNEKFKNR  540
VTLTTDSSTT TAYMELKSLQ FDDTAVYYCA RRDYRFDMGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGGGTK  720
VEIKR                                                             725

SEQ ID NO: 3              moltype = AA  length = 725
FEATURE                   Location/Qualifiers
source                    1..725
                          mol_type = protein
                          organism = synthetic construct
SEQUENCE: 3
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVLHEALHS HYTQKSLSLS PGKGGGGSGG GGSGGGGSGG GGSQVQLVQS  480
GVEVKKPGAS VKVSCKASGY TFTNYYMYWV RQAPGQGLEW MGGINPSNGG TNFNEKFKNR  540
VTLTTDSSTT TAYMELKSLQ FDDTAVYYCA RRDYRFDMGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGGGTK  720
VEIKR                                                             725

SEQ ID NO: 4              moltype = AA  length = 725
FEATURE                   Location/Qualifiers
source                    1..725
                          mol_type = protein
                          organism = synthetic construct
SEQUENCE: 4
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQGLEW MGGINPSQGG TNFNEKFKNR  540
VTLTTDSSTT TAYMELKSLQ FDDTAVYYCA RRDYRFDLGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGGGTK  720
VEIKR                                                             725

SEQ ID NO: 5              moltype = AA  length = 725
FEATURE                   Location/Qualifiers
source                    1..725
                          mol_type = protein
                          organism = synthetic construct
SEQUENCE: 5
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQGLEW MGGINPSQGG TNFNEKFKNR  540
VTLTTDSSTT TAYMELKSLQ FDDTAVYYCA RRDYRFDLGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGGGTK  720
VEIKR                                                             725

SEQ ID NO: 6              moltype = AA  length = 725
FEATURE                   Location/Qualifiers
source                    1..725
                          mol_type = protein
                          organism = synthetic construct
SEQUENCE: 6
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
```

-continued

```
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVLHEALHS HYTQKSLSLS PGKGGGGSGG GGSGGGGSGG GGSQVQLVQS   480
GVEVKKPGAS VKVSCKASGY TFTNYYMYWV RQAPGQGLEW MGGINPSQGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                               725

SEQ ID NO: 7           moltype = AA  length = 725
FEATURE                Location/Qualifiers
source                 1..725
                       mol_type = protein
                       organism = synthetic construct
SEQUENCE: 7
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSRGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                               725

SEQ ID NO: 8           moltype = AA  length = 725
FEATURE                Location/Qualifiers
source                 1..725
                       mol_type = protein
                       organism = synthetic construct
SEQUENCE: 8
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSRGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                               725

SEQ ID NO: 9           moltype = AA  length = 725
FEATURE                Location/Qualifiers
source                 1..725
                       mol_type = protein
                       organism = synthetic construct
SEQUENCE: 9
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVLHEALHS HYTQKSLSLS PGKGGGGSGG GGSGGGGSGG GGSQVQLVQS   480
GVEVKKPGAS VKVSCKASGY TFTNYYMYWV RQAPGQGLEW MGGINPSRGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                               725

SEQ ID NO: 10          moltype = AA  length = 725
FEATURE                Location/Qualifiers
source                 1..725
                       mol_type = protein
                       organism = synthetic construct
SEQUENCE: 10
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
```

-continued

```
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQCLEW MGGINPSNGG TNFNEKFKNR   540
VTLTTDSSTT TAYMELKSLQ FDDTAVYYCA RRDYRFDMGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGCGTK   720
VEIKR                                                              725
```

```
SEQ ID NO: 11                moltype = AA  length = 725
FEATURE                      Location/Qualifiers
source                       1..725
                             mol_type = protein
                             organism = synthetic construct
SEQUENCE: 11
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQCLEW MGGINPSNGG TNFNEKFKNR   540
VTLTTDSSTT TAYMELKSLQ FDDTAVYYCA RRDYRFDMGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGCGTK   720
VEIKR                                                              725
```

```
SEQ ID NO: 12                moltype = AA  length = 725
FEATURE                      Location/Qualifiers
source                       1..725
                             mol_type = protein
                             organism = synthetic construct
SEQUENCE: 12
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVLHEALHS HYTQKSLSLS PGKGGGGSGG GGSGGGGSGG GGSQVQLVQS   480
GVEVKKPGAS VKVSCKASGY TFTNYYMYWV RQAPGQCLEW MGGINPSNGG TNFNEKFKNR   540
VTLTTDSSTT TAYMELKSLQ FDDTAVYYCA RRDYRFDMGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGCGTK   720
VEIKR                                                              725
```

```
SEQ ID NO: 13                moltype = AA  length = 725
FEATURE                      Location/Qualifiers
source                       1..725
                             mol_type = protein
                             organism = synthetic construct
SEQUENCE: 13
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQCLEW MGGINPSQGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGCGTK   720
VEIKR                                                              725
```

```
SEQ ID NO: 14                moltype = AA  length = 725
FEATURE                      Location/Qualifiers
source                       1..725
                             mol_type = protein
                             organism = synthetic construct
SEQUENCE: 14
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
```

-continued

```
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLYIT REPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSQVQLVQS    480
GVEVKKPGAS VKVSCKASGY TFTNYYMYWV RQAPGQCLEW MGGINPSQGG TNFNEKFKNR    540
VTLTTDSSTT TAYMELKSLQ FDDTAVYYCA RRDYRFDLGF DYWGQGTTVT VSSGGGGSGG    600
GGSGGGGSGG GGSEIVLTQS PATLSLSPGE RATLSCRASK GVSTSGYSYL HWYQQKPGQA    660
PRLLIYLASY LESGVPARFS GSGSGTDFTL TISSLEPEDF AVYYCQHSRD LPLTFGCGTK    720
VEIKR                                                                725

SEQ ID NO: 15           moltype = AA  length = 725
FEATURE                 Location/Qualifiers
source                  1..725
                        mol_type = protein
                        organism = synthetic construct
SEQUENCE: 15
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVLHEALHS HYTQKSLSLS PGKGGGGSGG GGSGGGGSGG GGSQVQLVQS    480
GVEVKKPGAS VKVSCKASGY TFTNYYMYWV RQAPGQCLEW MGGINPSQGG TNFNEKFKNR    540
VTLTTDSSTT TAYMELKSLQ FDDTAVYYCA RRDYRFDLGF DYWGQGTTVT VSSGGGGSGG    600
GGSGGGGSGG GGSEIVLTQS PATLSLSPGE RATLSCRASK GVSTSGYSYL HWYQQKPGQA    660
PRLLIYLASY LESGVPARFS GSGSGTDFTL TISSLEPEDF AVYYCQHSRD LPLTFGCGTK    720
VEIKR                                                                725

SEQ ID NO: 16           moltype = AA  length = 725
FEATURE                 Location/Qualifiers
source                  1..725
                        mol_type = protein
                        organism = synthetic construct
SEQUENCE: 16
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSQVQLVQS    480
GVEVKKPGAS VKVSCKASGY TFTNYYMYWV RQAPGQCLEW MGGINPSRGG TNFNEKFKNR    540
VTLTTDSSTT TAYMELKSLQ FDDTAVYYCA RRDYRFDLGF DYWGQGTTVT VSSGGGGSGG    600
GGSGGGGSGG GGSEIVLTQS PATLSLSPGE RATLSCRASK GVSTSGYSYL HWYQQKPGQA    660
PRLLIYLASY LESGVPARFS GSGSGTDFTL TISSLEPEDF AVYYCQHSRD LPLTFGCGTK    720
VEIKR                                                                725

SEQ ID NO: 17           moltype = AA  length = 725
FEATURE                 Location/Qualifiers
source                  1..725
                        mol_type = protein
                        organism = synthetic construct
SEQUENCE: 17
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLYIT REPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSQVQLVQS    480
GVEVKKPGAS VKVSCKASGY TFTNYYMYWV RQAPGQCLEW MGGINPSRGG TNFNEKFKNR    540
VTLTTDSSTT TAYMELKSLQ FDDTAVYYCA RRDYRFDLGF DYWGQGTTVT VSSGGGGSGG    600
GGSGGGGSGG GGSEIVLTQS PATLSLSPGE RATLSCRASK GVSTSGYSYL HWYQQKPGQA    660
PRLLIYLASY LESGVPARFS GSGSGTDFTL TISSLEPEDF AVYYCQHSRD LPLTFGCGTK    720
VEIKR                                                                725

SEQ ID NO: 18           moltype = AA  length = 725
FEATURE                 Location/Qualifiers
source                  1..725
                        mol_type = protein
                        organism = synthetic construct
SEQUENCE: 18
EVQLVESGGG LVQPGGSLRL SCAASGYTFT NYGMNWVRQA PGKGLEWVGW INTYTGEPTY    60
```

-continued

```
AADFKRRFTF SLDTSKSTAY LQMNSLRAED TAVYYCAKYP HYYGSSHWYF DVWGQGTLVT    120
VSSSASTKGPS VFPLAPSSKS TSGGTAALGC LVKDYFPEPV TVSWNSGALT SGVHTFPAVL    180
QSSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVLHEALHS HYTQKSLSLS PGKGGGGSGG GGSGGGGSGG GGSQVQLVQS    480
GVEVKKPGAS VKVSCKASGY TFTNYYMYWV RQAPGQCLEW MGGINPSRGG TNFNEKFKNR    540
VTLTTDSSTT TAYMELKSLQ FDDTAVYYCA RRDYRFDLGF DYWGQGTTVT VSSGGGGSGG    600
GGSGGGGSGG GGSEIVLTQS PATLSLSPGE RATLSCRASK GVSTSGYSYL HWYQQKPGQA    660
PRLLIYLASY LESGVPARFS GSGSGTDFTL TISSLEPEDF AVYYCQHSRD LPLTFGCGTK    720
VEIKR                                                                725

SEQ ID NO: 19              moltype = AA  length = 726
FEATURE                    Location/Qualifiers
source                     1..726
                           mol_type = protein
                           organism = synthetic construct
SEQUENCE: 19
EVQLVESGGG LVQPGGSLRL SCAASGYTFT NYGMNWVRQA PGKGLEWVGW INTYTGEPTY     60
AADFKRRFTF SLDTSKSTAY LQMNSLRAED TAVYYCAKYP HYYGSSHWYF DVWGQGTLVT    120
VSSSASTKGPS VFPLAPSSKS TSGGTAALGC LVKDYFPEPV TVSWNSGALT SGVHTFPAVL    180
QSSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSEIVLTQS    480
PATLSLSPGE RATLSCRASK GVSTSGYSYL HWYQQKPGQA PRLLIYLASY LESGVPARFS    540
GSGSGTDFTL TISSLEPEDF AVYYCQHSRD LPLTFGGGTK VEIKSSGGGG SGGGGSGGGG    600
SGGGGSQVQL VQSGVEVKKP GASVKVSCKA SGYTFTNYYM YWVRQAPGQG LEWMGGINPS    660
QGGTNFNEKF KNRVTLTTDS STTTAYMELK SLQFDDTAVY YCARRDYRFD LGFDYWGQGT    720
TVTVSS                                                                726

SEQ ID NO: 20              moltype = AA  length = 726
FEATURE                    Location/Qualifiers
source                     1..726
                           mol_type = protein
                           organism = synthetic construct
SEQUENCE: 20
EVQLVESGGG LVQPGGSLRL SCAASGYTFT NYGMNWVRQA PGKGLEWVGW INTYTGEPTY     60
AADFKRRFTF SLDTSKSTAY LQMNSLRAED TAVYYCAKYP HYYGSSHWYF DVWGQGTLVT    120
VSSSASTKGPS VFPLAPSSKS TSGGTAALGC LVKDYFPEPV TVSWNSGALT SGVHTFPAVL    180
QSSSGLYSLSS VVTVPSSSLG TQTYICNVNH KPSNTKVDKK VEPKSCDKTH TCPPCPAPEA    240
AGGPSVFLFP PKPKDTLYIT REPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSEIVLTQS    480
PATLSLSPGE RATLSCRASK GVSTSGYSYL HWYQQKPGQA PRLLIYLASY LESGVPARFS    540
GSGSGTDFTL TISSLEPEDF AVYYCQHSRD LPLTFGGGTK VEIKSSGGGG SGGGGSGGGG    600
SGGGGSQVQL VQSGVEVKKP GASVKVSCKA SGYTFTNYYM YWVRQAPGQG LEWMGGINPS    660
QGGTNFNEKF KNRVTLTTDS STTTAYMELK SLQFDDTAVY YCARRDYRFD LGFDYWGQGT    720
TVTVSS                                                                726

SEQ ID NO: 21              moltype = AA  length = 724
FEATURE                    Location/Qualifiers
source                     1..724
                           mol_type = protein
                           organism = synthetic construct
SEQUENCE: 21
EVQLVESGGG LVQPGGSLRL SCAASGYTFT NYGMNWVRQA PGKGLEWVGW INTYTGEPTY     60
AADFKRRFTF SLDTSKSTAY LQMNSLRAED TAVYYCAKYP HYYGSSHWYF DVWGQGTLVT    120
VSSSASTKGPS VFPLAPSSKS TSGGTAALGC LVKDYFPEPV TVSWNSGALT SGVHTFPAVL    180
QSSSGLYSLSS VVTVPSSSLG TQTYICNVNH KPSNTKVDKK VEPKSCDKTH TCPPCPAPEA    240
AGGPSVFLFP PKPKDTLYIT REPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSEIVLTQS    480
PATLSLSPGE RATLSCRASK GVSTSGYSYL HWYQQKPGQA PRLLIYLASY LESGVPARFS    540
GSGSGTDFTL TISSLEPEDF AVYYCQHSRD LPLTFGCGTK VEIKGGGGSG GGGSGGGGSG    600
GGGSQVQLVQ SGVEVKKPGA SVKVSCKASG YTFTNYYMYW VRQAPGQCLE WMGGINPSQG    660
GTNFNEKFKN RVTLTTDSST TTAYMELKSL QFDDTAVYYC ARRDYRFDLG FDYWGQGTTV    720
TVSS                                                                  724

SEQ ID NO: 22              moltype = AA  length = 725
FEATURE                    Location/Qualifiers
source                     1..725
                           mol_type = protein
                           organism = synthetic construct
SEQUENCE: 22
```

```
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLVES   480
GGGLVQPGGS LRLSCAASGY TFTNYYMYWV RQAPGKGLEW MGGINPSQGG TNFNEKFKNR   540
FTISRDNSKN TLYLQMNSLR AEDTAVYYCA RRDYRFDLGF DYWGQGTLVT VSSGGGGSGG   600
GGSGGGGSGG GGSEIVLTQS PATLSVSPGE RATLSCRASK GVSTSGYSYL HWYQQKPGQA   660
PRLLIYLASY LESGIPARFS GSGSGTEFTL TISSLQSEDF AVYYCQHSRD LPLTFGGGTK   720
VEIKR                                                              725

SEQ ID NO: 23           moltype = AA  length = 725
FEATURE                 Location/Qualifiers
source                  1..725
                        mol_type = protein
                        organism = synthetic construct
SEQUENCE: 23
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLVES   480
GGGLVQPGGS LRLSCAASGY TFTNYYMYWV RQAPGKCLEW MGGINPSQGG TNFNEKFKNR   540
FTISRDNSKN TLYLQMNSLR AEDTAVYYCA RRDYRFDLGF DYWGQGTLVT VSSGGGGSGG   600
GGSGGGGSGG GGSEIVLTQS PATLSVSPGE RATLSCRASK GVSTSGYSYL HWYQQKPGQA   660
PRLLIYLASY LESGIPARFS GSGSGTEFTL TISSLQSEDF AVYYCQHSRD LPLTFGCGTK   720
VEIKR                                                              725

SEQ ID NO: 24           moltype = AA  length = 725
FEATURE                 Location/Qualifiers
source                  1..725
                        mol_type = protein
                        organism = synthetic construct
SEQUENCE: 24
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSQGG TNFNEKFKNR   540
VTLTTDSSTT TAYMELKSLQ FDDTAVYYCA RRDYRFDLGF DYWGQGTVR VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                              725

SEQ ID NO: 25           moltype = AA  length = 725
FEATURE                 Location/Qualifiers
source                  1..725
                        mol_type = protein
                        organism = synthetic construct
SEQUENCE: 25
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQCLEW MGGINPSQGG TNFNEKFKNR   540
VTLTTDSSTT TAYMELKSLQ FDDTAVYYCA RRDYRFDLGF DYWGQGTVR VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGCGTK   720
VEIKR                                                              725

SEQ ID NO: 26           moltype = AA  length = 725
FEATURE                 Location/Qualifiers
source                  1..725
                        mol_type = protein
                        organism = synthetic construct
```

```
SEQUENCE: 26
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSNGG TNFNEKFKNR   540
VTLTTDSSTT TAYMELKSLR FDDTAVYYCA RRDYRFDMGF DYWGQGTTVT VSSGGGGSGG   600
GGSGGGGSGG GGSEIVLTQS PSTLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                              725

SEQ ID NO: 27         moltype = AA   length = 725
FEATURE               Location/Qualifiers
source                1..725
                      mol_type = protein
                      organism = synthetic construct
SEQUENCE: 27
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSNGG TNFNEKFKNR   540
VTLTTDSSTT TAYMELKSLR FDDTAVYYCA RRDYRFDMGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                              725

SEQ ID NO: 28         moltype = AA   length = 725
FEATURE               Location/Qualifiers
source                1..725
                      mol_type = protein
                      organism = synthetic construct
SEQUENCE: 28
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSNGG TNFNEKFKNR   540
VTLTTDSSTT TAYMELKSLR FDDTAVYYCA RRDYRFDMGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                              725

SEQ ID NO: 29         moltype = AA   length = 725
FEATURE               Location/Qualifiers
source                1..725
                      mol_type = protein
                      organism = synthetic construct
SEQUENCE: 29
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSNGG TNFNEKFKNR   540
VTLTTDSSTT TAYMELKSLR FDDTAVYYCA RRDYRFDMGF DYWGQGTTVT VSSGGGGSGG   600
GGSGGGGSGG GGSEIVLTQS PSTLSLSPGE RATLSCRASK GVSTSGYSYL HWYQQKPGQA   660
PRLLIYLASY LESGVPARFS GSGSGTDFTL TISGLEPEDF AVYYCQHSRD LPLTFGGGTK   720
VEIKR                                                              725

SEQ ID NO: 30         moltype = AA   length = 725
FEATURE               Location/Qualifiers
source                1..725
                      mol_type = protein
```

-continued

```
                          organism = synthetic construct
SEQUENCE: 30
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSNGG TNFNEKFKNR   540
VTLTTDSSTT TAYMELKSLQ FDDTAVYYCA RRDYRFDMGF DYWGQGTTVT VSSGGGGSGG   600
GGSGGGGSGG GGSEIVLTQS PSTLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                             725

SEQ ID NO: 31             moltype = AA  length = 725
FEATURE                   Location/Qualifiers
source                    1..725
                          mol_type = protein
                          organism = synthetic construct
SEQUENCE: 31
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSNGG TNFNEKFKNR   540
VTLTTDSSTT TAYMELKSLQ FDDTAVYYCA RRDYRFDMGF DYWGQGTTVT VSSGGGGSGG   600
GGSGGGGSGG GGSEIVLTQS PSTLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                             725

SEQ ID NO: 32             moltype = AA  length = 725
FEATURE                   Location/Qualifiers
source                    1..725
                          mol_type = protein
                          organism = synthetic construct
SEQUENCE: 32
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSNGG TNFNEKFKNR   540
VTLTTDSSTT TAYMELKSLQ FDDTAVYYCA RRDYRFDMGF DYWGQGTTVT VSSGGGGSGG   600
GGSGGGGSGG GGSEIVLTQS PSTLSLSPGE RATLSCRASK GVSTSGYSYL HWYQQKPGQA   660
PRLLIYLASY LESGVPARFS GSGSGTDFTL TISGLEPEDF AVYYCQHSRD LPLTFGGGTK   720
VEIKR                                                             725

SEQ ID NO: 33             moltype = AA  length = 725
FEATURE                   Location/Qualifiers
source                    1..725
                          mol_type = protein
                          organism = synthetic construct
SEQUENCE: 33
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSQGG TNFNEKFKNR   540
VTLTTDSSTT TAYMELKSLR FDDTAVYYCA RRDYRFDLGF DYWGQGTTVT VSSGGGGSGG   600
GGSGGGGSGG GGSEIVLTQS PSTLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                             725

SEQ ID NO: 34             moltype = AA  length = 725
FEATURE                   Location/Qualifiers
source                    1..725
```

```
                             mol_type = protein
                             organism = synthetic construct
        SEQUENCE: 34
        EVQLVESGGG LVQPGGSLRL SCAASGYTFT NYGMNWVRQA PGKGLEWVGW INTYTGEPTY  60
        AADFKRRFTF SLDTSKSTAY LQMNSLRAED TAVYYCAKYP HYYGSSHWYF DVWGQGTLVT  120
        VSSSASTKGPS VFPLAPSSKS TSGGTAALGC LVKDYFPEPV TVSWNSGALT SGVHTFPAVL  180
        QSSGLYSLSS VVTVPSSSLG TQTYICNVNH KPSNTKVDKK VEPKSCDKTH TCPPCPAPEA  240
        AGGPSVFLFP PKPKDTLYIT REPEVTCVVV DVSHEDPEVK FNWYVDGVEV HNAKTKPREE  300
        QYNSTYRVVS VLTVLHQDWL NGKEYKCKVS NKALPAPIEK TISKAKGQPR EPQVYTLPPS  360
        RDELTKNQVS LTCLVKGFYP SDIAVEWESN GQPENNYKTT PPVLDSDGSF FLYSKLTVDK  420
        SRWQQGNVFS CSVMHEALHN HYTQKSLSLS PGKGGGGSGG GGSGGGGSGG GGSQVQLVQS  480
        GVEVKKPGAS VKVSCKASGY TFTNYYMYWV RQAPGQGLEW MGGINPSQGG TNFNEKFKNR  540
        VTLTTDSSTT TAYMELKSLR FDDTAVYYCA RRDYRFDLGF DYWGQGTTVT VSSGGGGSGG  600
        GGSGGGGSGG GGSEIVLTQS PATLSLSPGE RATLSCRASK GVSTSGYSYL HWYQQKPGQA  660
        PRLLIYLASY LESGVPARFS GSGSGTDFTL TISSLEPEDF AVYYCQHSRD LPLTFGGGTK  720
        VEIKR                                                              725

SEQ ID NO: 35          moltype = AA   length = 725
        FEATURE                Location/Qualifiers
        source                 1..725
                               mol_type = protein
                               organism = synthetic construct
        SEQUENCE: 35
        EVQLVESGGG LVQPGGSLRL SCAASGYTFT NYGMNWVRQA PGKGLEWVGW INTYTGEPTY  60
        AADFKRRFTF SLDTSKSTAY LQMNSLRAED TAVYYCAKYP HYYGSSHWYF DVWGQGTLVT  120
        VSSSASTKGPS VFPLAPSSKS TSGGTAALGC LVKDYFPEPV TVSWNSGALT SGVHTFPAVL  180
        QSSGLYSLSS VVTVPSSSLG TQTYICNVNH KPSNTKVDKK VEPKSCDKTH TCPPCPAPEA  240
        AGGPSVFLFP PKPKDTLYIT REPEVTCVVV DVSHEDPEVK FNWYVDGVEV HNAKTKPREE  300
        QYNSTYRVVS VLTVLHQDWL NGKEYKCKVS NKALPAPIEK TISKAKGQPR EPQVYTLPPS  360
        RDELTKNQVS LTCLVKGFYP SDIAVEWESN GQPENNYKTT PPVLDSDGSF FLYSKLTVDK  420
        SRWQQGNVFS CSVMHEALHN HYTQKSLSLS PGKGGGGSGG GGSGGGGSGG GGSQVQLVQS  480
        GVEVKKPGAS VKVSCKASGY TFTNYYMYWV RQAPGQGLEW MGGINPSQGG TNFNEKFKNR  540
        VTLTTDSSTT TAYMELKSLR FDDTAVYYCA RRDYRFDLGF DYWGQGTTVT VSSGGGGSGG  600
        GGSGGGGSGG GGSEIVLTQS PSTLSLSPGE RATLSCRASK GVSTSGYSYL HWYQQKPGQA  660
        PRLLIYLASY LESGVPARFS GSGSGTDFTL TISGLEPEDF AVYYCQHSRD LPLTFGGGTK  720
        VEIKR                                                              725

SEQ ID NO: 36          moltype = AA   length = 725
        FEATURE                Location/Qualifiers
        source                 1..725
                               mol_type = protein
                               organism = synthetic construct
        SEQUENCE: 36
        EVQLVESGGG LVQPGGSLRL SCAASGYTFT NYGMNWVRQA PGKGLEWVGW INTYTGEPTY  60
        AADFKRRFTF SLDTSKSTAY LQMNSLRAED TAVYYCAKYP HYYGSSHWYF DVWGQGTLVT  120
        VSSSASTKGPS VFPLAPSSKS TSGGTAALGC LVKDYFPEPV TVSWNSGALT SGVHTFPAVL  180
        QSSGLYSLSS VVTVPSSSLG TQTYICNVNH KPSNTKVDKK VEPKSCDKTH TCPPCPAPEA  240
        AGGPSVFLFP PKPKDTLYIT REPEVTCVVV DVSHEDPEVK FNWYVDGVEV HNAKTKPREE  300
        QYNSTYRVVS VLTVLHQDWL NGKEYKCKVS NKALPAPIEK TISKAKGQPR EPQVYTLPPS  360
        RDELTKNQVS LTCLVKGFYP SDIAVEWESN GQPENNYKTT PPVLDSDGSF FLYSKLTVDK  420
        SRWQQGNVFS CSVMHEALHN HYTQKSLSLS PGKGGGGSGG GGSGGGGSGG GGSQVQLVQS  480
        GVEVKKPGAS VKVSCKASGY TFTNYYMYWV RQAPGQGLEW MGGINPSQGG TNFNEKFKNR  540
        VTLTTDSSTT TAYMELKSLQ FDDTAVYYCA RRDYRFDLGF DYWGQGTTVT VSSGGGGSGG  600
        GGSGGGGSGG GGSEIVLTQS PSTLSLSPGE RATLSCRASK GVSTSGYSYL HWYQQKPGQA  660
        PRLLIYLASY LESGVPARFS GSGSGTDFTL TISGLEPEDF AVYYCQHSRD LPLTFGGGTK  720
        VEIKR                                                              725

SEQ ID NO: 37          moltype = AA   length = 725
        FEATURE                Location/Qualifiers
        source                 1..725
                               mol_type = protein
                               organism = synthetic construct
        SEQUENCE: 37
        EVQLVESGGG LVQPGGSLRL SCAASGYTFT NYGMNWVRQA PGKGLEWVGW INTYTGEPTY  60
        AADFKRRFTF SLDTSKSTAY LQMNSLRAED TAVYYCAKYP HYYGSSHWYF DVWGQGTLVT  120
        VSSSASTKGPS VFPLAPSSKS TSGGTAALGC LVKDYFPEPV TVSWNSGALT SGVHTFPAVL  180
        QSSGLYSLSS VVTVPSSSLG TQTYICNVNH KPSNTKVDKK VEPKSCDKTH TCPPCPAPEA  240
        AGGPSVFLFP PKPKDTLYIT REPEVTCVVV DVSHEDPEVK FNWYVDGVEV HNAKTKPREE  300
        QYNSTYRVVS VLTVLHQDWL NGKEYKCKVS NKALPAPIEK TISKAKGQPR EPQVYTLPPS  360
        RDELTKNQVS LTCLVKGFYP SDIAVEWESN GQPENNYKTT PPVLDSDGSF FLYSKLTVDK  420
        SRWQQGNVFS CSVMHEALHN HYTQKSLSLS PGKGGGGSGG GGSGGGGSGG GGSQVQLVQS  480
        GVEVKKPGAS VKVSCKASGY TFTNYYMYWV RQAPGQGLEW MGGINPSQGG TNFNEKFKNR  540
        VTLTTDSSTT TAYMELKSLQ FDDTAVYYCA RRDYRFDLGF DYWGQGTTVT VSSGGGGSGG  600
        GGSGGGGSGG GGSEIVLTQS PSTLSLSPGE RATLSCRASK GVSTSGYSYL HWYQQKPGQA  660
        PRLLIYLASY LESGVPARFS GSGSGTDFTL TISGLEPEDF AVYYCQHSRD LPLTFGGGTK  720
        VEIKR                                                              725

SEQ ID NO: 38          moltype = AA   length = 725
        FEATURE                Location/Qualifiers
```

```
source                  1..725
                        mol_type = protein
                        organism = synthetic construct
SEQUENCE: 38
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSRGG TNFNEKFKNR   540
VTLTTDSSTT TAYMELKSLR FDDTAVYYCA RRDYRFDLGF DYWGQGTTVT VSSGGGGSGG   600
GGSGGGGSGG GGSEIVLTQS PSTLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                               725

SEQ ID NO: 39            moltype = AA   length = 725
FEATURE                  Location/Qualifiers
source                   1..725
                         mol_type = protein
                         organism = synthetic construct
SEQUENCE: 39
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSRGG TNFNEKFKNR   540
VTLTTDSSTT TAYMELKSLR FDDTAVYYCA RRDYRFDLGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                               725

SEQ ID NO: 40            moltype = AA   length = 725
FEATURE                  Location/Qualifiers
source                   1..725
                         mol_type = protein
                         organism = synthetic construct
SEQUENCE: 40
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSRGG TNFNEKFKNR   540
VTLTTDSSTT TAYMELKSLR FDDTAVYYCA RRDYRFDLGF DYWGQGTTVT VSSGGGGSGG   600
GGSGGGGSGG GGSEIVLTQS PSTLSLSPGE RATLSCRASK GVSTSGYSYL HWYQQKPGQA   660
PRLLIYLASY LESGVPARFS GSGSGTDFTL TISGLEPEDF AVYYCQHSRD LPLTFGGGTK   720
VEIKR                                                               725

SEQ ID NO: 41            moltype = AA   length = 725
FEATURE                  Location/Qualifiers
source                   1..725
                         mol_type = protein
                         organism = synthetic construct
SEQUENCE: 41
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSRGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSEIVLTQS PSTLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                               725

SEQ ID NO: 42            moltype = AA   length = 725
```

-continued

```
FEATURE            Location/Qualifiers
source             1..725
                   mol_type = protein
                   organism = synthetic construct
        SEQUENCE: 42
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT 120
VSSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEA 240
AGGPSVFLFP PKPKDTLYIT REPEVTCVVV DVSHEDPEVK FNWYVDGVEV HNAKTKPREE 300
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVMHEALHN HYTQKSLSLS PGKGGGGSGG GGSGGGGSGG GGSQVQLVQS 480
GVEVKKPGAS VKVSCKASGY TFTNYYMYWV RQAPGQGLEW MGGINPSRGG TNFNEKFKNR 540
VTLTTDSSTT TAYMELKSLQ FDDTAVYYCA RRDYRFDLGF DYWGQGTTVT VSSGGGGSGG 600
GGSGGGGSGG GGSEIVLTQS PSTLSLSPGE RATLSCRASK GVSTSGYSYL HWYQQKPGQA 660
PRLLIYLASY LESGVPARFS GSGSGTDFTL TISGLEPEDF AVYYCQHSRD LPLTFGGGTK 720
VEIKR                                                            725
```

```
SEQ ID NO: 43        moltype = AA  length = 725
FEATURE              Location/Qualifiers
source               1..725
                     mol_type = protein
                     organism = synthetic construct
        SEQUENCE: 43
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT 120
VSSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEA 240
AGGPSVFLFP PKPKDTLYIT REPEVTCVVV DVSHEDPEVK FNWYVDGVEV HNAKTKPREE 300
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVMHEALHN HYTQKSLSLS PGKGGGGSGG GGSGGGGSGG GGSQVQLVQS 480
GVEVKKPGAS VKVSCKASGY TFTNYYMYWV RQAPGQCLEW MGGINPSNGG TNFNEKFKNR 540
VTLTTDSSTT TAYMELKSLR FDDTAVYYCA RRDYRFDMGF DYWGQGTTVT VSSGGGGSGG 600
GGSGGGGSGG GGSEIVLTQS PSTLSLSPGE RATLSCRASK GVSTSGYSYL HWYQQKPGQA 660
PRLLIYLASY LESGVPARFS GSGSGTDFTL TISSLEPEDF AVYYCQHSRD LPLTFGCGTK 720
VEIKR                                                            725
```

```
SEQ ID NO: 44        moltype = AA  length = 725
FEATURE              Location/Qualifiers
source               1..725
                     mol_type = protein
                     organism = synthetic construct
        SEQUENCE: 44
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT 120
VSSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEA 240
AGGPSVFLFP PKPKDTLYIT REPEVTCVVV DVSHEDPEVK FNWYVDGVEV HNAKTKPREE 300
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVMHEALHN HYTQKSLSLS PGKGGGGSGG GGSGGGGSGG GGSQVQLVQS 480
GVEVKKPGAS VKVSCKASGY TFTNYYMYWV RQAPGQCLEW MGGINPSNGG TNFNEKFKNR 540
VTLTTDSSTT TAYMELKSLR FDDTAVYYCA RRDYRFDMGF DYWGQGTTVT VSSGGGGSGG 600
GGSGGGGSGG GGSEIVLTQS PATLSLSPGE RATLSCRASK GVSTSGYSYL HWYQQKPGQA 660
PRLLIYLASY LESGVPARFS GSGSGTDFTL TISSLEPEDF AVYYCQHSRD LPLTFGCGTK 720
VEIKR                                                            725
```

```
SEQ ID NO: 45        moltype = AA  length = 725
FEATURE              Location/Qualifiers
source               1..725
                     mol_type = protein
                     organism = synthetic construct
        SEQUENCE: 45
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT 120
VSSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEA 240
AGGPSVFLFP PKPKDTLYIT REPEVTCVVV DVSHEDPEVK FNWYVDGVEV HNAKTKPREE 300
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVMHEALHN HYTQKSLSLS PGKGGGGSGG GGSGGGGSGG GGSQVQLVQS 480
GVEVKKPGAS VKVSCKASGY TFTNYYMYWV RQAPGQCLEW MGGINPSNGG TNFNEKFKNR 540
VTLTTDSSTT TAYMELKSLR FDDTAVYYCA RRDYRFDMGF DYWGQGTTVT VSSGGGGSGG 600
GGSGGGGSGG GGSEIVLTQS PSTLSLSPGE RATLSCRASK GVSTSGYSYL HWYQQKPGQA 660
PRLLIYLASY LESGVPARFS GSGSGTDFTL TISGLEPEDF AVYYCQHSRD LPLTFGCGTK 720
VEIKR                                                            725
```

-continued

```
SEQ ID NO: 46          moltype = AA  length = 725
FEATURE                Location/Qualifiers
source                 1..725
                       mol_type = protein
                       organism = synthetic construct
SEQUENCE: 46
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSNGG TNFNEKFKNR  540
VTLTTDSSTT TAYMELKSLQ FDDTAVYYCA RRDYRFDMGF DYWGQGTTVT VSSGGGGSGG  600
GGSGGGGSGG GGSEIVLTQS PSTLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGCGTK  720
VEIKR                                                              725

SEQ ID NO: 47          moltype = AA  length = 725
FEATURE                Location/Qualifiers
source                 1..725
                       mol_type = protein
                       organism = synthetic construct
SEQUENCE: 47
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSNGG TNFNEKFKNR  540
VTLTTDSSTT TAYMELKSLQ FDDTAVYYCA RRDYRFDMGF DYWGQGTTVT VSSGGGGSGG  600
GGSGGGGSGG GGSEIVLTQS PSTLSLSPGE RATLSCRASK GVSTSGYSYL HWYQQKPGQA  660
PRLLIYLASY LESGVPARFS GSGSGTDFTL TISGLEPEDF AVYYCQHSRD LPLTFGCGTK  720
VEIKR                                                              725

SEQ ID NO: 48          moltype = AA  length = 725
FEATURE                Location/Qualifiers
source                 1..725
                       mol_type = protein
                       organism = synthetic construct
SEQUENCE: 48
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSNGG TNFNEKFKNR  540
VTLTTDSSTT TAYMELKSLR FDDTAVYYCA RRDYRFDLGF DYWGQGTTVT VSSGGGGSGG  600
GGSGGGGSGG GGSEIVLTQS PSTLSLSPGE RATLSCRASK GVSTSGYSYL HWYQQKPGQA  660
PRLLIYLASY LESGVPARFS GSGSGTDFTL TISGLEPEDF AVYYCQHSRD LPLTFGCGTK  720
VEIKR                                                              725

SEQ ID NO: 49          moltype = AA  length = 725
FEATURE                Location/Qualifiers
source                 1..725
                       mol_type = protein
                       organism = synthetic construct
SEQUENCE: 49
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSQGG TNFNEKFKNR  540
VTLTTDSSTT TAYMELKSLR FDDTAVYYCA RRDYRFDLGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISGLEPEDF AVYYCQHSRD LPLTFGCGTK  720
VEIKR                                                              725
```

-continued

```
SEQ ID NO: 50           moltype = AA  length = 725
FEATURE                 Location/Qualifiers
source                  1..725
                        mol_type = protein
                        organism = synthetic construct
SEQUENCE: 50
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSQGG TNFNEKFKNR  540
VTLTTDSSTT TAYMELKSLR FDDTAVYYCA RRDYRFDLGF DYWGQGTTVT VSSGGGGSGG  600
GGSGGGGSGG GGSEIVLTQS PSTLSLSPGE RATLSCRASK GVSTSGYSYL HWYQQKPGQA  660
PRLLIYLASY LESGVPARFS GSGSGTDFTL TISGLEPEDF AVYYCQHSRD LPLTFGCGTK  720
VEIKR                                                             725

SEQ ID NO: 51           moltype = AA  length = 725
FEATURE                 Location/Qualifiers
source                  1..725
                        mol_type = protein
                        organism = synthetic construct
SEQUENCE: 51
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSQGG TNFNEKFKNR  540
VTLTTDSSTT TAYMELKSLQ FDDTAVYYCA RRDYRFDLGF DYWGQGTTVT VSSGGGGSGG  600
GGSGGGGSGG GGSEIVLTQS PSTLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGCGTK  720
VEIKR                                                             725

SEQ ID NO: 52           moltype = AA  length = 725
FEATURE                 Location/Qualifiers
source                  1..725
                        mol_type = protein
                        organism = synthetic construct
SEQUENCE: 52
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSQGG TNFNEKFKNR  540
VTLTTDSSTT TAYMELKSLQ FDDTAVYYCA RRDYRFDLGF DYWGQGTTVT VSSGGGGSGG  600
GGSGGGGSGG GGSEIVLTQS PSTLSLSPGE RATLSCRASK GVSTSGYSYL HWYQQKPGQA  660
PRLLIYLASY LESGVPARFS GSGSGTDFTL TISGLEPEDF AVYYCQHSRD LPLTFGCGTK  720
VEIKR                                                             725

SEQ ID NO: 53           moltype = AA  length = 725
FEATURE                 Location/Qualifiers
source                  1..725
                        mol_type = protein
                        organism = synthetic construct
SEQUENCE: 53
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSRGG TNFNEKFKNR  540
VTLTTDSSTT TAYMELKSLR FDDTAVYYCA RRDYRFDLGF DYWGQGTTVT VSSGGGGSGG  600
GGSGGGGSGG GGSEIVLTQS PSTLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGCGTK  720
```

-continued

```
VEIKR                                                                 725

SEQ ID NO: 54          moltype = AA  length = 725
FEATURE                Location/Qualifiers
source                 1..725
                       mol_type = protein
                       organism = synthetic construct
SEQUENCE: 54
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSRGG TNFNEKFKNR  540
VTLTTDSSTT TAYMELKSLR FDDTAVYYCA RRDYRFDLGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGCGTK  720
VEIKR                                                               725

SEQ ID NO: 55          moltype = AA  length = 725
FEATURE                Location/Qualifiers
source                 1..725
                       mol_type = protein
                       organism = synthetic construct
SEQUENCE: 55
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSRGG TNFNEKFKNR  540
VTLTTDSSTT TAYMELKSLR FDDTAVYYCA RRDYRFDLGF DYWGQGTTVT VSSGGGGSGG  600
GGSGGGGSGG GGSEIVLTQS PSTLSLSPGE RATLSCRASK GVSTSGYSYL HWYQQKPGQA  660
PRLLIYLASY LESGVPARFS GSGSGTDFTL TISGLEPEDF AVYYCQHSRD LPLTFGCGTK  720
VEIKR                                                               725

SEQ ID NO: 56          moltype = AA  length = 725
FEATURE                Location/Qualifiers
source                 1..725
                       mol_type = protein
                       organism = synthetic construct
SEQUENCE: 56
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSRGG TNFNEKFKNR  540
VTLTTDSSTT TAYMELKSLQ FDDTAVYYCA RRDYRFDLGF DYWGQGTTVT VSSGGGGSGG  600
GGSGGGGSGG GGSEIVLTQS PSTLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGCGTK  720
VEIKR                                                               725

SEQ ID NO: 57          moltype = AA  length = 725
FEATURE                Location/Qualifiers
source                 1..725
                       mol_type = protein
                       organism = synthetic construct
SEQUENCE: 57
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSRGG TNFNEKFKNR  540
VTLTTDSSTT TAYMELKSLQ FDDTAVYYCA RRDYRFDLGF DYWGQGTTVT VSSGGGGSGG  600
GGSGGGGSGG GGSEIVLTQS PSTLSLSPGE RATLSCRASK GVSTSGYSYL HWYQQKPGQA  660
```

-continued

```
PRLLIYLASY LESGVPARFS GSGSGTDFTL TISGLEPEDF AVYYCQHSRD LPLTFGCGTK   720
VEIKR                                                                725

SEQ ID NO: 58              moltype = AA  length = 725
FEATURE                    Location/Qualifiers
source                     1..725
                           mol_type = protein
                           organism = synthetic construct
SEQUENCE: 58
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSQGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                                725

SEQ ID NO: 59              moltype = AA  length = 725
FEATURE                    Location/Qualifiers
source                     1..725
                           mol_type = protein
                           organism = synthetic construct
SEQUENCE: 59
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSQGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSEIVLTQS PATLSVSPGE RATLSCRASK GVSTSGYSYL HWYQQKPGQA   660
PRLLIYLASY LESGIPARFS GSGSGTEFTL TISSLQSEDF AVYYCQHSRD LPLTFGGGTK   720
VEIKR                                                                725

SEQ ID NO: 60              moltype = AA  length = 725
FEATURE                    Location/Qualifiers
source                     1..725
                           mol_type = protein
                           organism = synthetic construct
SEQUENCE: 60
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSQGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSDIQLTQS PSSLSASVGD RVTITCRASK GVSTSGYSYL HWYQQKPGKA   660
PKLLIYLASY LESGVPSRFS GSGSGTDFTL TISSLQPEDF ATYYCQHSRD LPLTFGGGTK   720
VEIKR                                                                725

SEQ ID NO: 61              moltype = AA  length = 725
FEATURE                    Location/Qualifiers
source                     1..725
                           mol_type = protein
                           organism = synthetic construct
SEQUENCE: 61
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLVQS   480
GAEVKKPGAS VKVSCKASGY TFTNYYMYWV RQAPGQGLEW MGGINPSQGG TNFNEKFKNR   540
VTLTTDSSTS TAYMELSSLR SEDTAVYYCA RRDYRFDLGF DYWGQGTTVT VSSGGGGSGG   600
```

-continued

```
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGGGTK  720
VEIKR                                                               725

SEQ ID NO: 62          moltype = AA  length = 725
FEATURE                Location/Qualifiers
source                 1..725
                       mol_type = protein
                       organism = synthetic construct
SEQUENCE: 62
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVQS  480
GAEVKKPGAS VKVSCKASGY TFTNYYMYWV RQAPGQGLEW MGGINPSQGG TNFNEKFKNR  540
VTLTTDSSTS TAYMELSSLR SEDTAVYYCA RRDYRFDLGF DYWGQGTTVT VSSGGGGSGG  600
GGSGGGGSGG GGSEIVLTQS PATLSVSPGE RATLSCRASK GVSTSGYSYL HWYQQKPGQA  660
PRLLIYLASY LESGIPARFS GSGSGTEFTL TISSLQSEDF AVYYCQHSRD LPLTFGGGTK  720
VEIKR                                                               725

SEQ ID NO: 63          moltype = AA  length = 725
FEATURE                Location/Qualifiers
source                 1..725
                       mol_type = protein
                       organism = synthetic construct
SEQUENCE: 63
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVQS  480
GAEVKKPGAS VKVSCKASGY TFTNYYMYWV RQAPGQGLEW MGGINPSQGG TNFNEKFKNR  540
VTLTTDSSTS TAYMELSSLR SEDTAVYYCA RRDYRFDLGF DYWGQGTTVT VSSGGGGSGG  600
GGSGGGGSGG GGSDIQLTQS PSSLSASVGD RVTITCRASK GVSTSGYSYL HWYQQKPGKA  660
PKLLIYLASY LESGVPSRFS GSGSGTDFTL TISSLQPEDF ATYYCQHSRD LPLTFGGGTK  720
VEIKR                                                               725

SEQ ID NO: 64          moltype = AA  length = 725
FEATURE                Location/Qualifiers
source                 1..725
                       mol_type = protein
                       organism = synthetic construct
SEQUENCE: 64
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVQS  480
GAEVKKPGAS VKVSCKASGY TFTNYYMYWV RQAPGQGLEW MGGINPSQGG TNFNEKFKNR  540
VTLTTDSSTS TAYMELSSLR SEDTAVYYCA RRDYRFDLGF DYWGQGTTVT VSSGGGGSGG  600
GGSGGGGSGG GGSDIQLTQS PSSLSASVGD RVTITCRASK GVSTSGYSYL HWYQQKPGKA  660
PKLLIYLASY LESGVPSRFS GSGSGTDFTL TISSLQPEDF ATYYCQHSRD LPLTFGGGTK  720
VEIKR                                                               725

SEQ ID NO: 65          moltype = AA  length = 725
FEATURE                Location/Qualifiers
source                 1..725
                       mol_type = protein
                       organism = synthetic construct
SEQUENCE: 65
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLLES  480
GGGLVQPGGS LRLSCKASGY TFTNYYMYWV RQAPGKGLEW MGGINPSQGG TNFNEKFKNR  540
```

-continued

```
VTLSTDSSKN TAYLQMNSLR AEDTAVYYCA RRDYRFDLGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                              725

SEQ ID NO: 66          moltype = AA  length = 725
FEATURE                Location/Qualifiers
source                 1..725
                       mol_type = protein
                       organism = synthetic construct
SEQUENCE: 66
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLLES   480
GGGLVQPGGS LRLSCKASGY TFTNYYMYWV RQAPGKGLEW MGGINPSQGG TNFNEKFKNR   540
VTLSTDSSKN TAYLQMNSLR AEDTAVYYCA RRDYRFDLGF DYWGQGTTVT VSSGGGGSGG   600
GGSGGGGSGG GGSEIVLTQS PATLSVSPGE RATLSCRASK GVSTSGYSYL HWYQQKPGQA   660
PRLLIYLASY LESGIPARFS GSGSGTEFTL TISSLQSEDF AVYYCQHSRD LPLTFGGGTK   720
VEIKR                                                              725

SEQ ID NO: 67          moltype = AA  length = 725
FEATURE                Location/Qualifiers
source                 1..725
                       mol_type = protein
                       organism = synthetic construct
SEQUENCE: 67
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLLES   480
GGGLVQPGGS LRLSCKASGY TFTNYYMYWV RQAPGKGLEW MGGINPSQGG TNFNEKFKNR   540
VTLSTDSSKN TAYLQMNSLR AEDTAVYYCA RRDYRFDLGF DYWGQGTTVT VSSGGGGSGG   600
GGSGGGGSGG GGSDIQLTQS PSSLSASVGD RVTITCRASK GVSTSGYSYL HWYQQKPGKA   660
PKLLIYLASY LESGVPSRFS GSGSGTDFTL TISSLQPEDF ATYYCQHSRD LPLTFGGGTK   720
VEIKR                                                              725

SEQ ID NO: 68          moltype = AA  length = 725
FEATURE                Location/Qualifiers
source                 1..725
                       mol_type = protein
                       organism = synthetic construct
SEQUENCE: 68
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQCLEW MGGINPSQGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGCGTK   720
VEIKR                                                              725

SEQ ID NO: 69          moltype = AA  length = 725
FEATURE                Location/Qualifiers
source                 1..725
                       mol_type = protein
                       organism = synthetic construct
SEQUENCE: 69
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
```

```
GVEVKKPGAS VKVSCKASGY TFTNYYMYWV RQAPGQCLEW MGGINPSQGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSEIVLTQS PATLSVSPGE RATLSCRASK GVSTSGYSYL HWYQQKPGQA   660
PRLLIYLASY LESGIPARFS GSGSGTEFTL TISSLQSEDF AVYYCQHSRD LPLTFGCGTK   720
VEIKR                                                              725

SEQ ID NO: 70              moltype = AA   length = 725
FEATURE                    Location/Qualifiers
source                     1..725
                           mol_type = protein
                           organism = synthetic construct
SEQUENCE: 70
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQCLEW MGGINPSQGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSDIQLTQS PSSLSASVGD RVTITCRASK GVSTSGYSYL HWYQQKPGKA   660
PKLLIYLASY LESGVPSRFS GSGSGTDFTL TISSLQPEDF ATYYCQHSRD LPLTFGCGTK   720
VEIKR                                                              725

SEQ ID NO: 71              moltype = AA   length = 725
FEATURE                    Location/Qualifiers
source                     1..725
                           mol_type = protein
                           organism = synthetic construct
SEQUENCE: 71
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLVQS   480
GAEVKKPGAS VKVSCKASGY TFTNYYMYWV RQAPGQCLEW MGGINPSQGG TNFNEKFKNR   540
VTLTTDSSTS TAYMELSSLR SEDTAVYYCA RRDYRFDLGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGCGTK   720
VEIKR                                                              725

SEQ ID NO: 72              moltype = AA   length = 725
FEATURE                    Location/Qualifiers
source                     1..725
                           mol_type = protein
                           organism = synthetic construct
SEQUENCE: 72
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLVQS   480
GAEVKKPGAS VKVSCKASGY TFTNYYMYWV RQAPGQCLEW MGGINPSQGG TNFNEKFKNR   540
VTLTTDSSTS TAYMELSSLR SEDTAVYYCA RRDYRFDLGF DYWGQGTTVT VSSGGGGSGG   600
GGSGGGGSGG GGSEIVLTQS PATLSVSPGE RATLSCRASK GVSTSGYSYL HWYQQKPGQA   660
PRLLIYLASY LESGIPARFS GSGSGTEFTL TISSLQSEDF AVYYCQHSRD LPLTFGCGTK   720
VEIKR                                                              725

SEQ ID NO: 73              moltype = AA   length = 725
FEATURE                    Location/Qualifiers
source                     1..725
                           mol_type = protein
                           organism = synthetic construct
SEQUENCE: 73
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
```

```
SRWQQGNVFS CSVMHEALHN HYTQKSLSLS PGKGGGGSGG GGSGGGGSGG GGSEVQLVQS  480
GAEVKKPGAS VKVSCKASGY TFTNYYMYWV RQAPGQCLEW MGGINPSQGG TNFNEKFKNR  540
VTLTTDSSTS TAYMELSSLR SEDTAVYYCA RRDYRFDLGF DYWGQGTTVT VSSGGGGSGG  600
GGSGGGGSGG GGSDIQLTQS PSSLSASVGD RVTITCRASK GVSTSGYSYL HWYQQKPGKA  660
PKLLIYLASY LESGVPSRFS GSGSGTDFTL TISSLQPEDF ATYYCQHSRD LPLTFGCGTK  720
VEIKR                                                              725

SEQ ID NO: 74            moltype = AA  length = 725
FEATURE                  Location/Qualifiers
source                   1..725
                         mol_type = protein
                         organism = synthetic construct
SEQUENCE: 74
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVQS  480
GAEVKKPGAS VKVSCKASGY TFTNYYMYWV RQAPGQCLEW MGGINPSQGG TNFNEKFKNR  540
VTLTTDSSTS TAYMELSSLR SEDTAVYYCA RRDYRFDLGF DYWGQGTTVT VSSGGGGSGG  600
GGSGGGGSGG GGSDIQLTQS PSSLSASVGD RVTITCRASK GVSTSGYSYL HWYQQKPGKA  660
PKLLIYLASY LESGVPSRFS GSGSGTDFTL TISSLQPEDF ATYYCQHSRD LPLTFGCGTK  720
VEIKR                                                              725

SEQ ID NO: 75            moltype = AA  length = 725
FEATURE                  Location/Qualifiers
source                   1..725
                         mol_type = protein
                         organism = synthetic construct
SEQUENCE: 75
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLLES  480
GGGLVQPGGS LRLSCKASGY TFTNYYMYWV RQAPGKCLEW MGGINPSQGG TNFNEKFKNR  540
VTLSTDSSKN TAYLQMNSLR AEDTAVYYCA RRDYRFDLGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGCGTK  720
VEIKR                                                              725

SEQ ID NO: 76            moltype = AA  length = 725
FEATURE                  Location/Qualifiers
source                   1..725
                         mol_type = protein
                         organism = synthetic construct
SEQUENCE: 76
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLLES  480
GGGLVQPGGS LRLSCKASGY TFTNYYMYWV RQAPGKCLEW MGGINPSQGG TNFNEKFKNR  540
VTLSTDSSKN TAYLQMNSLR AEDTAVYYCA RRDYRFDLGF DYWGQGTTVT VSSGGGGSGG  600
GGSGGGGSGG GGSEIVLTQS PATLSVSPGE RATLSCRASK GVSTSGYSYL HWYQQKPGQA  660
PRLLIYLASY LESGIPARFS GSGSGTEFTL TISSLQSEDF AVYYCQHSRD LPLTFGCGTK  720
VEIKR                                                              725

SEQ ID NO: 77            moltype = AA  length = 725
FEATURE                  Location/Qualifiers
source                   1..725
                         mol_type = protein
                         organism = synthetic construct
SEQUENCE: 77
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
```

-continued

```
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLLES  480
GGGLVQPGGS LRLSCKASGY TFTNYYMYWV RQAPGKCLEW MGGINPSQGG TNFNEKFKNR  540
VTLSTDSSKN TAYLQMNSLR AEDTAVYYCA RRDYRFDLGF DYWGQGTTVT VSSGGGGSGG  600
GGSGGGGSGG GGSDIQLTQS PSSLSASVGD RVTITCRASK GVSTSGYSYL HWYQQKPGKA  660
PKLLIYLASY LESGVPSRFS GSGSGTDFTL TISSLQPEDF ATYYCQHSRD LPLTFGCGTK  720
VEIKR                                                             725

SEQ ID NO: 78            moltype = AA  length = 724
FEATURE                  Location/Qualifiers
source                   1..724
                         mol_type = protein
                         organism = synthetic construct
SEQUENCE: 78
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEIVLTQS  480
PATLSLSPGE RATLSCRASK GVSTSGYSYL HWYQQKPGQA PRLLIYLASY LESGVPARFS  540
GSGSGTDFTL TISSLEPEDF AVYYCQHSRD LPLTFGGGTK VEIKGGGGSG GGGSGGGGSG  600
GGGSQVQLVQ SGVEVKKPGA SVKVSCKASG YTFTNYYMYW VRQAPGQGLE WMGGINPSNG  660
GTNFNEKFKN RVTLTTDSST TTAYMELKSL QFDDTAVYYC ARRDYRFDMG FDYWGQGTTV  720
TVSS                                                              724

SEQ ID NO: 79            moltype = AA  length = 724
FEATURE                  Location/Qualifiers
source                   1..724
                         mol_type = protein
                         organism = synthetic construct
SEQUENCE: 79
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEIVLTQS  480
PATLSLSPGE RATLSCRASK GVSTSGYSYL HWYQQKPGQA PRLLIYLASY LESGVPARFS  540
GSGSGTDFTL TISSLEPEDF AVYYCQHSRD LPLTFGGGTK VEIKGGGGSG GGGSGGGGSG  600
GGGSQVQLVQ SGVEVKKPGA SVKVSCKASG YTFTNYYMYW VRQAPGQGLE WMGGINPSNG  660
GTNFNEKFKN RVTLTTDSST TTAYMELKSL QFDDTAVYYC ARRDYRFDMG FDYWGQGTTV  720
TVSS                                                              724

SEQ ID NO: 80            moltype = AA  length = 724
FEATURE                  Location/Qualifiers
source                   1..724
                         mol_type = protein
                         organism = synthetic construct
SEQUENCE: 80
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEIVLTQS  480
PATLSLSPGE RATLSCRASK GVSTSGYSYL HWYQQKPGQA PRLLIYLASY LESGVPARFS  540
GSGSGTDFTL TISSLEPEDF AVYYCQHSRD LPLTFGGGTK VEIKGGGGSG GGGSGGGGSG  600
GGGSQVQLVQ SGVEVKKPGA SVKVSCKASG YTFTNYYMYW VRQAPGQGLE WMGGINPSRG  660
GTNFNEKFKN RVTLTTDSST TTAYMELKSL QFDDTAVYYC ARRDYRFDLG FDYWGQGTTV  720
TVSS                                                              724

SEQ ID NO: 81            moltype = AA  length = 724
FEATURE                  Location/Qualifiers
source                   1..724
                         mol_type = protein
                         organism = synthetic construct
SEQUENCE: 81
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
```

```
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVMHEALHN HYTQKSLSLS PGKGGGGSGG GGSGGGGSGG GGSEIVLTQS 480
PATLSLSPGE RATLSCRASK GVSTSGYSYL HWYQQKPGQA PRLLIYLASY LESGVPARFS 540
GSGSGTDFTL TISSLEPEDF AVYYCQHSRD LPLTFGGGTK VEIKGGGSGG GGGSGGGGSG 600
GGGSQVQLVQ SGVEVKKPGA SVKVSCKASG YTFTNYYMYW VRQAPGQGLE WMGGINPSRG 660
GTNFNEKFKN RVTLTTDSST TTAYMELKSL QFDDTAVYYC ARRDYRFDLG FDYWGQGTTV 720
TVSS                                                           724

SEQ ID NO: 82          moltype = AA  length = 724
FEATURE                Location/Qualifiers
source                 1..724
                       mol_type = protein
                       organism = synthetic construct
SEQUENCE: 82
EVQLVESGGG LVQPGGSLRL SCAASGYTFT NYGMNWVRQA PGKGLEWVGW INTYTGEPTY 60
AADFKRRFTF SLDTSKSTAY LQMNSLRAED TAVYYCAKYP HYYGSSHWYF DVWGQGTLVT 120
VSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEA 240
AGGPSVFLFP PKPKDTLMIS RTPEVTCVVV DVSHEDPEVK FNWYVDGVEV HNAKTKPREE 300
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVMHEALHN HYTQKSLSLS PGKGGGGSGG GGSGGGGSGG GGSEIVLTQS 480
PATLSLSPGE RATLSCRASK GVSTSGYSYL HWYQQKPGQA PRLLIYLASY LESGVPARFS 540
GSGSGTDFTL TISSLEPEDF AVYYCQHSRD LPLTFGGGTK VEIKGGGSGG GGGSGGGGSG 600
GGGSQVQLVQ SGVEVKKPGA SVKVSCKASG YTFTNYYMYW VRQAPGQGLE WMGGINPSNG 660
GTNFNEKFKN RVTLTTDSST TTAYMELKSL RFDDTAVYYC ARRDYRFDMG FDYWGQGTTV 720
TVSS                                                           724

SEQ ID NO: 83          moltype = AA  length = 724
FEATURE                Location/Qualifiers
source                 1..724
                       mol_type = protein
                       organism = synthetic construct
SEQUENCE: 83
EVQLVESGGG LVQPGGSLRL SCAASGYTFT NYGMNWVRQA PGKGLEWVGW INTYTGEPTY 60
AADFKRRFTF SLDTSKSTAY LQMNSLRAED TAVYYCAKYP HYYGSSHWYF DVWGQGTLVT 120
VSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEA 240
AGGPSVFLFP PKPKDTLYIT REPEVTCVVV DVSHEDPEVK FNWYVDGVEV HNAKTKPREE 300
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVMHEALHN HYTQKSLSLS PGKGGGGSGG GGSGGGGSGG GGSEIVLTQS 480
PATLSLSPGE RATLSCRASK GVSTSGYSYL HWYQQKPGQA PRLLIYLASY LESGVPARFS 540
GSGSGTDFTL TISSLEPEDF AVYYCQHSRD LPLTFGGGTK VEIKGGGSGG GGGSGGGGSG 600
GGGSQVQLVQ SGVEVKKPGA SVKVSCKASG YTFTNYYMYW VRQAPGQGLE WMGGINPSNG 660
GTNFNEKFKN RVTLTTDSST TTAYMELKSL RFDDTAVYYC ARRDYRFDMG FDYWGQGTTV 720
TVSS                                                           724

SEQ ID NO: 84          moltype = AA  length = 724
FEATURE                Location/Qualifiers
source                 1..724
                       mol_type = protein
                       organism = synthetic construct
SEQUENCE: 84
EVQLVESGGG LVQPGGSLRL SCAASGYTFT NYGMNWVRQA PGKGLEWVGW INTYTGEPTY 60
AADFKRRFTF SLDTSKSTAY LQMNSLRAED TAVYYCAKYP HYYGSSHWYF DVWGQGTLVT 120
VSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEA 240
AGGPSVFLFP PKPKDTLMIS RTPEVTCVVV DVSHEDPEVK FNWYVDGVEV HNAKTKPREE 300
QYNSTYRVVS VLTVLHQDWL NGKEYKCKVS NKALPAPIEK TISKAKGQPR EPQVYTLPPS 360
RDELTKNQVS LTCLVKGFYP SDIAVEWESN GQPENNYKTT PPVLDSDGSF FLYSKLTVDK 420
SRWQQGNVFS CSVMHEALHN HYTQKSLSLS PGKGGGGSGG GGSGGGGSGG GGSEIVLTQS 480
PSTLSLSPGE RATLSCRASK GVSTSGYSYL HWYQQKPGQA PRLLIYLASY LESGVPARFS 540
GSGSGTDFTL TISSLEPEDF AVYYCQHSRD LPLTFGGGTK VEIKGGGSGG GGGSGGGGSG 600
GGGSQVQLVQ SGVEVKKPGA SVKVSCKASG YTFTNYYMYW VRQAPGQGLE WMGGINPSNG 660
GTNFNEKFKN RVTLTTDSST TTAYMELKSL QFDDTAVYYC ARRDYRFDMG FDYWGQGTTV 720
TVSS                                                           724

SEQ ID NO: 85          moltype = AA  length = 724
FEATURE                Location/Qualifiers
source                 1..724
                       mol_type = protein
                       organism = synthetic construct
SEQUENCE: 85
EVQLVESGGG LVQPGGSLRL SCAASGYTFT NYGMNWVRQA PGKGLEWVGW INTYTGEPTY 60
AADFKRRFTF SLDTSKSTAY LQMNSLRAED TAVYYCAKYP HYYGSSHWYF DVWGQGTLVT 120
VSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEA 240
```

```
AGGPSVFLFP PKPKDTLYIT REPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSEIVLTQS    480
PSTLSLSPGE RATLSCRASK GVSTSGYSYL HWYQQKPGQA PRLLIYLAST LESGVPARFS    540
GSGSGTDFTL TISSLEPEDF AVYYCQHSRD LPLTFGGGTK VEIKGGGGSG GGGSGGGGSG    600
GGGSQVQLVQ SGVEVKKPGA SVKVSCKASG YTFTNYYMYW VRQAPGQGLE WMGGINPSNG    660
GTNFNEKFKN RVTLTTDSST TTAYMELKSL QFDDTAVYYC ARRDYRFDMG FDYWGQGTTV    720
TVSS                                                                724

SEQ ID NO: 86          moltype = AA  length = 725
FEATURE                Location/Qualifiers
source                 1..725
                       mol_type = protein
                       organism = synthetic construct
SEQUENCE: 86
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSEVQLVQS    480
GAEVKKPGAS VKVSCKASGY TFTNYYMYWV RQAPGQGLEW MGGINPSNGG TNFNEKFKNR    540
VTLTTDSSTS TAYMELSSLR SEDTAVYYCA RRDYRFDMGF DYWGQGTTVT VSSGGGGSGG    600
GGSGGGGSGG GGSDIQLTQS PSSLSASVGD RVTITCRASK GVSTSGYSYL HWYQQKPGKA    660
PKLLIYLASY LESGVPSRFS GSGSGTDFTL TISSLQPEDF ATYYCQHSRD LPLTFGGGTK    720
VEIKR                                                               725

SEQ ID NO: 87          moltype = AA  length = 725
FEATURE                Location/Qualifiers
source                 1..725
                       mol_type = protein
                       organism = synthetic construct
SEQUENCE: 87
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLYIT REPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSEVQLVQS    480
GAEVKKPGAS VKVSCKASGY TFTNYYMYWV RQAPGQGLEW MGGINPSNGG TNFNEKFKNR    540
VTLTTDSSTS TAYMELSSLR SEDTAVYYCA RRDYRFDMGF DYWGQGTTVT VSSGGGGSGG    600
GGSGGGGSGG GGSDIQLTQS PSSLSASVGD RVTITCRASK GVSTSGYSYL HWYQQKPGKA    660
PKLLIYLASY LESGVPSRFS GSGSGTDFTL TISSLQPEDF ATYYCQHSRD LPLTFGGGTK    720
VEIKR                                                               725

SEQ ID NO: 88          moltype = AA  length = 725
FEATURE                Location/Qualifiers
source                 1..725
                       mol_type = protein
                       organism = synthetic construct
SEQUENCE: 88
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSEVQLVQS    480
GAEVKKPGAS VKVSCKASGY TFTNYYMYWV RQAPGQCLEW MGGINPSNGG TNFNEKFKNR    540
VTLTTDSSTS TAYMELSSLR SEDTAVYYCA RRDYRFDMGF DYWGQGTTVT VSSGGGGSGG    600
GGSGGGGSGG GGSDIQLTQS PSSLSASVGD RVTITCRASK GVSTSGYSYL HWYQQKPGKA    660
PKLLIYLASY LESGVPSRFS GSGSGTDFTL TISSLQPEDF ATYYCQHSRD LPLTFGCGTK    720
VEIKR                                                               725

SEQ ID NO: 89          moltype = AA  length = 725
FEATURE                Location/Qualifiers
source                 1..725
                       mol_type = protein
                       organism = synthetic construct
SEQUENCE: 89
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSSASTKGPS VFPLAPSSKS TSGGTAALGC LVKDYFPEPV TVSWNSGALT SGVHTFPAVL    180
```

-continued

```
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVQS  480
GAEVKKPGAS VKVSCKASGY TFTNYYMYWV RQAPGQCLEW MGGINPSNGG TNFNEKFKNR  540
VTLTTDSSTS TAYMELSSLR SEDTAVYYCA RRDYRFDMGF DYWGQGTTVT VSSGGGGSGG  600
GGSGGGGSGG GGSDIQLTQS PSSLSASVGD RVTITCRASK GVSTSGYSYL HWYQQKPGKA  660
PKLLIYLASY LESGVPSRFS GSGSGTDFTL TISSLQPEDF ATYYCQHSRD LPLTFGCGTK  720
VEIKR                                                              725
```

SEQ ID NO: 90            moltype = AA  length = 725
FEATURE                  Location/Qualifiers
source                   1..725
                         mol_type = protein
                         organism = synthetic construct
SEQUENCE: 90

```
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVQS  480
GAEVKKPGAS VKVSCKASGY TFTNYYMYWV RQAPGQCLEW MGGINPSRGG TNFNEKFKNR  540
VTLTTDSSTS TAYMELSSLR SEDTAVYYCA RRDYRFDLGF DYWGQGTTVT VSSGGGGSGG  600
GGSGGGGSGG GGSDIQLTQS PSSLSASVGD RVTITCRASK GVSTSGYSYL HWYQQKPGKA  660
PKLLIYLASY LESGVPSRFS GSGSGTDFTL TISSLQPEDF ATYYCQHSRD LPLTFGCGTK  720
VEIKR                                                              725
```

SEQ ID NO: 91            moltype = AA  length = 725
FEATURE                  Location/Qualifiers
source                   1..725
                         mol_type = protein
                         organism = synthetic construct
SEQUENCE: 91

```
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVQS  480
GAEVKKPGAS VKVSCKASGY TFTNYYMYWV RQAPGQCLEW MGGINPSRGG TNFNEKFKNR  540
VTLTTDSSTS TAYMELSSLR SEDTAVYYCA RRDYRFDLGF DYWGQGTTVT VSSGGGGSGG  600
GGSGGGGSGG GGSDIQLTQS PSSLSASVGD RVTITCRASK GVSTSGYSYL HWYQQKPGKA  660
PKLLIYLASY LESGVPSRFS GSGSGTDFTL TISSLQPEDF ATYYCQHSRD LPLTFGCGTK  720
VEIKR                                                              725
```

SEQ ID NO: 92            moltype = AA  length = 725
FEATURE                  Location/Qualifiers
source                   1..725
                         mol_type = protein
                         organism = synthetic construct
SEQUENCE: 92

```
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVQS  480
GAEVKKPGAS VKVSCKASGY TFTNYYMYWV RQAPGQCLEW MGGINPSQGG TNFNEKFKNR  540
VTLTTDSSTS TAYMELSSLR SEDTAVYYCA RRDYRFDMGF DYWGQGTTVT VSSGGGGSGG  600
GGSGGGGSGG GGSDIQLTQS PSSLSASVGD RVTITCRASK GVSTSGYSYL HWYQQKPGKA  660
PKLLIYLASY LESGVPSRFS GSGSGTDFTL TISSLQPEDF ATYYCQHSRD LPLTFGCGTK  720
VEIKR                                                              725
```

SEQ ID NO: 93            moltype = AA  length = 725
FEATURE                  Location/Qualifiers
source                   1..725
                         mol_type = protein
                         organism = synthetic construct
SEQUENCE: 93

```
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
```

-continued

```
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLYIT REPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSEVQLVQS    480
GAEVKKPGAS VKVSCKASGY TFTNYYMYWV RQAPGQCLEW MGGINPSQGG TNFNEKFKNR    540
VTLTTDSSTS TAYMELSSLR SEDTAVYYCA RRDYRFDMGF DYWGQGTTVT VSSGGGGSGG    600
GGSGGGGSGG GGSDIQLTQS PSSLSASVGD RVTITCRASK GVSTSGYSYL HWYQQKPGKA    660
PKLLIYLASY LESGVPSRFS GSGSGTDFTL TISSLQPEDF ATYYCQHSRD LPLTFGCGTK    720
VEIKR                                                               725
```

SEQ ID NO: 94          moltype = AA  length = 725
FEATURE                Location/Qualifiers
source                 1..725
                       mol_type = protein
                       organism = synthetic construct
SEQUENCE: 94

```
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSEVQLVQS    480
GAEVKKPGAS VKVSCKASGY TFTNYYMYWV RQAPGQCLEW MGGINPSRGG TNFNEKFKNR    540
VTLTTDSSTS TAYMELSSLR SEDTAVYYCA RRDYRFDMGF DYWGQGTTVT VSSGGGGSGG    600
GGSGGGGSGG GGSDIQLTQS PSSLSASVGD RVTITCRASK GVSTSGYSYL HWYQQKPGKA    660
PKLLIYLASY LESGVPSRFS GSGSGTDFTL TISSLQPEDF ATYYCQHSRD LPLTFGCGTK    720
VEIKR                                                               725
```

SEQ ID NO: 95          moltype = AA  length = 725
FEATURE                Location/Qualifiers
source                 1..725
                       mol_type = protein
                       organism = synthetic construct
SEQUENCE: 95

```
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLYIT REPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSEVQLVQS    480
GAEVKKPGAS VKVSCKASGY TFTNYYMYWV RQAPGQCLEW MGGINPSRGG TNFNEKFKNR    540
VTLTTDSSTS TAYMELSSLR SEDTAVYYCA RRDYRFDMGF DYWGQGTTVT VSSGGGGSGG    600
GGSGGGGSGG GGSDIQLTQS PSSLSASVGD RVTITCRASK GVSTSGYSYL HWYQQKPGKA    660
PKLLIYLASY LESGVPSRFS GSGSGTDFTL TISSLQPEDF ATYYCQHSRD LPLTFGCGTK    720
VEIKR                                                               725
```

SEQ ID NO: 96          moltype = AA  length = 725
FEATURE                Location/Qualifiers
source                 1..725
                       mol_type = protein
                       organism = synthetic construct
SEQUENCE: 96

```
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSEVQLVQS    480
GAEVKKPGAS VKVSCKASGY TFTNYYMYWV RQAPGQCLEW MGGINPSNGG TNFNEKFKNR    540
VTLTTDSSTS TAYMELSSLR SEDTAVYYCA RRDYRFDLGF DYWGQGTTVT VSSGGGGSGG    600
GGSGGGGSGG GGSDIQLTQS PSSLSASVGD RVTITCRASK GVSTSGYSYL HWYQQKPGKA    660
PKLLIYLASY LESGVPSRFS GSGSGTDFTL TISSLQPEDF ATYYCQHSRD LPLTFGCGTK    720
VEIKR                                                               725
```

SEQ ID NO: 97          moltype = AA  length = 725
FEATURE                Location/Qualifiers
source                 1..725
                       mol_type = protein
                       organism = synthetic construct
SEQUENCE: 97

```
EVQLVESGGG LVQPGGSLRL SCAASGYTFT NYGMNWVRQA PGKGLEWVGW INTYTGEPTY    60
```

```
AADFKRRFTF  SLDTSKSTAY  LQMNSLRAED  TAVYYCAKYP  HYYGSSHWYF  DVWGQGTLVT  120
VSSASTKGPS  VFPLAPSSKS  TSGGTAALGC  LVKDYFPEPV  TVSWNSGALT  SGVHTFPAVL  180
QSSGLYSLSS  VVTVPSSSLG  TQTYICNVNH  KPSNTKVDKK  VEPKSCDKTH  TCPPCPAPEA  240
AGGPSVFLFP  PKPKDTLYIT  REPEVTCVVV  DVSHEDPEVK  FNWYVDGVEV  HNAKTKPREE  300
QYNSTYRVVS  VLTVLHQDWL  NGKEYKCKVS  NKALPAPIEK  TISKAKGQPR  EPQVYTLPPS  360
RDELTKNQVS  LTCLVKGFYP  SDIAVEWESN  GQPENNYKTT  PPVLDSDGSF  FLYSKLTVDK  420
SRWQQGNVFS  CSVMHEALHN  HYTQKSLSLS  PGKGGGGSGG  GGSGGGGSGG  GGSEVQLVQS  480
GAEVKKPGAS  VKVSCKASGY  TFTNYYMYWV  RQAPGQCLEW  MGGINPSNGG  TNFNEKFKNR  540
VTLTTDSSTS  TAYMELSSLR  SEDTAVYYCA  RRDYRFDLGF  DYWGQGTTVT  VSSGGGGSGG  600
GGSGGGGSGG  GGSDIQLTQS  PSSLSASVGD  RVTITCRASK  GVSTSGYSYL  HWYQQKPGKA  660
PKLLIYLASY  LESGVPSRFS  GSGSGTDFTL  TISSLQPEDF  ATYYCQHSRD  LPLTFGCGTK  720
VEIKR                                                                  725
```

```
SEQ ID NO: 98            moltype = AA  length = 721
FEATURE                  Location/Qualifiers
source                   1..721
                         mol_type = protein
                         organism = synthetic construct
SEQUENCE: 98
QVQLVQSGVE  VKKPGASVKV  SCKASGYTFT  NYYMYWVRQA  PGQGLEWMGG  INPSNGGTNF  60
NEKFKNRVTL  TTDSSTTTAY  MELKSLQFDD  TAVYYCARRD  YRFDMGFDYW  GQGTTVTVSS  120
ASTKGPSVFP  LAPSSKSTSG  GTAALGCLVK  DYFPEPVTVS  WNSGALTSGV  HTFPAVLQSS  180
GLYSLSSVVT  VPSSSLGTQT  YICNVNHKPS  NTKVDKKVEP  KSCDKTHTCP  PCPAPEAAGG  240
PSVFLFPPKP  KDTLMISRTP  EVTCVVVDVS  HEDPEVKFNW  YVDGVEVHNA  KTKPREEQYN  300
STYRVVSVLT  VLHQDWLNGK  EYKCKVSNKA  LPAPIEKTIS  KAKGQPREPQ  VYTLPPSRDE  360
LTKNQVSLTC  LVKGFYPSDI  AVEWESNGQP  ENNYKTTPPV  LDSDGSFFLY  SKLTVDKSRW  420
QQGNVFSCSV  MHEALHNHYT  QKSLSLSPGK  GGGGSGGGGS  GGGGSGGGGS  EVQLVESGGG  480
LVQPGGSLRL  SCAASGYTFT  NYGMNWVRQA  PGKGLEWVGW  INTYTGEPTY  AADFKRRFTF  540
SLDTSKSTAY  LQMNSLRAED  TAVYYCAKYP  HYYGSSHWYF  DVWGQGTLVT  VSSGGGGSGG  600
GGSGGGGSGG  GGSDIQMTQS  PSSLSASVGD  RVTITCSASQ  DISNYLNWYQ  QKPGKAPKVL  660
IYFTSSLHSG  VPSRFSGSGS  GTDFTLTISS  LQPEDFATYY  CQQYSTVPWT  FGQGTKVEIK  720
R                                                                      721
```

```
SEQ ID NO: 99            moltype = AA  length = 721
FEATURE                  Location/Qualifiers
source                   1..721
                         mol_type = protein
                         organism = synthetic construct
SEQUENCE: 99
QVQLVQSGVE  VKKPGASVKV  SCKASGYTFT  NYYMYWVRQA  PGQGLEWMGG  INPSNGGTNF  60
NEKFKNRVTL  TTDSSTTTAY  MELKSLQFDD  TAVYYCARRD  YRFDMGFDYW  GQGTTVTVSS  120
ASTKGPSVFP  LAPSSKSTSG  GTAALGCLVK  DYFPEPVTVS  WNSGALTSGV  HTFPAVLQSS  180
GLYSLSSVVT  VPSSSLGTQT  YICNVNHKPS  NTKVDKKVEP  KSCDKTHTCP  PCPAPEAAGG  240
PSVFLFPPKP  KDTLYITREP  EVTCVVVDVS  HEDPEVKFNW  YVDGVEVHNA  KTKPREEQYN  300
STYRVVSVLT  VLHQDWLNGK  EYKCKVSNKA  LPAPIEKTIS  KAKGQPREPQ  VYTLPPSRDE  360
LTKNQVSLTC  LVKGFYPSDI  AVEWESNGQP  ENNYKTTPPV  LDSDGSFFLY  SKLTVDKSRW  420
QQGNVFSCSV  MHEALHNHYT  QKSLSLSPGK  GGGGSGGGGS  GGGGSGGGGS  EVQLVESGGG  480
LVQPGGSLRL  SCAASGYTFT  NYGMNWVRQA  PGKGLEWVGW  INTYTGEPTY  AADFKRRFTF  540
SLDTSKSTAY  LQMNSLRAED  TAVYYCAKYP  HYYGSSHWYF  DVWGQGTLVT  VSSGGGGSGG  600
GGSGGGGSGG  GGSDIQMTQS  PSSLSASVGD  RVTITCSASQ  DISNYLNWYQ  QKPGKAPKVL  660
IYFTSSLHSG  VPSRFSGSGS  GTDFTLTISS  LQPEDFATYY  CQQYSTVPWT  FGQGTKVEIK  720
R                                                                      721
```

```
SEQ ID NO: 100           moltype = AA  length = 721
FEATURE                  Location/Qualifiers
source                   1..721
                         mol_type = protein
                         organism = synthetic construct
SEQUENCE: 100
QVQLVQSGVE  VKKPGASVKV  SCKASGYTFT  NYYMYWVRQA  PGQGLEWMGG  INPSNGGTNF  60
NEKFKNRVTL  TTDSSTTTAY  MELKSLQFDD  TAVYYCARRD  YRFDMGFDYW  GQGTTVTVSS  120
ASTKGPSVFP  LAPSSKSTSG  GTAALGCLVK  DYFPEPVTVS  WNSGALTSGV  HTFPAVLQSS  180
GLYSLSSVVT  VPSSSLGTQT  YICNVNHKPS  NTKVDKKVEP  KSCDKTHTCP  PCPAPEAAGG  240
PSVFLFPPKP  KDTLMISRTP  EVTCVVVDVS  HEDPEVKFNW  YVDGVEVHNA  KTKPREEQYN  300
STYRVSVLT   VLHQDWLNGK  EYKCKVSNKA  LPAPIEKTIS  KAKGQPREPQ  VYTLPPSRDE  360
LTKNQVSLTC  LVKGFYPSDI  AVEWESNGQP  ENNYKTTPPV  LDSDGSFFLY  SKLTVDKSRW  420
QQGNVFSCSV  LHEALHSHYT  QKSLSLSPGK  GGGGSGGGGS  GGGGSGGGGS  EVQLVESGGG  480
LVQPGGSLRL  SCAASGYTFT  NYGMNWVRQA  PGKGLEWVGW  INTYTGEPTY  AADFKRRFTF  540
SLDTSKSTAY  LQMNSLRAED  TAVYYCAKYP  HYYGSSHWYF  DVWGQGTLVT  VSSGGGGSGG  600
GGSGGGGSGG  GGSDIQMTQS  PSSLSASVGD  RVTITCSASQ  DISNYLNWYQ  QKPGKAPKVL  660
IYFTSSLHSG  VPSRFSGSGS  GTDFTLTISS  LQPEDFATYY  CQQYSTVPWT  FGQGTKVEIK  720
R                                                                      721
```

```
SEQ ID NO: 101           moltype = AA  length = 721
FEATURE                  Location/Qualifiers
source                   1..721
                         mol_type = protein
                         organism = synthetic construct
SEQUENCE: 101
```

```
QVQLVQSGVE VKKPGASVKV SCKASGYTFT NYYMYWVRQA PGQGLEWMGG INPSQGGTNF   60
NEKFKNRVTL TTDSSTTTAY MELKSLQFDD TAVYYCARRD YRFDLGFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK GGGGSGGGGS GGGGSGGGGS EVQLVESGGG  480
LVQPGGSLRL SCAASGYTFT NYGMNWVRQA PGKGLEWVGW INTYTGEPTY AADFKRRFTF  540
SLDTSKSTAY LQMNSLRAED TAVYYCAKYP HYYGSSHWYF DVWGQGTLVT VSSGGGGSGG  600
GGSGGGGSGG GGSDIQMTQS PSSLSASVGD RVTITCSASQ DISNYLNWYQ QKPGKAPKVL  660
IYFTSSLHSG VPSRFSGSGS GTDFTLTISS LQPEDFATYY CQQYSTVPWT FGQGTKVEIK  720
R                                                                 721

SEQ ID NO: 102          moltype = AA   length = 721
FEATURE                 Location/Qualifiers
source                  1..721
                        mol_type = protein
                        organism = synthetic construct
SEQUENCE: 102
QVQLVQSGVE VKKPGASVKV SCKASGYTFT NYYMYWVRQA PGQGLEWMGG INPSQGGTNF   60
NEKFKNRVTL TTDSSTTTAY MELKSLQFDD TAVYYCARRD YRFDLGFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLYITREP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK GGGGSGGGGS GGGGSGGGGS EVQLVESGGG  480
LVQPGGSLRL SCAASGYTFT NYGMNWVRQA PGKGLEWVGW INTYTGEPTY AADFKRRFTF  540
SLDTSKSTAY LQMNSLRAED TAVYYCAKYP HYYGSSHWYF DVWGQGTLVT VSSGGGGSGG  600
GGSGGGGSGG GGSDIQMTQS PSSLSASVGD RVTITCSASQ DISNYLNWYQ QKPGKAPKVL  660
IYFTSSLHSG VPSRFSGSGS GTDFTLTISS LQPEDFATYY CQQYSTVPWT FGQGTKVEIK  720
R                                                                 721

SEQ ID NO: 103          moltype = AA   length = 721
FEATURE                 Location/Qualifiers
source                  1..721
                        mol_type = protein
                        organism = synthetic construct
SEQUENCE: 103
QVQLVQSGVE VKKPGASVKV SCKASGYTFT NYYMYWVRQA PGQGLEWMGG INPSQGGTNF   60
NEKFKNRVTL TTDSSTTTAY MELKSLQFDD TAVYYCARRD YRFDLGFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV LHEALHSHYT QKSLSLSPGK GGGGSGGGGS GGGGSGGGGS EVQLVESGGG  480
LVQPGGSLRL SCAASGYTFT NYGMNWVRQA PGKGLEWVGW INTYTGEPTY AADFKRRFTF  540
SLDTSKSTAY LQMNSLRAED TAVYYCAKYP HYYGSSHWYF DVWGQGTLVT VSSGGGGSGG  600
GGSGGGGSGG GGSDIQMTQS PSSLSASVGD RVTITCSASQ DISNYLNWYQ QKPGKAPKVL  660
IYFTSSLHSG VPSRFSGSGS GTDFTLTISS LQPEDFATYY CQQYSTVPWT FGQGTKVEIK  720
R                                                                 721

SEQ ID NO: 104          moltype = AA   length = 721
FEATURE                 Location/Qualifiers
source                  1..721
                        mol_type = protein
                        organism = synthetic construct
SEQUENCE: 104
QVQLVQSGVE VKKPGASVKV SCKASGYTFT NYYMYWVRQA PGQGLEWMGG INPSRGGTNF   60
NEKFKNRVTL TTDSSTTTAY MELKSLQFDD TAVYYCARRD YRFDLGFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK GGGGSGGGGS GGGGSGGGGS EVQLVESGGG  480
LVQPGGSLRL SCAASGYTFT NYGMNWVRQA PGKGLEWVGW INTYTGEPTY AADFKRRFTF  540
SLDTSKSTAY LQMNSLRAED TAVYYCAKYP HYYGSSHWYF DVWGQGTLVT VSSGGGGSGG  600
GGSGGGGSGG GGSDIQMTQS PSSLSASVGD RVTITCSASQ DISNYLNWYQ QKPGKAPKVL  660
IYFTSSLHSG VPSRFSGSGS GTDFTLTISS LQPEDFATYY CQQYSTVPWT FGQGTKVEIK  720
R                                                                 721

SEQ ID NO: 105          moltype = AA   length = 721
FEATURE                 Location/Qualifiers
source                  1..721
                        mol_type = protein
                        organism = synthetic construct
```

-continued

```
SEQUENCE: 105
QVQLVQSGVE VKKPGASVKV SCKASGYTFT NYYMYWVRQA PGQGLEWMGG INPSRGGTNF    60
NEKFKNRVTL TTDSSTTTAY MELKSLQFDD TAVYYCARRD YRFDLGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLYITREP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK GGGGSGGGGS GGGGSGGGGS EVQLVESGGG   480
LVQPGGSLRL SCAASGYTFT NYGMNWVRQA PGKGLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGQGTKVEIK   720
R                                                                  721

SEQ ID NO: 106           moltype = AA  length = 721
FEATURE                  Location/Qualifiers
source                   1..721
                         mol_type = protein
                         organism = synthetic construct
SEQUENCE: 106
QVQLVQSGVE VKKPGASVKV SCKASGYTFT NYYMYWVRQA PGQGLEWMGG INPSRGGTNF    60
NEKFKNRVTL TTDSSTTTAY MELKSLQFDD TAVYYCARRD YRFDLGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV LHEALHSHYT QKSLSLSPGK GGGGSGGGGS GGGGSGGGGS EVQLVESGGG   480
LVQPGGSLRL SCAASGYTFT NYGMNWVRQA PGKGLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGQGTKVEIK   720
R                                                                  721

SEQ ID NO: 107           moltype = AA  length = 721
FEATURE                  Location/Qualifiers
source                   1..721
                         mol_type = protein
                         organism = synthetic construct
SEQUENCE: 107
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK GGGGSGGGGS GGGGSGGGGS EVQLVESGGG   480
LVQPGGSLRL SCAASGYTFT NYGMNWVRQA PGKCLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGCGTKVEIK   720
R                                                                  721

SEQ ID NO: 108           moltype = AA  length = 721
FEATURE                  Location/Qualifiers
source                   1..721
                         mol_type = protein
                         organism = synthetic construct
SEQUENCE: 108
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLYITREP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK GGGGSGGGGS GGGGSGGGGS EVQLVESGGG   480
LVQPGGSLRL SCAASGYTFT NYGMNWVRQA PGKCLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGCGTKVEIK   720
R                                                                  721

SEQ ID NO: 109           moltype = AA  length = 721
FEATURE                  Location/Qualifiers
source                   1..721
                         mol_type = protein
```

-continued

```
                          organism = synthetic construct
SEQUENCE: 109
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV LHEALHSHYT QKSLSLSPGK GGGGSGGGGS GGGGSGGGGS EVQLVESGGG   480
LVQPGGSLRL SCAASGYTFT NYGMNWVRQA PGKCLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGCGTKVEIK   720
R                                                                  721

SEQ ID NO: 110        moltype = AA  length = 721
FEATURE               Location/Qualifiers
source                1..721
                      mol_type = protein
                      organism = synthetic construct
SEQUENCE: 110
QVQLVQSGVE VKKPGASVKV SCKASGYTFT NYYMYWVRQA PGQGLEWMGG INPSQGGTNF    60
NEKFKNRVTL TTDSSTTTAY MELKSLQFDD TAVYYCARRD YRFDLGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK GGGGSGGGGS GGGGSGGGGS EVQLVESGGG   480
LVQPGGSLRL SCAASGYTFT NYGMNWVRQA PGKCLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGCGTKVEIK   720
R                                                                  721

SEQ ID NO: 111        moltype = AA  length = 721
FEATURE               Location/Qualifiers
source                1..721
                      mol_type = protein
                      organism = synthetic construct
SEQUENCE: 111
QVQLVQSGVE VKKPGASVKV SCKASGYTFT NYYMYWVRQA PGQGLEWMGG INPSQGGTNF    60
NEKFKNRVTL TTDSSTTTAY MELKSLQFDD TAVYYCARRD YRFDLGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLYITREP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK GGGGSGGGGS GGGGSGGGGS EVQLVESGGG   480
LVQPGGSLRL SCAASGYTFT NYGMNWVRQA PGKCLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGCGTKVEIK   720
R                                                                  721

SEQ ID NO: 112        moltype = AA  length = 721
FEATURE               Location/Qualifiers
source                1..721
                      mol_type = protein
                      organism = synthetic construct
SEQUENCE: 112
QVQLVQSGVE VKKPGASVKV SCKASGYTFT NYYMYWVRQA PGQGLEWMGG INPSQGGTNF    60
NEKFKNRVTL TTDSSTTTAY MELKSLQFDD TAVYYCARRD YRFDLGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV LHEALHSHYT QKSLSLSPGK GGGGSGGGGS GGGGSGGGGS EVQLVESGGG   480
LVQPGGSLRL SCAASGYTFT NYGMNWVRQA PGKCLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGCGTKVEIK   720
R                                                                  721

SEQ ID NO: 113        moltype = AA  length = 721
FEATURE               Location/Qualifiers
source                1..721
```

-continued

```
                          mol_type = protein
                          organism = synthetic construct
SEQUENCE: 113
QVQLVQSGVE VKKPGASVKV SCKASGYTFT NYYMYWVRQA PGQGLEWMGG INPSRGGTNF    60
NEKFKNRVTL TTDSSTTTAY MELKSLQFDD TAVYYCARRD YRFDLGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK GGGGSGGGGS GGGGSGGGGS EVQLVESGGG   480
LVQPGGSLRL SCAASGYTFT NYGMNWVRQA PGKCLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGCGTKVEIK   720
R                                                                  721

SEQ ID NO: 114         moltype = AA  length = 721
FEATURE                Location/Qualifiers
source                 1..721
                       mol_type = protein
                       organism = synthetic construct
SEQUENCE: 114
QVQLVQSGVE VKKPGASVKV SCKASGYTFT NYYMYWVRQA PGQGLEWMGG INPSRGGTNF    60
NEKFKNRVTL TTDSSTTTAY MELKSLQFDD TAVYYCARRD YRFDLGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLYITREP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK GGGGSGGGGS GGGGSGGGGS EVQLVESGGG   480
LVQPGGSLRL SCAASGYTFT NYGMNWVRQA PGKCLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGCGTKVEIK   720
R                                                                  721

SEQ ID NO: 115         moltype = AA  length = 721
FEATURE                Location/Qualifiers
source                 1..721
                       mol_type = protein
                       organism = synthetic construct
SEQUENCE: 115
QVQLVQSGVE VKKPGASVKV SCKASGYTFT NYYMYWVRQA PGQGLEWMGG INPSRGGTNF    60
NEKFKNRVTL TTDSSTTTAY MELKSLQFDD TAVYYCARRD YRFDLGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV LHEALHSHYT QKSLSLSPGK GGGGSGGGGS GGGGSGGGGS EVQLVESGGG   480
LVQPGGSLRL SCAASGYTFT NYGMNWVRQA PGKCLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGCGTKVEIK   720
R                                                                  721

SEQ ID NO: 116         moltype = AA  length = 592
FEATURE                Location/Qualifiers
source                 1..592
                       mol_type = protein
                       organism = synthetic construct
SEQUENCE: 116
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGGGGGSGG GGSEVQLVES   480
GGGLVQPGGS LRLSCAASGS IASIHAMGWV RQAPGKEREW VSVITWSGGI TYYADSVKGR   540
FTISRDNSKN TLYLQMNSLR AEDTAVYYCA GDKHQSSWYD YWGQGTLVTV SS           592

SEQ ID NO: 117         moltype = AA  length = 592
FEATURE                Location/Qualifiers
source                 1..592
                       mol_type = protein
                       organism = synthetic construct
```

-continued

```
SEQUENCE: 117
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVES  480
GGGLVQPGGS LRLSCAASGS IASIHAMGWV RQAPGKEREW VSVITWSGGI TYYADSVKGR  540
FTISRDNSKN TLYLQMNSLR AEDTAVYYCA GDKHQSSWYD YWGQGTLVTV SS          592

SEQ ID NO: 118       moltype = AA   length = 592
FEATURE              Location/Qualifiers
source               1..592
                     mol_type = protein
                     organism = synthetic construct
SEQUENCE: 118
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVES  480
GGGLVQPGGS LRLSCAASGS IASIHAMGWV RQAPGKEREW VSVITWSGGI TYYADSVKGR  540
FTISRDNSKN TVYLQMNSLR AEDTAVYYCA GDKHQSSWYD YWGQGTLVTV SS          592

SEQ ID NO: 119       moltype = AA   length = 592
FEATURE              Location/Qualifiers
source               1..592
                     mol_type = protein
                     organism = synthetic construct
SEQUENCE: 119
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVES  480
GGGLVQPGGS LRLSCAASGS IASIHAMGWV RQAPGKEREW VSVITWSGGI TYYADSVKGR  540
FTISRDNSKN TVYLQMNSLR AEDTAVYYCA GDKHQSSWYD YWGQGTLVTV SS          592

SEQ ID NO: 120       moltype = AA   length = 592
FEATURE              Location/Qualifiers
source               1..592
                     mol_type = protein
                     organism = synthetic construct
SEQUENCE: 120
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVES  480
GGGLVQPGGS LRLSCAASGS IASIHAMGWV RQAPGKEREF VSVITWSGGI TYYADSVKGR  540
FTISRDNSKN TLYLQMNSLR AEDTAVYYCA GDKHQSSWYD YWGQGTLVTV SS          592

SEQ ID NO: 121       moltype = AA   length = 592
FEATURE              Location/Qualifiers
source               1..592
                     mol_type = protein
                     organism = synthetic construct
SEQUENCE: 121
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVES  480
GGGLVQPGGS LRLSCAASGS IASIHAMGWV RQAPGKEREF VSVITWSGGI TYYADSVKGR  540
FTISRDNSKN TLYLQMNSLR AEDTAVYYCA GDKHQSSWYD YWGQGTLVTV SS          592
```

-continued

```
SEQ ID NO: 122          moltype = AA  length = 592
FEATURE                 Location/Qualifiers
source                  1..592
                        mol_type = protein
                        organism = synthetic construct
SEQUENCE: 122
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLVES   480
GGGLVQPGGS LRLSCAASGS IASIHAMGWV RQAPGKEREF VSVITWSGGI TYYADSVKGR   540
FTISRDNSKN TVYLQMNSLR AEDTAVYYCA GDKHQSSWYD YWGQGTLVTV SS           592

SEQ ID NO: 123          moltype = AA  length = 592
FEATURE                 Location/Qualifiers
source                  1..592
                        mol_type = protein
                        organism = synthetic construct
SEQUENCE: 123
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLVES   480
GGGLVQPGGS LRLSCAASGS IASIHAMGWV RQAPGKEREF VSVITWSGGI TYYADSVKGR   540
FTISRDNSKN TVYLQMNSLR AEDTAVYYCA GDKHQSSWYD YWGQGTLVTV SS           592

SEQ ID NO: 124          moltype = AA  length = 592
FEATURE                 Location/Qualifiers
source                  1..592
                        mol_type = protein
                        organism = synthetic construct
SEQUENCE: 124
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLVES   480
GGGLVQPGGS LRLSCAASGS IASIHAMGWV RQAPGKEREF VAVITWSGGI TYYADSVKGR   540
FTISRDNSKN TVYLQMNSLR AEDTAVYYCA GDKHQSSWYD YWGQGTLVTV SS           592

SEQ ID NO: 125          moltype = AA  length = 592
FEATURE                 Location/Qualifiers
source                  1..592
                        mol_type = protein
                        organism = synthetic construct
SEQUENCE: 125
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLVES   480
GGGLVQPGGS LRLSCAASGS IASIHAMGWV RQAPGKEREF VAVITWSGGI TYYADSVKGR   540
FTISRDNSKN TVYLQMNSLR AEDTAVYYCA GDKHQSSWYD YWGQGTLVTV SS           592

SEQ ID NO: 126          moltype = AA  length = 592
FEATURE                 Location/Qualifiers
source                  1..592
                        mol_type = protein
                        organism = synthetic construct
SEQUENCE: 126
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
```

```
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVES  480
GGGLVQPGGS LRLSCAASGS IASIHAMGWV RQAPGKEREW VAVITWSGGI TYYADSVKGR  540
FTISRDNSKN TVYLQMNSLR AEDTAVYYCA GDKHQSSWYD YWGQGTLVTV SS          592

SEQ ID NO: 127          moltype = AA  length = 592
FEATURE                 Location/Qualifiers
source                  1..592
                        mol_type = protein
                        organism = synthetic construct
SEQUENCE: 127
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVES  480
GGGLVQPGGS LRLSCAASGS IASIHAMGWV RQAPGKEREW VAVITWSGGI TYYADSVKGR  540
FTISRDNSKN TVYLQMNSLR AEDTAVYYCA GDKHQSSWYD YWGQGTLVTV SS          592

SEQ ID NO: 128          moltype = AA  length = 719
FEATURE                 Location/Qualifiers
source                  1..719
                        mol_type = protein
                        organism = synthetic construct
SEQUENCE: 128
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVES  480
GGGLVQPGGS LRLSCAASGF AFSSYDMSWV RQAPGKGLDW VATISGGGRY TYYPDSVKGR  540
FTISRDNSKN NLYLQMNSLR AEDTALYYCA NRYGEAWFAY WGQGTLVTVS SGGGGSGGGG  600
SGGGGSGGGG SDIQMTQSPS SMSASVGDRV TFTCRASQDI NTYLSWFQQK PGKSPKTLIY  660
RANRLVSGVP SRFSGSGSGQ DYTLTISSLQ PEDMATYYCL QYDEFPLTFG AGTKLELKR   719

SEQ ID NO: 129          moltype = AA  length = 719
FEATURE                 Location/Qualifiers
source                  1..719
                        mol_type = protein
                        organism = synthetic construct
SEQUENCE: 129
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVES  480
GGGLVQPGGS LRLSCAASGF AFSSYDMSWV RQAPGKGLDW VATISGGGRY TYYPDSVKGR  540
FTISRDNSKN NLYLQMNSLR AEDTALYYCA NRYGEAWFAY WGQGTLVTVS SGGGGSGGGG  600
SGGGGSGGGG SDIQMTQSPS SMSASVGDRV TFTCRASQDI NTYLSWFQQK PGKSPKTLIY  660
RANRLVSGVP SRFSGSGSGQ DYTLTISSLQ PEDMATYYCL QYDEFPLTFG AGTKLELKR   719

SEQ ID NO: 130          moltype = AA  length = 725
FEATURE                 Location/Qualifiers
source                  1..725
                        mol_type = protein
                        organism = synthetic construct
SEQUENCE: 130
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQGLEW MGGINPSNGG TNFNEKFKNR  540
VTLTTDSSTT TAYMELKSLQ FDDTAVYYCA RRDYRFDMGF DYWGQGTTVT VSSGGGGSGG  600
GGSGGGGSGG GGSEIVLTQS PATLSLSPGE RATLSCRASK GVSTSGYSYL HWYQQKPGQA  660
```

-continued

```
PRLLIYLASY LESGVPARFS GSGSGTDFTL TISSLEPEDF AVYYCQHSRD LPLTFGGGTK   720
VEIKR                                                                725

SEQ ID NO: 131          moltype = AA  length = 725
FEATURE                 Location/Qualifiers
source                  1..725
                        mol_type = protein
                        organism = synthetic construct
SEQUENCE: 131
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSNGG TNFNEKFKNR   540
VTLTTDSSTT TAYMELKSLQ FDDTAVYYCA RRDYRFDMGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                                725

SEQ ID NO: 132          moltype = AA  length = 725
FEATURE                 Location/Qualifiers
source                  1..725
                        mol_type = protein
                        organism = synthetic construct
SEQUENCE: 132
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSQGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                                725

SEQ ID NO: 133          moltype = AA  length = 725
FEATURE                 Location/Qualifiers
source                  1..725
                        mol_type = protein
                        organism = synthetic construct
SEQUENCE: 133
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSQGG TNFNEKFKNR   540
VTLTTDSSTT TAYMELKSLQ FDDTAVYYCA RRDYRFDLGF DYWGQGTTVT VSSGGGGSGG   600
GGSGGGGSGG GGSEIVLTQS PATLSLSPGE RATLSCRASK GVSTSGYSYL HWYQQKPGQA   660
PRLLIYLASY LESGVPARFS GSGSGTDFTL TISSLEPEDF AVYYCQHSRD LPLTFGGGTK   720
VEIKR                                                                725

SEQ ID NO: 134          moltype = AA  length = 725
FEATURE                 Location/Qualifiers
source                  1..725
                        mol_type = protein
                        organism = synthetic construct
SEQUENCE: 134
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVQS   480
GVEVKKPGAS VKVSCKASGY TFTNYYMYWV RQAPGQGLEW MGGINPSRGG TNFNEKFKNR   540
VTLTTDSSTT TAYMELKSLQ FDDTAVYYCA RRDYRFDLGF DYWGQGTTVT VSSGGGGSGG   600
```

-continued

```
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGGGTK  720
VEIKR                                                             725

SEQ ID NO: 135           moltype = AA  length = 725
FEATURE                  Location/Qualifiers
source                   1..725
                         mol_type = protein
                         organism = synthetic construct
SEQUENCE: 135
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQGLEW MGGINPSRGG TNFNEKFKNR  540
VTLTTDSSTT TAYMELKSLQ FDDTAVYYCA RRDYRFDLGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGGGTK  720
VEIKR                                                             725

SEQ ID NO: 136           moltype = AA  length = 725
FEATURE                  Location/Qualifiers
source                   1..725
                         mol_type = protein
                         organism = synthetic construct
SEQUENCE: 136
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSNGG TNFNEKFKNR  540
VTLTTDSSTT TAYMELKSLQ FDDTAVYYCA RRDYRFDMGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGCGTK  720
VEIKR                                                             725

SEQ ID NO: 137           moltype = AA  length = 725
FEATURE                  Location/Qualifiers
source                   1..725
                         mol_type = protein
                         organism = synthetic construct
SEQUENCE: 137
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSNGG TNFNEKFKNR  540
VTLTTDSSTT TAYMELKSLQ FDDTAVYYCA RRDYRFDMGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGCGTK  720
VEIKR                                                             725

SEQ ID NO: 138           moltype = AA  length = 725
FEATURE                  Location/Qualifiers
source                   1..725
                         mol_type = protein
                         organism = synthetic construct
SEQUENCE: 138
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSQGG TNFNEKFKNR  540
```

-continued

```
VTLTTDSSTT TAYMELKSLQ FDDTAVYYCA RRDYRFDLGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGCGTK  720
VEIKR                                                             725

SEQ ID NO: 139          moltype = AA  length = 725
FEATURE                 Location/Qualifiers
source                  1..725
                        mol_type = protein
                        organism = synthetic construct
SEQUENCE: 139
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSQGG TNFNEKFKNR  540
VTLTTDSSTT TAYMELKSLQ FDDTAVYYCA RRDYRFDLGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGCGTK  720
VEIKR                                                             725

SEQ ID NO: 140          moltype = AA  length = 725
FEATURE                 Location/Qualifiers
source                  1..725
                        mol_type = protein
                        organism = synthetic construct
SEQUENCE: 140
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSRGG TNFNEKFKNR  540
VTLTTDSSTT TAYMELKSLQ FDDTAVYYCA RRDYRFDLGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGCGTK  720
VEIKR                                                             725

SEQ ID NO: 141          moltype = AA  length = 725
FEATURE                 Location/Qualifiers
source                  1..725
                        mol_type = protein
                        organism = synthetic construct
SEQUENCE: 141
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSQVQLVQS  480
GVEVKKPGAS VKVSCKASGY TFTNYYMYWV RQAPGQCLEW MGGINPSRGG TNFNEKFKNR  540
VTLTTDSSTT TAYMELKSLQ FDDTAVYYCA RRDYRFDLGF DYWGQGTTVT VSSGGGGSGG  600
GGSGGGGSGG GGSEIVLTQS PATLSLSPGE RATLSCRASK GVSTSGYSYL HWYQQKPGQA  660
PRLLIYLASY LESGVPARFS GSGSGTDFTL TISSLEPEDF AVYYCQHSRD LPLTFGCGTK  720
VEIKR                                                             725

SEQ ID NO: 142          moltype = AA  length = 725
FEATURE                 Location/Qualifiers
source                  1..725
                        mol_type = protein
                        organism = synthetic construct
SEQUENCE: 142
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGKGGGGSGG GGSGGGGSGG GGSEVQLVES  480
```

-continued

```
GGGLVQPGGS LRLSCAASGY TFTNYYMYWV RQAPGKGLEW MGGINPSQGG TNFNEKFKNR   540
FTISRDNSKN TLYLQMNSLR AEDTAVYYCA RRDYRFDLGF DYWGQGTLVT VSSGGGGSGG   600
GGSGGGGSGG GGSEIVLTQS PATLSVSPGE RATLSCRASK GVSTSGYSYL HWYQQKPGQA   660
PRLLIYLASY LESGIPARFS GSGSGTEFTL TISSLQSEDF AVYYCQHSRD LPLTFGGGTK   720
VEIKR                                                             725

SEQ ID NO: 143          moltype = AA  length = 725
FEATURE                 Location/Qualifiers
source                  1..725
                        mol_type = protein
                        organism = synthetic construct
SEQUENCE: 143
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLVES   480
GGGLVQPGGS LRLSCAASGY TFTNYYMYWV RQAPGKCLEW MGGINPSQGG TNFNEKFKNR   540
FTISRDNSKN TLYLQMNSLR AEDTAVYYCA RRDYRFDLGF DYWGQGTLVT VSSGGGGSGG   600
GGSGGGGSGG GGSEIVLTQS PATLSVSPGE RATLSCRASK GVSTSGYSYL HWYQQKPGQA   660
PRLLIYLASY LESGIPARFS GSGSGTEFTL TISSLQSEDF AVYYCQHSRD LPLTFGCGTK   720
VEIKR                                                             725

SEQ ID NO: 144          moltype = AA  length = 721
FEATURE                 Location/Qualifiers
source                  1..721
                        mol_type = protein
                        organism = synthetic construct
SEQUENCE: 144
QVQLVQSGVE VKKPGASVKV SCKASGYTFT NYYMYWVRQA PGQGLEWMGG INPSQGGTNF   60
NEKFKNRVTL TTDSSTTTAY MELKSLQFDD TAVYYCARRD YRFDLGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLYITREP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK GGGGSGGGGS GGGGSGGGGS EVQLVESGGG   480
LVQPGGSLRL SCAASGYTFT NYGMNWVRQA PGKGLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGQGTKVEIK   720
R                                                                 721

SEQ ID NO: 145          moltype = AA  length = 721
FEATURE                 Location/Qualifiers
source                  1..721
                        mol_type = protein
                        organism = synthetic construct
SEQUENCE: 145
QVQLVQSGVE VKKPGASVKV SCKASGYTFT NYYMYWVRQA PGQGLEWMGG INPSRGGTNF   60
NEKFKNRVTL TTDSSTTTAY MELKSLQFDD TAVYYCARRD YRFDLGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLYITREP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK GGGGSGGGGS GGGGSGGGGS EVQLVESGGG   480
LVQPGGSLRL SCAASGYTFT NYGMNWVRQA PGKGLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGQGTKVEIK   720
R                                                                 721

SEQ ID NO: 146          moltype = AA  length = 721
FEATURE                 Location/Qualifiers
source                  1..721
                        mol_type = protein
                        organism = synthetic construct
SEQUENCE: 146
QVQLVQSGVE VKKPGASVKV SCKASGYTFT NYYMYWVRQA PGQGLEWMGG INPSQGGTNF   60
NEKFKNRVTL TTDSSTTTAY MELKSLQFDD TAVYYCARRD YRFDLGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLYITREP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
```

```
QQGNVFSCSV MHEALHNHYT QKSLSLSPGK GGGGSGGGGS GGGGSGGGGS EVQLVESGGG   480
LVQPGGSLRL SCAASGYTFT NYGMNWVRQA PGKCLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGCGTKVEIK   720
R                                                                  721

SEQ ID NO: 147            moltype = AA   length = 721
FEATURE                   Location/Qualifiers
source                    1..721
                          mol_type = protein
                          organism = synthetic construct
SEQUENCE: 147
QVQLVQSGVE VKKPGASVKV SCKASGYTFT NYYMYWVRQA PGQGLEWMGG INPSRGGTNF   60
NEKFKNRVTL TTDSSTTTAY MELKSLQFDD TAVYYCARRD YRFDLGFDYW GQGTTVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPEAAGG   240
PSVFLFPPKP KDTLYITREP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK GGGGSGGGGS GGGGSGGGGS EVQLVESGGG   480
LVQPGGSLRL SCAASGYTFT NYGMNWVRQA PGKCLEWVGW INTYTGEPTY AADFKRRFTF   540
SLDTSKSTAY LQMNSLRAED TAVYYCAKYP HYYGSSHWYF DVWGQGTLVT VSSGGGGSGG   600
GGSGGGGSGG GGSDIQMTQS PSSLSASVGD RVTITCSASQ DISNYLNWYQ QKPGKAPKVL   660
IYFTSSLHSG VPSRFSGSGS GTDFTLTISS LQPEDFATYY CQQYSTVPWT FGCGTKVEIK   720
R                                                                  721

SEQ ID NO: 148            moltype = AA   length = 214
FEATURE                   Location/Qualifiers
source                    1..214
                          mol_type = protein
                          organism = synthetic construct
SEQUENCE: 148
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 149            moltype = AA   length = 214
FEATURE                   Location/Qualifiers
source                    1..214
                          mol_type = protein
                          organism = synthetic construct
SEQUENCE: 149
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 150            moltype = AA   length = 214
FEATURE                   Location/Qualifiers
source                    1..214
                          mol_type = protein
                          organism = synthetic construct
SEQUENCE: 150
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 151            moltype = AA   length = 214
FEATURE                   Location/Qualifiers
source                    1..214
                          mol_type = protein
                          organism = synthetic construct
SEQUENCE: 151
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 152            moltype = AA   length = 214
FEATURE                   Location/Qualifiers
source                    1..214
                          mol_type = protein
                          organism = synthetic construct
SEQUENCE: 152
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
```

-continued

```
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 153          moltype = AA  length = 214
FEATURE                 Location/Qualifiers
source                  1..214
                        mol_type = protein
                        organism = synthetic construct
SEQUENCE: 153
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 154          moltype = AA  length = 214
FEATURE                 Location/Qualifiers
source                  1..214
                        mol_type = protein
                        organism = synthetic construct
SEQUENCE: 154
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 155          moltype = AA  length = 214
FEATURE                 Location/Qualifiers
source                  1..214
                        mol_type = protein
                        organism = synthetic construct
SEQUENCE: 155
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 156          moltype = AA  length = 214
FEATURE                 Location/Qualifiers
source                  1..214
                        mol_type = protein
                        organism = synthetic construct
SEQUENCE: 156
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 157          moltype = AA  length = 214
FEATURE                 Location/Qualifiers
source                  1..214
                        mol_type = protein
                        organism = synthetic construct
SEQUENCE: 157
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 158          moltype = AA  length = 214
FEATURE                 Location/Qualifiers
source                  1..214
                        mol_type = protein
                        organism = synthetic construct
SEQUENCE: 158
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 159          moltype = AA  length = 214
FEATURE                 Location/Qualifiers
source                  1..214
                        mol_type = protein
                        organism = synthetic construct
SEQUENCE: 159
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

-continued

```
SEQ ID NO: 160            moltype = AA  length = 214
FEATURE                   Location/Qualifiers
source                    1..214
                          mol_type = protein
                          organism = synthetic construct
SEQUENCE: 160
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 161            moltype = AA  length = 214
FEATURE                   Location/Qualifiers
source                    1..214
                          mol_type = protein
                          organism = synthetic construct
SEQUENCE: 161
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 162            moltype = AA  length = 214
FEATURE                   Location/Qualifiers
source                    1..214
                          mol_type = protein
                          organism = synthetic construct
SEQUENCE: 162
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 163            moltype = AA  length = 214
FEATURE                   Location/Qualifiers
source                    1..214
                          mol_type = protein
                          organism = synthetic construct
SEQUENCE: 163
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 164            moltype = AA  length = 214
FEATURE                   Location/Qualifiers
source                    1..214
                          mol_type = protein
                          organism = synthetic construct
SEQUENCE: 164
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 165            moltype = AA  length = 214
FEATURE                   Location/Qualifiers
source                    1..214
                          mol_type = protein
                          organism = synthetic construct
SEQUENCE: 165
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 166            moltype = AA  length = 214
FEATURE                   Location/Qualifiers
source                    1..214
                          mol_type = protein
                          organism = synthetic construct
SEQUENCE: 166
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 167            moltype = AA  length = 214
```

-continued

```
FEATURE                  Location/Qualifiers
source                   1..214
                         mol_type = protein
                         organism = synthetic construct
SEQUENCE: 167
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 168           moltype = AA   length = 214
FEATURE                  Location/Qualifiers
source                   1..214
                         mol_type = protein
                         organism = synthetic construct
SEQUENCE: 168
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 169           moltype = AA   length = 214
FEATURE                  Location/Qualifiers
source                   1..214
                         mol_type = protein
                         organism = synthetic construct
SEQUENCE: 169
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 170           moltype = AA   length = 214
FEATURE                  Location/Qualifiers
source                   1..214
                         mol_type = protein
                         organism = synthetic construct
SEQUENCE: 170
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 171           moltype = AA   length = 214
FEATURE                  Location/Qualifiers
source                   1..214
                         mol_type = protein
                         organism = synthetic construct
SEQUENCE: 171
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 172           moltype = AA   length = 214
FEATURE                  Location/Qualifiers
source                   1..214
                         mol_type = protein
                         organism = synthetic construct
SEQUENCE: 172
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 173           moltype = AA   length = 214
FEATURE                  Location/Qualifiers
source                   1..214
                         mol_type = protein
                         organism = synthetic construct
SEQUENCE: 173
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 174           moltype = AA   length = 214
FEATURE                  Location/Qualifiers
source                   1..214
```

```
                              mol_type = protein
                              organism = synthetic construct
SEQUENCE: 174
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 175            moltype = AA  length = 214
FEATURE                   Location/Qualifiers
source                    1..214
                          mol_type = protein
                          organism = synthetic construct
SEQUENCE: 175
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 176            moltype = AA  length = 214
FEATURE                   Location/Qualifiers
source                    1..214
                          mol_type = protein
                          organism = synthetic construct
SEQUENCE: 176
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 177            moltype = AA  length = 214
FEATURE                   Location/Qualifiers
source                    1..214
                          mol_type = protein
                          organism = synthetic construct
SEQUENCE: 177
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 178            moltype = AA  length = 214
FEATURE                   Location/Qualifiers
source                    1..214
                          mol_type = protein
                          organism = synthetic construct
SEQUENCE: 178
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 179            moltype = AA  length = 214
FEATURE                   Location/Qualifiers
source                    1..214
                          mol_type = protein
                          organism = synthetic construct
SEQUENCE: 179
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 180            moltype = AA  length = 214
FEATURE                   Location/Qualifiers
source                    1..214
                          mol_type = protein
                          organism = synthetic construct
SEQUENCE: 180
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 181            moltype = AA  length = 214
FEATURE                   Location/Qualifiers
source                    1..214
                          mol_type = protein
                          organism = synthetic construct
```

-continued

```
SEQUENCE: 181
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 182         moltype = AA   length = 214
FEATURE                Location/Qualifiers
source                 1..214
                       mol_type = protein
                       organism = synthetic construct
SEQUENCE: 182
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 183         moltype = AA   length = 214
FEATURE                Location/Qualifiers
source                 1..214
                       mol_type = protein
                       organism = synthetic construct
SEQUENCE: 183
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 184         moltype = AA   length = 214
FEATURE                Location/Qualifiers
source                 1..214
                       mol_type = protein
                       organism = synthetic construct
SEQUENCE: 184
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 185         moltype = AA   length = 214
FEATURE                Location/Qualifiers
source                 1..214
                       mol_type = protein
                       organism = synthetic construct
SEQUENCE: 185
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 186         moltype = AA   length = 214
FEATURE                Location/Qualifiers
source                 1..214
                       mol_type = protein
                       organism = synthetic construct
SEQUENCE: 186
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 187         moltype = AA   length = 214
FEATURE                Location/Qualifiers
source                 1..214
                       mol_type = protein
                       organism = synthetic construct
SEQUENCE: 187
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 188         moltype = AA   length = 214
FEATURE                Location/Qualifiers
source                 1..214
                       mol_type = protein
                       organism = synthetic construct
SEQUENCE: 188
DIQMTQSPSS LSASVGDRVT ITCSASQDIS NYLNWYQQKP GKAPKVLIYF TSSLHSGVPS    60
```

-continued

```
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 189          moltype = AA  length = 214
FEATURE                 Location/Qualifiers
source                  1..214
                        mol_type = protein
                        organism = synthetic construct
SEQUENCE: 189
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 190          moltype = AA  length = 214
FEATURE                 Location/Qualifiers
source                  1..214
                        mol_type = protein
                        organism = synthetic construct
SEQUENCE: 190
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 191          moltype = AA  length = 214
FEATURE                 Location/Qualifiers
source                  1..214
                        mol_type = protein
                        organism = synthetic construct
SEQUENCE: 191
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 192          moltype = AA  length = 214
FEATURE                 Location/Qualifiers
source                  1..214
                        mol_type = protein
                        organism = synthetic construct
SEQUENCE: 192
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 193          moltype = AA  length = 214
FEATURE                 Location/Qualifiers
source                  1..214
                        mol_type = protein
                        organism = synthetic construct
SEQUENCE: 193
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 194          moltype = AA  length = 214
FEATURE                 Location/Qualifiers
source                  1..214
                        mol_type = protein
                        organism = synthetic construct
SEQUENCE: 194
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 195          moltype = AA  length = 214
FEATURE                 Location/Qualifiers
source                  1..214
                        mol_type = protein
                        organism = synthetic construct
SEQUENCE: 195
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
```

-continued

```
LSKADYEKHK VYACEVTHQG LSSPVTKSFN RGEC                              214

SEQ ID NO: 196          moltype = AA  length = 214
FEATURE                 Location/Qualifiers
source                  1..214
                        mol_type = protein
                        organism = synthetic construct
SEQUENCE: 196
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 197          moltype = AA  length = 214
FEATURE                 Location/Qualifiers
source                  1..214
                        mol_type = protein
                        organism = synthetic construct
SEQUENCE: 197
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 198          moltype = AA  length = 214
FEATURE                 Location/Qualifiers
source                  1..214
                        mol_type = protein
                        organism = synthetic construct
SEQUENCE: 198
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 199          moltype = AA  length = 214
FEATURE                 Location/Qualifiers
source                  1..214
                        mol_type = protein
                        organism = synthetic construct
SEQUENCE: 199
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 200          moltype = AA  length = 214
FEATURE                 Location/Qualifiers
source                  1..214
                        mol_type = protein
                        organism = synthetic construct
SEQUENCE: 200
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 201          moltype = AA  length = 214
FEATURE                 Location/Qualifiers
source                  1..214
                        mol_type = protein
                        organism = synthetic construct
SEQUENCE: 201
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 202          moltype = AA  length = 214
FEATURE                 Location/Qualifiers
source                  1..214
                        mol_type = protein
                        organism = synthetic construct
SEQUENCE: 202
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214
```

-continued

```
SEQ ID NO: 203           moltype = AA  length = 214
FEATURE                  Location/Qualifiers
source                   1..214
                         mol_type = protein
                         organism = synthetic construct
SEQUENCE: 203
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 204           moltype = AA  length = 214
FEATURE                  Location/Qualifiers
source                   1..214
                         mol_type = protein
                         organism = synthetic construct
SEQUENCE: 204
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 205           moltype = AA  length = 214
FEATURE                  Location/Qualifiers
source                   1..214
                         mol_type = protein
                         organism = synthetic construct
SEQUENCE: 205
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 206           moltype = AA  length = 214
FEATURE                  Location/Qualifiers
source                   1..214
                         mol_type = protein
                         organism = synthetic construct
SEQUENCE: 206
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 207           moltype = AA  length = 214
FEATURE                  Location/Qualifiers
source                   1..214
                         mol_type = protein
                         organism = synthetic construct
SEQUENCE: 207
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 208           moltype = AA  length = 214
FEATURE                  Location/Qualifiers
source                   1..214
                         mol_type = protein
                         organism = synthetic construct
SEQUENCE: 208
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 209           moltype = AA  length = 214
FEATURE                  Location/Qualifiers
source                   1..214
                         mol_type = protein
                         organism = synthetic construct
SEQUENCE: 209
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 210           moltype = AA  length = 214
FEATURE                  Location/Qualifiers
```

-continued

```
source                   1..214
                         mol_type = protein
                         organism = synthetic construct
SEQUENCE: 210
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 211          moltype = AA  length = 214
FEATURE                 Location/Qualifiers
source                  1..214
                        mol_type = protein
                        organism = synthetic construct
SEQUENCE: 211
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 212          moltype = AA  length = 214
FEATURE                 Location/Qualifiers
source                  1..214
                        mol_type = protein
                        organism = synthetic construct
SEQUENCE: 212
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 213          moltype = AA  length = 214
FEATURE                 Location/Qualifiers
source                  1..214
                        mol_type = protein
                        organism = synthetic construct
SEQUENCE: 213
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 214          moltype = AA  length = 214
FEATURE                 Location/Qualifiers
source                  1..214
                        mol_type = protein
                        organism = synthetic construct
SEQUENCE: 214
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 215          moltype = AA  length = 214
FEATURE                 Location/Qualifiers
source                  1..214
                        mol_type = protein
                        organism = synthetic construct
SEQUENCE: 215
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 216          moltype = AA  length = 214
FEATURE                 Location/Qualifiers
source                  1..214
                        mol_type = protein
                        organism = synthetic construct
SEQUENCE: 216
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 217          moltype = AA  length = 214
FEATURE                 Location/Qualifiers
source                  1..214
                        mol_type = protein
```

-continued

```
                          organism = synthetic construct
SEQUENCE: 217
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 218           moltype = AA  length = 214
FEATURE                  Location/Qualifiers
source                   1..214
                         mol_type = protein
                         organism = synthetic construct
SEQUENCE: 218
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 219           moltype = AA  length = 214
FEATURE                  Location/Qualifiers
source                   1..214
                         mol_type = protein
                         organism = synthetic construct
SEQUENCE: 219
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 220           moltype = AA  length = 214
FEATURE                  Location/Qualifiers
source                   1..214
                         mol_type = protein
                         organism = synthetic construct
SEQUENCE: 220
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 221           moltype = AA  length = 214
FEATURE                  Location/Qualifiers
source                   1..214
                         mol_type = protein
                         organism = synthetic construct
SEQUENCE: 221
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 222           moltype = AA  length = 214
FEATURE                  Location/Qualifiers
source                   1..214
                         mol_type = protein
                         organism = synthetic construct
SEQUENCE: 222
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 223           moltype = AA  length = 214
FEATURE                  Location/Qualifiers
source                   1..214
                         mol_type = protein
                         organism = synthetic construct
SEQUENCE: 223
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 224           moltype = AA  length = 214
FEATURE                  Location/Qualifiers
source                   1..214
                         mol_type = protein
                         organism = synthetic construct
SEQUENCE: 224
```

-continued

```
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 225          moltype = AA  length = 214
FEATURE                 Location/Qualifiers
source                  1..214
                        mol_type = protein
                        organism = synthetic construct
SEQUENCE: 225
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 226          moltype = AA  length = 214
FEATURE                 Location/Qualifiers
source                  1..214
                        mol_type = protein
                        organism = synthetic construct
SEQUENCE: 226
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 227          moltype = AA  length = 214
FEATURE                 Location/Qualifiers
source                  1..214
                        mol_type = protein
                        organism = synthetic construct
SEQUENCE: 227
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 228          moltype = AA  length = 214
FEATURE                 Location/Qualifiers
source                  1..214
                        mol_type = protein
                        organism = synthetic construct
SEQUENCE: 228
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 229          moltype = AA  length = 214
FEATURE                 Location/Qualifiers
source                  1..214
                        mol_type = protein
                        organism = synthetic construct
SEQUENCE: 229
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 230          moltype = AA  length = 214
FEATURE                 Location/Qualifiers
source                  1..214
                        mol_type = protein
                        organism = synthetic construct
SEQUENCE: 230
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 231          moltype = AA  length = 214
FEATURE                 Location/Qualifiers
source                  1..214
                        mol_type = protein
                        organism = synthetic construct
SEQUENCE: 231
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
```

-continued

```
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 232          moltype = AA  length = 214
FEATURE                 Location/Qualifiers
source                  1..214
                        mol_type = protein
                        organism = synthetic construct
SEQUENCE: 232
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 233          moltype = AA  length = 214
FEATURE                 Location/Qualifiers
source                  1..214
                        mol_type = protein
                        organism = synthetic construct
SEQUENCE: 233
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 234          moltype = AA  length = 214
FEATURE                 Location/Qualifiers
source                  1..214
                        mol_type = protein
                        organism = synthetic construct
SEQUENCE: 234
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 235          moltype = AA  length = 214
FEATURE                 Location/Qualifiers
source                  1..214
                        mol_type = protein
                        organism = synthetic construct
SEQUENCE: 235
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 236          moltype = AA  length = 214
FEATURE                 Location/Qualifiers
source                  1..214
                        mol_type = protein
                        organism = synthetic construct
SEQUENCE: 236
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 237          moltype = AA  length = 214
FEATURE                 Location/Qualifiers
source                  1..214
                        mol_type = protein
                        organism = synthetic construct
SEQUENCE: 237
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 238          moltype = AA  length = 214
FEATURE                 Location/Qualifiers
source                  1..214
                        mol_type = protein
                        organism = synthetic construct
SEQUENCE: 238
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

-continued

```
SEQ ID NO: 239              moltype = AA   length = 214
FEATURE                     Location/Qualifiers
source                      1..214
                            mol_type = protein
                            organism = synthetic construct
SEQUENCE: 239
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 240              moltype = AA   length = 214
FEATURE                     Location/Qualifiers
source                      1..214
                            mol_type = protein
                            organism = synthetic construct
SEQUENCE: 240
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 241              moltype = AA   length = 214
FEATURE                     Location/Qualifiers
source                      1..214
                            mol_type = protein
                            organism = synthetic construct
SEQUENCE: 241
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 242              moltype = AA   length = 214
FEATURE                     Location/Qualifiers
source                      1..214
                            mol_type = protein
                            organism = synthetic construct
SEQUENCE: 242
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 243              moltype = AA   length = 214
FEATURE                     Location/Qualifiers
source                      1..214
                            mol_type = protein
                            organism = synthetic construct
SEQUENCE: 243
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 244              moltype = AA   length = 214
FEATURE                     Location/Qualifiers
source                      1..214
                            mol_type = protein
                            organism = synthetic construct
SEQUENCE: 244
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 245              moltype = AA   length = 218
FEATURE                     Location/Qualifiers
source                      1..218
                            mol_type = protein
                            organism = synthetic construct
SEQUENCE: 245
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KRTVAAPSVF   120
IPPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                            218

SEQ ID NO: 246              moltype = AA   length = 218
```

-continued

```
FEATURE              Location/Qualifiers
source               1..218
                     mol_type = protein
                     organism = synthetic construct
SEQUENCE: 246
EIVLTQSPAT LSLSPGERAT LSCRASKGVS TSGYSYLHWY QQKPGQAPRL LIYLASYLES      60
GVPARFSGSG SGTDFTLTIS SLEPEDFAVY YCQHSRDLPL TFGGGTKVEI KRTVAAPSVF     120
IFPPSDEQLK SGTASVVCLL NNFYPREAKV QWKVDNALQS GNSQESVTEQ DSKDSTYSLS     180
STLTLSKADY EKHKVYACEV THQGLSSPVT KSFNRGEC                             218

SEQ ID NO: 247         moltype = AA  length = 218
FEATURE                Location/Qualifiers
source                 1..218
                       mol_type = protein
                       organism = synthetic construct
SEQUENCE: 247
EIVLTQSPAT LSLSPGERAT LSCRASKGVS TSGYSYLHWY QQKPGQAPRL LIYLASYLES      60
GVPARFSGSG SGTDFTLTIS SLEPEDFAVY YCQHSRDLPL TFGGGTKVEI KRTVAAPSVF     120
IFPPSDEQLK SGTASVVCLL NNFYPREAKV QWKVDNALQS GNSQESVTEQ DSKDSTYSLS     180
STLTLSKADY EKHKVYACEV THQGLSSPVT KSFNRGEC                             218

SEQ ID NO: 248         moltype = AA  length = 218
FEATURE                Location/Qualifiers
source                 1..218
                       mol_type = protein
                       organism = synthetic construct
SEQUENCE: 248
EIVLTQSPAT LSLSPGERAT LSCRASKGVS TSGYSYLHWY QQKPGQAPRL LIYLASYLES      60
GVPARFSGSG SGTDFTLTIS SLEPEDFAVY YCQHSRDLPL TFGGGTKVEI KRTVAAPSVF     120
IFPPSDEQLK SGTASVVCLL NNFYPREAKV QWKVDNALQS GNSQESVTEQ DSKDSTYSLS     180
STLTLSKADY EKHKVYACEV THQGLSSPVT KSFNRGEC                             218

SEQ ID NO: 249         moltype = AA  length = 218
FEATURE                Location/Qualifiers
source                 1..218
                       mol_type = protein
                       organism = synthetic construct
SEQUENCE: 249
EIVLTQSPAT LSLSPGERAT LSCRASKGVS TSGYSYLHWY QQKPGQAPRL LIYLASYLES      60
GVPARFSGSG SGTDFTLTIS SLEPEDFAVY YCQHSRDLPL TFGGGTKVEI KRTVAAPSVF     120
IFPPSDEQLK SGTASVVCLL NNFYPREAKV QWKVDNALQS GNSQESVTEQ DSKDSTYSLS     180
STLTLSKADY EKHKVYACEV THQGLSSPVT KSFNRGEC                             218

SEQ ID NO: 250         moltype = AA  length = 218
FEATURE                Location/Qualifiers
source                 1..218
                       mol_type = protein
                       organism = synthetic construct
SEQUENCE: 250
EIVLTQSPAT LSLSPGERAT LSCRASKGVS TSGYSYLHWY QQKPGQAPRL LIYLASYLES      60
GVPARFSGSG SGTDFTLTIS SLEPEDFAVY YCQHSRDLPL TFGGGTKVEI KRTVAAPSVF     120
IFPPSDEQLK SGTASVVCLL NNFYPREAKV QWKVDNALQS GNSQESVTEQ DSKDSTYSLS     180
STLTLSKADY EKHKVYACEV THQGLSSPVT KSFNRGEC                             218

SEQ ID NO: 251         moltype = AA  length = 218
FEATURE                Location/Qualifiers
source                 1..218
                       mol_type = protein
                       organism = synthetic construct
SEQUENCE: 251
EIVLTQSPAT LSLSPGERAT LSCRASKGVS TSGYSYLHWY QQKPGQAPRL LIYLASYLES      60
GVPARFSGSG SGTDFTLTIS SLEPEDFAVY YCQHSRDLPL TFGGGTKVEI KRTVAAPSVF     120
IFPPSDEQLK SGTASVVCLL NNFYPREAKV QWKVDNALQS GNSQESVTEQ DSKDSTYSLS     180
STLTLSKADY EKHKVYACEV THQGLSSPVT KSFNRGEC                             218

SEQ ID NO: 252         moltype = AA  length = 218
FEATURE                Location/Qualifiers
source                 1..218
                       mol_type = protein
                       organism = synthetic construct
SEQUENCE: 252
EIVLTQSPAT LSLSPGERAT LSCRASKGVS TSGYSYLHWY QQKPGQAPRL LIYLASYLES      60
GVPARFSGSG SGTDFTLTIS SLEPEDFAVY YCQHSRDLPL TFGGGTKVEI KRTVAAPSVF     120
IFPPSDEQLK SGTASVVCLL NNFYPREAKV QWKVDNALQS GNSQESVTEQ DSKDSTYSLS     180
STLTLSKADY EKHKVYACEV THQGLSSPVT KSFNRGEC                             218

SEQ ID NO: 253         moltype = AA  length = 218
FEATURE                Location/Qualifiers
source                 1..218
```

-continued

```
                              mol_type = protein
                              organism = synthetic construct
SEQUENCE: 253
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 254           moltype = AA  length = 218
FEATURE                  Location/Qualifiers
source                   1..218
                         mol_type = protein
                         organism = synthetic construct
SEQUENCE: 254
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 255           moltype = AA  length = 218
FEATURE                  Location/Qualifiers
source                   1..218
                         mol_type = protein
                         organism = synthetic construct
SEQUENCE: 255
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 256           moltype = AA  length = 218
FEATURE                  Location/Qualifiers
source                   1..218
                         mol_type = protein
                         organism = synthetic construct
SEQUENCE: 256
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 257           moltype = AA  length = 218
FEATURE                  Location/Qualifiers
source                   1..218
                         mol_type = protein
                         organism = synthetic construct
SEQUENCE: 257
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 258           moltype = AA  length = 218
FEATURE                  Location/Qualifiers
source                   1..218
                         mol_type = protein
                         organism = synthetic construct
SEQUENCE: 258
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 259           moltype = AA  length = 218
FEATURE                  Location/Qualifiers
source                   1..218
                         mol_type = protein
                         organism = synthetic construct
SEQUENCE: 259
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 260           moltype = AA  length = 218
FEATURE                  Location/Qualifiers
source                   1..218
                         mol_type = protein
                         organism = synthetic construct
```

```
SEQUENCE: 260
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

SEQ ID NO: 261           moltype = AA   length = 218
FEATURE                  Location/Qualifiers
source                   1..218
                         mol_type = protein
                         organism = synthetic construct
SEQUENCE: 261
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

SEQ ID NO: 262           moltype = AA   length = 218
FEATURE                  Location/Qualifiers
source                   1..218
                         mol_type = protein
                         organism = synthetic construct
SEQUENCE: 262
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

SEQ ID NO: 263           moltype = AA   length = 214
FEATURE                  Location/Qualifiers
source                   1..214
                         mol_type = protein
                         organism = synthetic construct
SEQUENCE: 263
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 264           moltype = AA   length = 214
FEATURE                  Location/Qualifiers
source                   1..214
                         mol_type = protein
                         organism = synthetic construct
SEQUENCE: 264
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 265           moltype = AA   length = 214
FEATURE                  Location/Qualifiers
source                   1..214
                         mol_type = protein
                         organism = synthetic construct
SEQUENCE: 265
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 266           moltype = AA   length = 214
FEATURE                  Location/Qualifiers
source                   1..214
                         mol_type = protein
                         organism = synthetic construct
SEQUENCE: 266
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 267           moltype = AA   length = 214
FEATURE                  Location/Qualifiers
source                   1..214
                         mol_type = protein
                         organism = synthetic construct
SEQUENCE: 267
DIQMTQSPSS LSASVGDRVT ITCSASQDIS NYLNWYQQKP GKAPKVLIYF TSSLHSGVPS   60
```

```
RFSGSGSGTD FTLTISSLQP EDFATYYCQQ YSTVPWTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 268              moltype = AA  length = 214
FEATURE                     Location/Qualifiers
source                      1..214
                            mol_type = protein
                            organism = synthetic construct
SEQUENCE: 268
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 269              moltype = AA  length = 214
FEATURE                     Location/Qualifiers
source                      1..214
                            mol_type = protein
                            organism = synthetic construct
SEQUENCE: 269
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 270              moltype = AA  length = 214
FEATURE                     Location/Qualifiers
source                      1..214
                            mol_type = protein
                            organism = synthetic construct
SEQUENCE: 270
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 271              moltype = AA  length = 214
FEATURE                     Location/Qualifiers
source                      1..214
                            mol_type = protein
                            organism = synthetic construct
SEQUENCE: 271
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 272              moltype = AA  length = 214
FEATURE                     Location/Qualifiers
source                      1..214
                            mol_type = protein
                            organism = synthetic construct
SEQUENCE: 272
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 273              moltype = AA  length = 214
FEATURE                     Location/Qualifiers
source                      1..214
                            mol_type = protein
                            organism = synthetic construct
SEQUENCE: 273
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 274              moltype = AA  length = 214
FEATURE                     Location/Qualifiers
source                      1..214
                            mol_type = protein
                            organism = synthetic construct
SEQUENCE: 274
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP     120
SDEQLKSGTA SVVCLLNNFY PREAKVQWKV DNALQSGNSQ ESVTEQDSKD STYSLSSTLT     180
```

-continued

```
LSKADYEKHK VYACEVTHQG LSSPVTKSFN RGEC                                 214

SEQ ID NO: 275          moltype = AA  length = 214
FEATURE                 Location/Qualifiers
source                  1..214
                        mol_type = protein
                        organism = synthetic construct
SEQUENCE: 275
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214

SEQ ID NO: 276          moltype = AA  length = 214
FEATURE                 Location/Qualifiers
source                  1..214
                        mol_type = protein
                        organism = synthetic construct
SEQUENCE: 276
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214

SEQ ID NO: 277          moltype = AA  length = 214
FEATURE                 Location/Qualifiers
source                  1..214
                        mol_type = protein
                        organism = synthetic construct
SEQUENCE: 277
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214

SEQ ID NO: 278          moltype = AA  length = 214
FEATURE                 Location/Qualifiers
source                  1..214
                        mol_type = protein
                        organism = synthetic construct
SEQUENCE: 278
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214

SEQ ID NO: 279          moltype = AA  length = 214
FEATURE                 Location/Qualifiers
source                  1..214
                        mol_type = protein
                        organism = synthetic construct
SEQUENCE: 279
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214

SEQ ID NO: 280          moltype = AA  length = 214
FEATURE                 Location/Qualifiers
source                  1..214
                        mol_type = protein
                        organism = synthetic construct
SEQUENCE: 280
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214

SEQ ID NO: 281          moltype = AA  length = 214
FEATURE                 Location/Qualifiers
source                  1..214
                        mol_type = protein
                        organism = synthetic construct
SEQUENCE: 281
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214
```

-continued

```
SEQ ID NO: 282            moltype = AA  length = 214
FEATURE                   Location/Qualifiers
source                    1..214
                          mol_type = protein
                          organism = synthetic construct
SEQUENCE: 282
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 283            moltype = AA  length = 214
FEATURE                   Location/Qualifiers
source                    1..214
                          mol_type = protein
                          organism = synthetic construct
SEQUENCE: 283
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 284            moltype = AA  length = 214
FEATURE                   Location/Qualifiers
source                    1..214
                          mol_type = protein
                          organism = synthetic construct
SEQUENCE: 284
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 285            moltype = AA  length = 214
FEATURE                   Location/Qualifiers
source                    1..214
                          mol_type = protein
                          organism = synthetic construct
SEQUENCE: 285
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 286            moltype = AA  length = 214
FEATURE                   Location/Qualifiers
source                    1..214
                          mol_type = protein
                          organism = synthetic construct
SEQUENCE: 286
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 287            moltype = AA  length = 214
FEATURE                   Location/Qualifiers
source                    1..214
                          mol_type = protein
                          organism = synthetic construct
SEQUENCE: 287
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 288            moltype = AA  length = 214
FEATURE                   Location/Qualifiers
source                    1..214
                          mol_type = protein
                          organism = synthetic construct
SEQUENCE: 288
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 289            moltype = AA  length = 214
FEATURE                   Location/Qualifiers
```

-continued

```
source                   1..214
                         mol_type = protein
                         organism = synthetic construct
SEQUENCE: 289
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 290          moltype = AA  length = 214
FEATURE                 Location/Qualifiers
source                  1..214
                        mol_type = protein
                        organism = synthetic construct
SEQUENCE: 290
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 291          moltype = AA  length = 218
FEATURE                 Location/Qualifiers
source                  1..218
                        mol_type = protein
                        organism = synthetic construct
SEQUENCE: 291
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 292          moltype = AA  length = 218
FEATURE                 Location/Qualifiers
source                  1..218
                        mol_type = protein
                        organism = synthetic construct
SEQUENCE: 292
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 293          moltype = AA  length = 218
FEATURE                 Location/Qualifiers
source                  1..218
                        mol_type = protein
                        organism = synthetic construct
SEQUENCE: 293
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 294          moltype = AA  length = 218
FEATURE                 Location/Qualifiers
source                  1..218
                        mol_type = protein
                        organism = synthetic construct
SEQUENCE: 294
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 295          moltype = AA  length = 123
FEATURE                 Location/Qualifiers
source                  1..123
                        mol_type = protein
                        organism = synthetic construct
SEQUENCE: 295
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSS                                                               123

SEQ ID NO: 296          moltype = AA  length = 123
FEATURE                 Location/Qualifiers
source                  1..123
                        mol_type = protein
                        organism = synthetic construct
```

```
SEQUENCE: 296
EVQLVESGGG LVQPGGSLRL SCAASGYTFT NYGMNWVRQA PGKCLEWVGW INTYTGEPTY   60
AADFKRRFTF SLDTSKSTAY LQMNSLRAED TAVYYCAKYP HYYGSSHWYF DVWGQGTLVT   120
VSS                                                                 123

SEQ ID NO: 297        moltype =   length =
SEQUENCE: 297
000

SEQ ID NO: 298        moltype = AA   length = 107
FEATURE               Location/Qualifiers
source                1..107
                      mol_type = protein
                      organism = synthetic construct
SEQUENCE: 298
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIK                 107

SEQ ID NO: 299        moltype = AA   length = 108
FEATURE               Location/Qualifiers
source                1..108
                      mol_type = protein
                      organism = synthetic construct
SEQUENCE: 299
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKR                108

SEQ ID NO: 300        moltype = AA   length = 108
FEATURE               Location/Qualifiers
source                1..108
                      mol_type = protein
                      organism = synthetic construct
SEQUENCE: 300
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGC GTKVEIKR                108

SEQ ID NO: 301        moltype = AA   length = 120
FEATURE               Location/Qualifiers
source                1..120
                      mol_type = protein
                      organism = synthetic construct
SEQUENCE: 301
QVQLVQSGVE VKKPGASVKV SCKASGYTFT NYYMYWVRQA PGQGLEWMGG INPSNGGTNF   60
NEKFKNRVTL TTDSSTTTAY MELKSLQFDD TAVYYCARRD YRFDMGFDYW GQGTTVTVSS   120

SEQ ID NO: 302        moltype = AA   length = 120
FEATURE               Location/Qualifiers
source                1..120
                      mol_type = protein
                      organism = synthetic construct
SEQUENCE: 302
QVQLVQSGVE VKKPGASVKV SCKASGYTFT NYYMYWVRQA PGQGLEWMGG INPSQGGTNF   60
NEKFKNRVTL TTDSSTTTAY MELKSLQFDD TAVYYCARRD YRFDLGFDYW GQGTTVTVSS   120

SEQ ID NO: 303        moltype = AA   length = 120
FEATURE               Location/Qualifiers
source                1..120
                      mol_type = protein
                      organism = synthetic construct
SEQUENCE: 303
QVQLVQSGVE VKKPGASVKV SCKASGYTFT NYYMYWVRQA PGQGLEWMGG INPSRGGTNF   60
NEKFKNRVTL TTDSSTTTAY MELKSLQFDD TAVYYCARRD YRFDLGFDYW GQGTTVTVSS   120

SEQ ID NO: 304        moltype = AA   length = 120
FEATURE               Location/Qualifiers
source                1..120
                      mol_type = protein
                      organism = synthetic construct
SEQUENCE: 304
QVQLVQSGVE VKKPGASVKV SCKASGYTFT NYYMYWVRQA PGQGLEWMGG INPSNGGTNF   60
NEKFKNRVTL TTDSSTTTAY MELKSLQFDD TAVYYCARRD YRFDMGFDYW GQGTTVTVSS   120

SEQ ID NO: 305        moltype = AA   length = 120
FEATURE               Location/Qualifiers
source                1..120
                      mol_type = protein
                      organism = synthetic construct
SEQUENCE: 305
QVQLVQSGVE VKKPGASVKV SCKASGYTFT NYYMYWVRQA PGQCLEWMGG INPSNGGTNF   60
```

```
NEKFKNRVTL TTDSSTTTAY MELKSLQFDD TAVYYCARRD YRFDMGFDYW GQGTTVTVSS   120

SEQ ID NO: 306              moltype = AA   length = 120
FEATURE                    Location/Qualifiers
source                     1..120
                           mol_type = protein
                           organism = synthetic construct
SEQUENCE: 306
QVQLVQSGVE VKKPGASVKV SCKASGYTFT NYYMYWVRQA PGQCLEWMGG INPSQGGTNF   60
NEKFKNRVTL TTDSSTTTAY MELKSLQFDD TAVYYCARRD YRFDLGFDYW GQGTTVTVSS   120

SEQ ID NO: 307              moltype = AA   length = 120
FEATURE                    Location/Qualifiers
source                     1..120
                           mol_type = protein
                           organism = synthetic construct
SEQUENCE: 307
QVQLVQSGVE VKKPGASVKV SCKASGYTFT NYYMYWVRQA PGQCLEWMGG INPSRGGTNF   60
NEKFKNRVTL TTDSSTTTAY MELKSLQFDD TAVYYCARRD YRFDLGFDYW GQGTTVTVSS   120

SEQ ID NO: 308              moltype = AA   length = 120
FEATURE                    Location/Qualifiers
source                     1..120
                           mol_type = protein
                           organism = synthetic construct
SEQUENCE: 308
EVQLVESGGG LVQPGGSLRL SCAASGYTFT NYYMYWVRQA PGKGLEWMGG INPSQGGTNF   60
NEKFKNRFTI SRDNSKNTLY LQMNSLRAED TAVYYCARRD YRFDLGFDYW GQGTLVTVSS   120

SEQ ID NO: 309              moltype = AA   length = 120
FEATURE                    Location/Qualifiers
source                     1..120
                           mol_type = protein
                           organism = synthetic construct
SEQUENCE: 309
EVQLVESGGG LVQPGGSLRL SCAASGYTFT NYYMYWVRQA PGKCLEWMGG INPSQGGTNF   60
NEKFKNRFTI SRDNSKNTLY LQMNSLRAED TAVYYCARRD YRFDLGFDYW GQGTLVTVSS   120

SEQ ID NO: 310              moltype = AA   length = 120
FEATURE                    Location/Qualifiers
source                     1..120
                           mol_type = protein
                           organism = synthetic construct
SEQUENCE: 310
QVQLVQSGVE VKKPGASVKV SCKASGYTFT NYYMYWVRQA PGQGLEWMGG INPSQGGTNF   60
NEKFKNRVTL TTDSSTTTAY MELKSLQFDD TAVYYCARRD YRFDLGFDYW GQGTGVRVSS   120

SEQ ID NO: 311              moltype = AA   length = 120
FEATURE                    Location/Qualifiers
source                     1..120
                           mol_type = protein
                           organism = synthetic construct
SEQUENCE: 311
QVQLVQSGVE VKKPGASVKV SCKASGYTFT NYYMYWVRQA PGQCLEWMGG INPSQGGTNF   60
NEKFKNRVTL TTDSSTTTAY MELKSLQFDD TAVYYCARRD YRFDLGFDYW GQGTGVRVSS   120

SEQ ID NO: 312              moltype = AA   length = 120
FEATURE                    Location/Qualifiers
source                     1..120
                           mol_type = protein
                           organism = synthetic construct
SEQUENCE: 312
QVQLVQSGVE VKKPGASVKV SCKASGYTFT NYYMYWVRQA PGQGLEWMGG INPSNGGTNF   60
NEKFKNRVTL TTDSSTTTAY MELKSLRFDD TAVYYCARRD YRFDMGFDYW GQGTTVTVSS   120

SEQ ID NO: 313              moltype = AA   length = 120
FEATURE                    Location/Qualifiers
source                     1..120
                           mol_type = protein
                           organism = synthetic construct
SEQUENCE: 313
QVQLVQSGVE VKKPGASVKV SCKASGYTFT NYYMYWVRQA PGQGLEWMGG INPSQGGTNF   60
NEKFKNRVTL TTDSSTTTAY MELKSLRFDD TAVYYCARRD YRFDLGFDYW GQGTTVTVSS   120

SEQ ID NO: 314              moltype = AA   length = 120
FEATURE                    Location/Qualifiers
source                     1..120
                           mol_type = protein
                           organism = synthetic construct
```

-continued

```
SEQUENCE: 314
QVQLVQSGVE VKKPGASVKV SCKASGYTFT NYYMYWVRQA PGQGLEWMGG INPSRGGTNF    60
NEKFKNRVTL TTDSSTTTAY MELKSLRFDD TAVYYCARRD YRFDLGFDYW GQGTTVTVSS    120

SEQ ID NO: 315          moltype = AA   length = 120
FEATURE                 Location/Qualifiers
source                  1..120
                        mol_type = protein
                        organism = synthetic construct
SEQUENCE: 315
QVQLVQSGVE VKKPGASVKV SCKASGYTFT NYYMYWVRQA PGQCLEWMGG INPSNGGTNF    60
NEKFKNRVTL TTDSSTTTAY MELKSLRFDD TAVYYCARRD YRFDMGFDYW GQGTTVTVSS    120

SEQ ID NO: 316          moltype = AA   length = 120
FEATURE                 Location/Qualifiers
source                  1..120
                        mol_type = protein
                        organism = synthetic construct
SEQUENCE: 316
QVQLVQSGVE VKKPGASVKV SCKASGYTFT NYYMYWVRQA PGQCLEWMGG INPSQGGTNF    60
NEKFKNRVTL TTDSSTTTAY MELKSLRFDD TAVYYCARRD YRFDLGFDYW GQGTTVTVSS    120

SEQ ID NO: 317          moltype = AA   length = 120
FEATURE                 Location/Qualifiers
source                  1..120
                        mol_type = protein
                        organism = synthetic construct
SEQUENCE: 317
QVQLVQSGVE VKKPGASVKV SCKASGYTFT NYYMYWVRQA PGQCLEWMGG INPSRGGTNF    60
NEKFKNRVTL TTDSSTTTAY MELKSLRFDD TAVYYCARRD YRFDLGFDYW GQGTTVTVSS    120

SEQ ID NO: 318          moltype = AA   length = 120
FEATURE                 Location/Qualifiers
source                  1..120
                        mol_type = protein
                        organism = synthetic construct
SEQUENCE: 318
EVQLVQSGAE VKKPGASVKV SCKASGYTFT NYYMYWVRQA PGQGLEWMGG INPSQGGTNF    60
NEKFKNRVTL TTDSSTSTAY MELSSLRSED TAVYYCARRD YRFDLGFDYW GQGTTVTVSS    120

SEQ ID NO: 319          moltype = AA   length = 120
FEATURE                 Location/Qualifiers
source                  1..120
                        mol_type = protein
                        organism = synthetic construct
SEQUENCE: 319
EVQLLESGGG LVQPGGSLRL SCKASGYTFT NYYMYWVRQA PGKGLEWMGG INPSQGGTNF    60
NEKFKNRVTL STDSSKNTAY LQMNSLRAED TAVYYCARRD YRFDLGFDYW GQGTTVTVSS    120

SEQ ID NO: 320          moltype = AA   length = 120
FEATURE                 Location/Qualifiers
source                  1..120
                        mol_type = protein
                        organism = synthetic construct
SEQUENCE: 320
EVQLVQSGAE VKKPGASVKV SCKASGYTFT NYYMYWVRQA PGQCLEWMGG INPSQGGTNF    60
NEKFKNRVTL TTDSSTSTAY MELSSLRSED TAVYYCARRD YRFDLGFDYW GQGTTVTVSS    120

SEQ ID NO: 321          moltype = AA   length = 120
FEATURE                 Location/Qualifiers
source                  1..120
                        mol_type = protein
                        organism = synthetic construct
SEQUENCE: 321
EVQLLESGGG LVQPGGSLRL SCKASGYTFT NYYMYWVRQA PGKCLEWMGG INPSQGGTNF    60
NEKFKNRVTL STDSSKNTAY LQMNSLRAED TAVYYCARRD YRFDLGFDYW GQGTTVTVSS    120

SEQ ID NO: 322          moltype = AA   length = 120
FEATURE                 Location/Qualifiers
source                  1..120
                        mol_type = protein
                        organism = synthetic construct
SEQUENCE: 322
EVQLVQSGAE VKKPGASVKV SCKASGYTFT NYYMYWVRQA PGQGLEWMGG INPSNGGTNF    60
NEKFKNRVTL TTDSSTSTAY MELSSLRSED TAVYYCARRD YRFDMGFDYW GQGTTVTVSS    120

SEQ ID NO: 323          moltype = AA   length = 120
FEATURE                 Location/Qualifiers
source                  1..120
```

```
                         mol_type = protein
                         organism = synthetic construct
SEQUENCE: 323
EVQLVQSGAE VKKPGASVKV SCKASGYTFT NYYMYWVRQA PGQCLEWMGG INPSNGGTNF   60
NEKFKNRVTL TTDSSTSTAY MELSSLRSED TAVYYCARRD YRFDMGFDYW GQGTTVTVSS   120

SEQ ID NO: 324          moltype = AA  length = 120
FEATURE                 Location/Qualifiers
source                  1..120
                        mol_type = protein
                        organism = synthetic construct
SEQUENCE: 324
EVQLVQSGAE VKKPGASVKV SCKASGYTFT NYYMYWVRQA PGQCLEWMGG INPSRGGTNF   60
NEKFKNRVTL TTDSSTSTAY MELSSLRSED TAVYYCARRD YRFDLGFDYW GQGTTVTVSS   120

SEQ ID NO: 325          moltype = AA  length = 120
FEATURE                 Location/Qualifiers
source                  1..120
                        mol_type = protein
                        organism = synthetic construct
SEQUENCE: 325
EVQLVQSGAE VKKPGASVKV SCKASGYTFT NYYMYWVRQA PGQCLEWMGG INPSQGGTNF   60
NEKFKNRVTL TTDSSTSTAY MELSSLRSED TAVYYCARRD YRFDMGFDYW GQGTTVTVSS   120

SEQ ID NO: 326          moltype = AA  length = 120
FEATURE                 Location/Qualifiers
source                  1..120
                        mol_type = protein
                        organism = synthetic construct
SEQUENCE: 326
EVQLVQSGAE VKKPGASVKV SCKASGYTFT NYYMYWVRQA PGQCLEWMGG INPSRGGTNF   60
NEKFKNRVTL TTDSSTSTAY MELSSLRSED TAVYYCARRD YRFDMGFDYW GQGTTVTVSS   120

SEQ ID NO: 327          moltype = AA  length = 120
FEATURE                 Location/Qualifiers
source                  1..120
                        mol_type = protein
                        organism = synthetic construct
SEQUENCE: 327
EVQLVQSGAE VKKPGASVKV SCKASGYTFT NYYMYWVRQA PGQCLEWMGG INPSNGGTNF   60
NEKFKNRVTL TTDSSTSTAY MELSSLRSED TAVYYCARRD YRFDLGFDYW GQGTTVTVSS   120

SEQ ID NO: 328          moltype = AA  length = 119
FEATURE                 Location/Qualifiers
source                  1..119
                        mol_type = protein
                        organism = synthetic construct
SEQUENCE: 328
EVQLVESGGG LVQPGGSLRL SCAASGSIAS IHAMGWVRQA PGKEREWVSV ITWSGGITYY   60
ADSVKGRFTI SRDNSKNTLY LQMNSLRAED TAVYYCAGDK HQSSWYDYWG QGTLVTVSS   119

SEQ ID NO: 329          moltype = AA  length = 119
FEATURE                 Location/Qualifiers
source                  1..119
                        mol_type = protein
                        organism = synthetic construct
SEQUENCE: 329
EVQLVESGGG LVQPGGSLRL SCAASGSIAS IHAMGWVRQA PGKEREWVSV ITWSGGITYY   60
ADSVKGRFTI SRDNSKNTVY LQMNSLRAED TAVYYCAGDK HQSSWYDYWG QGTLVTVSS   119

SEQ ID NO: 330          moltype = AA  length = 119
FEATURE                 Location/Qualifiers
source                  1..119
                        mol_type = protein
                        organism = synthetic construct
SEQUENCE: 330
EVQLVESGGG LVQPGGSLRL SCAASGSIAS IHAMGWVRQA PGKEREFVSV ITWSGGITYY   60
ADSVKGRFTI SRDNSKNTLY LQMNSLRAED TAVYYCAGDK HQSSWYDYWG QGTLVTVSS   119

SEQ ID NO: 331          moltype = AA  length = 119
FEATURE                 Location/Qualifiers
source                  1..119
                        mol_type = protein
                        organism = synthetic construct
SEQUENCE: 331
EVQLVESGGG LVQPGGSLRL SCAASGSIAS IHAMGWVRQA PGKEREFVSV ITWSGGITYY   60
ADSVKGRFTI SRDNSKNTVY LQMNSLRAED TAVYYCAGDK HQSSWYDYWG QGTLVTVSS   119

SEQ ID NO: 332          moltype = AA  length = 119
```

-continued

```
FEATURE             Location/Qualifiers
source              1..119
                    mol_type = protein
                    organism = synthetic construct
SEQUENCE: 332
EVQLVESGGG LVQPGGSLRL SCAASGSIAS IHAMGWVRQA PGKEREFVAV ITWSGGITYY   60
ADSVKGRFTI SRDNSKNTVY LQMNSLRAED TAVYYCAGDK HQSSWYDYWG QGTLVTVSS   119

SEQ ID NO: 333      moltype = AA  length = 119
FEATURE             Location/Qualifiers
source              1..119
                    mol_type = protein
                    organism = synthetic construct
SEQUENCE: 333
EVQLVESGGG LVQPGGSLRL SCAASGSIAS IHAMGWVRQA PGKEREWVAV ITWSGGITYY   60
ADSVKGRFTI SRDNSKNTVY LQMNSLRAED TAVYYCAGDK HQSSWYDYWG QGTLVTVSS   119

SEQ ID NO: 334      moltype = AA  length = 118
FEATURE             Location/Qualifiers
source              1..118
                    mol_type = protein
                    organism = synthetic construct
SEQUENCE: 334
EVQLVESGGG LVQPGGSLRL SCAASGFAFS SYDMSWVRQA PGKGLDWVAT ISGGGRYTYY   60
PDSVKGRFTI SRDNSKNNLY LQMNSLRAED TALYYCANRY GEAWFAYWGQ GTLVTVSS    118

SEQ ID NO: 335      moltype = AA  length = 111
FEATURE             Location/Qualifiers
source              1..111
                    mol_type = protein
                    organism = synthetic construct
SEQUENCE: 335
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI K          111

SEQ ID NO: 336      moltype = AA  length = 112
FEATURE             Location/Qualifiers
source              1..112
                    mol_type = protein
                    organism = synthetic construct
SEQUENCE: 336
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KR         112

SEQ ID NO: 337      moltype = AA  length = 112
FEATURE             Location/Qualifiers
source              1..112
                    mol_type = protein
                    organism = synthetic construct
SEQUENCE: 337
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGCGTKVEI KR         112

SEQ ID NO: 338      moltype = AA  length = 113
FEATURE             Location/Qualifiers
source              1..113
                    mol_type = protein
                    organism = synthetic construct
SEQUENCE: 338
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KSS        113

SEQ ID NO: 339      moltype = AA  length = 111
FEATURE             Location/Qualifiers
source              1..111
                    mol_type = protein
                    organism = synthetic construct
SEQUENCE: 339
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGCGTKVEI K          111

SEQ ID NO: 340      moltype = AA  length = 112
FEATURE             Location/Qualifiers
source              1..112
                    mol_type = protein
                    organism = synthetic construct
SEQUENCE: 340
EIVLTQSPAT LSVSPGERAT LSCRASKGVS TSGYSYLHWY QQKPGQAPRL LIYLASYLES   60
GIPARFSGSG SGTEFTLTIS SLQSEDFAVY YCQHSRDLPL TFGGGTKVEI KR         112
```

```
SEQ ID NO: 341          moltype = AA   length = 112
FEATURE                 Location/Qualifiers
source                  1..112
                        mol_type = protein
                        organism = synthetic construct
SEQUENCE: 341
EIVLTQSPAT LSVSPGERAT LSCRASKGVS TSGYSYLHWY QQKPGQAPRL LIYLASYLES    60
GIPARFSGSG SGTEFTLTIS SLQSEDFAVY YCQHSRDLPL TFGCGTKVEI KR            112

SEQ ID NO: 342          moltype = AA   length = 112
FEATURE                 Location/Qualifiers
source                  1..112
                        mol_type = protein
                        organism = synthetic construct
SEQUENCE: 342
EIVLTQSPST LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KR            112

SEQ ID NO: 343          moltype = AA   length = 112
FEATURE                 Location/Qualifiers
source                  1..112
                        mol_type = protein
                        organism = synthetic construct
SEQUENCE: 343
EIVLTQSPST LSLSPGERAT LSCRASKGVS TSGYSYLHWY QQKPGQAPRL LIYLASYLES    60
GVPARFSGSG SGTDFTLTIS GLEPEDFAVY YCQHSRDLPL TFGGGTKVEI KR            112

SEQ ID NO: 344          moltype = AA   length = 112
FEATURE                 Location/Qualifiers
source                  1..112
                        mol_type = protein
                        organism = synthetic construct
SEQUENCE: 344
EIVLTQSPST LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGCGTKVEI KR            112

SEQ ID NO: 345          moltype = AA   length = 112
FEATURE                 Location/Qualifiers
source                  1..112
                        mol_type = protein
                        organism = synthetic construct
SEQUENCE: 345
EIVLTQSPST LSLSPGERAT LSCRASKGVS TSGYSYLHWY QQKPGQAPRL LIYLASYLES    60
GVPARFSGSG SGTDFTLTIS GLEPEDFAVY YCQHSRDLPL TFGCGTKVEI KR            112

SEQ ID NO: 346          moltype = AA   length = 112
FEATURE                 Location/Qualifiers
source                  1..112
                        mol_type = protein
                        organism = synthetic construct
SEQUENCE: 346
DIQLTQSPSS LSASVGDRVT ITCRASKGVS TSGYSYLHWY QQKPGKAPKL LIYLASYLES    60
GVPSRFSGSG SGTDFTLTIS SLQPEDFATY YCQHSRDLPL TFGGGTKVEI KR            112

SEQ ID NO: 347          moltype = AA   length = 112
FEATURE                 Location/Qualifiers
source                  1..112
                        mol_type = protein
                        organism = synthetic construct
SEQUENCE: 347
DIQLTQSPSS LSASVGDRVT ITCRASKGVS TSGYSYLHWY QQKPGKAPKL LIYLASYLES    60
GVPSRFSGSG SGTDFTLTIS SLQPEDFATY YCQHSRDLPL TFGCGTKVEI KR            112

SEQ ID NO: 348          moltype = AA   length = 111
FEATURE                 Location/Qualifiers
source                  1..111
                        mol_type = protein
                        organism = synthetic construct
SEQUENCE: 348
EIVLTQSPST LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI K             111

SEQ ID NO: 349          moltype = AA   length = 108
FEATURE                 Location/Qualifiers
source                  1..108
                        mol_type = protein
                        organism = synthetic construct
SEQUENCE: 349
```

```
DIQMTQSPSS MSASVGDRVT FTCRASQDIN TYLSWFQQKP GKSPKTLIYR ANRLVSGVPS    60
RFSGSGSGQD YTLTISSLQP EDMATYYCLQ YDEFPLTFGA GTKLELKR                108

SEQ ID NO: 350         moltype = AA   length = 330
FEATURE                Location/Qualifiers
source                 1..330
                       mol_type = protein
                       organism = synthetic construct
SEQUENCE: 350
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 351         moltype = AA   length = 330
FEATURE                Location/Qualifiers
source                 1..330
                       mol_type = protein
                       organism = synthetic construct
SEQUENCE: 351
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 352         moltype = AA   length = 330
FEATURE                Location/Qualifiers
source                 1..330
                       mol_type = protein
                       organism = synthetic construct
SEQUENCE: 352
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV LHEALHSHYT QKSLSLSPGK                                    330

SEQ ID NO: 353         moltype = AA   length = 107
FEATURE                Location/Qualifiers
source                 1..107
                       mol_type = protein
                       organism = synthetic construct
SEQUENCE: 353
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 354         moltype = AA   length = 252
FEATURE                Location/Qualifiers
source                 1..252
                       mol_type = protein
                       organism = synthetic construct
SEQUENCE: 354
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS   120
GGGGSGGGGS GGGGSGGGGS EIVLTQSPAT LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGGGTKVEI KR                                                      252

SEQ ID NO: 355         moltype = AA   length = 252
FEATURE                Location/Qualifiers
source                 1..252
                       mol_type = protein
                       organism = synthetic construct
SEQUENCE: 355
QVQLVQSGVE VKKPGASVKV SCKASGYTFT NYYMYWVRQA PGQGLEWMGG INPSQGGTNF    60
NEKFKNRVTL TTDSSTTTAY MELKSLQFDD TAVYYCARRD YRFDLGFDYW GQGTTVTVSS   120
GGGGSGGGGS GGGGSGGGGS EIVLTQSPAT LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGGGTKVEI KR                                                      252

SEQ ID NO: 356         moltype = AA   length = 252
FEATURE                Location/Qualifiers
source                 1..252
                       mol_type = protein
```

-continued

```
                            organism = synthetic construct
SEQUENCE: 356
QVQLVQSGVE VKKPGASVKV SCKASGYTFT NYYMYWVRQA PGQGLEWMGG INPSRGGTNF    60
NEKFKNRVTL TTDSSTTTAY MELKSLQFDD TAVYYCARRD YRFDLGFDYW GQGTTVTVSS   120
GGGGSGGGGS GGGGSGGGGS EIVLTQSPAT LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGGGTKVEI KR                                                       252

SEQ ID NO: 357            moltype = AA   length = 252
FEATURE                   Location/Qualifiers
source                    1..252
                          mol_type = protein
                          organism = synthetic construct
SEQUENCE: 357
QVQLVQSGVE VKKPGASVKV SCKASGYTFT NYYMYWVRQA PGQCLEWMGG INPSNGGTNF    60
NEKFKNRVTL TTDSSTTTAY MELKSLQFDD TAVYYCARRD YRFDMGFDYW GQGTTVTVSS   120
GGGGSGGGGS GGGGSGGGGS EIVLTQSPAT LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGCGTKVEI KR                                                       252

SEQ ID NO: 358            moltype = AA   length = 252
FEATURE                   Location/Qualifiers
source                    1..252
                          mol_type = protein
                          organism = synthetic construct
SEQUENCE: 358
QVQLVQSGVE VKKPGASVKV SCKASGYTFT NYYMYWVRQA PGQCLEWMGG INPSQGGTNF    60
NEKFKNRVTL TTDSSTTTAY MELKSLQFDD TAVYYCARRD YRFDLGFDYW GQGTTVTVSS   120
GGGGSGGGGS GGGGSGGGGS EIVLTQSPAT LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGCGTKVEI KR                                                       252

SEQ ID NO: 359            moltype = AA   length = 252
FEATURE                   Location/Qualifiers
source                    1..252
                          mol_type = protein
                          organism = synthetic construct
SEQUENCE: 359
QVQLVQSGVE VKKPGASVKV SCKASGYTFT NYYMYWVRQA PGQCLEWMGG INPSRGGTNF    60
NEKFKNRVTL TTDSSTTTAY MELKSLQFDD TAVYYCARRD YRFDLGFDYW GQGTTVTVSS   120
GGGGSGGGGS GGGGSGGGGS EIVLTQSPAT LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGCGTKVEI KR                                                       252

SEQ ID NO: 360            moltype = AA   length = 253
FEATURE                   Location/Qualifiers
source                    1..253
                          mol_type = protein
                          organism = synthetic construct
SEQUENCE: 360
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KSSGGGGSGG   120
GGSGGGGSGG GGSQVQLVQS GVEVKKPGAS VKVSCKASGY TFTNYYMYWV RQAPGQGLEW   180
MGGINPSQGG TNFNEKFKNR VTLTTDSSTT TAYMELKSLQ FDDTAVYYCA RRDYRFDLGF   240
DYWGQGTTVT VSS                                                      253

SEQ ID NO: 361            moltype = AA   length = 251
FEATURE                   Location/Qualifiers
source                    1..251
                          mol_type = protein
                          organism = synthetic construct
SEQUENCE: 361
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGCGTKVEI KGGGGSGGGG   120
SGGGGSGGGG SQVQLVQSGV EVKKPGASVK VSCKASGYTF TNYYMYWVRQ APGQCLEWMG   180
GINPSQGGTN FNEKFKNRVT LTTDSSTTTA YMELKSLQFD DTAVYYCARR DYRFDLGFDY   240
WGQGTTVTVS S                                                        251

SEQ ID NO: 362            moltype = AA   length = 252
FEATURE                   Location/Qualifiers
source                    1..252
                          mol_type = protein
                          organism = synthetic construct
SEQUENCE: 362
EVQLVESGGG LVQPGGSLRL SCAASGYTFT NYYMYWVRQA PGKGLEWMGG INPSQGGTNF    60
NEKFKNRFTI SRDNSKNTLY LQMNSLRAED TAVYYCARRD YRFDLGFDYW GQGTLVTVSS   120
GGGGSGGGGS GGGGSGGGGS EIVLTQSPAT LSVSPGERAT LSCRASKGVS TSGYSYLHWY   180
QQKPGQAPRL LIYLASYLES GIPARFSGSG SGTEFTLTIS SLQSEDFAVY YCQHSRDLPL   240
TFGGGTKVEI KR                                                       252
```

-continued

```
SEQ ID NO: 363               moltype = AA   length = 252
FEATURE                      Location/Qualifiers
source                       1..252
                             mol_type = protein
                             organism = synthetic construct
SEQUENCE: 363
EVQLVESGGG LVQPGGSLRL SCAASGYTFT NYYMYWVRQA PGKCLEWMGG INPSQGGTNF   60
NEKFKNRFTI SRDNSKNTLY LQMNSLRAED TAVYYCARRD YRFDLGFDYW GQGTLVTVSS  120
GGGGSGGGGS GGGGSGGGGS EIVLTQSPAT LSVSPGERAT LSCRASKGVS TSGYSYLHWY  180
QQKPGQAPRL LIYLASYLES GIPARFSGSG SGTEFTLTIS SLQSEDFAVY YCQHSRDLPL  240
TFGCGTKVEI KR                                                      252

SEQ ID NO: 364               moltype = AA   length = 252
FEATURE                      Location/Qualifiers
source                       1..252
                             mol_type = protein
                             organism = synthetic construct
SEQUENCE: 364
QVQLVQSGVE VKKPGASVKV SCKASGYTFT NYYMYWVRQA PGQGLEWMGG INPSQGGTNF   60
NEKFKNRVTL TTDSSTTTAY MELKSLQFDD TAVYYCARRD YRFDLGFDYW GQGTGVRVSS  120
GGGGSGGGGS GGGGSGGGGS EIVLTQSPAT LSLSPGERAT LSCRASKGVS TSGYSYLHWY  180
QQKPGQAPRL LIYLASYLES GVPARFSGSG SGTDFTLTIS SLEPEDFAVY YCQHSRDLPL  240
TFGGGTKVEI KR                                                      252

SEQ ID NO: 365               moltype = AA   length = 252
FEATURE                      Location/Qualifiers
source                       1..252
                             mol_type = protein
                             organism = synthetic construct
SEQUENCE: 365
QVQLVQSGVE VKKPGASVKV SCKASGYTFT NYYMYWVRQA PGQCLEWMGG INPSQGGTNF   60
NEKFKNRVTL TTDSSTTTAY MELKSLQFDD TAVYYCARRD YRFDLGFDYW GQGTGVRVSS  120
GGGGSGGGGS GGGGSGGGGS EIVLTQSPAT LSLSPGERAT LSCRASKGVS TSGYSYLHWY  180
QQKPGQAPRL LIYLASYLES GVPARFSGSG SGTDFTLTIS SLEPEDFAVY YCQHSRDLPL  240
TFGCGTKVEI KR                                                      252

SEQ ID NO: 366               moltype = AA   length = 252
FEATURE                      Location/Qualifiers
source                       1..252
                             mol_type = protein
                             organism = synthetic construct
SEQUENCE: 366
QVQLVQSGVE VKKPGASVKV SCKASGYTFT NYYMYWVRQA PGQGLEWMGG INPSNGGTNF   60
NEKFKNRVTL TTDSSTTTAY MELKSLRFDD TAVYYCARRD YRFDMGFDYW GQGTTVTVSS  120
GGGGSGGGGS GGGGSGGGGS EIVLTQSPST LSLSPGERAT LSCRASKGVS TSGYSYLHWY  180
QQKPGQAPRL LIYLASYLES GVPARFSGSG SGTDFTLTIS SLEPEDFAVY YCQHSRDLPL  240
TFGGGTKVEI KR                                                      252

SEQ ID NO: 367               moltype = AA   length = 252
FEATURE                      Location/Qualifiers
source                       1..252
                             mol_type = protein
                             organism = synthetic construct
SEQUENCE: 367
QVQLVQSGVE VKKPGASVKV SCKASGYTFT NYYMYWVRQA PGQGLEWMGG INPSNGGTNF   60
NEKFKNRVTL TTDSSTTTAY MELKSLRFDD TAVYYCARRD YRFDMGFDYW GQGTTVTVSS  120
GGGGSGGGGS GGGGSGGGGS EIVLTQSPAT LSLSPGERAT LSCRASKGVS TSGYSYLHWY  180
QQKPGQAPRL LIYLASYLES GVPARFSGSG SGTDFTLTIS SLEPEDFAVY YCQHSRDLPL  240
TFGGGTKVEI KR                                                      252

SEQ ID NO: 368               moltype = AA   length = 252
FEATURE                      Location/Qualifiers
source                       1..252
                             mol_type = protein
                             organism = synthetic construct
SEQUENCE: 368
QVQLVQSGVE VKKPGASVKV SCKASGYTFT NYYMYWVRQA PGQGLEWMGG INPSNGGTNF   60
NEKFKNRVTL TTDSSTTTAY MELKSLRFDD TAVYYCARRD YRFDMGFDYW GQGTTVTVSS  120
GGGGSGGGGS GGGGSGGGGS EIVLTQSPST LSLSPGERAT LSCRASKGVS TSGYSYLHWY  180
QQKPGQAPRL LIYLASYLES GVPARFSGSG SGTDFTLTIS GLEPEDFAVY YCQHSRDLPL  240
TFGGGTKVEI KR                                                      252

SEQ ID NO: 369               moltype = AA   length = 252
FEATURE                      Location/Qualifiers
source                       1..252
                             mol_type = protein
                             organism = synthetic construct
SEQUENCE: 369
```

-continued

```
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGGGTKVEI KR                                                      252

SEQ ID NO: 370            moltype = AA   length = 252
FEATURE                   Location/Qualifiers
source                    1..252
                          mol_type = protein
                          organism = synthetic construct
SEQUENCE: 370
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS GLEPEDFAVY YCQHSRDLPL   240
TFGGGTKVEI KR                                                      252

SEQ ID NO: 371            moltype = AA   length = 252
FEATURE                   Location/Qualifiers
source                    1..252
                          mol_type = protein
                          organism = synthetic construct
SEQUENCE: 371
QVQLVQSGVE VKKPGASVKV SCKASGYTFT NYYMYWVRQA PGQGLEWMGG INPSQGGTNF    60
NEKFKNRVTL TTDSSTTTAY MELKSLRFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGGGTKVEI KR                                                      252

SEQ ID NO: 372            moltype = AA   length = 252
FEATURE                   Location/Qualifiers
source                    1..252
                          mol_type = protein
                          organism = synthetic construct
SEQUENCE: 372
QVQLVQSGVE VKKPGASVKV SCKASGYTFT NYYMYWVRQA PGQGLEWMGG INPSQGGTNF    60
NEKFKNRVTL TTDSSTTTAY MELKSLRFDD TAVYYCARRD YRFDLGFDYW GQGTTVTVSS   120
GGGGSGGGGS GGGGSGGGGS EIVLTQSPAT LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGGGTKVEI KR                                                      252

SEQ ID NO: 373            moltype = AA   length = 252
FEATURE                   Location/Qualifiers
source                    1..252
                          mol_type = protein
                          organism = synthetic construct
SEQUENCE: 373
QVQLVQSGVE VKKPGASVKV SCKASGYTFT NYYMYWVRQA PGQGLEWMGG INPSQGGTNF    60
NEKFKNRVTL TTDSSTTTAY MELKSLRFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS GLEPEDFAVY YCQHSRDLPL   240
TFGGGTKVEI KR                                                      252

SEQ ID NO: 374            moltype = AA   length = 252
FEATURE                   Location/Qualifiers
source                    1..252
                          mol_type = protein
                          organism = synthetic construct
SEQUENCE: 374
QVQLVQSGVE VKKPGASVKV SCKASGYTFT NYYMYWVRQA PGQGLEWMGG INPSQGGTNF    60
NEKFKNRVTL TTDSSTTTAY MELKSLQFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGGGTKVEI KR                                                      252

SEQ ID NO: 375            moltype = AA   length = 252
FEATURE                   Location/Qualifiers
source                    1..252
                          mol_type = protein
                          organism = synthetic construct
SEQUENCE: 375
QVQLVQSGVE VKKPGASVKV SCKASGYTFT NYYMYWVRQA PGQGLEWMGG INPSQGGTNF    60
NEKFKNRVTL TTDSSTTTAY MELKSLQFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS GLEPEDFAVY YCQHSRDLPL   240
TFGGGTKVEI KR                                                      252

SEQ ID NO: 376            moltype = AA   length = 252
```

```
FEATURE              Location/Qualifiers
source               1..252
                     mol_type = protein
                     organism = synthetic construct
SEQUENCE: 376
QVQLVQSGVE VKKPGASVKV SCKASGYTFT NYYMYWVRQA PGQGLEWMGG INPSRGGTNF    60
NEKFKNRVTL TTDSSTTTAY MELKSLRFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGGGTKVEI KR                                                      252

SEQ ID NO: 377          moltype = AA  length = 252
FEATURE              Location/Qualifiers
source               1..252
                     mol_type = protein
                     organism = synthetic construct
SEQUENCE: 377
QVQLVQSGVE VKKPGASVKV SCKASGYTFT NYYMYWVRQA PGQGLEWMGG INPSRGGTNF    60
NEKFKNRVTL TTDSSTTTAY MELKSLRFDD TAVYYCARRD YRFDLGFDYW GQGTTVTVSS   120
GGGGSGGGGS GGGGSGGGGS EIVLTQSPAT LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGGGTKVEI KR                                                      252

SEQ ID NO: 378          moltype = AA  length = 252
FEATURE              Location/Qualifiers
source               1..252
                     mol_type = protein
                     organism = synthetic construct
SEQUENCE: 378
QVQLVQSGVE VKKPGASVKV SCKASGYTFT NYYMYWVRQA PGQGLEWMGG INPSRGGTNF    60
NEKFKNRVTL TTDSSTTTAY MELKSLRFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS GLEPEDFAVY YCQHSRDLPL   240
TFGGGTKVEI KR                                                      252

SEQ ID NO: 379          moltype = AA  length = 252
FEATURE              Location/Qualifiers
source               1..252
                     mol_type = protein
                     organism = synthetic construct
SEQUENCE: 379
QVQLVQSGVE VKKPGASVKV SCKASGYTFT NYYMYWVRQA PGQGLEWMGG INPSRGGTNF    60
NEKFKNRVTL TTDSSTTTAY MELKSLQFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGGGTKVEI KR                                                      252

SEQ ID NO: 380          moltype = AA  length = 252
FEATURE              Location/Qualifiers
source               1..252
                     mol_type = protein
                     organism = synthetic construct
SEQUENCE: 380
QVQLVQSGVE VKKPGASVKV SCKASGYTFT NYYMYWVRQA PGQGLEWMGG INPSRGGTNF    60
NEKFKNRVTL TTDSSTTTAY MELKSLQFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS GLEPEDFAVY YCQHSRDLPL   240
TFGGGTKVEI KR                                                      252

SEQ ID NO: 381          moltype = AA  length = 252
FEATURE              Location/Qualifiers
source               1..252
                     mol_type = protein
                     organism = synthetic construct
SEQUENCE: 381
QVQLVQSGVE VKKPGASVKV SCKASGYTFT NYYMYWVRQA PGQCLEWMGG INPSNGGTNF    60
NEKFKNRVTL TTDSSTTTAY MELKSLRFDD TAVYYCARRD YRFDMGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGCGTKVEI KR                                                      252

SEQ ID NO: 382          moltype = AA  length = 252
FEATURE              Location/Qualifiers
source               1..252
                     mol_type = protein
                     organism = synthetic construct
SEQUENCE: 382
QVQLVQSGVE VKKPGASVKV SCKASGYTFT NYYMYWVRQA PGQCLEWMGG INPSNGGTNF    60
NEKFKNRVTL TTDSSTTTAY MELKSLRFDD TAVYYCARRD YRFDMGFDYW GQGTTVTVSS   120
```

```
GGGGSGGGGS GGGGSGGGGS EIVLTQSPAT LSLSPGERAT LSCRASKGVS TSGYSYLHWY    180
QQKPGQAPRL LIYLASYLES GVPARFSGSG SGTDFTLTIS SLEPEDFAVY YCQHSRDLPL    240
TFGCGTKVEI KR                                                        252

SEQ ID NO: 383            moltype = AA   length = 252
FEATURE                   Location/Qualifiers
source                    1..252
                          mol_type = protein
                          organism = synthetic construct
SEQUENCE: 383
QVQLVQSGVE VKKPGASVKV SCKASGYTFT NYYMYWVRQA PGQCLEWMGG INPSNGGTNF     60
NEKFKNRVTL TTDSSTTTAY MELKSLRFDD TAVYYCARRD YRFDMGFDYW GQGTTVTVSS    120
GGGGSGGGGS GGGGSGGGGS EIVLTQSPST LSLSPGERAT LSCRASKGVS TSGYSYLHWY    180
QQKPGQAPRL LIYLASYLES GVPARFSGSG SGTDFTLTIS GLEPEDFAVY YCQHSRDLPL    240
TFGCGTKVEI KR                                                        252

SEQ ID NO: 384            moltype = AA   length = 252
FEATURE                   Location/Qualifiers
source                    1..252
                          mol_type = protein
                          organism = synthetic construct
SEQUENCE: 384
QVQLVQSGVE VKKPGASVKV SCKASGYTFT NYYMYWVRQA PGQCLEWMGG INPSNGGTNF     60
NEKFKNRVTL TTDSSTTTAY MELKSLQFDD TAVYYCARRD YRFDMGFDYW GQGTTVTVSS    120
GGGGSGGGGS GGGGSGGGGS EIVLTQSPST LSLSPGERAT LSCRASKGVS TSGYSYLHWY    180
QQKPGQAPRL LIYLASYLES GVPARFSGSG SGTDFTLTIS SLEPEDFAVY YCQHSRDLPL    240
TFGCGTKVEI KR                                                        252

SEQ ID NO: 385            moltype = AA   length = 252
FEATURE                   Location/Qualifiers
source                    1..252
                          mol_type = protein
                          organism = synthetic construct
SEQUENCE: 385
QVQLVQSGVE VKKPGASVKV SCKASGYTFT NYYMYWVRQA PGQCLEWMGG INPSNGGTNF     60
NEKFKNRVTL TTDSSTTTAY MELKSLQFDD TAVYYCARRD YRFDMGFDYW GQGTTVTVSS    120
GGGGSGGGGS GGGGSGGGGS EIVLTQSPST LSLSPGERAT LSCRASKGVS TSGYSYLHWY    180
QQKPGQAPRL LIYLASYLES GVPARFSGSG SGTDFTLTIS GLEPEDFAVY YCQHSRDLPL    240
TFGCGTKVEI KR                                                        252

SEQ ID NO: 386            moltype = AA   length = 252
FEATURE                   Location/Qualifiers
source                    1..252
                          mol_type = protein
                          organism = synthetic construct
SEQUENCE: 386
QVQLVQSGVE VKKPGASVKV SCKASGYTFT NYYMYWVRQA PGQCLEWMGG INPSQGGTNF     60
NEKFKNRVTL TTDSSTTTAY MELKSLRFDD TAVYYCARRD YRFDLGFDYW GQGTTVTVSS    120
GGGGSGGGGS GGGGSGGGGS EIVLTQSPST LSLSPGERAT LSCRASKGVS TSGYSYLHWY    180
QQKPGQAPRL LIYLASYLES GVPARFSGSG SGTDFTLTIS SLEPEDFAVY YCQHSRDLPL    240
TFGCGTKVEI KR                                                        252

SEQ ID NO: 387            moltype = AA   length = 252
FEATURE                   Location/Qualifiers
source                    1..252
                          mol_type = protein
                          organism = synthetic construct
SEQUENCE: 387
QVQLVQSGVE VKKPGASVKV SCKASGYTFT NYYMYWVRQA PGQCLEWMGG INPSQGGTNF     60
NEKFKNRVTL TTDSSTTTAY MELKSLRFDD TAVYYCARRD YRFDLGFDYW GQGTTVTVSS    120
GGGGSGGGGS GGGGSGGGGS EIVLTQSPAT LSLSPGERAT LSCRASKGVS TSGYSYLHWY    180
QQKPGQAPRL LIYLASYLES GVPARFSGSG SGTDFTLTIS SLEPEDFAVY YCQHSRDLPL    240
TFGCGTKVEI KR                                                        252

SEQ ID NO: 388            moltype = AA   length = 252
FEATURE                   Location/Qualifiers
source                    1..252
                          mol_type = protein
                          organism = synthetic construct
SEQUENCE: 388
QVQLVQSGVE VKKPGASVKV SCKASGYTFT NYYMYWVRQA PGQCLEWMGG INPSQGGTNF     60
NEKFKNRVTL TTDSSTTTAY MELKSLRFDD TAVYYCARRD YRFDLGFDYW GQGTTVTVSS    120
GGGGSGGGGS GGGGSGGGGS EIVLTQSPST LSLSPGERAT LSCRASKGVS TSGYSYLHWY    180
QQKPGQAPRL LIYLASYLES GVPARFSGSG SGTDFTLTIS GLEPEDFAVY YCQHSRDLPL    240
TFGCGTKVEI KR                                                        252

SEQ ID NO: 389            moltype = AA   length = 252
FEATURE                   Location/Qualifiers
source                    1..252
```

-continued

```
                                  mol_type = protein
                                  organism = synthetic construct
SEQUENCE: 389
QVQLVQSGVE VKKPGASVKV SCKASGYTFT NYYMYWVRQA PGQCLEWMGG INPSQGGTNF    60
NEKFKNRVTL TTDSSTTTAY MELKSLQFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGCGTKVEI KR                                                      252

SEQ ID NO: 390            moltype = AA  length = 252
FEATURE                   Location/Qualifiers
source                    1..252
                          mol_type = protein
                          organism = synthetic construct
SEQUENCE: 390
QVQLVQSGVE VKKPGASVKV SCKASGYTFT NYYMYWVRQA PGQCLEWMGG INPSQGGTNF    60
NEKFKNRVTL TTDSSTTTAY MELKSLQFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS GLEPEDFAVY YCQHSRDLPL   240
TFGCGTKVEI KR                                                      252

SEQ ID NO: 391            moltype = AA  length = 252
FEATURE                   Location/Qualifiers
source                    1..252
                          mol_type = protein
                          organism = synthetic construct
SEQUENCE: 391
QVQLVQSGVE VKKPGASVKV SCKASGYTFT NYYMYWVRQA PGQCLEWMGG INPSRGGTNF    60
NEKFKNRVTL TTDSSTTTAY MELKSLRFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGCGTKVEI KR                                                      252

SEQ ID NO: 392            moltype = AA  length = 252
FEATURE                   Location/Qualifiers
source                    1..252
                          mol_type = protein
                          organism = synthetic construct
SEQUENCE: 392
QVQLVQSGVE VKKPGASVKV SCKASGYTFT NYYMYWVRQA PGQCLEWMGG INPSRGGTNF    60
NEKFKNRVTL TTDSSTTTAY MELKSLRFDD TAVYYCARRD YRFDLGFDYW GQGTTVTVSS   120
GGGGSGGGGS GGGGSGGGGS EIVLTQSPAT LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGCGTKVEI KR                                                      252

SEQ ID NO: 393            moltype = AA  length = 252
FEATURE                   Location/Qualifiers
source                    1..252
                          mol_type = protein
                          organism = synthetic construct
SEQUENCE: 393
QVQLVQSGVE VKKPGASVKV SCKASGYTFT NYYMYWVRQA PGQCLEWMGG INPSRGGTNF    60
NEKFKNRVTL TTDSSTTTAY MELKSLRFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS GLEPEDFAVY YCQHSRDLPL   240
TFGCGTKVEI KR                                                      252

SEQ ID NO: 394            moltype = AA  length = 252
FEATURE                   Location/Qualifiers
source                    1..252
                          mol_type = protein
                          organism = synthetic construct
SEQUENCE: 394
QVQLVQSGVE VKKPGASVKV SCKASGYTFT NYYMYWVRQA PGQCLEWMGG INPSRGGTNF    60
NEKFKNRVTL TTDSSTTTAY MELKSLQFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGCGTKVEI KR                                                      252

SEQ ID NO: 395            moltype = AA  length = 252
FEATURE                   Location/Qualifiers
source                    1..252
                          mol_type = protein
                          organism = synthetic construct
SEQUENCE: 395
QVQLVQSGVE VKKPGASVKV SCKASGYTFT NYYMYWVRQA PGQCLEWMGG INPSRGGTNF    60
NEKFKNRVTL TTDSSTTTAY MELKSLQFDD TAVYYCARRD YRFDLGFDYW GQGTTVTVSS   120
GGGGSGGGGS GGGGSGGGGS EIVLTQSPST LSLSPGERAT LSCRASKGVS TSGYSYLHWY   180
QQKPGQAPRL LIYLASYLES GVPARFSGSG SGTDFTLTIS GLEPEDFAVY YCQHSRDLPL   240
```

```
TFGCGTKVEI KR                                                           252

SEQ ID NO: 396              moltype = AA  length = 252
FEATURE                     Location/Qualifiers
source                      1..252
                            mol_type = protein
                            organism = synthetic construct
SEQUENCE: 396
QVQLVQSGVE VKKPGASVKV SCKASGYTFT NYYMYWVRQA PGQGLEWMGG INPSQGGTNF       60
NEKFKNRVTL TTDSSTTTAY MELKSLQFDD TAVYYCARRD YRFDLGFDYW GQGTTVTVSS      120
GGGGSGGGGS GGGGSGGGGS EIVLTQSPAT LSVSPGERAT LSCRASKGVS TSGYSYLHWY      180
QQKPGQAPRL LIYLASYLES GIPARFSGSG SGTEFTLTIS SLQSEDFAVY YCQHSRDLPL      240
TFGGGTKVEI KR                                                          252

SEQ ID NO: 397              moltype = AA  length = 252
FEATURE                     Location/Qualifiers
source                      1..252
                            mol_type = protein
                            organism = synthetic construct
SEQUENCE: 397
QVQLVQSGVE VKKPGASVKV SCKASGYTFT NYYMYWVRQA PGQGLEWMGG INPSQGGTNF       60
NEKFKNRVTL TTDSSTTTAY MELKSLQFDD TAVYYCARRD YRFDLGFDYW GQGTTVTVSS      120
GGGGSGGGGS GGGGSGGGGS DIQLTQSPSS LSASVGDRVT ITCRASKGVS TSGYSYLHWY      180
QQKPGKAPKL LIYLASYLES GVPSRFSGSG SGTDFTLTIS SLQPEDFATY YCQHSRDLPL      240
TFGGGTKVEI KR                                                          252

SEQ ID NO: 398              moltype = AA  length = 252
FEATURE                     Location/Qualifiers
source                      1..252
                            mol_type = protein
                            organism = synthetic construct
SEQUENCE: 398
EVQLVQSGAE VKKPGASVKV SCKASGYTFT NYYMYWVRQA PGQGLEWMGG INPSQGGTNF       60
NEKFKNRVTL TTDSSTSTAY MELSSLRSED TAVYYCARRD YRFDLGFDYW GQGTTVTVSS      120
GGGGSGGGGS GGGGSGGGGS EIVLTQSPAT LSLSPGERAT LSCRASKGVS TSGYSYLHWY      180
QQKPGQAPRL LIYLASYLES GVPARFSGSG SGTDFTLTIS SLEPEDFAVY YCQHSRDLPL      240
TFGGGTKVEI KR                                                          252

SEQ ID NO: 399              moltype = AA  length = 252
FEATURE                     Location/Qualifiers
source                      1..252
                            mol_type = protein
                            organism = synthetic construct
SEQUENCE: 399
EVQLVQSGAE VKKPGASVKV SCKASGYTFT NYYMYWVRQA PGQGLEWMGG INPSQGGTNF       60
NEKFKNRVTL TTDSSTSTAY MELSSLRSED TAVYYCARRD YRFDLGFDYW GQGTTVTVSS      120
GGGGSGGGGS GGGGSGGGGS EIVLTQSPAT LSVSPGERAT LSCRASKGVS TSGYSYLHWY      180
QQKPGQAPRL LIYLASYLES GIPARFSGSG SGTEFTLTIS SLQSEDFAVY YCQHSRDLPL      240
TFGGGTKVEI KR                                                          252

SEQ ID NO: 400              moltype = AA  length = 252
FEATURE                     Location/Qualifiers
source                      1..252
                            mol_type = protein
                            organism = synthetic construct
SEQUENCE: 400
EVQLVQSGAE VKKPGASVKV SCKASGYTFT NYYMYWVRQA PGQGLEWMGG INPSQGGTNF       60
NEKFKNRVTL TTDSSTSTAY MELSSLRSED TAVYYCARRD YRFDLGFDYW GQGTTVTVSS      120
GGGGSGGGGS GGGGSGGGGS DIQLTQSPSS LSASVGDRVT ITCRASKGVS TSGYSYLHWY      180
QQKPGKAPKL LIYLASYLES GVPSRFSGSG SGTDFTLTIS SLQPEDFATY YCQHSRDLPL      240
TFGGGTKVEI KR                                                          252

SEQ ID NO: 401              moltype = AA  length = 252
FEATURE                     Location/Qualifiers
source                      1..252
                            mol_type = protein
                            organism = synthetic construct
SEQUENCE: 401
EVQLLESGGG LVQPGGSLRL SCKASGYTFT NYYMYWVRQA PGKGLEWMGG INPSQGGTNF       60
NEKFKNRVTL STDSSKNTAY LQMNSLRAED TAVYYCARRD YRFDLGFDYW GQGTTVTVSS      120
GGGGSGGGGS GGGGSGGGGS EIVLTQSPAT LSLSPGERAT LSCRASKGVS TSGYSYLHWY      180
QQKPGQAPRL LIYLASYLES GVPARFSGSG SGTDFTLTIS SLEPEDFAVY YCQHSRDLPL      240
TFGGGTKVEI KR                                                          252

SEQ ID NO: 402              moltype = AA  length = 252
FEATURE                     Location/Qualifiers
source                      1..252
                            mol_type = protein
                            organism = synthetic construct
```

-continued

```
SEQUENCE: 402
EVQLLESGGG LVQPGGSLRL SCKASGYTFT NYYMYWVRQA PGKGLEWMGG INPSQGGTNF    60
NEKFKNRVTL STDSSKNTAY LQMNSLRAED TAVYYCARRD YRFDLGFDYW GQGTTVTVSS   120
GGGGSGGGGS GGGGSGGGGS EIVLTQSPAT LSVSPGERAT LSCRASKGVS TSGYSYLHWY   180
QQKPGQAPRL LIYLASYLES GIPARFSGSG SGTEFTLTIS SLQSEDFAVY YCQHSRDLPL   240
TFGGGTKVEI KR                                                      252

SEQ ID NO: 403          moltype = AA  length = 252
FEATURE                 Location/Qualifiers
source                  1..252
                        mol_type = protein
                        organism = synthetic construct
SEQUENCE: 403
EVQLLESGGG LVQPGGSLRL SCKASGYTFT NYYMYWVRQA PGKGLEWMGG INPSQGGTNF    60
NEKFKNRVTL STDSSKNTAY LQMNSLRAED TAVYYCARRD YRFDLGFDYW GQGTTVTVSS   120
GGGGSGGGGS GGGGSGGGGS DIQLTQSPSS LSASVGDRVT ITCRASKGVS TSGYSYLHWY   180
QQKPGKAPKL LIYLASYLES GVPSRFSGSG SGTDFTLTIS SLQPEDFATY YCQHSRDLPL   240
TFGGGTKVEI KR                                                      252

SEQ ID NO: 404          moltype = AA  length = 252
FEATURE                 Location/Qualifiers
source                  1..252
                        mol_type = protein
                        organism = synthetic construct
SEQUENCE: 404
QVQLVQSGVE VKKPGASVKV SCKASGYTFT NYYMYWVRQA PGQCLEWMGG INPSQGGTNF    60
NEKFKNRVTL TTDSSTTTAY MELKSLQFDD TAVYYCARRD YRFDLGFDYW GQGTTVTVSS   120
GGGGSGGGGS GGGGSGGGGS EIVLTQSPAT LSVSPGERAT LSCRASKGVS TSGYSYLHWY   180
QQKPGQAPRL LIYLASYLES GIPARFSGSG SGTEFTLTIS SLQSEDFAVY YCQHSRDLPL   240
TFGCGTKVEI KR                                                      252

SEQ ID NO: 405          moltype = AA  length = 252
FEATURE                 Location/Qualifiers
source                  1..252
                        mol_type = protein
                        organism = synthetic construct
SEQUENCE: 405
QVQLVQSGVE VKKPGASVKV SCKASGYTFT NYYMYWVRQA PGQCLEWMGG INPSQGGTNF    60
NEKFKNRVTL TTDSSTTTAY MELKSLQFDD TAVYYCARRD YRFDLGFDYW GQGTTVTVSS   120
GGGGSGGGGS GGGGSGGGGS DIQLTQSPSS LSASVGDRVT ITCRASKGVS TSGYSYLHWY   180
QQKPGKAPKL LIYLASYLES GVPSRFSGSG SGTDFTLTIS SLQPEDFATY YCQHSRDLPL   240
TFGCGTKVEI KR                                                      252

SEQ ID NO: 406          moltype = AA  length = 252
FEATURE                 Location/Qualifiers
source                  1..252
                        mol_type = protein
                        organism = synthetic construct
SEQUENCE: 406
EVQLVQSGAE VKKPGASVKV SCKASGYTFT NYYMYWVRQA PGQCLEWMGG INPSQGGTNF    60
NEKFKNRVTL TTDSSTSTAY MELSSLRSED TAVYYCARRD YRFDLGFDYW GQGTTVTVSS   120
GGGGSGGGGS GGGGSGGGGS EIVLTQSPAT LSLSPGERAT LSCRASKGVS TSGYSYLHWY   180
QQKPGQAPRL LIYLASYLES GVPARFSGSG SGTDFTLTIS SLEPEDFAVY YCQHSRDLPL   240
TFGCGTKVEI KR                                                      252

SEQ ID NO: 407          moltype = AA  length = 252
FEATURE                 Location/Qualifiers
source                  1..252
                        mol_type = protein
                        organism = synthetic construct
SEQUENCE: 407
EVQLVQSGAE VKKPGASVKV SCKASGYTFT NYYMYWVRQA PGQCLEWMGG INPSQGGTNF    60
NEKFKNRVTL TTDSSTSTAY MELSSLRSED TAVYYCARRD YRFDLGFDYW GQGTTVTVSS   120
GGGGSGGGGS GGGGSGGGGS EIVLTQSPAT LSVSPGERAT LSCRASKGVS TSGYSYLHWY   180
QQKPGQAPRL LIYLASYLES GIPARFSGSG SGTEFTLTIS SLQSEDFAVY YCQHSRDLPL   240
TFGCGTKVEI KR                                                      252

SEQ ID NO: 408          moltype = AA  length = 252
FEATURE                 Location/Qualifiers
source                  1..252
                        mol_type = protein
                        organism = synthetic construct
SEQUENCE: 408
EVQLVQSGAE VKKPGASVKV SCKASGYTFT NYYMYWVRQA PGQCLEWMGG INPSQGGTNF    60
NEKFKNRVTL TTDSSTSTAY MELSSLRSED TAVYYCARRD YRFDLGFDYW GQGTTVTVSS   120
GGGGSGGGGS GGGGSGGGGS DIQLTQSPSS LSASVGDRVT ITCRASKGVS TSGYSYLHWY   180
QQKPGKAPKL LIYLASYLES GVPSRFSGSG SGTDFTLTIS SLQPEDFATY YCQHSRDLPL   240
TFGCGTKVEI KR                                                      252
```

-continued

```
SEQ ID NO: 409          moltype = AA  length = 252
FEATURE                 Location/Qualifiers
source                  1..252
                        mol_type = protein
                        organism = synthetic construct
SEQUENCE: 409
EVQLLESGGG LVQPGGSLRL SCKASGYTFT NYYMYWVRQA PGKCLEWMGG INPSQGGTNF  60
NEKFKNRVTL STDSSKNTAY LQMNSLRAED TAVYYCARRD YRFDLGFDYW GQGTTVTVSS 120
GGGGSGGGGS GGGGSGGGGS EIVLTQSPAT LSLSPGERAT LSCRASKGVS TSGYSYLHWY 180
QQKPGQAPRL LIYLASYLES GVPARFSGSG SGTDFTLTIS SLEPEDFAVY YCQHSRDLPL 240
TFGCGTKVEI KR                                                     252

SEQ ID NO: 410          moltype = AA  length = 252
FEATURE                 Location/Qualifiers
source                  1..252
                        mol_type = protein
                        organism = synthetic construct
SEQUENCE: 410
EVQLLESGGG LVQPGGSLRL SCKASGYTFT NYYMYWVRQA PGKCLEWMGG INPSQGGTNF  60
NEKFKNRVTL STDSSKNTAY LQMNSLRAED TAVYYCARRD YRFDLGFDYW GQGTTVTVSS 120
GGGGSGGGGS GGGGSGGGGS EIVLTQSPAT LSVSPGERAT LSCRASKGVS TSGYSYLHWY 180
QQKPGQAPRL LIYLASYLES GIPARFSGSG SGTEFTLTIS SLQSEDFAVY YCQHSRDLPL 240
TFGCGTKVEI KR                                                     252

SEQ ID NO: 411          moltype = AA  length = 252
FEATURE                 Location/Qualifiers
source                  1..252
                        mol_type = protein
                        organism = synthetic construct
SEQUENCE: 411
EVQLLESGGG LVQPGGSLRL SCKASGYTFT NYYMYWVRQA PGKCLEWMGG INPSQGGTNF  60
NEKFKNRVTL STDSSKNTAY LQMNSLRAED TAVYYCARRD YRFDLGFDYW GQGTTVTVSS 120
GGGGSGGGGS GGGGSGGGGS DIQLTQSPSS LSASVGDRVT ITCRASKGVS TSGYSYLHWY 180
QQKPGKAPKL LIYLASYLES GVPSRFSGSG SGTDFTLTIS SLQPEDFATY YCQHSRDLPL 240
TFGCGTKVEI KR                                                     252

SEQ ID NO: 412          moltype = AA  length = 251
FEATURE                 Location/Qualifiers
source                  1..251
                        mol_type = protein
                        organism = synthetic construct
SEQUENCE: 412
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KGGGGSGGGG 120
SGGGGSGGGG SQVQLVQSGV EVKKPGASVK VSCKASGYTF TNYYMYWVRQ APGQGLEWMG 180
GINPSNGGTN FNEKFKNRVT LTTDSSTTTA YMELKSLQFD DTAVYYCARR DYRFDMGFDY 240
WGQGTTVTVS S                                                      251

SEQ ID NO: 413          moltype = AA  length = 251
FEATURE                 Location/Qualifiers
source                  1..251
                        mol_type = protein
                        organism = synthetic construct
SEQUENCE: 413
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KGGGGSGGGG 120
SGGGGSGGGG SQVQLVQSGV EVKKPGASVK VSCKASGYTF TNYYMYWVRQ APGQGLEWMG 180
GINPSRGGTN FNEKFKNRVT LTTDSSTTTA YMELKSLQFD DTAVYYCARR DYRFDLGFDY 240
WGQGTTVTVS S                                                      251

SEQ ID NO: 414          moltype = AA  length = 251
FEATURE                 Location/Qualifiers
source                  1..251
                        mol_type = protein
                        organism = synthetic construct
SEQUENCE: 414
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KGGGGSGGGG 120
SGGGGSGGGG SQVQLVQSGV EVKKPGASVK VSCKASGYTF TNYYMYWVRQ APGQGLEWMG 180
GINPSNGGTN FNEKFKNRVT LTTDSSTTTA YMELKSLRFD DTAVYYCARR DYRFDMGFDY 240
WGQGTTVTVS S                                                      251

SEQ ID NO: 415          moltype = AA  length = 251
FEATURE                 Location/Qualifiers
source                  1..251
                        mol_type = protein
                        organism = synthetic construct
SEQUENCE: 415
EIVLTQSPST LSLSPGERAT LSCRASKGVS TSGYSYLHWY QQKPGQAPRL LIYLASYLES  60
```

-continued

```
GVPARFSGSG SGTDFTLTIS SLEPEDFAVY YCQHSRDLPL TFGGGTKVEI KGGGGSGGGG   120
SGGGGSGGGG SQVQLVQSGV EVKKPGASVK VSCKASGYTF TNYYMYWVRQ APGQGLEWMG   180
GINPSNGGTN FNEKFKNRVT LTTDSSTTTA YMELKSLQFD DTAVYYCARR DYRFDMGFDY   240
WGQGTTVTVS S                                                       251

SEQ ID NO: 416            moltype = AA  length = 252
FEATURE                   Location/Qualifiers
source                    1..252
                          mol_type = protein
                          organism = synthetic construct
SEQUENCE: 416
EVQLVQSGAE VKKPGASVKV SCKASGYTFT NYYMYWVRQA PGQGLEWMGG INPSNGGTNF   60
NEKFKNRVTL TTDSSTSTAY MELSSLRSED TAVYYCARRD YRFDMGFDYW GQGTTVTVSS   120
GGGGSGGGGS GGGGSGGGGS DIQLTQSPSS LSASVGDRVT ITCRASKGVS TSGYSYLHWY   180
QQKPGKAPKL LIYLASYLES GVPSRFSGSG SGTDFTLTIS SLQPEDFATY YCQHSRDLPL   240
TFGGGTKVEI KR                                                      252

SEQ ID NO: 417            moltype = AA  length = 252
FEATURE                   Location/Qualifiers
source                    1..252
                          mol_type = protein
                          organism = synthetic construct
SEQUENCE: 417
EVQLVQSGAE VKKPGASVKV SCKASGYTFT NYYMYWVRQA PGQCLEWMGG INPSNGGTNF   60
NEKFKNRVTL TTDSSTSTAY MELSSLRSED TAVYYCARRD YRFDMGFDYW GQGTTVTVSS   120
GGGGSGGGGS GGGGSGGGGS DIQLTQSPSS LSASVGDRVT ITCRASKGVS TSGYSYLHWY   180
QQKPGKAPKL LIYLASYLES GVPSRFSGSG SGTDFTLTIS SLQPEDFATY YCQHSRDLPL   240
TFGCGTKVEI KR                                                      252

SEQ ID NO: 418            moltype = AA  length = 252
FEATURE                   Location/Qualifiers
source                    1..252
                          mol_type = protein
                          organism = synthetic construct
SEQUENCE: 418
EVQLVQSGAE VKKPGASVKV SCKASGYTFT NYYMYWVRQA PGQCLEWMGG INPSRGGTNF   60
NEKFKNRVTL TTDSSTSTAY MELSSLRSED TAVYYCARRD YRFDLGFDYW GQGTTVTVSS   120
GGGGSGGGGS GGGGSGGGGS DIQLTQSPSS LSASVGDRVT ITCRASKGVS TSGYSYLHWY   180
QQKPGKAPKL LIYLASYLES GVPSRFSGSG SGTDFTLTIS SLQPEDFATY YCQHSRDLPL   240
TFGCGTKVEI KR                                                      252

SEQ ID NO: 419            moltype = AA  length = 252
FEATURE                   Location/Qualifiers
source                    1..252
                          mol_type = protein
                          organism = synthetic construct
SEQUENCE: 419
EVQLVQSGAE VKKPGASVKV SCKASGYTFT NYYMYWVRQA PGQCLEWMGG INPSQGGTNF   60
NEKFKNRVTL TTDSSTSTAY MELSSLRSED TAVYYCARRD YRFDMGFDYW GQGTTVTVSS   120
GGGGSGGGGS GGGGSGGGGS DIQLTQSPSS LSASVGDRVT ITCRASKGVS TSGYSYLHWY   180
QQKPGKAPKL LIYLASYLES GVPSRFSGSG SGTDFTLTIS SLQPEDFATY YCQHSRDLPL   240
TFGCGTKVEI KR                                                      252

SEQ ID NO: 420            moltype = AA  length = 252
FEATURE                   Location/Qualifiers
source                    1..252
                          mol_type = protein
                          organism = synthetic construct
SEQUENCE: 420
EVQLVQSGAE VKKPGASVKV SCKASGYTFT NYYMYWVRQA PGQCLEWMGG INPSRGGTNF   60
NEKFKNRVTL TTDSSTSTAY MELSSLRSED TAVYYCARRD YRFDMGFDYW GQGTTVTVSS   120
GGGGSGGGGS GGGGSGGGGS DIQLTQSPSS LSASVGDRVT ITCRASKGVS TSGYSYLHWY   180
QQKPGKAPKL LIYLASYLES GVPSRFSGSG SGTDFTLTIS SLQPEDFATY YCQHSRDLPL   240
TFGCGTKVEI KR                                                      252

SEQ ID NO: 421            moltype = AA  length = 252
FEATURE                   Location/Qualifiers
source                    1..252
                          mol_type = protein
                          organism = synthetic construct
SEQUENCE: 421
EVQLVQSGAE VKKPGASVKV SCKASGYTFT NYYMYWVRQA PGQCLEWMGG INPSNGGTNF   60
NEKFKNRVTL TTDSSTSTAY MELSSLRSED TAVYYCARRD YRFDLGFDYW GQGTTVTVSS   120
GGGGSGGGGS GGGGSGGGGS DIQLTQSPSS LSASVGDRVT ITCRASKGVS TSGYSYLHWY   180
QQKPGKAPKL LIYLASYLES GVPSRFSGSG SGTDFTLTIS SLQPEDFATY YCQHSRDLPL   240
TFGCGTKVEI KR                                                      252

SEQ ID NO: 422            moltype = AA  length = 251
FEATURE                   Location/Qualifiers
```

-continued

```
source                     1..251
                           mol_type = protein
                           organism = synthetic construct
SEQUENCE: 422
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSGGGGSGG GGSGGGGSGG GGSDIQMTQS PSSLSASVGD RVTITCSASQ DISNYLNWYQ   180
QKPGKAPKVL IYFTSSLHSG VPSRFSGSGS GTDFTLTISS LQPEDFATYY CQQYSTVPWT   240
FGQGTKVEIK R                                                        251

SEQ ID NO: 423            moltype = AA   length = 251
FEATURE                   Location/Qualifiers
source                    1..251
                          mol_type = protein
                          organism = synthetic construct
SEQUENCE: 423
EVQLVESGGG LVQPGGSLRL SCAASGYTFT NYGMNWVRQA PGKCLEWVGW INTYTGEPTY    60
AADFKRRFTF SLDTSKSTAY LQMNSLRAED TAVYYCAKYP HYYGSSHWYF DVWGQGTLVT   120
VSSGGGGSGG GGSGGGGSGG GGSDIQMTQS PSSLSASVGD RVTITCSASQ DISNYLNWYQ   180
QKPGKAPKVL IYFTSSLHSG VPSRFSGSGS GTDFTLTISS LQPEDFATYY CQQYSTVPWT   240
FGCGTKVEIK R                                                        251

SEQ ID NO: 424            moltype = AA   length = 119
FEATURE                   Location/Qualifiers
source                    1..119
                          mol_type = protein
                          organism = synthetic construct
SEQUENCE: 424
EVQLVESGGG LVQPGGSLRL SCAASGSIAS IHAMGWVRQA PGKEREWVSV ITWSGGITYY    60
ADSVKGRFTI SRDNSKNTLY LQMNSLRAED TAVYYCAGDK HQSSWYDYWG QGTLVTVSS    119

SEQ ID NO: 425            moltype = AA   length = 119
FEATURE                   Location/Qualifiers
source                    1..119
                          mol_type = protein
                          organism = synthetic construct
SEQUENCE: 425
EVQLVESGGG LVQPGGSLRL SCAASGSIAS IHAMGWVRQA PGKEREWVSV ITWSGGITYY    60
ADSVKGRFTI SRDNSKNTVY LQMNSLRAED TAVYYCAGDK HQSSWYDYWG QGTLVTVSS    119

SEQ ID NO: 426            moltype = AA   length = 119
FEATURE                   Location/Qualifiers
source                    1..119
                          mol_type = protein
                          organism = synthetic construct
SEQUENCE: 426
EVQLVESGGG LVQPGGSLRL SCAASGSIAS IHAMGWVRQA PGKEREFVSV ITWSGGITYY    60
ADSVKGRFTI SRDNSKNTLY LQMNSLRAED TAVYYCAGDK HQSSWYDYWG QGTLVTVSS    119

SEQ ID NO: 427            moltype = AA   length = 119
FEATURE                   Location/Qualifiers
source                    1..119
                          mol_type = protein
                          organism = synthetic construct
SEQUENCE: 427
EVQLVESGGG LVQPGGSLRL SCAASGSIAS IHAMGWVRQA PGKEREFVSV ITWSGGITYY    60
ADSVKGRFTI SRDNSKNTVY LQMNSLRAED TAVYYCAGDK HQSSWYDYWG QGTLVTVSS    119

SEQ ID NO: 428            moltype = AA   length = 119
FEATURE                   Location/Qualifiers
source                    1..119
                          mol_type = protein
                          organism = synthetic construct
SEQUENCE: 428
EVQLVESGGG LVQPGGSLRL SCAASGSIAS IHAMGWVRQA PGKEREFVAV ITWSGGITYY    60
ADSVKGRFTI SRDNSKNTVY LQMNSLRAED TAVYYCAGDK HQSSWYDYWG QGTLVTVSS    119

SEQ ID NO: 429            moltype = AA   length = 119
FEATURE                   Location/Qualifiers
source                    1..119
                          mol_type = protein
                          organism = synthetic construct
SEQUENCE: 429
EVQLVESGGG LVQPGGSLRL SCAASGSIAS IHAMGWVRQA PGKEREWVAV ITWSGGITYY    60
ADSVKGRFTI SRDNSKNTVY LQMNSLRAED TAVYYCAGDK HQSSWYDYWG QGTLVTVSS    119

SEQ ID NO: 430            moltype = AA   length = 246
FEATURE                   Location/Qualifiers
source                    1..246
```

-continued

```
                                mol_type = protein
                                organism = synthetic construct
SEQUENCE: 430
EVQLVESGGG LVQPGGSLRL SCAASGFAFS SYDMSWVRQA PGKGLDWVAT ISGGGRYTYY    60
PDSVKGRFTI SRDNSKNNLY LQMNSLRAED TALYYCANRY GEAWFAYWGQ GTLVTVSSGG   120
GGSGGGGSGG GGSGGGGSDI QMTQSPSSMS ASVGDRVTFT CRASQDINTY LSWFQQKPGK   180
SPKTLIYRAN RLVSGVPSRF SGSGSGQDYT LTISSLQPED MATYYCLQYD EFPLTFGAGT   240
KLELKR                                                             246

SEQ ID NO: 431           moltype = AA   length = 123
FEATURE                  Location/Qualifiers
source                   1..123
                         mol_type = protein
                         organism = synthetic construct
SEQUENCE: 431
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSS                                                                123

SEQ ID NO: 432           moltype = AA   length = 107
FEATURE                  Location/Qualifiers
source                   1..107
                         mol_type = protein
                         organism = synthetic construct
SEQUENCE: 432
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIK                107

SEQ ID NO: 433           moltype = AA   length = 5
FEATURE                  Location/Qualifiers
source                   1..5
                         mol_type = protein
                         organism = synthetic construct
SEQUENCE: 433
NYGMN                                                                5

SEQ ID NO: 434           moltype = AA   length = 17
FEATURE                  Location/Qualifiers
source                   1..17
                         mol_type = protein
                         organism = synthetic construct
SEQUENCE: 434
WINTYTGEPT YAADFKR                                                  17

SEQ ID NO: 435           moltype = AA   length = 14
FEATURE                  Location/Qualifiers
source                   1..14
                         mol_type = protein
                         organism = synthetic construct
SEQUENCE: 435
YPHYYGSSHW YFDV                                                     14

SEQ ID NO: 436           moltype = AA   length = 11
FEATURE                  Location/Qualifiers
source                   1..11
                         mol_type = protein
                         organism = synthetic construct
SEQUENCE: 436
SASQDISNYL N                                                        11

SEQ ID NO: 437           moltype = AA   length = 7
FEATURE                  Location/Qualifiers
source                   1..7
                         mol_type = protein
                         organism = synthetic construct
SEQUENCE: 437
FTSSLHS                                                              7

SEQ ID NO: 438           moltype = AA   length = 9
FEATURE                  Location/Qualifiers
source                   1..9
                         mol_type = protein
                         organism = synthetic construct
SEQUENCE: 438
QQYSTVPWT                                                            9

SEQ ID NO: 439           moltype = AA   length = 8
FEATURE                  Location/Qualifiers
source                   1..8
```

-continued

```
                          mol_type = protein
                          organism = synthetic construct
SEQUENCE: 439
GYTFTNYG                                                     8

SEQ ID NO: 440           moltype = AA  length = 8
FEATURE                  Location/Qualifiers
source                   1..8
                         mol_type = protein
                         organism = synthetic construct
SEQUENCE: 440
INTYTGEP                                                     8

SEQ ID NO: 441           moltype = AA  length = 16
FEATURE                  Location/Qualifiers
source                   1..16
                         mol_type = protein
                         organism = synthetic construct
SEQUENCE: 441
AKYPHYYGSS HWYFDV                                            16

SEQ ID NO: 442           moltype = AA  length = 6
FEATURE                  Location/Qualifiers
source                   1..6
                         mol_type = protein
                         organism = synthetic construct
SEQUENCE: 442
QDISNY                                                       6

SEQ ID NO: 443           moltype = AA  length = 7
FEATURE                  Location/Qualifiers
source                   1..7
                         mol_type = protein
                         organism = synthetic construct
SEQUENCE: 443
GYTFTNY                                                      7

SEQ ID NO: 444           moltype = AA  length = 6
FEATURE                  Location/Qualifiers
source                   1..6
                         mol_type = protein
                         organism = synthetic construct
SEQUENCE: 444
NTYTGE                                                       6

SEQ ID NO: 445           moltype = AA  length = 5
FEATURE                  Location/Qualifiers
source                   1..5
                         mol_type = protein
                         organism = synthetic construct
SEQUENCE: 445
NYYMY                                                        5

SEQ ID NO: 446           moltype = AA  length = 17
FEATURE                  Location/Qualifiers
source                   1..17
                         mol_type = protein
                         organism = synthetic construct
SEQUENCE: 446
GINPSNGGTN FNEKFKN                                           17

SEQ ID NO: 447           moltype = AA  length = 11
FEATURE                  Location/Qualifiers
source                   1..11
                         mol_type = protein
                         organism = synthetic construct
SEQUENCE: 447
RDYRFDMGFD Y                                                 11

SEQ ID NO: 448           moltype = AA  length = 15
FEATURE                  Location/Qualifiers
source                   1..15
                         mol_type = protein
                         organism = synthetic construct
SEQUENCE: 448
RASKGVSTSG YSYLH                                             15

SEQ ID NO: 449           moltype = AA  length = 7
FEATURE                  Location/Qualifiers
```

```
source                    1..7
                          mol_type = protein
                          organism = synthetic construct
SEQUENCE: 449
LASYLES                                                            7

SEQ ID NO: 450            moltype = AA   length = 9
FEATURE                   Location/Qualifiers
source                    1..9
                          mol_type = protein
                          organism = synthetic construct
SEQUENCE: 450
QHSRDLPLT                                                          9

SEQ ID NO: 451            moltype = AA   length = 8
FEATURE                   Location/Qualifiers
source                    1..8
                          mol_type = protein
                          organism = synthetic construct
SEQUENCE: 451
GYTFTNYY                                                           8

SEQ ID NO: 452            moltype = AA   length = 8
FEATURE                   Location/Qualifiers
source                    1..8
                          mol_type = protein
                          organism = synthetic construct
SEQUENCE: 452
INPSNGGT                                                           8

SEQ ID NO: 453            moltype = AA   length = 13
FEATURE                   Location/Qualifiers
source                    1..13
                          mol_type = protein
                          organism = synthetic construct
SEQUENCE: 453
ARRDYRFDMG FDY                                                     13

SEQ ID NO: 454            moltype = AA   length = 10
FEATURE                   Location/Qualifiers
source                    1..10
                          mol_type = protein
                          organism = synthetic construct
SEQUENCE: 454
KGVSTSGYSY                                                         10

SEQ ID NO: 455            moltype = AA   length = 6
FEATURE                   Location/Qualifiers
source                    1..6
                          mol_type = protein
                          organism = synthetic construct
SEQUENCE: 455
NPSNGG                                                             6

SEQ ID NO: 456            moltype = AA   length = 17
FEATURE                   Location/Qualifiers
source                    1..17
                          mol_type = protein
                          organism = synthetic construct
SEQUENCE: 456
GINPSQGGTN FNEKFKN                                                 17

SEQ ID NO: 457            moltype = AA   length = 11
FEATURE                   Location/Qualifiers
source                    1..11
                          mol_type = protein
                          organism = synthetic construct
SEQUENCE: 457
RDYRFDLGFD Y                                                       11

SEQ ID NO: 458            moltype = AA   length = 8
FEATURE                   Location/Qualifiers
source                    1..8
                          mol_type = protein
                          organism = synthetic construct
SEQUENCE: 458
INPSQGGT                                                           8

SEQ ID NO: 459            moltype = AA   length = 13
```

-continued

```
FEATURE              Location/Qualifiers
source               1..13
                     mol_type = protein
                     organism = synthetic construct
SEQUENCE: 459
ARRDYRFDLG FDY                                                  13

SEQ ID NO: 460       moltype = AA  length = 6
FEATURE              Location/Qualifiers
source               1..6
                     mol_type = protein
                     organism = synthetic construct
SEQUENCE: 460
NPSQGG                                                          6

SEQ ID NO: 461       moltype = AA  length = 17
FEATURE              Location/Qualifiers
source               1..17
                     mol_type = protein
                     organism = synthetic construct
SEQUENCE: 461
GINPSRGGTN FNEKFKN                                              17

SEQ ID NO: 462       moltype = AA  length = 8
FEATURE              Location/Qualifiers
source               1..8
                     mol_type = protein
                     organism = synthetic construct
SEQUENCE: 462
INPSRGGT                                                        8

SEQ ID NO: 463       moltype = AA  length = 6
FEATURE              Location/Qualifiers
source               1..6
                     mol_type = protein
                     organism = synthetic construct
SEQUENCE: 463
NPSRGG                                                          6

SEQ ID NO: 464       moltype = AA  length = 120
FEATURE              Location/Qualifiers
source               1..120
                     mol_type = protein
                     organism = synthetic construct
SEQUENCE: 464
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120

SEQ ID NO: 465       moltype = AA  length = 120
FEATURE              Location/Qualifiers
source               1..120
                     mol_type = protein
                     organism = synthetic construct
SEQUENCE: 465
QVQLVQSGVE VKKPGASVKV SCKASGYTFT NYYMYWVRQA PGQGLEWMGG INPSNGGTNF  60
NEKFKNRVTL TTDSSTTTAY MELKSLRFDD TAVYYCARRD YRFDMGFDYW GQGTTVTVSS  120

SEQ ID NO: 466       moltype = AA  length = 120
FEATURE              Location/Qualifiers
source               1..120
                     mol_type = protein
                     organism = synthetic construct
SEQUENCE: 466
QVQLVQSGVE VKKPGASVKV SCKASGYTFT NYYMYWVRQA PGQGLEWMGG INPSQGGTNF  60
NEKFKNRVTL TTDSSTTTAY MELKSLQFDD TAVYYCARRD YRFDLGFDYW GQGTGVRVSS  120

SEQ ID NO: 467       moltype = AA  length = 120
FEATURE              Location/Qualifiers
source               1..120
                     mol_type = protein
                     organism = synthetic construct
SEQUENCE: 467
EVQLVQSGAE VKKPGASVKV SCKASGYTFT NYYMYWVRQA PGQGLEWMGG INPSQGGTNF  60
NEKFKNRVTL TTDSSTSTAY MELSSLRSED TAVYYCARRD YRFDLGFDYW GQGTTVTVSS  120

SEQ ID NO: 468       moltype = AA  length = 120
FEATURE              Location/Qualifiers
source               1..120
                     mol_type = protein
```

```
                        organism = synthetic construct
SEQUENCE: 468
EVQLLESGGG LVQPGGSLRL SCKASGYTFT NYYMYWVRQA PGKGLEWMGG INPSQGGTNF   60
NEKFKNRVTL STDSSKNTAY LQMNSLRAED TAVYYCARRD YRFDLGFDYW GQGTTVTVSS   120

SEQ ID NO: 469          moltype = AA  length = 120
FEATURE                 Location/Qualifiers
source                  1..120
                        mol_type = protein
                        organism = synthetic construct
SEQUENCE: 469
QVQLVQSGVE VKKPGASVKV SCKASGYTFT NYYMYWVRQA PGQCLEWMGG INPSQGGTNF   60
NEKFKNRVTL TTDSSTTTAY MELKSLQFDD TAVYYCARRD YRFDLGFDYW GQGTTVTVSS   120

SEQ ID NO: 470          moltype = AA  length = 120
FEATURE                 Location/Qualifiers
source                  1..120
                        mol_type = protein
                        organism = synthetic construct
SEQUENCE: 470
EVQLVESGGG LVQPGGSLRL SCAASGYTFT NYYMYWVRQA PGKGLEWMGG INPSQGGTNF   60
NEKFKNRFTI SRDNSKNTLY LQMNSLRAED TAVYYCARRD YRFDLGFDYW GQGTLVTVSS   120

SEQ ID NO: 471          moltype = AA  length = 112
FEATURE                 Location/Qualifiers
source                  1..112
                        mol_type = protein
                        organism = synthetic construct
SEQUENCE: 471
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KR           112

SEQ ID NO: 472          moltype = AA  length = 112
FEATURE                 Location/Qualifiers
source                  1..112
                        mol_type = protein
                        organism = synthetic construct
SEQUENCE: 472
EIVLTQSPST LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KR           112

SEQ ID NO: 473          moltype = AA  length = 112
FEATURE                 Location/Qualifiers
source                  1..112
                        mol_type = protein
                        organism = synthetic construct
SEQUENCE: 473
EIVLTQSPST LSLSPGERAT LSCRASKGVS TSGYSYLHWY QQKPGQAPRL LIYLASYLES   60
GVPARFSGSG SGTDFTLTIS GLEPEDFAVY YCQHSRDLPL TFGGGTKVEI KR           112

SEQ ID NO: 474          moltype = AA  length = 112
FEATURE                 Location/Qualifiers
source                  1..112
                        mol_type = protein
                        organism = synthetic construct
SEQUENCE: 474
EIVLTQSPAT LSVSPGERAT LSCRASKGVS TSGYSYLHWY QQKPGQAPRL LIYLASYLES   60
GIPARFSGSG SGTEFTLTIS SLQSEDFAVY YCQHSRDLPL TFGGGTKVEI KR           112

SEQ ID NO: 475          moltype = AA  length = 112
FEATURE                 Location/Qualifiers
source                  1..112
                        mol_type = protein
                        organism = synthetic construct
SEQUENCE: 475
DIQLTQSPSS LSASVGDRVT ITCRASKGVS TSGYSYLHWY QQKPGKAPKL LIYLASYLES   60
GVPSRFSGSG SGTDFTLTIS SLQPEDFATY YCQHSRDLPL TFGGGTKVEI KR           112

SEQ ID NO: 476          moltype = AA  length = 112
FEATURE                 Location/Qualifiers
source                  1..112
                        mol_type = protein
                        organism = synthetic construct
SEQUENCE: 476
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGCGTKVEI KR           112

SEQ ID NO: 477          moltype =    length =
SEQUENCE: 477
```

-continued

```
000

SEQ ID NO: 478          moltype =   length =
SEQUENCE: 478
000

SEQ ID NO: 479          moltype =   length =
SEQUENCE: 479
000

SEQ ID NO: 480          moltype =   length =
SEQUENCE: 480
000

SEQ ID NO: 481          moltype =   length =
SEQUENCE: 481
000

SEQ ID NO: 482          moltype =   length =
SEQUENCE: 482
000

SEQ ID NO: 483          moltype =   length =
SEQUENCE: 483
000

SEQ ID NO: 484          moltype =   length =
SEQUENCE: 484
000

SEQ ID NO: 485          moltype =   length =
SEQUENCE: 485
000

SEQ ID NO: 486          moltype =   length =
SEQUENCE: 486
000

SEQ ID NO: 487          moltype =   length =
SEQUENCE: 487
000

SEQ ID NO: 488          moltype =   length =
SEQUENCE: 488
000

SEQ ID NO: 489          moltype =   length =
SEQUENCE: 489
000

SEQ ID NO: 490          moltype =   length =
SEQUENCE: 490
000

SEQ ID NO: 491          moltype =   length =
SEQUENCE: 491
000

SEQ ID NO: 492          moltype =   length =
SEQUENCE: 492
000

SEQ ID NO: 493          moltype =   length =
SEQUENCE: 493
000

SEQ ID NO: 494          moltype =   length =
SEQUENCE: 494
000

SEQ ID NO: 495          moltype =   length =
SEQUENCE: 495
000

SEQ ID NO: 496          moltype =   length =
SEQUENCE: 496
000

SEQ ID NO: 497          moltype =   length =
```

```
SEQUENCE: 497
000

SEQ ID NO: 498        moltype =   length =
SEQUENCE: 498
000

SEQ ID NO: 499        moltype =   length =
SEQUENCE: 499
000

SEQ ID NO: 500        moltype =   length =
SEQUENCE: 500
000

SEQ ID NO: 501        moltype =   length =
SEQUENCE: 501
000

SEQ ID NO: 502        moltype =   length =
SEQUENCE: 502
000

SEQ ID NO: 503        moltype =   length =
SEQUENCE: 503
000

SEQ ID NO: 504        moltype =   length =
SEQUENCE: 504
000

SEQ ID NO: 505        moltype =   length =
SEQUENCE: 505
000

SEQ ID NO: 506        moltype =   length =
SEQUENCE: 506
000

SEQ ID NO: 507        moltype =   length =
SEQUENCE: 507
000

SEQ ID NO: 508        moltype =   length =
SEQUENCE: 508
000

SEQ ID NO: 509        moltype =   length =
SEQUENCE: 509
000

SEQ ID NO: 510        moltype =   length =
SEQUENCE: 510
000

SEQ ID NO: 511        moltype =   length =
SEQUENCE: 511
000

SEQ ID NO: 512        moltype =   length =
SEQUENCE: 512
000

SEQ ID NO: 513        moltype =   length =
SEQUENCE: 513
000

SEQ ID NO: 514        moltype =   length =
SEQUENCE: 514
000

SEQ ID NO: 515        moltype =   length =
SEQUENCE: 515
000

SEQ ID NO: 516        moltype =   length =
SEQUENCE: 516
000
```

US 12,673,997 B2

479                                                        480

-continued

```
SEQ ID NO: 517          moltype =    length =
SEQUENCE: 517
000

SEQ ID NO: 518          moltype =    length =
SEQUENCE: 518
000

SEQ ID NO: 519          moltype =    length =
SEQUENCE: 519
000

SEQ ID NO: 520          moltype =    length =
SEQUENCE: 520
000

SEQ ID NO: 521          moltype =    length =
SEQUENCE: 521
000

SEQ ID NO: 522          moltype =    length =
SEQUENCE: 522
000

SEQ ID NO: 523          moltype =    length =
SEQUENCE: 523
000

SEQ ID NO: 524          moltype =    length =
SEQUENCE: 524
000

SEQ ID NO: 525          moltype =    length =
SEQUENCE: 525
000

SEQ ID NO: 526          moltype =    length =
SEQUENCE: 526
000

SEQ ID NO: 527          moltype =    length =
SEQUENCE: 527
000

SEQ ID NO: 528          moltype =    length =
SEQUENCE: 528
000

SEQ ID NO: 529          moltype =    length =
SEQUENCE: 529
000

SEQ ID NO: 530          moltype =    length =
SEQUENCE: 530
000

SEQ ID NO: 531          moltype =    length =
SEQUENCE: 531
000

SEQ ID NO: 532          moltype =    length =
SEQUENCE: 532
000

SEQ ID NO: 533          moltype =    length =
SEQUENCE: 533
000

SEQ ID NO: 534          moltype =    length =
SEQUENCE: 534
000

SEQ ID NO: 535          moltype =    length =
SEQUENCE: 535
000

SEQ ID NO: 536          moltype =    length =
SEQUENCE: 536
000
```

-continued

```
SEQ ID NO: 537          moltype =   length =
SEQUENCE: 537
000

SEQ ID NO: 538          moltype =   length =
SEQUENCE: 538
000

SEQ ID NO: 539          moltype =   length =
SEQUENCE: 539
000

SEQ ID NO: 540          moltype =   length =
SEQUENCE: 540
000

SEQ ID NO: 541          moltype =   length =
SEQUENCE: 541
000

SEQ ID NO: 542          moltype =   length =
SEQUENCE: 542
000

SEQ ID NO: 543          moltype =   length =
SEQUENCE: 543
000

SEQ ID NO: 544          moltype =   length =
SEQUENCE: 544
000

SEQ ID NO: 545          moltype =   length =
SEQUENCE: 545
000

SEQ ID NO: 546          moltype =   length =
SEQUENCE: 546
000

SEQ ID NO: 547          moltype =   length =
SEQUENCE: 547
000

SEQ ID NO: 548          moltype =   length =
SEQUENCE: 548
000

SEQ ID NO: 549          moltype =   length =
SEQUENCE: 549
000

SEQ ID NO: 550          moltype =   length =
SEQUENCE: 550
000

SEQ ID NO: 551          moltype =   length =
SEQUENCE: 551
000

SEQ ID NO: 552          moltype =   length =
SEQUENCE: 552
000

SEQ ID NO: 553          moltype =   length =
SEQUENCE: 553
000

SEQ ID NO: 554          moltype =   length =
SEQUENCE: 554
000

SEQ ID NO: 555          moltype =   length =
SEQUENCE: 555
000

SEQ ID NO: 556          moltype =   length =
SEQUENCE: 556
```

-continued

```
000

SEQ ID NO: 557          moltype =    length =
SEQUENCE: 557
000

SEQ ID NO: 558          moltype =    length =
SEQUENCE: 558
000

SEQ ID NO: 559          moltype =    length =
SEQUENCE: 559
000

SEQ ID NO: 560          moltype =    length =
SEQUENCE: 560
000

SEQ ID NO: 561          moltype =    length =
SEQUENCE: 561
000

SEQ ID NO: 562          moltype =    length =
SEQUENCE: 562
000

SEQ ID NO: 563          moltype =    length =
SEQUENCE: 563
000

SEQ ID NO: 564          moltype =    length =
SEQUENCE: 564
000

SEQ ID NO: 565          moltype =    length =
SEQUENCE: 565
000

SEQ ID NO: 566          moltype =    length =
SEQUENCE: 566
000

SEQ ID NO: 567          moltype =    length =
SEQUENCE: 567
000

SEQ ID NO: 568          moltype =    length =
SEQUENCE: 568
000

SEQ ID NO: 569          moltype =    length =
SEQUENCE: 569
000

SEQ ID NO: 570          moltype =    length =
SEQUENCE: 570
000

SEQ ID NO: 571          moltype =    length =
SEQUENCE: 571
000

SEQ ID NO: 572          moltype =    length =
SEQUENCE: 572
000

SEQ ID NO: 573          moltype =    length =
SEQUENCE: 573
000

SEQ ID NO: 574          moltype =    length =
SEQUENCE: 574
000

SEQ ID NO: 575          moltype =    length =
SEQUENCE: 575
000

SEQ ID NO: 576          moltype =    length =
```

-continued

```
SEQUENCE: 576
000

SEQ ID NO: 577          moltype =   length =
SEQUENCE: 577
000

SEQ ID NO: 578          moltype =   length =
SEQUENCE: 578
000

SEQ ID NO: 579          moltype =   length =
SEQUENCE: 579
000

SEQ ID NO: 580          moltype =   length =
SEQUENCE: 580
000

SEQ ID NO: 581          moltype =   length =
SEQUENCE: 581
000

SEQ ID NO: 582          moltype =   length =
SEQUENCE: 582
000

SEQ ID NO: 583          moltype =   length =
SEQUENCE: 583
000

SEQ ID NO: 584          moltype =   length =
SEQUENCE: 584
000

SEQ ID NO: 585          moltype =   length =
SEQUENCE: 585
000

SEQ ID NO: 586          moltype =   length =
SEQUENCE: 586
000

SEQ ID NO: 587          moltype =   length =
SEQUENCE: 587
000

SEQ ID NO: 588          moltype =   length =
SEQUENCE: 588
000

SEQ ID NO: 589          moltype =   length =
SEQUENCE: 589
000

SEQ ID NO: 590          moltype =   length =
SEQUENCE: 590
000

SEQ ID NO: 591          moltype =   length =
SEQUENCE: 591
000

SEQ ID NO: 592          moltype =   length =
SEQUENCE: 592
000

SEQ ID NO: 593          moltype =   length =
SEQUENCE: 593
000

SEQ ID NO: 594          moltype =   length =
SEQUENCE: 594
000

SEQ ID NO: 595          moltype =   length =
SEQUENCE: 595
000
```

-continued

```
SEQ ID NO: 596        moltype =   length =
SEQUENCE: 596
000

SEQ ID NO: 597        moltype =   length =
SEQUENCE: 597
000

SEQ ID NO: 598        moltype =   length =
SEQUENCE: 598
000

SEQ ID NO: 599        moltype =   length =
SEQUENCE: 599
000

SEQ ID NO: 600        moltype =   length =
SEQUENCE: 600
000

SEQ ID NO: 601        moltype =   length =
SEQUENCE: 601
000

SEQ ID NO: 602        moltype =   length =
SEQUENCE: 602
000

SEQ ID NO: 603        moltype =   length =
SEQUENCE: 603
000

SEQ ID NO: 604        moltype =   length =
SEQUENCE: 604
000

SEQ ID NO: 605        moltype =   length =
SEQUENCE: 605
000

SEQ ID NO: 606        moltype =   length =
SEQUENCE: 606
000

SEQ ID NO: 607        moltype =   length =
SEQUENCE: 607
000

SEQ ID NO: 608        moltype =   length =
SEQUENCE: 608
000

SEQ ID NO: 609        moltype =   length =
SEQUENCE: 609
000

SEQ ID NO: 610        moltype =   length =
SEQUENCE: 610
000

SEQ ID NO: 611        moltype =   length =
SEQUENCE: 611
000

SEQ ID NO: 612        moltype =   length =
SEQUENCE: 612
000

SEQ ID NO: 613        moltype =   length =
SEQUENCE: 613
000

SEQ ID NO: 614        moltype =   length =
SEQUENCE: 614
000

SEQ ID NO: 615        moltype =   length =
SEQUENCE: 615
000
```

-continued

```
SEQ ID NO: 616          moltype =   length =
SEQUENCE: 616
000

SEQ ID NO: 617          moltype =   length =
SEQUENCE: 617
000

SEQ ID NO: 618          moltype =   length =
SEQUENCE: 618
000

SEQ ID NO: 619          moltype =   length =
SEQUENCE: 619
000

SEQ ID NO: 620          moltype =   length =
SEQUENCE: 620
000

SEQ ID NO: 621          moltype =   length =
SEQUENCE: 621
000

SEQ ID NO: 622          moltype =   length =
SEQUENCE: 622
000

SEQ ID NO: 623          moltype =   length =
SEQUENCE: 623
000

SEQ ID NO: 624          moltype =   length =
SEQUENCE: 624
000

SEQ ID NO: 625          moltype =   length =
SEQUENCE: 625
000

SEQ ID NO: 626          moltype =   length =
SEQUENCE: 626
000

SEQ ID NO: 627          moltype =   length =
SEQUENCE: 627
000

SEQ ID NO: 628          moltype =   length =
SEQUENCE: 628
000

SEQ ID NO: 629          moltype =   length =
SEQUENCE: 629
000

SEQ ID NO: 630          moltype =   length =
SEQUENCE: 630
000

SEQ ID NO: 631          moltype =   length =
SEQUENCE: 631
000

SEQ ID NO: 632          moltype =   length =
SEQUENCE: 632
000

SEQ ID NO: 633          moltype =   length =
SEQUENCE: 633
000

SEQ ID NO: 634          moltype =   length =
SEQUENCE: 634
000

SEQ ID NO: 635          moltype =   length =
SEQUENCE: 635
```

-continued

```
000

SEQ ID NO: 636          moltype =    length =
SEQUENCE: 636
000

SEQ ID NO: 637          moltype =    length =
SEQUENCE: 637
000

SEQ ID NO: 638          moltype =    length =
SEQUENCE: 638
000

SEQ ID NO: 639          moltype =    length =
SEQUENCE: 639
000

SEQ ID NO: 640          moltype =    length =
SEQUENCE: 640
000

SEQ ID NO: 641          moltype =    length =
SEQUENCE: 641
000

SEQ ID NO: 642          moltype =    length =
SEQUENCE: 642
000

SEQ ID NO: 643          moltype =    length =
SEQUENCE: 643
000

SEQ ID NO: 644          moltype =    length =
SEQUENCE: 644
000

SEQ ID NO: 645          moltype =    length =
SEQUENCE: 645
000

SEQ ID NO: 646          moltype =    length =
SEQUENCE: 646
000

SEQ ID NO: 647          moltype =    length =
SEQUENCE: 647
000

SEQ ID NO: 648          moltype =    length =
SEQUENCE: 648
000

SEQ ID NO: 649          moltype =    length =
SEQUENCE: 649
000

SEQ ID NO: 650          moltype =    length =
SEQUENCE: 650
000

SEQ ID NO: 651          moltype =    length =
SEQUENCE: 651
000

SEQ ID NO: 652          moltype =    length =
SEQUENCE: 652
000

SEQ ID NO: 653          moltype =    length =
SEQUENCE: 653
000

SEQ ID NO: 654          moltype =    length =
SEQUENCE: 654
000

SEQ ID NO: 655          moltype =    length =
```

-continued

```
SEQUENCE: 655
000

SEQ ID NO: 656          moltype = AA  length = 723
FEATURE                 Location/Qualifiers
source                  1..723
                        mol_type = protein
                        organism = synthetic construct
SEQUENCE: 656
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGGGSGGG GSGGGGSGGG GSEVQLVQSG  480
AEVKKPGASV KVSCKASGYT FTNYYMYWVR QAPGQCLEWM QAPGQCLEWM NFNEKFKNRV  540
TLTTDSSTST AYMELSSLRS EDTAVYYCAR RDYRFDLGFD YWGQGTTVTV SSGGGGSGGG  600
GSGGGGSGGG GSDIQLTQSP SSLSASVGDR VTITCRASKG VSTSGYSYLH WYQQKPGKAP  660
KLLIYLASYL ESGVPSRFSG SGSGTDFTLT ISSLQPEDFA TYYCQHSRDL PLTFGCGTKV  720
EIK                                                                723

SEQ ID NO: 657          moltype = AA  length = 723
FEATURE                 Location/Qualifiers
source                  1..723
                        mol_type = protein
                        organism = synthetic construct
SEQUENCE: 657
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGGGSGGG GSGGGGSGGG GSEVQLVQSG  480
AEVKKPGASV KVSCKASGYT FTNYYMYWVR QAPGQCLEWM QAPGQCLEWM NFNEKFKNRV  540
TLTTDSSTST AYMELSSLRS EDTAVYYCAR RDYRFDLGFD YWGQGTTVTV SSGGGGSGGG  600
GSGGGGSGGG GSDIQLTQSP SSLSASVGDR VTITCRASKG VSTSGYSYLH WYQQKPGKAP  660
KLLIYLASYL ESGVPSRFSG SGSGTDFTLT ISSLQPEDFA TYYCQHSRDL PLTFGCGTKV  720
EIK                                                                723

SEQ ID NO: 658          moltype = AA  length = 723
FEATURE                 Location/Qualifiers
source                  1..723
                        mol_type = protein
                        organism = synthetic construct
SEQUENCE: 658
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGGGSGGG GSGGGGSGGG GSEVQLVQSG  480
AEVKKPGASV KVSCKASGYT FTNYYMYWVR QAPGQCLEWM GGINPSNGGT NFNEKFKNRV  540
TLTTDSSTST AYMELSSLRS EDTAVYYCAR RDYRFDMGFD YWGQGTTVTV SSGGGGSGGG  600
GSGGGGSGGG GSDIQLTQSP SSLSASVGDR VTITCRASKG VSTSGYSYLH WYQQKPGKAP  660
KLLIYLASYL ESGVPSRFSG SGSGTDFTLT ISSLQPEDFA TYYCQHSRDL PLTFGCGTKV  720
EIK                                                                723

SEQ ID NO: 659          moltype = AA  length = 723
FEATURE                 Location/Qualifiers
source                  1..723
                        mol_type = protein
                        organism = synthetic construct
SEQUENCE: 659
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGGGSGGG GSGGGGSGGG GSEVQLVQSG  480
AEVKKPGASV KVSCKASGYT FTNYYMYWVR QAPGQCLEWM GGINPSNGGT NFNEKFKNRV  540
TLTTDSSTST AYMELSSLRS EDTAVYYCAR RDYRFDMGFD YWGQGTTVTV SSGGGGSGGG  600
```

```
GSGGGGSGGG GSDIQLTQSP SSLSASVGDR VTITCRASKG VSTSGYSYLH WYQQKPGKAP    660
KLLIYLASYL ESGVPSRFSG SGSGTDFTLT ISSLQPEDFA TYYCQHSRDL PLTFGCGTKV    720
EIK                                                                 723

SEQ ID NO: 660          moltype = AA  length = 723
FEATURE                 Location/Qualifiers
source                  1..723
                        mol_type = protein
                        organism = synthetic construct
SEQUENCE: 660
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGGGGGSGGG GSGGGGSGGG GSEVQLVQSG    480
AEVKKPGASV KVSCKASGYT FTNYYMYWVR QAPGQCLEWM GGINPSQGGT NFNEKFKNRV    540
TLTTDSSTST AYMELSSLRS EDTAVYYCAR RDYRFDMGFD YWGQGTTVTV SSGGGGSGGG    600
GSGGGGSGGG GSDIQLTQSP SSLSASVGDR VTITCRASKG VSTSGYSYLH WYQQKPGKAP    660
KLLIYLASYL ESGVPSRFSG SGSGTDFTLT ISSLQPEDFA TYYCQHSRDL PLTFGCGTKV    720
EIK                                                                 723

SEQ ID NO: 661          moltype = AA  length = 723
FEATURE                 Location/Qualifiers
source                  1..723
                        mol_type = protein
                        organism = synthetic construct
SEQUENCE: 661
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGGGGGSGGG GSGGGGSGGG GSEVQLVQSG    480
AEVKKPGASV KVSCKASGYT FTNYYMYWVR QAPGQCLEWM GGINPSRGGT NFNEKFKNRV    540
TLTTDSSTST AYMELSSLRS EDTAVYYCAR RDYRFDMGFD YWGQGTTVTV SSGGGGSGGG    600
GSGGGGSGGG GSDIQLTQSP SSLSASVGDR VTITCRASKG VSTSGYSYLH WYQQKPGKAP    660
KLLIYLASYL ESGVPSRFSG SGSGTDFTLT ISSLQPEDFA TYYCQHSRDL PLTFGCGTKV    720
EIK                                                                 723

SEQ ID NO: 662          moltype = AA  length = 723
FEATURE                 Location/Qualifiers
source                  1..723
                        mol_type = protein
                        organism = synthetic construct
SEQUENCE: 662
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGGGGGSGGG GSGGGGSGGG GSEVQLVQSG    480
AEVKKPGASV KVSCKASGYT FTNYYMYWVR QAPGQCLEWM GGINPSNGGT NFNEKFKNRV    540
TLTTDSSTST AYMELSSLRS EDTAVYYCAR RDYRFDLGFD YWGQGTTVTV SSGGGGSGGG    600
GSGGGGSGGG GSDIQLTQSP SSLSASVGDR VTITCRASKG VSTSGYSYLH WYQQKPGKAP    660
KLLIYLASYL ESGVPSRFSG SGSGTDFTLT ISSLQPEDFA TYYCQHSRDL PLTFGCGTKV    720
EIK                                                                 723

SEQ ID NO: 663          moltype = AA  length = 591
FEATURE                 Location/Qualifiers
source                  1..591
                        mol_type = protein
                        organism = synthetic construct
SEQUENCE: 663
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT    120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGGGGGSGGG GSGGGGSGGG GSEVQLVESG    480
GGLVQPGGSL RLSCAASGSI ASIHAMGWVR QAPGKEREFV AVITWSGGIT YYADSVKGRF    540
```

-continued

```
TISRDNSKNT VYLQMNSLRP EDTAVYYCAG DKHQSSWYDY WGQGTLVTVS S          591

SEQ ID NO: 664          moltype = AA   length = 591
FEATURE                 Location/Qualifiers
source                  1..591
                        mol_type = protein
                        organism = synthetic construct
SEQUENCE: 664
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGGGSGGG GSGGGGSGGG GSEVQLVESG  480
GGLVQPGGSL RLSCAASGSI ASIHAMGWVR QAPGKEREFV AVITWSGGIT YYADSVKGRF  540
TISRDNSKNT VYLQMNSLRP EDTALYYCAG DKHQSSWYDY WGQGTLVTVS S          591

SEQ ID NO: 665          moltype = AA   length = 591
FEATURE                 Location/Qualifiers
source                  1..591
                        mol_type = protein
                        organism = synthetic construct
SEQUENCE: 665
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGGGSGGG GSGGGGSGGG GSEVQLVESG  480
GGLVQPGGSL RLSCAASGSI ASIHAMGWFR QAPGKEREFV AVITWSGGIT YYADSVKGRF  540
TISRDNSKNT VYLQMNSLRP EDTAVYYCAG DKHQSSWYDY WGQGTLVTVS S          591

SEQ ID NO: 666          moltype = AA   length = 591
FEATURE                 Location/Qualifiers
source                  1..591
                        mol_type = protein
                        organism = synthetic construct
SEQUENCE: 666
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGGGSGGG GSGGGGSGGG GSEVQLVESG  480
GGLVQPGGSL RLSCAASGSI ASIHAMGWFR QAPGKEREFV AVITWSGGIT YYADSVKGRF  540
TISRDNSKNT VYLQMNSLRP EDTALYYCAG DKHQSSWYDY WGQGTLVTVS S          591

SEQ ID NO: 667          moltype = AA   length = 976
FEATURE                 Location/Qualifiers
source                  1..976
                        mol_type = protein
                        organism = synthetic construct
SEQUENCE: 667
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL 180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGSGGGGS GGGGSGGGGS EIVLTQSPAT  480
LSLSPGERAT LSCRASKGVS TSGYSYLHWY QQKPGQAPRL LIYLASYLES GVPARFSGSG  540
SGTDFTLTIS SLEPEDFAVY YCQHSRDLPL TFGGGTKVEI KRTVAAPSVF IFPPSDEQLK  600
SGTASVVCLL NNFYPREAKV QWKVDNALQS GNSQESVTEQ DSKDSTYSLS STLTLSKADY  660
EKHKVYACEV THQGLSSPVT KSFNRGECGG SSGSGSGSTG TSSSGTGTSA GTTGTSASTS  720
GSGSGGGGGS GGGGSAGGTA TAGASSGSQV QLVQSGVEVK KPGASVKVSC KASGYTFTNY  780
YMYWVRQAPG QGLEWMGGIN PSNGGTNFNE KFKNRVTLTT DSSTTAYME LKSLQFDDTA  840
VYYCARRDYR FDMGFDYWGQ GTTVTVSSAS TKGPSVFPLA PSSKSTSGGT AALGCLVKDY  900
FPEPVTVSWN SGALTSGVHT FPAVLQSSGL YSLSSVVTVP SSSLGTQTYI CNVNHKPSNT  960
KVDKKVEPKS CDKTHT                                                976

SEQ ID NO: 668          moltype = AA   length = 976
FEATURE                 Location/Qualifiers
```

-continued

```
source                  1..976
                        mol_type = protein
                        organism = synthetic construct
SEQUENCE: 668
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGSGGGGS GGGGSGGGGS EIVLTQSPAT  480
LSLSPGERAT LSCRASKGVS TSGYSYLHWY QQKPGQAPRL LIYLASYLES GVPARFSGSG  540
SGTDFTLTIS SLEPEDFAVY YCQHSRDLPL TFGGGTKVEI KRTVAAPSVF IFPPSDEQLK  600
SGTASVVCLL NNFYPREAKV QWKVDNALQS GNSQESVTEQ DSKDSTYSLS STLTLSKADY  660
EKHKVYACEV THQGLSSPVT KSFNRGECGG SSGSGSGSTG TSSSGTGTSA GTTGTSASTS  720
GSGSGGGGS GGGGSAGGTA TAGASSGSQV QLVQSGVEVK KPGASVKVSC KASGYTFTNY  780
YMYWVRQAPG QGLEWMGGIN PSNGGTNFNE KFKNRVTLTT DSSTTTAYME LKSLQFDDTA  840
VYYCARRDYR FDMGFDYWGQ GTTVTVSSAS TKGPSVFPLA PSSKSTSGGT AALGCLVKDY  900
FPEPVTVSWN SGALTSGVHT FPAVLQSSGL YSLSSVVTVP SSSLGTQTYI CNVNHKPSNT  960
KVDKKVEPKS CDKTHT                                                  976

SEQ ID NO: 669          moltype = AA   length = 976
FEATURE                 Location/Qualifiers
source                  1..976
                        mol_type = protein
                        organism = synthetic construct
SEQUENCE: 669
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGSGGGGS GGGGSGGGGS EIVLTQSPAT  480
LSLSPGERAT LSCRASKGVS TSGYSYLHWY QQKPGQAPRL LIYLASYLES GVPARFSGSG  540
SGTDFTLTIS SLEPEDFAVY YCQHSRDLPL TFGGGTKVEI KRTVAAPSVF IFPPSDEQLK  600
SGTASVVCLL NNFYPREAKV QWKVDNALQS GNSQESVTEQ DSKDSTYSLS STLTLSKADY  660
EKHKVYACEV THQGLSSPVT KSFNRGECGG SSGSGSGSTG TSSSGTGTSA GTTGTSASTS  720
GSGSGGGGS GGGGSAGGTA TAGASSGSQV QLVQSGVEVK KPGASVKVSC KASGYTFTNY  780
YMYWVRQAPG QGLEWMGGIN PSQGGTNFNE KFKNRVTLTT DSSTTTAYME LKSLQFDDTA  840
VYYCARRDYR FDLGFDYWGQ GTTVTVSSAS TKGPSVFPLA PSSKSTSGGT AALGCLVKDY  900
FPEPVTVSWN SGALTSGVHT FPAVLQSSGL YSLSSVVTVP SSSLGTQTYI CNVNHKPSNT  960
KVDKKVEPKS CDKTHT                                                  976

SEQ ID NO: 670          moltype = AA   length = 976
FEATURE                 Location/Qualifiers
source                  1..976
                        mol_type = protein
                        organism = synthetic construct
SEQUENCE: 670
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGSGGGGS GGGGSGGGGS EIVLTQSPAT  480
LSLSPGERAT LSCRASKGVS TSGYSYLHWY QQKPGQAPRL LIYLASYLES GVPARFSGSG  540
SGTDFTLTIS SLEPEDFAVY YCQHSRDLPL TFGGGTKVEI KRTVAAPSVF IFPPSDEQLK  600
SGTASVVCLL NNFYPREAKV QWKVDNALQS GNSQESVTEQ DSKDSTYSLS STLTLSKADY  660
EKHKVYACEV THQGLSSPVT KSFNRGECGG SSGSGSGSTG TSSSGTGTSA GTTGTSASTS  720
GSGSGGGGS GGGGSAGGTA TAGASSGSQV QLVQSGVEVK KPGASVKVSC KASGYTFTNY  780
YMYWVRQAPG QGLEWMGGIN PSQGGTNFNE KFKNRVTLTT DSSTTTAYME LKSLQFDDTA  840
VYYCARRDYR FDLGFDYWGQ GTTVTVSSAS TKGPSVFPLA PSSKSTSGGT AALGCLVKDY  900
FPEPVTVSWN SGALTSGVHT FPAVLQSSGL YSLSSVVTVP SSSLGTQTYI CNVNHKPSNT  960
KVDKKVEPKS CDKTHT                                                  976

SEQ ID NO: 671          moltype = AA   length = 976
FEATURE                 Location/Qualifiers
source                  1..976
                        mol_type = protein
                        organism = synthetic construct
SEQUENCE: 671
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
```

```
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGSGGGGS GGGGSGGGGS EIVLTQSPAT  480
LSLSPGERAT LSCRASKGVS TSGYSYLHWY QQKPGQAPRL LIYLASYLES GVPARFSGSG  540
SGTDFTLTIS SLEPEDFAVY YCQHSRDLPL TFGGGTKVEI KRTVAAPSVF IFPPSDEQLK  600
SGTASVVCLL NNFYPREAKV QWKVDNALQS GNSQESVTEQ DSKDSTYSLS STLTLSKADY  660
EKHKVYACEV THQGLSSPVT KSFNRGECGG SSGSGSGSTG TSSSGTGTSA GTTGTSASTS  720
GSGSGGGGGS GGGGSAGGTA TAGASSGSQV QLVQSGVEVK KPGASVKVSC KASGYTFTNY  780
YMYWVRQAPG QGLEWMGGIN PSRGGTNFNE KFKNRVTLTT DSSTTTAYME LKSLQFDDTA  840
VYYCARRDYR FDLGFDYWGQ GTTVTVSSAS TKGPSVFPLA PSSKSTSGGT AALGCLVKDY  900
FPEPVTVSWN SGALTSGVHT FPAVLQSSGL YSLSSVVTVP SSSLGTQTYI CNVNHKPSNT  960
KVDKKVEPKS CDKTHT                                                  976
```

SEQ ID NO: 672    moltype = AA  length = 976
FEATURE           Location/Qualifiers
source            1..976
                  mol_type = protein
                  organism = synthetic construct
SEQUENCE: 672

```
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGSGGGGS GGGGSGGGGS EIVLTQSPAT  480
LSLSPGERAT LSCRASKGVS TSGYSYLHWY QQKPGQAPRL LIYLASYLES GVPARFSGSG  540
SGTDFTLTIS SLEPEDFAVY YCQHSRDLPL TFGGGTKVEI KRTVAAPSVF IFPPSDEQLK  600
SGTASVVCLL NNFYPREAKV QWKVDNALQS GNSQESVTEQ DSKDSTYSLS STLTLSKADY  660
EKHKVYACEV THQGLSSPVT KSFNRGECGG SSGSGSGSTG TSSSGTGTSA GTTGTSASTS  720
GSGSGGGGGS GGGGSAGGTA TAGASSGSQV QLVQSGVEVK KPGASVKVSC KASGYTFTNY  780
YMYWVRQAPG QGLEWMGGIN PSRGGTNFNE KFKNRVTLTT DSSTTTAYME LKSLQFDDTA  840
VYYCARRDYR FDLGFDYWGQ GTTVTVSSAS TKGPSVFPLA PSSKSTSGGT AALGCLVKDY  900
FPEPVTVSWN SGALTSGVHT FPAVLQSSGL YSLSSVVTVP SSSLGTQTYI CNVNHKPSNT  960
KVDKKVEPKS CDKTHT                                                  976
```

SEQ ID NO: 673    moltype = AA  length = 976
FEATURE           Location/Qualifiers
source            1..976
                  mol_type = protein
                  organism = synthetic construct
SEQUENCE: 673

```
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGSGGGGS GGGGSGGGGS DIQLTQSPSS  480
LSASVGDRVT ITCRASKGVS TSGYSYLHWY QQKPGKAPKL LIYLASYLES GVPSRFSGSG  540
SGTDFTLTIS SLQPEDFATY YCQHSRDLPL TFGGGTKVEI KRTVAAPSVF IFPPSDEQLK  600
SGTASVVCLL NNFYPREAKV QWKVDNALQS GNSQESVTEQ DSKDSTYSLS STLTLSKADY  660
EKHKVYACEV THQGLSSPVT KSFNRGECGG SSGSGSGSTG TSSSGTGTSA GTTGTSASTS  720
GSGSGGGGGS GGGGSAGGTA TAGASSGSEV QLVQSGAEVK KPGASVKVSC KASGYTFTNY  780
YMYWVRQAPG QGLEWMGGIN PSNGGTNFNE KFKNRVTLTT DSSTSTAYME LSSLRSEDTA  840
VYYCARRDYR FDMGFDYWGQ GTTVTVSSAS TKGPSVFPLA PSSKSTSGGT AALGCLVKDY  900
FPEPVTVSWN SGALTSGVHT FPAVLQSSGL YSLSSVVTVP SSSLGTQTYI CNVNHKPSNT  960
KVDKKVEPKS CDKTHT                                                  976
```

SEQ ID NO: 674    moltype = AA  length = 976
FEATURE           Location/Qualifiers
source            1..976
                  mol_type = protein
                  organism = synthetic construct
SEQUENCE: 674

```
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGSGGGGS GGGGSGGGGS DIQLTQSPSS  480
LSASVGDRVT ITCRASKGVS TSGYSYLHWY QQKPGKAPKL LIYLASYLES GVPSRFSGSG  540
SGTDFTLTIS SLQPEDFATY YCQHSRDLPL TFGGGTKVEI KRTVAAPSVF IFPPSDEQLK  600
```

```
SGTASVVCLL NNFYPREAKV QWKVDNALQS GNSQESVTEQ DSKDSTYSLS STLTLSKADY   660
EKHKVYACEV THQGLSSPVT KSFNRGECGG SSGSGSGSTG TSSSGTGTSA GTTGTSASTS   720
GSGSGGGGGS GGGGSAGGTA TAGASSGSEV QLVQSGAEVK KPGASVKVSC KASGYTFTNY   780
YMYWVRQAPG QGLEWMGGIN PSNGGTNFNE KFKNRVTLTT DSSTSTAYME LSSLRSEDTA   840
VYYCARRDYR FDMGFDYWGQ GTTVTVSSAS TKGPSVFPLA PSSKSTSGGT AALGCLVKDY   900
FPEPVTVSWN SGALTSGVHT FPAVLQSSGL YSLSSVVTVP SSSLGTQTYI CNVNHKPSNT   960
KVDKKVEPKS CDKTHT                                                   976

SEQ ID NO: 675            moltype = AA  length = 976
FEATURE                   Location/Qualifiers
source                    1..976
                          mol_type = protein
                          organism = synthetic construct
SEQUENCE: 675
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGGGSGGGGS GGGGSGGGGS DIQLTQSPSS   480
LSASVGDRVT ITCRASKGVS TSGYSYLHWY QQKPGKAPKL LIYLASYLES GVPSRFSGSG   540
SGTDFTLTIS SLQPEDFATY YCQHSRDLPL TFGGGTKVEI KRTVAAPSVF IFPPSDEQLK   600
SGTASVVCLL NNFYPREAKV QWKVDNALQS GNSQESVTEQ DSKDSTYSLS STLTLSKADY   660
EKHKVYACEV THQGLSSPVT KSFNRGECGG SSGSGSGSTG TSSSGTGTSA GTTGTSASTS   720
GSGSGGGGGS GGGGSAGGTA TAGASSGSEV QLVQSGAEVK KPGASVKVSC KASGYTFTNY   780
YMYWVRQAPG QGLEWMGGIN PSQGGTNFNE KFKNRVTLTT DSSTSTAYME LSSLRSEDTA   840
VYYCARRDYR FDLGFDYWGQ GTTVTVSSAS TKGPSVFPLA PSSKSTSGGT AALGCLVKDY   900
FPEPVTVSWN SGALTSGVHT FPAVLQSSGL YSLSSVVTVP SSSLGTQTYI CNVNHKPSNT   960
KVDKKVEPKS CDKTHT                                                   976

SEQ ID NO: 676            moltype = AA  length = 976
FEATURE                   Location/Qualifiers
source                    1..976
                          mol_type = protein
                          organism = synthetic construct
SEQUENCE: 676
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGGGSGGGGS GGGGSGGGGS DIQLTQSPSS   480
LSASVGDRVT ITCRASKGVS TSGYSYLHWY QQKPGKAPKL LIYLASYLES GVPSRFSGSG   540
SGTDFTLTIS SLQPEDFATY YCQHSRDLPL TFGGGTKVEI KRTVAAPSVF IFPPSDEQLK   600
SGTASVVCLL NNFYPREAKV QWKVDNALQS GNSQESVTEQ DSKDSTYSLS STLTLSKADY   660
EKHKVYACEV THQGLSSPVT KSFNRGECGG SSGSGSGSTG TSSSGTGTSA GTTGTSASTS   720
GSGSGGGGGS GGGGSAGGTA TAGASSGSEV QLVQSGAEVK KPGASVKVSC KASGYTFTNY   780
YMYWVRQAPG QGLEWMGGIN PSQGGTNFNE KFKNRVTLTT DSSTSTAYME LSSLRSEDTA   840
VYYCARRDYR FDLGFDYWGQ GTTVTVSSAS TKGPSVFPLA PSSKSTSGGT AALGCLVKDY   900
FPEPVTVSWN SGALTSGVHT FPAVLQSSGL YSLSSVVTVP SSSLGTQTYI CNVNHKPSNT   960
KVDKKVEPKS CDKTHT                                                   976

SEQ ID NO: 677            moltype = AA  length = 976
FEATURE                   Location/Qualifiers
source                    1..976
                          mol_type = protein
                          organism = synthetic construct
SEQUENCE: 677
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGGGSGGGGS GGGGSGGGGS DIQLTQSPSS   480
LSASVGDRVT ITCRASKGVS TSGYSYLHWY QQKPGKAPKL LIYLASYLES GVPSRFSGSG   540
SGTDFTLTIS SLQPEDFATY YCQHSRDLPL TFGGGTKVEI KRTVAAPSVF IFPPSDEQLK   600
SGTASVVCLL NNFYPREAKV QWKVDNALQS GNSQESVTEQ DSKDSTYSLS STLTLSKADY   660
EKHKVYACEV THQGLSSPVT KSFNRGECGG SSGSGSGSTG TSSSGTGTSA GTTGTSASTS   720
GSGSGGGGGS GGGGSAGGTA TAGASSGSEV QLVQSGAEVK KPGASVKVSC KASGYTFTNY   780
YMYWVRQAPG QGLEWMGGIN PSRGGTNFNE KFKNRVTLTT DSSTSTAYME LSSLRSEDTA   840
VYYCARRDYR FDLGFDYWGQ GTTVTVSSAS TKGPSVFPLA PSSKSTSGGT AALGCLVKDY   900
FPEPVTVSWN SGALTSGVHT FPAVLQSSGL YSLSSVVTVP SSSLGTQTYI CNVNHKPSNT   960
KVDKKVEPKS CDKTHT                                                   976
```

```
SEQ ID NO: 678            moltype = AA   length = 976
FEATURE                   Location/Qualifiers
source                    1..976
                          mol_type = protein
                          organism = synthetic construct
SEQUENCE: 678
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGSGGGGS GGGGSGGGGS DIQLTQSPSS  480
LSASVGDRVT ITCRASKGVS TSGYSYLHWY QQKPGKAPKL LIYLASYLES GVPSRFSGSG  540
SGTDFTLTIS SLQPEDFATY YCQHSRDLPL TFGGGTKVEI KRTVAAPSVF IFPPSDEQLK  600
SGTASVVCLL NNFYPREAKV QWKVDNALQS GNSQESVTEQ DSKDSTYSLS STLTLSKADY  660
EKHKVYACEV THQGLSSPVT KSFNRGECGG SSGSGSGSTG TSSSGTGTSA GTTGTSASTS  720
GSGSGGGGGS GGGGSAGGTA TAGASSGSEV QLVQSGAEVK KPGASVKVSC KASGYTFTNY  780
YMYWVRQAPG QGLEWMGGIN PSRGGTNFNE KFKNRVTLTT DSSTSTAYME LSSLRSEDTA  840
VYYCARRDYR FDLGFDYWGQ GTTVTVSSAS TKGPSVFPLA PSSKSTSGGT AALGCLVKDY  900
FPEPVTVSWN SGALTSGVHT FPAVLQSSGL YSLSSVVTVP SSSLGTQTYI CNVNHKPSNT  960
KVDKKVEPKS CDKTHT                                                 976

SEQ ID NO: 679            moltype = AA   length = 214
FEATURE                   Location/Qualifiers
source                    1..214
                          mol_type = protein
                          organism = synthetic construct
SEQUENCE: 679
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 680            moltype = AA   length = 214
FEATURE                   Location/Qualifiers
source                    1..214
                          mol_type = protein
                          organism = synthetic construct
SEQUENCE: 680
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 681            moltype = AA   length = 214
FEATURE                   Location/Qualifiers
source                    1..214
                          mol_type = protein
                          organism = synthetic construct
SEQUENCE: 681
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 682            moltype = AA   length = 214
FEATURE                   Location/Qualifiers
source                    1..214
                          mol_type = protein
                          organism = synthetic construct
SEQUENCE: 682
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 683            moltype = AA   length = 214
FEATURE                   Location/Qualifiers
source                    1..214
                          mol_type = protein
                          organism = synthetic construct
SEQUENCE: 683
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214
```

-continued

```
SEQ ID NO: 684              moltype = AA  length = 214
FEATURE                     Location/Qualifiers
source                      1..214
                            mol_type = protein
                            organism = synthetic construct
SEQUENCE: 684
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 685              moltype = AA  length = 214
FEATURE                     Location/Qualifiers
source                      1..214
                            mol_type = protein
                            organism = synthetic construct
SEQUENCE: 685
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 686              moltype = AA  length = 214
FEATURE                     Location/Qualifiers
source                      1..214
                            mol_type = protein
                            organism = synthetic construct
SEQUENCE: 686
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 687              moltype = AA  length = 214
FEATURE                     Location/Qualifiers
source                      1..214
                            mol_type = protein
                            organism = synthetic construct
SEQUENCE: 687
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 688              moltype = AA  length = 214
FEATURE                     Location/Qualifiers
source                      1..214
                            mol_type = protein
                            organism = synthetic construct
SEQUENCE: 688
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 689              moltype = AA  length = 214
FEATURE                     Location/Qualifiers
source                      1..214
                            mol_type = protein
                            organism = synthetic construct
SEQUENCE: 689
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 690              moltype = AA  length = 214
FEATURE                     Location/Qualifiers
source                      1..214
                            mol_type = protein
                            organism = synthetic construct
SEQUENCE: 690
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 691              moltype = AA  length = 214
```

```
FEATURE              Location/Qualifiers
source               1..214
                     mol_type = protein
                     organism = synthetic construct
SEQUENCE: 691
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 692         moltype = AA  length = 214
FEATURE              Location/Qualifiers
source               1..214
                     mol_type = protein
                     organism = synthetic construct
SEQUENCE: 692
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 693         moltype = AA  length = 214
FEATURE              Location/Qualifiers
source               1..214
                     mol_type = protein
                     organism = synthetic construct
SEQUENCE: 693
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 694         moltype = AA  length = 214
FEATURE              Location/Qualifiers
source               1..214
                     mol_type = protein
                     organism = synthetic construct
SEQUENCE: 694
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 695         moltype = AA  length = 214
FEATURE              Location/Qualifiers
source               1..214
                     mol_type = protein
                     organism = synthetic construct
SEQUENCE: 695
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 696         moltype = AA  length = 214
FEATURE              Location/Qualifiers
source               1..214
                     mol_type = protein
                     organism = synthetic construct
SEQUENCE: 696
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 697         moltype = AA  length = 214
FEATURE              Location/Qualifiers
source               1..214
                     mol_type = protein
                     organism = synthetic construct
SEQUENCE: 697
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 698         moltype = AA  length = 214
FEATURE              Location/Qualifiers
source               1..214
```

-continued

```
                              mol_type = protein
                              organism = synthetic construct
SEQUENCE: 698
DIQMTQSPSS LSASVGDRVT ITCSASQDIS NYLNWYQQKP GKAPKVLIYF TSSLHSGVPS      60
RFSGSGSGTD FTLTISSLQP EDFATYYCQQ YSTVPWTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 699          moltype = AA   length = 214
FEATURE                 Location/Qualifiers
source                  1..214
                        mol_type = protein
                        organism = synthetic construct
SEQUENCE: 699
DIQMTQSPSS LSASVGDRVT ITCSASQDIS NYLNWYQQKP GKAPKVLIYF TSSLHSGVPS      60
RFSGSGSGTD FTLTISSLQP EDFATYYCQQ YSTVPWTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 700          moltype = AA   length = 214
FEATURE                 Location/Qualifiers
source                  1..214
                        mol_type = protein
                        organism = synthetic construct
SEQUENCE: 700
DIQMTQSPSS LSASVGDRVT ITCSASQDIS NYLNWYQQKP GKAPKVLIYF TSSLHSGVPS      60
RFSGSGSGTD FTLTISSLQP EDFATYYCQQ YSTVPWTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 701          moltype = AA   length = 214
FEATURE                 Location/Qualifiers
source                  1..214
                        mol_type = protein
                        organism = synthetic construct
SEQUENCE: 701
DIQMTQSPSS LSASVGDRVT ITCSASQDIS NYLNWYQQKP GKAPKVLIYF TSSLHSGVPS      60
RFSGSGSGTD FTLTISSLQP EDFATYYCQQ YSTVPWTFGQ GTKVEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 702          moltype = AA   length = 697
FEATURE                 Location/Qualifiers
source                  1..697
                        mol_type = protein
                        organism = synthetic construct
SEQUENCE: 702
EVQLVESGGG LVQPGGSLRL SCAASGYTFT NYGMNWVRQA PGKGLEWVGW INTYTGEPTY      60
AADFKRRFTF SLDTSKSTAY LQMNSLRAED TAVYYCAKYP HYYGSSHWYF DVWGQGTLVT     120
VSSASTKGPS VFPLAPSSKS TSGGTAALGC LVKDYFPEPV TVSWNSGALT SGVHTFPAVL     180
QSSGLYSLSS VVTVPSSSLG TQTYICNVNH KPSNTKVDKK VEPKSCDKTH TCPPCPAPEA     240
AGGPSVFLFP PKPKDTLMIS RTPEVTCVVV DVSHEDPEVK FNWYVDGVEV HNAKTKPREE     300
QYNSTYRVVS VLTVLHQDWL NGKEYKCKVS NKALPAPIEK TISKAKGQPR EPQVYTLPPS     360
RDELTKNQVS LTCLVKGFYP SDIAVEWESN GQPENNYKTT PPVLDSDGSF FLYSKLTVDK     420
SRWQQGNVFS CSVMHEALHN HYTQKSLSLS PGGGSGGGGS GGGGSGGGGS QVQLVQSGVE     480
VKKPGASVKV SCKASGYTFT NYYMYWVRQA PGQGLEWMGG INPSNGGTNF NEKFKNRVTL     540
TTDSSTTTAY MELKSLQFDD TAVYYCARRD YRFDMGFDYW GQGTTVTVSS ASVAAPSVFI     600
FPPSDEQLKS GTASVVCLLN NFYPREAKVQ WKVDNALQSG NSQESVTEQD SKDSTYSLSS     660
TLTLSKADYE KHKVYACEVT HQGLSSPVTK SFNRGEC                             697

SEQ ID NO: 703          moltype = AA   length = 697
FEATURE                 Location/Qualifiers
source                  1..697
                        mol_type = protein
                        organism = synthetic construct
SEQUENCE: 703
EVQLVESGGG LVQPGGSLRL SCAASGYTFT NYGMNWVRQA PGKGLEWVGW INTYTGEPTY      60
AADFKRRFTF SLDTSKSTAY LQMNSLRAED TAVYYCAKYP HYYGSSHWYF DVWGQGTLVT     120
VSSASTKGPS VFPLAPSSKS TSGGTAALGC LVKDYFPEPV TVSWNSGALT SGVHTFPAVL     180
QSSGLYSLSS VVTVPSSSLG TQTYICNVNH KPSNTKVDKK VEPKSCDKTH TCPPCPAPEA     240
AGGPSVFLFP PKPKDTLYIT REPEVTCVVV DVSHEDPEVK FNWYVDGVEV HNAKTKPREE     300
QYNSTYRVVS VLTVLHQDWL NGKEYKCKVS NKALPAPIEK TISKAKGQPR EPQVYTLPPS     360
RDELTKNQVS LTCLVKGFYP SDIAVEWESN GQPENNYKTT PPVLDSDGSF FLYSKLTVDK     420
SRWQQGNVFS CSVMHEALHN HYTQKSLSLS PGGGSGGGGS GGGGSGGGGS QVQLVQSGVE     480
VKKPGASVKV SCKASGYTFT NYYMYWVRQA PGQGLEWMGG INPSNGGTNF NEKFKNRVTL     540
TTDSSTTTAY MELKSLQFDD TAVYYCARRD YRFDMGFDYW GQGTTVTVSS ASVAAPSVFI     600
FPPSDEQLKS GTASVVCLLN NFYPREAKVQ WKVDNALQSG NSQESVTEQD SKDSTYSLSS     660
TLTLSKADYE KHKVYACEVT HQGLSSPVTK SFNRGEC                             697
```

-continued

```
SEQ ID NO: 704            moltype = AA   length = 697
FEATURE                   Location/Qualifiers
source                    1..697
                          mol_type = protein
                          organism = synthetic construct
SEQUENCE: 704
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGGGSGGGGS GGGGSGGGGS QVQLVQSGVE   480
VKKPGASVKV SCKASGYTFT NYYMWVRQA PGQGLEWMGG INPSQGGTNF NEKFKNRVTL   540
TTDSSTTTAY MELKSLQFDD TAVYYCARRD YRFDLGFDYW GQGTTVTVSS ASVAAPSVFI   600
FPPSDEQLKS GTASVVCLLN NFYPREAKVQ WKVDNALQSG NSQESVTEQD SKDSTYSLSS   660
TLTLSKADYE KHKVYACEVT HQGLSSPVTK SFNRGEC                           697

SEQ ID NO: 705            moltype = AA   length = 697
FEATURE                   Location/Qualifiers
source                    1..697
                          mol_type = protein
                          organism = synthetic construct
SEQUENCE: 705
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGGGSGGGGS GGGGSGGGGS QVQLVQSGVE   480
VKKPGASVKV SCKASGYTFT NYYMWVRQA PGQGLEWMGG INPSQGGTNF NEKFKNRVTL   540
TTDSSTTTAY MELKSLQFDD TAVYYCARRD YRFDLGFDYW GQGTTVTVSS ASVAAPSVFI   600
FPPSDEQLKS GTASVVCLLN NFYPREAKVQ WKVDNALQSG NSQESVTEQD SKDSTYSLSS   660
TLTLSKADYE KHKVYACEVT HQGLSSPVTK SFNRGEC                           697

SEQ ID NO: 706            moltype = AA   length = 697
FEATURE                   Location/Qualifiers
source                    1..697
                          mol_type = protein
                          organism = synthetic construct
SEQUENCE: 706
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGGGSGGGGS GGGGSGGGGS QVQLVQSGVE   480
VKKPGASVKV SCKASGYTFT NYYMWVRQA PGQGLEWMGG INPSRGGTNF NEKFKNRVTL   540
TTDSSTTTAY MELKSLQFDD TAVYYCARRD YRFDLGFDYW GQGTTVTVSS ASVAAPSVFI   600
FPPSDEQLKS GTASVVCLLN NFYPREAKVQ WKVDNALQSG NSQESVTEQD SKDSTYSLSS   660
TLTLSKADYE KHKVYACEVT HQGLSSPVTK SFNRGEC                           697

SEQ ID NO: 707            moltype = AA   length = 697
FEATURE                   Location/Qualifiers
source                    1..697
                          mol_type = protein
                          organism = synthetic construct
SEQUENCE: 707
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGGGSGGGGS GGGGSGGGGS QVQLVQSGVE   480
VKKPGASVKV SCKASGYTFT NYYMWVRQA PGQGLEWMGG INPSRGGTNF NEKFKNRVTL   540
TTDSSTTTAY MELKSLQFDD TAVYYCARRD YRFDLGFDYW GQGTTVTVSS ASVAAPSVFI   600
FPPSDEQLKS GTASVVCLLN NFYPREAKVQ WKVDNALQSG NSQESVTEQD SKDSTYSLSS   660
TLTLSKADYE KHKVYACEVT HQGLSSPVTK SFNRGEC                           697

SEQ ID NO: 708            moltype = AA   length = 697
FEATURE                   Location/Qualifiers
source                    1..697
```

-continued

```
                              mol_type = protein
                              organism = synthetic construct
SEQUENCE: 708
EVQLVESGGG LVQPGGSLRL SCAASGYTFT NYGMNWVRQA PGKGLEWVGW INTYTGEPTY     60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGGGSGGGGS GGGGSGGGGS EVQLVQSGAE    480
VKKPGASVKV SCKASGYTFT NYYMYWVRQA PGQGLEWMGG INPSNGGTNF NEKFKNRVTL    540
TTDSSTSTAY MELSSLRSED TAVYYCARRD YRFDMGFDYW GQGTTVTVSS ASVAAPSVFI    600
FPPSDEQLKS GTASVVCLLN NFYPREAKVQ WKVDNALQSG NSQESVTEQD SKDSTYSLSS    660
TLTLSKADYE KHKVYACEVT HQGLSSPVTK SFNRGEC                            697

SEQ ID NO: 709            moltype = AA  length = 697
FEATURE                   Location/Qualifiers
source                    1..697
                          mol_type = protein
                          organism = synthetic construct
SEQUENCE: 709
EVQLVESGGG LVQPGGSLRL SCAASGYTFT NYGMNWVRQA PGKGLEWVGW INTYTGEPTY     60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLYIT REPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGGGSGGGGS GGGGSGGGGS EVQLVQSGAE    480
VKKPGASVKV SCKASGYTFT NYYMYWVRQA PGQGLEWMGG INPSNGGTNF NEKFKNRVTL    540
TTDSSTSTAY MELSSLRSED TAVYYCARRD YRFDMGFDYW GQGTTVTVSS ASVAAPSVFI    600
FPPSDEQLKS GTASVVCLLN NFYPREAKVQ WKVDNALQSG NSQESVTEQD SKDSTYSLSS    660
TLTLSKADYE KHKVYACEVT HQGLSSPVTK SFNRGEC                            697

SEQ ID NO: 710            moltype = AA  length = 697
FEATURE                   Location/Qualifiers
source                    1..697
                          mol_type = protein
                          organism = synthetic construct
SEQUENCE: 710
EVQLVESGGG LVQPGGSLRL SCAASGYTFT NYGMNWVRQA PGKGLEWVGW INTYTGEPTY     60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGGGSGGGGS GGGGSGGGGS EVQLVQSGAE    480
VKKPGASVKV SCKASGYTFT NYYMYWVRQA PGQGLEWMGG INPSQGGTNF NEKFKNRVTL    540
TTDSSTSTAY MELSSLRSED TAVYYCARRD YRFDLGFDYW GQGTTVTVSS ASVAAPSVFI    600
FPPSDEQLKS GTASVVCLLN NFYPREAKVQ WKVDNALQSG NSQESVTEQD SKDSTYSLSS    660
TLTLSKADYE KHKVYACEVT HQGLSSPVTK SFNRGEC                            697

SEQ ID NO: 711            moltype = AA  length = 697
FEATURE                   Location/Qualifiers
source                    1..697
                          mol_type = protein
                          organism = synthetic construct
SEQUENCE: 711
EVQLVESGGG LVQPGGSLRL SCAASGYTFT NYGMNWVRQA PGKGLEWVGW INTYTGEPTY     60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLYIT REPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGGGSGGGGS GGGGSGGGGS EVQLVQSGAE    480
VKKPGASVKV SCKASGYTFT NYYMYWVRQA PGQGLEWMGG INPSQGGTNF NEKFKNRVTL    540
TTDSSTSTAY MELSSLRSED TAVYYCARRD YRFDLGFDYW GQGTTVTVSS ASVAAPSVFI    600
FPPSDEQLKS GTASVVCLLN NFYPREAKVQ WKVDNALQSG NSQESVTEQD SKDSTYSLSS    660
TLTLSKADYE KHKVYACEVT HQGLSSPVTK SFNRGEC                            697

SEQ ID NO: 712            moltype = AA  length = 697
FEATURE                   Location/Qualifiers
source                    1..697
                          mol_type = protein
                          organism = synthetic construct
SEQUENCE: 712
```

```
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGSGGGGS GGGGSGGGGS EVQLVQSGAE  480
VKKPGASVKV SCKASGYTFT NYYMYWVRQA PGQGLEWMGG INPSRGGTNF NEKFKNRVTL  540
TTDSSTSTAY MELSSLRSED TAVYYCARRD YRFDLGFDYW GQGTTVTVSS ASVAAPSVFI  600
FPPSDEQLKS GTASVVCLLN NFYPREAKVQ WKVDNALQSG NSQESVTEQD SKDSTYSLSS  660
TLTLSKADYE KHKVYACEVT HQGLSSPVTK SFNRGEC                          697
```

SEQ ID NO: 713        moltype = AA   length = 697
FEATURE               Location/Qualifiers
source                1..697
                      mol_type = protein
                      organism = synthetic construct
SEQUENCE: 713

```
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLYIT REPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGSGGGGS GGGGSGGGGS EVQLVQSGAE  480
VKKPGASVKV SCKASGYTFT NYYMYWVRQA PGQGLEWMGG INPSRGGTNF NEKFKNRVTL  540
TTDSSTSTAY MELSSLRSED TAVYYCARRD YRFDLGFDYW GQGTTVTVSS ASVAAPSVFI  600
FPPSDEQLKS GTASVVCLLN NFYPREAKVQ WKVDNALQSG NSQESVTEQD SKDSTYSLSS  660
TLTLSKADYE KHKVYACEVT HQGLSSPVTK SFNRGEC                          697
```

SEQ ID NO: 714        moltype = AA   length = 214
FEATURE               Location/Qualifiers
source                1..214
                      mol_type = protein
                      organism = synthetic construct
SEQUENCE: 714

```
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214
```

SEQ ID NO: 715        moltype = AA   length = 214
FEATURE               Location/Qualifiers
source                1..214
                      mol_type = protein
                      organism = synthetic construct
SEQUENCE: 715

```
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214
```

SEQ ID NO: 716        moltype = AA   length = 214
FEATURE               Location/Qualifiers
source                1..214
                      mol_type = protein
                      organism = synthetic construct
SEQUENCE: 716

```
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214
```

SEQ ID NO: 717        moltype = AA   length = 214
FEATURE               Location/Qualifiers
source                1..214
                      mol_type = protein
                      organism = synthetic construct
SEQUENCE: 717

```
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214
```

SEQ ID NO: 718        moltype = AA   length = 214
FEATURE               Location/Qualifiers
source                1..214

-continued

```
                          mol_type = protein
                          organism = synthetic construct
SEQUENCE: 718
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 719          moltype = AA  length = 214
FEATURE                 Location/Qualifiers
source                  1..214
                        mol_type = protein
                        organism = synthetic construct
SEQUENCE: 719
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 720          moltype = AA  length = 214
FEATURE                 Location/Qualifiers
source                  1..214
                        mol_type = protein
                        organism = synthetic construct
SEQUENCE: 720
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 721          moltype = AA  length = 214
FEATURE                 Location/Qualifiers
source                  1..214
                        mol_type = protein
                        organism = synthetic construct
SEQUENCE: 721
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 722          moltype = AA  length = 214
FEATURE                 Location/Qualifiers
source                  1..214
                        mol_type = protein
                        organism = synthetic construct
SEQUENCE: 722
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 723          moltype = AA  length = 214
FEATURE                 Location/Qualifiers
source                  1..214
                        mol_type = protein
                        organism = synthetic construct
SEQUENCE: 723
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 724          moltype = AA  length = 214
FEATURE                 Location/Qualifiers
source                  1..214
                        mol_type = protein
                        organism = synthetic construct
SEQUENCE: 724
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 725          moltype = AA  length = 214
FEATURE                 Location/Qualifiers
source                  1..214
                        mol_type = protein
                        organism = synthetic construct
```

```
SEQUENCE: 725
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 726           moltype = AA   length = 216
FEATURE                  Location/Qualifiers
source                   1..216
                         mol_type = protein
                         organism = synthetic construct
SEQUENCE: 726
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KSSASTKGPS   120
VFPLAPSSKS TSGGTAALGC LVKDYFPEPV TVSWNSGALT SGVHTFPAVL QSSGLYSLSS   180
VVTVPSSSLG TQTYICNVNH KPSNTKVDKK VEPKSC                             216

SEQ ID NO: 727           moltype = AA   length = 216
FEATURE                  Location/Qualifiers
source                   1..216
                         mol_type = protein
                         organism = synthetic construct
SEQUENCE: 727
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KSSASTKGPS   120
VFPLAPSSKS TSGGTAALGC LVKDYFPEPV TVSWNSGALT SGVHTFPAVL QSSGLYSLSS   180
VVTVPSSSLG TQTYICNVNH KPSNTKVDKK VEPKSC                             216

SEQ ID NO: 728           moltype = AA   length = 216
FEATURE                  Location/Qualifiers
source                   1..216
                         mol_type = protein
                         organism = synthetic construct
SEQUENCE: 728
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KSSASTKGPS   120
VFPLAPSSKS TSGGTAALGC LVKDYFPEPV TVSWNSGALT SGVHTFPAVL QSSGLYSLSS   180
VVTVPSSSLG TQTYICNVNH KPSNTKVDKK VEPKSC                             216

SEQ ID NO: 729           moltype = AA   length = 216
FEATURE                  Location/Qualifiers
source                   1..216
                         mol_type = protein
                         organism = synthetic construct
SEQUENCE: 729
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KSSASTKGPS   120
VFPLAPSSKS TSGGTAALGC LVKDYFPEPV TVSWNSGALT SGVHTFPAVL QSSGLYSLSS   180
VVTVPSSSLG TQTYICNVNH KPSNTKVDKK VEPKSC                             216

SEQ ID NO: 730           moltype = AA   length = 216
FEATURE                  Location/Qualifiers
source                   1..216
                         mol_type = protein
                         organism = synthetic construct
SEQUENCE: 730
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KSSASTKGPS   120
VFPLAPSSKS TSGGTAALGC LVKDYFPEPV TVSWNSGALT SGVHTFPAVL QSSGLYSLSS   180
VVTVPSSSLG TQTYICNVNH KPSNTKVDKK VEPKSC                             216

SEQ ID NO: 731           moltype = AA   length = 216
FEATURE                  Location/Qualifiers
source                   1..216
                         mol_type = protein
                         organism = synthetic construct
SEQUENCE: 731
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KSSASTKGPS   120
VFPLAPSSKS TSGGTAALGC LVKDYFPEPV TVSWNSGALT SGVHTFPAVL QSSGLYSLSS   180
VVTVPSSSLG TQTYICNVNH KPSNTKVDKK VEPKSC                             216

SEQ ID NO: 732           moltype = AA   length = 216
FEATURE                  Location/Qualifiers
source                   1..216
                         mol_type = protein
                         organism = synthetic construct
SEQUENCE: 732
DIQLTQSPSS LSASVGDRVT ITCRASKGVS TSGYSYLHWY QQKPGKAPKL LIYLASYLES    60
```

-continued

```
GVPSRFSGSG SGTDFTLTIS SLQPEDFATY YCQHSRDLPL TFGGGTKVEI KSSASTKGPS    120
VFPLAPSSKS TSGGTAALGC LVKDYFPEPV TVSWNSGALT SGVHTFPAVL QSSGLYSLSS    180
VVTVPSSSLG TQTYICNVNH KPSNTKVDKK VEPKSC                              216

SEQ ID NO: 733          moltype = AA   length = 216
FEATURE                 Location/Qualifiers
source                  1..216
                        mol_type = protein
                        organism = synthetic construct
SEQUENCE: 733
DIQLTQSPSS LSASVGDRVT ITCRASKGVS TSGYSYLHWY QQKPGKAPKL LIYLASYLES    60
GVPSRFSGSG SGTDFTLTIS SLQPEDFATY YCQHSRDLPL TFGGGTKVEI KSSASTKGPS    120
VFPLAPSSKS TSGGTAALGC LVKDYFPEPV TVSWNSGALT SGVHTFPAVL QSSGLYSLSS    180
VVTVPSSSLG TQTYICNVNH KPSNTKVDKK VEPKSC                              216

SEQ ID NO: 734          moltype = AA   length = 216
FEATURE                 Location/Qualifiers
source                  1..216
                        mol_type = protein
                        organism = synthetic construct
SEQUENCE: 734
DIQLTQSPSS LSASVGDRVT ITCRASKGVS TSGYSYLHWY QQKPGKAPKL LIYLASYLES    60
GVPSRFSGSG SGTDFTLTIS SLQPEDFATY YCQHSRDLPL TFGGGTKVEI KSSASTKGPS    120
VFPLAPSSKS TSGGTAALGC LVKDYFPEPV TVSWNSGALT SGVHTFPAVL QSSGLYSLSS    180
VVTVPSSSLG TQTYICNVNH KPSNTKVDKK VEPKSC                              216

SEQ ID NO: 735          moltype = AA   length = 216
FEATURE                 Location/Qualifiers
source                  1..216
                        mol_type = protein
                        organism = synthetic construct
SEQUENCE: 735
DIQLTQSPSS LSASVGDRVT ITCRASKGVS TSGYSYLHWY QQKPGKAPKL LIYLASYLES    60
GVPSRFSGSG SGTDFTLTIS SLQPEDFATY YCQHSRDLPL TFGGGTKVEI KSSASTKGPS    120
VFPLAPSSKS TSGGTAALGC LVKDYFPEPV TVSWNSGALT SGVHTFPAVL QSSGLYSLSS    180
VVTVPSSSLG TQTYICNVNH KPSNTKVDKK VEPKSC                              216

SEQ ID NO: 736          moltype = AA   length = 216
FEATURE                 Location/Qualifiers
source                  1..216
                        mol_type = protein
                        organism = synthetic construct
SEQUENCE: 736
DIQLTQSPSS LSASVGDRVT ITCRASKGVS TSGYSYLHWY QQKPGKAPKL LIYLASYLES    60
GVPSRFSGSG SGTDFTLTIS SLQPEDFATY YCQHSRDLPL TFGGGTKVEI KSSASTKGPS    120
VFPLAPSSKS TSGGTAALGC LVKDYFPEPV TVSWNSGALT SGVHTFPAVL QSSGLYSLSS    180
VVTVPSSSLG TQTYICNVNH KPSNTKVDKK VEPKSC                              216

SEQ ID NO: 737          moltype = AA   length = 216
FEATURE                 Location/Qualifiers
source                  1..216
                        mol_type = protein
                        organism = synthetic construct
SEQUENCE: 737
DIQLTQSPSS LSASVGDRVT ITCRASKGVS TSGYSYLHWY QQKPGKAPKL LIYLASYLES    60
GVPSRFSGSG SGTDFTLTIS SLQPEDFATY YCQHSRDLPL TFGGGTKVEI KSSASTKGPS    120
VFPLAPSSKS TSGGTAALGC LVKDYFPEPV TVSWNSGALT SGVHTFPAVL QSSGLYSLSS    180
VVTVPSSSLG TQTYICNVNH KPSNTKVDKK VEPKSC                              216

SEQ ID NO: 738          moltype = AA   length = 119
FEATURE                 Location/Qualifiers
source                  1..119
                        mol_type = protein
                        organism = synthetic construct
SEQUENCE: 738
EVQLVESGGG LVQPGGSLRL SCAASGSIAS IHAMGWVRQA PGKEREFVAV ITWSGGITYY    60
ADSVKGRFTI SRDNSKNTVY LQMNSLRPED TAVYYCAGDK HQSSWYDYWG QGTLVTVSS    119

SEQ ID NO: 739          moltype = AA   length = 119
FEATURE                 Location/Qualifiers
source                  1..119
                        mol_type = protein
                        organism = synthetic construct
SEQUENCE: 739
EVQLVESGGG LVQPGGSLRL SCAASGSIAS IHAMGWVRQA PGKEREFVAV ITWSGGITYY    60
ADSVKGRFTI SRDNSKNTVY LQMNSLRPED TALYYCAGDK HQSSWYDYWG QGTLVTVSS    119

SEQ ID NO: 740          moltype = AA   length = 119
FEATURE                 Location/Qualifiers
```

-continued

```
source                1..119
                      mol_type = protein
                      organism = synthetic construct
SEQUENCE: 740
EVQLVESGGG LVQPGGSLRL SCAASGSIAS IHAMGWFRQA PGKEREFVAV ITWSGGITYY   60
ADSVKGRFTI SRDNSKNTVY LQMNSLRPED TAVYYCAGDK HQSSWYDYWG QGTLVTVSS    119

SEQ ID NO: 741        moltype = AA  length = 119
FEATURE               Location/Qualifiers
source                1..119
                      mol_type = protein
                      organism = synthetic construct
SEQUENCE: 741
EVQLVESGGG LVQPGGSLRL SCAASGSIAS IHAMGWFRQA PGKEREFVAV ITWSGGITYY   60
ADSVKGRFTI SRDNSKNTVY LQMNSLRPED TALYYCAGDK HQSSWYDYWG QGTLVTVSS    119

SEQ ID NO: 742        moltype = AA  length = 120
FEATURE               Location/Qualifiers
source                1..120
                      mol_type = protein
                      organism = synthetic construct
SEQUENCE: 742
EVQLVQSGAE VKKPGASVKV SCKASGYTFT NYYMYWVRQA PGQGLEWMGG INPSRGGTNF   60
NEKFKNRVTL TTDSSTSTAY MELSSLRSED TAVYYCARRD YRFDLGFDYW GQGTTVTVSS   120

SEQ ID NO: 743        moltype = AA  length = 111
FEATURE               Location/Qualifiers
source                1..111
                      mol_type = protein
                      organism = synthetic construct
SEQUENCE: 743
DIQLTQSPSS LSASVGDRVT ITCRASKGVS TSGYSYLHWY QQKPGKAPKL LIYLASYLES   60
GVPSRFSGSG SGTDFTLTIS SLQPEDFATY YCQHSRDLPL TFGCGTKVEI K            111

SEQ ID NO: 744        moltype = AA  length = 111
FEATURE               Location/Qualifiers
source                1..111
                      mol_type = protein
                      organism = synthetic construct
SEQUENCE: 744
DIQLTQSPSS LSASVGDRVT ITCRASKGVS TSGYSYLHWY QQKPGKAPKL LIYLASYLES   60
GVPSRFSGSG SGTDFTLTIS SLQPEDFATY YCQHSRDLPL TFGGGTKVEI K            111

SEQ ID NO: 745        moltype = AA  length = 448
FEATURE               Location/Qualifiers
source                1..448
                      mol_type = protein
                      organism = synthetic construct
SEQUENCE: 745
EVQLVESGGG LVQPGGSLRL SCAASGFAFS SYDMSWVRQA PGKGLDWVAT ISGGGRYTYY   60
PDSVKGRFTI SRDNSKNNLY LQMNSLRAED TALYYCANRY GEAWFAYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPEAAGAPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                      448

SEQ ID NO: 746        moltype = AA  length = 214
FEATURE               Location/Qualifiers
source                1..214
                      mol_type = protein
                      organism = synthetic construct
SEQUENCE: 746
DIQMTQSPSS MSASVGDRVT FTCRASQDIN TYLSWFQQKP GKSPKTLIYR ANRLVSGVPS   60
RFSGSGSGQD YTLTISSLQP EDMATYYCLQ YDEFPLTFGA GTKLELKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 747        moltype = AA  length = 498
FEATURE               Location/Qualifiers
source                1..498
                      mol_type = protein
                      organism = synthetic construct
SEQUENCE: 747
EPKSCDKTHT CPPCPAPEAA GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GKGGGGSGGG   240
```

```
GSGGGGSGGG GSEVQLVESG GGLVQPGGSL RLSCAASGFA FSSYDMSWVR QAPGKGLDWV    300
ATISGGGRYT YYPDSVKGRF TISRDNSKNN LYLQMNSLRA EDTALYYCAN RYGEAWFAYW    360
GQGTLVTVSS GGGGSGGGGS GGGGSGGGGS DIQMTQSPSS MSASVGDRVT FTCRASQDIN    420
TYLSWFQQKP GKSPKTLIYR ANRLVSGVPS RFSGSGSGQD YTLTISSLQP EDMATYYCLQ    480
YDEFPLTFGA GTKLELKR                                                  498

SEQ ID NO: 748            moltype = AA   length = 447
FEATURE                   Location/Qualifiers
source                    1..447
                          mol_type = protein
                          organism = synthetic construct
SEQUENCE: 748
QVQLVQSGVE VKKPGASVKV SCKASGYTFT NYYMYWVRQA PGQGLEWMGG INPSNGGTNF     60
NEKFKNRVTL TTDSSTTTAY MELKSLQFDD TAVYYCARRD YRFDMGFDYW GQGTTVTVSS    120
ASTKGPSVFP LAPCSRSTSE STAALGCLVK DYFPEPVTVS WNSGALTSGV HTFPAVLQSS    180
GLYSLSSVVT VPSSSLGTKT YTCNVDHKPS NTKVDKRVES KYGPPCPPCP APEFLGGPSV    240
FLFPPKPKDT LMISRTPEVT CVVVDVSQED PEVQFNWYVD GVEVHNAKTK PREEQFNSTY    300
RVVSVLTVLH QDWLNGKEYK CKVSNKGLPS SIEKTISKAK GQPREPQVYT LPPSQEEMTK    360
NQVSLTCLVK GFYPSDIAVE WESNGQPENN YKTTPPVLDS DGSFFLYSRL TVDKSRWQEG    420
NVFSCSVMHE ALHNHYTQKS LSLSLGK                                        447

SEQ ID NO: 749            moltype = AA   length = 218
FEATURE                   Location/Qualifiers
source                    1..218
                          mol_type = protein
                          organism = synthetic construct
SEQUENCE: 749
EIVLTQSPAT LSLSPGERAT LSCRASKGVS TSGYSYLHWY QQKPGQAPRL LIYLASYLES     60
GVPARFSGSG SGTDFTLTIS SLEPEDFAVY YCQHSRDLPL TFGGGTKVEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 750            moltype = AA   length = 504
FEATURE                   Location/Qualifiers
source                    1..504
                          mol_type = protein
                          organism = synthetic construct
SEQUENCE: 750
EPKSCDKTHT CPPCPAPEAA GGPSVFLFPP KPKDTLMISR TPEVTCVVVD VSHEDPEVKF     60
NWYVDGVEVH NAKTKPREEQ YNSTYRVVSV LTVLHQDWLN GKEYKCKVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GKGGGGSGGGG    240
GSGGGGSGGG GSQVQLVQSG VEVKKPGASV KVSCKASGYT FTNYYMYWVR QAPGQGLEWM    300
GGINPSNGGT NFNEKFKNRV TLTTDSSTTT AYMELKSLQF DDTAVYYCAR RDYRFDMGFD    360
YWGQGTTVTV SSGGGGSGGG GSGGGGSGGG GSEIVLTQSP ATLSLSPGER ATLSCRASKG    420
VSTSGYSYLH WYQQKPGQAP RLLIYLASYL ESGVPARFSG SGSGTDFTLT ISSLEPEDFA    480
VYYCQHSRDL PLTFGGGTKV EIKR                                           504

SEQ ID NO: 751            moltype = AA   length = 504
FEATURE                   Location/Qualifiers
source                    1..504
                          mol_type = protein
                          organism = synthetic construct
SEQUENCE: 751
EPKSCDKTHT CPPCPAPEAA GGPSVFLFPP KPKDTLMISR TPEVTCVVVD VSHEDPEVKF     60
NWYVDGVEVH NAKTKPREEQ YNSTYRVVSV LTVLHQDWLN GKEYKCKVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GKGGGGSGGGG    240
GSGGGGSGGG GSQVQLVQSG VEVKKPGASV KVSCKASGYT FTNYYMYWVR QAPGQCLEWM    300
GGINPSNGGT NFNEKFKNRV TLTTDSSTTT AYMELKSLQF DDTAVYYCAR RDYRFDMGFD    360
YWGQGTTVTV SSGGGGSGGG GSGGGGSGGG GSEIVLTQSP ATLSLSPGER ATLSCRASKG    420
VSTSGYSYLH WYQQKPGQAP RLLIYLASYL ESGVPARFSG SGSGTDFTLT ISSLEPEDFA    480
VYYCQHSRDL PLTFGCGTKV EIKR                                           504

SEQ ID NO: 752            moltype = AA   length = 453
FEATURE                   Location/Qualifiers
source                    1..453
                          mol_type = protein
                          organism = synthetic construct
SEQUENCE: 752
EVQLVESGGG LVQPGGSLRL SCAASGYTFT NYGMNWVRQA PGKGLEWVGW INTYTGEPTY     60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEL    240
LGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
REEMTKNQVS LTCLVKGFYP SDIAVEWESN GQPENNYKTT PPVLDSDGSF FLYSKLTVDK    420
SRWQQGNVFS CSVMHEALHN HYTQKSLSLS PGK                                 453
```

SEQ ID NO: 753          moltype = AA  length = 214
FEATURE                 Location/Qualifiers
source                  1..214
                        mol_type = protein
                        organism = synthetic construct
SEQUENCE: 753
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 754          moltype = AA  length = 714
FEATURE                 Location/Qualifiers
source                  1..714
                        mol_type = protein
                        organism = synthetic construct
SEQUENCE: 754
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVES   480
GGGVVQPGRS LRLDCKASGI TFSNSGMHWV RQAPGKGLEW VAVIWYDGSK RYYADSVKGR   540
FTISRDNSKN TLFLQMNSLR AEDTAVYYCA TNDDYWGQGT GVRVSSGGGG SGGGGSGGGG   600
SGGGGSEIVL TQSPATLSLS PGERATLSCR ASQSVSSYLA WYQQKPGQAP RLLIYDASNR   660
ATGIPARFSG SGSGTDFTLT ISSLEPEDFA VYYCQQSSNW PRTFGQGTKV EIKR         714

SEQ ID NO: 755          moltype = AA  length = 214
FEATURE                 Location/Qualifiers
source                  1..214
                        mol_type = protein
                        organism = synthetic construct
SEQUENCE: 755
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 756          moltype = AA  length = 714
FEATURE                 Location/Qualifiers
source                  1..714
                        mol_type = protein
                        organism = synthetic construct
SEQUENCE: 756
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120
VSSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSQVQLVES   480
GGGVVQPGRS LRLDCKASGI TFSNSGMHWV RQAPGKGLEW VAVIWYDGSK RYYADSVKGR   540
FTISRDNSKN TLFLQMNSLR AEDTAVYYCA TNDDYWGQGT GVRVSSGGGG SGGGGSGGGG   600
SGGGGSEIVL TQSPATLSLS PGERATLSCR ASQSVSSYLA WYQQKPGQAP RLLIYDASNR   660
ATGIPARFSG SGSGTDFTLT ISSLEPEDFA VYYCQQSSNW PRTFGQGTKV EIKR         714

SEQ ID NO: 757          moltype = AA  length = 214
FEATURE                 Location/Qualifiers
source                  1..214
                        mol_type = protein
                        organism = synthetic construct
SEQUENCE: 757
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 758          moltype = AA  length = 717
FEATURE                 Location/Qualifiers
source                  1..717
                        mol_type = protein
                        organism = synthetic construct
SEQUENCE: 758
EVQLVESGGG LVQPGGSLRL SCAASGYTFT NYGMNWVRQA PGKGLEWVGW INTYTGEPTY    60
AADFKRRFTF SLDTSKSTAY LQMNSLRAED TAVYYCAKYP HYYGSSHWYF DVWGQGTLVT   120

-continued

```
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLMIS RTPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLLES   480
GGVLVQPGGS LRLSCAASGF TFSNFGMTWV RQAPGKGLEW VSGISGGGRD TYFADSVKGR   540
FTISRDNSKN TLYLQMNSLK GEDTAVYYCV KWGNIYFDYW GQGTLVTVSS GGGGSGGGGS   600
GGGGSGGGGS DIQMTQSPSS LSASVGDSIT ITCRASLSIN TFLNWYQQKP GKAPNLLIYA   660
ASSLHGGVPS RFSGSGSGTD FTLTIRTLQP EDFATYYCQQ SSNTPFTFGP GTVVDFR      717
```

```
SEQ ID NO: 759        moltype = AA  length = 214
FEATURE               Location/Qualifiers
source                1..214
                      mol_type = protein
                      organism = synthetic construct
SEQUENCE: 759
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

```
SEQ ID NO: 760        moltype = AA  length = 717
FEATURE               Location/Qualifiers
source                1..717
                      mol_type = protein
                      organism = synthetic construct
SEQUENCE: 760
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLLES   480
GGVLVQPGGS LRLSCAASGF TFSNFGMTWV RQAPGKGLEW VSGISGGGRD TYFADSVKGR   540
FTISRDNSKN TLYLQMNSLK GEDTAVYYCV KWGNIYFDYW GQGTLVTVSS GGGGSGGGGS   600
GGGGSGGGGS DIQMTQSPSS LSASVGDSIT ITCRASLSIN TFLNWYQQKP GKAPNLLIYA   660
ASSLHGGVPS RFSGSGSGTD FTLTIRTLQP EDFATYYCQQ SSNTPFTFGP GTVVDFR      717
```

```
SEQ ID NO: 761        moltype = AA  length = 214
FEATURE               Location/Qualifiers
source                1..214
                      mol_type = protein
                      organism = synthetic construct
SEQUENCE: 761
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214
```

```
SEQ ID NO: 762        moltype = AA  length = 717
FEATURE               Location/Qualifiers
source                1..717
                      mol_type = protein
                      organism = synthetic construct
SEQUENCE: 762
EVQLVESGGG LVQPGGSLRL SCAASGYTFT NYGMNWVRQA PGKGLEWVGW INTYTGEPTY   60
AADFKRRFTF SLDTSKSTAY LQMNSLRAED TAVYYCAKYP HYYGSSHWYF DVWGQGTLVT   120
VSSASTKGPS VFPLAPSSKS TSGGTAALGC LVKDYFPEPV TVSWNSGALT SGVHTFPAVL   180
QSSGLYSLSS VVTVPSSSLG TQTYICNVNH KPSNTKVDKK VEPKSCDKTH TCPPCPAPEA   240
AGGPSVFLFP PKPKDTLYIT REPEVTCVVV DVSHEDPEVK FNWYVDGVEV HNAKTKPREE   300
QYNSTYRVVS VLTVLHQDWL NGKEYKCKVS NKALPAPIEK TISKAKGQPR EPQVYTLPPS   360
RDELTKNQVS LTCLVKGFYP SDIAVEWESN GQPENNYKTT PPVLDSDGSF FLYSKLTVDK   420
SRWQQGNVFS CSVMHEALHN HYTQKSLSLS PGKGGGGSGG GGSGGGGSGG GGSEVQLLES   480
GGVLVQPGGS LRLSCAASGF TFSNFGMTWV RQAPGKCLEW VSGISGGGRD TYFADSVKGR   540
FTISRDNSKN TLYLQMNSLK GEDTAVYYCV KWGNIYFDYW GQGTLVTVSS GGGGSGGGGS   600
GGGGSGGGGS DIQMTQSPSS LSASVGDSIT ITCRASLSIN TFLNWYQQKP GKAPNLLIYA   660
ASSLHGGVPS RFSGSGSGTD FTLTIRTLQP EDFATYYCQQ SSNTPFTFGC GTVVDFR      717
```

```
SEQ ID NO: 763        moltype = AA  length = 214
FEATURE               Location/Qualifiers
source                1..214
                      mol_type = protein
                      organism = synthetic construct
SEQUENCE: 763
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
```

-continued

```
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214

SEQ ID NO: 764              moltype = AA   length = 592
FEATURE                     Location/Qualifiers
source                      1..592
                            mol_type = protein
                            organism = synthetic construct
SEQUENCE: 764
EVQLVESGGG LVQPGGSLRL SCAASGYTFT NYGMNWVRQA PGKGLEWVGW INTYTGEPTY     60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSDVQLVES    480
GGGVVQPGGS LRLSCAASGS IASIHAMGWF RQAPGKEREF VAVITWSGGI TYYADSVKGR    540
FTISRDNSKN TVYLQMNSLR PEDTALYYCA GDKHQSSWYD YWGQGTLVTV SS            592

SEQ ID NO: 765              moltype = AA   length = 214
FEATURE                     Location/Qualifiers
source                      1..214
                            mol_type = protein
                            organism = synthetic construct
SEQUENCE: 765
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214

SEQ ID NO: 766              moltype = AA   length = 592
FEATURE                     Location/Qualifiers
source                      1..592
                            mol_type = protein
                            organism = synthetic construct
SEQUENCE: 766
EVQLVESGGG LVQPGGSLRL SCAASGYTFT NYGMNWVRQA PGKGLEWVGW INTYTGEPTY     60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLYIT REPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGKGGGGSGG GGSGGGGSGG GGSDVQLVES    480
GGGVVQPGGS LRLSCAASGS IASIHAMGWF RQAPGKEREF VAVITWSGGI TYYADSVKGR    540
FTISRDNSKN TVYLQMNSLR PEDTALYYCA GDKHQSSWYD YWGQGTLVTV SS            592

SEQ ID NO: 767              moltype = AA   length = 214
FEATURE                     Location/Qualifiers
source                      1..214
                            mol_type = protein
                            organism = synthetic construct
SEQUENCE: 767
DIQMTQSPSS LSASVGDRVT ITCSASQDIS NYLNWYQQKP GKAPKVLIYF TSSLHSGVPS     60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214

SEQ ID NO: 768              moltype = AA   length = 578
FEATURE                     Location/Qualifiers
source                      1..578
                            mol_type = protein
                            organism = synthetic construct
SEQUENCE: 768
EVQLVESGGG LVQPGGSLRL SCAASGYTFT NYGMNWVRQA PGKGLEWVGW INTYTGEPTY     60
AADFKRRFTF SLDTSKSTAY LQMNSLRAED TAVYYCAKYP HYYGSSHWYF DVWGQGTLVT    120
VSSASTKGPS VFPLAPSSKS TSGGTAALGC LVKDYFPEPV TVSWNSGALT SGVHTFPAVL    180
QSSGLYSLSS VVTVPSSSLG TQTYICNVNH KPSNTKVDKK VEPKSCDKTH TCPPCPAPEA    240
AGGPSVFLFP PKPKDTLMIS RTPEVTCVVV DVSHEDPEVK FNWYVDGVEV HNAKTKPREE    300
QYNSTYRVVS VLTVLHQDWL NGKEYKCKVS NKALPAPIEK TISKAKGQPR EPQVYTLPPS    360
RDELTKNQVS LTCLVKGFYP SDIAVEWESN GQPENNYKTT PPVLDSDGSF FLYSKLTVDK    420
SRWQQGNVFS CSVMHEALHN HYTQKSLSLS PGGGGSGGG GSGEVQLQES GGGLVQPGGS    480
LRLSCAASGF TFSSYWMYWL RQAPGKGLEW VSSINSDSSS TYYRDSVKGR FTISRDNAKN    540
TLYLQMNSLK SEDTAVYYCA KDPGGYAKGQ GTQVTVSS                            578

SEQ ID NO: 769              moltype = AA   length = 214
FEATURE                     Location/Qualifiers
source                      1..214
```

```
                         mol_type = protein
                         organism = synthetic construct
SEQUENCE: 769
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 770          moltype = AA  length = 562
FEATURE                 Location/Qualifiers
source                  1..562
                        mol_type = protein
                        organism = synthetic construct
SEQUENCE: 770
SDTGRPFVEM YSEIPEIIHM TEGRELVIPC RVTSPNITVT LKKFPLDTLI PDGKRIIWDS  60
RKGFIISAAT YKEIGLLTCE ATVNGHLYKT NYLTHRQTNT GGGGSGGGGS GGGGSEVQLV  120
ESGGGLVQPG GSLRLSCAAS GFTFSDSWIH WVRQAPGKGL EWVAWISPYG GSTYYADSVK  180
GRFTISADTS KNTAYLQMNS LRAEDTAVYY CARRHWPGGF DYWGQGTLVT VSSASTKGPS  240
VFPLAPSSKS TSGGTAALGC LVKDYFPEPV TVSWNSGALT SGVHTFPAVL QSSGLYSLSS  300
VVTVPSSSLG TQTYICNVNH KPSNTKVDKR VEPKSCDKTH TCPPCPAPEL LGGPSVFLFP  360
PKPKDTLMIS RTPEVTCVVV DVSHEDPEVK FNWYVDGVEV HNAKTKPREE QYNATYRVVS  420
VLTVLHQDWL NGKEYKCKVS NKALPAPIAA TISKAKGQPR EPQVYTLPPS REEMTKNQVS  480
LTCLVKGFYP SDIAVEWESN GQPENNYKTT PPVLDSDGSF FLYSKLTVDK SRWQQGNVFS  540
CSVMHEALHN HYTQKSLSLS PG                                          562

SEQ ID NO: 771          moltype = AA  length = 214
FEATURE                 Location/Qualifiers
source                  1..214
                        mol_type = protein
                        organism = synthetic construct
SEQUENCE: 771
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 772          moltype = AA  length = 595
FEATURE                 Location/Qualifiers
source                  1..595
                        mol_type = protein
                        organism = synthetic construct
SEQUENCE: 772
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKK VEPKSCDKTH TCPPCPAPEA  240
AGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGGGGSGGG GSGGGGSGGG GSEVQLVESG  480
GGLVQPGGSL RLSCAVSGNI YNRNFMGWFR QAPGKGREGV SAIYTGTSRT YYADSVKGRF  540
TISRDNAKNT VYLQMNSLRP EDTAVYYCAA DLRDGFWDTG VWNTWGQGTL VTVSS       595

SEQ ID NO: 773          moltype = AA  length = 214
FEATURE                 Location/Qualifiers
source                  1..214
                        mol_type = protein
                        organism = synthetic construct
SEQUENCE: 773
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 774          moltype = AA  length = 450
FEATURE                 Location/Qualifiers
source                  1..450
                        mol_type = protein
                        organism = synthetic construct
SEQUENCE: 774
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYA  300
STYRVSVLT VLHQDWLNGK EYKCKVSNKA LPAPIEKTIS KAKGQPREPQ VYTLPPSRDE  360
LTKNQVSLLC LVKGFYPSDI AVEWESNGQP ENNYKTTPPV LRSDGSFFLY SKLTVDKSRW  420
QQGNVFSCSV MHEALHNHYT QKSLSLSPGK                                  450
```

```
SEQ ID NO: 775          moltype = AA  length = 218
FEATURE                 Location/Qualifiers
source                  1..218
                        mol_type = protein
                        organism = synthetic construct
SEQUENCE: 775
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF   120
IPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                           218

SEQ ID NO: 776          moltype = AA  length = 450
FEATURE                 Location/Qualifiers
source                  1..450
                        mol_type = protein
                        organism = synthetic construct
SEQUENCE: 776
EVQLVESGGG LVQPGGSLRL SCAASGFTIS DYWIHWVRQA PGKGLEWVAG ITPAGGYTYY   60
ADSVKGRFTI SADTSKNTAY LQMNSLRAED TAVYYCARFV FFLPYAMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYA   300
STYRVVSVLT VLHQDWLNGK EYKCKVSNKA LPAPIEKTIS KAKGQPREPQ VYTEPPSRDE   360
LTKNQVSLTC LVKGFYPSDI AVEWESNGQP ENNYKTTPPV LDSDGSFFLL SVLTVDKSRW   420
QQGNVFSCSV MHEALHNHYT QKSLSLSPGK                                   450

SEQ ID NO: 777          moltype = AA  length = 214
FEATURE                 Location/Qualifiers
source                  1..214
                        mol_type = protein
                        organism = synthetic construct
SEQUENCE: 777
DIQMTQSPSS LSASVGDRVT ITCRASQDVS TAVAWYQQKP GKAPKLLIYS ASFLYSGVPS   60
RFSGSGSGTD FTLTISSLQP EDFATYYCQQ GYGNPFTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 778          moltype = AA  length = 713
FEATURE                 Location/Qualifiers
source                  1..713
                        mol_type = protein
                        organism = synthetic construct
SEQUENCE: 778
QVQLVESGGG LVQPGGSLRL SCAASGFAFS SYDMSWVRQA PGKCLEWVAT ISGGGRYTYY   60
PDSVKGRFTI SRDNSKNNLY LQMNSLRAED TAVYYCAVRY GETWFAYWGQ GTLVTVSSGG   120
GGSGGGGSGG GGSGGGGSDI QMTQSPSSLS ASVGDRVTIT CRASQDINTY LAWFQQKPGK   180
APKSLIYRAN RLVSGVPSRF SGSGSGTDFT LTISSLQPED MATYYCLQYD EFPLTFGCGT   240
KLELKGGGAS GGGGSGGGGS EVQLVESGGG LVQPGGSLRL SCAASGYTFT NYGMNWVRQA   300
PGKGLEWVGW INTYTGEPTY AADFKRRFTF SLDTSKSTAY LQMNSLRAED TAVYYCAKYP   360
HYYGSSHWYF DVWGQGTLVT VSSASTKGPS VFPLAPSSKS TSGGTAALGC LVKDYFPEPV   420
TVSWNSGALT SGVHTFPAVL QSSGLYSLSS VVTVPSSSLG TQTYICNVNH KPSNTKVDKK   480
VEPKSCDKTH TCPPCPAPEA AGGPSVFLFP PKPKDTLMIS RTPEVTCVVV DVSHEDPEVK   540
FNWYVDGVEV HNAKTKPREE QYNSTYRVVS VLTVLHQDWL NGKEYKCKVS NKALPAPIEK   600
TISKAKGQPR EPQVYTLPPS REEMTKNQVS LTCLVKGFYP SDIAVEWESN GQPENNYKTT   660
PPVLDSDGSF FLYSKLTVDK SRWQQGNVFS CSVMHEALHN HYTQKSLSLS PGK          713

SEQ ID NO: 779          moltype = AA  length = 214
FEATURE                 Location/Qualifiers
source                  1..214
                        mol_type = protein
                        organism = synthetic construct
SEQUENCE: 779
DIQMTQSPSS LSASVGDRVT ITCSASQDIS NYLNWYQQKP GKAPKVLIYF TSSLHSGVPS   60
RFSGSGSGTD FTLTISSLQP EDFATYYCQQ YSTVPWTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 780          moltype = AA  length = 681
FEATURE                 Location/Qualifiers
source                  1..681
                        mol_type = protein
                        organism = synthetic construct
SEQUENCE: 780
EVQLVESGGG LVQPGGSLRL SCAASGFVFS NYDMSWVRQA PGKRLEWVAT ISGGGGYTYY   60
SDSVKGRFTI SRDNAKNSLY LQMNSLRAED TAVYYCASPY GHYGFEYWGQ GTLVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVGGGG SGGGGSGGGG SEVQLVESGG   240
GLVQPGGSLR LSCAASGYDF THYGMNWVRQ APGKGLEWVG WINTYTGEPT YAADFKRRFT   300
FSLDTSKSTA YLQMNSLRAE DTAVYYCAKY PYYYGTSHWY FDVWGQGTLV TVSSASTKGP   360
```

```
SVFPLAPCSR STSESTAALG CLVKDYFPEP VTVSWNSGAL TSGVHTFPAV LQSSGLYSLS    420
SVVTVPSSSL GTKTYTCNVD HKPSNTKVDK RVESKYGPPC PPCPAPEFLG GPSVFLFPPK    480
PKDTLMISRT PEVTCVVVDV SQEDPEVQFN WYVDGVEVHN AKTKPREEQF NSTYRVVSVL    540
TVLHQDWLNG KEYKCKVSNK GLPSSIEKTI SKAKGQPREP QVYTLPPSQE EMTKNQVSLT    600
CLVKGFYPSD IAVEWESNGQ PENNYKTTPP VLDSDGSFFL YSRLTVDKSR WQEGNVFSCS    660
VMHEALHNHY TQKSLSLSLG K                                             681

SEQ ID NO: 781          moltype = AA   length = 214
FEATURE                 Location/Qualifiers
source                  1..214
                        mol_type = protein
                        organism = synthetic construct
SEQUENCE: 781
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTLPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 782          moltype = AA   length = 586
FEATURE                 Location/Qualifiers
source                  1..586
                        mol_type = protein
                        organism = synthetic construct
SEQUENCE: 782
QVQLVESGGG LVQPGGSLRL SCATSGSRRS IYAMGWFRQA PGKGLEFVAG IGWAYATTYY    60
ADSVKGRFTI SRDNTKNTLY LQMNSLRAED TAVYYCAADL DHSGFDYWGQ GTLVTVSSGG    120
GGSGGGGSGG GGSEVQLVQS GGGVVQPGGS LRLSCAASGY TFTNYGMNWV RQAPGKGLEW    180
VGWINTYTGE PTYAADFKRR FTFSLDTSKS TAYLQMNSLR AEDTAVYYCA KYPHYYGSSH    240
WYFDVWGQGT LVTVSSASTK GPSVFPLAPS SKSTSGGTAA LGCLVKDYFP EPVTVSWNSG    300
ALTSGVHTFP AVLQSSGLYS LSSVVTVPSS SLGTQTYICN VNHKPSNTKV DKKVEPKSCD    360
KTHTCPPCPA PEAAGGPSVF LFPPKPKDTL MISRTPEVTC VVVDVSHEDP EVKFNWYVDG    420
VEVHNAKTKP REEQYNSTYR VVSVLTVLHQ DWLNGKEYKC KVSNKALPAP IEKTISKAKG    480
QPREPQVYTL PPSREEMTKN QVSLTCLVKG FYPSDIAVEW ESNGQPENNY KTTPPVLDSD    540
GSFFLYSKLT VDKSRWQQGN VFSCSVMHEA LHNHYTQKSL SLSPGK                 586

SEQ ID NO: 783          moltype = AA   length = 214
FEATURE                 Location/Qualifiers
source                  1..214
                        mol_type = protein
                        organism = synthetic construct
SEQUENCE: 783
DIQMTQSPSS LSASVGDRVT ITCSASQDIS NYLNWYQQKP GKAPKVLIYF TSSLHSGVPS    60
RFSGSGSGTD FTLTISSLQP EDFATYYCQQ YSTVPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 784          moltype = AA   length = 450
FEATURE                 Location/Qualifiers
source                  1..450
                        mol_type = protein
                        organism = synthetic construct
SEQUENCE: 784
QVQLVQSGVE VKKPGASVKV SCKASGYTFT NYYMYWVRQA PGQGLEWMGG INPSQGGTNF    60
NEKFKNRVTL TTDSSTTTAY MELKSLQFDD TAVYYCARRD YRFDLGFDYW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPEAAGG    240
PSVFLFPPKP KDTLYITREP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                    450

SEQ ID NO: 785          moltype = AA   length = 218
FEATURE                 Location/Qualifiers
source                  1..218
                        mol_type = protein
                        organism = synthetic construct
SEQUENCE: 785
EIVLTQSPAT LSLSPGERAT LSCRASKGVS TSGYSYLHWY QQKPGQAPRL LIYLASYLES    60
GVPARFSGSG SGTDFTLTIS SLEPEDFAVY YCQHSRDLPL TFGGGTKVEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                           218

SEQ ID NO: 786          moltype = AA   length = 450
FEATURE                 Location/Qualifiers
source                  1..450
                        mol_type = protein
                        organism = synthetic construct
SEQUENCE: 786
QVQLVQSGVE VKKPGASVKV SCKASGYTFT NYYMYWVRQA PGQGLEWMGG INPSRGGTNF    60
```

```
NEKFKNRVTL TTDSSTTTAY MELKSLQFDD TAVYYCARRD YRFDLGFDYW GQGTTVTVSS    120
ASTKGPSVFP LAPSSKSTSG GTAALGCLVK DYFPEPVTVS WNSGALTSGV HTFPAVLQSS    180
GLYSLSSVVT VPSSSLGTQT YICNVNHKPS NTKVDKKVEP KSCDKTHTCP PCPAPEAAGG    240
PSVFLFPPKP KDTLYITREP EVTCVVVDVS HEDPEVKFNW YVDGVEVHNA KTKPREEQYN    300
STYRVVSVLT VLHQDWLNGK EYKCKVSNKA LPAPIEKTIS KAKGQPREPQ VYTLPPSRDE    360
LTKNQVSLTC LVKGFYPSDI AVEWESNGQP ENNYKTTPPV LDSDGSFFLY SKLTVDKSRW    420
QQGNVFSCSV MHEALHNHYT QKSLSLSPGK                                      450

SEQ ID NO: 787              moltype = AA  length = 218
FEATURE                     Location/Qualifiers
source                      1..218
                            mol_type = protein
                            organism = synthetic construct
SEQUENCE: 787
EIVLTQSPAT LSLSPGERAT LSCRASKGVS TSGYSYLHWY QQKPGQAPRL LIYLASYLES     60
GVPARFSGSG SGTDFTLTIS SLEPEDFAVY YCQHSRDLPL TFGGGTKVEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 788              moltype = AA  length = 504
FEATURE                     Location/Qualifiers
source                      1..504
                            mol_type = protein
                            organism = synthetic construct
SEQUENCE: 788
EPKSCDKTHT CPPCPAPEAA GGPSVFLFPP KPKDTLYITR EPEVTCVVVD VSHEDPEVKF     60
NWYVDGVEVH NAKTKPREEQ YNSTYRVVSV LTVLHQDWLN GKEYKCKVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GKGGGGSGGG    240
GSGGGGSGGG GSQVQLVQSG VEVKKPGASV KVSCKASGYT FTNYYMYWVR QAPGQGLEWM    300
GGINPSQGGT NFNEKFKNRV TLTTDSSTTT AYMELKSLQF DDTAVYYCAR RDYRFDLGFD    360
YWGQGTTVTV SSGGGGSGGG GSGGGGSGGG GSEIVLTQSP ATLSLSPGER ATLSCRASKG    420
VSTSGYSYLH WYQQKPGQAP RLLIYLASYL ESGVPARFSG SGSGTDFTLT ISSLEPEDFA    480
VYYCQHSRDL PLTFGGGTKV EIKR                                          504

SEQ ID NO: 789              moltype = AA  length = 504
FEATURE                     Location/Qualifiers
source                      1..504
                            mol_type = protein
                            organism = synthetic construct
SEQUENCE: 789
EPKSCDKTHT CPPCPAPEAA GGPSVFLFPP KPKDTLYITR EPEVTCVVVD VSHEDPEVKF     60
NWYVDGVEVH NAKTKPREEQ YNSTYRVVSV LTVLHQDWLN GKEYKCKVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GKGGGGSGGG    240
GSGGGGSGGG GSQVQLVQSG VEVKKPGASV KVSCKASGYT FTNYYMYWVR QAPGQGLEWM    300
GGINPSQGGT NFNEKFKNRV TLTTDSSTTT AYMELKSLQF DDTAVYYCAR RDYRFDLGFD    360
YWGQGTTVTV SSGGGGSGGG GSGGGGSGGG GSEIVLTQSP ATLSLSPGER ATLSCRASKG    420
VSTSGYSYLH WYQQKPGQAP RLLIYLASYL ESGVPARFSG SGSGTDFTLT ISSLEPEDFA    480
VYYCQHSRDL PLTFGGGTKV EIKR                                          504

SEQ ID NO: 790              moltype = AA  length = 504
FEATURE                     Location/Qualifiers
source                      1..504
                            mol_type = protein
                            organism = synthetic construct
SEQUENCE: 790
EPKSCDKTHT CPPCPAPEAA GGPSVFLFPP KPKDTLYITR EPEVTCVVVD VSHEDPEVKF     60
NWYVDGVEVH NAKTKPREEQ YNSTYRVVSV LTVLHQDWLN GKEYKCKVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GKGGGGSGGG    240
GSGGGGSGGG GSQVQLVQSG VEVKKPGASV KVSCKASGYT FTNYYMYWVR QAPGQCLEWM    300
GGINPSQGGT NFNEKFKNRV TLTTDSSTTT AYMELKSLQF DDTAVYYCAR RDYRFDLGFD    360
YWGQGTTVTV SSGGGGSGGG GSGGGGSGGG GSEIVLTQSP ATLSLSPGER ATLSCRASKG    420
VSTSGYSYLH WYQQKPGQAP RLLIYLASYL ESGVPARFSG SGSGTDFTLT ISSLEPEDFA    480
VYYCQHSRDL PLTFGCGTKV EIKR                                          504

SEQ ID NO: 791              moltype = AA  length = 504
FEATURE                     Location/Qualifiers
source                      1..504
                            mol_type = protein
                            organism = synthetic construct
SEQUENCE: 791
EPKSCDKTHT CPPCPAPEAA GGPSVFLFPP KPKDTLYITR EPEVTCVVVD VSHEDPEVKF     60
NWYVDGVEVH NAKTKPREEQ YNSTYRVVSV LTVLHQDWLN GKEYKCKVSN KALPAPIEKT    120
ISKAKGQPRE PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP GKGGGGSGGG    240
GSGGGGSGGG GSQVQLVQSG VEVKKPGASV KVSCKASGYT FTNYYMYWVR QAPGQCLEWM    300
GGINPSRGGT NFNEKFKNRV TLTTDSSTTT AYMELKSLQF DDTAVYYCAR RDYRFDLGFD    360
```

```
YWGQGTTVTV SSGGGGSGGG GSGGGGSGGG GSEIVLTQSP ATLSLSPGER ATLSCRASKG    420
VSTSGYSYLH WYQQKPGQAP RLLIYLASYL ESGVPARFSG SGSGTDFTLT ISSLEPEDFA    480
VYYCQHSRDL PLTFGCGTKV EIKR                                           504

SEQ ID NO: 792            moltype = AA   length = 329
FEATURE                   Location/Qualifiers
source                    1..329
                          mol_type = protein
                          organism = Homo sapiens
SEQUENCE: 792
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 793            moltype = AA   length = 325
FEATURE                   Location/Qualifiers
source                    1..325
                          mol_type = protein
                          organism = Homo sapiens
SEQUENCE: 793
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF    120
LFPPKPKDTL MISRTPEVTC VVVDVSHEDP EVQFNWYVDG VEVHNAKTKP REEQFNSTFR    180
VVSVLTVVHQ DWLNGKEYKC KVSNKGLPAP IEKTISKTKG QPREPQVYTL PPSREEMTKN    240
QVSLTCLVKG FYPSDIAVEW ESNGQPENNY KTTPPMLDSD GSFFLYSKLT VDKSRWQQGN    300
VFSCSVMHEA LHNHYTQKSL SLSPG                                          325

SEQ ID NO: 794            moltype = AA   length = 326
FEATURE                   Location/Qualifiers
source                    1..326
                          mol_type = protein
                          organism = Homo sapiens
SEQUENCE: 794
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLG                                         326

SEQ ID NO: 795            moltype = AA   length = 326
FEATURE                   Location/Qualifiers
source                    1..326
                          mol_type = protein
                          organism = synthetic construct
SEQUENCE: 795
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLG                                         326

SEQ ID NO: 796            moltype = AA   length = 326
FEATURE                   Location/Qualifiers
source                    1..326
                          mol_type = protein
                          organism = synthetic construct
SEQUENCE: 796
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEELGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLG                                         326

SEQ ID NO: 797            moltype = AA   length = 329
FEATURE                   Location/Qualifiers
source                    1..329
                          mol_type = protein
                          organism = synthetic construct
SEQUENCE: 797
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLT VLHQDWLNGK EYKCKVSNKA LPAPIEKTIS KAKGQPREPQ VYTLPPSRDE    240
```

-continued

```
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                      329

SEQ ID NO: 798          moltype = AA  length = 329
FEATURE                 Location/Qualifiers
source                  1..329
                        mol_type = protein
                        organism = synthetic construct
SEQUENCE: 798
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVAVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                      329

SEQ ID NO: 799          moltype = AA  length = 329
FEATURE                 Location/Qualifiers
source                  1..329
                        mol_type = protein
                        organism = synthetic construct
SEQUENCE: 799
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                      329

SEQ ID NO: 800          moltype = AA  length = 329
FEATURE                 Location/Qualifiers
source                  1..329
                        mol_type = protein
                        organism = synthetic construct
SEQUENCE: 800
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                      329

SEQ ID NO: 801          moltype = AA  length = 329
FEATURE                 Location/Qualifiers
source                  1..329
                        mol_type = protein
                        organism = synthetic construct
SEQUENCE: 801
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                      329

SEQ ID NO: 802          moltype = AA  length = 329
FEATURE                 Location/Qualifiers
source                  1..329
                        mol_type = protein
                        organism = synthetic construct
SEQUENCE: 802
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                      329

SEQ ID NO: 803          moltype = AA  length = 329
FEATURE                 Location/Qualifiers
source                  1..329
                        mol_type = protein
                        organism = synthetic construct
SEQUENCE: 803
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
```

-continued

```
QQGNVFSCSV MHEALHNHYT QKSLSLSPG                                        329

SEQ ID NO: 804          moltype = AA  length = 329
FEATURE                 Location/Qualifiers
source                  1..329
                        mol_type = protein
                        organism = synthetic construct
SEQUENCE: 804
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKKVEP KSCDKTHTCP PCPAPELLGG     120
PSVFLFPPKP KDTLYITREP EVTCVVVDVS HEDPEVKFNW YVDGVEVHNA KTKPREEQYA     180
STYRVVSVLT VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPG                                        329

SEQ ID NO: 805          moltype = AA  length = 329
FEATURE                 Location/Qualifiers
source                  1..329
                        mol_type = protein
                        organism = synthetic construct
SEQUENCE: 805
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKKVEP KSCDKTHTCP PCPAPELLGG     120
PSVFLFPPKP KDTLYITREP EVTCVVVAVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPG                                        329

SEQ ID NO: 806          moltype = AA  length = 329
FEATURE                 Location/Qualifiers
source                  1..329
                        mol_type = protein
                        organism = synthetic construct
SEQUENCE: 806
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKKVEP KSCDKTHTCP PCPAPEAAGG     120
PSVFLFPPKP KDTLYITREP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPG                                        329

SEQ ID NO: 807          moltype = AA  length = 329
FEATURE                 Location/Qualifiers
source                  1..329
                        mol_type = protein
                        organism = synthetic construct
SEQUENCE: 807
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKKVEP KSCDKTHTCP PCPAPELAGA     120
PSVFLFPPKP KDTLYITREP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPG                                        329

SEQ ID NO: 808          moltype = AA  length = 329
FEATURE                 Location/Qualifiers
source                  1..329
                        mol_type = protein
                        organism = synthetic construct
SEQUENCE: 808
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKKVEP KSCDKTHTCP PCPAPEAAGA     120
PSVFLFPPKP KDTLYITREP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPG                                        329

SEQ ID NO: 809          moltype = AA  length = 329
FEATURE                 Location/Qualifiers
source                  1..329
                        mol_type = protein
                        organism = synthetic construct
SEQUENCE: 809
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKKVEP KSCDKTHTCP PCPAPEAAGG     120
PSVFLFPPKP KDTLYITREP EVTCVVVDVS HEDPEVKFNW YVDGVEVHNA KTKPREEQYN     180
STYRVVSVLT VLHQDWLNGK EYKCKVSNKA LGAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPG                                        329
```

```
SEQ ID NO: 810              moltype = AA   length = 329
FEATURE                     Location/Qualifiers
source                      1..329
                            mol_type = protein
                            organism = synthetic construct
SEQUENCE: 810
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 811              moltype = AA   length = 329
FEATURE                     Location/Qualifiers
source                      1..329
                            mol_type = protein
                            organism = synthetic construct
SEQUENCE: 811
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 812              moltype = AA   length = 329
FEATURE                     Location/Qualifiers
source                      1..329
                            mol_type = protein
                            organism = synthetic construct
SEQUENCE: 812
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 813              moltype = AA   length = 329
FEATURE                     Location/Qualifiers
source                      1..329
                            mol_type = protein
                            organism = synthetic construct
SEQUENCE: 813
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 814              moltype = AA   length = 329
FEATURE                     Location/Qualifiers
source                      1..329
                            mol_type = protein
                            organism = synthetic construct
SEQUENCE: 814
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 815              moltype = AA   length = 329
FEATURE                     Location/Qualifiers
source                      1..329
                            mol_type = protein
                            organism = synthetic construct
SEQUENCE: 815
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329
```

-continued

```
SEQ ID NO: 816            moltype = AA   length = 329
FEATURE                   Location/Qualifiers
source                    1..329
                          mol_type = protein
                          organism = synthetic construct
SEQUENCE: 816
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 817            moltype = AA   length = 329
FEATURE                   Location/Qualifiers
source                    1..329
                          mol_type = protein
                          organism = synthetic construct
SEQUENCE: 817
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VDHHDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 818            moltype = AA   length = 329
FEATURE                   Location/Qualifiers
source                    1..329
                          mol_type = protein
                          organism = synthetic construct
SEQUENCE: 818
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VDHHDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 819            moltype = AA   length = 329
FEATURE                   Location/Qualifiers
source                    1..329
                          mol_type = protein
                          organism = synthetic construct
SEQUENCE: 819
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VDHHDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 820            moltype = AA   length = 329
FEATURE                   Location/Qualifiers
source                    1..329
                          mol_type = protein
                          organism = synthetic construct
SEQUENCE: 820
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VDHHDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 821            moltype = AA   length = 329
FEATURE                   Location/Qualifiers
source                    1..329
                          mol_type = protein
                          organism = synthetic construct
SEQUENCE: 821
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VDHHDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 822            moltype = AA   length = 329
```

```
FEATURE             Location/Qualifiers
source              1..329
                    mol_type = protein
                    organism = synthetic construct
SEQUENCE: 822
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VDHHDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 823      moltype = AA  length = 329
FEATURE             Location/Qualifiers
source              1..329
                    mol_type = protein
                    organism = synthetic construct
SEQUENCE: 823
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VDHHDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 824      moltype = AA  length = 326
FEATURE             Location/Qualifiers
source              1..326
                    mol_type = protein
                    organism = synthetic construct
SEQUENCE: 824
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LYITREPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLG                                       326

SEQ ID NO: 825      moltype = AA  length = 326
FEATURE             Location/Qualifiers
source              1..326
                    mol_type = protein
                    organism = synthetic construct
SEQUENCE: 825
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LYITREPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLG                                       326

SEQ ID NO: 826      moltype = AA  length = 326
FEATURE             Location/Qualifiers
source              1..326
                    mol_type = protein
                    organism = synthetic construct
SEQUENCE: 826
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEELGGPSV  120
FLFPPKPKDT LYITREPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLG                                       326

SEQ ID NO: 827      moltype = AA  length = 326
FEATURE             Location/Qualifiers
source              1..326
                    mol_type = protein
                    organism = synthetic construct
SEQUENCE: 827
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVLHE ALHSHYTQKS LSLSLG                                       326

SEQ ID NO: 828      moltype = AA  length = 326
FEATURE             Location/Qualifiers
```

-continued

```
source                  1..326
                        mol_type = protein
                        organism = synthetic construct
SEQUENCE: 828
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVLHE ALHSHYTQKS LSLSLG                                        326

SEQ ID NO: 829          moltype = AA  length = 326
FEATURE                 Location/Qualifiers
source                  1..326
                        mol_type = protein
                        organism = synthetic construct
SEQUENCE: 829
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEELGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVLHE ALHSHYTQKS LSLSLG                                        326

SEQ ID NO: 830          moltype = AA  length = 326
FEATURE                 Location/Qualifiers
source                  1..326
                        mol_type = protein
                        organism = synthetic construct
SEQUENCE: 830
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVDH HDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHSHYTQKS LSLSLG                                        326

SEQ ID NO: 831          moltype = AA  length = 326
FEATURE                 Location/Qualifiers
source                  1..326
                        mol_type = protein
                        organism = synthetic construct
SEQUENCE: 831
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVDH HDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHSHYTQKS LSLSLG                                        326

SEQ ID NO: 832          moltype = AA  length = 326
FEATURE                 Location/Qualifiers
source                  1..326
                        mol_type = protein
                        organism = synthetic construct
SEQUENCE: 832
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEELGGPSV   120
FLFPPKPKDT LMISRTPEVT CVVVDVSQED PEVQFNWYVD GVEVHNAKTK PREEQFNSTY   180
RVVSVLTVDH HDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHSHYTQKS LSLSLG                                        326

SEQ ID NO: 833          moltype = AA  length = 325
FEATURE                 Location/Qualifiers
source                  1..325
                        mol_type = protein
                        organism = synthetic construct
SEQUENCE: 833
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF   120
LFPPKPKDTL YITREPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVMHEA LHNHYTQKSL SLSPG                                         325

SEQ ID NO: 834          moltype = AA  length = 325
FEATURE                 Location/Qualifiers
source                  1..325
```

```
                         mol_type = protein
                         organism = synthetic construct
SEQUENCE: 834
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVLHEA LHSHYTQKSL SLSPG                                       325

SEQ ID NO: 835          moltype = AA   length = 325
FEATURE                 Location/Qualifiers
source                  1..325
                        mol_type = protein
                        organism = synthetic construct
SEQUENCE: 835
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVDHH DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHSHYTQKSL SLSPG                                       325

SEQ ID NO: 836          moltype = AA   length = 329
FEATURE                 Location/Qualifiers
source                  1..329
                        mol_type = protein
                        organism = synthetic construct
SEQUENCE: 836
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                   329

SEQ ID NO: 837          moltype = AA   length = 329
FEATURE                 Location/Qualifiers
source                  1..329
                        mol_type = protein
                        organism = synthetic construct
SEQUENCE: 837
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                   329

SEQ ID NO: 838          moltype = AA   length = 329
FEATURE                 Location/Qualifiers
source                  1..329
                        mol_type = protein
                        organism = synthetic construct
SEQUENCE: 838
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                   329

SEQ ID NO: 839          moltype = AA   length = 329
FEATURE                 Location/Qualifiers
source                  1..329
                        mol_type = protein
                        organism = synthetic construct
SEQUENCE: 839
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                   329

SEQ ID NO: 840          moltype = AA   length = 329
FEATURE                 Location/Qualifiers
source                  1..329
                        mol_type = protein
```

-continued

```
                         organism = synthetic construct
SEQUENCE: 840
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                    329

SEQ ID NO: 841        moltype = AA  length = 329
FEATURE               Location/Qualifiers
source                1..329
                      mol_type = protein
                      organism = synthetic construct
SEQUENCE: 841
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                    329

SEQ ID NO: 842        moltype = AA  length = 329
FEATURE               Location/Qualifiers
source                1..329
                      mol_type = protein
                      organism = synthetic construct
SEQUENCE: 842
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                    329

SEQ ID NO: 843        moltype = AA  length = 329
FEATURE               Location/Qualifiers
source                1..329
                      mol_type = protein
                      organism = synthetic construct
SEQUENCE: 843
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHAHYT QKSLSLSPG                                    329

SEQ ID NO: 844        moltype = AA  length = 329
FEATURE               Location/Qualifiers
source                1..329
                      mol_type = protein
                      organism = synthetic construct
SEQUENCE: 844
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHAHYT QKSLSLSPG                                    329

SEQ ID NO: 845        moltype = AA  length = 329
FEATURE               Location/Qualifiers
source                1..329
                      mol_type = protein
                      organism = synthetic construct
SEQUENCE: 845
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHAHYT QKSLSLSPG                                    329

SEQ ID NO: 846        moltype = AA  length = 329
FEATURE               Location/Qualifiers
source                1..329
                      mol_type = protein
                      organism = synthetic construct
```

-continued

```
SEQUENCE: 846
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                     329

SEQ ID NO: 847         moltype = AA  length = 329
FEATURE                Location/Qualifiers
source                 1..329
                       mol_type = protein
                       organism = synthetic construct
SEQUENCE: 847
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                     329

SEQ ID NO: 848         moltype = AA  length = 329
FEATURE                Location/Qualifiers
source                 1..329
                       mol_type = protein
                       organism = synthetic construct
SEQUENCE: 848
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                     329

SEQ ID NO: 849         moltype = AA  length = 329
FEATURE                Location/Qualifiers
source                 1..329
                       mol_type = protein
                       organism = synthetic construct
SEQUENCE: 849
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                     329

SEQ ID NO: 850         moltype = AA  length = 329
FEATURE                Location/Qualifiers
source                 1..329
                       mol_type = protein
                       organism = synthetic construct
SEQUENCE: 850
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                     329

SEQ ID NO: 851         moltype = AA  length = 329
FEATURE                Location/Qualifiers
source                 1..329
                       mol_type = protein
                       organism = synthetic construct
SEQUENCE: 851
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                     329

SEQ ID NO: 852         moltype = AA  length = 329
FEATURE                Location/Qualifiers
source                 1..329
                       mol_type = protein
                       organism = synthetic construct
SEQUENCE: 852
```

-continued

```
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVAVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                     329

SEQ ID NO: 853           moltype = AA   length = 329
FEATURE                  Location/Qualifiers
source                   1..329
                         mol_type = protein
                         organism = synthetic construct
SEQUENCE: 853
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                     329

SEQ ID NO: 854           moltype = AA   length = 329
FEATURE                  Location/Qualifiers
source                   1..329
                         mol_type = protein
                         organism = synthetic construct
SEQUENCE: 854
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                     329

SEQ ID NO: 855           moltype = AA   length = 329
FEATURE                  Location/Qualifiers
source                   1..329
                         mol_type = protein
                         organism = synthetic construct
SEQUENCE: 855
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                     329

SEQ ID NO: 856           moltype = AA   length = 329
FEATURE                  Location/Qualifiers
source                   1..329
                         mol_type = protein
                         organism = synthetic construct
SEQUENCE: 856
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                     329

SEQ ID NO: 857           moltype = AA   length = 329
FEATURE                  Location/Qualifiers
source                   1..329
                         mol_type = protein
                         organism = synthetic construct
SEQUENCE: 857
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRDP EVTCVVVDVS HEDPEVKFNW YVDGVEVHNA KTKPREEQYN   180
STYRVVSVLQ VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 858           moltype = AA   length = 329
FEATURE                  Location/Qualifiers
source                   1..329
                         mol_type = protein
                         organism = synthetic construct
SEQUENCE: 858
ASTKGPSVFP LAPSSKSTSG GTAALGCLVK DYFPEPVTVS WNSGALTSGV HTFPAVLQSS    60
```

```
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVHNA KTKPREEQYA  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                     329

SEQ ID NO: 859                moltype = AA   length = 329
FEATURE                       Location/Qualifiers
source                        1..329
                              mol_type = protein
                              organism = synthetic construct
SEQUENCE: 859
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRDP EVTCVVVAVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                     329

SEQ ID NO: 860                moltype = AA   length = 329
FEATURE                       Location/Qualifiers
source                        1..329
                              mol_type = protein
                              organism = synthetic construct
SEQUENCE: 860
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                     329

SEQ ID NO: 861                moltype = AA   length = 329
FEATURE                       Location/Qualifiers
source                        1..329
                              mol_type = protein
                              organism = synthetic construct
SEQUENCE: 861
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                     329

SEQ ID NO: 862                moltype = AA   length = 329
FEATURE                       Location/Qualifiers
source                        1..329
                              mol_type = protein
                              organism = synthetic construct
SEQUENCE: 862
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                     329

SEQ ID NO: 863                moltype = AA   length = 329
FEATURE                       Location/Qualifiers
source                        1..329
                              mol_type = protein
                              organism = synthetic construct
SEQUENCE: 863
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                     329

SEQ ID NO: 864                moltype = AA   length = 329
FEATURE                       Location/Qualifiers
source                        1..329
                              mol_type = protein
                              organism = synthetic construct
SEQUENCE: 864
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
```

-continued

```
PSVFLFPPKP KDTLMISRDP EVTCVVVDVS HEDPEVKFNW YVDGVEVHNA KTKPREEQYN   180
STYRVVSVLW VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 865              moltype = AA  length = 329
FEATURE                     Location/Qualifiers
source                      1..329
                            mol_type = protein
                            organism = synthetic construct
SEQUENCE: 865
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRDP EVTCVVVDVS HEDPEVKFNW YVDGVEVHNA KTKPREEQYA   180
STYRVVSVLW VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 866              moltype = AA  length = 329
FEATURE                     Location/Qualifiers
source                      1..329
                            mol_type = protein
                            organism = synthetic construct
SEQUENCE: 866
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRDP EVTCVVVAVS HEDPEVKFNW YVDGVEVHNA KTKPREEQYN   180
STYRVVSVLW VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 867              moltype = AA  length = 329
FEATURE                     Location/Qualifiers
source                      1..329
                            mol_type = protein
                            organism = synthetic construct
SEQUENCE: 867
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRDP EVTCVVVDVS HEDPEVKFNW YVDGVEVHNA KTKPREEQYN   180
STYRVVSVLW VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 868              moltype = AA  length = 329
FEATURE                     Location/Qualifiers
source                      1..329
                            mol_type = protein
                            organism = synthetic construct
SEQUENCE: 868
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLMISRDP EVTCVVVDVS HEDPEVKFNW YVDGVEVHNA KTKPREEQYN   180
STYRVVSVLW VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 869              moltype = AA  length = 329
FEATURE                     Location/Qualifiers
source                      1..329
                            mol_type = protein
                            organism = synthetic construct
SEQUENCE: 869
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRDP EVTCVVVDVS HEDPEVKFNW YVDGVEVHNA KTKPREEQYN   180
STYRVVSVLW VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 870              moltype = AA  length = 329
FEATURE                     Location/Qualifiers
source                      1..329
                            mol_type = protein
                            organism = synthetic construct
SEQUENCE: 870
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRDP EVTCVVVDVS HEDPEVKFNW YVDGVEVHNA KTKPREEQYN   180
```

-continued

```
STYRVVSVLW VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 871        moltype = AA  length = 329
FEATURE               Location/Qualifiers
source                1..329
                      mol_type = protein
                      organism = synthetic construct
SEQUENCE: 871
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 872        moltype = AA  length = 329
FEATURE               Location/Qualifiers
source                1..329
                      mol_type = protein
                      organism = synthetic construct
SEQUENCE: 872
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLYISRDP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 873        moltype = AA  length = 329
FEATURE               Location/Qualifiers
source                1..329
                      mol_type = protein
                      organism = synthetic construct
SEQUENCE: 873
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLYISRDP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 874        moltype = AA  length = 329
FEATURE               Location/Qualifiers
source                1..329
                      mol_type = protein
                      organism = synthetic construct
SEQUENCE: 874
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 875        moltype = AA  length = 329
FEATURE               Location/Qualifiers
source                1..329
                      mol_type = protein
                      organism = synthetic construct
SEQUENCE: 875
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 876        moltype = AA  length = 329
FEATURE               Location/Qualifiers
source                1..329
                      mol_type = protein
                      organism = synthetic construct
SEQUENCE: 876
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
```

```
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                       329

SEQ ID NO: 877          moltype = AA  length = 329
FEATURE                 Location/Qualifiers
source                  1..329
                        mol_type = protein
                        organism = synthetic construct
SEQUENCE: 877
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLYISRDP EVTCVVVDVS HEDPEVKFNW YVDGVEVHNA KTKPREEQYN    180
STYRVVSVLT VLHQDWLNGK EYKCKVSNKA LGAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                       329

SEQ ID NO: 878          moltype = AA  length = 329
FEATURE                 Location/Qualifiers
source                  1..329
                        mol_type = protein
                        organism = synthetic construct
SEQUENCE: 878
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                       329

SEQ ID NO: 879          moltype = AA  length = 329
FEATURE                 Location/Qualifiers
source                  1..329
                        mol_type = protein
                        organism = synthetic construct
SEQUENCE: 879
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                       329

SEQ ID NO: 880          moltype = AA  length = 329
FEATURE                 Location/Qualifiers
source                  1..329
                        mol_type = protein
                        organism = synthetic construct
SEQUENCE: 880
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVAVS HEDPEVKFNW YVDGVEVHNA KTKPREEQYN    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                       329

SEQ ID NO: 881          moltype = AA  length = 329
FEATURE                 Location/Qualifiers
source                  1..329
                        mol_type = protein
                        organism = synthetic construct
SEQUENCE: 881
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                       329

SEQ ID NO: 882          moltype = AA  length = 329
FEATURE                 Location/Qualifiers
source                  1..329
                        mol_type = protein
                        organism = synthetic construct
SEQUENCE: 882
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA    120
PSVFLFPPKP KDTLMISRTP EVTCVVVDVS HEDPEVKFNW YVDGVEVHNA KTKPREEQYN    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
```

-continued

```
QQGNVFSCSV MHEALHNHYT QKSLSLSPG                                   329

SEQ ID NO: 883           moltype = AA   length = 329
FEATURE                  Location/Qualifiers
source                   1..329
                         mol_type = protein
                         organism = synthetic construct
SEQUENCE: 883
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLQ VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                   329

SEQ ID NO: 884           moltype = AA   length = 329
FEATURE                  Location/Qualifiers
source                   1..329
                         mol_type = protein
                         organism = synthetic construct
SEQUENCE: 884
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLQ VLHVDWLNGK EYKCKVSNKA LGAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                   329

SEQ ID NO: 885           moltype = AA   length = 329
FEATURE                  Location/Qualifiers
source                   1..329
                         mol_type = protein
                         organism = synthetic construct
SEQUENCE: 885
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                   329

SEQ ID NO: 886           moltype = AA   length = 329
FEATURE                  Location/Qualifiers
source                   1..329
                         mol_type = protein
                         organism = synthetic construct
SEQUENCE: 886
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVDNA KTKPREEQYA  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                   329

SEQ ID NO: 887           moltype = AA   length = 329
FEATURE                  Location/Qualifiers
source                   1..329
                         mol_type = protein
                         organism = synthetic construct
SEQUENCE: 887
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRDP EVTCVVVAVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                   329

SEQ ID NO: 888           moltype = AA   length = 329
FEATURE                  Location/Qualifiers
source                   1..329
                         mol_type = protein
                         organism = synthetic construct
SEQUENCE: 888
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                   329
```

-continued

```
SEQ ID NO: 889               moltype = AA   length = 329
FEATURE                      Location/Qualifiers
source                       1..329
                             mol_type = protein
                             organism = synthetic construct
SEQUENCE: 889
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                    329

SEQ ID NO: 890               moltype = AA   length = 329
FEATURE                      Location/Qualifiers
source                       1..329
                             mol_type = protein
                             organism = synthetic construct
SEQUENCE: 890
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                    329

SEQ ID NO: 891               moltype = AA   length = 329
FEATURE                      Location/Qualifiers
source                       1..329
                             mol_type = protein
                             organism = synthetic construct
SEQUENCE: 891
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LGAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPG                                    329

SEQ ID NO: 892               moltype = AA   length = 329
FEATURE                      Location/Qualifiers
source                       1..329
                             mol_type = protein
                             organism = synthetic construct
SEQUENCE: 892
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 893               moltype = AA   length = 326
FEATURE                      Location/Qualifiers
source                       1..326
                             mol_type = protein
                             organism = synthetic construct
SEQUENCE: 893
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH RDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVLHE ALHNHYTQKS LSLSLG                                       326

SEQ ID NO: 894               moltype = AA   length = 326
FEATURE                      Location/Qualifiers
source                       1..326
                             mol_type = protein
                             organism = synthetic construct
SEQUENCE: 894
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH RDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVLHE ALHNHYTQKS LSLSLG                                       326
```

-continued

```
SEQ ID NO: 895          moltype = AA  length = 326
FEATURE                 Location/Qualifiers
source                  1..326
                        mol_type = protein
                        organism = synthetic construct
SEQUENCE: 895
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEELGGPSV  120
FLFPPKPKDT LMISRTPEVT CVVVDVSQED PEVQFNWYVD GVEVHNAKTK PREEQFNSTY  180
RVVSVLTVLH RDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVLHE ALHNHYTQKS LSLSLG                                       326

SEQ ID NO: 896          moltype = AA  length = 325
FEATURE                 Location/Qualifiers
source                  1..325
                        mol_type = protein
                        organism = synthetic construct
SEQUENCE: 896
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHR DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVLHEA LHNHYTQKSL SLSPG                                        325

SEQ ID NO: 897          moltype = AA  length = 329
FEATURE                 Location/Qualifiers
source                  1..329
                        mol_type = protein
                        organism = synthetic construct
SEQUENCE: 897
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 898          moltype = AA  length = 329
FEATURE                 Location/Qualifiers
source                  1..329
                        mol_type = protein
                        organism = synthetic construct
SEQUENCE: 898
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 899          moltype = AA  length = 329
FEATURE                 Location/Qualifiers
source                  1..329
                        mol_type = protein
                        organism = synthetic construct
SEQUENCE: 899
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 900          moltype = AA  length = 329
FEATURE                 Location/Qualifiers
source                  1..329
                        mol_type = protein
                        organism = synthetic construct
SEQUENCE: 900
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 901          moltype = AA  length = 329
```

-continued

```
FEATURE              Location/Qualifiers
source               1..329
                     mol_type = protein
                     organism = synthetic construct
SEQUENCE: 901
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 902        moltype = AA  length = 329
FEATURE              Location/Qualifiers
source               1..329
                     mol_type = protein
                     organism = synthetic construct
SEQUENCE: 902
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 903        moltype = AA  length = 329
FEATURE              Location/Qualifiers
source               1..329
                     mol_type = protein
                     organism = synthetic construct
SEQUENCE: 903
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 904        moltype = AA  length = 329
FEATURE              Location/Qualifiers
source               1..329
                     mol_type = protein
                     organism = synthetic construct
SEQUENCE: 904
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV LHEALHSHYT QKSLSLSPG                                    329

SEQ ID NO: 905        moltype = AA  length = 329
FEATURE              Location/Qualifiers
source               1..329
                     mol_type = protein
                     organism = synthetic construct
SEQUENCE: 905
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLYITREP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 906        moltype = AA  length = 329
FEATURE              Location/Qualifiers
source               1..329
                     mol_type = protein
                     organism = synthetic construct
SEQUENCE: 906
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV LHEALHAHYT QKSLSLSPG                                    329

SEQ ID NO: 907        moltype = AA  length = 329
FEATURE              Location/Qualifiers
```

-continued

```
source                  1..329
                        mol_type = protein
                        organism = synthetic construct
SEQUENCE: 907
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALKFHYT QKSLSLSPG                                    329

SEQ ID NO: 908         moltype = AA  length = 329
FEATURE                Location/Qualifiers
source                 1..329
                       mol_type = protein
                       organism = synthetic construct
SEQUENCE: 908
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VDHHDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHSHYT QKSLSLSPG                                    329

SEQ ID NO: 909         moltype = AA  length = 329
FEATURE                Location/Qualifiers
source                 1..329
                       mol_type = protein
                       organism = synthetic construct
SEQUENCE: 909
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 910         moltype = AA  length = 329
FEATURE                Location/Qualifiers
source                 1..329
                       mol_type = protein
                       organism = synthetic construct
SEQUENCE: 910
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLYITREP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                    329

SEQ ID NO: 911         moltype = AA  length = 330
FEATURE                Location/Qualifiers
source                 1..330
                       mol_type = protein
                       organism = Homo sapiens
SEQUENCE: 911
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 912         moltype = AA  length = 326
FEATURE                Location/Qualifiers
source                 1..326
                       mol_type = protein
                       organism = Homo sapiens
SEQUENCE: 912
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                       326

SEQ ID NO: 913         moltype = AA  length = 327
FEATURE                Location/Qualifiers
source                 1..327
```

```
                              mol_type = protein
                              organism = Homo sapiens
SEQUENCE: 913
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327

SEQ ID NO: 914          moltype = AA   length = 327
FEATURE                 Location/Qualifiers
source                  1..327
                        mol_type = protein
                        organism = synthetic construct
SEQUENCE: 914
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327

SEQ ID NO: 915          moltype = AA   length = 327
FEATURE                 Location/Qualifiers
source                  1..327
                        mol_type = protein
                        organism = synthetic construct
SEQUENCE: 915
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEELGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327

SEQ ID NO: 916          moltype = AA   length = 330
FEATURE                 Location/Qualifiers
source                  1..330
                        mol_type = protein
                        organism = synthetic construct
SEQUENCE: 916
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 917          moltype = AA   length = 330
FEATURE                 Location/Qualifiers
source                  1..330
                        mol_type = protein
                        organism = synthetic construct
SEQUENCE: 917
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVAVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 918          moltype = AA   length = 330
FEATURE                 Location/Qualifiers
source                  1..330
                        mol_type = protein
                        organism = synthetic construct
SEQUENCE: 918
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 919          moltype = AA   length = 330
FEATURE                 Location/Qualifiers
source                  1..330
                        mol_type = protein
```

-continued

```
                               organism = synthetic construct
SEQUENCE: 919
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 920           moltype = AA   length = 330
FEATURE                  Location/Qualifiers
source                   1..330
                         mol_type = protein
                         organism = synthetic construct
SEQUENCE: 920
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 921           moltype = AA   length = 330
FEATURE                  Location/Qualifiers
source                   1..330
                         mol_type = protein
                         organism = synthetic construct
SEQUENCE: 921
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 922           moltype = AA   length = 330
FEATURE                  Location/Qualifiers
source                   1..330
                         mol_type = protein
                         organism = synthetic construct
SEQUENCE: 922
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 923           moltype = AA   length = 330
FEATURE                  Location/Qualifiers
source                   1..330
                         mol_type = protein
                         organism = synthetic construct
SEQUENCE: 923
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLYITREP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 924           moltype = AA   length = 330
FEATURE                  Location/Qualifiers
source                   1..330
                         mol_type = protein
                         organism = synthetic construct
SEQUENCE: 924
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLYITREP EVTCVVVAVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 925           moltype = AA   length = 330
FEATURE                  Location/Qualifiers
source                   1..330
                         mol_type = protein
                         organism = synthetic construct
```

-continued

```
SEQUENCE: 925
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 926           moltype = AA   length = 330
FEATURE                  Location/Qualifiers
source                   1..330
                         mol_type = protein
                         organism = synthetic construct
SEQUENCE: 926
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 927           moltype = AA   length = 330
FEATURE                  Location/Qualifiers
source                   1..330
                         mol_type = protein
                         organism = synthetic construct
SEQUENCE: 927
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 928           moltype = AA   length = 330
FEATURE                  Location/Qualifiers
source                   1..330
                         mol_type = protein
                         organism = synthetic construct
SEQUENCE: 928
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 929           moltype = AA   length = 330
FEATURE                  Location/Qualifiers
source                   1..330
                         mol_type = protein
                         organism = synthetic construct
SEQUENCE: 929
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV LHEALHSHYT QKSLSLSPGK                                    330

SEQ ID NO: 930           moltype = AA   length = 330
FEATURE                  Location/Qualifiers
source                   1..330
                         mol_type = protein
                         organism = synthetic construct
SEQUENCE: 930
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV LHEALHSHYT QKSLSLSPGK                                    330

SEQ ID NO: 931           moltype = AA   length = 330
FEATURE                  Location/Qualifiers
source                   1..330
                         mol_type = protein
                         organism = synthetic construct
SEQUENCE: 931
```

```
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPGK                                   330

SEQ ID NO: 932             moltype = AA   length = 330
FEATURE                    Location/Qualifiers
source                     1..330
                           mol_type = protein
                           organism = synthetic construct
SEQUENCE: 932
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPGK                                   330

SEQ ID NO: 933             moltype = AA   length = 330
FEATURE                    Location/Qualifiers
source                     1..330
                           mol_type = protein
                           organism = synthetic construct
SEQUENCE: 933
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPGK                                   330

SEQ ID NO: 934             moltype = AA   length = 330
FEATURE                    Location/Qualifiers
source                     1..330
                           mol_type = protein
                           organism = synthetic construct
SEQUENCE: 934
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPGK                                   330

SEQ ID NO: 935             moltype = AA   length = 330
FEATURE                    Location/Qualifiers
source                     1..330
                           mol_type = protein
                           organism = synthetic construct
SEQUENCE: 935
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW  300
QQGNVFSCSV LHEALHSHYT QKSLSLSPGK                                   330

SEQ ID NO: 936             moltype = AA   length = 330
FEATURE                    Location/Qualifiers
source                     1..330
                           mol_type = protein
                           organism = synthetic construct
SEQUENCE: 936
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VDHHDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPGK                                   330

SEQ ID NO: 937             moltype = AA   length = 330
FEATURE                    Location/Qualifiers
source                     1..330
                           mol_type = protein
                           organism = synthetic construct
SEQUENCE: 937
ASTKGPSVFP LAPSSKSTSG GTAALGCLVK DYFPEPVTVS WNSGALTSGV HTFPAVLQSS   60
```

```
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLT VDHHDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHSHYT QKSLSLSPGK                                     330

SEQ ID NO: 938          moltype = AA   length = 330
FEATURE                 Location/Qualifiers
source                  1..330
                        mol_type = protein
                        organism = synthetic construct
SEQUENCE: 938
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVAVS HEDPEVKFNW YVDGVEVHNA KTKPREEQYN    180
STYRVVSVLT VDHHDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHSHYT QKSLSLSPGK                                     330

SEQ ID NO: 939          moltype = AA   length = 330
FEATURE                 Location/Qualifiers
source                  1..330
                        mol_type = protein
                        organism = synthetic construct
SEQUENCE: 939
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLT VDHHDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHSHYT QKSLSLSPGK                                     330

SEQ ID NO: 940          moltype = AA   length = 330
FEATURE                 Location/Qualifiers
source                  1..330
                        mol_type = protein
                        organism = synthetic construct
SEQUENCE: 940
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA    120
PSVFLFPPKP KDTLMISRTP EVTCVVVDVS HEDPEVKFNW YVDGVEVHNA KTKPREEQYN    180
STYRVVSVLT VDHHDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHSHYT QKSLSLSPGK                                     330

SEQ ID NO: 941          moltype = AA   length = 330
FEATURE                 Location/Qualifiers
source                  1..330
                        mol_type = protein
                        organism = synthetic construct
SEQUENCE: 941
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA    120
PSVFLFPPKP KDTLMISRTP EVTCVVVDVS HEDPEVKFNW YVDGVEVHNA KTKPREEQYN    180
STYRVVSVLT VDHHDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHSHYT QKSLSLSPGK                                     330

SEQ ID NO: 942          moltype = AA   length = 330
FEATURE                 Location/Qualifiers
source                  1..330
                        mol_type = protein
                        organism = synthetic construct
SEQUENCE: 942
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLT VDHHDWLNGK EYKCKVSNKA LGAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHSHYT QKSLSLSPGK                                     330

SEQ ID NO: 943          moltype = AA   length = 327
FEATURE                 Location/Qualifiers
source                  1..327
                        mol_type = protein
                        organism = synthetic construct
SEQUENCE: 943
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV    120
```

-continued

```
FLFPPKPKDT LYITREPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLGK                                        327

SEQ ID NO: 944            moltype = AA   length = 327
FEATURE                   Location/Qualifiers
source                    1..327
                          mol_type = protein
                          organism = synthetic construct
SEQUENCE: 944
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPPCP APEFLGGPSV    120
FLFPPKPKDT LYITREPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLGK                                        327

SEQ ID NO: 945            moltype = AA   length = 327
FEATURE                   Location/Qualifiers
source                    1..327
                          mol_type = protein
                          organism = synthetic construct
SEQUENCE: 945
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPPCP APEELGGPSV    120
FLFPPKPKDT LYITREPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLGK                                        327

SEQ ID NO: 946            moltype = AA   length = 327
FEATURE                   Location/Qualifiers
source                    1..327
                          mol_type = protein
                          organism = synthetic construct
SEQUENCE: 946
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPSCP APEFLGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVLHE ALHSHYTQKS LSLSLGK                                        327

SEQ ID NO: 947            moltype = AA   length = 327
FEATURE                   Location/Qualifiers
source                    1..327
                          mol_type = protein
                          organism = synthetic construct
SEQUENCE: 947
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPPCP APEFLGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVLHE ALHSHYTQKS LSLSLGK                                        327

SEQ ID NO: 948            moltype = AA   length = 327
FEATURE                   Location/Qualifiers
source                    1..327
                          mol_type = protein
                          organism = synthetic construct
SEQUENCE: 948
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPPCP APEELGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVLHE ALHSHYTQKS LSLSLGK                                        327

SEQ ID NO: 949            moltype = AA   length = 327
FEATURE                   Location/Qualifiers
source                    1..327
                          mol_type = protein
                          organism = synthetic construct
SEQUENCE: 949
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPSCP APEFLGGPSV    120
FLFPPKPKDT LMISRTPEVT CVVVDVSQED PEVQFNWYVD GVEVHNAKTK PREEQFNSTY    180
```

```
RVVSVLTVDH HDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHSHYTQKS LSLSLGK                                      327

SEQ ID NO: 950         moltype = AA  length = 327
FEATURE                Location/Qualifiers
source                 1..327
                       mol_type = protein
                       organism = synthetic construct
SEQUENCE: 950
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPPKPKDT LMISRTPEVT CVVVDVSQED PEVQFNWYVD GVEVHNAKTK PREEQFNSTY  180
RVVSVLTVDH HDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHSHYTQKS LSLSLGK                                      327

SEQ ID NO: 951         moltype = AA  length = 327
FEATURE                Location/Qualifiers
source                 1..327
                       mol_type = protein
                       organism = synthetic construct
SEQUENCE: 951
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEELGGPSV  120
FLFPPPKPKDT LMISRTPEVT CVVVDVSQED PEVQFNWYVD GVEVHNAKTK PREEQFNSTY  180
RVVSVLTVDH HDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHSHYTQKS LSLSLGK                                      327

SEQ ID NO: 952         moltype = AA  length = 326
FEATURE                Location/Qualifiers
source                 1..326
                       mol_type = protein
                       organism = synthetic construct
SEQUENCE: 952
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL YITREPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                       326

SEQ ID NO: 953         moltype = AA  length = 326
FEATURE                Location/Qualifiers
source                 1..326
                       mol_type = protein
                       organism = synthetic construct
SEQUENCE: 953
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVLHEA LHSHYTQKSL SLSPGK                                       326

SEQ ID NO: 954         moltype = AA  length = 326
FEATURE                Location/Qualifiers
source                 1..326
                       mol_type = protein
                       organism = synthetic construct
SEQUENCE: 954
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVDHH DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHSHYTQKSL SLSPGK                                       326

SEQ ID NO: 955         moltype = AA  length = 330
FEATURE                Location/Qualifiers
source                 1..330
                       mol_type = protein
                       organism = synthetic construct
SEQUENCE: 955
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
```

-continued

```
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPGK                                   330

SEQ ID NO: 956          moltype = AA  length = 330
FEATURE                 Location/Qualifiers
source                  1..330
                        mol_type = protein
                        organism = synthetic construct
SEQUENCE: 956
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPGK                                   330

SEQ ID NO: 957          moltype = AA  length = 330
FEATURE                 Location/Qualifiers
source                  1..330
                        mol_type = protein
                        organism = synthetic construct
SEQUENCE: 957
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPGK                                   330

SEQ ID NO: 958          moltype = AA  length = 330
FEATURE                 Location/Qualifiers
source                  1..330
                        mol_type = protein
                        organism = synthetic construct
SEQUENCE: 958
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPGK                                   330

SEQ ID NO: 959          moltype = AA  length = 330
FEATURE                 Location/Qualifiers
source                  1..330
                        mol_type = protein
                        organism = synthetic construct
SEQUENCE: 959
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPGK                                   330

SEQ ID NO: 960          moltype = AA  length = 330
FEATURE                 Location/Qualifiers
source                  1..330
                        mol_type = protein
                        organism = synthetic construct
SEQUENCE: 960
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHAHYT QKSLSLSPGK                                   330

SEQ ID NO: 961          moltype = AA  length = 330
FEATURE                 Location/Qualifiers
source                  1..330
                        mol_type = protein
                        organism = synthetic construct
SEQUENCE: 961
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
```

-continued

```
QQGNVFSCSV LHEALHAHYT QKSLSLSPGK                                    330

SEQ ID NO: 962          moltype = AA   length = 330
FEATURE                 Location/Qualifiers
source                  1..330
                        mol_type = protein
                        organism = synthetic construct
SEQUENCE: 962
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPGK                                    330

SEQ ID NO: 963          moltype = AA   length = 330
FEATURE                 Location/Qualifiers
source                  1..330
                        mol_type = protein
                        organism = synthetic construct
SEQUENCE: 963
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPGK                                    330

SEQ ID NO: 964          moltype = AA   length = 330
FEATURE                 Location/Qualifiers
source                  1..330
                        mol_type = protein
                        organism = synthetic construct
SEQUENCE: 964
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVAVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPGK                                    330

SEQ ID NO: 965          moltype = AA   length = 330
FEATURE                 Location/Qualifiers
source                  1..330
                        mol_type = protein
                        organism = synthetic construct
SEQUENCE: 965
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPGK                                    330

SEQ ID NO: 966          moltype = AA   length = 330
FEATURE                 Location/Qualifiers
source                  1..330
                        mol_type = protein
                        organism = synthetic construct
SEQUENCE: 966
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPGK                                    330

SEQ ID NO: 967          moltype = AA   length = 330
FEATURE                 Location/Qualifiers
source                  1..330
                        mol_type = protein
                        organism = synthetic construct
SEQUENCE: 967
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPGK                                    330
```

-continued

```
SEQ ID NO: 968            moltype = AA  length = 330
FEATURE                   Location/Qualifiers
source                    1..330
                          mol_type = protein
                          organism = synthetic construct
SEQUENCE: 968
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHAHYT QKSLSLSPGK                                   330

SEQ ID NO: 969            moltype = AA  length = 330
FEATURE                   Location/Qualifiers
source                    1..330
                          mol_type = protein
                          organism = synthetic construct
SEQUENCE: 969
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPGK                                   330

SEQ ID NO: 970            moltype = AA  length = 330
FEATURE                   Location/Qualifiers
source                    1..330
                          mol_type = protein
                          organism = synthetic construct
SEQUENCE: 970
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPGK                                   330

SEQ ID NO: 971            moltype = AA  length = 330
FEATURE                   Location/Qualifiers
source                    1..330
                          mol_type = protein
                          organism = synthetic construct
SEQUENCE: 971
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPGK                                   330

SEQ ID NO: 972            moltype = AA  length = 330
FEATURE                   Location/Qualifiers
source                    1..330
                          mol_type = protein
                          organism = synthetic construct
SEQUENCE: 972
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPGK                                   330

SEQ ID NO: 973            moltype = AA  length = 330
FEATURE                   Location/Qualifiers
source                    1..330
                          mol_type = protein
                          organism = synthetic construct
SEQUENCE: 973
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPGK                                   330
```

-continued

```
SEQ ID NO: 974            moltype = AA   length = 330
FEATURE                   Location/Qualifiers
source                    1..330
                          mol_type = protein
                          organism = synthetic construct
SEQUENCE: 974
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPGK                                    330

SEQ ID NO: 975            moltype = AA   length = 330
FEATURE                   Location/Qualifiers
source                    1..330
                          mol_type = protein
                          organism = synthetic construct
SEQUENCE: 975
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHWHYT QKSLSLSPGK                                    330

SEQ ID NO: 976            moltype = AA   length = 330
FEATURE                   Location/Qualifiers
source                    1..330
                          mol_type = protein
                          organism = synthetic construct
SEQUENCE: 976
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 977            moltype = AA   length = 330
FEATURE                   Location/Qualifiers
source                    1..330
                          mol_type = protein
                          organism = synthetic construct
SEQUENCE: 977
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVHNA KTKPREEQYA  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 978            moltype = AA   length = 330
FEATURE                   Location/Qualifiers
source                    1..330
                          mol_type = protein
                          organism = synthetic construct
SEQUENCE: 978
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRDP EVTCVVVAVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 979            moltype = AA   length = 330
FEATURE                   Location/Qualifiers
source                    1..330
                          mol_type = protein
                          organism = synthetic construct
SEQUENCE: 979
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                    330

SEQ ID NO: 980            moltype = AA   length = 330
```

-continued

```
FEATURE                  Location/Qualifiers
source                   1..330
                         mol_type = protein
                         organism = synthetic construct
SEQUENCE: 980
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 981           moltype = AA  length = 330
FEATURE                  Location/Qualifiers
source                   1..330
                         mol_type = protein
                         organism = synthetic construct
SEQUENCE: 981
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 982           moltype = AA  length = 330
FEATURE                  Location/Qualifiers
source                   1..330
                         mol_type = protein
                         organism = synthetic construct
SEQUENCE: 982
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVHNA KTKPREEQYN  180
STYRVVSVLQ VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 983           moltype = AA  length = 330
FEATURE                  Location/Qualifiers
source                   1..330
                         mol_type = protein
                         organism = synthetic construct
SEQUENCE: 983
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVHNA KTKPREEQYN  180
STYRVVSVLW VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 984           moltype = AA  length = 330
FEATURE                  Location/Qualifiers
source                   1..330
                         mol_type = protein
                         organism = synthetic construct
SEQUENCE: 984
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVHNA KTKPREEQYA  180
STYRVVSVLW VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 985           moltype = AA  length = 330
FEATURE                  Location/Qualifiers
source                   1..330
                         mol_type = protein
                         organism = synthetic construct
SEQUENCE: 985
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRDP EVTCVVVAVS HEDPEVKFNW YVDGVEVHNA KTKPREEQYN  180
STYRVVSVLW VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 986           moltype = AA  length = 330
FEATURE                  Location/Qualifiers
```

-continued

```
source                    1..330
                          mol_type = protein
                          organism = synthetic construct
SEQUENCE: 986
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVHNA KTKPREEQYN  180
STYRVVSVLW VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 987          moltype = AA  length = 330
FEATURE                 Location/Qualifiers
source                    1..330
                          mol_type = protein
                          organism = synthetic construct
SEQUENCE: 987
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRDP EVTCVVVDVS HEDPEVKFNW YVDGVEVHNA KTKPREEQYN  180
STYRVVSVLW VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 988          moltype = AA  length = 330
FEATURE                 Location/Qualifiers
source                    1..330
                          mol_type = protein
                          organism = synthetic construct
SEQUENCE: 988
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRDP EVTCVVVDVS HEDPEVKFNW YVDGVEVHNA KTKPREEQYN  180
STYRVVSVLW VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 989          moltype = AA  length = 330
FEATURE                 Location/Qualifiers
source                    1..330
                          mol_type = protein
                          organism = synthetic construct
SEQUENCE: 989
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVHNA KTKPREEQYN  180
STYRVVSVLW VLHQDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 990          moltype = AA  length = 330
FEATURE                 Location/Qualifiers
source                    1..330
                          mol_type = protein
                          organism = synthetic construct
SEQUENCE: 990
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLYISRDP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 991          moltype = AA  length = 330
FEATURE                 Location/Qualifiers
source                    1..330
                          mol_type = protein
                          organism = synthetic construct
SEQUENCE: 991
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLYISRDP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 992          moltype = AA  length = 330
FEATURE                 Location/Qualifiers
source                    1..330
```

-continued

```
                              mol_type = protein
                              organism = synthetic construct
SEQUENCE: 992
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLYISRDP EVTCVVVAVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 993            moltype = AA   length = 330
FEATURE                   Location/Qualifiers
source                    1..330
                          mol_type = protein
                          organism = synthetic construct
SEQUENCE: 993
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLYISRDP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 994            moltype = AA   length = 330
FEATURE                   Location/Qualifiers
source                    1..330
                          mol_type = protein
                          organism = synthetic construct
SEQUENCE: 994
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLYISRDP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 995            moltype = AA   length = 330
FEATURE                   Location/Qualifiers
source                    1..330
                          mol_type = protein
                          organism = synthetic construct
SEQUENCE: 995
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLYISRDP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 996            moltype = AA   length = 330
FEATURE                   Location/Qualifiers
source                    1..330
                          mol_type = protein
                          organism = synthetic construct
SEQUENCE: 996
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLYISRDP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 997            moltype = AA   length = 330
FEATURE                   Location/Qualifiers
source                    1..330
                          mol_type = protein
                          organism = synthetic construct
SEQUENCE: 997
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLQ VLHVDWLNGK EYKCKVSNKA LPAPIEKTIS KAKGQPREPQ VYTLPPSRDE   240
LTKNQVSLTC LVKGFYPSDI VVEWESNGQP ENNYKTTPPV LDSDGSFFLY SKLTVDKSRW   300
QQGNVFSCSV MHEALHNHYT QKSLSLSPGK                                    330

SEQ ID NO: 998            moltype = AA   length = 330
FEATURE                   Location/Qualifiers
source                    1..330
                          mol_type = protein
```

-continued

```
                          organism = synthetic construct
SEQUENCE: 998
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLQ VLHVDWLNGK EYKCKVSNKA LPAPIEKTIS KAKGQPREPQ VYTLPPSRDE   240
LTKNQVSLTC LVKGFYPSDI VVEWESNGQP ENNYKTTPPV LDSDGSFFLY SKLTVDKSRW   300
QQGNVFSCSV MHEALHNHYT QKSLSLSPGK                                    330

SEQ ID NO: 999             moltype = AA   length = 330
FEATURE                    Location/Qualifiers
source                     1..330
                           mol_type = protein
                           organism = synthetic construct
SEQUENCE: 999
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVAVS HEDPEVKFNW YVDGVEVHNA KTKPREEQYN   180
STYRVVSVLQ VLHVDWLNGK EYCKVSNKA LPAPIEKTIS KAKGQPREPQ VYTLPPSRDE   240
LTKNQVSLTC LVKGFYPSDI VVEWESNGQP ENNYKTTPPV LDSDGSFFLY SKLTVDKSRW   300
QQGNVFSCSV MHEALHNHYT QKSLSLSPGK                                    330

SEQ ID NO: 1000            moltype = AA   length = 330
FEATURE                    Location/Qualifiers
source                     1..330
                           mol_type = protein
                           organism = synthetic construct
SEQUENCE: 1000
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLQ VLHVDWLNGK EYCKVSNKA LPAPIEKTIS KAKGQPREPQ VYTLPPSRDE   240
LTKNQVSLTC LVKGFYPSDI VVEWESNGQP ENNYKTTPPV LDSDGSFFLY SKLTVDKSRW   300
QQGNVFSCSV MHEALHNHYT QKSLSLSPGK                                    330

SEQ ID NO: 1001            moltype = AA   length = 330
FEATURE                    Location/Qualifiers
source                     1..330
                           mol_type = protein
                           organism = synthetic construct
SEQUENCE: 1001
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLQ VLHVDWLNGK EYCKVSNKA LPAPIEKTIS KAKGQPREPQ VYTLPPSRDE   240
LTKNQVSLTC LVKGFYPSDI VVEWESNGQP ENNYKTTPPV LDSDGSFFLY SKLTVDKSRW   300
QQGNVFSCSV MHEALHNHYT QKSLSLSPGK                                    330

SEQ ID NO: 1002            moltype = AA   length = 330
FEATURE                    Location/Qualifiers
source                     1..330
                           mol_type = protein
                           organism = synthetic construct
SEQUENCE: 1002
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLQ VLHVDWLNGK EYCKVSNKA LPAPIEKTIS KAKGQPREPQ VYTLPPSRDE   240
LTKNQVSLTC LVKGFYPSDI VVEWESNGQP ENNYKTTPPV LDSDGSFFLY SKLTVDKSRW   300
QQGNVFSCSV MHEALHNHYT QKSLSLSPGK                                    330

SEQ ID NO: 1003            moltype = AA   length = 330
FEATURE                    Location/Qualifiers
source                     1..330
                           mol_type = protein
                           organism = synthetic construct
SEQUENCE: 1003
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLQ VLHVDWLNGK EYCKVSNKA LGAPIEKTIS KAKGQPREPQ VYTLPPSRDE   240
LTKNQVSLTC LVKGFYPSDI VVEWESNGQP ENNYKTTPPV LDSDGSFFLY SKLTVDKSRW   300
QQGNVFSCSV MHEALHNHYT QKSLSLSPGK                                    330

SEQ ID NO: 1004            moltype = AA   length = 330
FEATURE                    Location/Qualifiers
source                     1..330
                           mol_type = protein
                           organism = synthetic construct
```

-continued

```
SEQUENCE: 1004
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPGK                                   330

SEQ ID NO: 1005        moltype = AA   length = 330
FEATURE                Location/Qualifiers
source                 1..330
                       mol_type = protein
                       organism = synthetic construct
SEQUENCE: 1005
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRDP EVTCVVVDVS HEDPEVKFNW YVDGVEVDNA KTKPREEQYA  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPGK                                   330

SEQ ID NO: 1006        moltype = AA   length = 330
FEATURE                Location/Qualifiers
source                 1..330
                       mol_type = protein
                       organism = synthetic construct
SEQUENCE: 1006
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRDP EVTCVVVAVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPGK                                   330

SEQ ID NO: 1007        moltype = AA   length = 330
FEATURE                Location/Qualifiers
source                 1..330
                       mol_type = protein
                       organism = synthetic construct
SEQUENCE: 1007
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPGK                                   330

SEQ ID NO: 1008        moltype = AA   length = 330
FEATURE                Location/Qualifiers
source                 1..330
                       mol_type = protein
                       organism = synthetic construct
SEQUENCE: 1008
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPGK                                   330

SEQ ID NO: 1009        moltype = AA   length = 330
FEATURE                Location/Qualifiers
source                 1..330
                       mol_type = protein
                       organism = synthetic construct
SEQUENCE: 1009
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LPAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPGK                                   330

SEQ ID NO: 1010        moltype = AA   length = 330
FEATURE                Location/Qualifiers
source                 1..330
                       mol_type = protein
                       organism = synthetic construct
SEQUENCE: 1010
```

```
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRDP EVTCVVVDVS HEDPEVKFNW YVDGVEVDNA KTKPREEQYN  180
STYRVVSVLR VLHVDWLNGK EYKCKVSNKA LGAPIEKTIS KAKGQPREPQ VYTLPPSRDE  240
LTKNQVSLTC LVKGFYPSDI VVEWESNGQP ENNYKTTPPV LDSDGSFFLY SKLTVDKSRW  300
QQGNVFSCSV MHEALHNHYT QKSLSLSPGK                                   330
```

```
SEQ ID NO: 1011          moltype = AA   length = 330
FEATURE                  Location/Qualifiers
source                   1..330
                         mol_type = protein
                         organism = synthetic construct
SEQUENCE: 1011
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPGK                                   330
```

```
SEQ ID NO: 1012          moltype = AA   length = 327
FEATURE                  Location/Qualifiers
source                   1..327
                         mol_type = protein
                         organism = synthetic construct
SEQUENCE: 1012
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH RDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVLHE ALHNHYTQKS LSLSLGK                                      327
```

```
SEQ ID NO: 1013          moltype = AA   length = 327
FEATURE                  Location/Qualifiers
source                   1..327
                         mol_type = protein
                         organism = synthetic construct
SEQUENCE: 1013
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH RDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVLHE ALHNHYTQKS LSLSLGK                                      327
```

```
SEQ ID NO: 1014          moltype = AA   length = 327
FEATURE                  Location/Qualifiers
source                   1..327
                         mol_type = protein
                         organism = synthetic construct
SEQUENCE: 1014
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEELGGPSV  120
FLFPPKPKDT LMISRTPEVT CVVVDVSQED PEVQFNWYVD GVEVHNAKTK PREEQFNSTY  180
RVVSVLTVLH RDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVLHE ALHNHYTQKS LSLSLGK                                      327
```

```
SEQ ID NO: 1015          moltype = AA   length = 326
FEATURE                  Location/Qualifiers
source                   1..326
                         mol_type = protein
                         organism = synthetic construct
SEQUENCE: 1015
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHR DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVLHEA LHNHYTQKSL SLSPGK                                       326
```

```
SEQ ID NO: 1016          moltype = AA   length = 330
FEATURE                  Location/Qualifiers
source                   1..330
                         mol_type = protein
                         organism = synthetic construct
SEQUENCE: 1016
ASTKGPSVFP LAPSSKSTSG GTAALGCLVK DYFPEPVTVS WNSGALTSGV HTFPAVLQSS  60
```

-continued

```
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPGK                                   330

SEQ ID NO: 1017          moltype = AA   length = 330
FEATURE                  Location/Qualifiers
source                   1..330
                         mol_type = protein
                         organism = synthetic construct
SEQUENCE: 1017
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPGK                                   330

SEQ ID NO: 1018          moltype = AA   length = 330
FEATURE                  Location/Qualifiers
source                   1..330
                         mol_type = protein
                         organism = synthetic construct
SEQUENCE: 1018
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPGK                                   330

SEQ ID NO: 1019          moltype = AA   length = 330
FEATURE                  Location/Qualifiers
source                   1..330
                         mol_type = protein
                         organism = synthetic construct
SEQUENCE: 1019
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELAGA  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPGK                                   330

SEQ ID NO: 1020          moltype = AA   length = 330
FEATURE                  Location/Qualifiers
source                   1..330
                         mol_type = protein
                         organism = synthetic construct
SEQUENCE: 1020
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPGK                                   330

SEQ ID NO: 1021          moltype = AA   length = 330
FEATURE                  Location/Qualifiers
source                   1..330
                         mol_type = protein
                         organism = synthetic construct
SEQUENCE: 1021
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LGAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPGK                                   330

SEQ ID NO: 1022          moltype = AA   length = 330
FEATURE                  Location/Qualifiers
source                   1..330
                         mol_type = protein
                         organism = synthetic construct
SEQUENCE: 1022
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
```

-continued

```
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 1023            moltype = AA   length = 330
FEATURE                    Location/Qualifiers
source                     1..330
                           mol_type = protein
                           organism = synthetic construct
SEQUENCE: 1023
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV LHEALHSHYT QKSLSLSPGK                                   330

SEQ ID NO: 1024            moltype = AA   length = 330
FEATURE                    Location/Qualifiers
source                     1..330
                           mol_type = protein
                           organism = synthetic construct
SEQUENCE: 1024
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLYITREP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                   330

SEQ ID NO: 1025            moltype = AA   length = 330
FEATURE                    Location/Qualifiers
source                     1..330
                           mol_type = protein
                           organism = synthetic construct
SEQUENCE: 1025
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV LHEALHAHYT QKSLSLSPGK                                   330

SEQ ID NO: 1026            moltype = AA   length = 330
FEATURE                    Location/Qualifiers
source                     1..330
                           mol_type = protein
                           organism = synthetic construct
SEQUENCE: 1026
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALKFHYT QKSLSLSPGK                                   330

SEQ ID NO: 1027            moltype = AA   length = 330
FEATURE                    Location/Qualifiers
source                     1..330
                           mol_type = protein
                           organism = synthetic construct
SEQUENCE: 1027
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VDHHDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHSHYT QKSLSLSPGK                                   330

SEQ ID NO: 1028            moltype = AA   length = 330
FEATURE                    Location/Qualifiers
source                     1..330
                           mol_type = protein
                           organism = synthetic construct
SEQUENCE: 1028
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYA  180
```

-continued

```
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 1029        moltype = AA  length = 330
FEATURE                Location/Qualifiers
source                 1..330
                       mol_type = protein
                       organism = synthetic construct
SEQUENCE: 1029
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA   120
PSVFLFPPKP KDTLYITREP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 1030        moltype = AA  length = 20
FEATURE                Location/Qualifiers
source                 1..20
                       mol_type = protein
                       organism = synthetic construct
SEQUENCE: 1030
GGGGSGGGGS GGGGSGGGGS                                               20

SEQ ID NO: 1031        moltype = AA  length = 5
FEATURE                Location/Qualifiers
source                 1..5
                       mol_type = protein
                       organism = Homo sapiens
SEQUENCE: 1031
SRDEL                                                               5

SEQ ID NO: 1032        moltype = AA  length = 5
FEATURE                Location/Qualifiers
source                 1..5
                       mol_type = protein
                       organism = Homo sapiens
SEQUENCE: 1032
SREEM                                                               5
```

The invention claimed is:

1. A bispecific binding protein comprising:

(a) a PD-1 binding region comprising an anti-PD-1 immunoglobulin heavy chain variable domain (anti-PD-1 V$_H$) that comprises, according to Kabat numbering, a heavy chain complementarity determining region 1 (CDR-H1) comprising the amino acid sequence of SEQ ID NO: 445, a CDR-H2 comprising the amino acid sequence of SEQ ID NO: 446, and a CDR-H3 comprising the amino acid sequence of SEQ ID NO: 457; and an anti-PD-1 immunoglobulin light chain variable domain (anti-PD-1 V$_L$) that comprises, according to Kabat numbering, a light chain complementarity determining region 1 (CDR-L1) comprising the amino acid sequence of SEQ ID NO: 448, a CDR-L2 comprising the amino acid sequence of SEQ ID NO: 449, and a CDR-L3 comprising the amino acid sequence of SEQ ID NO: 450; and (b) a VEGF binding region comprising an anti-VEGF immunoglobulin heavy chain variable domain (anti-VEGF V$_H$) that comprises, according to Kabat numbering, a heavy chain complementarity determining region 1 (CDR-H1) comprising the amino acid sequence of SEQ ID NO: 433, a CDR-H2 comprising the amino acid sequence of SEQ ID NO: 434, and a CDR-H3 comprising the amino acid sequence of SEQ ID NO: 435; and an anti-VEGF immunoglobulin light chain variable domain (anti-VEGF V$_L$) that comprises, according to Kabat numbering, a light chain complementarity determining region 1 (CDR-L1) comprising the amino acid sequence of SEQ ID NO: 436, a CDR-L2 comprising the amino acid sequence of SEQ ID NO: 437, and a CDR-L3 comprising the amino acid sequence of SEQ ID NO: 438.

2. The bispecific binding protein of claim 1, wherein the anti-PD-1 V$_H$ comprises the amino acid sequence of SEQ ID NO: 327, and the anti-PD-1 V$_L$ comprises the amino acid sequence of SEQ ID NO: 347.

3. The bispecific binding protein of claim 2, wherein the PD-1 binding region is an anti-PD-1 scFv that comprises the anti-PD-1 V$_H$ and the anti-PD-1 V$_L$.

4. The bispecific binding protein of claim 3, wherein the anti-PD-1 scFv comprises the amino acid sequence of SEQ ID NO: 421.

5. The bispecific binding protein of claim 1, wherein the anti-VEGF V$_H$ comprises the amino acid sequence of SEQ ID NO: 431, and the anti-VEGF V$_L$ comprises the amino acid sequence of SEQ ID NO: 432.

6. The bispecific binding protein of claim 4, wherein the anti-VEGF V$_H$ comprises the amino acid sequence of SEQ ID NO: 431, and the anti-VEGF V$_L$ comprises the amino acid sequence of SEQ ID NO: 432.

7. The bispecific binding protein of claim 1, further comprising an IgG1 Fc region.

8. The bispecific binding protein of claim 6, wherein the VEGF binding region further comprises an IgG1 Fc region.

9. The bispecific binding protein of claim 8, wherein the IgG1 Fc region comprises L234A/L235A (LALA) substitutions.

10. The bispecific binding protein of claim 8, wherein the anti-PD-1 scFv is linked to the VEGF binding region.

11. The bispecific binding protein of claim 10, wherein the anti-PD-1 scFv is linked to the C-terminal of the VEGF binding region.

12. The bispecific binding protein of claim 11, wherein the anti-PD-1 scFv is linked to the VEGF binding region directly.

13. The bispecific binding protein of claim 11, wherein the anti-PD-1 scFv is linked to the VEGF binding region via a linker.

14. The bispecific binding protein of claim 13, wherein the linker comprises the amino acid sequence of SEQ ID NO: 1030.

15. The bispecific binding protein of claim 1, wherein the bispecific binding protein comprises a heavy chain that comprises the amino acid sequence of SEQ ID NO: 96, and a light chain that comprises the amino acid sequence of SEQ ID NO: 243.

16. The bispecific binding protein of claim 1, comprising two PD-1 binding regions and two VEGF binding regions.

17. A pharmaceutical composition comprising the bispecific binding protein of claim 1 and a pharmaceutically acceptable carrier.

18. A bispecific binding protein comprising a first polypeptide chain having the sequence of SEQ ID NO: 96 and a second polypeptide chain having the sequence of SEQ ID NO: 243, wherein the bispecific binding protein comprises two PD-1 binding regions and two VEGF-binding regions.

19. A pharmaceutical composition comprising the bispecific binding protein of claim 18 and a pharmaceutically acceptable carrier.

\* \* \* \* \*